United States Patent
Romero et al.

(10) Patent No.: US 10,889,571 B2
(45) Date of Patent: Jan. 12, 2021

(54) SUBSTITUTED BENZOIMIDAZOLES AND IMIDAZO[4,5-C]PYRIDINES FOR TREATING CERTAIN LEUKEMIAS

(71) Applicant: Terns, Inc., Foster City, CA (US)

(72) Inventors: F. Anthony Romero, Redwood City, CA (US); Thorsten A. Kirschberg, San Carlos, CA (US); Randall Halcomb, Foster City, CA (US); Yingzi Xu, Palo Alto, CA (US)

(73) Assignee: Terns, Inc., Foster City, CA (US)

(*) Notice: Subject to any disclaimer, the term of this patent is extended or adjusted under 35 U.S.C. 154(b) by 0 days.

(21) Appl. No.: 16/573,860

(22) Filed: Sep. 17, 2019

(65) Prior Publication Data

US 2020/0087283 A1    Mar. 19, 2020

Related U.S. Application Data

(60) Provisional application No. 62/889,929, filed on Aug. 21, 2019, provisional application No. 62/816,637, filed on Mar. 11, 2019, provisional application No. 62/733,029, filed on Sep. 18, 2018.

(51) Int. Cl.

| | | |
|---|---|---|
| A61K 31/4184 | (2006.01) | |
| A61K 31/4188 | (2006.01) | |
| C07D 235/04 | (2006.01) | |
| C07D 471/04 | (2006.01) | |
| C07D 403/04 | (2006.01) | |
| C07D 413/04 | (2006.01) | |
| C07D 235/16 | (2006.01) | |
| C07D 409/14 | (2006.01) | |
| C07D 417/04 | (2006.01) | |
| A61P 35/00 | (2006.01) | |
| C07D 513/04 | (2006.01) | |
| C07D 405/14 | (2006.01) | |
| C07D 498/04 | (2006.01) | |
| C07D 403/14 | (2006.01) | |

(52) U.S. Cl.
CPC ............ *C07D 403/04* (2013.01); *A61P 35/00* (2018.01); *C07D 235/16* (2013.01); *C07D 403/14* (2013.01); *C07D 405/14* (2013.01); *C07D 409/14* (2013.01); *C07D 413/04* (2013.01); *C07D 417/04* (2013.01); *C07D 471/04* (2013.01); *C07D 498/04* (2013.01); *C07D 513/04* (2013.01)

(58) Field of Classification Search
CPC ............ A61K 31/4184; A61K 31/4188; C07D 235/64; C07D 471/04
USPC ............... 514/393, 394; 548/303.1, 304.4
See application file for complete search history.

(56) References Cited

U.S. PATENT DOCUMENTS

| | | |
|---|---|---|
| 2002/0010343 A1 | 1/2002 | Sircar et al. |
| 2005/0197375 A1 | 9/2005 | Sircar et al. |
| 2011/0046133 A1 | 2/2011 | Sung et al. |

OTHER PUBLICATIONS

International Search Report and Written Opinion of the International Searching Authority dated Jan. 15, 2020, for Patent Application No. PCT/US2019/051567, filed Sep. 17, 2019, 13 pages.
Invitation to Pay Additional Fees dated Oct. 28, 2019, for Patent Application No. PCT/US2019/051567, filed Sep. 17, 2019, 2 pages.

*Primary Examiner* — Douglas M Willis
(74) *Attorney, Agent, or Firm* — Morrison & Foerster LLP

(57) ABSTRACT

Provided herein are compounds of formula (I) or formula (Ia) that inhibit tyrosine kinase enzymatic activity of a protein selected from Abelson protein (ABL1), Abelson-related protein (ABL2), or a chimeric protein BCR-ABL1, compositions thereof, and methods of their preparation, and methods of inhibiting tyrosine kinase enzymatic activity of a protein selected from Abelson protein (ABL1), Abelson-related protein (ABL2), or a chimeric protein BCR-ABL1, and methods for treating diseases wherein modulation of BCR-ABL1 activity prevents, inhibits, or ameliorates the pathology and/or symptomology of the disease.

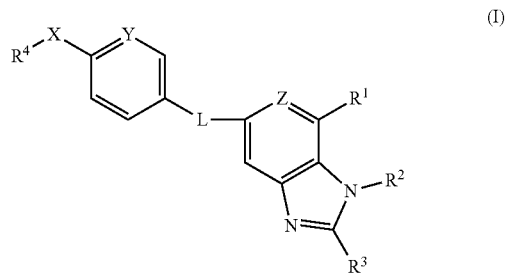

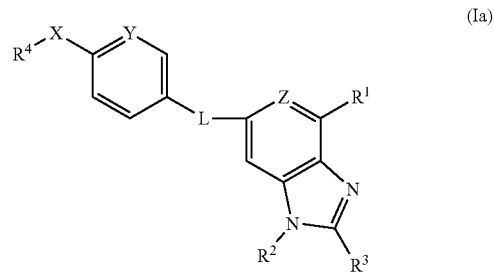

34 Claims, No Drawings

SUBSTITUTED BENZOIMIDAZOLES AND IMIDAZO[4,5-C]PYRIDINES FOR TREATING CERTAIN LEUKEMIAS

CROSS-REFERENCE TO RELATED APPLICATIONS

This application claims priority to U.S. Provisional Application No. 62/733,029, filed Sep. 18, 2018, U.S. Provisional Application No. 62/816,637, filed Mar. 11, 2019, and U.S. Provisional Application No. 62/889,929, filed Aug. 21, 2019, the disclosures of each of which are hereby incorporated by reference in their entireties for all purposes.

FIELD OF THE INVENTION

Provided herein are compounds, preferably compounds inhibiting tyrosine kinase enzymatic activity of a protein selected from Abelson protein (ABL1), Abelson-related protein (ABL2), or a chimeric protein BCR-ABL1, compositions thereof, and methods of their preparation, and methods of inhibiting tyrosine kinase enzymatic activity of a protein selected from Abelson protein (ABL1), Abelson-related protein (ABL2), or a chimeric protein BCR-ABL1, and methods for treating diseases wherein modulation of BCR-ABL1 activity prevents, inhibits, or ameliorates the pathology and/or symptomology of the disease.

STATE OF THE ART

In chronic myeloid leukemia (CML) the Philadelphia chromosome (Ph), formed by the t(9,22) reciprocal chromosome, translocates in a haematopoietic stem cell. This chromosome carries the BCR-ABL1 oncogene which encodes the chimeric BCR-ABL1 protein. Drugs that inhibit the tyrosine kinase activity of BCR-ABL1 via an ATP competitive mechanism, such as Gleevec®/Glivec® (imatinib), Tasigna® (nilotinib) and Sprycel® (dasatinib), may be effective in treating CML; however, some patients relapse due to the emergence of drug-resistant clones. For example, small molecules, or combinations thereof, may be useful to inhibit the activity of BCR-ABL1 and BCR-ABL1 mutations via the ATP binding site, the myristoyl binding site or a combination of both sites.

SUMMARY

In one aspect, provided herein is a compound of formula (I) or (Ia):

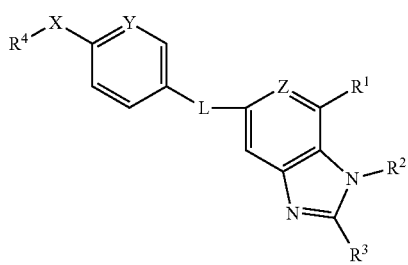

(I)

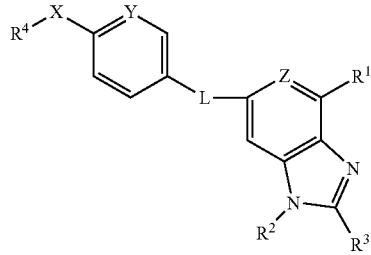

(Ia)

or a tautomer or an N-oxide thereof, or a pharmaceutically acceptable salt of any of the foregoing, wherein:

L is —NH—CO—, —CO—NH—, —NH—SO$_2$—, or —SO$_2$—NH—;

$R^1$ is optionally substituted $C_6$-$C_{10}$ aryl, optionally substituted 5-10 membered heteroaryl, optionally substituted 4-10 membered heterocycle, C(O)NR$^6$R$^7$, S(O)$_2$NR$^6$R$^7$, NR$^6$COR$^7$, NR$^6$SO$_2$R$^7$, or C(O)OR$^6$;

$R^2$ is H, optionally substituted $C_1$-$C_6$ alkyl, optionally substituted $C_3$-$C_8$ cycloalkyl, optionally substituted 4-10 membered heterocycloalkyl, optionally substituted $C_2$-$C_6$ alkenyl, optionally substituted $C_2$-$C_6$ alkynyl, optionally substituted $C_6$-$C_{10}$ aryl, or optionally substituted 5-10 membered heteroaryl;

$R^3$ is H, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, optionally substituted heteroaryl, OR$^6$, or NR$^6$R$^7$;

or $R^2$ and $R^3$ together with the intervening atoms form optionally substituted $C_3$-$C_8$ cycloalkyl or optionally substituted 4-10 membered heterocycloalkyl;

$R^4$ is optionally substituted $C_1$-$C_6$ alkyl, optionally substituted $C_2$-$C_6$ alkenyl, or optionally substituted $C_2$-$C_6$ alkynyl;

X is O or S;

Y is CH, C—($C_1$-$C_2$ alkyl), or C-halo or N;

Z is CR$^5$ or N;

$R^5$ is H or halogen;

$R^6$ is H, optionally substituted $C_1$-$C_6$ alkyl, optionally substituted $C_3$-$C_8$ cycloalkyl, optionally substituted 4-10 membered heterocycloalkyl, optionally substituted $C_6$-$C_{10}$ aryl, or optionally substituted 5-10 membered heteroaryl; and $R^7$ is H, optionally substituted $C_1$-$C_6$ alkyl, optionally substituted $C_3$-$C_8$ cycloalkyl, optionally substituted 4-10 membered heterocycloalkyl, optionally substituted $C_6$-$C_{10}$ aryl, or optionally substituted 5-10 membered heteroaryl;

or $R^6$ and $R^7$ together with the nitrogen to which they are attached form an optionally substituted 4-7 membered heterocycle, provided that the compound is other than (i) 1H-Benzimidazole-7-carboxylic acid, 5-[[(4-methoxyphenyl)sulfonyl]amino]-1-methyl- or (ii) 1H-Benzimidazole-7-carboxylic acid, 5-[[(4-ethoxyphenyl)sulfonyl]amino]-1-methyl-.

In some embodiments, the compound is of formula (IA-1):

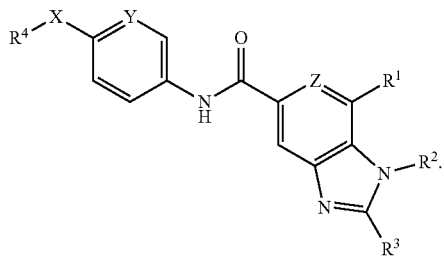

(IA-1)

In one aspect, provided herein is a method of inhibiting tyrosine kinase enzymatic activity of a protein selected from the group consisting of Abelson protein (ABL1), Abelson-related protein (ABL2), and a chimeric protein BCR-ABL1, comprising contacting an effective amount of a compound or composition provided herein, to the protein.

In one aspect, provided herein is a method of treating a disease, wherein modulation of BCR-ABL1 activity prevents, inhibits, or ameliorates the pathology and/or symptomology of the disease, in a patient, comprising administering to the patient a therapeutically effective amount of a compound or composition provided herein.

In one aspect, provided herein is a method of treating leukemia in a patient comprising administering to the patient a therapeutically effective amount of a compound or composition provided herein, wherein the leukemia is chronic myeloid leukemia (CML), acute myeloid leukemia (AML), or acute lymphoblastic leukemia (ALL).

DETAILED DESCRIPTION

Definitions

As used herein, the following definitions shall apply unless otherwise indicated. Further, if any term or symbol used herein is not defined as set forth below, it shall have its ordinary meaning in the art.

"Comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of, e.g., other ingredients and substantial method steps recited. Embodiments defined by each of these transition terms are within the scope of this invention.

"Effective amount" or dose of a compound or a composition, refers to that amount of the compound or the composition that results in an intended result as desired based on the disclosure herein. Effective amounts can be determined by standard pharmaceutical procedures in cell cultures or experimental animals, e.g., and without limitation, by determining the $LD_{50}$ (the dose lethal to 50% of the population) and the $ED_{50}$ (the dose therapeutically effective in 50% of the population).

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Patient" refers to mammals and includes humans and non-human mammals. Examples of patients include, but are not limited to mice, rats, hamsters, guinea pigs, pigs, rabbits, cats, dogs, goats, sheep, cows, and humans. In some embodiments, patient refers to a human.

"Pharmaceutically acceptable" refers to safe and non-toxic, preferably for in vivo, more preferably, for human administration.

"Pharmaceutically acceptable salt" refers to a salt that is pharmaceutically acceptable. A compound described herein may be administered as a pharmaceutically acceptable salt.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than employing the corresponding drug. For illustration and without limitation, prodrugs include, carboxy esters, linear and cyclic phosphate esters and phosphoramide and phosphoramidates, carbamates, preferably phenolic carbamates (i.e., carbamates where the hydroxy group is part of an aryl or heteroaryl moiety, where the aryl and heteroaryl may be optionally substituted), and the likes.

"Salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary and non-limiting cations useful in pharmaceutically acceptable salts include Na, K, Rb, Cs, $NH_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisulfate, mono-, di-, and tribasic phosphate, mesylate, tosylate, and the likes.

"Therapeutically effective amount" or dose of a compound or a composition refers to that amount of the compound or the composition that results in reduction or inhibition of symptoms or a prolongation of survival in a patient. The results may require multiple doses of the compound or the composition.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease. As used herein, "treatment" or "treating" is an approach for obtaining beneficial or desired results including clinical results. For purposes of this disclosure, beneficial or desired results include, but are not limited to, one or more of the following: decreasing one more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delay or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient. Also encompassed by "treatment" is a reduction of pathological consequence of the disease or disorder. The methods of the invention contemplate any one or more of these aspects of treatment.

An "isotopomer" of a compound is a compound in which one or more atoms of the compound have been replaced with isotopes of those same atoms. For example, where H has been replaced by D or T, or $^{12}C$ has been replaced by $^{11}C$ or $^{14}N$ has been replaced by $^{15}N$. For example, and without limitation, replacement of with D can in some instances lead to reduced rates of metabolism and therefore longer half-lives. Replacement of H with T can provide radioligands potentially useful in binding studies. Replacement of $^{12}C$ with the short-lived isotope $^{11}C$ can provide ligands useful in Positron Emission Tomography (PET) scanning. Replacement of $^{14}N$ with $^{15}N$ provides compounds that can be detected/monitored by $^{15}N$ NMR spectroscopy. For example, an isotopomer of a compound containing —$CH_2CH_3$ is that compound but containing —$CD_2CD_3$ instead of the —$CH_2CH_3$.

"Stereoisomer" or "stereoisomers" refer to compounds that differ in the stereogenicity of the constituent atoms such as, without limitation, in the chirality of one or more stereocenters or related to the cis or trans configuration of a carbon-carbon or carbon-nitrogen double bond. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N-moiety such as pyrazoles, imidazoles, benzimidazoles, triazoles, and tetrazoles.

"Alkyl" refers to monovalent saturated aliphatic hydrocarbyl groups having from 1 to 12 carbon atoms, preferably from 1 to 10 carbon atoms, and more preferably from 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—). $C_x$ alkyl refers to an alkyl group having x number of carbon atoms.

"Alkenyl" refers to straight or branched monovalent hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers. $C_x$ alkenyl refers to an alkenyl group having x number of carbon atoms.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH). $C_x$ alkynyl refers to an alkynyl group having x number of carbon atoms.

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, sulfonylamino, thioacyl, thiol, alkylthio, and substituted alkylthio, wherein said substituents are defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein and with the proviso that any hydroxyl or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group CH$_3$C(O)—.

"Acylamino" refers to the groups —NR$^{30}$C(O)alkyl, —NR$^{30}$C(O)substituted alkyl, —NR$^{30}$C(O)cycloalkyl, —NR$^{30}$C(O)substituted cycloalkyl, —NR$^{30}$C(O)alkenyl, —NR$^{30}$C(O)substituted alkenyl, alkoxy, substituted alkoxy-NR$^{30}$C(O)alkynyl, —NR$^{30}$C(O)substituted alkynyl, —NR$^{30}$C(O)aryl, —NR$^{30}$C(O)substituted aryl, —NR$^{30}$C(O)heteroaryl, —NR$^{30}$C(O)substituted heteroaryl, —NR$^{30}$C(O)heterocyclic, and —NR$^{30}$C(O)substituted heterocyclic wherein R$^{30}$ is hydrogen, alkyl, substituted alkyl, aryl, substituted aryl, heteroaryl, substituted heteroaryl, cycloalkyl, or substituted cycloalkyl; and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —NH$_2$.

"Substituted amino" refers to the group —NR$^{31}$R$^{32}$ where R$^{31}$ and R$^{32}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, substituted heterocyclic, acylamino, substituted acylamino, heteroarylamino, substituted heteroarylamino, cycloalkylamino, substituted cycloalkylamino, heterocycloalkylamino, substituted heterocyclylamino, sulfonylamino, and substituted sulfonyl and wherein R$^{31}$ and R$^{32}$ are optionally joined, together with the nitrogen bound thereto to form a heterocyclic or substituted heterocyclic group, provided that R$^{31}$ and R$^{32}$ are both not hydrogen, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic, and substituted heterocyclic are as defined herein. When R$^{31}$ is hydrogen and R$^{32}$ is alkyl, the substituted amino group is sometimes referred to herein as alkylamino. When R$^{31}$ and R$^{32}$ are alkyl, the substituted amino group is sometimes referred to herein as dialkylamino. When referring to a monosubstituted amino, it is meant that either R$^{31}$ or R$^{32}$ is hydrogen but not both. When referring to a disubstituted amino, it is meant that neither R$^{31}$ nor R$^{32}$ are hydrogen.

"Aminocarbonyl" refers to the group —C(O)NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —C(S)NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{30}$C(O) NR$^{33}$R$^{34}$ where $R^{30}$ is hydrogen, alkyl, substituted alkyl, aryl, substituted aryl, heteroaryl, substituted heteroaryl, cycloalkyl, or substituted cycloalkyl, and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR$^{30}$C (S)NR$^{33}$R$^{34}$ where $R^{30}$ is hydrogen, alkyl, substituted alkyl, aryl, substituted aryl, heteroaryl, substituted heteroaryl, cycloalkyl, or substituted cycloalkyl, and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O) NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{30}$—SO$_2$NR$^{33}$R$^{34}$ where $R^{30}$ is hydrogen, alkyl, substituted alkyl, aryl, substituted aryl, heteroaryl, substituted heteroaryl, cycloalkyl, or substituted cycloalkyl, and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{35}$)NR$^{33}$R$^{34}$ where $R^{33}$, $R^{34}$, and $R^{35}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl (Ph)) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Acylamino" refers to the group —NR$^{37}$(aryl), where aryl is as defined herein and R$^{37}$ is hydrogen, alkyl, or substituted alkyl.

"Substituted arylamino" refers to the group —NR$^{37}$(substituted aryl), where R$^{37}$ is hydrogen, alkyl, or substituted alkyl where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester) amino" refers to the group —NR$^{30}$—C(O)O-alkyl, —NR$^{30}$—C(O)O-substituted alkyl, —NR$^{30}$—C(O)O-alkenyl, —NR$^{30}$—C(O)O-substituted alkenyl, —NR$^{30}$—C(O)O-alkynyl, —NR$^{30}$—C(O)O-substituted alkynyl, —NR$^{30}$—C(O)O-aryl, —NR$^{30}$—C(O)O-substituted aryl, —NR$^{30}$—C(O)O-cycloalkyl, —NR$^{30}$—C(O)O-substituted cycloalkyl, —NR$^{30}$—C(O)O-heteroaryl, —NR$^{30}$—C(O)O-substituted heteroaryl, —NR$^{30}$—C(O)O-heterocyclic, and —NR$^{30}$—C(O)O-substituted heterocyclic wherein R$^{30}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to saturated or unsaturated but non-aromatic cyclic alkyl groups of from 3 to 10 carbon atoms, preferably from 3 to 8 carbon atoms, and more preferably from 3 to 6 carbon atoms, having single or multiple cyclic rings including fused, bridged, and spiro ring systems. C$_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylamino" refers to the group —NR$^{37}$(cycloalkyl) where R$^{37}$ is hydrogen, alkyl, or substituted alkyl.

"Substituted cycloalkylamino" refers to the group —NR$^{37}$(substituted cycloalkyl) where R$^{37}$ is hydrogen, alkyl, or substituted alkyl and substituted cycloalkyl is as defined herein.

"Cycloalkylthio" refers to —S-cycloalkyl.

"Substituted cycloalkylthio" refers to —S-(substituted cycloalkyl).

"Guanidino" refers to the group —NHC(⊚NH)NH$_2$.

"Substituted guanidino" refers to —NR$^{36}$C(=NR$^{36}$)N(R$^{36}$)$_2$ where each R$^{36}$ is independently selected from the group consisting of hydrogen, alkyl, substituted alkyl, aryl, substituted aryl, heteroaryl, substituted heteroaryl, heterocyclic, and substituted heterocyclic and two R$^{36}$ groups attached to a common guanidino nitrogen atom are optionally joined together with the nitrogen bound thereto to form a heterocyclic or substituted heterocyclic group, provided that at least one R$^{36}$ is not hydrogen, and wherein said substituents are as defined herein.

"Halo" or "halogen" refers to fluoro, chloro, bromo and iodo and preferably is fluoro or chloro.

"Hydroxy" or "hydroxyl" refers to the group —OH.

"Heteroalkylene" refers to an alkylene group wherein one or more carbons is replaced with —O—, —S—, SO$_2$, —NR$^Q$—,

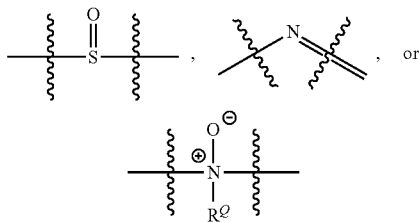

moieties where R$^Q$ is H or C$_1$-C$_6$ alkyl. "Substituted heteroalkylene" refers to heteroalkynylene groups having from 1 to 3 substituents, and preferably 1 to 2 substituents, selected from the substituents disclosed for substituted alkylene.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, thiophenyl, and furanyl. Other preferred heteroaryls include 9 or 10 membered heteroaryls, such as indolyl, quinolinyl, quinolonyl, isoquinolinyl, and isoquinolonyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heteroarylamino" refers to the group —NR$^{37}$(heteroaryl) where R$^{37}$ is hydrogen, alkyl, or substituted alkyl.

"Substituted heteroarylamino" refers to the group —NR$^{37}$(substituted heteroaryl), where R$^{37}$ is hydrogen, alkyl, or substituted alkyl and substituted heteroaryl is defined as herein.

"Heterocycle" or "heterocyclic" or "heterocycloalkyl" or "heterocyclyl" refers to a saturated or partially saturated, but not aromatic, group having from 1 to 10 ring carbon atoms, preferably from 1 to 8 carbon atoms, and more preferably from 1 to 6 carbon atoms, and from 1 to 4 ring heteroatoms, preferably from 1 to 3 heteroatoms, and more preferably from 1 to 2 heteroatoms selected from the group consisting of nitrogen, sulfur, or oxygen. C$_x$ heterocycloalkyl refers to a heterocycloalkyl group having x number of ring atoms including the ring heteroatoms. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring.

In one embodiment, the nitrogen and/or sulfur atom(s) of the heterocyclic group are optionally oxidized to provide for the N-oxide, sulfinyl, sulfonyl moieties.

"Heterocyclylene" refers to a divalent saturated or partially saturated, but not aromatic, group having from 1 to 10 ring carbon atoms and from 1 to 4 ring heteroatoms selected from the group consisting of nitrogen, sulfur, or oxygen. "Substituted heterocyclylene" refers to heterocyclylene groups that are substituted with from 1 to 5 or preferably 1 to 3 of the same substituents as defined for substituted cycloalkyl "Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

"Heterocyclylamino" refers to the group —NR$^{37}$(heterocyclyl) where R$^{37}$ is hydrogen, alkyl, or substituted alkyl.

"Substituted heterocyclylamino" refers to the group —NR$^{37}$(substituted heterocyclyl), where R$^{37}$ is hydrogen, alkyl, or substituted alkyl and substituted heterocyclyl is defined as herein.

Examples of heterocyclyl and heteroaryl include, but are not limited to, azetidinyl, pyrrolyl, imidazolyl, pyrazolyl, pyridyl, pyrazyl, pyrimidyl, pyridazyl, indolizyl, isoindolyl, indolyl, dihydroindolyl, indazolyl, purinyl, quinolizinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, isoxazolyl, phenoxazinyl, phenothiazinyl, imidazolidinyl, imidazolinyl, piperidinyl, piperazinyl, indolinyl, phthalimidyl, 1,2,3,4-tetrahydroisoquinolinyl, 4,5,6,7-tetrahydrobenzo[b]thiophenyl, thiazolyl, thiazolidinyl, thiophenyl, benzo[b]thiophenyl, morpholinyl, thiomorpholinyl (also referred to as thiamorpholinyl), 1,1-dioxothiomorpholinyl, piperidinyl, pyrrolidinyl, and tetrahydrofuranyl.

"Nitro" refers to the group —NO$_2$.

"Oxo" refers to the atom (=O) or (O).

"Spiro ring systems" refers to bicyclic ring systems that have a single ring carbon atom common to both rings.

"Sulfinyl" refers to the divalent group —S(O)— or —S(=O)—.

"Sulfonyl" refers to the divalent group —S(O)$_2$— or —S(=O)$_2$—.

"Substituted sulfonyl" refers to the group —SO$_2$-alkyl, —SO$_2$-substituted alkyl, —SO$_2$—OH, —SO$_2$-alkenyl, —SO$_2$-substituted alkenyl, —SO$_2$-cycloalkyl, —SO$_2$-substituted cylcoalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—. Preferred substituted alkyl groups on the substituted alkyl-SO$_2$— include halogenated alkyl groups and particularly halogenated methyl groups such as trifluoromethyl, difluoromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cylcoalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluromethyl, fluoromethyl and the like.

"Sulfonyloxy" or "substituted sulfonyloxy" refers to the group —$OSO_2$-alkyl, —$OSO_2$-substituted alkyl, —$OSO_2$—OH, —$OSO_2$-alkenyl, —$OSO_2$-substituted alkenyl, —$OSO_2$-cycloalkyl, —$OSO_2$-substituted cylcoalkyl, —$OSO_2$-aryl, —$OSO_2$-substituted aryl, —$OSO_2$-heteroaryl, —$OSO_2$-substituted heteroaryl, —$OSO_2$-heterocyclic, —$OSO_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the group —$NR^{37}$(substituted sulfonyl) where $R^{37}$ is hydrogen, alkyl, or substituted alkyl and substituted sulfonyl is as defined here.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluromethyl, fluoromethyl and the like.

"Vinyl" refers to unsaturated hydrocarbon radical —CH=$CH_2$, derived from ethylene.

The terms "optional" or "optionally" as used throughout the specification means that the subsequently described event or circumstance may but need not occur, and that the description includes instances where the event or circumstance occurs and instances in which it does not. For example, "the nitrogen atom is optionally oxidized to provide for the N-oxide (N→O) moiety" means that the nitrogen atom may but need not be oxidized, and the description includes situations where the nitrogen atom is not oxidized and situations where the nitrogen atom is oxidized.

The term "optionally substituted" refers to a substituted or unsubstituted group. The substituted group may be substituted with one or more substituents, such as e.g., 1, 2, 3, 4 or 5 substituents. Preferably, the substituents are selected from the functional groups provided herein. In certain more preferred embodiments, the substituents are selected from oxo, halo, —CN, $NO_2$, —$CO_2R^{100}$, —$OR^{100}$, —$OR^{100}$, —$SR^{100}$, —$SOR^{100}$, —$SO_2R^{100}$, —$NR^{101}R^{102}$, —$CONR^{101}R^{102}$, —$SO_2NR^{101}R^{102}$, $C_1$-$C_6$ alkoxy, —$CR^{100}$=C($R^{100}$)$_2$, —$CCR^{100}$, $C_3$-$C_{10}$ cycloalkyl, $C_4$-$C_{10}$ heterocyclyl, $C_6$-$C_{14}$ aryl and $C_5$-$C_{12}$ heteroaryl, wherein each $R^{100}$ independently is hydrogen or $C_1$-$C_8$ alkyl; $C_3$-$C_{12}$ cycloalkyl; $C_4$-$C_{10}$ heterocyclyl; $C_6$-$C_{14}$ aryl; or $C_2$-$C_{12}$ heteroaryl; wherein each alkyl, cycloalkyl, heterocyclyl, aryl, or heteroaryl is optionally substituted with 1-3 halo, 1-3 $C_1$-$C_6$ alkyl, 1-3 $C_1$-$C_6$ haloalkyl or 1-3 $C_1$-$C_6$ alkoxy groups. More preferably, the substituents are selected from the group consisting of chloro, fluoro, —$OCH_3$, methyl, ethyl, iso-propyl, cyclopropyl, —$OCF_3$, —$CF_3$ and —$OCHF_2$.

$R^{101}$ and $R^{102}$ independently are hydrogen; $C_1$-$C_8$ alkyl, optionally substituted with —$CO_2H$ or an ester thereof, $C_1$-$C_6$ alkoxy, oxo, —$CR^{103}$=C($R^{103}$)$_2$, —CCR, $C_3$-$C_{10}$ cycloalkyl, $C_3$-$C_{10}$ heterocyclyl, $C_6$-$C_{14}$ aryl, or $C_2$-$C_{12}$ heteroaryl, wherein each $R^{103}$ independently is hydrogen or $C_1$-$C_8$ alkyl; $C_3$-$C_{12}$ cycloalkyl; $C_4$-$C_{10}$ heterocyclyl; $C_6$-$C_{14}$ aryl; or $C_2$-$C_{12}$ heteroaryl; wherein each cycloalkyl, heterocyclyl, aryl, or heteroaryl is optionally substituted with 1-3 alkyl groups or 1-3 halo groups, or $R^{101}$ and $R^{102}$ together with the nitrogen atom they are attached to form a 5-7 membered heterocycle.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to—substituted aryl-(substituted aryl)-substituted aryl.

In some embodiments of a substituted moiety, the moiety is substituted with a group that may also be substituted with a further group, but the further group cannot be additionally substituted. For example, in some embodiments of "substituted alkyl", the alkyl moiety is substituted with a group that may be further substituted (e.g., substituted alkoxy, substituted amino, substituted aryl, substituted aryloxy, substituted arylthio, substituted acylamino, substituted heteroarylamino, substituted cycloalkylamino, substituted heterocyclylamino, substituted cycloalkyl, substituted cycloalkyloxy, substituted cycloalkylthio, substituted guanidino, substituted heteroaryl, substituted heteroaryloxy, substituted heteroarylthio, substituted heterocyclic, substituted heterocyclyloxy, substituted heterocyclylthio, substituted sulfonyl, substituted alkylthio), but the substituted alkoxy, substituted amino, substituted aryl, substituted aryloxy, substituted arylthio, substituted acylamino, substituted heteroarylamino, substituted cycloalkylamino, substituted heterocyclylamino, substituted cycloalkyl, substituted cycloalkyloxy, substituted cycloalkylthio, substituted guanidino, substituted heteroaryl, substituted heteroaryloxy, substituted heteroarylthio, substituted heterocyclic, substituted heterocyclyloxy, substituted heterocyclylthio, substituted sulfonyl or substituted alkylthio on the alkyl moiety is not substituted with a moiety that is itself further substituted. Although "substituted alkyl" is provided as an example, such an embodiment is intended for each substituted moiety described herein.

In some embodiments of a substituted moiety, the moiety is substituted with a group that is not further substituted. Thus, in some embodiments, "substituted alkyl" is an alkyl moiety substituted with one or more, and in some aspects, 1 or 2 or 3 or 4 or 5 moieties independently selected from the group consisting of alkoxy, acyl, acylamino, acyloxy, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, aryloxy, arylthio, arylamino, heteroarylamino, cycloalkylamino, heterocycloalkylamino, carboxyl, carboxyl ester, (carboxyl ester)amino, (carboxyl ester)oxy, cyano, cycloalkyl, cycloalkyloxy, cycloalkylthio, guanidino, halo, hydroxy, heteroaryl, heteroaryloxy, heteroarylthio, heterocyclic, heterocyclyloxy, heterocyclylthio, nitro, SO$_3$H, sulfonyloxy, sulfonylamino, thioacyl, thiol, and alkylthio. Although "substituted alkyl" is provided as an example, such an embodiment is intended for each substituted moiety described herein.

It is understood that the above definitions are not intended to include impermissible substitution patterns (e.g., methyl substituted with 4 fluoro groups). Such impermissible substitution patterns are well known to the skilled artisan.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Compounds

In one aspect, is provided a compound of formula (I):

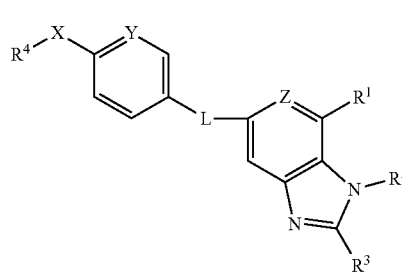

(I)

or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding, wherein:

L is —NH—CO—, —CO—NH—, —NH—SO$_2$—, or —SO$_2$—NH—;

$R^1$ is optionally substituted $C_6$-$C_{10}$ aryl, optionally substituted 5-10 membered heteroaryl, optionally substituted 4-10 membered heterocycle, C(O)NR$^6$R$^7$, S(O)$_2$NR$^6$R$^7$, NR$^6$COR$^7$, or NR$^6$SO$_2$R$^7$, or C(O)OR$^6$;

$R^2$ is H, optionally substituted $C_1$-$C_6$ alkyl, optionally substituted $C_3$-$C_8$ cycloalkyl, optionally substituted 4-10 membered heterocycloalkyl, optionally substituted $C_2$-$C_6$ alkenyl, optionally substituted $C_2$-$C_6$ alkynyl, optionally substituted $C_6$-$C_{10}$ aryl, or optionally substituted 5-10 membered heteroaryl;

$R^3$ is H, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, optionally substituted heteroaryl, OR$^6$, or NR$^6$R$^7$; or $R^2$ and $R^3$ together with the intervening atoms form cycloalkyl or heterocycloalkyl, preferably an optionally substituted $C_3$-$C_8$ cycloalkyl or an optionally substituted 4-10 membered heterocycloalkyl;

$R^4$ is optionally substituted $C_1$-$C_6$ alkyl, preferably $C_1$-$C_3$ haloalkyl, such as CF$_3$ or CF$_2$Cl, optionally substituted $C_2$-$C_6$ alkenyl, optionally substituted $C_2$-$C_6$ alkynyl;

X is O or S;

Y is CH, C—($C_1$-$C_2$ alkyl), or C-halo or N;

Z is CR$^5$ or N;

$R^5$ is H or halogen;

$R^6$ is H, optionally substituted $C_1$-$C_6$ alkyl, optionally substituted $C_3$-$C_8$ cycloalkyl, optionally substituted 4-10 membered heterocycloalkyl, optionally substituted $C_6$-$C_{10}$ aryl, or optionally substituted 5-10 membered heteroaryl; and $R^7$ is H, optionally substituted $C_1$-$C_6$ alkyl, optionally substituted $C_3$-$C_8$ cycloalkyl, optionally substituted 4-10 membered heterocycloalkyl, optionally substituted $C_6$-$C_{10}$ aryl, or optionally substituted 5-10 membered heteroaryl; or $R^6$ and $R^7$ together with the nitrogen to which they are attached form an optionally substituted 4-7 membered heterocycle, provided that the compound is other than (i) 1H-Benzimidazole-7-carboxylic acid, 5-[[(4-methoxyphenyl)sulfonyl]amino]-1-methyl- or (ii) 1H-Benzimidazole-7-carboxylic acid, 5-[[(4-ethoxyphenyl)sulfonyl]amino]-1-methyl-.

In some embodiments, provided is a compound of formula (I-i):

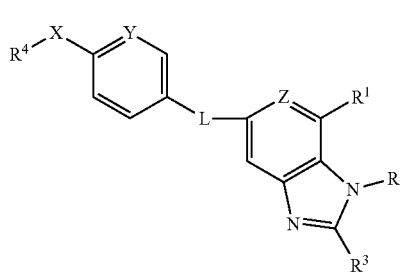

(I-i)

or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding, wherein:

L is —NH—CO—, —CO—NH—, or —NH—SO$_2$—;

$R^1$ is optionally substituted $C_6$-$C_{10}$ aryl, optionally substituted 5-10 membered heteroaryl, optionally substituted 4-10 membered heterocycle, C(O)NR$^6$R$^7$, S(O)$_2$NR$^6$R$^7$, NR$^6$COR$^7$, or NR$^6$SO$_2$R$^7$, or C(O)OR$^6$;

$R^2$ is H, optionally substituted $C_1$-$C_6$ alkyl, optionally substituted $C_3$-$C_8$ cycloalkyl, optionally substituted 4-10 membered heterocycloalkyl, optionally substituted $C_2$-$C_6$ alkenyl, optionally substituted $C_2$-$C_6$ alkynyl, optionally substituted $C_6$-$C_{10}$ aryl, or optionally substituted 5-10 membered heteroaryl;

$R^3$ is H, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, optionally substituted heteroaryl, OR$^6$, or NR$^6$R$^7$; or $R^2$ and $R^3$ together with the intervening atoms form cycloalkyl or heterocycloalkyl, preferably an optionally substituted $C_3$-$C_8$ cycloalkyl or an optionally substituted 4-10 membered heterocycloalkyl;

$R^4$ is optionally substituted $C_1$-$C_6$ alkyl, preferably $C_1$-$C_3$ haloalkyl, such as CF$_3$ or CF$_2$Cl, optionally substituted $C_2$-$C_6$ alkenyl, optionally substituted $C_2$-$C_6$ alkynyl;

X is O or S;

Y is CH, C—($C_1$-$C_2$ alkyl), or C-halo or N;

Z is CR$^5$ or N;

$R^5$ is H or halogen;

$R^6$ is H, optionally substituted $C_1$-$C_6$ alkyl, optionally substituted $C_3$-$C_8$ cycloalkyl, optionally substituted 4-10 membered heterocycloalkyl, optionally substituted $C_6$-$C_{10}$ aryl, or optionally substituted 5-10 membered heteroaryl; and $R^7$ is H, optionally substituted $C_1$-$C_6$ alkyl, optionally substituted $C_3$-$C_8$ cycloalkyl, optionally substituted 4-10 membered heterocycloalkyl, optionally substituted $C_6$-$C_{10}$ aryl, or optionally substituted 5-10 membered heteroaryl; or $R^6$ and $R^7$ together with the nitrogen to which they are attached form an optionally substituted 4-7 membered heterocycle.

Also provided herein is a compound of formula (I-a):

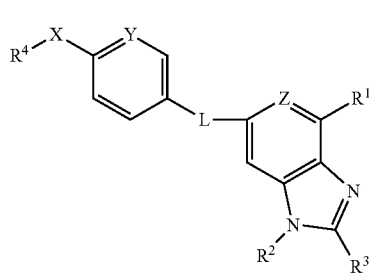

(Ia)

wherein $R^1$, $R^2$, $R^3$, $R^4$, X, Y, Z, and L are as defined for the compound of formula (I).

In some embodiments, the compound is of formula (IA):

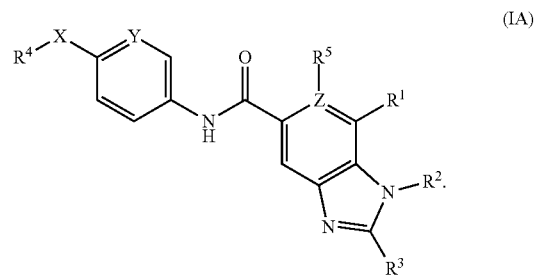

(IA)

It is understood that when Z is N, then $R^5$ is absent. Similarly, it is understood that when $R^5$ is present, then $R^5$ is bound to a carbon atom in the aryl ring such that Z is CR$^5$.

In some embodiments, the compound is of formula (IA-1):

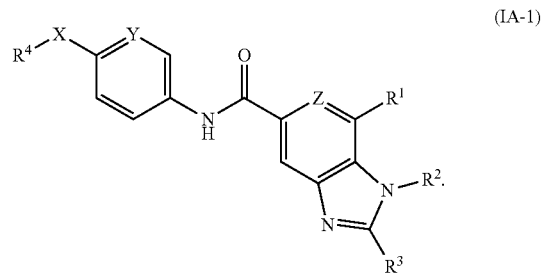

(IA-1)

In some embodiments, the compound is selected from formula (IIA)-(IIH):

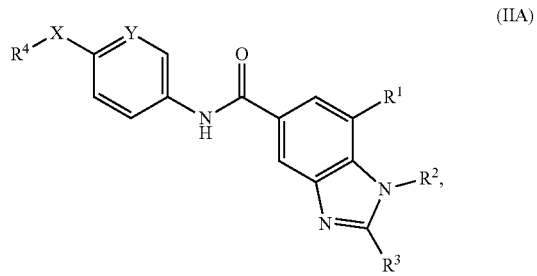

(IIA)

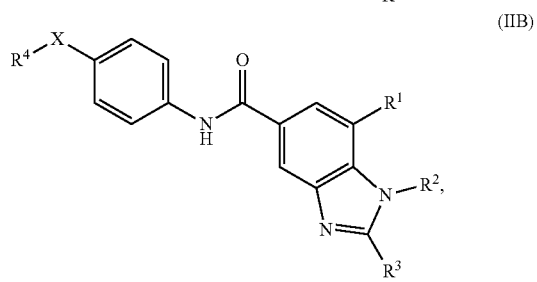

(IIB)

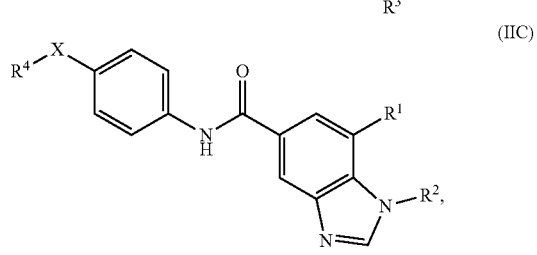

(IIC)

-continued

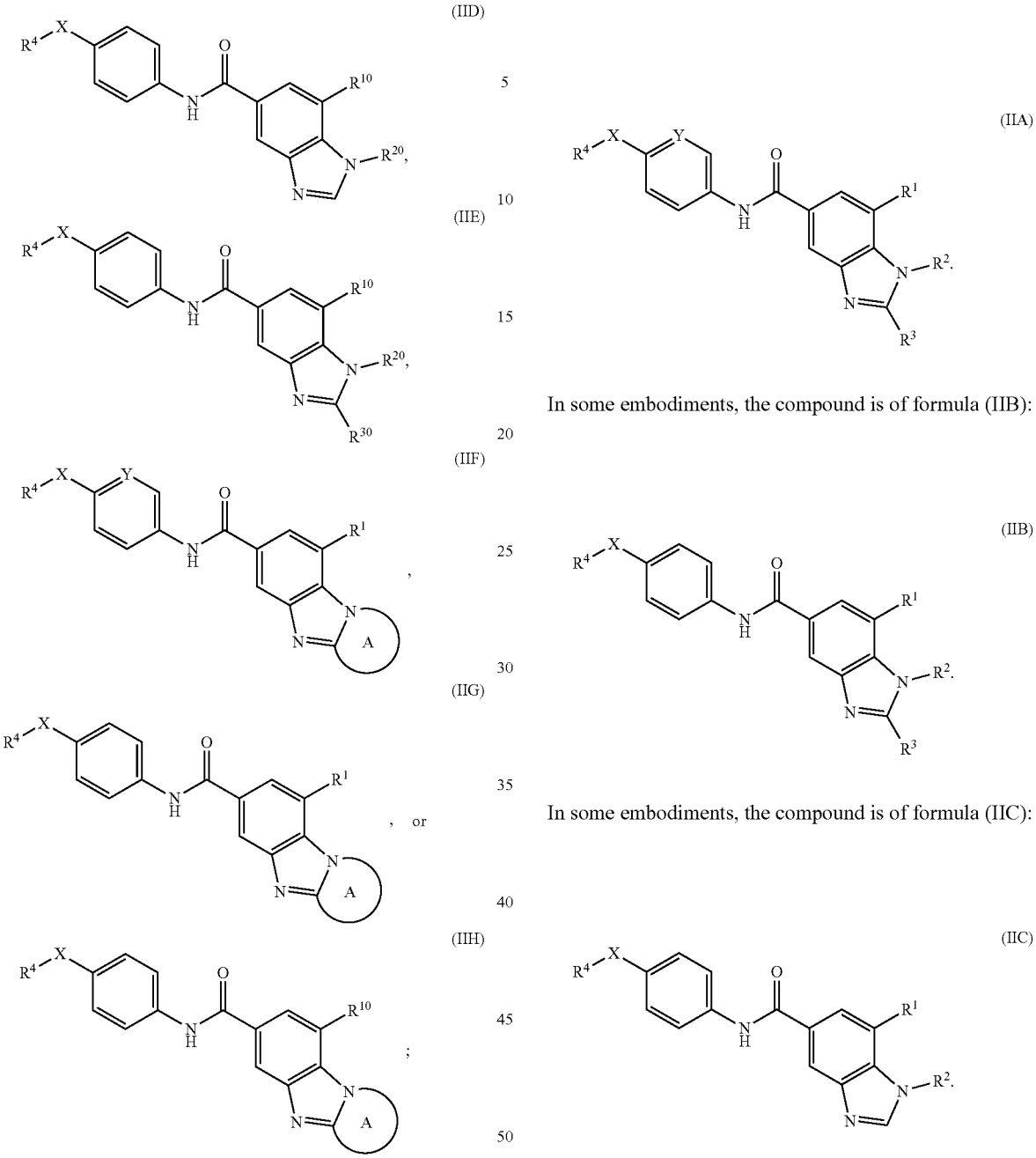

wherein R[10] is an optionally substituted 5-6 membered heteroaryl, preferably the heteroaryl moiety has up to 2 ring nitrogen atoms;

R[20] is optionally substituted $C_1$-$C_3$ alkyl, optionally substituted $C_3$-$C_4$ cycloalkyl, or optionally substituted 4-6 membered heterocycloalkyl, preferably, R[20] is methyl, optionally substituted isopropyl, or cyclopropyl;

R[30] is H, optionally substituted $C_1$-$C_3$ alkyl, optionally substituted $C_3$-$C_4$ cycloalkyl, or optionally substituted 5-6 membered heterocycloalkyl, preferably optionally substituted cyclopropyl;

Ring A is optionally substituted 5-6 membered heterocycloalkyl; and the remaining variables are defined as herein.

In some embodiments, the compound is of formula (IIA):

In some embodiments, the compound is of formula (IIB):

In some embodiments, the compound is of formula (IIC):

In some embodiments, the compound is of formula (IID):

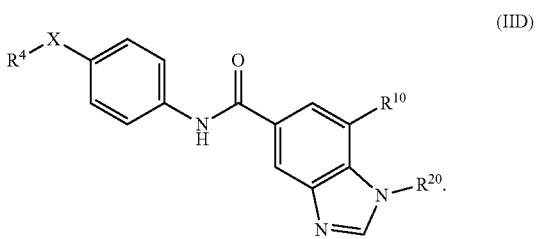

In some embodiments, the compound is of formula (IIE):

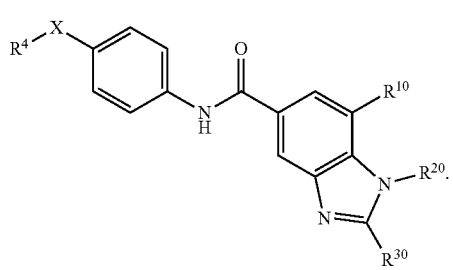
(IIE)

In some embodiments, the compound provided herein is of formula (IIF):

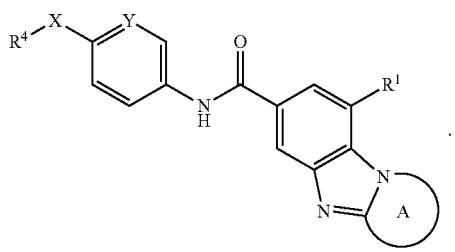
(IIF)

In some embodiments, the compound provided herein is of formula (IIG):

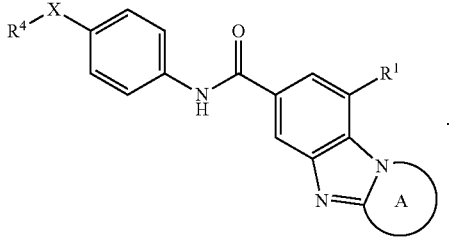
(IIG)

In some embodiments, the compound provided herein is of formula (IIH):

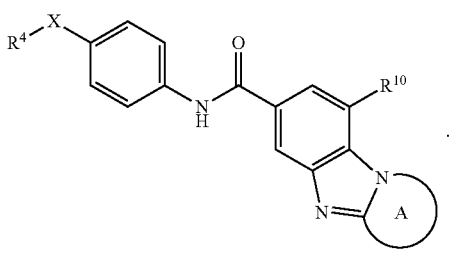
(IIH)

In some embodiments, the compound provided herein is of formula (Ib):

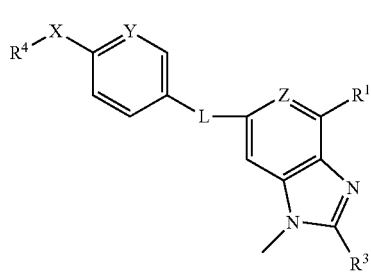
(Ib)

wherein the remaining variables are defined as herein.

In some embodiments, the compound provided herein is of formula (Ic):

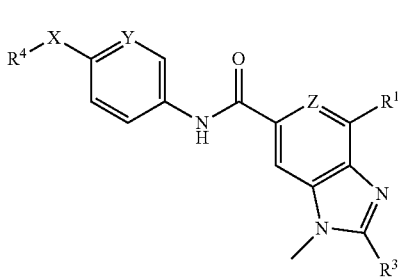
(Ic)

wherein the remaining variables are defined as herein.

In some embodiments, the compound provided herein is of formula (Id) or (Ie):

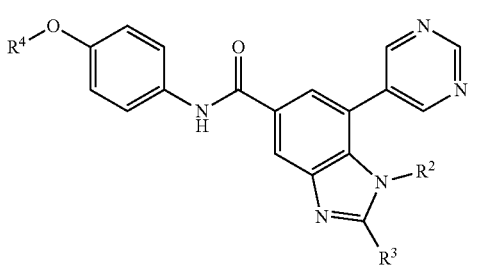
(Id)

or

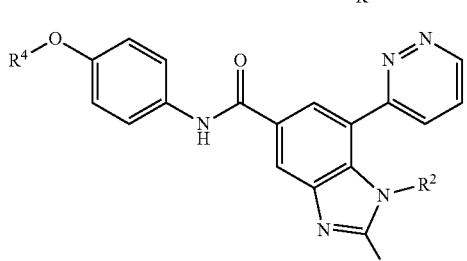
(Ie)

wherein the remaining variables are defined as herein.

In some embodiments, L is —NH—CO—. In some embodiments, L is —CO—NH—. In some embodiments, L is —NH—SO$_2$—. In some embodiments, L is —SO$_2$—NH—.

In some embodiments, $R^1$ is optionally substituted $C_6$-$C_{10}$ aryl. In some embodiments, $R^1$ is optionally substituted 5-10 membered heteroaryl. In some embodiments, $R^1$ is optionally substituted 4-10 membered heterocycle. In some embodiments, $R^1$ is C(O)NR$^6$R$^7$. In some embodiments, $R^1$ is $S(O)_2NR^6R^7$. In some embodiments, $R^1$ is $NR^6COR^7$. In some embodiments, $R^1$ is or $NR^6SO_2R^7$. In some embodiments, $R^1$ is $C(O)OR^6$.

In some embodiments, $R^2$ is H. In some embodiments, $R^2$ is optionally substituted $C_1$-$C_6$ alkyl. In some embodiments, $R^2$ is cycloalkylalkyl. In some embodiments, $R^2$ is heterocyclylalkyl. In some embodiments, $R^2$ is arylalkyl. In some embodiments, $R^2$ is heteroarylalkyl. In some embodiments, $R^2$ is optionally substituted $C_3$-$C_8$ cycloalkyl. In some embodiments, $R^2$ is optionally substituted 4-10 membered heterocycloalkyl. In some embodiments, $R^2$ is optionally substituted $C_2$-$C_6$ alkenyl. In some embodiments, $R^2$ is optionally substituted $C_2$-$C_6$ alkynyl. In some embodiments, $R^2$ is optionally substituted $C_6$-$C_{10}$ aryl. In some embodiments, $R^2$ is optionally substituted 5-10 membered heteroaryl.

In some embodiments, $R^3$ is H. In some embodiments, $R^3$ is optionally substituted $C_1$-$C_6$ alkyl. In some embodiments, $R^3$ is optionally substituted $C_2$-$C_6$ alkenyl. In some embodiments, $R^3$ is optionally substituted $C_2$-$C_6$ alkynyl. In some embodiments, $R^3$ is optionally substituted cycloalkyl. In some embodiments, $R^3$ is optionally substituted heterocycloalkyl. In some embodiments, $R^3$ is optionally substituted 4-6 membered heterocycloalkyl. In some embodiments, $R^3$ is optionally substituted aryl. In some embodiments, $R^3$ is optionally substituted $C_6$-$C_{10}$ aryl. In some embodiments, $R^3$ is optionally substituted heteroaryl. In some embodiments, $R^3$ is optionally substituted 5-10 membered heteroaryl. In some embodiments, $R^3$ is $C_1$-$C_6$ alkyl, $C_2$-$C_6$ alkenyl, $C_2$-$C_6$ alkynyl, $C_3$-$C_6$ cycloalkyl, 4- to 6-membered heterocycloalkyl, $C_6$-$C_{10}$ aryl, or 5- to 10-membered heteroaryl, each of which is optionally substituted by 1-3 substituents selected from the group consisting of halogen, hydroxyl, and $C_1$-$C_6$ alkyl. In some embodiments, $R^3$ is $OR^6$. In some embodiments, $R^3$ is $NR^6R^7$.

In some embodiments, $R^2$ and $R^3$ together with the intervening atoms form ring A, which is cycloalkyl. It is understood that $R^2$ and $R^3$ taken together with the intervening atoms to form ring A, which is cycloalkyl, does not include the nitrogen atom to which $R^2$ is attached. Rather, it is understood that no further heteroatoms, other than the nitrogen atom to which $R^2$ is attached, make up ring A. In some embodiments, $R^2$ and $R^3$ together with the intervening atoms form ring A, which is heterocycloalkyl. It is understood that $R^2$ and $R^3$ taken together with the intervening atoms to form ring A, which is heterocycloalkyl, includes the nitrogen atom to which $R^2$ is attached. It is also understood that additional heteroatoms, further to the nitrogen atom to which $R^2$ is attached, can make up ring A. In some embodiments, $R^2$ and $R^3$ are taken together with the intervening atoms to form ring A, which is heterocycloalkyl, and does not include any heteroatoms other than the nitrogen atom to which $R^2$ is attached. In some embodiments, $R^2$ and $R^3$ are taken together with the intervening atoms to form ring A, which is heterocycloalkyl, and includes the nitrogen atom to which $R^2$ is attached as well as additional heteroatoms. In some embodiments, $R^2$ and $R^3$ together with the intervening atoms form ring A, which is an optionally substituted $C_3$-$C_8$ cycloalkyl. Suitable cycloalkyl substituents include, without limitation, $C_1$-$C_6$ alkyl, hydroxy$C_1$-$C_6$ alkyl, and $C_1$-$C_6$ alkyl substituted with 1-3 halo, preferably fluoro atoms. In some embodiments, $R^2$ and $R^3$ together with the intervening atoms form ring A, which is an optionally substituted 4-10 membered heterocycloalkyl. Suitable heterocycloalkyl substituents include, without limitation $C_1$-$C_6$ alkyl, hydroxy$C_1$-$C_6$ alkyl, and $C_1$-$C_6$ alkyl substituted with 1-3 halo, preferably fluoro atoms.

In some embodiments, $R^4$ is optionally substituted $C_1$-$C_6$ alkyl. In some embodiments, $R^4$ is $C_1$-$C_3$ haloalkyl. In some embodiments, $R^4$ is $CF_3$. In some embodiments, $R^4$ is $CF_2Cl$. In some embodiments, $R^4$ is optionally substituted $C_2$-$C_6$ alkenyl. In some embodiments, $R^4$ is optionally substituted $C_2$-$C_6$ alkynyl.

In some embodiments, X is O. In some embodiments, X is S.

In some embodiments, Y is CH. In some embodiments, Y is C—($C_1$-$C_2$ alkyl). In some embodiments, Y is C-halo. In some embodiments, Y is N.

In some embodiments, Z is $CR^5$. In some embodiments, Z is N.

In some embodiments, $R^5$ is H. In some embodiments, $R^5$ is halogen.

In some embodiments, $R^6$ is H. In some embodiments, $R^6$ is optionally substituted $C_1$-$C_6$ alkyl. In some embodiments, $R^6$ is optionally substituted $C_3$-$C_8$ cycloalkyl. In some embodiments, $R^6$ is optionally substituted 4-10 membered heterocycloalkyl. In some embodiments, $R^6$ is optionally substituted $C_6$-$C_{10}$ aryl. In some embodiments, $R^6$ is optionally substituted 5-10 membered heteroaryl. In some embodiments, $R^6$ is $C_1$-$C_6$ alkyl, $C_3$-$C_8$ cycloalkyl, 4-10 membered heterocycloalkyl, $C_6$-$C_{10}$ aryl, or 5-10 membered heteroaryl, each of which is optionally substituted by 1-3 substituents selected from the group consisting of halogen, hydroxyl, and $C_1$-$C_6$ alkyl.

In some embodiments, $R^7$ is H. In some embodiments, $R^7$ is optionally substituted $C_1$-$C_6$ alkyl. In some embodiments, $R^7$ is optionally substituted $C_3$-$C_8$ cycloalkyl. In some embodiments, $R^7$ is optionally substituted 4-10 membered heterocycloalkyl. In some embodiments, $R^7$ is optionally substituted $C_6$-$C_{10}$ aryl. In some embodiments, $R^7$ is optionally substituted 5-10 membered heteroaryl. In some embodiments, $R^7$ is $C_1$-$C_6$ alkyl, $C_3$-$C_8$ cycloalkyl, 4-10 membered heterocycloalkyl, $C_6$-$C_{10}$ aryl, or 5-10 membered heteroaryl, each of which is optionally substituted by 1-3 substituents selected from the group consisting of halogen, hydroxyl, and $C_1$-$C_6$ alkyl.

In some embodiments, $R^6$ is H; and $R^7$ is H, optionally substituted $C_1$-$C_6$ alkyl, optionally substituted $C_3$-$C_8$ cycloalkyl, optionally substituted 4-10 membered heterocycloalkyl, optionally substituted $C_6$-$C_{10}$ aryl, or optionally substituted 5-10 membered heteroaryl.

In some embodiments, $R^6$ and $R^7$ together with the nitrogen to which they are attached form an optionally substituted 4-7 membered heterocycle. In some embodiments, $R^6$ and $R^7$ together with the nitrogen to which they are attached form 4-7 membered heterocycle optionally substituted by 1-3 substituents selected from the group consisting of halogen, hydroxyl, and $C_1$-$C_6$ alkyl.

In some embodiments, $R^{10}$ is a 5-6 membered heteroaryl. In some embodiments, $R^{10}$ is a 5-6 membered heteroaryl, wherein the heteroaryl moiety has up to 2 ring nitrogen atoms. In some embodiments, $R^{10}$ is 5-6 membered heteroaryl optionally substituted by 1-3 substituents selected from the group consisting of halogen, cyano, hydroxyl, $C_1$-$C_6$ alkoxy, $C_1$-$C_6$ alkyl, and $C_3$-$C_6$ cycloalkyl.

In some embodiments, $R^{20}$ is optionally substituted $C_1$-$C_3$ alkyl. In some embodiments, $R^{20}$ is optionally substituted $C_3$-$C_4$ cycloalkyl. In some embodiments, $R^{20}$ is methyl. In some embodiments, $R^{20}$ is optionally substituted isopropyl. In some embodiments, $R^{20}$ is cyclopropyl. In some embodiments, $R^{20}$ is $C_1$-$C_3$ alkyl, $C_3$-$C_4$ cycloalkyl, or 4-6 membered heterocycloalkyl, each of which is optionally substituted by 1-3 substituents selected from the group consisting of halogen, hydroxyl, $C_1$-$C_6$ alkoxy, $C_1$-$C_6$ alkyl, $C_3$-$C_6$ cycloalkyl, 4- to 6-membered heterocyclyl, cyano, oxo, —C(O)NH(C₁-C₆ alkyl), and —C(O)NH(C₃-C₆ cycloalkyl), In some embodiments, $R^{30}$ is H. In some embodiments, $R^{30}$ is optionally substituted $C_1$-$C_3$ alkyl. In some embodiments, $R^{30}$ is optionally substituted $C_3$-$C_4$ cycloalkyl. In some embodiments, $R^{30}$ is optionally substituted cyclopropyl. In some embodiments, $R^{30}$ is $C_1$-$C_3$ alkyl, $C_3$-$C_4$ cycloalkyl, or 5-6 membered heterocycloalkyl, each of which is optionally substituted by 1-3 substituents selected from the group consisting of halogen, hydroxyl, and $C_1$-$C_6$ alkyl.

In some embodiments, $R^1$ is a 5-6 membered heteroaryl. In some embodiments, $R^1$ is a 5-6 membered heteroaryl containing up to 2 ring nitrogen atoms. In some embodiments, $R^1$ is a 5-6 membered heteroaryl containing 2 ring nitrogen atoms. In some embodiments, $R^1$ is a 5-6 membered heteroaryl containing 1 ring nitrogen atom. In some embodiments, $R^1$ is a 5-6 membered heteroaryl containing 3 ring nitrogen atoms. In some embodiments, $R^1$ is pyrimidinyl. In some embodiments, $R^1$ is pyrazolyl. In some embodiments, $R^1$ is pyridyl. In some embodiments, $R^1$ is triazolyl. In some embodiments, $R^1$ is imidazolyl. In some embodiments, $R^1$ is pyridazinyl. In some embodiments, $R^1$ is a 5-6 membered heteroaryl containing 1 ring nitrogen atom and 1 ring sulfur atom. In some embodiments, $R^1$ is a 5-6 membered heteroaryl containing 1 ring nitrogen atom and 1 ring oxygen atom. In some embodiments, $R^1$ is thiazolyl. In some embodiments, $R^1$ is oxazolyl. In some embodiments, $R^1$ is isothiazolyl. In some embodiments, $R^1$ is isoxazolyl. In some embodiments, $R^1$ is a 4-5 membered heterocyclyl containing 1 ring nitrogen atom. In some embodiments, $R^1$ is a 4-5 membered heterocyclyl which is optionally substited by 1-2 oxo groups. In some embodiments, $R^1$ is azetidinyl. In some embodiments, $R^1$ is pyrrolidinyl. In any of these embodiments, $R^1$ is optionally substituted by 1-3 substituents selected from the group consisting of halogen, cyano, hydroxyl, $C_1$-$C_6$ alkoxy, $C_1$-$C_6$ alkyl, and $C_3$-$C_6$ cycloalkyl. In some variations, $R^1$ is substituted by 1-2 substituents selected from the group consisting of halogen, cyano, hydroxyl, $C_1$-$C_3$ alkoxy, $C_1$-$C_3$ alkyl, and $C_3$-$C_6$ cycloalkyl. In some variations, $R^1$ is substituted by 1 substituent selected from the group consisting of halogen, cyano, hydroxyl, $C_1$-$C_3$ alkoxy, $C_1$-$C_3$ alkyl, and $C_3$-$C_6$ cycloalkyl. In some variations, $R^1$ is substituted by 1 substituent selected from the group consisting of fluoro, chloro, bromo, cyano, hydroxyl, methoxy, ethoxy, methyl, ethyl, cyclopropyl, cyclobutyl, cyclopentyl, and cyclohexyl.

In some embodiments, $R^1$ is

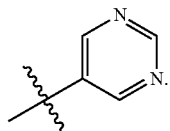

In some embodiments, $R^1$ is

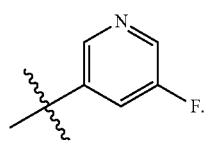 [SMILES: *c1cncc(F)c1]

In some embodiments, $R^1$ is

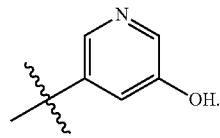

In some embodiments, $R^1$ is

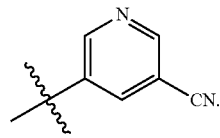 [SMILES: *c1cncc(C#N)c1]

In some embodiments, $R^1$ is

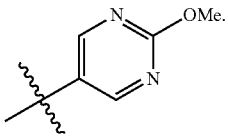 [SMILES: *c1cnc(OC)nc1]

In some embodiments, $R^1$ is

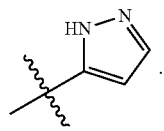

In some embodiments, $R^1$ is

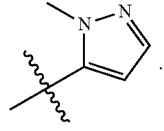 [SMILES: *c1ccnn1C]

In some embodiments, $R^1$ is

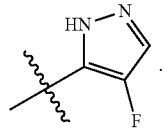

In some embodiments, $R^1$ is

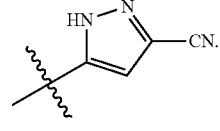 [SMILES: *c1cc(C#N)n[nH]1]

In some embodiments, R¹ is
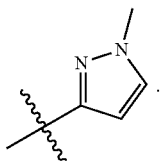 [SMILES: *c1ccn(C)n1]
In some embodiments, R¹ is
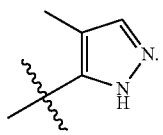 [SMILES: *c1[nH]ncc1C]
In some embodiments, R¹ is
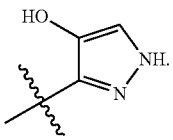
In some embodiments, R¹ is
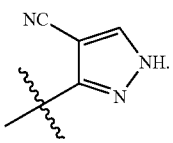 [SMILES: *c1n[nH]cc1C#N]
In some embodiments, R¹ is
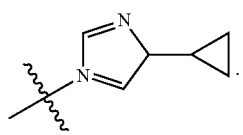
In some embodiments, R¹ is
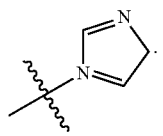
In some embodiments, R¹ is
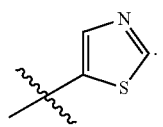
In some embodiments, R¹ is
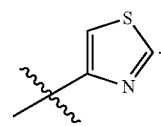
In some embodiments, R¹ is
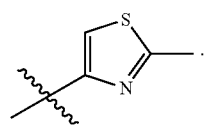 [SMILES: *c1csc(C)n1]
In some embodiments, R¹ is
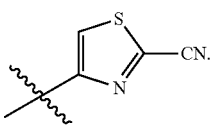 [SMILES: *c1csc(C#N)n1]
In some embodiments, R¹ is
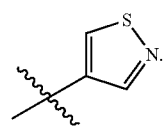 [SMILES: *c1cnsc1]
In some embodiments, R¹ is
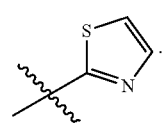
In some embodiments, R¹ is
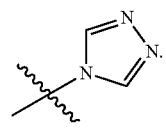 [SMILES: *n1cnnc1]
In some embodiments, R¹ is
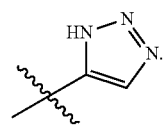 [SMILES: *c1cnn[nH]1]

In some embodiments, $R^1$ is

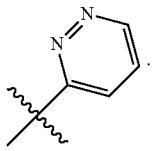

In some embodiments, $R^1$ is

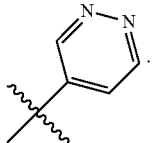

In some embodiments, $R^1$ is

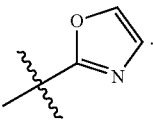

In some embodiments, $R^1$ is

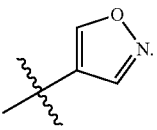 [SMILES: *c1cnoc1]

In some embodiments, $R^1$ is

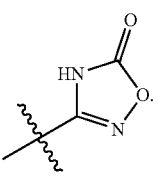

In some embodiments, $R^1$ is

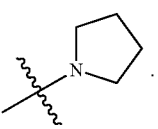

In some embodiments, $R^1$ is

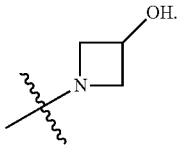

In some embodiments, $R^1$ is

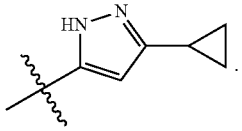 [SMILES: *c1cc(C2CC2)n[nH]1]

In some embodiments, $R^1$ is

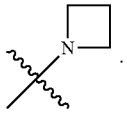

In some embodiments, $R^1$—$CONHR^7$, wherein $R^7$ is H, $C_3$-$C_6$ cycloalkyl, or $C_1$-$C_6$ alkyl.

In some embodiments, $R^1$ is —$CONH(C_3$-$C_6$ cycloalkyl). In some embodiments, $R^1$ is —$CONH(C_3$-$C_5$ cycloalkyl). In some embodiments, $R^1$ is —$CONH(C_3$-$C_4$ cycloalkyl).

In some embodiments, $R^1$ is —$CONH$(cyclopropyl).

In some embodiments, $R^1$ is —$CONH_2$.

In some embodiments, $R^1$ is —$CONH(C_1$-$C_6$ alkyl). In some embodiments, $R^1$ is —$CONH(C_1$-$C_3$ alkyl). In some embodiments, $R^1$ is —$CON(H)(CH_3)$ or —$CON(H)(C_2H_5)$.

In some embodiments, $R^2$ is optionally substituted $C_1$-$C_3$ alkyl. In some embodiments, $R^2$ is methyl. In some embodiments, $R^2$ is ethyl. In some embodiments, $R^2$ is propyl. In some embodiments, $R^2$ is optionally substituted isopropyl. In some embodiments, $R^2$ is isopropyl. In some embodiments, $R^2$ is butyl. In some embodiments, $R^2$ is tertiary butyl. In some embodiments, $R^2$ is pentyl. In some embodiments, $R^2$ is n-pentyl, sec-pentyl, 3-pentyl, or sec-isopentyl. In some embodiments, $R^2$ is optionally substituted $C_3$-$C_4$ cycloalkyl. In some embodiments, $R^2$ is cyclopropyl. In some embodiments, $R^2$ is cyclobutyl. In some embodiments, $R^2$ is cyclopentyl. In some embodiments, $R^2$ is 4- to 6-membered heterocyclyl. In some embodiments, $R^2$ is 4- to 6-membered heterocyclyl containing 1 or 2 heteroatoms selected from the group consisting of nitrogen, sulfur, and oxygen. In some embodiments, $R^2$ is tetrahydrofuranyl. In some embodiments, $R^2$ is tetrahydropyranyl. In some embodiments, $R^2$ is thietanyl. In some embodiments, $R^2$ is pyrrolidinyl. In any of these embodiments, $R^2$ is optionally substituted by 1-3 substituents selected from the group consisting of halogen, hydroxyl, $C_1$-$C_6$ alkoxy, $C_1$-$C_6$ alkyl, $C_3$-$C_6$ cycloalkyl, 4- to 6-membered heterocyclyl, cyano, oxo, —$C(O)NH(C_1$-$C_6$ alkyl), and —$C(O)NH(C_3$-$C_6$ cycloalkyl). In some variations, $R^2$ is substituted by 1-3 substituents selected from the group consisting of halogen, hydroxyl, $C_1$-$C_3$ alkoxy, $C_1$-$C_3$ alkyl, $C_3$-$C_5$ cycloalkyl, 4- to 6-membered heterocyclyl, cyano, oxo, —$C(O)NH(C_1$-$C_3$ alkyl), and —$C(O)NH(C_3$-$C_6$ cycloalkyl). In some variations, $R^2$ is substituted by 1-3 substituents selected from the group consisting of fluoro, chloro, bromo, hydroxyl, methyoxy, ethyoxy, methyl, ethyl, cyclopropyl, cyclobutyl, oxetanyl, cyano, oxo, —C(O)NH(CH$_3$), —C(O)NH (CH$_2$CH$_3$), —C(O)NH(cyclopropyl), —C(O)NH(cyclobutyl), —C(O)NH(cyclopentyl), and —C(O)NH(cyclohexyl).

In some embodiments, $R^2$ is H.

In some embodiments, $R^2$ is

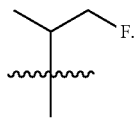 [SMILES: *C(C)CF]

In some embodiments, $R^2$ is

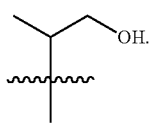 [SMILES: *C(C)CO]

In some embodiments, $R^2$ is

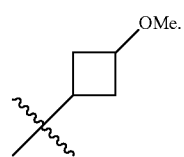 [SMILES: *C1CC(OC)C1]

In some embodiments, $R^2$ is

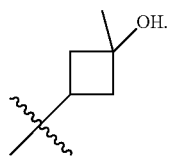 [SMILES: *C1CC(C)(O)C1]

In some embodiments, $R^2$ is

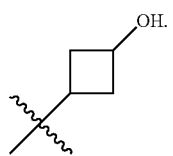 [SMILES: *C1CC(O)C1]

In some embodiments, $R^2$ is

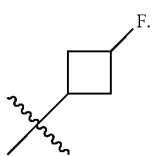 [SMILES: *C1CC(F)C1]

In some embodiments, $R^2$ is

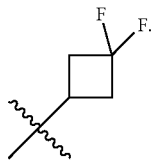

In some embodiments, $R^2$ is

In some embodiments, $R^2$ is

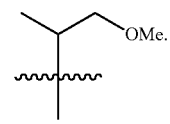 [SMILES: *C(C)COC]

In some embodiments, $R^2$ is

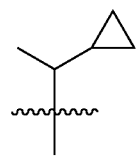

In some embodiments, $R^2$ is

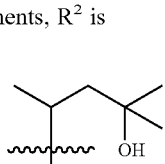

In some embodiments, $R^2$ is

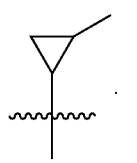

In some embodiments, $R^2$ is

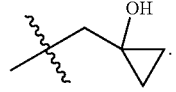 [SMILES: *CC1(O)CC1]

In some embodiments, $R^2$ is

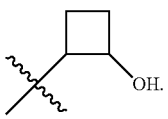 [SMILES: *C1CCC1O]

In some embodiments, $R^2$ is

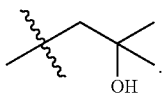 [SMILES: *CC(C)(C)O]

In some embodiments, $R^2$ is

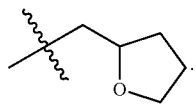 [SMILES: *CC1CCCO1]

In some embodiments, $R^2$ is

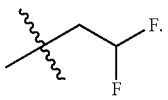

In some embodiments, $R^2$ is

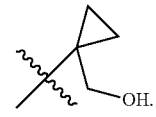 [SMILES: *C1(CO)CC1]

In some embodiments, $R^2$ is

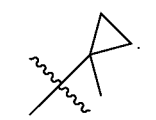

In some embodiments, $R^2$ is

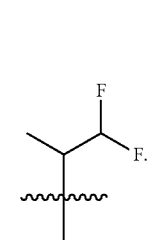 [SMILES: *C(C)C(F)F]

In some embodiments, $R^2$ is

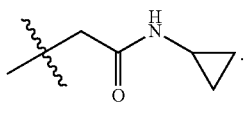 [SMILES: *CC(=O)NC1CC1]

In some embodiments, $R^2$ is

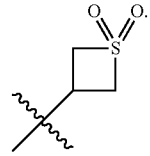

In some embodiments, $R^2$ is

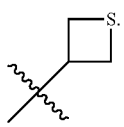

In some embodiments, $R^2$ is

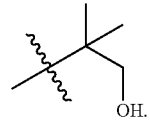

In some embodiments, $R^2$ is

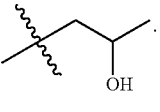

In some embodiments, $R^2$ is

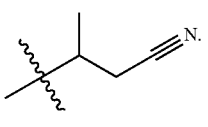 [SMILES: *C(C)CC#N]

In some embodiments, $R^2$ is

In some embodiments, R² is

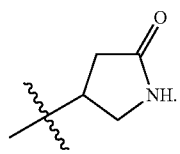 [SMILES: *C1CNC(=O)C1]

In some embodiments, R² is

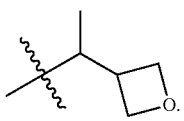 [SMILES: *C(C)C1COC1]

In some embodiments, R² is

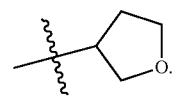

In some embodiments, R² is

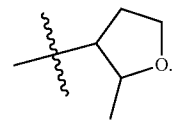 [SMILES: *C1CCOC1C]

In some embodiments, R² is

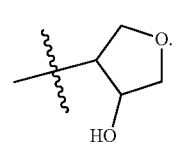 [SMILES: *C1COCC1O]

In some embodiments, R² is

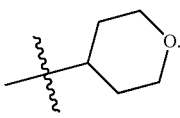 [SMILES: *C1CCOCC1]

In some embodiments, R² and R³ together with the intervening atoms form ring A, which is optionally substituted 5- to 6-membered heterocycloalkyl. In some embodiments, ring A is optionally substituted by 1-3 substituents selected from the group consisting of $C_1$-$C_6$ alkyl, hydroxyl, $C_1$-$C_6$ alkyl-OH, —C(O)($C_1$-$C_6$ alkyl), and oxo. In some variations, ring A is substituted by 1-3 substituents selected from the group consisting of $C_1$-$C_3$ alkyl, hydroxyl, $C_1$-$C_3$ alkyl-OH, —C(O)($C_1$-$C_3$ alkyl), and oxo. In some variations, ring A is substituted by 1-3 substituents selected from the group consisting of methyl, ethyl, hydroxyl, —CH₂OH, —CH₂CH₂—OH, —C(O)CH₃, —C(O)CH₂CH₃, and oxo.

In some embodiments, R² and R³ together form:

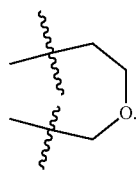 [SMILES: *CCOC*]

In some embodiments, R² and R³ together form:

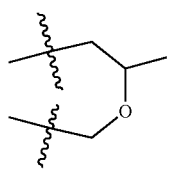

In some embodiments, R² and R³ together form:

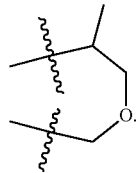 [SMILES: *COCC(*)C]

In some embodiments, R² and R³ together form:

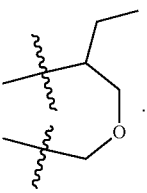 [SMILES: *COCC(*)CC]

In some embodiments, R² and R³ together form:

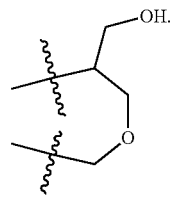 [SMILES: *COCC(*)CO]

In some embodiments, R² and R³ together form:

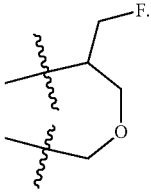 [SMILES: *COCC(*)CF]

In some embodiments, R² and R³ together form:

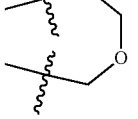

In some embodiments, $R^2$ and $R^3$ together form:

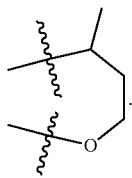 [SMILES: *OCCC(*)C]

In some embodiments, $R^2$ and $R^3$ together form:

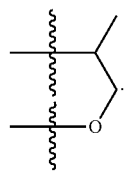

In some embodiments, $R^2$ and $R^3$ together form:

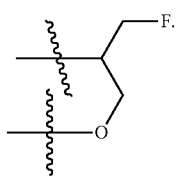

In some embodiments, $R^2$ and $R^3$ together form:

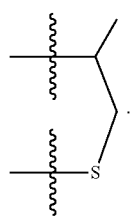

In some embodiments, $R^2$ and $R^3$ together form:

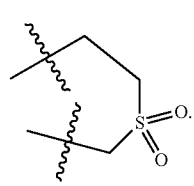 [SMILES: *CCS(=O)(=O)C*]

In some embodiments, $R^2$ and $R^3$ together form:

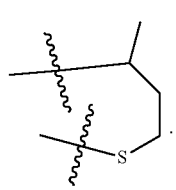 [SMILES: *SCCC(*)C]

In some embodiments, $R^2$ and $R^3$ together form:

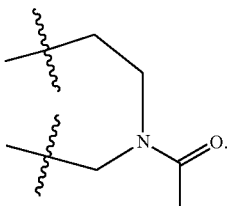 [SMILES: *CCN(C*)C(C)=O]

In some embodiments, $R^2$ and $R^3$ together form:

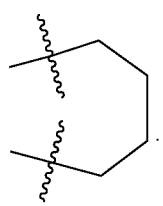

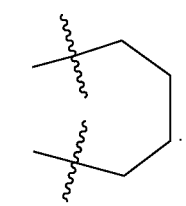

In some embodiments, $R^2$ and $R^3$ together form:

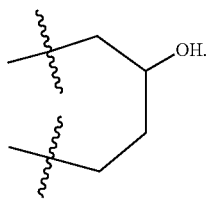 [SMILES: *CCC(O)C*]

In some embodiments, $R^2$ and $R^3$ together form:

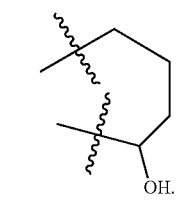 [SMILES: *CCCC(*)O]

In some embodiments, $R^2$ and $R^3$ together form:

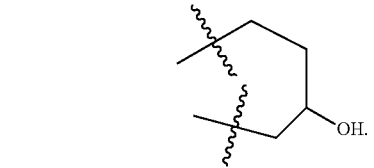 [SMILES: *CCC(O)C*]

In some embodiments, R² and R³ together form:

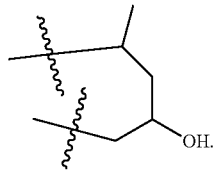 [SMILES: *CC(O)CC(*)C]

In some embodiments, R² and R³ together form:

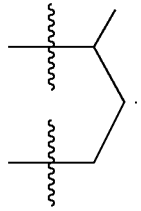 [SMILES: *CCC(*)C]

In some embodiments, R² and R³ together form:

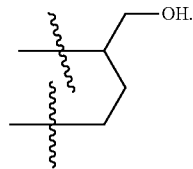

In some embodiments, R² and R³ together form:

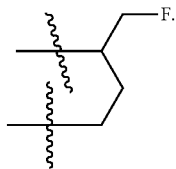 [SMILES: *CCC(*)CF]

In some embodiments, R² and R³ together form:

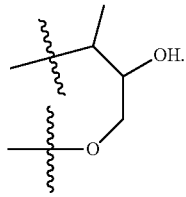 [SMILES: *OCC(O)C(*)C]

In some embodiments, R² and R³ together form:

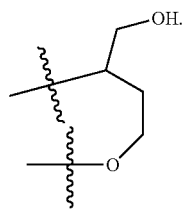 [SMILES: *OCCC(*)CO]

In some embodiments, R² and R³ together form:

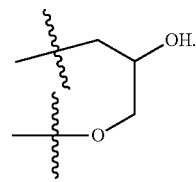 [SMILES: *CC(O)CO*]

In some embodiments, R² and R³ together form:

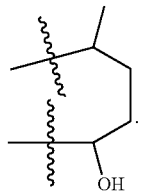

In some embodiments, R² and R³ together form:

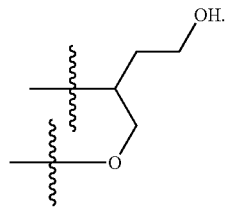 [SMILES: *OCC(*)CCO]

In some embodiments, R³ is H. In some embodiment, R³ is $C_1$-$C_6$ alkyl optionally substituted with 1-3 substituents selected from the group consisting of halogen, hydroxyl, and —O($C_1$-$C_6$ alkyl). In some embodiments, R³ is methyl. In some embodiments, R³ is isopropyl. In some embodiments, R³ is difluoromethyl. In some embodiments, R³ is hydroxyethyl. In some embodiments, R³ is —$CH_2CH_2OH$. In some embodiments, R³ is —$C(Me)_2OH$. In some embodiments, R³ is —CH(Me)OH. In some embodiments, R³ is methoxymethyl. In some embodiments, R³ is hydroxymethyl. In some embodiments, R³ is $C_3$-$C_6$ cycloalkyl. In some embodiments, R³ is $C_3$-$C_6$ cycloalkyl substituted by 1-3 substituents selected from the group consisting of halogen, $C_1$-$C_6$ alkyl, and hydroxyl. In some embodiments, R³ is cyclopropyl. In some embodiments, R³ is cyclobutyl. In some embodiments, R³ is —OR⁶, wherein R⁶ is $C_1$-$C_6$ alkyl. In some embodiments, R³ is methoxy. In some embodiments, R³ is ethoxy. In some embodiments, R³ is 4- to 6-membered heterocyclyl. In some embodiments, R³ is 4- to 6-membered heterocyclyl substituted by 1-3 substituents selected from the group consisting of halogen, $C_1$-$C_6$ alkyl, and hydroxyl. In some embodiments, R³ is tetrahydropyranyl.

In some embodiments, R⁴ is optionally substituted $C_1$-$C_3$ alkyl. In some embodiments, R⁴ is $C_1$-$C_3$ alkyl, wherein the alkyl group is substituted with one or more halo substituents. In some embodiments, R⁴ is $C_1$-$C_3$ alkyl substituted with 1-3 halo substituents. In some embodiments, R⁴ is $CF_3$. In some embodiments, R⁴ is $CF_2Cl$.

In one aspect, provided is a compound of formula (I) wherein the compound has any one or more of the following features:

(I) $R^1$ is:
  (i) 5-6 membered heteroaryl optionally substituted by 1-3 substituents selected from the group consisting of halogen, cyano, hydroxyl, $C_1$-$C_6$ alkoxy, $C_3$-$C_6$ cycloalkyl, and $C_1$-$C_6$ alkyl; or
  (ii) 4-5 membered heterocyclyl optionally substituted by 1-3 substituents selected from the group consisting of halogen, cyano, hydroxyl, $C_1$-$C_6$ alkoxy, $C_3$-$C_6$ cycloalkyl, $C_1$-$C_6$ alkyl, and oxo; or
  (iii) $R^1$—CONHR$^7$, wherein $R^7$ is H, $C_3$-$C_6$ cycloalkyl, or $C_1$-$C_6$ alkyl;
(II) $R^2$ is:
  (iv) $C_1$-$C_6$ alkyl optionally substituted by 1-3 substituents selected from the group consisting of halogen, hydroxyl, $C_1$-$C_6$ alkoxy, $C_1$-$C_6$ alkyl, $C_3$-$C_6$ cycloalkyl, 4- to 6-membered heterocyclyl, cyano, —C(O)NH($C_1$-$C_6$ alkyl), and —C(O)NH($C_3$-$C_6$ cycloalkyl); or
  (v) $R^2$ is $C_3$-$C_6$ cycloalkyl optionally substituted by 1-3 substituents selected from the group consisting of halogen, hydroxyl, $C_1$-$C_6$ alkoxy, $C_1$-$C_6$ alkyl, $C_3$-$C_6$ cycloalkyl, 4- to 6-membered heterocyclyl, cyano, oxo, —C(O)NH($C_1$-$C_3$ alkyl), and —C(O)NH($C_3$-$C_6$ cycloalkyl); or
  (vi) 4- to 6-membered heterocyclyl optionally substituted by 1-3 substituents selected from the group consisting of halogen, hydroxyl, $C_1$-$C_6$ alkoxy, $C_1$-$C_6$ alkyl, $C_3$-$C_6$ cycloalkyl, 4- to 6-membered heterocyclyl, cyano, oxo, —C(O)NH($C_1$-$C_3$ alkyl), and —C(O)NH($C_3$-$C_6$ cycloalkyl); or
  (vii) H;
(III) $R^3$ is:
  (viii) H; or
  (ix) $C_1$-$C_6$ alkyl optionally substituted by 1-3 substitutents selected from the group consisting of halogen, hydroxyl, and —O($C_1$-$C_6$ alkyl); or
  (x) —OR$^6$, wherein $R^6$ is $C_1$-$C_6$ alkyl; or
  (xi) $C_3$-$C_6$ cycloalkyl optionally substituted by 1-3 substituents selected from the group consisting of halogen, $C_1$-$C_6$ alkyl, and hydroxyl; or
  (xii) 4- to 6-membered heterocyclyl optionally substituted by 1-3 substituents selected from the group consisting of halogen, $C_1$-$C_6$ alkyl, and hydroxyl;
(IV) $R^2$ and $R^3$ together with the intervening atoms form ring A, which is 5- to 6-membered heterocycloalkyl optionally substituted by 1-3 substituents selected from the group consisting of $C_1$-$C_6$ alkyl, hydroxyl, $C_1$-$C_6$ alkyl-OH, —C(O)O($C_1$-$C_6$ alkyl), and oxo;
(V) $R^4$ is $C_1$-$C_3$ alkyl optionally substituted by 1-3 halogen;
(VI) L is —NH—CO—;
(VII) Z is CH, C-halo, or N;
(VIII) X is O.

In one variation, (I) applies. In one variation, (II) applies. In one variation, (III) applies. In one variation, (IV) applies. In one variation, (V) applies. In one variation, (VI) applies. In one variation, (VII) applies. In one variation, (VIII) applies. In one aspect of this variation, (I), (II), (III), (V), (VI), (VII), and (VIII) apply. In another aspect of this variation, (I), (IV), (V), (VI), (VII), and (VIII) apply. In one variation, (V), (VI), (VII), and (VIII) apply. In one variation, (i), (iv), and (viii) apply. In one variation, (i), (v), and (viii) apply. In one variation, (iv), (iv), and (ix) apply. In one variation, (iv), (iv), and (x) apply. In one variation, (i), (v), and (ix) apply. In one variation, (i), (vi), and (viii) apply. In one variation, (i), (iv), and (xi) apply. In one variation, (i), (vii), and (viii) apply. In one variation, (i), (iv), and (xii) apply. In one variation, (i) and (IV) apply. In one variation, (ii), (iv), and (viii) apply. In one variation, (ii) and (IV) apply. In one variation, (iii), (iv), and (viii) apply. In one variation, (iii) and (IV) apply.

In one aspect, provided is a compound of formula (I) such as those provided in the Examples (e.g., Examples 1-49) below and tabulated in Table 1 (Examples 50-232), or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding.

This disclosure also includes all salts, such as pharmaceutically acceptable salts, of compounds referred to herein. This disclosure also includes any or all of the stereochemical forms, including any enantiomeric or diastereomeric forms, and any tautomers or other forms, such as N-oxides, solvates, prodrugs, or isotopomers, of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

In the descriptions herein, it is understood that every description, variation, embodiment, or aspect of a moiety can be combined with every description, variation, embodiment, or aspect of other moieties the same as if each and every combination of descriptions is specifically and individually listed. For example, every description, variation, embodiment, or aspect provided herein with respect to $R^1$ of formula (I) may be combined with every description, variation, embodiment, or aspect of $R^2$, $R^3$, $R^4$, $R^5$, $R^6$, $R^7$, X, L, Y, and/or Z the same as if each and every combination were specifically and individually listed. It is also understood that all descriptions, variations, embodiments or aspects of formula (I), where applicable, apply equally to other formulae detailed herein, and are equally described, the same as if each and every description, variation, embodiment or aspect were separately and individually listed for all formulae. For example, all descriptions, variations, embodiments, or aspects of formula (I), where applicable, apply equally to any of formulae (I-i), (Ia), (IA), (IA-1), (IIA), (IIB), (IIC), (IID), (IIE), (IIF), (IIG), (IIH), (Ib), (Ic), (Id), and (Ie) detailed herein, and are equally described, the same as if each and every description, variation, embodiment or aspect were separately and individually listed for all formulae.

The invention also includes all salts, such as pharmaceutically acceptable salts, of compounds referred to herein. The invention also includes any or all of the stereochemical forms, including any enantiomeric or diastereomeric forms, and any tautomers or other forms, such as N-oxides, solvates, prodrugs, or isotopomers, of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

Pharmaceutical Compositions and Formulations

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. For example, a composition of a substantially pure compound selected from a compound of Table 1 (A, B, etc.) intends a composition that contains no more than 35% impurity, wherein the impurity denotes a compound other than the compound or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 15% or preferably no more than 10% or more preferably no more than 5% or even more preferably no more than 3% and most preferably no more than 1% impurity, which impurity may be the compound in a different stereochemical form. For instance, and without limitation, a composition of substantially pure (S) compound means that the composition contains no more than 15% or no more than 10% or no more than 5% or no more than 3% or no more than 1% of the (R) form of the compound.

In one variation, the compounds herein are synthetic compounds prepared for administration to an individual such as a human. In another variation, compositions are provided containing a compound in substantially pure form. In another variation, the invention embraces pharmaceutical compositions comprising a compound detailed herein and a pharmaceutically acceptable carrier or excipient. In another variation, methods of administering a compound are provided. The purified forms, pharmaceutical compositions and methods of administering the compounds are suitable for any compound or form thereof detailed herein.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington: The Science and Practice of Pharmacy*, Lippincott Williams & Wilkins, $21^{st}$ ed. (2005), which is incorporated herein by reference.

Compounds as described herein may be administered to individuals (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid polyols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described.

Compositions comprising a compound provided herein are also described. In one variation, the composition comprises a compound and a pharmaceutically acceptable carrier or excipient. In another variation, a composition of substantially pure compound is provided.

Methods of Use/Treatments

Compounds and compositions detailed herein, such as a pharmaceutical composition containing a compound provided herein, or a salt thereof, and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In one aspect, provided herein is a method of inhibiting tyrosine kinase enzymatic activity of a protein selected from Abelson protein (ABL1), Abelson-related protein (ABL2), or a chimeric protein BCR-ABL1, comprising contacting an effective amount of a compound or composition provided herein, to the protein. In one embodiment, provided herein is a method of inhibiting tyrosine kinase enzymatic activity of Abelson protein (ABL1) comprising contacting an effective amount of a compound or composition provided herein to ABL1. In another embodiment, provided herein is a method of inhibiting tyrosine kinase enzymatic activity of Abelson-related protein (ABL2) comprising contacting an effective amount of a compound or composition provided herein to ABL2. In a further embodiment, provided herein is a method of inhibiting tyrosine kinase enzymatic activity of a chimeric protein BCR-ABL1 comprising contacting an effective amount of a compound or composition provided herein to the chimeric protein.

In one aspect, provided herein is a method of treating a disease in a patient in need thereof, comprising administering to the patient a therapeutically effective amount of a compound provided herein or a salt thereof, or a composition provided herein. In some embodiments, the compound, or salt thereof, or the composition is administered according to a dosage described herein.

The compounds, or salts thereof, described herein and compositions described herein are believed to be effective for treating a variety of diseases and disorders. In some embodiments, a compound, or salt thereof, described herein or a composition described herein may be used in a method of treating a disease mediated by ABL1, ABL2, and/or BCR-ABL1.

In one aspect, provided herein is a method of treating a disease, wherein modulation of BCR-ABL1 activity prevents, inhibits, or ameliorates the pathology and/or symptomology of the disease, in a patient, comprising administering to the patient a therapeutically effective amount of a compound or composition provided herein. In one embodiment, provided herein is a method of treating a disease, wherein modulation of BCR-ABL1 activity prevents the pathology and/or symptomology of the disease, in a patient, comprising administering to the patient a therapeutically effective amount of a compound or composition provided herein. In one embodiment, provided herein is a method of treating a disease, wherein modulation of BCR-ABL1 activity inhibits the pathology and/or symptomology of the disease, in a patient, comprising administering to the patient a therapeutically effective amount of a compound or composition provided herein. In one embodiment, provided herein is a method of treating a disease, wherein modulation of BCR-ABL1 activity ameliorates the pathology and/or symptomology of the disease, in a patient, comprising administering to the patient a therapeutically effective amount of a compound or composition provided herein.

In some embodiments, the disease is leukemia. In some embodiments, the leukemia is chronic myeloid leukemia (CML), acute myeloid leukemia (AML), or acute lymphoblastic leukemia (ALL). In some embodiments, the leukemia is chronic myeloid leukemia (CML).

In one aspect, provided herein is a method of treating leukemia in a patient comprising administering to the patient a therapeutically effective amount of a compound or composition provided herein. In one aspect, provided herein is a method of treating leukemia in a patient comprising administering to the patient a therapeutically effective amount of a compound or composition provided herein, wherein the leukemia is chronic myeloid leukemia (CML), acute myeloid leukemia (AML), or acute lymphoblastic leukemia (ALL).

In some embodiments, the leukemia treated herein is CML or ALL, and the method further comprises administering a therapeutically effective amount of a compound selected from imatinib, nilotinib, dasatinib, bosutinib, ponatinib and bafetinib. In some embodiments, the leukemia is CML or ALL, and the method further comprises administering a therapeutically effective amount of a compound selected from imatinib, nilotinib, dasatinib, bosutinib, ponatinib and bafetinib.

In some embodiments, the leukemia is resistant to treatment. In some embodiments, the leukemia is resistant to treatment with imatinib, nilotinib, dasatinib, bosutinib, ponatinib, and/or bafetinib. In some embodiments, the CML is resistant to standard-of-care treatment such as treatment with one or more of imatinib, nilotinib, and dasatinib. In some embodiments, the leukemia progressed during a prior treatment. In some embodiments the prior treatment comprised administration of imatinib, nilotinib, dasatinib, bosutinib, ponatinib, and/or bafetinib.

In some embodiments, the method further comprises administering a therapeutically effective amount of a compound selected from imatinib, nilotinib, dasatinib, bosutinib, ponatinib and bafetinib.

In some embodiments, the AML is secondary AML, which develops after myelodysplastic syndromes (MDS) or myeloproliferative neo-plasms (MPN).

In one aspect, provided herein is a method of treating a cancer in a patient comprising administering to the patient a therapeutically effective amount of a compound or composition provided herein. In some embodiments, the cancer is melanoma, hereditary leiomyomatosis, renal cell carcinoma (HLRCC), or other solid tumors.

In one aspect, provided herein is a method of treating a neurodegenerative disease in a patient comprising administering to the patient a therapeutically effective amount of a compound or composition provided herein. In some embodiments, the neurodegenerative disease is Alzheimer's or Parkinson's disease.

In another aspect is provided a method of delaying the onset and/or development of a disease or disorder that is mediated by BCR-ABL1 activity in a patient (such as a human) who is at risk for developing the disease or disorder. It is appreciated that delayed development may encompass prevention in the event the individual or patient does not develop the disease or disorder. In one aspect, an individual or patient at risk of developing a disease or disorder that is mediated by BCR-ABL1 activity has one or more risk factors for developing the disease or disorder, such as a family history of an individual or patient having the disease or disorder, or having an underlying genetic condition that is associated with an increased likelihood of developing the disease or disorder.

In one aspect, provided herein is a method of delaying the onset and/or development of leukemia in a patient in need thereof, comprising administering to the patient a therapeutically effective amount of a compound or composition provided herein. In one variation, provided herein is a method of delaying the onset and/or development of CML in a patient in need thereof, comprising administering to the patient a therapeutically effective amount of a compound or composition provided herein. In one variation, provided herein is a method of delaying the onset and/or development of AML in a patient in need thereof, comprising administering to the patient a therapeutically effective amount of a compound or composition provided herein. In one variation, provided herein is a method of delaying the onset and/or development of ALL in a patient in need thereof, comprising administering to the patient a therapeutically effective amount of a compound or composition provided herein.

Methods of treating a disease mediated by BCR-ABL1, such as various leukemias and the like, are well known to the skilled artisan and can be adapted to treating such a disease with a compound or composition provided herein.

In some embodiments, the patient is a mammal. In some embodiments, the patient is a primate, dog, cat, rabbit, or rodent. In some embodiments, the patient is a primate. In some embodiments, the patient is a human. In some embodiments, the human is at least about or is about any of 18, 21, 30, 50, 60, 65, 70, 75, 80, or 85 years old. In some embodiments, the human is a child. In some embodiments, the human is less than about or about any of 21, 18, 15, 10, 5, 4, 3, 2, or 1 years old. In some embodiments, the patient has a genetic condition that is associated with an increased likelihood of developing the disease, such as the leukemia. In some embodiments, the patient has a mutation in the ABL1 and/or ABL2 gene. In some embodiments, the patient is Philadelphia chromosome positive.

A compound or composition provided herein may be administered to a patient in accordance with an effective dosing regimen for a desired period of time or duration, such as at least about one month, at least about 2 months, at least about 3 months, at least about 6 months, or at least about 12 months or longer, which in some variations may be for the duration of the patient's life. In one variation, the compound is administered on a daily or intermittent schedule. The compound can be administered to an patient continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to a patient via various routes, including, e.g., intravenous, intramuscular, subcutaneous, oral and transdermal.

The dose of a compound administered to a patient may vary with the particular compound or salt thereof, the method of administration, and the particular disease. In some embodiments, the amount of the compound or salt thereof is a therapeutically effective amount.

The effective amount of the compound may in one aspect be a dose of between about 0.01 and about 100 mg/kg. Effective amounts or doses of the compounds of the present disclosure may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g in a day, or about 7 mg to 350 mg in a day, or about 350 mg to 1.75 g in a day, or about 1.75 to 7 g in a day.

Also provided herein are uses of a compound described herein or a salt thereof, or a composition described herein, in the manufacture of a medicament. In some embodiments, the manufacture of a medicament is for the treatment of a disease described herein. In some embodiments, the manufacture of a medicament is for the treatment of a disease mediated by ABL1, ABL2, and/or BCR-ABL1.

Articles of Manufacture and Kits

The present disclosure further provides articles of manufacture comprising a compound described herein or a salt thereof, a composition described herein, or one or more unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the present disclosure, which comprises one or more compounds described herein or a composition comprising a compound described herein. The kits may employ any of the compounds disclosed herein. In one variation, the kit employs a compound described herein or a salt thereof. The kits may be used for any one or more of the uses described herein, and, accordingly, may contain instructions for the treatment of any disease or described herein, for example for the treatment of cancer.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of a patient for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to a patient.

EXEMPLARY EMBODIMENTS

The present disclosure is further described by the following embodiments. The features of each of the embodiments are combinable with any of the other embodiments where appropriate and practical.

Embodiment 1. A compound of formula (I) or (Ia):

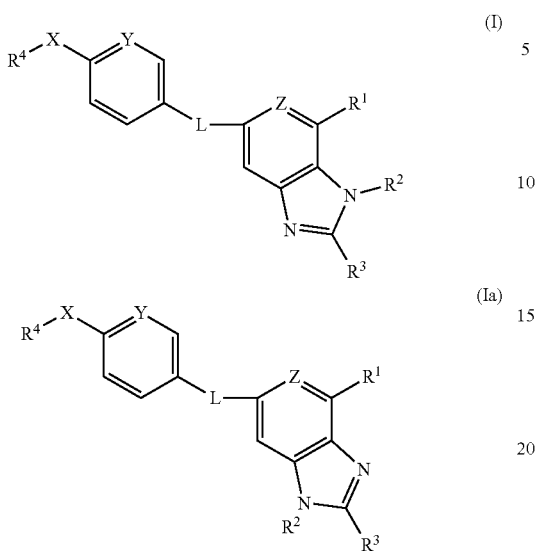

or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding, wherein:

L is —NH—CO—, —CO—NH—, —NH—SO$_2$—, or —SO$_2$—NH—;

R$^1$ is optionally substituted C$_6$-C$_{10}$ aryl, optionally substituted 5-10 membered heteroaryl, optionally substituted 4-10 membered heterocycle, C(O)NR$^6$R$^7$, S(O)$_2$NR$^6$R$^7$, NR$^6$COR$^7$, or NR$^6$SO$_2$R$^7$, or C(O)OR$^6$;

R$^2$ is H, optionally substituted C$_1$-C$_6$ alkyl, optionally substituted C$_3$-C$_8$ cycloalkyl, optionally substituted 4-10 membered heterocycloalkyl, optionally substituted C$_2$-C$_6$ alkenyl, optionally substituted C$_2$-C$_6$ alkynyl, optionally substituted C$_6$-C$_{10}$ aryl, or optionally substituted 5-10 membered heteroaryl;

R$^3$ is H, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted heterocycloalkyl, optionally substituted aryl, optionally substituted heteroaryl, OR$^6$, or NR$^6$R$^7$; or R$^2$ and R$^3$ together with the intervening atoms form cycloalkyl or heterocycloalkyl, preferably an optionally substituted C$_3$-C$_8$ cycloalkyl or an optionally substituted 4-10 membered heterocycloalkyl;

R$^4$ is optionally substituted C$_1$-C$_6$ alkyl, preferably C$_1$-C$_3$ haloalkyl, such as CF$_3$ or CF$_2$Cl, optionally substituted C$_2$-C$_6$ alkenyl, optionally substituted C$_2$-C$_6$ alkynyl;

X is O or S;

Y is CH, C—(C$_1$-C$_2$ alkyl), or C-halo or N;

Z is CR$^5$ or N;

R$^5$ is H or halogen when Z is CH;

R$^6$ is H, optionally substituted C$_1$-C$_6$ alkyl, optionally substituted C$_3$-C$_8$ cycloalkyl, optionally substituted 4-10 membered heterocycloalkyl, optionally substituted C$_6$-C$_{10}$ aryl, or optionally substituted 5-10 membered heteroaryl; and R$^7$ is H, optionally substituted C$_1$-C$_6$ alkyl, optionally substituted C$_3$-C$_8$ cycloalkyl, optionally substituted 4-10 membered heterocycloalkyl, optionally substituted C$_6$-C$_{10}$ aryl, or optionally substituted 5-10 membered heteroaryl; or R$^6$ and R$^7$ together with the nitrogen to which they are attached form an optionally substituted 4-7 membered heterocycle.

Embodiment 2. A compound of embodiment 1 of formula (IA):

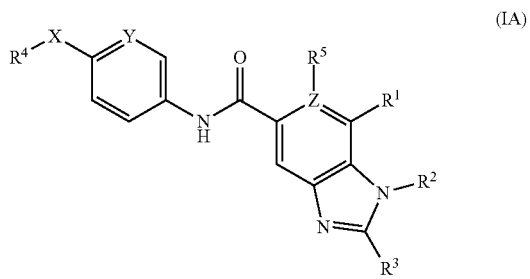

wherein the variables are defined as in embodiment 1.

Embodiment 3. A compound of embodiment 2 selected from formula IIA-IIE:

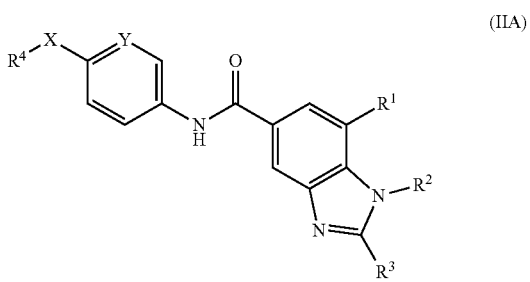

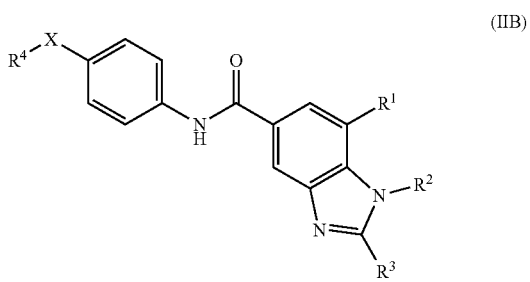

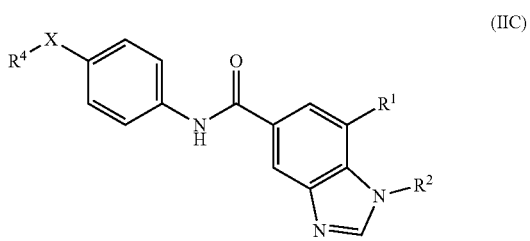

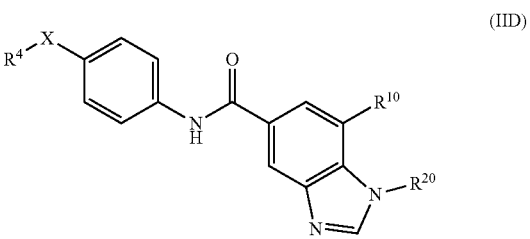

-continued

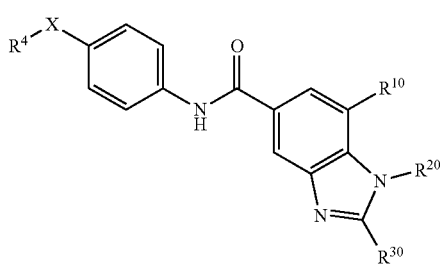
(IIE)

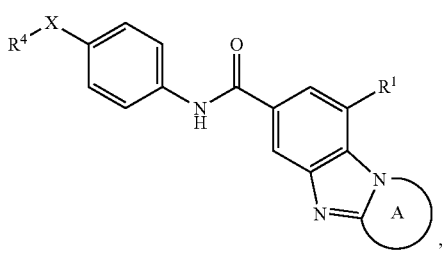
(IIF)

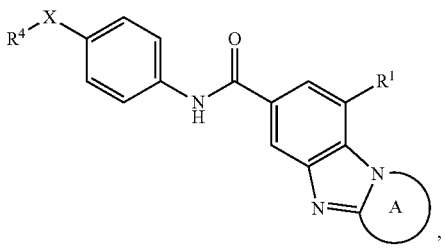
(IIG)

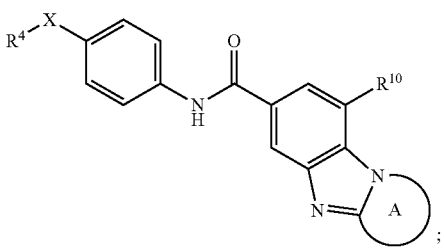
(IIH)

wherein R[10] is a 5-6 membered heteroaryl, preferably the heteroaryl moiety has up to 2 ring nitrogen atoms;

R[20] is optionally substituted $C_1$-$C_3$ alkyl or optionally substituted $C_3$-$C_4$ cycloalkyl, preferably, R[20] is methyl, optionally substituted isopropyl, or cyclopropyl;

R[30] is H, optionally substituted $C_1$-$C_3$ alkyl or optionally substituted $C_3$-$C_4$ cycloalkyl, preferably optionally substituted cyclopropyl; and the remaining variables are defined as in embodiment 1.

Embodiment 4. The compound of embodiment 2 or 3, wherein X is O.

Embodiment 5. The compound of any one of embodiments 2-4, wherein R[1] is 5-10 membered heteroaryl, preferably the heteroaryl moiety containing up to 2 ring nitrogen atoms, or R[1] is 4-10 membered heterocycle, preferably the heterocyclyl moiety containing up to 2 ring nitrogen atoms.

Embodiment 6. The compound of any one embodiments 2-5, wherein R[1] is:

—CONH(cyclopropyl), —CONH$_2$, —CONHMe

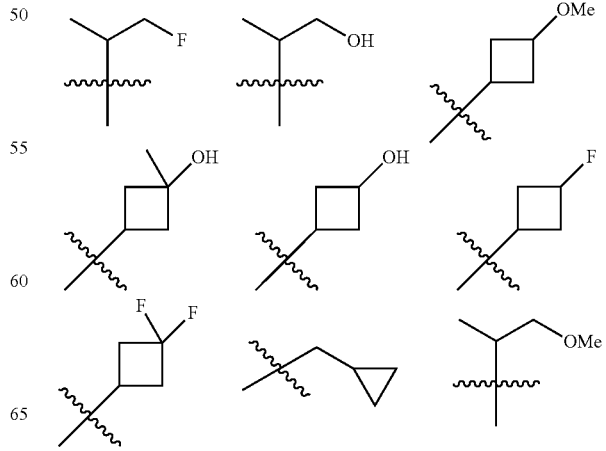

Embodiment 7. The compound of any one of embodiments 2-6, wherein R[1] is pyrimidinyl or pyrazolyl.

Embodiment 8. The compound of any one of embodiments 2-7, wherein R[2] is optionally substituted $C_1$-$C_3$ alkyl or optionally substituted $C_3$-$C_4$ cycloalkyl, preferably, R[2] is methyl, optionally substituted isopropyl, or cyclopropyl.

Embodiment 9. The compound of any one of embodiments 2-7, wherein R[2] is: methyl, isopropyl, tertiary butyl, cyclopropyl, cyclobutyl, cyclopentyl, tetrahydrofuranyl, tetrahydropyranyl, -continued

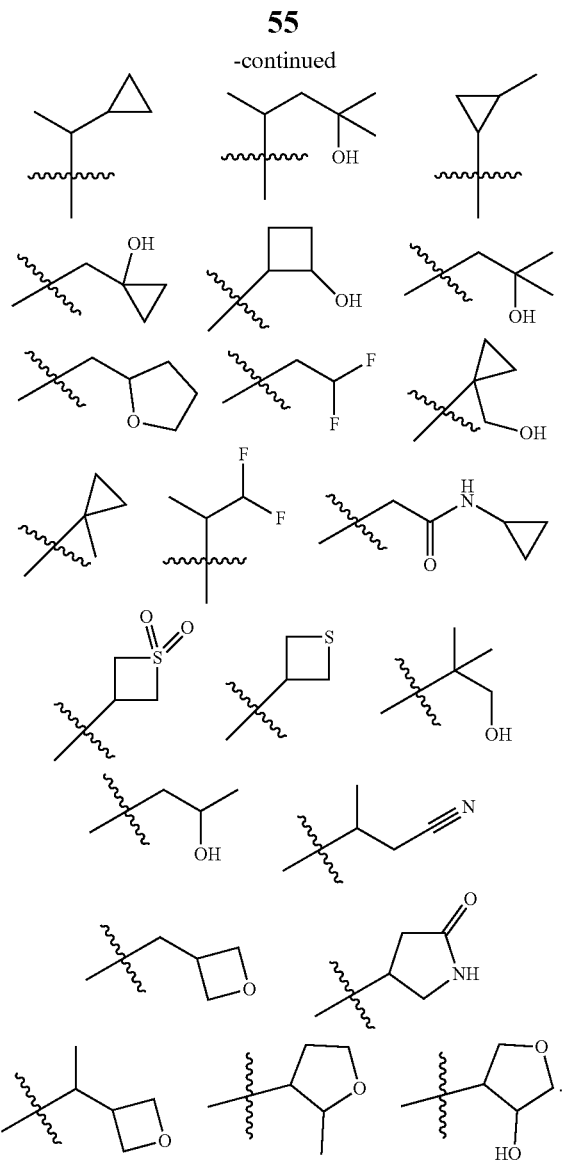

Embodiment 10. The compound of any one embodiments 2-9, wherein $R^3$ is: H, methyl, isopropyl, difluoromethyl, hydroxyethyl, cyclopropyl, cyclobutyl, —C(Me)$_2$OH, methoxymethyl, hydroxymethyl, methoxy, hydroxyethyl, —CH$_2$CH$_2$OH, or tetrahydropyranyl.

Embodiment 11. The compound of any one of embodiments 2-6, wherein $R^2$ and $R^3$ together form:

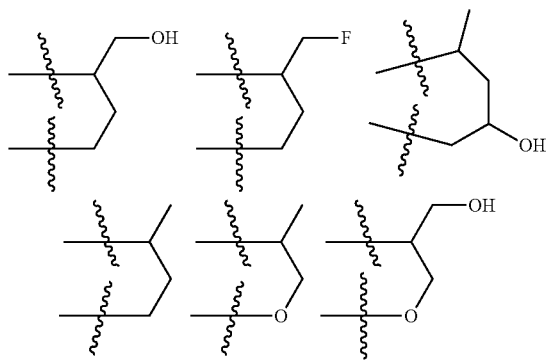

-continued

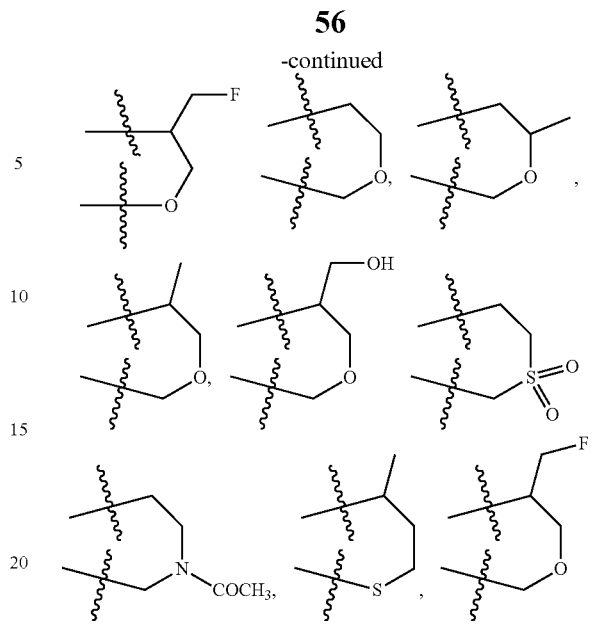

Embodiment 12. The compound of any one of embodiments 2-11, wherein $R^4$ is optionally substituted $C_1$-$C_3$ alkyl, preferably wherein the alkyl group is substituted with one or more halo substituents, more preferably, $R^4$ is CF$_3$ or CF$_2$Cl.

Embodiment 13. The compound of any one of embodiments 2-12, wherein $R^5$ is H.

Embodiment 14. The compound of any one of embodiments 2-13, wherein Y is CH.

Embodiment 15. The compound of embodiment 1 of formula (Ib) or (Ic):

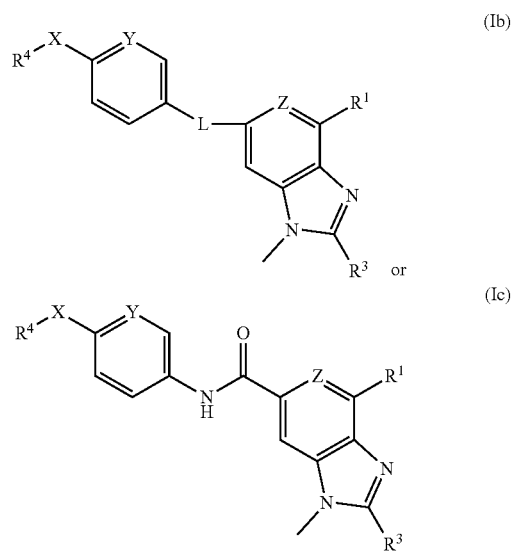

wherein the remaining variables are defined as in embodiment 1.

Embodiment 16. A compound selected from Compounds of formula (I) of Examples 1-26 and from Table 1, or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding.

Embodiment 17. A composition comprising a compound of any one of embodiments 2 to 16, and at least one pharmaceutically acceptable excipient.

Embodiment 18. A method of inhibiting tyrosine kinase enzymatic activity of a protein selected from Abelson protein (ABL1), Abelson-related protein (ABL2), or a chimeric protein BCR-ABL1, comprising contacting an effective amount of a compound of any one of embodiments 2 to 16, or the composition of embodiment 17, to the protein.

Embodiment 19. A method of treating a disease, wherein modulation of BCR-ABL1 activity prevents, inhibits, or ameliorates the pathology and/or symptomology of the disease, in a patient, comprising administering to the patient a therapeutically effective amount of a compound of any one of embodiments 2 to 16, or the composition of embodiment 17.

Embodiment 20. A method of treating leukemia in a patient comprising administering to the patient a therapeutically effective amount of the compound of any one of embodiments 2 to 16, or the composition of embodiment 17, wherein the leukemia is chronic myeloid leukemia (CML), acute myeloid leukemia (AML), or acute lymphoblastic leukemia (ALL).

Embodiment 21. The method of embodiment 20, wherein the leukemia is CML or ALL, and the method further comprising administering a therapeutically effective amount of a compound selected from imatinib, nilotinib, dasatinib, bosutinib, ponatinib and bafetinib.

Embodiment 22. The method of embodiment 20 or 21, wherein the CML is resistant to standard-of-care treatment such as treatment with one or more of imatinib, nilotinib, and dasatinib.

Embodiment 23. The method of embodiment 20 or 21, wherein the AML is secondary AML, which develops after myelodysplastic syndromes (MDS) or myeloproliferative neo-plasms (MPN).

Embodiment 24. A compound of formula (I) or (Ia):

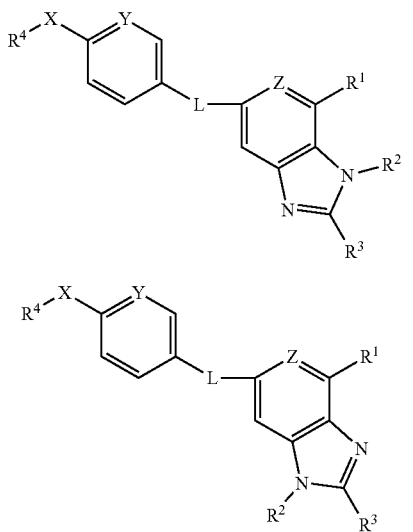

or a tautomer thereof, or a pharmaceutically acceptable salt of any of the foregoing, wherein:

L is —NH—CO—, —CO—NH—, —NH—SO$_2$—, or —SO$_2$—NH—;

$R^1$ is optionally substituted $C_6$-$C_{10}$ aryl, optionally substituted 5-10 membered heteroaryl, optionally substituted 4-10 membered heterocycle, C(O)NR$^6$R$^7$, S(O)$_2$NR$^6$R$^7$, NR$^6$COR$^7$, NR$^6$SO$_2$R$^7$, or C(O)OR$^6$;

$R^2$ is H, optionally substituted $C_1$-$C_6$ alkyl, optionally substituted $C_3$-$C_8$ cycloalkyl, optionally substituted 4-10 membered heterocycloalkyl, optionally substituted $C_2$-$C_6$ alkenyl, optionally substituted $C_2$-$C_6$ alkynyl, optionally substituted $C_6$-$C_{10}$ aryl, or optionally substituted 5-10 membered heteroaryl;

$R^3$ is H, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, optionally substituted heteroaryl, OR$^6$, or NR$^6$R$^7$;

or $R^2$ and $R^3$ together with the intervening atoms form optionally substituted $C_3$-$C_8$ cycloalkyl or optionally substituted 4-10 membered heterocycloalkyl;

$R^4$ is optionally substituted $C_1$-$C_6$ alkyl, optionally substituted $C_2$-$C_6$ alkenyl, or optionally substituted $C_2$-$C_6$ alkynyl;

X is O or S;

Y is CH, C—($C_1$-$C_2$ alkyl), C-halo or N;

Z is CR$^5$ or N;

$R^5$ is H or halogen;

$R^6$ is H, optionally substituted $C_1$-$C_6$ alkyl, optionally substituted $C_3$-$C_8$ cycloalkyl, optionally substituted 4-10 membered heterocycloalkyl, optionally substituted $C_6$-$C_{10}$ aryl, or optionally substituted 5-10 membered heteroaryl; and $R^7$ is H, optionally substituted $C_1$-$C_6$ alkyl, optionally substituted $C_3$-$C_8$ cycloalkyl, optionally substituted 4-10 membered heterocycloalkyl, optionally substituted $C_6$-$C_{10}$ aryl, or optionally substituted 5-10 membered heteroaryl;

or $R^6$ and $R^7$ together with the nitrogen to which they are attached form an optionally substituted 4-7 membered heterocycle, provided that the compound is other than (i) 1H-Benzimidazole-7-carboxylic acid, 5-[[(4-methoxyphenyl)sulfonyl]amino]-1-methyl- or (ii) 1H-Benzimidazole-7-carboxylic acid, 5-[[(4-ethoxy phenyl)sulfonyl]amino]-1-methyl-.

Embodiment 25. The compound of embodiment 24, or a pharmaceutically acceptable salt thereof, wherein:

$R^1$ is $C_6$-$C_{10}$ aryl, 5-10 membered heteroaryl, or 4-10 membered heterocycle, each of which is optionally substituted by 1-3 substituents selected from the group consisting of halogen, cyano, hydroxyl, $C_1$-$C_6$ alkoxy, $C_1$-$C_6$ alkyl, and $C_3$-$C_6$ cycloalkyl;

$R^2$ is $C_1$-$C_6$ alkyl, $C_3$-$C_8$ cycloalkyl, 4-10 membered heterocycloalkyl, $C_2$-$C_6$ alkenyl, $C_2$-$C_6$ alkynyl, $C_6$-$C_{10}$ aryl, or 5-10 membered heteroaryl, each of which is optionally substituted by 1-3 substituents selected from the group consisting of halogen, hydroxyl, $C_1$-$C_6$ alkoxy, $C_1$-$C_6$ alkyl, $C_3$-$C_6$ cycloalkyl, 4- to 6-membered heterocyclyl, cyano, oxo, —C(O)NH($C_1$-$C_6$ alkyl), and —C(O)NH($C_3$-$C_6$ cycloalkyl);

$R^3$ is $C_1$-$C_6$ alkyl, $C_2$-$C_6$ alkenyl, $C_2$-$C_6$ alkynyl, $C_3$-$C_6$ cycloalkyl, 4- to 6-membered heterocycloalkyl, $C_6$-$C_{10}$ aryl, or 5- to 10-membered heteroaryl, each of which is optionally substituted by 1-3 substituents selected from the group consisting of halogen, hydroxyl, and $C_1$-$C_6$ alkyl; or $R^2$ and $R^3$ together with the intervening atoms form $C_3$-$C_8$ cycloalkyl or 4-10 membered heterocycloalkyl, each of which is optionally substituted by 1-3 substituents selected from the group consisting of $C_1$-$C_6$ alkyl, hydroxyl, $C_1$-$C_6$ alkyl-OH, —C(O)($C_1$-$C_6$ alkyl), and oxo;

$R^4$ is $C_1$-$C_6$ alkyl, $C_2$-$C_6$ alkenyl, or $C_2$-$C_6$ alkynyl, each of which is optionally substituted by 1-3 halogens;

$R^6$ is $C_1$-$C_6$ alkyl, $C_3$-$C_8$ cycloalkyl, 4-10 membered heterocycloalkyl, $C_6$-$C_{10}$ aryl, or 5-10 membered heteroaryl, each of which is optionally substituted by 1-3 substituents selected from the group consisting of halogen, hydroxyl, and $C_1$-$C_6$ alkyl; and is $C_1$-$C_6$ alkyl, $C_3$-$C_8$ cycloalkyl, 4-10 membered heterocycloalkyl, $C_6$-$C_{10}$ aryl, or 5-10 membered heteroaryl, each of which is optionally substituted by 1-3 substituents selected from the group consisting of halogen, hydroxyl, and $C_1$-$C_6$ alkyl;

or $R^6$ and $R^7$ together with the nitrogen to which they are attached form 4-7 membered heterocycle optionally substituted by 1-3 substituents selected from the group consisting of halogen, hydroxyl, and $C_1$-$C_6$ alkyl.

Embodiment 26. The compound of embodiment 24 or 25, or a pharmaceutically acceptable salt thereof, which is of formula (IA-1):

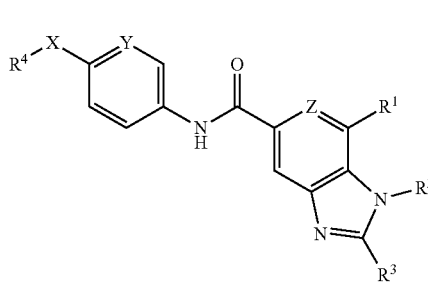

(IA-1)

Embodiment 27. The compound of embodiment 26, or a pharmaceutically acceptable salt thereof, wherein the compound is selected from formula (IIA)-(IIH):

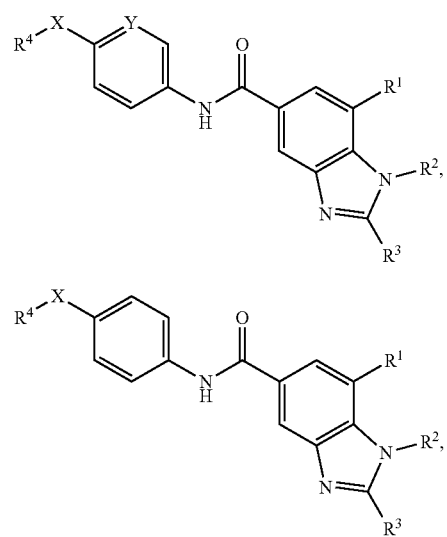

(IIA)

(IIB)

(IIC)

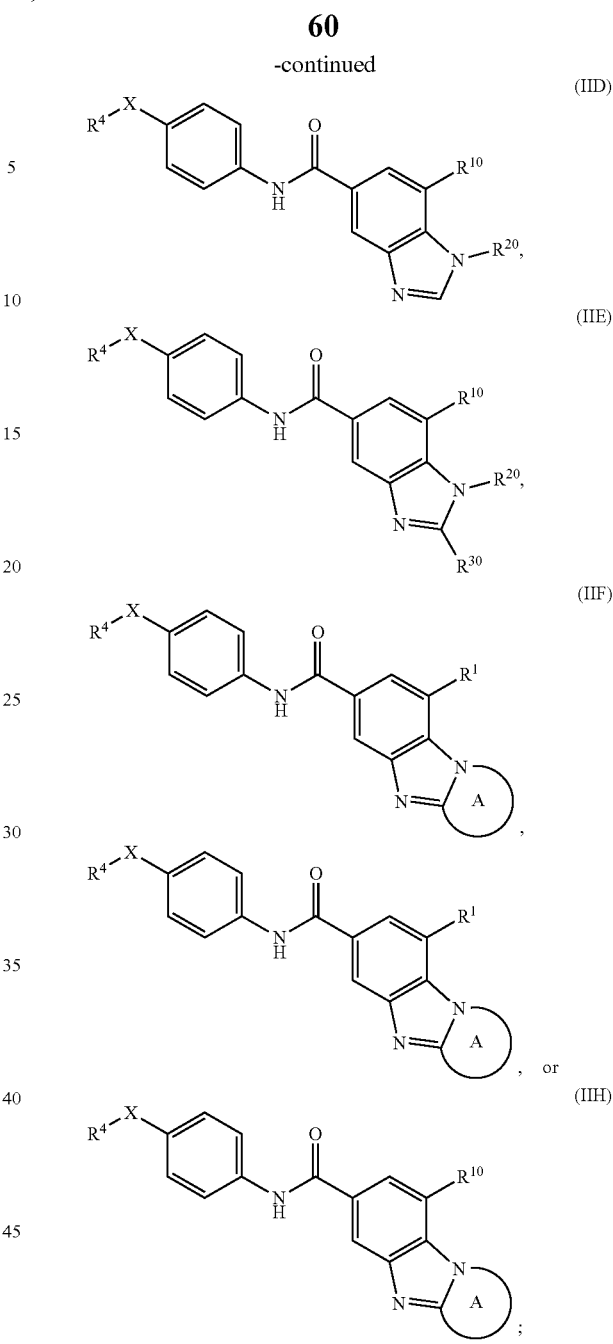

(IID)

(IIE)

(IIF)

(IIG)

(IIH)

wherein:

$R^{10}$ is an optionally substituted 5-6 membered heteroaryl;

$R^{20}$ is optionally substituted $C_1$-$C_3$ alkyl, optionally substituted $C_3$-$C_4$ cycloalkyl, or optionally substituted 4-6 membered heterocycloalkyl;

$R^{30}$ is H, optionally substituted $C_1$-$C_3$ alkyl, optionally substituted $C_3$-$C_4$ cycloalkyl, or optionally substituted 5-6 membered heterocycloalkyl; and Ring A is optionally substituted 5-6 membered heterocycloalkyl.

Embodiment 28. The compound of embodiment 27, or a pharmaceutically acceptable salt thereof, wherein:

$R^{10}$ is 5-6 membered heteroaryl optionally substituted by 1-3 substituents selected from the group consisting of halogen, cyano, hydroxyl, $C_1$-$C_6$ alkoxy, $C_1$-$C_6$ alkyl, and $C_3$-$C_6$ cycloalkyl;

$R^{20}$ is $C_1$-$C_3$ alkyl, $C_3$-$C_4$ cycloalkyl, or 4-6 membered heterocycloalkyl, each of which is optionally substituted by 1-3 substituents selected from the group consisting of halogen, hydroxyl, $C_1$-$C_6$ alkoxy, $C_1$-$C_6$ alkyl, $C_3$-$C_6$ cycloalkyl, 4- to 6-membered heterocyclyl, cyano, oxo, —C(O)NH($C_1$-$C_6$ alkyl), and —C(O)NH($C_3$-$C_6$ cycloalkyl);

$R^{30}$ is $C_1$-$C_3$ alkyl, $C_3$-$C_4$ cycloalkyl, or 5-6 membered heterocycloalkyl, each of which is optionally substituted by 1-3 substituents selected from the group consisting of halogen, hydroxyl, and $C_1$-$C_6$ alkyl;

Ring A is 5-6 membered heterocycloalkyl optionally substituted by 1-3 substituents selected from the group consisting of $C_1$-$C_6$ alkyl, hydroxyl, $C_1$-$C_6$ alkyl-OH, —C(O)($C_1$-$C_6$ alkyl), and oxo.

Embodiment 29. The compound of any one of embodiments 26-28, or a pharmaceutically acceptable salt thereof, wherein:

X is O.

Embodiment 30. The compound of any one of embodiments 26-29, or a pharmaceutically acceptable salt thereof, wherein:

$R^1$ is 5-10 membered heteroaryl or 4-10 membered heterocycle, each of which is optionally substituted by 1-3 substituents selected from the group consisting of halogen, cyano, hydroxyl, $C_1$-$C_6$ alkoxy, $C_1$-$C_6$ alkyl, and $C_3$-$C_6$ cycloalkyl.

Embodiment 31. The compound of any one of embodiments 26-29, or a pharmaceutically acceptable salt thereof, wherein:

$R^1$ is —CONH(cyclopropyl), —CONH$_2$, —CONHMe,

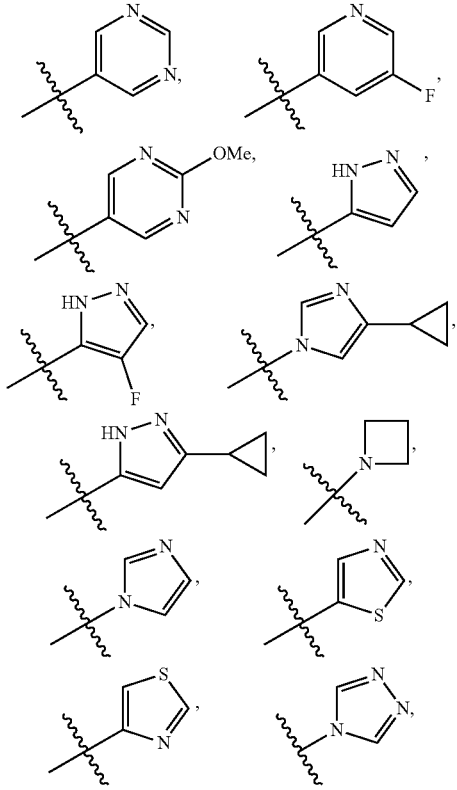

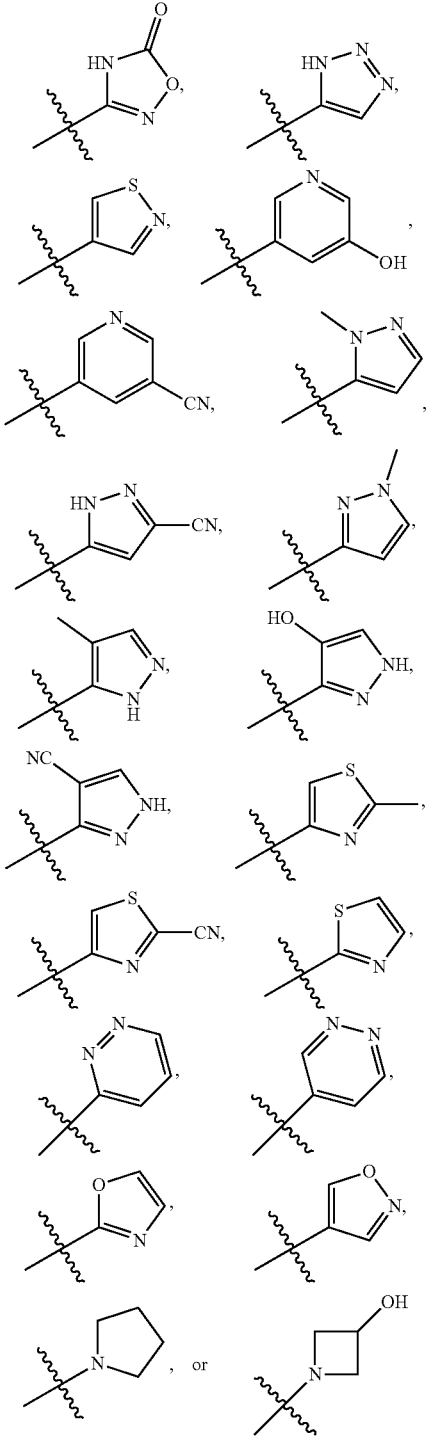

Embodiment 32. The compound of any one of embodiments 26-30, or a pharmaceutically acceptable salt thereof, wherein:

$R^1$ is pyrimidinyl or pyrazolyl, each of which is optionally substituted by 1-3 substituents selected from the group consisting of halogen, cyano, hydroxyl, $C_1$-$C_6$ alkoxy, $C_1$-$C_6$ alkyl, and $C_3$-$C_6$ cycloalkyl.

Embodiment 33. The compound of any one of embodiments 26-32, or a pharmaceutically acceptable salt thereof, wherein:

$R^2$ is $C_1$-$C_3$ alkyl or $C_3$-$C_4$ cycloalkyl, each of which is optionally substituted by 1-3 substituents selected from the group consisting of halogen, hydroxyl, $C_1$-$C_6$ alkoxy, $C_1$-$C_6$ alkyl, $C_3$-$C_6$ cycloalkyl, 4- to 6-membered heterocyclyl, cyano, oxo, —C(O)NH($C_1$-$C_6$ alkyl), and —C(O)NH($C_3$-$C_6$ cycloalkyl).

Embodiment 34. The compound of any one of embodiments 26-32, or a pharmaceutically acceptable salt thereof, wherein:

$R^2$ is methyl, ethyl, isopropyl, tertiary butyl, cyclopropyl, cyclobutyl, cyclopentyl, tetrahydrofuranyl, tetrahydropyranyl,

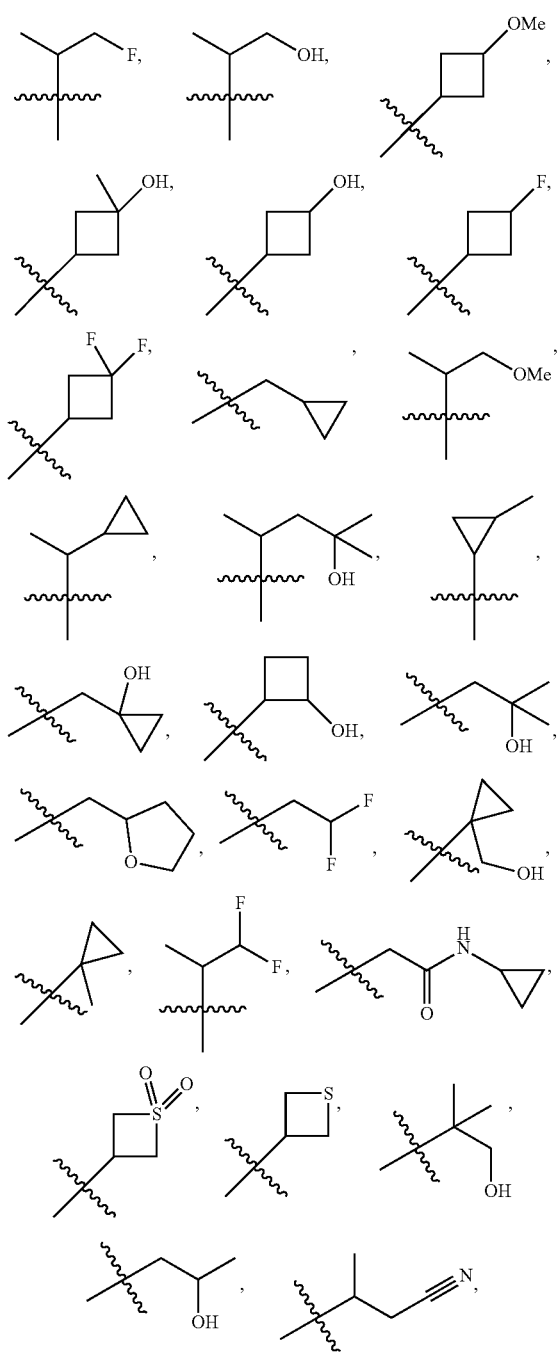

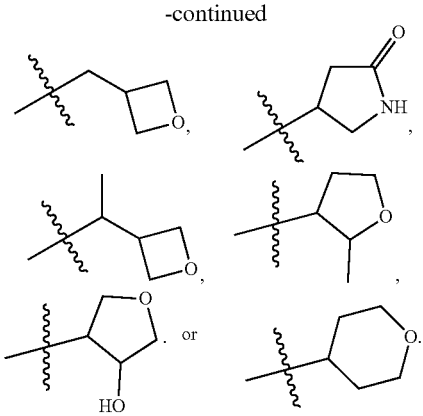

Embodiment 35. The compound of any one of embodiments 26-34, or a pharmaceutically acceptable salt thereof, wherein:

$R^3$ is H, methyl, isopropyl, difluoromethyl, hydroxyethyl, cyclopropyl, cyclobutyl, —C(Me)$_2$OH, —CH(Me)OH, methoxymethyl, hydroxymethyl, methoxy, ethoxy, —CH$_2$CH$_2$OH, or tetrahydropyranyl.

Embodiment 36. The compound of any one of embodiments 26-32, or a pharmaceutically acceptable salt thereof, wherein $R^2$ and $R^3$ together form:

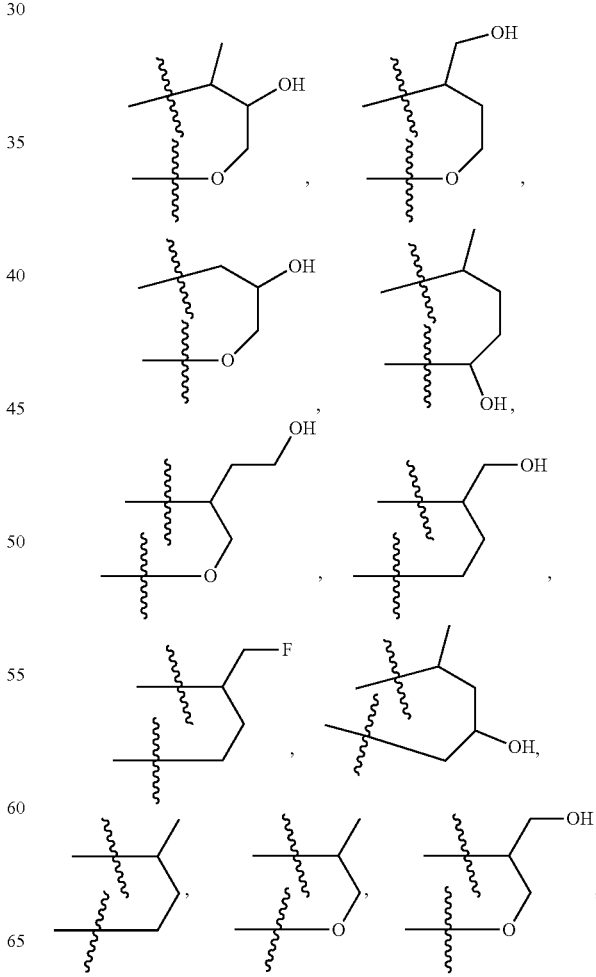

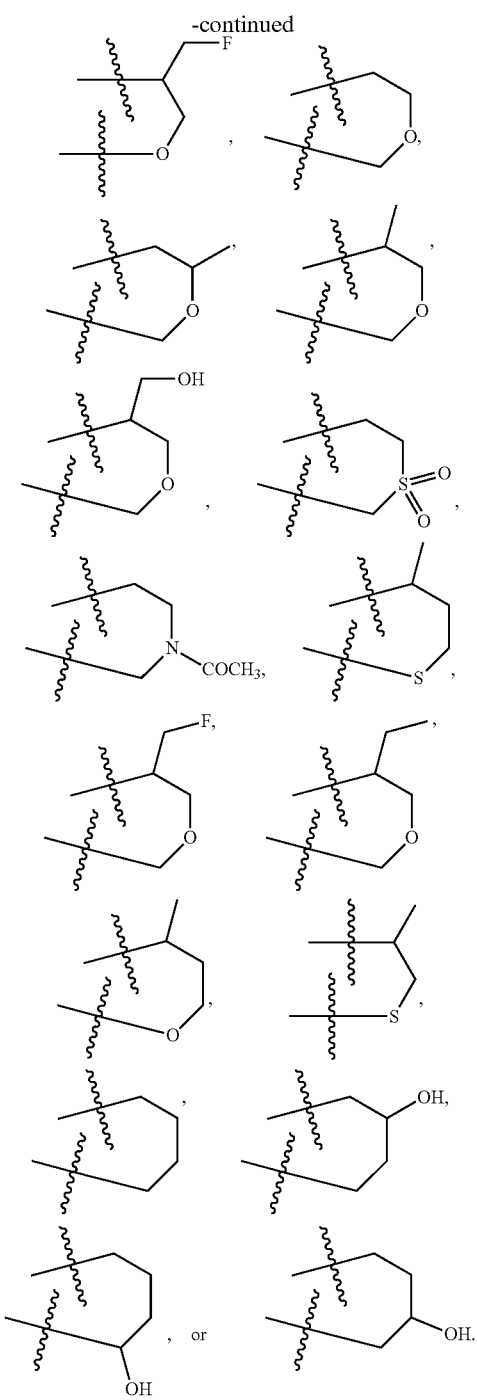

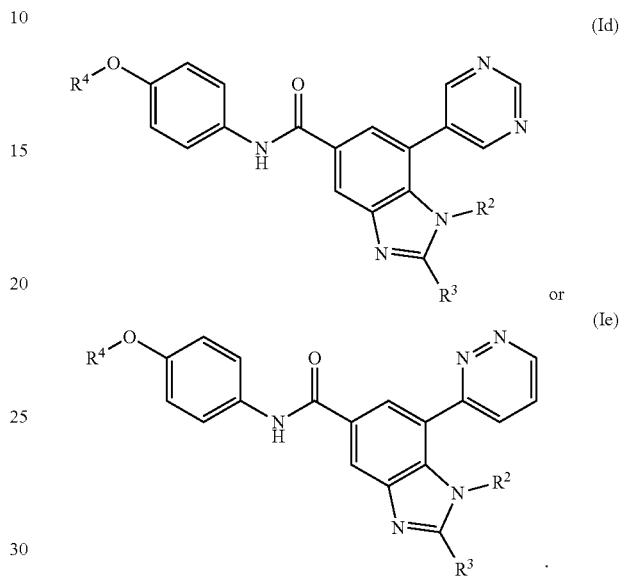

Embodiment 37. The compound of any one of embodiments 26-36, or a pharmaceutically acceptable salt thereof, wherein:
R$^4$ is C$_1$-C$_3$ alkyl optionally substituted with 1-3 halo substituents.

Embodiment 38. The compound of any one of embodiments 26-37, or a pharmaceutically acceptable salt thereof, wherein:
R$^4$ is CF$_3$ or CF$_2$Cl.

Embodiment 39. The compound of any one of embodiments 26-38, or a pharmaceutically acceptable salt thereof, wherein:
R$^5$ is H.

Embodiment 40. The compound of any one of embodiments 26-39, or a pharmaceutically acceptable salt thereof, wherein:
Y is CH.

Embodiment 41. The compound of embodiment 26, or a pharmaceutically acceptable salt thereof, which is of formula (Id) or (Ie):

Embodiment 42. A compound selected from Examples 1-232, or a pharmaceutically acceptable salt thereof.

Embodiment 43. A composition comprising the compound of any one of embodiments 26-42, or a pharmaceutically acceptable salt thereof, and at least one pharmaceutically acceptable excipient.

Embodiment 44. A method of inhibiting tyrosine kinase enzymatic activity of a protein selected from the group consisting of Abelson protein (ABL1), Abelson-related protein (ABL2), and a chimeric protein BCR-ABL1, comprising contacting an effective amount of the compound of any one of embodiments 26-42, or a pharmaceutically acceptable salt thereof, or the composition of embodiment 43, to the protein.

Embodiment 45. A method of treating a disease, wherein modulation of BCR-ABL1 activity prevents, inhibits, or ameliorates the pathology and/or symptomology of the disease, in a patient, comprising administering to the patient a therapeutically effective amount of the compound of any one of embodiments 26-42, or a pharmaceutically acceptable salt thereof, or the composition of embodiment 43.

Embodiment 46. A method of treating leukemia in a patient comprising administering to the patient a therapeutically effective amount of the compound of any one of embodiments 26-42, or a pharmaceutically acceptable salt thereof, or the composition of embodiment 43, wherein the leukemia is chronic myeloid leukemia (CML), acute myeloid leukemia (AML), or acute lymphoblastic leukemia (ALL).

Embodiment 47. The method of embodiment 46, wherein the leukemia is CML or ALL, and the method further comprises administering a therapeutically effective amount of a compound selected from the group consisting of imatinib, nilotinib, dasatinib, bosutinib, ponatinib and bafetinib.

Embodiment 48. The method of embodiment 46 or 47, wherein the CML is resistant to standard-of-care treatment.

Embodiment 49. The method of embodiment 48, wherein the CML is resistant to treatment with one or more of imatinib, nilotinib, and dasatinib.

Embodiment 50. The method of embodiment 46, wherein the AML is secondary AML, which develops after myelodysplastic syndromes (MDS) or myeloproliferative neoplasms (MPN).

EXAMPLES

The following abbreviations may be relevant for the application.

Abbreviations

Ac: acetyl
Bn: benzyl
Bu: butyl
Bz: benzoyl
CMC: carboxymethyl cellulose
DCM: dichloromethane
DIPEA: diisopropylethylamine
DMF: dimethylformamide
DMEDA: N,N'-Dimethylethylenediamine
DSC: N,N'-Disuccinimidyl carbonate or bis(2,5-dioxopyrrolidin-1-yl) carbonate
dppf: 1,1'-bis(diphenylphosphino)ferrocene
Et: ethyl
HATU: 1-[Bis(dimethylamino)methylene]-1H-1,2,3-triazolo[4,5-b]pyridinium 3-oxid hexafluorophosphate,
NBS: N-bromosuccinimide
PEG: polyethylene glycol
PMB: paramethoxybenzyl
Pr: propyl
Py: pyridine
rt: room temperature
TEA: triethylamine
TBDPS: tertiarybutyldiphenylsilyl
TBAF: tetrabutylammonium fluoride
THF: tetrahydrofuran
TMS: trimethylsilyl
TFA: trifluoroacetic acid
Ts: tosyl
Xphos: 2-dicyclohexylphosphino-2',4',6'-triisopropylbiphenyl Synthetic Examples Preparing Compounds of Formula (I): Synthetic Schemes As depicted in the Examples of Compounds of Formula (I), below, in certain exemplary embodiments, compounds of Formula (I) are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Scheme 1

-continued

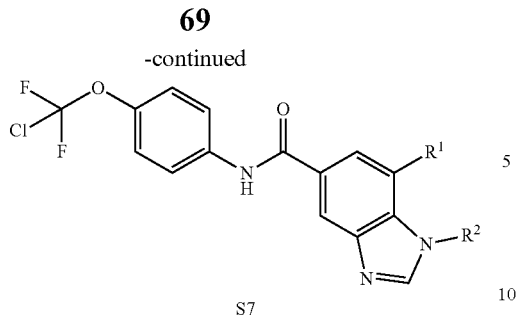

S7 wherein R¹ and R² are as defined for the compound of formula (I).

Compounds of formula (S7) may be prepared by general synthetic methods as shown in Scheme 1. Treatment of 1a with various primary amines (S1) in a suitable solvent such as ethanol with a base such as, but not limited to, triethylamine at a temperature from about room temperature to reflux and for a time varying from about 30 minutes to about 8 hours, can readily produce nitroaniline (S2). The phenylenediamine (S3) can be formed by reduction of nitroaniline (S2) using a reductant such as, but not limited to, iron in a solvent such as, but not limited to acetic acid at a temperature from about room temperature to reflux and for a time varying from about 1 hour. The cyclization of phenylenediamine (S3) to benzimidazole (S4) can be carried out using a reagent such as, but not limited to, trimethyl orthoformate in the presence of an acid such as, but not limited to p-TsOH at a temperature from about room temperature to 100° C. and for a time varying from about 10 min to 1 hour. Compounds of formula (S5) can be prepared from the bromide (S4) upon treatment with aryl, heteroaryl or heterocyclic boronic acids or boronate esters under palladium catalyst conditions such as, but not limited to, [1,1'-bis(diphenylphosphino)ferrocene] dichloropalladium(II) in the presence of water and an inorganic base such as, but not limited to, sodium carbonate, potassium carbonate, or potassium phosphate in an organic solvent such as, but not limited to, 1,4-dioxane at an elevated temperature. Treatment of the ester (S5) with hydroxide sources such as, but not limited to, lithium hydroxide in the presence of water and organic solvents such as, but not limited to, methanol and/or tetrahydrofuran yields carboxylic acid of formula (S6). Reaction of carboxylic acid (S6) with a coupling reagent such as, but not limited to, 1-[bis(dimethylamino)methylene]-1H-1,2,3-triazolo[4,5-b]pyridinium 3-oxide hexafluorophosphate, a base such as, but not limited to, diisopropylethylamine, and amine (1h) provides amide of formula (S7).

Scheme 2

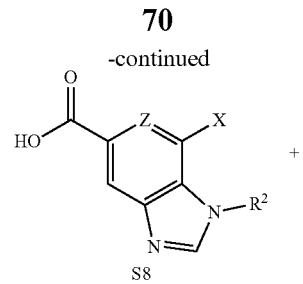

S5
X = halogen
Z = CH, N

-continued

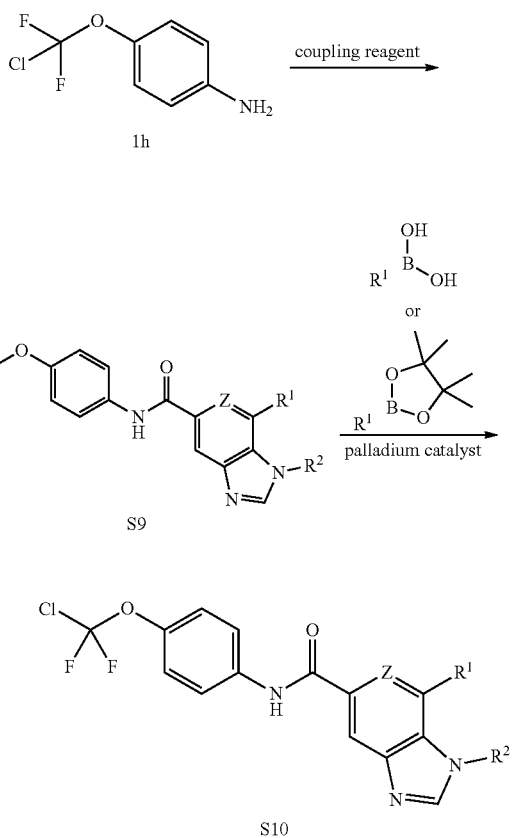

wherein R¹ and R² are as defined for the compound of formula (I); X is halogen; and Z is CH or N.

Compounds of formula (S10) may be prepared by general synthetic methods as shown in Scheme 2. Treatment of the ester (S5) with hydroxide sources such as, but not limited to, lithium hydroxide in the presence of water and organic solvents such as, but not limited to, methanol and/or tetrahydrofuran yields carboxylic acid of formula (S8). Reaction of carboxylic acid (S8) with a coupling reagent such as, but not limited to, 1-[bis(dimethylamino)methylene]-1H-1,2,3-triazolo[4,5-b]pyridinium 3-oxide hexafluorophosphate, a base such as, but not limited to, diisopropylethylamine, and amine (1h) provides amide of formula (S9). Compounds of formula (S10) can be prepared from the halide (S9) upon treatment with aryl, heteroaryl or heterocyclic boronic acids or boronate esters under palladium catalyst conditions such as, but not limited to, [1,1'-bis(diphenylphosphino)ferrocene] dichloropalladium(II) in the presence of water and an inorganic base such as, but not limited to, sodium carbonate, potassium carbonate, or potassium phosphate in an organic solvent such as, but not limited to, 1,4-dioxane at an elevated temperature.

Scheme 3

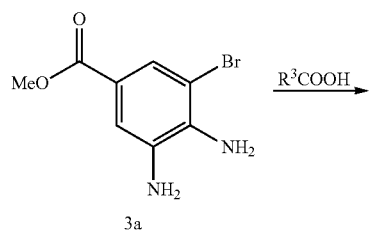

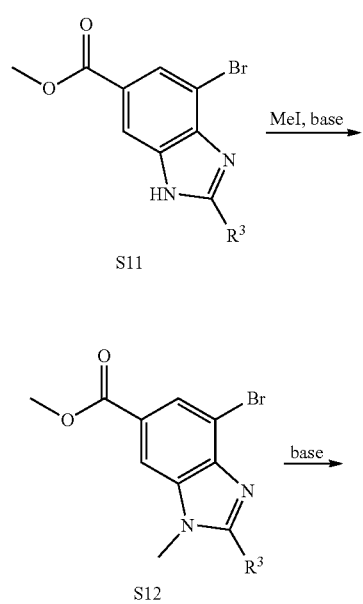

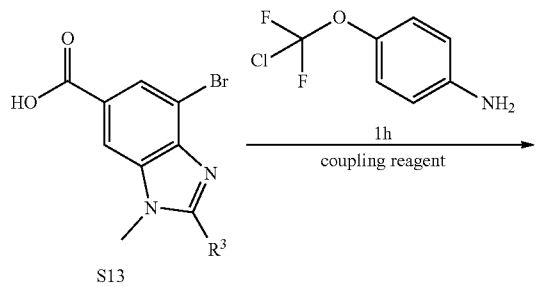

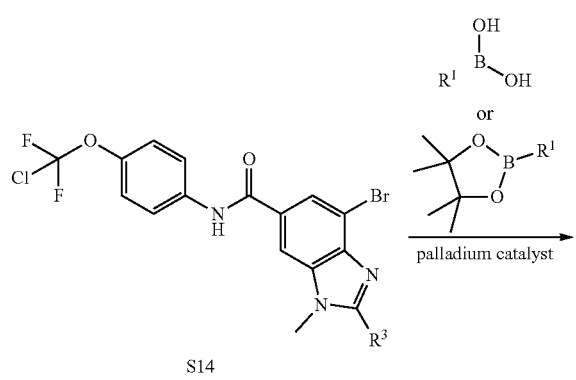

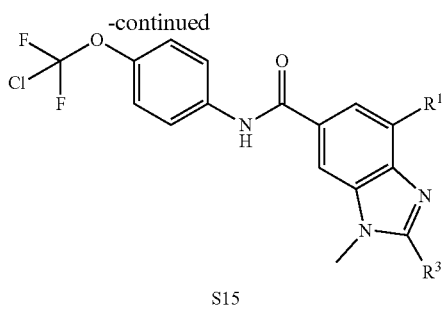

wherein $R^1$ and $R^3$ are as defined for the compound of formula (I).

Compounds of formula (S15) may be prepared by general synthetic methods as shown in Scheme 3. Compound (3a) can be treated with various carboxylic acids at a temperature from about 80° C. to 130° C. and for a time varying from about 1 hour to 2 hours to produce benzimidazoles of formula (S11). Treatment of benzimidazole (S11) with methyliodide in the presence of a base such as, but not limited to, potassium carbonate in an organic solvent such as, but not limited to, N,N-dimethylformamide at a temperature at about 50° C. and for a time for about 3 hours to produce benzimidazole (S12). Treatment of the ester (S12) with hydroxide sources such as, but not limited to, lithium hydroxide in the presence of water and organic solvents such as, but not limited to, methanol and/or tetrahydrofuran yields carboxylic acid of formula (S13). Reaction of carboxylic acid (S13) with a coupling reagent such as, but not limited to, [1-bis(dimethylamino)methylene]-1H-1,2,3-triazolo[4,5-b]pyridinium 3-oxide hexafluorophosphate, a base such as, but not limited to, diisopropylethylamine, and amine (1h) in an organic solvent such as, but not limited to, N,N-dimethylformamide at about room temperature and for a time of about 30 minutes provides amide of formula (S14). Compounds of formula (S15) can be prepared from the bromide (S14) upon treatment with aryl, heteroaryl or heterocyclic boronic acids or boronate esters under palladium catalyst conditions such as, but not limited to, [1,1'-bis(diphenylphosphino)ferrocene] dichloropalladium(II) in the presence of water and an inorganic base such as, but not limited to, sodium carbonate, potassium carbonate, or potassium phosphate in an organic solvent such as, but not limited to, 1,4-dioxane at an elevated temperature.

Scheme 4

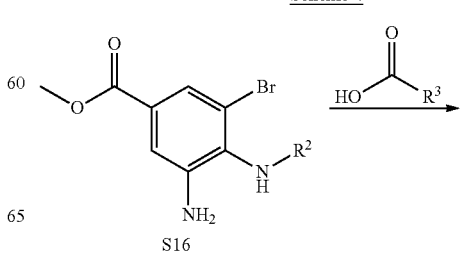

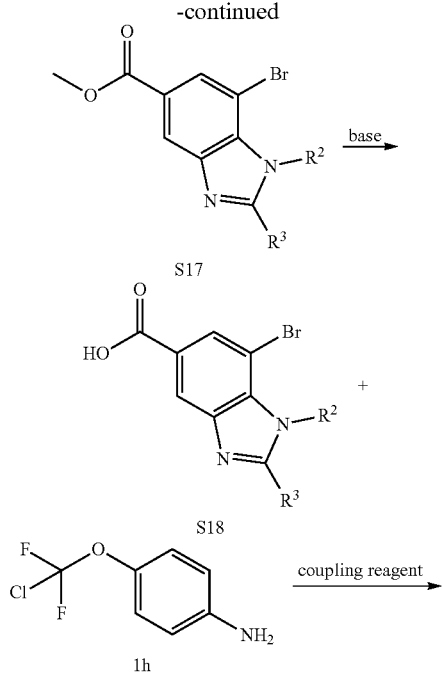

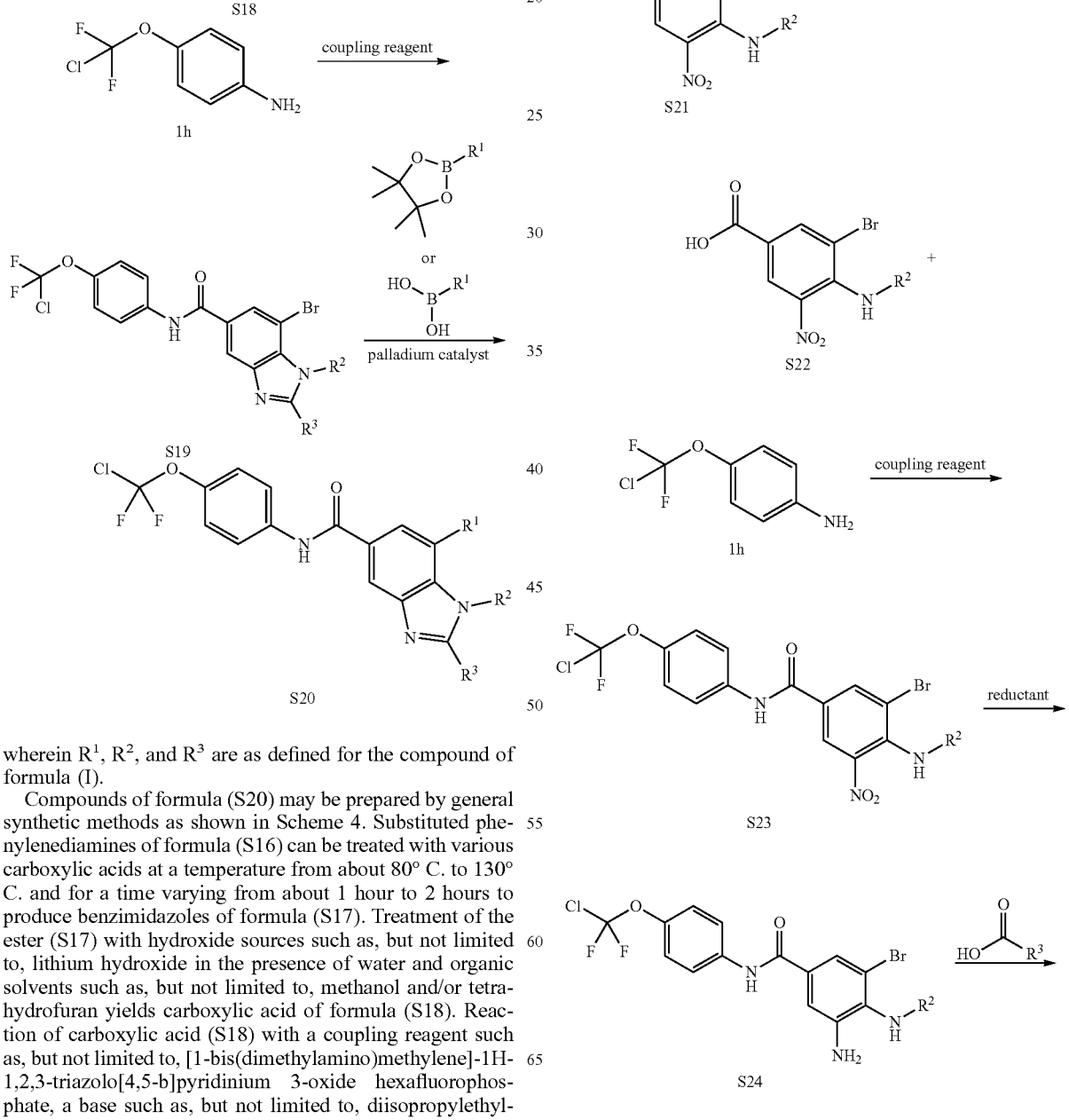

wherein $R^1$, $R^2$, and $R^3$ are as defined for the compound of formula (I).

Compounds of formula (S20) may be prepared by general synthetic methods as shown in Scheme 4. Substituted phenylenediamines of formula (S16) can be treated with various carboxylic acids at a temperature from about 80° C. to 130° C. and for a time varying from about 1 hour to 2 hours to produce benzimidazoles of formula (S17). Treatment of the ester (S17) with hydroxide sources such as, but not limited to, lithium hydroxide in the presence of water and organic solvents such as, but not limited to, methanol and/or tetrahydrofuran yields carboxylic acid of formula (S18). Reaction of carboxylic acid (S18) with a coupling reagent such as, but not limited to, [1-bis(dimethylamino)methylene]-1H-1,2,3-triazolo[4,5-b]pyridinium 3-oxide hexafluorophosphate, a base such as, but not limited to, diisopropylethylamine, and amine (1h) in an organic solvent such as, but not limited to, N,N-dimethylformamide at about room temperature and for a time of about 30 minutes provides amide of formula (S19). Compounds of formula (S20) can be prepared from the bromide (S19) upon treatment with aryl, heteroaryl or heterocyclic boronic acids or boronate esters under palladium catalyst conditions such as, but not limited to, [1,1'-bis(diphenylphosphino)ferrocene] dichloropalladium(II) in the presence of water and an inorganic base such as, but not limited to, sodium carbonate, potassium carbonate, or potassium phosphate in an organic solvent such as, but not limited to, 1,4-dioxane at an elevated temperature.

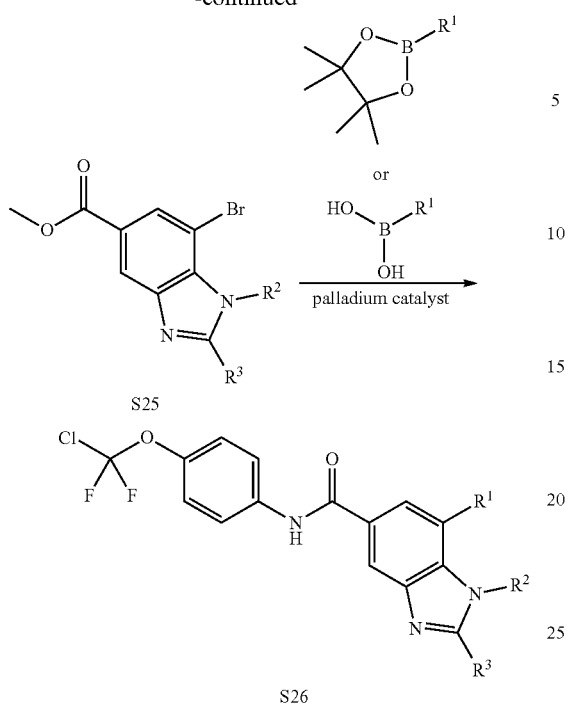

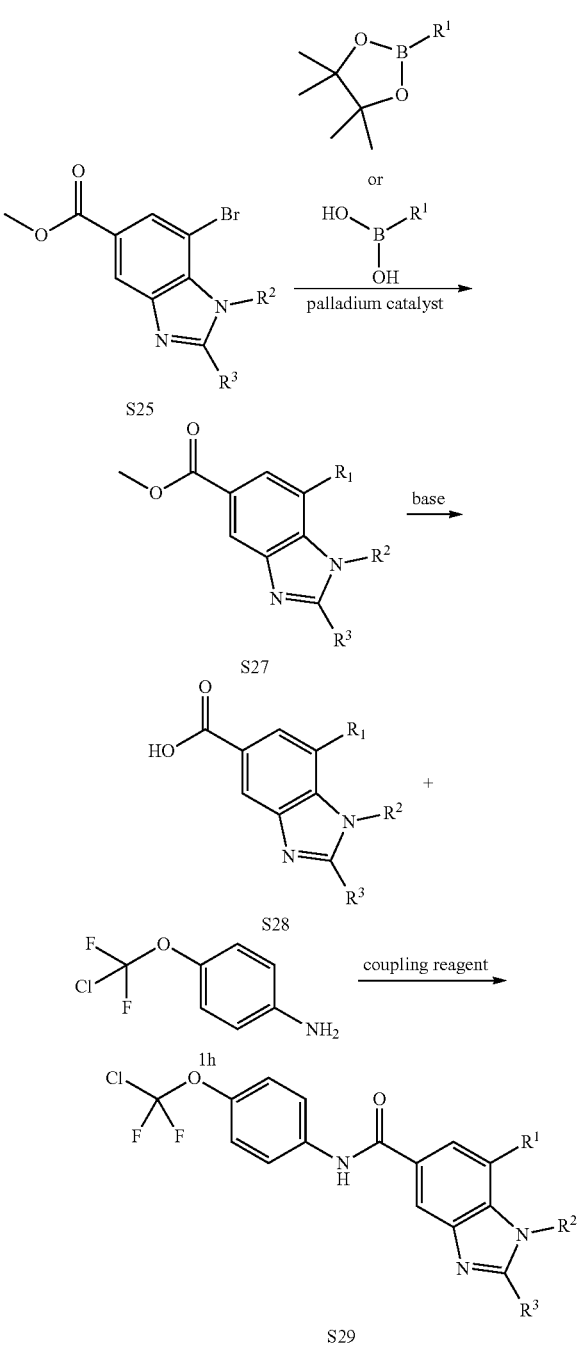

Scheme 6 wherein $R^1$, $R^2$, and $R^3$ are as defined for the compound of formula (I).

Compounds of formula (S26) may be prepared by general synthetic methods as shown in Scheme 5. Treatment of the ester (S21) with hydroxide sources such as, but not limited to, lithium hydroxide in the presence of water and organic solvents such as, but not limited to, methanol and/or tetrahydrofuran yields carboxylic acid of formula (S22). Reaction of carboxylic acid (S22) with a coupling reagent such as, but not limited to, 1-[bis(dimethylamino)methylene]-1H-1,2,3-triazolo[4,5-b]pyridinium 3-oxide hexafluorophosphate, a base such as, but not limited to, diisopropylethylamine, and amine (1h) in an organic solvent such as, but not limited to, N,N-dimethylformamide at a temperature from room temperature to 50° C. and for a time of about 2 hours provides amide of formula (S23). The phenylenediamine (S24) can be formed by reduction nitroaniline (S23) using a reductant such as, but not limited to, iron in a solvent such as, but not limited to acetic acid at a temperature from about 35° C. and for a time varying from about 3 hours. Substituted phenylenediamines of formula (S24) can be treated with various carboxylic acids at a temperature from about 80° C. to 130° C. and for a time varying from about 1 hour to 2 hours to produce benzimidazoles of formula (S25). Compounds of formula (S26) can be prepared from the bromide (S25) upon treatment with aryl, heteroaryl or heterocyclic boronic acids or boronate esters under palladium catalyst conditions such as, but not limited to, [1,1′-bis (diphenylphosphino)ferrocene] dichloropalladium(II) in the presence of water and an inorganic base such as, but not limited to, sodium carbonate, potassium carbonate, or potassium phosphate in an organic solvent such as, but not limited to, 1,4-dioxane at an elevated temperature.

wherein $R^1$, $R^2$, and $R^3$ are as defined for the compound of formula (I).

Compounds of formula (S29) may be prepared by general synthetic methods as shown in Scheme 6. Compounds of formula (S27) can be prepared from the bromide (S25) upon treatment with aryl, heteroaryl or heterocyclic boronic acids or boronate esters under palladium catalyst conditions such as, but not limited to, [1,1′-bis(diphenylphosphino)ferrocene] dichloropalladium(II) in the presence of water and an inorganic base such as, but not limited to, sodium carbonate, potassium carbonate, or potassium phosphate in an organic solvent such as, but not limited to, 1,4-dioxane at an elevated temperature. Treatment of the ester (S27) with hydroxide sources such as, but not limited to, lithium hydroxide in the presence of water and organic solvents such as, but not limited to, methanol and/or tetrahydrofuran yields carboxylic acid of formula (S28). Reaction of carboxylic acid (S28) with a coupling reagent such as, but not limited to, 1-[bis(dimethylamino)methylene]-1H-1,2,3-triazolo[4,5-b]pyridinium 3-oxide hexafluorophosphate, a base such as, but not limited to, diisopropylethylamine, and amine (1h) in an organic solvent such as, but not limited to, N,N-dimethylformamide at a temperature from room temperature to 50° C. and for a time of about 2 hours provides amide of formula (S29).

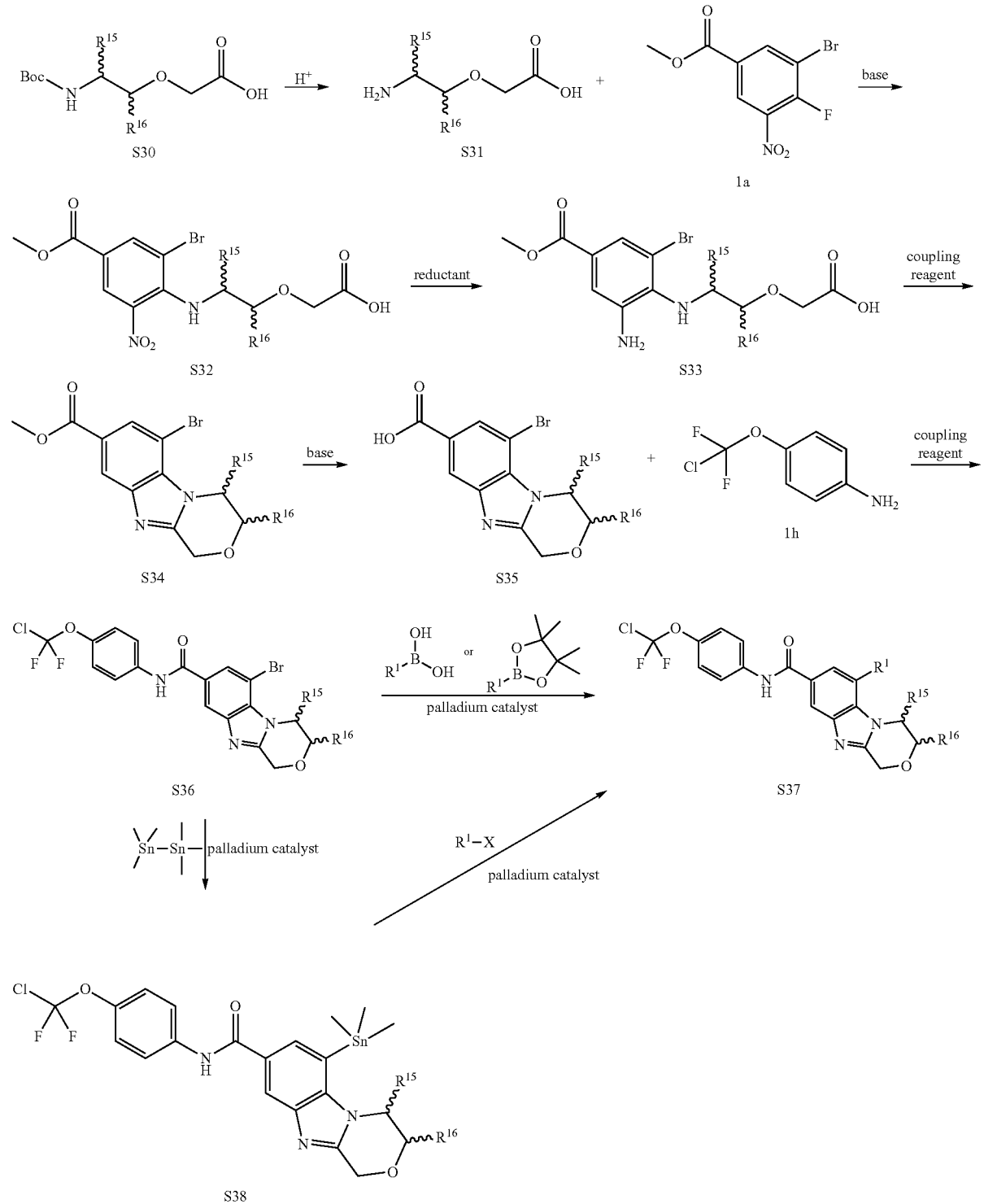

Scheme 7 wherein R¹ is as defined for the compound of formula (I); X is a halide; and as used herein, R¹⁵ and R¹⁶ are optional substituents.

Compounds of formula (S38) may be prepared by general synthetic methods as shown in Scheme 7. In the presence of an acid such as, but not limited to, hydrochloric acid in an organic solvent such as, but not limited to, ethyl acetate at a temperature at about 15° C. from a time of about 2 hours, compounds of formula (S30) can be converted to compounds of formula (S31). Treatment of amine (S31) with (1a) in a suitable solvent such as ethanol with a base such as, but not limited to, triethylamine at a temperature at about 15° C. and for a time of about 1 hour, can readily produce nitroaniline (S32). The phenylenediamine (S33) can be formed by reduction nitroaniline (S32) using a reductant such as, but not limited to, iron in a solvent such as, but not limited to acetic acid at a temperature from about room temperature to reflux and for a time varying from about 1 hour. Reaction of carboxylic acid (S33) with a coupling reagent such as, but not limited to, 1-[bis(dimethylamino)methylene]-1H-1,2,3-triazolo[4,5-b]pyridinium 3-oxide hexafluorophosphate, a base such as, but not limited to, diisopropylethylamine in an organic solvent such as, but not limited to, N,N-dimethylformamide at a temperature from about room temperature and for a time of about 16 hours provides benzimidazole of formula (S34). Treatment of the ester (S34) with hydroxide sources such as, but not limited to, lithium hydroxide in the presence of water and organic solvents such as, but not limited to, methanol and/or tetrahydrofuran yields carboxylic acid of formula (S35). Reaction of carboxylic acid (S35) with a coupling reagent such as, but not limited to, 1-[bis(dimethylamino)methylene]-1H-1,2,3-triazolo[4,5-b]pyridinium 3-oxide hexafluorophosphate, a base such as, but not limited to, pyridine, and amine (1h) in an organic solvent such as, but not limited to, N,N-dimethylformamide at a temperature at about 40° C. and for a time of about 6 hours provides amide of formula (S36). Compounds of formula (S37) can be prepared from the bromide (S36) upon treatment with aryl, heteroaryl or heterocyclic boronic acids or boronate esters under palladium catalyst conditions such as, but not limited to, [1,1'-bis(diphenylphosphino)ferrocene]dichloropalladium(II) in the presence of water and an inorganic base such as, but not limited to, sodium carbonate, potassium carbonate, or potassium phosphate in an organic solvent such as, but not limited to, 1,4-dioxane at an elevated temperature. Alternatively, compounds of formula (S37) can be prepared by Stille coupling. Bromide (S36) is converted to stannane (S38) under under palladium catalyst conditions such as, but not limited to, palladium tetrakis triphenylphosphine in an organic solvent such as, but not limited to, toluene at an elevated temperature. Stannane (S38) can be treated with various aryl or heteroaryl halides under under palladium catalyst conditions such as, but not limited to, palladium tetrakis triphenylphosphine in an organic solvent such as, but not limited to, DMSO at an elevated temperature.

Scheme 8

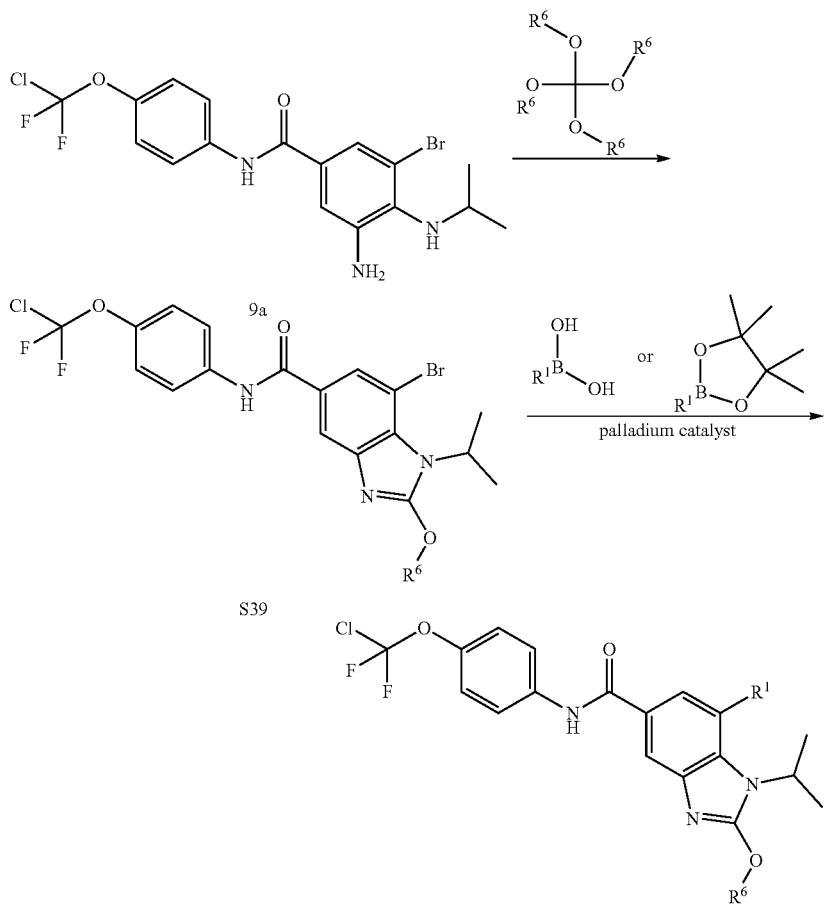

wherein R¹ and R⁶ are as defined for the compound of formula (I).

Compounds of formula (S40) may be prepared by general synthetic methods as shown in Scheme 8. Compound (S38) can be treated a tetramethoxy-alkane at a temperature at about 50° C. and for a time of about 16 hours can afford compounds of formula (S39). Compounds of formula (S40) can be prepared from the bromide (S39) upon treatment with aryl, heteroaryl or heterocyclic boronic acids or boronate esters under palladium catalyst conditions such as, but not limited to, [1,1'-bis(diphenylphosphino)ferrocene] dichloropalladium(II) in the presence of water and an inorganic base such as, but not limited to, sodium carbonate, potassium carbonate, or potassium phosphate in an organic solvent such as, but not limited to, 1,4-dioxane at an elevated temperature.

Scheme 10

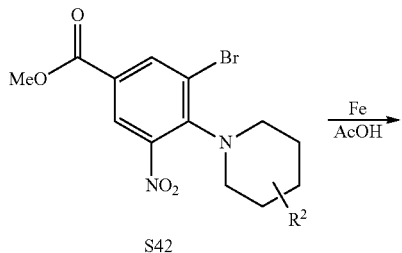

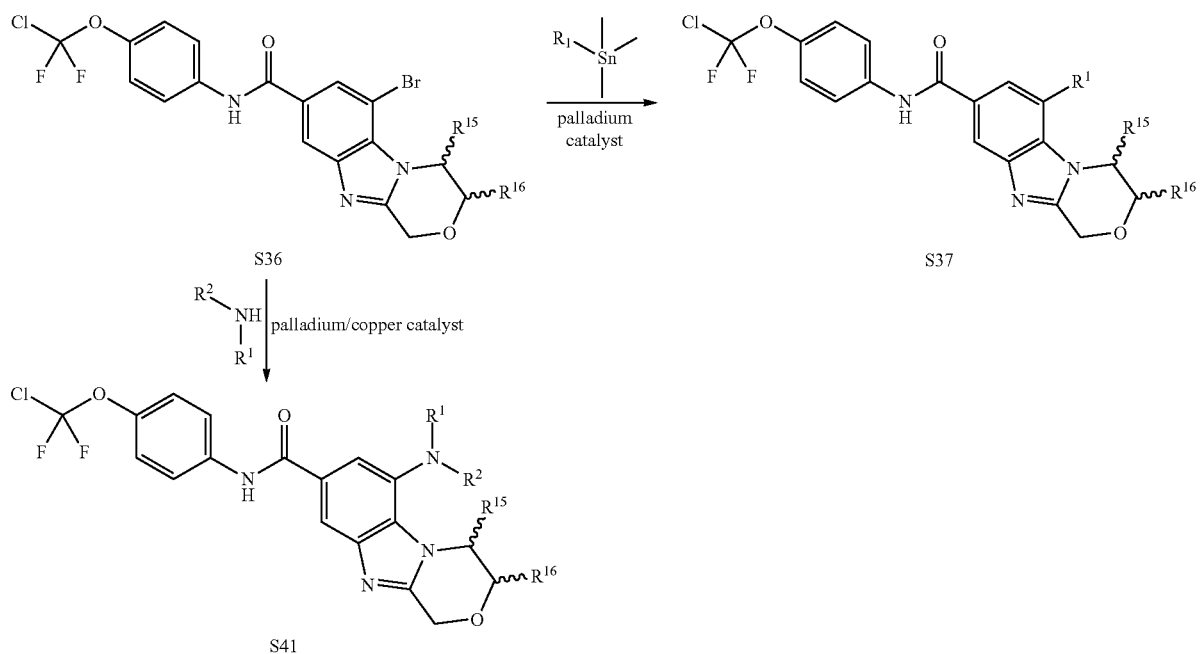

wherein R¹ and R² are as defined for the compound of formula (I); and R¹⁵ and R¹⁶ are optional substituents.

Compounds of formula (S37 and S41) may be prepared by general synthetic methods as shown in Scheme 9. Compound (S36) can be treated with various aryl and heteroaryl stannanes under palladium catalyst conditions such as, but not limited to, palladium tetrakis triphenylphosphine in an organic solvent such as, but not limited to, toluene at an elevated temperature to afford compound (S37). Additionally, bromide (S36) can be treated with various amines under palladium catalyst or copper conditions such as, but not limited to, [(2-di-cyclohexylphosphino-3,6-dimethoxy-2',4', 6'-triisopropyl-1,1'-biphenyl)-2-(2'-amino-1,1'-biphenyl)] palladium(II) methanesulfonate or (Bu₄NCuI₂)₂ in an organic solvent such as, but not limited to, tetrahydrofuran or 1,4-dioxane at an elevated temperature to afford compounds of formula (S41).

-continued

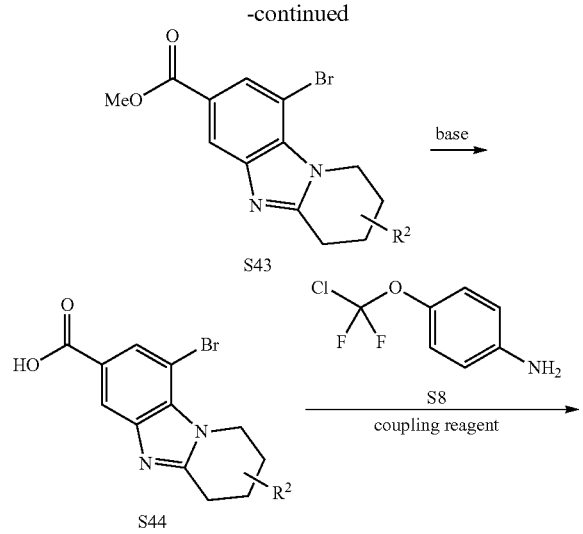

-continued

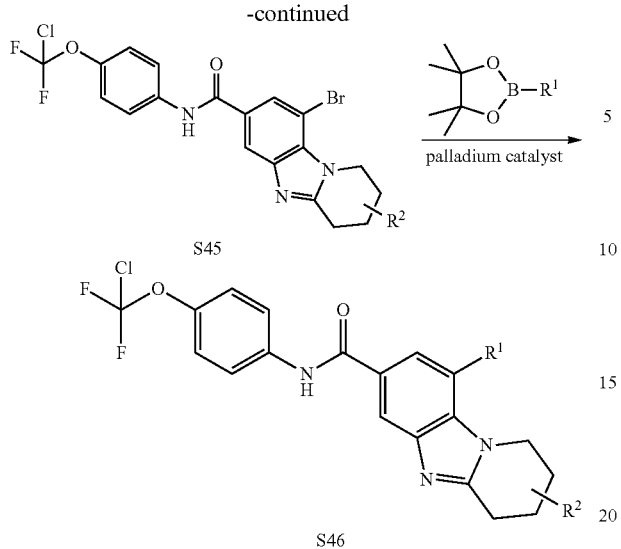

wherein R¹ and R² are as defined for the compound of formula (I).

Compounds of formula (S46) may be prepared by general synthetic methods as shown in Scheme 10. In the presence iron and acetic acid, compound (S42) can be cyclized to compounds of formula (S43). Treatment of the ester (S43) with hydroxide sources such as, but not limited to, lithium hydroxide in the presence of water and organic solvents such as, but not limited to, methanol and/or tetrahydrofuran yields carboxylic acid of formula (S44). Reaction of carboxylic acid (S44) with a coupling reagent such as, but not limited to, 1-[bis(dimethylamino)methylene]-1H-1,2,3-triazolo[4,5-b]pyridinium 3-oxide hexafluorophosphate, a base such as, but not limited to, pyridine, and amine (1h) in an organic solvent such as, but not limited to, N,N-dimethylformamide at a temperature at about 40° C. and for a time of about 6 hours provides amide of formula (S45). Compounds of formula (S46) can be prepared from the bromide (S45) upon treatment with aryl, heteroaryl or heterocyclic boronic acids or boronate esters under palladium catalyst conditions such as, but not limited to, [1,1'-bis(diphenylphosphino)ferrocene] dichloropalladium(II) in the presence of water and an inorganic base such as, but not limited to, sodium carbonate, potassium carbonate, or potassium phosphate in an organic solvent such as, but not limited to, 1,4-dioxane at an elevated temperature.

Example 1

General Procedure A

N-(4-(chlorodifluoromethoxy)phenyl)-1-methyl-7-(pyrimidin-5-yl)-1H-benzo[d]imidazole-5-carboxamide The title compound was prepared according to Scheme 1. This General Procedure A exemplifies Scheme 1 and provides particular synthetic details as applied to the title compound.

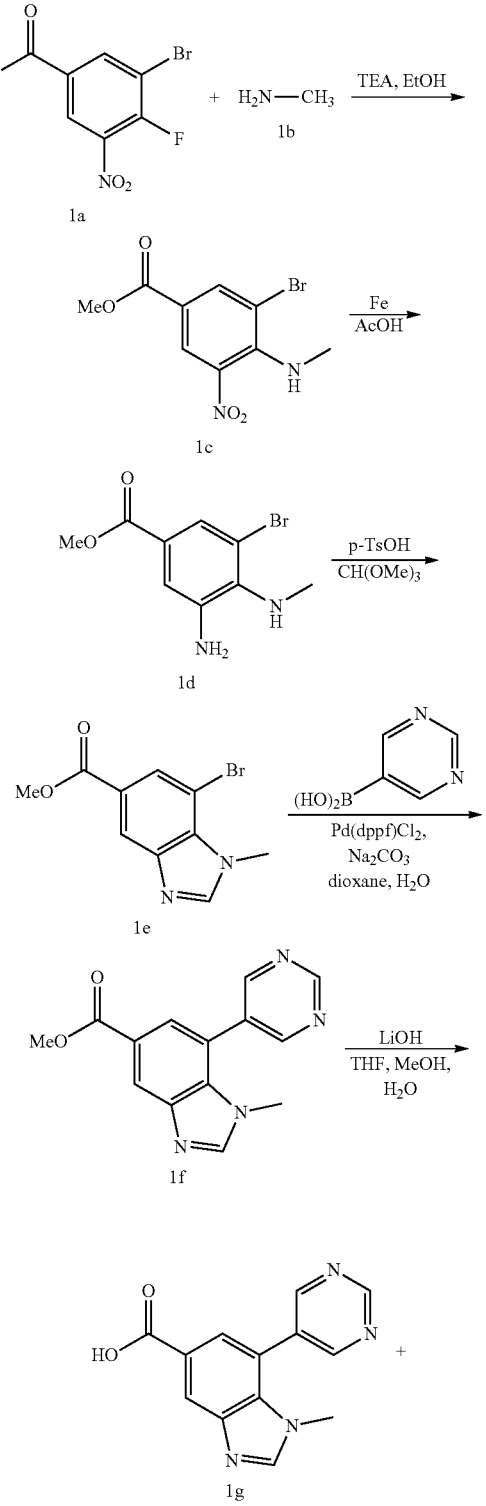

-continued

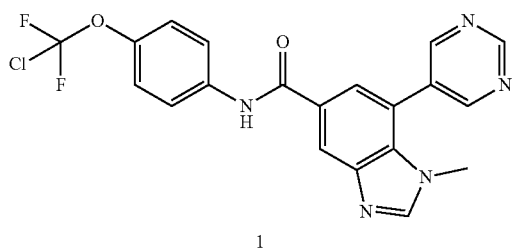 [SMILES: Cn1cnc2cc(C(=O)Nc3ccc(OC(F)(F)Cl)cc3)cc(-c3cncnc3)c21]

1

Methyl 3-bromo-4-(methylamino)-5-nitrobenzoate (1c). To a solution of methyl 3-bromo-4-fluoro-5-nitro-benzoate (1a, 3 g, 10.79 mmol, 1 eq) and methylamine hydrochloride (1b, 874.23 mg, 12.95 mmol, 1.2 eq) in EtOH (50 mL) was added TEA (3.28 g, 32.37 mmol, 4.51 mL, 3 eq). The mixture was stirred at 15° C. for 12 hours. TLC (petroleum ether:ethyl acetate=5:1, $R_f$=0.50) one major new spot with larger polarity was detected. The reaction mixture was concentrated under reduced pressure. The mixture was diluted with water and extracted with EtOAc. The combined organic layers were washed with brine, dried over $Na_2SO_4$, filtered and concentrated under reduced pressure to give 1c as a yellow solid. $^1$H NMR (400 MHz, $CDCl_3$-d) δ 8.52 (d, J=2.0 Hz, 1H), 8.30 (d, J=2.0 Hz, 1H), 6.54 (br s, 1H), 3.91 (s, 3H), 3.09 (d, J=5.5 Hz, 3H).

Methyl 3-amino-5-bromo-4-(methylamino)benzoate (1d). To a solution of methyl 3-bromo-4-(methylamino)-5-nitrobenzoate (1c, 1.5 g, 5.19 mmol, 1 eq) in AcOH (20 mL) at 15° C. was added Fe (2.90 g, 51.89 mmol, 10 eq) in one portion. The mixture was stirred at 15° C. for 1 hour. Another batch of Fe (869.31 mg, 15.57 mmol, 3 eq) was added in one portion at 15° C. and the mixture was stirred at 35° C. for 1 hour. TLC (petroleum ether:ethyl acetate=3:1, $R_f$=0.30) indicated 1c was consumed completely, and one major new spot with larger polarity was detected. Ethyl acetate (100 mL) was added. The organic layers were washed with $H_2O$ (50 mL×2), saturated $NaHCO_3$ (30 mL×4) and brine (30 mL), and dried over anhydrous $Na_2SO_4$, filtered and concentrated in vacuo. The product was used in the next step without further purification. Compound 1d was obtained as a brown oil. $^1$H NMR (400 MHz, $CDCl_3$-d) δ 7.63 (d, J=1.8 Hz, 1H), 7.31 (d, J=1.8 Hz, 1H), 4.05-3.93 (m, 2H), 3.89-3.84 (m, 3H), 3.61 (br s, 1H), 2.81-2.72 (m, 3H).

Methyl 7-bromo-1-methyl-1H-benzo[d]imidazole-5-carboxylate (1e). To a solution of methyl 3-amino-5-bromo-4-(methylamino)benzoate (1d, 0.1 g, 0.386 mmol, 1 eq) in trimethoxymethane (15 mL) was added p-TsOH (6.65 mg, 0.039 mmol, 0.1 eq). The mixture was stirred at 100° C. for 1 hr. LCMS showed 1d was consumed completely and one main peak with desired mass was detected. The mixture was concentrated and ethyl acetate (20 mL) was added. The organic layers were washed with saturated $NaHCO_3$ (5 mL) and brine (5 mL), dried over anhydrous $Na_2SO_4$, filtered and concentrated in vacuo to afford 1e as a white solid. The product was used in the next step without further purification. $^1$H NMR (400 MHz, $CDCl_3$-d) δ 8.43 (d, J=1.5 Hz, 1H), 8.16 (d, J=1.3 Hz, 1H), 7.91 (s, 1H), 4.18 (s, 3H), 4.00-3.92 (m, 3H).

Methyl 1-methyl-7-(pyrimidin-5-yl)-1H-benzo[d]imidazole-5-carboxylate (1F). To a mixture of methyl 7-bromo-1-methyl-1H-benzo[d]imidazole-5-carboxylate (1e, 0.1 g, 0.372 mmol, 1 eq) and pyrimidin-5-ylboronic acid (92.09 mg, 0.743 mmol, 2 eq) in dioxane (5 mL) and $H_2O$ (0.3 mL) under $N_2$ was added $Pd(dppf)Cl_2$ (19.03 mg, 0.026 mmol, 0.07 eq), $Na_2CO_3$ (78.77 mg, 0.743 mmol, 2 eq). The mixture was stirred at 100° C. for 12 hours. LCMS showed 1e remained and one main peak with desired mass was detected. The mixture was filtered and concentrated to give the crude residue. The residue was purified by prep-TLC ($SiO_2$, ethyl acetate:methanol=9:1). Compound 1f was obtained as a brown solid. $^1$H NMR (400 MHz, $CDCl_3$-d) δ 9.35 (s, 1H), 8.90 (s, 2H), 8.62 (d, J=1.5 Hz, 1H), 7.97-7.88 (m, 2H), 3.98 (s, 3H), 3.51 (s, 3H).

1-Methyl-7-(pyrimidin-5-yl)-1H-benzo[d]imidazole-5-carboxylic acid (1g). To a solution of methyl 1-methyl-7-(pyrimidin-5-yl)-1H-benzo[d]imidazole-5-carboxylate (1f, 0.045 g, 0.168 mmol, 1 eq) in THF (2 mL), MeOH (2 mL) and $H_2O$ (1 mL) at 15° C. under $N_2$ was added $LiOH \cdot H_2O$ (14.08 mg, 0.335 mmol, 2 eq). The mixture was stirred at 15° C. for 12 hours. LCMS showed 1f was consumed completely and one main peak with desired mass was detected. The mixture was adjusted to pH=5 with aqueous HCl (1M) and concentrated to give the crude product 1g as a brown solid. The product was used into the next step without further purification.

N-(4-(chlorodifluoromethoxy)phenyl)-1-methyl-7-(pyrimidin-5-yl)-1H-benzo[d]imidazole-5-carboxamide (1). To a solution of 1-methyl-7-(pyrimidin-5-yl)-1H-benzo[d]imidazole-5-carboxylic acid (1 g, 0.04 g, 0.157 mmol, 1 eq) and 4-(chlorodifluoromethoxy)aniline (33.50 mg, 0.173 mmol, 1.1 eq), HATU (71.79 mg, 0.189 mmol, 1.2 eq) in DMF (1 mL) at 15° C. was added DIEA (61.00 mg, 0.472 mmol, 82.21 uL, 3 eq). The mixture was stirred at 15° C. for 12 hours. LCMS showed 1g was consumed completely and desired mass was detected. The mixture was concentrated, and the resulting residue was purified by prep-HPLC (FA condition, column: Luna C18 100*30 5 u; mobile phase: [water (0.225% FA)-ACN]; B %: 35%-50%, 14 min) to afford the title compound 1 as a yellow solid. $^1$H NMR (400 MHz, MeOD-$d_4$) δ $^1$H NMR (400 MHz, MeOD-$d_4$) δ 9.31 (s, 1H), 9.06 (s, 2H), 8.45 (d, J=1.5 Hz, 1H), 8.39 (s, 1H), 7.91 (d, J=1.5 Hz, 1H), 7.84 (d, J=9.0 Hz, 2H), 7.31 (d, J=9.0 Hz, 2H), 3.60 (s, 3H).

Example 2

General Procedure B

N-(4-(chlorodifluoromethoxy)phenyl)-1-(1s,3s)-3-hydroxycyclobutyl)-7-(pyrimidin-5-yl)-1H-benzo[d]imidazole-5-carboxamide The title compound was prepared according to Scheme 2. This General Procedure B exemplifies Scheme 2 and provides particular synthetic details as applied to the title compound.

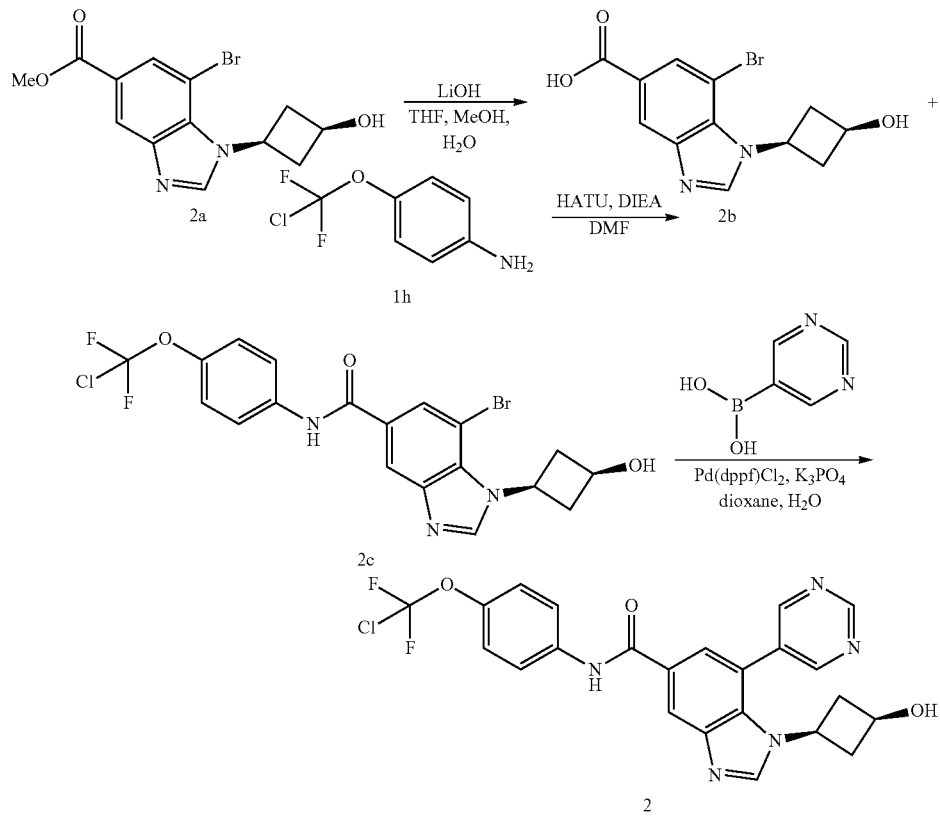

7-Bromo-1-(1s,3s)-3-hydroxycyclobutyl)-1H-benzo[d]imidazole-5-carboxylic acid (2b). To a solution of methyl 7-bromo-1-(1s,3s)-3-hydroxycyclobutyl)-1H-benzo[d]imidazole-5-carboxylate (synthesized in a similar fashion to 1e; 2a, 140 mg, 0.431 mmol, 1 eq) in THF (2 mL), MeOH (2 mL) and H$_2$O (1 mL) was added LiOH.H$_2$O (27.10 mg, 0.646 mmol, 1.5 eq). The mixture was stirred at 15° C. for 12 hr. LCMS showed 2a was consumed completely and desired MS was detected. The aqueous phase was acidified to pH=5 with the addition of aqueous HCl. The mixture was filtered and concentrated in vacuo and compound 2b obtained as a white solid. $^1$H NMR (400 MHz, DMSO-d$_6$) δ 13.10 (br s, 1H) 8.72 (s, 1H) 8.19 (d, J=1.1 Hz, 1H) 7.96 (s, 1H) 5.37 (br d, J=6.2 Hz, 1H) 4.94-5.07 (m, 1H) 4.01-4.11 (m, 1H) 2.86-2.95 (m, 2H) 2.37-2.44 (m, 2H).

7-Bromo-N-(4-(chlorodifluoromethoxy)phenyl)-1-(1s,3s)-3-hydroxycyclobutyl)-1H-benzo[d]imidazole-5-carboxamide (2c) To a solution of 7-bromo-1-((1s,3s)-3-hydroxycyclobutyl)-1H-benzo[d]imidazole-5-carboxylic acid (2b, 100 mg, 0.321 mmol, 1 eq) and 4-[chloro(difluoro)methoxy]aniline (74.66 mg, 0.386 mmol, 1.2 eq) in DMF (2 mL) was added HATU (146.65 mg, 0.386 mmol, 1.2 eq) and DIEA (83.08 mg, 0.643 mmol, 111.97 uL, 2 eq). The mixture was stirred at 15° C. for 12 hr. LCMS showed 2b was consumed completely and desired MS was detected. The mixture was diluted with water (3 mL) and extracted with EtOAc (10 mL×3). The combined organic layers were washed with brine (3 mL), dried over Na$_2$SO$_4$, filtered and concentrated under reduced pressure to give a residue. The residue was purified by prep-TLC (SiO$_2$, ethyl acetate:methanol=10:1) to give 2c as a white solid. $^1$H NMR (400 MHz, DMSO-d$_6$) δ10.48 (s, 1H) 8.72 (s, 1H) 8.40 (d, J=1.3 Hz, 1H) 8.05 (d, J=1.3 Hz, 1H) 7.92 (d, J=9.0 Hz, 2H) 7.36 (d, J=9.0 Hz, 2H) 5.37 (d, J=6.4 Hz, 1H) 4.96-5.08 (m, 1H) 4.01-4.13 (m, 1H) 2.89-2.98 (m, 2H) 2.36-2.43 (m, 2H).

N-(4-(chlorodifluoromethoxy)phenyl)-1-((1s,3s)-3-hydroxycyclobutyl)-7-(pyrimidin-5-yl)-1H-benzo[d]imidazole-5-carboxamide (2). To a solution of 7-bromo-N-(4-(chlorodifluoromethoxy)phenyl)-1-(1s,3s)-3-hydroxycyclobutyl)-1H-benzo[d]imidazole-5-carboxamide (2c, 40 mg, 0.082 mmol, 1 eq) and pyrimidin-5-ylboronic acid (20.37 mg, 0.164 mmol, 2 eq) in dioxane (3 mL) and H$_2$O (0.3 mL) was added Pd(dppf)Cl$_2$ (6.01 mg, 8.22 umol, 0.1 eq) and K$_3$PO$_4$ (52.34 mg, 0.247 mmol, 3 eq). The mixture was stirred at 100° C. for 12 hr. LCMS showed 2c was consumed completely and desired MS was detected. The aqueous phase was extracted with H$_2$O (5 mL) and ethyl acetate (5 mL×3). The combined organic layers were washed with brine (5 mL), dried over anhydrous Na$_2$SO$_4$, filtered and concentrated in vacuo. The mixture purified by prep-HPLC (NH$_4$HCO$_3$ condition, column: Waters Xbridge Prep OBD C18 150*30 10 u; mobile phase: [water (10 mM NH$_4$HCO$_3$)-ACN]; B %: 25%-45%,10 min) to give the title compound 2 as a white solid. MS mass calculated for [M−H]$^+$ (C$_{23}$H$_{18}$O$_3$N$_5$ClF$_2$) requires m/z 486.1, LCMS found m/z 486.1. $^1$H NMR (400 MHz, DMSO-d$_6$) δ 10.46 (s, 1H) 9.36 (s, 1H) 9.06 (s, 2H) 8.62 (s, 1H) 8.51 (d, J=1.5 Hz, 1H) 7.94 (d, J=9.0 Hz, 2H) 7.81 (d, J=1.5 Hz, 1H) 7.37 (d, J=8.8 Hz, 2H) 5.21 (d, J=6.6 Hz, 1H) 3.97 (quin, J=8.0 Hz, 1H) 3.66 (sxt, J=7.1 Hz, 1H) 2.06-2.16 (m, 4H).

Example 3

General Procedure C

N-(4-(chlorodifluoromethoxy)phenyl)-2-(difluoromethyl)-1-methyl-4-(pyrimidin-5-yl)-1H-benzo[d]imidazole-6-carboxamide The title compound was prepared according to Scheme 3. This General Procedure C exemplifies Scheme 3 and provides particular synthetic details as applied to the title compound.

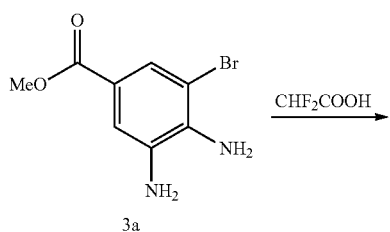

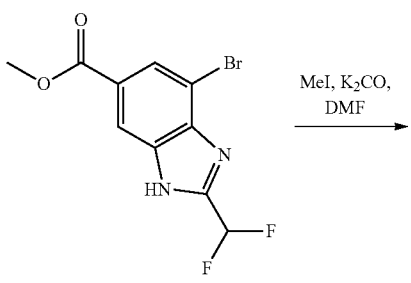

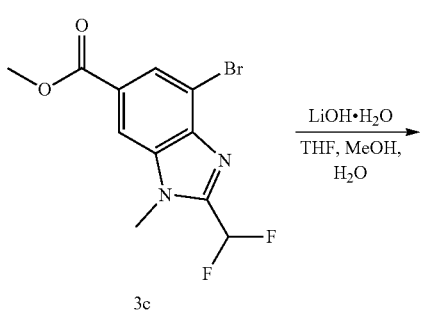

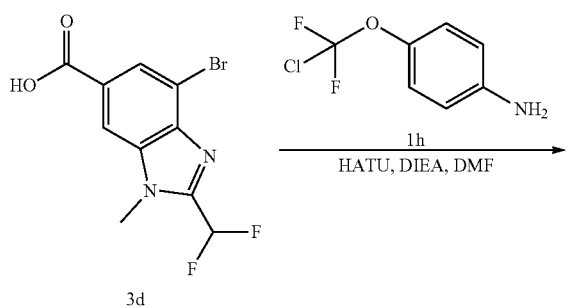

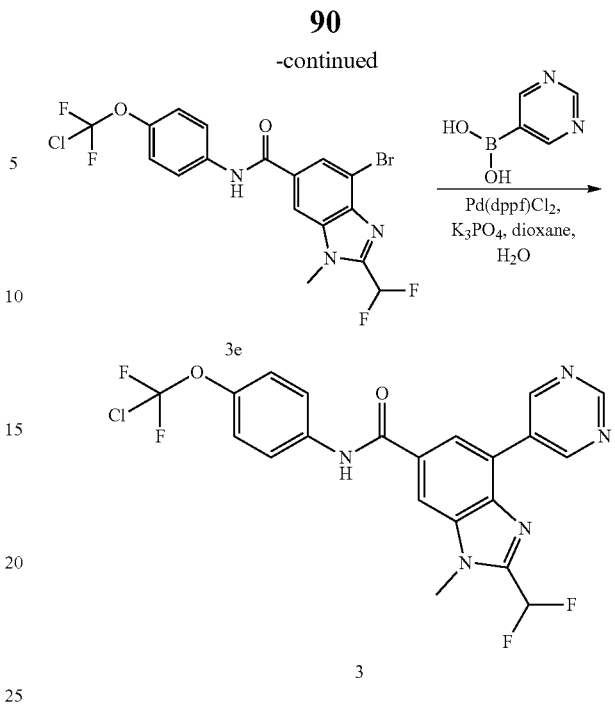

Methyl 4-bromo-2-(difluoromethyl)-1H-benzo[d]imidazole-6-carboxylate (3b). Methyl 3,4-diamino-5-bromobenzoate (synthesized in a similar fashion to 1d; 3a, 0.2 g, 0.816 mmol, 1 eq) was dissolved in CHF$_2$COOH (3 mL)), the mixture was stirred at 130° C. for 1 hr. TLC (petroleum ether:ethyl acetate=3:1) showed the starting material was consumed and LCMS showed the desired MS. The mixture was concentrated, and the residue was dissolved in EtOAc (10 ml). The organic layers were washed with aq. NaHCO$_3$ (5 mL×3) and then concentrated to afford 3b as a brown solid. The crude product was used in the next step without further purification.

Methyl 4-bromo-2-(difluoromethyl)-1-methyl-1H-benzo[d]imidazole-6-carboxylate (3c). To a solution of methyl 4-bromo-2-(difluoromethyl)-1H-benzo[d]imidazole-6-carboxylate (3b, 200 mg, 0.656 mmol, 1 eq) in DMF (2 mL) was added K$_2$CO$_3$ (271.82 mg, 1.97 mmol, 3 eq) and MeI (930.52 mg, 6.56 mmol, 408.12 uL, 10 eq). The mixture was stirred at 50° C. for 10 hr. TLC (petroleum ether:ethyl acetate=2:1) showed the starting material was consumed. The mixture was concentrated and the residue was purified by prep-TLC (SiO$_2$, petroleum ether:ethyl acetate=2:1) to afford 3c as a yellow solid. $^1$H NMR (400 MHz, CDCl$_3$-d) δ 8.24 (d, J=1.1 Hz, 1H), 8.17 (d, J=1.1 Hz, 1H), 7.17-6.85 (m, 1H), 4.04 (s, 3H), 3.98 (s, 3H).

4-Bromo-2-(difluoromethyl)-1-methyl-1H-benzo[d]imidazole-6-carboxylic acid (3d). To a solution of methyl 4-bromo-2-(difluoromethyl)-1-methyl-1H-benzo[d]imidazole-6-carboxylate (3c, 115 mg, 0.36 mmol, 1 eq) in THF (3 mL), MeOH (2 mL) and H$_2$O (1 mL) at 25° C. was added LiOH.H$_2$O (30.24 mg, 0.721 mmol, 2 eq). The mixture was stirred at 50° C. for 2 hr. TLC (petroleum ether:ethyl acetate=2:1) showed the starting material was consumed. The mixture was concentrated and aq. HCl (1M) was added until pH=3-4. The suspension was filtered, and the solid was washed with H$_2$O (1 mL) and dried to give 3d as a yellow solid. The crude product was used in the next step without further purification. $^1$H NMR (400 MHz, MeOD-d$_4$) δ 8.35 (s, 1H), 8.07 (s, 1H), 7.70-7.32 (m, 1H), 4.02 (s, 3H).

4-Bromo-N-(4-(chlorodifluoromethoxy)phenyl)-2-(difluoromethyl)-1-methyl-1H-benzo[d]imidazole-6-carboxamide (3e). To a solution of 4-bromo-2-(difluoromethyl)-1-methyl-1H-benzo[d]imidazole-6-carboxylic acid (3d, 110 mg, 0.361 mmol, 1 eq) in DMF (3 mL) was added DIPEA (93.20 mg, 0.721 mmol, 125.61 uL, 3 eq) and HATU (205.65 mg, 0.541 mmol, 1.2 eq). The mixture was stirred at 25° C. for 0.5 hr before 4-(chlorodifluoromethoxy)aniline (1h, 83.76 mg, 0.433 mmol, 1.2 eq) was added. The reaction mixture was stirred at 25° C. for 3.5 hrs. TLC (petroleum ether:ethyl acetate=3:1) showed the starting material was consumed and LCMS showed desired MS. The mixture was concentrated and the residue was purified by column chromatography by prep-TLC (SiO$_2$, petroleum ether:ethyl acetate=1:1) to afford 3e as a yellow solid. $^1$H NMR (400 MHz, CDCl$_3$-d) δ 8.10 (d, J=1.2 Hz, 1H), 7.98-7.91 (m, 2H), 7.74 (d, J=8.9 Hz, 2H), 7.30 (d, J=8.9 Hz, 2H), 7.18-6.88 (m, 1H), 4.07 (s, 3H).

N-(4-(chlorodifluoromethoxy)phenyl)-2-(difluoromethyl)-1-methyl-4-(pyrimidin-5-yl)-1H-benzo[d]imidazole-6-carboxamide (3). To a solution of 4-bromo-N-(4-(chlorodifluoromethoxy)phenyl)-2-(difluoromethyl)-1-methyl-1H-benzo[d]imidazole-6-carboxamide (3e, 100 mg, 0.208 mmol, 1 eq) and pyrimidin-5-ylboronic acid (51.56 mg, 0.416 mmol, 2 eq) in dioxane (4 mL) and H$_2$O (1 mL) under N$_2$ was added K$_3$PO$_4$ (132.49 mg, 0.624 mmol, 3 eq) and Pd(dppf)Cl$_2$ (15.22 mg, 0.021 mmol, 0.1 eq). The mixture was stirred under N$_2$ at 100° C. for 4 hrs. LCMS showed the starting material was consumed and desired product was detected. The mixture was poured into water and extracted with EtOAc. The organic layers were concentrated and the resulting residue was purified by prep-HPLC (NH$_4$HCO$_3$ condition, column: Waters Xbridge Prep OBD C18 150*30 10 u; mobile phase: [water (10 mM NH$_4$HCO$_3$)-ACN]; B %: 30%-50%,10 min) to give the title compound 3 as a white solid. MS mass calculated for [M+H]$^+$ (C$_{21}$H$_{14}$ClF$_4$N$_5$O$_2$) requires m/z 480.1, LCMS found m/z 480.1. $^1$H NMR (400 MHz, DMSO-d$_6$) δ 10.58 (s, 1H), 9.55 (s, 2H), 9.26 (s, 1H), 8.46 (s, 1H), 8.32 (s, 1H), 7.93 (d, J=9.2 Hz, 2H), 7.69-7.37 (m, 3H), 4.08 (s, 3H).

Example 4

N-(4-(chlorodifluoromethoxy)phenyl)-1,2-dimethyl-4-(pyrimidin-5-yl)-1H-benzo[d]imidazole-6-carboxamide

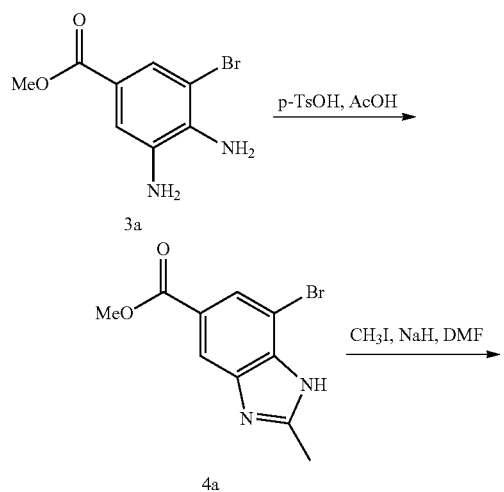

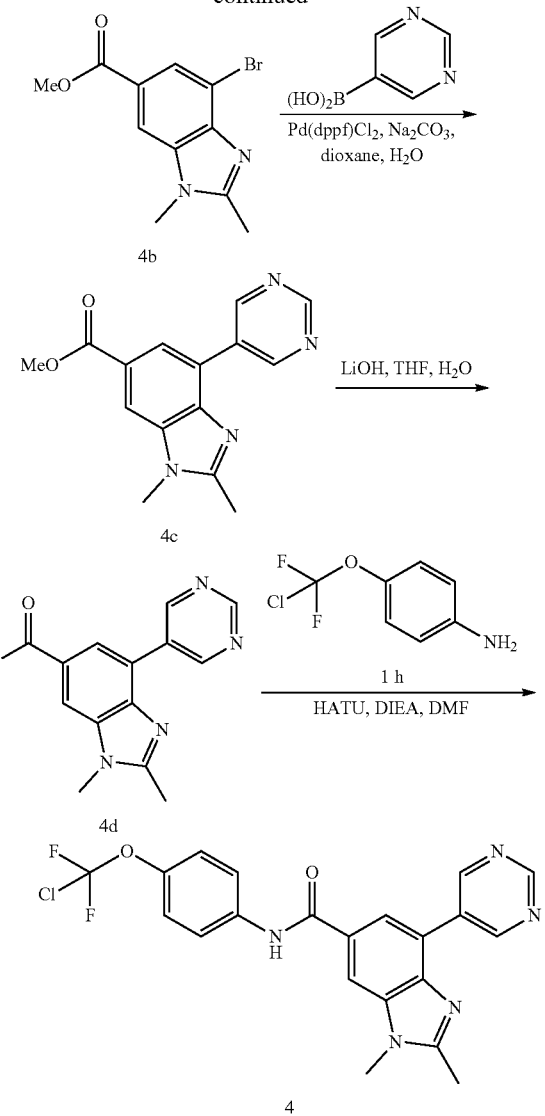

Methyl 7-bromo-2-methyl-1H-benzo[d]imidazole-5-carboxylate (4a). To a mixture of Methyl 3,4-diamino-5-bromobenzoate (synthesized in a similar fashion to 1d; 3a, 0.16 g, 0.653 mmol, 1 eq) in CH$_3$COOH (3 mL) at 20° C. was added 4-methylbenzenesulfonic acid (11.24 mg, 0.065 mmol, 0.1 eq). The mixture was stirred at 100° C. for 3 hours. LCMS showed desired MS. The mixture was poured into water (20 mL), and then was extracted with EtOAC (20 mL×3). The combined organic layers were dried with anhydrous Na$_2$SO$_4$, filtered and concentrated in vacuo to give 4a as a brown oil.

Methyl 4-bromo-1,2-dimethyl-1H-benzo[d]imidazole-6-carboxylate (4b). To a mixture of Methyl 7-bromo-2-methyl-1H-benzo[d]imidazole-5-carboxylate (4a, 0.15 g, 0.557 mmol, 1 eq) and NaH (44.59 mg, 1.11 mmol, 60% purity, 2 eq) in DMF (1 mL) was added CH$_3$I (158.24 mg, 1.11 mmol, 69.40 uL, 2 eq). The mixture was stirred at 15° C. for 16 hours. LCMS showed desired MS. The mixture was poured into water (20 mL), and then was extracted with EtOAC (20 mL×3). The combined organic layers were dried over anhydrous Na$_2$SO$_4$, filtered and concentrated in vacuo to give the product. The residue was purified by prep-TLC (Petroleum ether:Ethyl acetate=0:1, R$_f$=0.40) to give 4b as a brown oil.

Methyl 1,2-dimethyl-4-(pyrimidin-5-yl)-1H-benzo[d]imidazole-6-carboxylate (4c). To a mixture of methyl 4-bromo-1,2-dimethyl-1H-benzo[d]imidazole-6-carboxylate (4b, 0.02 g, 0.071 mmol, 1 eq), pyrimidin-5-yl-boronic acid (26.26 mg, 0.212 mmol, 3 eq) and $K_3PO_4$ (44.98 mg, 0.212 mmol, 3 eq) in dioxane (2 mL), $H_2O$ (0.2 mL) under $N_2$ was added Pd(dppf)$Cl_2$ (5.17 mg, 7.06 umol, 0.1 eq). The mixture was stirred at 110° C. for 16 hours. LCMS showed desired MS. The mixture was poured into water and extracted with EtOAc. The combined organic layers were dried over anhydrous $Na_2SO_4$, filtered and concentrated in vacuo to give the crude product. The residue was purified by prep-TLC (petroleum ether:ethyl acetate=0:1, $R_f$=0.37) to afford 4c as yellow oil.

1,2-Dimethyl-4-(pyrimidin-5-yl)-1H-benzo[d]imidazole-6-carboxylic acid (4d). To a mixture of 4c (0.015 g, 0.053 mmol, 1 eq) in $H_2O$ (0.5 mL), THF (1 mL), MeOH (1 mL) was added LiOH.$H_2O$ (4.46 mg, 0.106 mmol, 2 eq). The mixture was stirred at 15° C. for 16 hours. LCMS showed the desire MS. The mixture was poured into water and extracted with EtOAc, the combined organic layers were dried over anhydrous $Na_2SO_4$, filtered and concentrated in vacuo to give the 4d as red solid. The crude product was used in the next step without further purification.

N-(4-(chlorodifluoromethoxy)phenyl)-1,2-dimethyl-4-(pyrimidin-5-yl)-1H-benzo[d]imidazole-6-carboxamide (4). To a mixture of 1,2-dimethyl-4-(pyrimidin-5-yl)-1H-benzo[d]imidazole-6-carboxylic acid (4d, 15 mg, 0.056 mmol, 1 eq) and HATU (25.51 mg, 0.067 mmol, 1.2 eq), DIPEA (14.45 mg, 0.112 mmol, 19.48 uL, 2 eq) in DMF (1 mL) at 20° C. was added 4-[chloro(difluoro)methoxy]aniline (1h, 16.24 mg, 0.084 mmol, 1.5 eq). The mixture was stirred at 20° C. for 16 hours. The mixture was concentrated in vacuo. LCMS showed desired MS. The mixture was poured into water and extracted with EtOAc, and the combined organic layers were dried over anhydrous $Na_2SO_4$, filtered and concentrated in vacuo to give the crude product. The residue was purified by prep-HPLC (TFA condition, column: Nano-Micro UniSil 5-100 C18 ULTRA 100*250 mm 5 um; mobile phase: [water (0.1% TFA)-ACN]; B %: 25%-50%, 11 min) to afford the title compound 4 as a white solid. MS mass calculated for $[M+H]^+$ ($C_{21}H_{16}ClF_2N_5O_2$) requires m/z 444.1, LCMS found m/z 444.1. $^1$H NMR (400 MHz, MeOD-$d_4$) δ 9.33-9.25 (m, 3H), 8.48 (s, 1H), 8.25 (s, 1H), 7.88 (d, J=9.0 Hz, 2H), 7.33 (d, J=8.8 Hz, 2H), 4.07 (s, 3H), 2.85 (s, 3H).

Example 5

General Procedure D (R)—N-(4-(chlorodifluoromethoxy)phenyl)-2-(difluoromethyl)-1-(1-hydroxypropan-2-yl)-7-(pyrimidin-5-yl)-1H-benzo[d]imidazole-5-carboxamide The title compound was prepared according to Scheme 4. This General Procedure D exemplifies Scheme 4 and provides particular synthetic details as applied to the title compound.

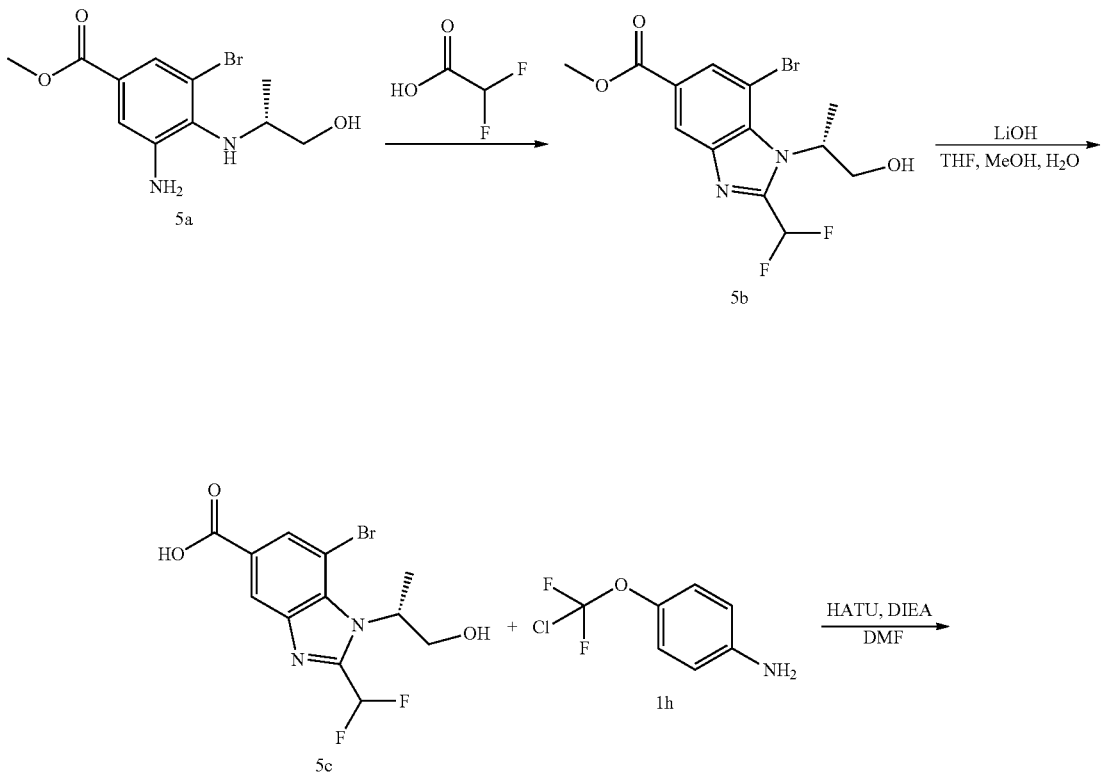

-continued

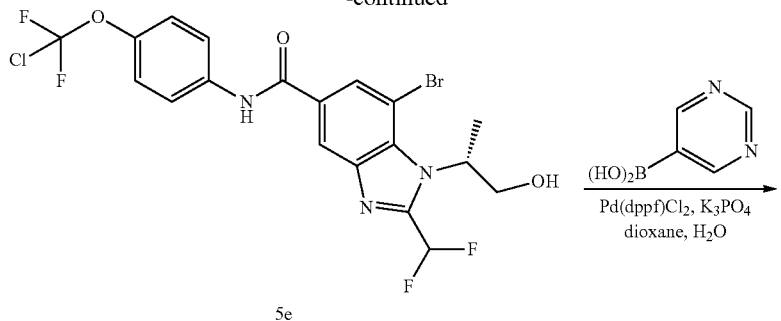

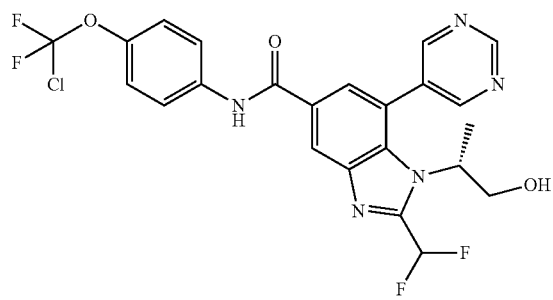

(R)-methyl 7-bromo-2-(difluoromethyl)-1-(1-hydroxypropan-2-yl)-1H-benzo[d]imidazole-5-carboxylate (5b). A solution of (R)-methyl 3-amino-5-bromo-4-(1-hydroxypropan-2-yl)amino)benzoate (synthesized in a similar fashion to 1d; 5a, 230 mg, 0.759 mmol, 1 eq) in 2,2-difluoroacetic acid (4.59 g, 0.048 mmol, 3 mL, 63 eq) was stirred at 110° C. for 3 hr. LCMS showed 5a was consumed completely and desired MS was detected. The mixture was filtered and concentrated under reduced pressure to give the crude residue. The residue was purified by prep-TLC (SiO$_2$, petroleum ether:ethyl acetate=0:1) to provide 5b as a white solid. $^1$H NMR (400 MHz, DMSO-d$_6$) δ 8.34 (s, 1H) 8.11 (s, 1H), 7.37-7.75 (m, 1H), 5.95-6.10 (m, 1H), 5.31 (t, J=5.2 Hz, 1H), 3.90 (s, 3H), 3.74-3.87 (m, 2H), 1.59 (br d, J=7.3 Hz, 3H).

(R)-7-bromo-2-(difluoromethyl)-1-(1-hydroxypropan-2-yl)-1H-benzo[d]imidazole-5-carboxylic acid (5c). To a solution of (R)-methyl 7-bromo-2-(difluoromethyl)-1-(1-hydroxypropan-2-yl)-1H-benzo[d]imidazole-5-carboxylate (5b, 130 mg, 0.358 mmol, 1 eq) in THF (1 mL), MeOH (1 mL) and H$_2$O (0.5 mL) was added LiOH.H$_2$O (30.04 mg, 0.716 mmol, 2 eq). The mixture was stirred at 15° C. for 2 hr. LCMS showed 5b was consumed completely and desired MS was detected. The aqueous phase was acidified to pH=5 with aqueous HCl. The mixture was filtered and concentrated in vacuo. The product was used in the next step without further purification. Compound 5c was obtained as a white solid.

(R)-7-bromo-N-(4-(chlorodifluoromethoxy)phenyl)-2-(difluoromethyl)-1-(1-hydroxypropan-2-yl)-1H-benzo[d]imidazole-5-carboxamide (5e). To a solution of (R)-7-bromo-2-(difluoromethyl)-1-(1-hydroxypropan-2-yl)-1H-benzo[d]imidazole-5-carboxylic acid (5c, 100 mg, 0.286 mmol, 1 eq) and 4-(chlorodifluoromethoxy)aniline (1h, 66.54 mg, 0.344 mmol, 1.2 eq) in DMF (2 mL) was added HATU (130.69 mg, 0.344 mmol, 1.2 eq) and DIEA (148.08 mg, 1.15 mmol, 199.56 uL, 4 eq). The mixture was stirred at 15° C. for 12 hr. LCMS showed 5c was consumed completely and desired MS was detected. The mixture was diluted with water (5 mL) and extracted with EtOAc (10 mL×3). The combined organic layers were washed with brine (5 mL), dried over Na$_2$SO$_4$, filtered and concentrated under reduced pressure to give the crude residue. The residue was purified by prep-TLC (SiO$_2$, ethyl acetate:methanol=10:1) to afford 5e as a yellow oil. $^1$H NMR (400 MHz, DMSO-d$_6$) δ 10.56 (s, 1H), 8.49 (s, 1H), 8.21 (s, 1H), 7.93 (d, J=9.3 Hz, 2H), 7.43-7.71 (m, 1H), 7.38 (br d, J=9.0 Hz, 2H), 6.02 (br d, J=6.2 Hz, 1H), 5.23-5.45 (m, 1H), 3.72-3.93 (m, 2H), 1.60 (br d, J=6.8 Hz, 3H).

(R)—N-(4-(chlorodifluoromethoxy)phenyl)-2-(difluoromethyl)-1-(1-hydroxypropan-2-yl)-7-(pyrimidin-5-yl)-1H-benzo[d]imidazole-5-carboxamide (5). To a solution of (R)-7-bromo-N-(4-(chlorodifluoromethoxy)phenyl)-2-(difluoromethyl)-1-(1-hydroxypropan-2-yl)-1H-benzo[d]imidazole-5-carboxamide (5e, 60 mg, 0.114 mmol, 1 eq) and pyrimidin-5-ylboronic acid (28.34 mg, 0.229 mmol, 2 eq) in dioxane (1 mL) and H$_2$O (0.1 mL) was added Pd(dppf)Cl$_2$ (8.37 mg, 11.44 umol, 0.1 eq) and K$_3$PO$_4$ (72.82 mg, 0.343 mmol, 3 eq). The mixture was stirred at 100° C. for 16 hr. LCMS showed 5e was consumed completely and desired MS was detected. The mixture was filtered and concentrated under reduced pressure to give the crude residue. The residue was purified by prep-TLC (SiO$_2$, ethyl acetate:methanol=10:1) to afford title compound 5 as a white solid. MS mass calculated for [M+H]$^+$ (C$_{23}$H$_{18}$O$_3$N$_5$ClF$_4$) requires m/z 524.1, LCMS found m/z 524.1. $^1$H NMR (400 MHz, DMSO-d$_6$) δ 10.50 (s, 1H) 9.35 (s, 1H) 9.07 (s, 2H) 8.58 (d, J=1.5 Hz, 1H) 7.93 (d, J=9.3 Hz, 2H) 7.84 (d, J=1.8 Hz, 1H) 7.42-7.70 (m, 1H) 7.38 (d, J=9.0 Hz, 2H) 5.11 (t, J=5.1 Hz, 1H) 4.25-4.45 (m, 1H) 3.41-3.63 (m, 2H) 1.37 (br d, J=7.1 Hz, 3H).

Example 6

General Procedure E

N-(4-(chlorodifluoromethoxy)phenyl)-2-isopropyl-1-methyl-7-(pyrimidin-5-yl)-1H-benzo[d]imidazole-5-carboxamide The title compound was prepared according to Scheme 5. This General Procedure E exemplifies Scheme 5 and provides particular synthetic details as applied to the title compound.

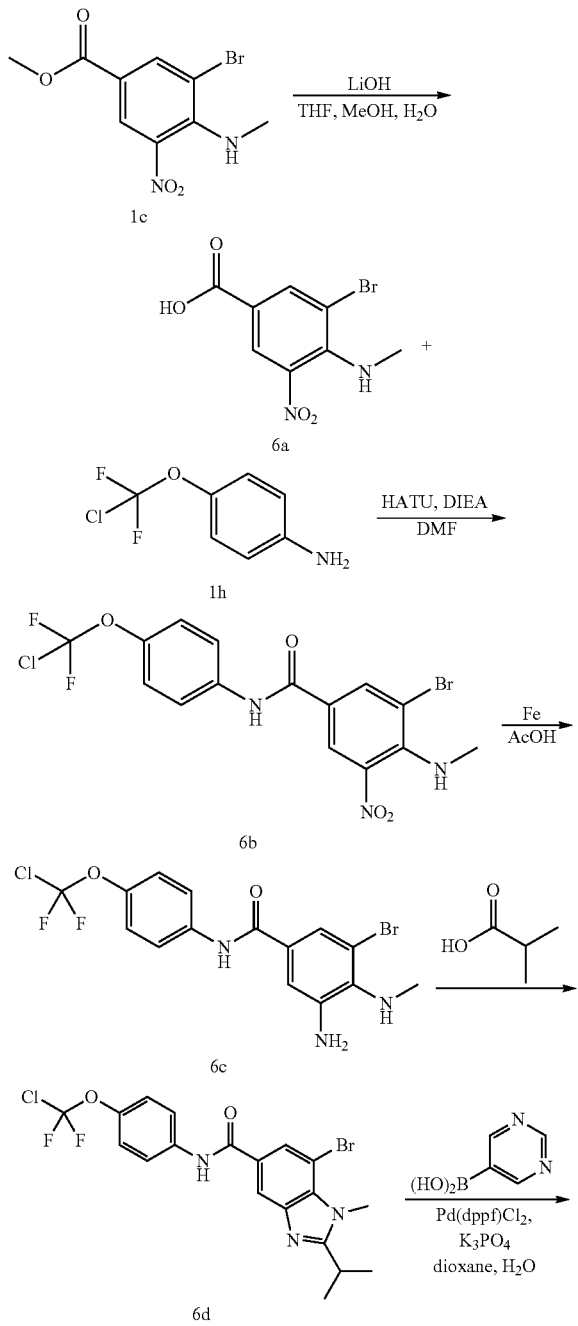

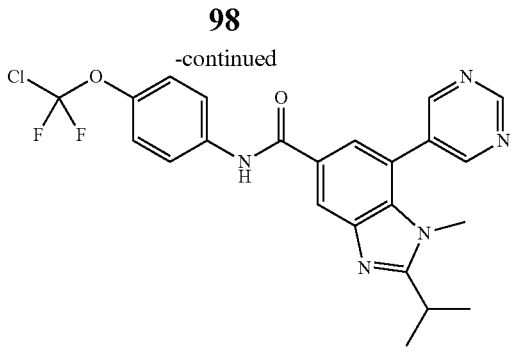

3-Bromo-4-(methylamino)-5-nitrobenzoic acid (6a). To a mixture of methyl 3-bromo-4-(methylamino)-5-nitrobenzoate (1c, 1.7 g, 5.88 mmol, 1 eq) in THF (20 mL) and H$_2$O (4 mL) was added LiOH.H$_2$O (493.55 mg, 11.76 mmol, 2 eq) in one portion. The mixture was stirred at 60° C. for 12 hours. TLC (petroleum ether:ethyl acetate=3:1, R$_f$=0.0) indicated 1c was consumed completely, and one major new spot with larger polarity was detected. The mixture was adjusted to pH=3 with aqueous HCl (1M). The mixture was filtered, and the yellow solid was washed with H$_2$O (10 mL) to give 6b as a yellow solid. The product was used in the next step without further purification.

3-Bromo-N-(4-(chlorodifluoromethoxy)phenyl)-4-(methylamino)-5-nitrobenzamide (6b) To a mixture of 3-bromo-4-(methylamino)-5-nitrobenzoic acid (6a, 1.27 g, 6.54 mmol, 1.2 eq) and 4-(chlorodifluoromethoxy)aniline (1h, 1.50 g, 5.45 mmol, 1 eq) in DMF (10 mL) was added HATU (2.28 g, 6.00 mmol, 1.1 eq) and DIEA (775.28 mg, 6.00 mmol, 1.04 mL, 1.1 eq) in one portion. The mixture was heated to 30° C. and stirred for 12 hours. LC-MS showed one main peak with desired mass was detected. The mixture was concentrated and the resulting residue was purified by column chromatography (SiO$_2$, petroleum ether:ethyl acetate=20:1 to 5:1) to yield 6b as a yellow solid.

3-Amino-5-bromo-N-(4-(chlorodifluoromethoxy)phenyl)-4-(methylamino)benzamide (6c). A solution of 3-bromo-N-(4-(chlorodifluoromethoxy)phenyl)-4-(methylamino)-5-nitrobenzamide (6b, 2.1 g, 4.66 mmol, 1 eq) in AcOH (15 mL) at 20° C. was added Fe (2.60 g, 46.60 mmol, 10 eq) in one portion. The mixture was stirred at 35° C. for 3 h. TLC (petroleum ether:ethyl acetate=1:1, R$_f$=0.6) indicated 6b was consumed completely and one new spot formed. Ethyl acetate (40 mL) was added and the mixture was filtered through a Celite® pad. The filtrate was washed with H$_2$O (30 mL), saturated NaHCO$_3$ solution (20 mL×3), and brine (20 mL) before being dried over anhydrous Na$_2$SO$_4$, filtered and concentrated in vacuo to afford 6c as a yellow solid. The crude product was used in the next step without further purification.

3-Amino-5-bromo-N-(4-(chlorodifluoromethoxy)phenyl)-4-(methylamino)benzamide (6d). A mixture of 3-amino-5-bromo-N-(4-(chlorodifluoromethoxy)phenyl)-4-(methylamino)benzamide (6c, 0.075 g, 0.178 mmol, 1 eq) in 2-methylpropanoic acid (314.18 mg, 3.57 mmol, 330.72 uL, 20 eq) was stirred at 130° C. for 12 hours. The mixture turned from brown to dark. LC-MS showed 6e was consumed completely and desired mass was detected. The residue was purified by prep-TLC (SiO$_2$, petroleum ether: ethyl acetate=1:1) to afford 6d as a yellow oil.

N-(4-(chlorodifluoromethoxy)phenyl)-2-isopropyl-1-methyl-7-(pyrimidin-5-yl)-1H-benzo[d]imidazole-5-carboxamide (6). To a mixture of 3-amino-5-bromo-N-(4-

(chlorodifluoromethoxy)phenyl)-4-(methylamino) benzamide (6d, 0.03 g, 0.063 mmol, 1 eq) and pyrimidin-5-ylboronic acid (15.73 mg, 0.127 mmol, 2 eq) in dioxane (4 mL) and H$_2$O (0.3 mL) at 15° C. under N$_2$ was added Pd(dppf)Cl$_2$ (4.64 mg, 6.35 umol, 0.1 eq), K$_3$PO$_4$ (40.41 mg, 0.190 mmol, 3 eq) in one portion. The mixture was stirred at 110° C. for 12 hours. LC-MS showed the starting material was consumed completely and one main peak with desired mass was detected. The mixture was filtered through a Celite® pad and the filtrate was concentrated to give a crude residue. The residue was purified by prep-HPLC (TFA condition: column: Luna C18 100*30 5 u; mobile phase: [water (0.1% TFA)-ACN]; B %: 15%-45%, 14 min) to provide the title compound 6 as a white solid. MS mass calculated for [M+H]$^+$ (C$_{23}$H$_{20}$O$_2$N$_5$ClF$_2$) requires m/z 472.1, LCMS found m/z 472.1. $^1$H NMR (400 MHz, MeOD-d$_4$) δ 9.34 (s, 1H), 9.07 (s, 2H), 8.43 (d, J=1.5 Hz, 1H), 8.01 (d, J=1.5 Hz, 1H), 7.84 (d, J=9.0 Hz, 2H), 7.31 (d, J=9.0 Hz, 2H), 3.64-3.55 (m, 4H), 1.52 (d, J=6.8 Hz, 6H).

Example 7

General Procedure F

N-(4-(chlorodifluoromethoxy)phenyl)-1,2-dimethyl-7-(pyrimidin-5-yl)-1H-benzo[d]imidazole-5-carboxamide The title compound was prepared according to Scheme 6. This General Procedure F exemplifies Scheme 6 and provides particular synthetic details as applied to the title compound.

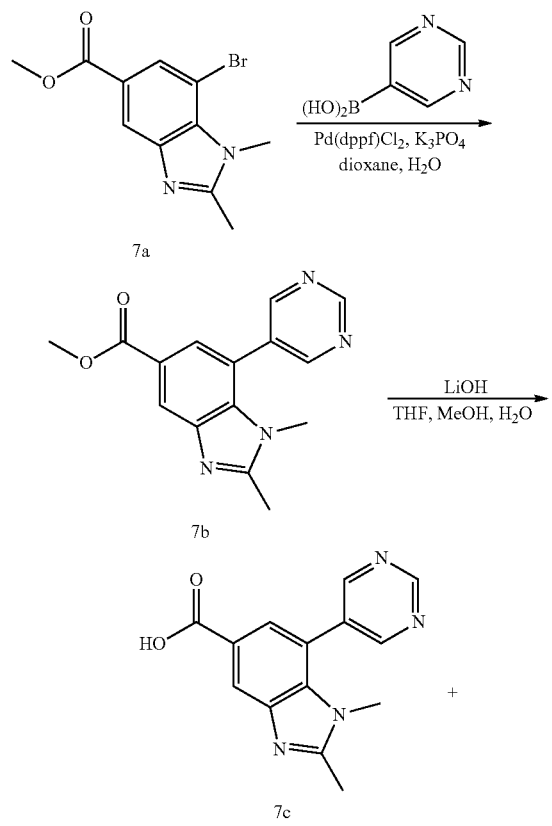

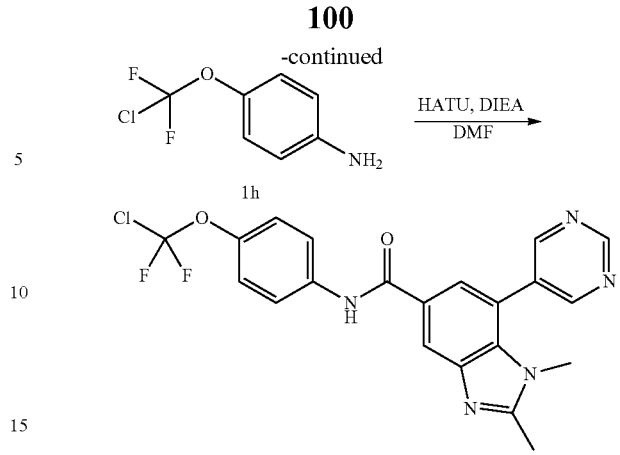

Methyl 1,2-dimethyl-7-(pyrimidin-5-yl)-1H-benzo[d] imidazole-5-carboxylate (7b). To a mixture of methyl 7-bromo-1,2-dimethyl-1H-benzo[d]imidazole-5-carboxylate (synthesized in a similar fashion to 1e; 7a, 0.15 g, 0.53 mmol, 1 eq) and pyrimidin-5-ylboronic acid (65.65 mg, 0.53 mmol, 1 eq) in dioxane (5 mL) and H$_2$O (0.5 mL) under N$_2$ was added Pd(dppf)Cl$_2$ (38.77 mg, 0.53 mmol, 0.1 eq) and K$_3$PO$_4$.3H$_2$O (423.28 mg, 1.59 mmol, 3 eq). The mixture was stirred at 110° C. for 16 hours. TLC (ethyl acetate:methanol=8:1, R$_f$=0.20) indicated 7a was consumed completely, and one major new spot with larger polarity was detected. LC-MS showed 7a was consumed completely and one main peak with desired mass was detected. The mixture was filtered and concentrated to give a residue that was purified by prep-TLC (SiO$_2$, ethyl acetate:methanol=8:1) to afford 7b as a light brown solid. $^1$H NMR (400 MHz, DMSO-d$_6$) δ 9.30 (s, 1H), 9.01 (s, 2H), 8.21 (d, J=1.3 Hz, 1H), 7.67 (d, J=1.3 Hz, 1H), 3.87 (s, 3H), 3.32-3.31 (m, 3H), 2.55 (s, 3H).

1,2-Dimethyl-7-(pyrimidin-5-yl)-1H-benzo[d]imidazole-5-carboxylic acid (7c). To a solution of methyl 1,2-dimethyl-7-(pyrimidin-5-yl)-1H-benzo[d]imidazole-5-carboxylate (7b, 0.06 g, 0.213 mmol, 1 eq) in THF (2 mL), MeOH (2 mL), H$_2$O (1 mL) was added LiOH.H$_2$O (17.84 mg, 0.425 mmol, 2 eq). The mixture was stirred at 50° C. for 3 hours. LC-MS showed 7b was consumed completely and one main peak with desired mass was detected. The mixture was adjusted to pH=5 with HCl aqueous (1M) and concentrated to give 7c as a brown solid. The product was used in the next step without further purification.

N-(4-(chlorodifluoromethoxy)phenyl)-1,2-dimethyl-7-(pyrimidin-5-yl)-1H-benzo[d]imidazole-5-carboxamide (7) To a mixture of 1,2-dimethyl-7-(pyrimidin-5-yl)-1H-benzo[d]imidazole-5-carboxylic acid (7c, 0.057 g, 0.212 mmol, 1 eq) and 4-(chlorodifluoromethoxy)aniline (1h, 45.24 mg, 0.234 mmol, 1.1 eq), HATU (96.95 mg, 0.255 mmol, 1.2 eq) in DMF (2 mL) was added DIEA (82.38 mg, 0.637 mmol, 111.03 uL, 3 eq). The mixture was stirred at 15° C. for 12 hours. LC-MS showed 7c was consumed completely and one main peak with desired mass was detected. The mixture was concentrated to give a crude residue that was purified by prep-HPLC (FA condition: column: Nano-micro Kromasil C18 100*30 mm 5 um; mobile phase: [water (0.225% FA)-ACN]; B %: 1%-50%, 15 min) to yield the title compound 7 as a white solid. MS mass calculated for [M+H]$^+$ (C$_{21}$H$_{16}$ClF$_2$N$_5$O$_2$) requires m/z 444.1, LCMS found m/z 444.2. $^1$H NMR (400 MHz, DMSO-d$_6$) δ 10.42 (s, 1H), 9.32

(s, 1H), 9.06 (s, 2H), 8.35 (d, J=1.3 Hz, 1H), 7.92 (d, J=9.0 Hz, 2H), 7.76 (d, J=1.5 Hz, 1H), 7.36 (d, J=9.0 Hz, 2H), 3.37 (s, 3H), 2.57 (s, 3H).

Example 8

General Procedure G

N-[4-[chloro(difluoro)methoxy]phenyl]-6-pyrimidin-5-yl-3,4-dihydro-1H-[1,4]oxazino[4,3-a]benzimidazole-8-carboxamide The title compound was prepared according to Scheme 7. This General Procedure G exemplifies Scheme 7 and provides particular synthetic details as applied to the title compound.

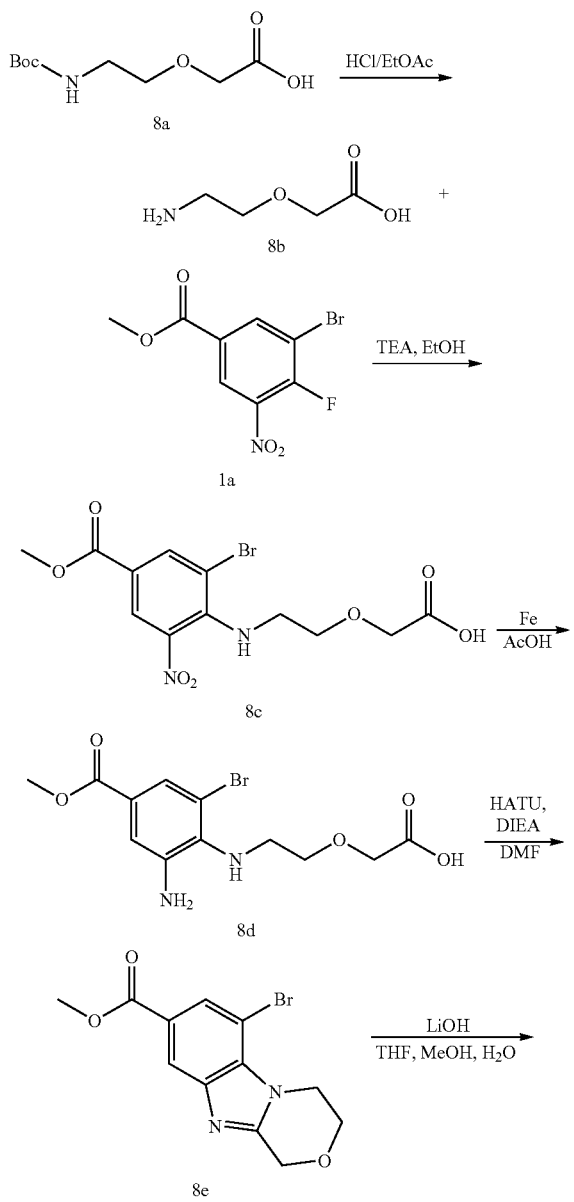

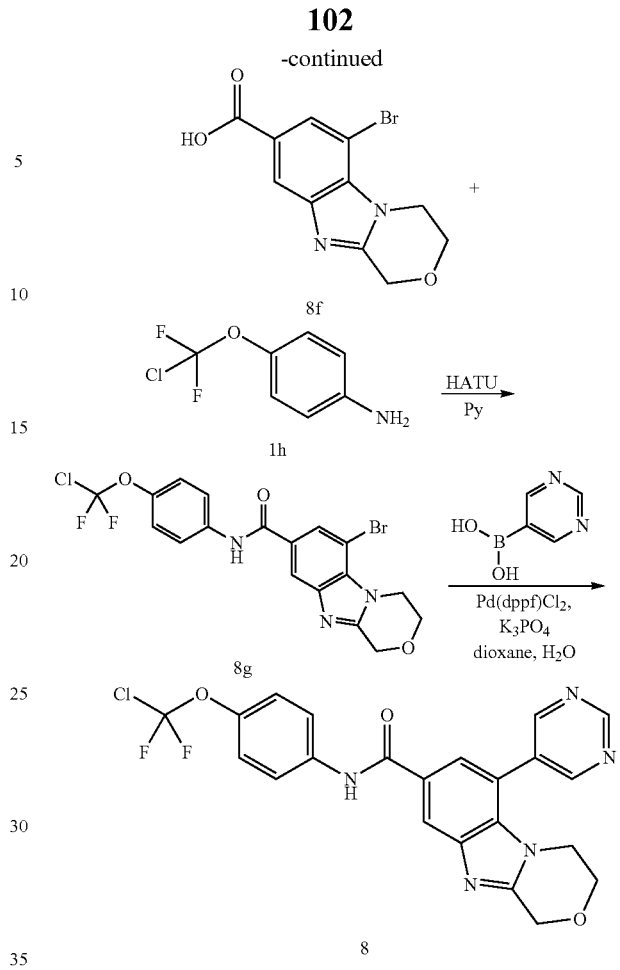

2-(2-Aminoethoxy)acetic acid (8b). A solution of 2-[2-(tert-butoxycarbonylamino)ethoxy]acetic acid (8a, 800 mg, 3.65 mmol, 1 eq) in HCl/EtOAc (5 mL) was stirred at 15° C. for 2 hr. LCMS showed 8) was consumed completely and desired MS was detected. The mixture was filtered and concentrated under reduced pressure to give 8b as a white solid. The product was used in the next step without further purification. $^1$H NMR (400 MHz, DMSO-$d_6$) δ 12.76 (br s, 1H) 8.09 (br s, 3H) 4.06 (s, 2H) 3.66 (t, J=5.2 Hz, 2H) 2.87-3.02 (m, 2H).

2-[2-(2-Bromo-4-methoxycarbonyl-6-nitro-anilino) ethoxy]acetic acid (8c). To a solution of methyl 3-bromo-4-fluoro-5-nitrobenzoate (1a, 500 mg, 1.80 mmol, 1 eq) and 2-(2-aminoethoxy)acetic acid (8b, 335.75 mg, 2.16 mmol, 1.2 eq, HCl) in EtOH (10 mL) was added TEA (454.94 mg, 4.50 mmol, 625.78 uL, 2.5 eq). The mixture was stirred at 15° C. for 1 hr. LCMS showed 1a was consumed completely and desired MS was detected. The reaction mixture was concentrated under reduced pressure. The mixture was diluted with water (25 mL) and extracted with EtOAc (20 mL×3). The combined organic layers were washed with brine (15 mL), dried over $Na_2SO_4$, filtered and concentrated under reduced pressure to give the crude residue. The residue was purified by silica gel chromatography (column height: 250 mm, diameter: 100 mm, 200-300 mesh silica gel, petroleum ether/ethyl acetate=5/1, ethyl acetate/methanol/$CH_3COOH$=5/1/0.1%) to afford 8c as a yellow solid. $^1$H NMR (400 MHz, DMSO-$d_6$) δ 8.28 (d, J=1.7 Hz, 1H) 8.18 (d, J=1.7 Hz, 1H) 7.09 (br s, 1H) 3.89 (s, 2H) 3.83 (s, 3H) 3.65 (br t, J=5.0 Hz, 2H) 3.19-3.28 (m, 2H).

2-[2-(2-Amino-6-bromo-4-methoxycarbonyl-anilino)ethoxy]acetic acid (8d). To a solution of 2-[2-(2-bromo-4-methoxycarbonyl-6-nitro-anilino)ethoxy]acetic acid (8c, 420 mg, 1.11 mmol, 1 eq) in AcOH (5 mL) was added Fe (621.91 mg, 11.14 mmol, 10 eq). The reaction mixture was stirred at 35° C. for 1 hr. LCMS showed 8c was consumed completely and desired MS was detected. The mixture was filtered through a Celite® pad and washed with ethyl acetate. The mixture was concentrated under reduced pressure to give the crude residue that was purified by prep-HPLC (HCl condition, column: Phenomenex Luna C18 200*40 mm*10 um; mobile phase: [water (0.05% HCl)-ACN]; B %: 15%-45%,10 min) to give 8d as a yellow solid. $^1$H NMR (400 MHz, DMSO-$d_6$) δ 7.53 (s, 1H) 7.49 (s, 1H) 4.16 (br s, 2H) 4.05 (s, 3H) 3.60 (br t, J=4.9 Hz, 2H) 3.26-3.35 (m, 2H).

Methyl 6-bromo-3,4-dihydro-1H-[1,4]oxazino[4,3-a]benzimidazole-8-carboxylate (8e). To a solution of 2-[2-(2-amino-6-bromo-4-methoxycarbonyl-anilino)ethoxy]acetic acid (8d, 100 mg, 0.261 mmol, 1 eq, HCl) in DMF (20 mL) was added HATU (109.03 mg, 0.287 mmol, 1.1 eq) and DIEA (101.07 mg, 0.782 mmol, 136.21 uL, 3 eq). The mixture was stirred at 20° C. for 16 hr. LCMS showed 8d was consumed completely and desired MS was detected. The mixture was diluted with water (5 mL) and extracted with EtOAc (5 mL×3). The combined organic layers were washed with brine (5 mL), dried over $Na_2SO_4$, filtered and concentrated under reduced pressure to give the crude residue. The residue was purified by prep-TLC ($SiO_2$, petroleum ether:ethyl acetate=0:1) to afford 8e as a white solid. $^1$H NMR (400 MHz, CDCl$_3$-d) δ 8.34 (d, J=1.3 Hz, 1H) 8.11 (d, J=1.3 Hz, 1H) 5.05 (s, 2H) 4.71 (t, J=5.3 Hz, 2H) 4.15-4.26 (m, 2H) 3.95 (s, 3H).

6-Bromo-3,4-dihydro-1H-[1,4]oxazino[4,3-a]benzimidazole-8-carboxylic acid (8f). To a solution of Methyl 6-bromo-3,4-dihydro-1H-[1,4]oxazino[4,3-a]benzimidazole-8-carboxylate (8e, 50 mg, 0.161 mmol, 1 eq) in MeOH (1 mL), THF (1 mL) and $H_2O$ (0.5 mL) was added LiOH.$H_2O$ (13.49 mg, 0.321 mmol, 2 eq). The mixture was stirred at 40° C. for 6 hr. TLC (petroleum ether:ethyl acetate=0:1, $R_f$=0) showed 8e was consumed completely and one major new spot with more polarity was detected. The mixture was concentrated in vacuo. The mixture was added to $H_2O$ (3 mL) and the aqueous phase was acidified to pH=5 with aqueous HCl. The mixture was concentrated in vacuo to afford 8f as a white solid. The product was used in the next step without further purification. $^1$H NMR (400 MHz, DMSO-$d_6$) δ 8.13 (d, J=1.2 Hz, 1H) 7.94 (d, J=1.3 Hz, 1H) 5.00 (s, 2H) 4.63 (t, J=5.3 Hz, 2H) 4.16 (t, J=5.3 Hz, 2H).

6-Bromo-N-[4-[chloro(difluoro)methoxy]phenyl]-3,4-dihydro-1H-[1,4]oxazino[4,3-a]benzimidazole-8-carboxamide (8g). To a solution of 6-bromo-3,4-dihydro-1H-[1,4]oxazino[4,3-a]benzimidazole-8-carboxylic acid (8f, 45 mg, 0.151 mmol, 1 eq) and 4-(chlorodifluoromethoxy)aniline (1h, 35.18 mg, 0.182 mmol, 1.2 eq) in pyridine (2 mL) was added HATU (69.11 mg, 0.182 mmol, 1.2 eq). The mixture was stirred at 40° C. for 6 hr. LCMS showed 8f was consumed completely and desired MS was detected. The mixture was diluted with water (5 mL) and extracted with EtOAc (5 mL×3). The combined organic layers were washed with brine (5 mL), dried over $Na_2SO_4$, filtered and concentrated under reduced pressure to give the crude residue. The residue was purified by prep-TLC ($SiO_2$, petroleum ether:ethyl acetate=0:1) to obtain 8g as a white solid. $^1$H NMR (400 MHz, CDCl$_3$-d) δ 8.11 (s, 1H) 8.00 (s, 1H) 7.96 (br s, 1H) 7.73 (d, J=8.9 Hz, 2H) 7.29 (br s, 2H) 5.06 (s, 2H) 4.73 (t, J=5.3 Hz, 2H) 4.22 (t, J=5.1 Hz, 2H).

N-[4-[chloro(difluoro)methoxy]phenyl]-6-pyrimidin-5-yl-3,4-dihydro-1H-[1,4]oxazino[4,3-a]benzimidazole-8-carboxamide (8). To a solution of 6-bromo-N-[4-[chloro(difluoro)methoxy]phenyl]-3,4-dihydro-1H-[1,4]oxazino[4,3-a]benzimidazole-8-carboxamide (8 g, 40 mg, 0.085 mmol, 1 eq) and pyrimidin-5-ylboronic acid (20.97 mg, 0.169 mmol, 2 eq) in dioxane (1 mL) and $H_2O$ (0.1 mL) was added Pd(dppf)Cl$_2$ (6.19 mg, 8.46 umol, 0.1 eq) and $K_3PO_4$ (53.89 mg, 0.254 mmol, 3 eq). The mixture was stirred at 110° C. for 16 hr. LCMS showed 8g was consumed completely and desired MS was detected. The mixture was diluted with water (15 mL) and extracted with EtOAc (15 mL×3). The combined organic layers were washed with brine (10 mL), dried over $Na_2SO_4$, filtered and concentrated under reduced pressure to give the crude residue. The residue was purified by prep-TLC ($SiO_2$, ethyl acetate:methanol=10:1) to afford the title compound 8 as a yellow solid. MS mass calculated for [M+H]$^+$ ($C_{22}H_{16}O_3N_5ClF_2$) requires m/z 472.1, LCMS found m/z 472.1 $^1$H NMR (400 MHz, DMSO-$d_6$) δ 10.46 (s, 1H) 9.32 (s, 1H) 9.10 (s, 2H) 8.42 (s, 1H) 7.93 (d, J=9.0 Hz, 2H) 7.82 (s, 1H) 7.26-7.45 (m, 1H) 7.36 (br d, J=8.8 Hz, 1H) 5.03 (s, 2H) 3.98 (br t, J=4.9 Hz, 2H) 3.70-3.83 (m, 2H).

Example 9

General Procedure H

N-(4-(chlorodifluoromethoxy)phenyl)-1-isopropyl-2-methoxy-7-(pyrimidin-5-yl)-1H-benzo[d]imidazole-5-carboxamide The title compound was prepared according to Scheme 8. This General Procedure H exemplifies Scheme 8 and provides particular synthetic details as applied to the title compound.

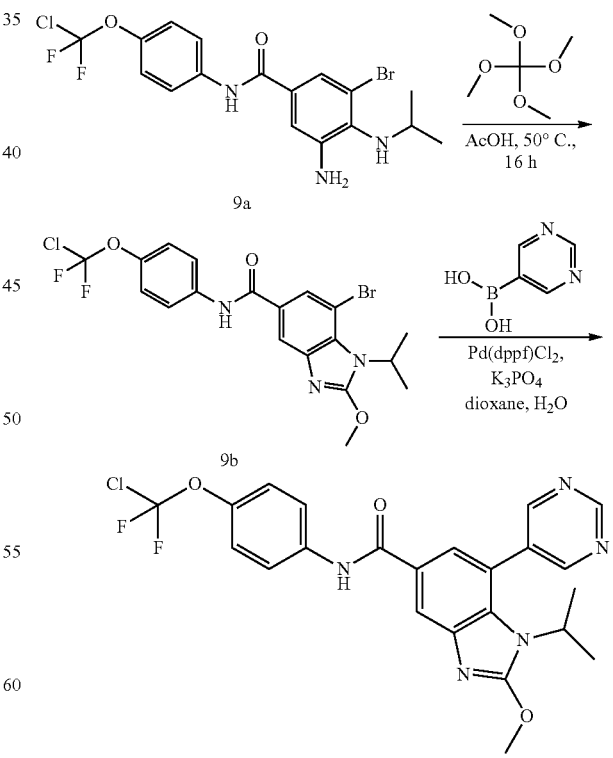

7-Bromo-N-(4-(chlorodifluoromethoxy)phenyl)-1-isopropyl-2-methoxy-1H-benzo[d]imidazole-5-carboxamide (9b). To a solution of 3-amino-5-bromo-N-(4-(chlorodifluoromethoxy)phenyl)-4-(isopropylamino)benzamide (synthesized in a similar fashion to 6c; 9a, 100 mg, 0.223 mmol, 1 eq) in AcOH (2 mL) was added tetramethoxymethane (197.23 mg, 1.45 mmol, 6.5 eq). The mixture was stirred at 50° C. for 16 hr. LCMS showed 9a was consumed completely and desired MS was detected. TLC (petroleum ether:ethyl acetate=3:1, $R_f$=0.4) showed 9a was consumed completely, one major new spot with less polarity was detected. The reaction mixture was concentrated under reduced pressure. The mixture was washed with saturated aqueous $NaHCO_3$, dried over $Na_2SO_4$ and evaporated to dryness. The crude residue was purified by prep-TLC ($SiO_2$, petroleum ether:ethyl acetate=3:1) to afford 9b as a white solid.

N-(4-(chlorodifluoromethoxy)phenyl)-1-isopropyl-2-methoxy-7-(pyrimidin-5-yl)-1H-benzo[d]imidazole-5-carboxamide (9). A mixture of 7-bromo-N-(4-(chlorodifluoromethoxy)phenyl)-1-isopropyl-2-methoxy-1H-benzo[d]imidazole-5-carboxamide (9b, 40 mg, 0.082 mmol, 1 eq), pyrimidin-5-ylboronic acid (30.42 mg, 0.246 mmol, 3 eq), Pd (dppf) $Cl_2$ (5.99 mg, 8.18 umol, 0.1 eq) and $K_3PO_4$ (52.12 mg, 0.246 mmol, 3 eq) in dioxane (4 mL) and $H_2O$ (0.4 mL) was degassed and purged with $N_2$ 3 times. The mixture was stirred at 110° C. for 16 hr under $N_2$ atmosphere. LCMS showed 9b was consumed completely and desired MS was detected. The reaction mixture was concentrated under reduced pressure. The residue was purified by prep-TLC ($SiO_2$, petroleum ether:ethyl acetate=1:1) to yield the title compound 9 as a white solid. MS mass calculated for $[M+1]^+$ ($C_{23}H_{20}ClF_2N_5O_3$) requires m/z 488.1, LCMS found m/z 488.0. $^1$H NMR (400 MHz, DMSO-$d_6$) δ 10.33 (s, 1H), 9.33 (s, 1H), 9.06 (s, 2H), 8.21 (d, J=1.5 Hz, 1H), 7.94-7.89 (m, 2H), 7.64 (d, J=1.5 Hz, 1H), 7.35 (d, J=9.0 Hz, 2H), 4.18 (s, 3H), 3.99-3.91 (m, 1H), 1.29 (d, J=6.8 Hz, 6H).

Example 10

N-(4-(chlorodifluoromethoxy)phenyl)-7-(4-cyclopropyl-1H-imidazol-1-yl)-1-isopropyl-1H-benzo[d]imidazole-5-carboxamide

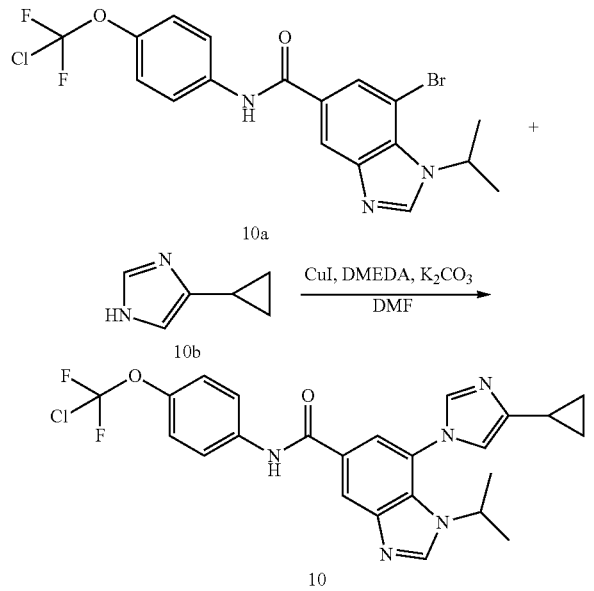

N-(4-(chlorodifluoromethoxy)phenyl)-7-(4-cyclopropyl-1H-imidazol-1-yl)-1-isopropyl-1H-benzo[d]imidazole-5-carboxamide (10). A mixture of 7-bromo-N-(4-(chlorodifluoromethoxy)phenyl)-1-isopropyl-1H-benzo[d]imidazole-5-carboxamide (synthesized in a similar fashion to 2c; 10a, 50 mg, 0.109 mmol, 1 eq), 4-cyclopropyl-1H-imidazole (10b, 23.58 mg, 0.218 mmol, 2 eq), CuI (20.76 mg, 0.109 mmol, 1 eq), $K_2CO_3$ (150.65 mg, 1.09 mmol, 10 eq) and DMEDA (19.22 mg, 0.218 mmol, 23.47 μL, 2 eq) in DMF (2 mL) was degassed and purged with $N_2$ 3 times before the mixture was stirred at 140° C. for 16 hr under $N_2$ atmosphere. The reaction mixture was concentrated, and the aqueous phase was extracted with ethyl acetate (30 mL). The combined organic layers were washed with brine (5 mL), dried over anhydrous $Na_2SO_4$, filtered and concentrated in vacuo. The crude product was purified by prep-TLC (ethyl acetate:methanol=10:1, $R_f$=0.2) to give the crude product, which was further purified by prep-HPLC ($NH_4HCO_3$, column: Waters Xbridge Prep OBD C18 150*30 10 u; mobile phase: [water (10 mM $NH_4HCO_3$)-ACN]; B %: 35%-55%,10 min) to give title compound 10 as a white solid. MS mass calculated for $[M+1]^+$ ($C_{24}H_{22}ClF_2N_5O_2$) requires m/z 486.1, LCMS found m/z 486.1; $^1$H NMR (400 MHz, MeOD-$d_4$) δ 8.61 (s, 1H), 8.49 (d, J=1.5 Hz, 1H), 7.92 (s, 2H), 7.87-7.81 (m, 2H), 7.33-7.24 (m, 3H), 3.78 (td, J=6.7, 13.4 Hz, 1H), 2.01-1.89 (m, 1H), 1.46 (br s, 6H), 0.93 (dd, J=2.0, 8.4 Hz, 2H), 0.77 (br s, 2H).

Example 11

N-(4-(chlorodifluoromethoxy)phenyl)-7-(1H-imidazol-1-yl)-1-isopropyl-1H-benzo[d]imidazole-5-carboxamide

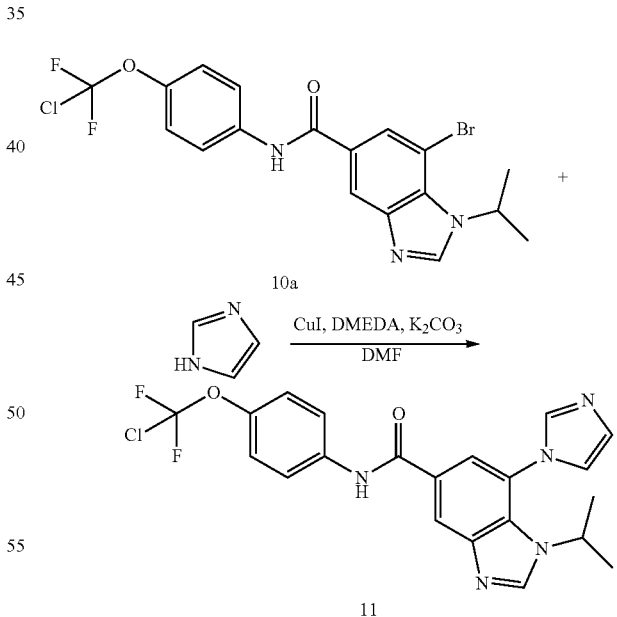

N-(4-(chlorodifluoromethoxy)phenyl)-7-(1H-imidazol-1-yl)-1-isopropyl-1H-benzo[d]imidazole-5-carboxamide (11). To a solution of 7-bromo-N-(4-(chlorodifluoromethoxy)phenyl)-1-isopropyl-1H-benzo[d]imidazole-5-carboxamide (10a, 200 mg, 0.436 mmol, 1 eq) and imidazole (148.42 mg, 2.18 mmol, 5 eq) in DMF (2 mL) was added $K_2CO_3$ (602.64 mg, 4.36 mmol, 10 eq), CuI (83.04 mg, 0.436 mmol, 1 eq) and DMEDA (115.31 mg, 1.31 mmol, 140.79 uL, 3 eq). The mixture was stirred at 120° C. for 12 hrs. The mixture was dissolved in EtOAc (20 ml), washed with water (10 mL×5) and the organic layers were concentrated. The residue was purified by prep-HPLC (NH$_4$HCO$_3$ condition, column: Waters Xbridge Prep OBD C18 150*30 10 u; mobile phase: [water (10 mM NH$_4$HCO$_3$)-ACN]; B %: 35%-55%,10 min) to give title compound 11 as a white solid. MS mass calculated for [M+1]$^+$ (C$_{21}$H$_{18}$ClF$_2$N$_5$O$_2$) requires m/z 446.1, LCMS found m/z 446.1; $^1$H NMR (400 MHz, MeOD-d$_4$) δ 8.63 (s, 1H), 8.51 (d, J=1.5 Hz, 1H), 8.11 (s, 1H), 7.95 (d, J=1.5 Hz, 1H), 7.89-7.78 (m, 2H), 7.58 (d, J=1.3 Hz, 1H), 7.35-7.21 (m, 3H), 3.70 (quin, J=6.7 Hz, 1H), 1.43 (br s, 6H).

Example 12

N-(4-(chlorodifluoromethoxy)phenyl)-2-(2-hydroxyethyl)-1-methyl-7-(pyrimidin-5-yl)-1H-benzo[d]imidazole-5-carboxamide

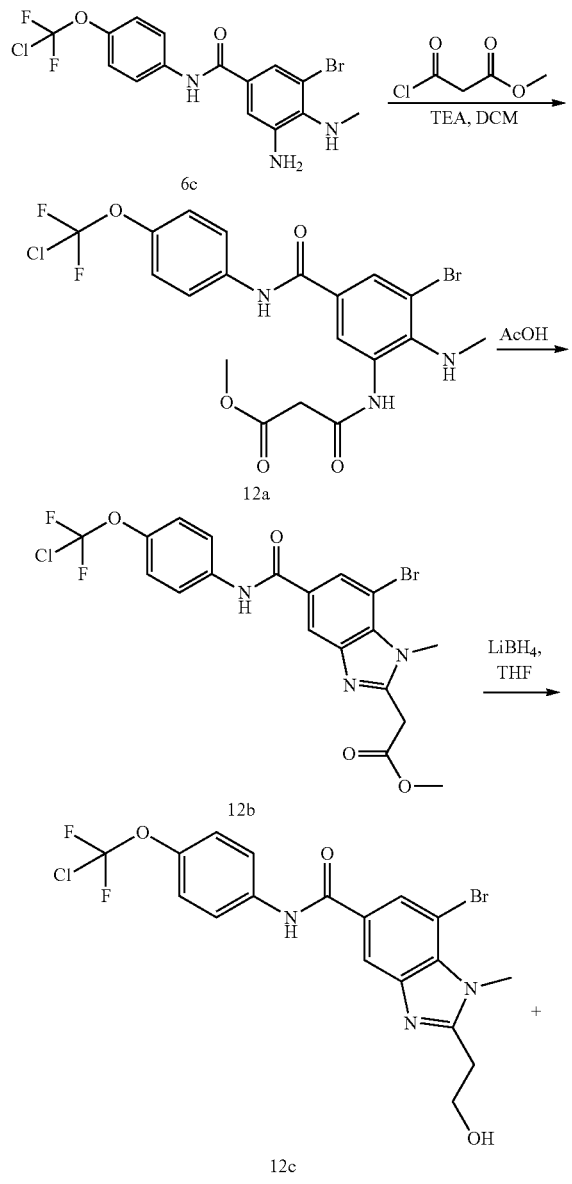

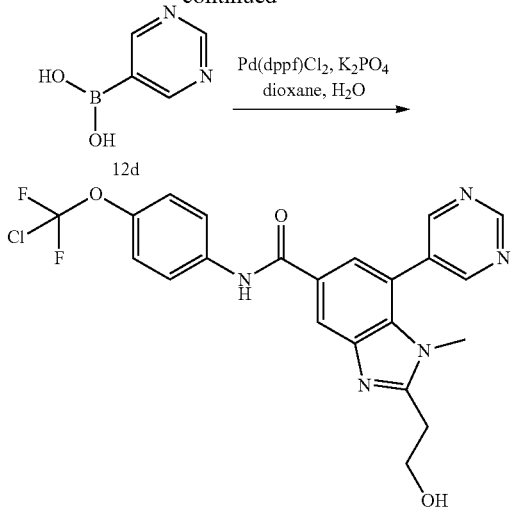

Methyl 3-((3-bromo-5-((4-(chlorodifluoromethoxy)phenyl)carbamoyl)-2-(methylamino)phenyl)amino)-3-oxopropanoate (12a). To a solution of 3-amino-5-bromo-N-(4-(chlorodifluoromethoxy)phenyl)-4-(methylamino) benzamide (6c, 300 mg, 0.713 mmol) and methyl 3-chloro-3-oxo-propanoate (107.11 mg, 0.784 mmol, 83.68 uL, 1.1 eq) in DCM was added TEA (72.17 mg, 0.713 mmol, 99.27 uL, 1 eq) drop-wise. The mixture was warmed to 30° C. and stirred for 0.5 hr. The reaction mixture was concentrated under reduced pressure to remove solvent. The residue was purified by prep-TLC (SiO$_2$, petroleum ether:ethyl acetate=1:1) to give 12a as a brown solid.

Methyl 2-(7-bromo-5-((4-(chlorodifluoromethoxy)phenyl)carbamoyl)-1-methyl-1H-benzo[d]imidazol-2-yl)acetate (12b). A solution of methyl 3-(3-bromo-5-(4-(chlorodifluoromethoxy)phenyl)carbamoyl)-2-(methylamino) phenyl)amino)-3-oxopropanoate (12a, 130 mg, 0.25 mmol) in AcOH was heated to 60° C. and stirred for 6 hours. LC-MS showed reactant was consumed completely and one main peak with desired mass was detected. The mixture was poured into EtOAc and the mixture was washed with water, saturated NaHCO$_3$ and brine. The combined organic layers were dried over Na$_2$SO$_4$ and concentrated. The residue was purified by prep-TLC to give 12b as a yellow solid.

7-Bromo-N-(4-(chlorodifluoromethoxy)phenyl)-2-(2-hydroxyethyl)-1-methyl-1H-benzo[d]imidazole-5-carboxamide (12c). To a solution of methyl 2-(7-bromo-5-((4-(chlorodifluoromethoxy)phenyl)carbamoyl)-1-methyl-1H-benzo[d]imidazol-2-yl)acetate (12b, 50 mg, 0.099 mmol, 1 eq) in THF at 20° C. was added LiBH$_4$ (10.83 mg, 0.497 mmol, 5 eq) slowly in one portion under N$_2$. The mixture was heated to 30° C. and stirred for 50 min. LC-MS showed reactant was consumed completely and one main peak with desired mass was detected. After the reaction mixture was cooled to 0° C., the reaction mixture was quenched by addition of H$_2$O, and acidified with 1N HCl to pH=6. The reaction mixture was concentrated under reduced pressure to remove solvent. The residue was purified by prep-TLC (SiO$_2$, ethyl acetate:methanol=10:1) to give 12c as a yellow solid.

N-(4-(chlorodifluoromethoxy)phenyl)-2-(2-hydroxyethyl)-1-methyl-7-(pyrimidin-5-yl)-1H-benzo[d]imidazole-5-carboxamide (12). To a mixture of 7-bromo-N-(4-(chlorodifluoromethoxy)phenyl)-2-(2-hydroxyethyl)-1-methyl-1H-benzo[d]imidazole-5-carboxamide (12c, 40 mg, 0.084 mmol, 1 eq) and pyrimidin-5-ylboronic acid (12e, 20.88 mg, 0.169 mmol, 2 eq) in dioxane (3 mL) and H$_2$O (0.3 mL) at 20° C. under N$_2$ was added Pd(dppf)Cl$_2$ (6.17 mg, 8.43 umol, 0.1 eq) and K$_3$PO$_4$ (53.66 mg, 0.253 mmol, 3 eq) in one portion. The mixture was heated to 110° C. and stirred for 12 hours. LC-MS showed reactant was consumed completely and one main peak with desired mass was detected. The mixture was filtered through a Celite® pad, and the filtrate was concentrated to give crude product, which was purified by prep-HPLC (FA condition, column: Waters Atlantis T3 150*30*5 um; mobile phase: [water (0.225% FA)-ACN]; B %: 10%-50%,13 min) to afford the title compound 12 as a white solid. MS mass calculated for [M+1]$^+$ (C$_{22}$H$_{18}$ClF$_2$N$_5$O$_3$) requires m/z 474.1, LCMS found m/z 474.0; $^1$H NMR (400 MHz, DMSO-d$_6$) δ 10.43 (s, 1H), 9.33 (s, 1H), 9.07 (s, 2H), 8.40 (s, 1H), 7.94 (d, J=9.2 Hz, 2H), 7.77 (s, 1H), 7.37 (d, J=9.0 Hz, 2H), 4.89 (t, J=5.6 Hz, 1H), 3.96-3.86 (m, 2H), 3.41 (s, 3H), 3.07 (t, J=6.9 Hz, 2H).

Example 13

N$^5$-(4-(chlorodifluoromethoxy)phenyl)-N$^7$-cyclopropyl-1-isopropyl-1H-benzo[d]imidazole-5,7-dicarboxamide

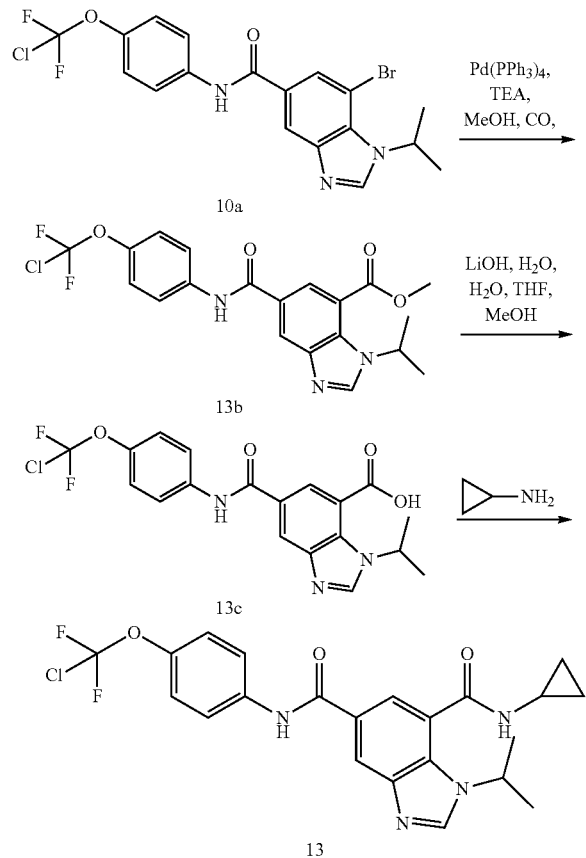

Methyl 5-((4-(chlorodifluoromethoxy)phenyl)carbamoyl)-1-isopropyl-1H-benzo[d]imidazole-7-carboxylate (13b). To a mixture of 7-bromo-N-(4-(chlorodifluoromethoxy)phenyl)-1-isopropyl-1H-benzo[d]imidazole-5-carboxamide (10a, 200 mg, 0.436 mmol, 1 eq) and TEA (176.49 mg, 1.74 mmol, 242.76 uL, 4 eq) in MeOH (20 mL) at 20° C. under N$_2$ was added Pd(PPh$_3$)$_4$ (50.39 mg, 0.044 mmol, 0.1 eq) in one portion. The mixture was heated to 100° C. and stirred for 24 hours under CO (0.436 mmol, 3 MPa). LC-MS showed ~60% of reactant remained. One new peak was observed by LC-MS and ~30% of the desired compound was detected. HPLC showed 60% of reactant remained. The mixture was filtered through a Celite® pad, and the filtrate was concentrated to give crude product. The residue was purified by prep-HPLC (NH$_4$HCO3, column: YMC-Actus Triart C18 100*30 mm*5 um; mobile phase: [water (10 mM NH4HCO3)-ACN]; B %: 45%-65%, 12 min) to give 13b as a white solid. $^1$H NMR (400 MHz, MeOD-d$_4$) δ 8.64 (s, 1H), 8.54 (d, J=1.7 Hz, 1H), 8.45 (d, J=1.7 Hz, 1H), 7.90-7.84 (m, 2H), 7.33 (d, J=9.0 Hz, 2H), 5.40 (td, J=6.6, 13.3 Hz, 1H), 4.06 (s, 3H), 1.62 (d, J=6.7 Hz, 6H).

5-((4-(Chlorodifluoromethoxy)phenyl)carbamoyl)-1-isopropyl-1H-benzo[d]imidazole-7-carboxylic acid (13c). To a mixture of methyl 5-(4-(chlorodifluoromethoxy)phenyl)carbamoyl)-1-isopropyl-1H-benzo[d]imidazole-7-carboxylate (13b, 10 mg, 0.023 mmol, 1 eq) in THF (1 mL), H$_2$O (1 mL) and MeOH (0.5 mL) at 20° C. was added LiOH.H$_2$O (1.92 mg, 0.046 mmol, 2 eq) in one portion. The mixture was heated to 45° C. and stirred for 2 hours. LC-MS showed that the reactant was consumed completely and one main peak with the desired mass was detected. The reaction mixture was concentrated under reduced pressure to remove solvent. The residue was poured into H$_2$O (0.5 mL) and acidified with 1N HCl to pH=5. The mixture was filtered, and the filter cake was washed with 0.5 mL of H$_2$O and dried in vacuo to give the crude product. The crude residue 13c was obtained as a white solid and used into the next step without further purification.

N$^5$-(4-(chlorodifluoromethoxy)phenyl)-N$^7$-cyclopropyl-1-isopropyl-1H-benzo[d]imidazole-5,7-dicarboxamide (13). To a mixture of 5-(4-(chlorodifluoromethoxy)phenyl)carbamoyl)-1-isopropyl-1H-benzo[d]imidazole-7-carboxylic acid (13c, 40 mg, 0.094 mmol, 1 eq) and cyclopropanamine (6.47 mg, 0.113 mmol, 7.85 uL, 1.2 eq) in DMF (2 mL) at 20° C. was added HATU (39.48 mg, 0.104 mmol, 1.1 eq) and DIEA (24.40 mg, 0.189 mmol, 32.88 uL, 2 eq) in one portion. The mixture was stirred at 20° C. for 12 h. LC-MS showed 40% of reactant remained. One new peak was observed on LC-MS and 60% of the desired compound was detected. The reaction mixture was concentrated under reduced pressure to remove solvent. EtOAc (15 mL) was added to the residue. The organic layers were washed with H$_2$O (10 mL) and brine (10 mL), dried by Na$_2$SO$_4$ and concentrated under reduced pressure to give the crude product. The residue was purified by prep-TLC (SiO$_2$, EtOAc:MeOH=10:1) to give the title compound 13 as a white solid. MS mass calculated for [M+1]$^+$ (C$_{22}$H$_{21}$ClF$_2$N$_4$O$_3$) requires m/z 463.1, LCMS found m/z 463.1; $^1$H NMR (400 MHz, DMSO-d$_6$) δ 10.49 (s, 1H), 8.88 (d, J=4.3 Hz, 1H), 8.61 (s, 1H), 8.48 (d, J=1.6 Hz, 1H), 7.96 (d, J=9.0 Hz, 2H), 7.89 (d, J=1.6 Hz, 1H), 7.37 (d, J=9.0 Hz, 2H), 4.96 (quin, J=6.7 Hz, 1H), 3.02-2.87 (m, 1H), 1.50 (d, J=6.7 Hz, 6H), 0.85-0.70 (m, 2H), 0.65-0.56 (m, 2H).

Example 14

N-(4-(chlorodifluoromethoxy)phenyl)-1-((1-hydroxy-cyclopropyl)methyl)-7-(pyrimidin-5-yl)-1H-benzo[d]imidazole-5-carboxamide

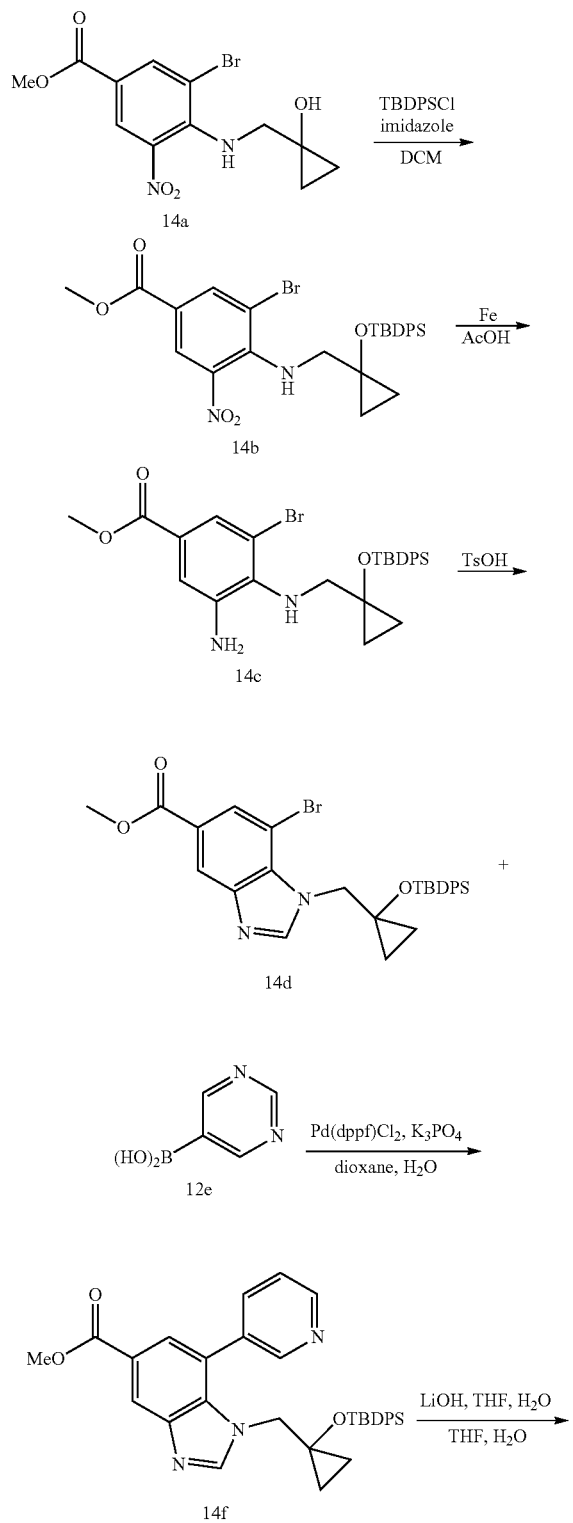

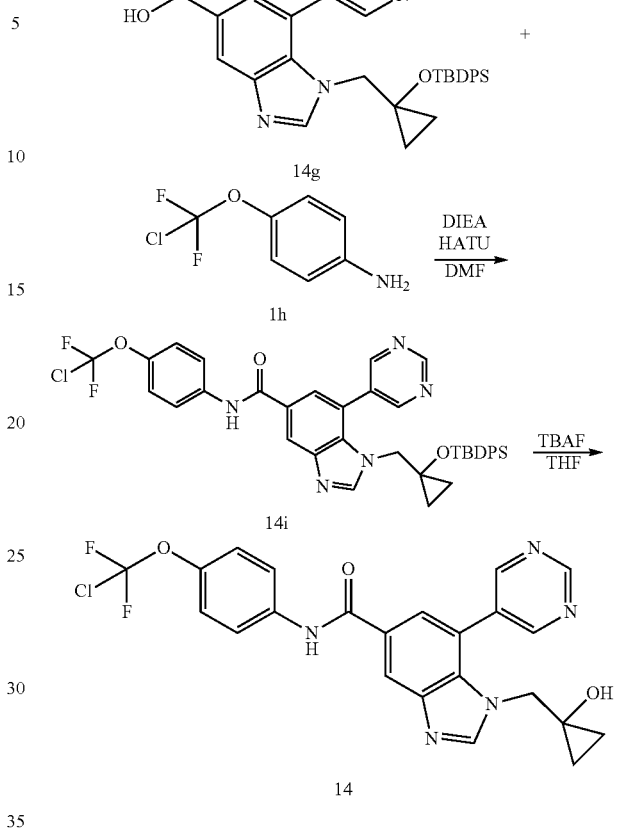

Methyl 3-bromo-4-(((1-((tert-butyldiphenylsilyl)oxy)cyclopropyl)methyl)amino)-5-nitrobenzoate (14b). A mixture of methyl 3-bromo-4-(((1-hydroxycyclopropyl)methyl)amino)-5-nitrobenzoate (synthesized in similar fashion to 1c; 14a, 0.48 g, 1.39 mmol, 1 eq), imidazole (142.02 mg, 2.09 mmol, 1.5 eq) and TBDPSCl (458.70 mg, 1.67 mmol, 428.69 uL, 1.2 eq) in DCM (5 mL) at 25° C. was stirred at 25° C. for 16 hrs. Water (10 ml) was added and the mixture was extracted with DCM (20 mL×3). The organic layers were dried over $Na_2SO_4$ and concentrated to give the crude product. The crude residue was purified by column chromatography to give 1c as a yellow oil. $^1H$ NMR (400 MHz, $CDCl_3$-d) δ 8.43 (d, J=2.0 Hz, 1H), 8.22 (d, J=2.0 Hz, 1H), 7.55-7.48 (m, 4H), 7.39-7.28 (m, 6H), 6.94-6.84 (m, 1H), 3.85 (s, 3H), 2.92 (d, J=4.4 Hz, 2H), 0.89 (s, 9H), 0.84-0.79 (m, 2H), 0.39-0.29 (m, 2H).

Methyl 3-amino-5-bromo-4-(((1-((tert-butyldiphenylsilyl)oxy)cyclopropyl)methyl)amino)benzoate (14c). A solution of methyl 3-bromo-4-(((1-((tert-butyldiphenylsilyl)oxy)cyclopropyl)methyl)amino)-5-nitrobenzoate (14b, 634 mg, 1.09 mmol, 1 eq) and Fe (606.79 mg, 10.86 mmol, 10 eq) in AcOH (7 mL) was stirred at 35° C. for 1 hr. EtOAc (20 ml) was added and the mixture was filtered. The filtrate was washed with water (20 mL×3), the organic layers were dried over $Na_2SO_4$ and the mixture was concentrated. Compound 14c was obtained as a yellow oil and required no further purification. $^1H$ NMR (400 MHz, CHLOROFORM-d) δ 7.67-7.63 (m, 4H), 7.54 (d, J=1.7 Hz, 1H), 7.37-7.30 (m, 6H), 7.17 (d, J=1.8 Hz, 1H), 3.79 (s, 3H), 2.84 (s, 2H), 1.00-0.98 (m, 9H), 0.76-0.67 (m, 2H), 0.33-0.21 (m, 2H).

Methyl 7-bromo-1-((1-(tert-butyldiphenylsilyl)oxy)cyclopropyl)methyl)-1H-benzo[d]imidazole-5-carboxylate (14d). A solution of methyl 3-amino-5-bromo-4-(((1-((tert-butyldiphenylsilyl)oxy)cyclopropyl)methyl)amino)benzoate (14c, 0.6 g, 1.08 mmol, 1 eq) and TsOH (18.66 mg, 0.108 mmol, 0.1 eq) in CH(OMe)$_3$ (10 mL) was stirred at 100° C. for 1 hr. The crude product was washed with TMBE/PE, the mixture was filtrated and the solid was concentrated. No further purification was required. Compound 14d was obtained as a yellow solid. $^1$H NMR (400 MHz, CDCl$_3$-d) δ 8.46 (s, 1H), 8.38 (s, 1H), 8.12 (s, 1H), 7.61 (d, J=7.1 Hz, 4H), 7.48-7.41 (m, 2H), 7.39-7.33 (m, 4H), 4.52 (s, 2H), 3.98 (s, 3H), 1.05-0.93 (m, 11H), 0.67-0.54 (m, 2H).

Methyl 1-((1-((tert-butyldiphenylsilyl)oxy)cyclopropyl)methyl)-7-(pyridin-3-yl)-1H-benzo[d]imidazole-5-carboxylate (14f). To a solution of methyl 7-bromo-1-((1-((tert-butyldiphenylsilyl)oxy)cyclopropyl)methyl)-1H-benzo[d]imidazole-5-carboxylate (14d, 440 mg, 0.781 mmol, 1 eq) and 12e (116.09 mg, 0.934 mmol, 1.2 eq) in dioxane (5 mL) and H$_2$O (1 mL) under N$_2$ was added K$_3$PO$_4$ (497.19 mg, 2.34 mmol, 3 eq) and Pd(dppf)Cl$_2$ (28.56 mg, 0.039 mmol, 0.05 eq). The mixture was stirred at 100° C. for 4 hrs. The mixture was concentrated, and the residue was purified by column chromatography. Compound 14f was obtained as a yellow solid. $^1$H NMR (400 MHz, CDCl$_3$-d) δ 9.20 (s, 1H), 8.60-8.52 (m, 2H), 8.39 (s, 2H), 7.70 (d, J=1.5 Hz, 1H), 7.34-7.23 (m, 6H), 7.16-7.09 (m, 4H), 3.92 (s, 3H), 3.36 (s, 2H), 0.87-0.76 (m, 11H), 0.30-0.23 (m, 2H).

1-((1-((Tert-butyldiphenylsilyl)oxy)cyclopropyl)methyl)-7-(pyridin-3-yl)-1H-benzo[d]imidazole-5-carboxylic acid (14g). To a solution of methyl 1-((1-((tert-butyldiphenylsilyl)oxy)cyclopropyl)methyl)-7-(pyridin-3-yl)-1H-benzo[d]imidazole-5-carboxylate (14f, 360 mg, 0.64 mmol, 1 eq) in THF (3 mL), MeOH and H$_2$O (2 mL) at 25° C. was added LiOH.H$_2$O (40.26 mg, 0.96 mmol, 1.5 eq). The reaction was stirred at 25° C. for 3 hrs. The reaction mixture was concentrated under reduced pressure. Water (5 ml) was added and the mixture was extracted with EtOAc (10 ml). Aqueous HCl (1M) was added until the aqueous phase reached pH=3~4. The aqueous phase was again extracted with EtOAc (10 mL×3), the organic layers were dried over Na$_2$SO$_4$, filtered and concentrated, to give the crude product. No further purification was required. Compound 14g was obtained as a red solid.

1-((1-((Tert-butyldiphenylsilyl)oxy)cyclopropyl)methyl)-N-(4-(chlorodifluoromethoxy)phenyl)-7-(pyrimidin-5-yl)-1H-benzo[d]imidazole-5-carboxamide (14i). To a solution of 1-((1-((tert-butyldiphenylsilyl)oxy)cyclopropyl)methyl)-7-(pyridin-3-yl)-1H-benzo[d]imidazole-5-carboxylic acid (14 g, 90 mg, 0.164 mmol, 1 eq) and 1 h (38.10 mg, 0.197 mmol, 1.2 eq) in DMF (3 mL) at 25° C. was added DIPEA (63.59 mg, 0.492 mmol, 85.71 uL, 3 eq) and HATU (93.55 mg, 0.246 mmol, 1.5 eq). The mixture was stirred at 25° C. for 12 hrs. EtOAc (10 ml) was added, the mixture was washed with water (10 mL×5), the organic layers were dried over Na$_2$SO$_4$ and concentrated to give the crude product. The residue was purified by column chromatography. Compound 14i was obtained as a light-yellow solid.

N-(4-(chlorodifluoromethoxy)phenyl)-1-((1-hydroxycyclopropyl)methyl)-7-(pyrimidin-5-yl)-1H-benzo[d]imidazole-5-carboxamide (14). To a solution of 1-((1-((tert-butyldiphenylsilyl)oxy)cyclopropyl)methyl)-N-(4-(chlorodifluoromethoxy)phenyl)-7-(pyrimidin-5-yl)-1H-benzo[d]imidazole-5-carboxamide (14i, 0.03 g, 0.041 mmol, 1 eq) in dry THF (3 mL) at 25° C. under N$_2$ was added TBAF (1M, 41.42 uL, 1 eq). The mixture was stirred at 25° C. for 2 hrs and was concentrated. The residue was purified by prep-HPLC (NH$_4$HCO$_3$ condition, column: Waters Xbridge Prep OBD C18 150*30 10 u; mobile phase: [water (10 mM NH$_4$HCO$_3$)-ACN]; B %: 35%-55%, 10 min) to yield the title compound 14 as a yellow solid. MS mass calculated for [M+1]$^+$ (C$_{23}$H$_{18}$ClF$_2$N$_5$O$_3$) requires m/z 486.1, LCMS found m/z 486.1; $^1$H NMR (400 MHz, DMSO-d$_6$) δ 10.45 (s, 1H), 9.33 (s, 1H), 9.04 (s, 2H), 8.53 (s, 2H), 7.98-7.93 (m, J=9.2 Hz, 2H), 7.81 (s, 1H), 7.42-7.33 (m, J=9.0 Hz, 2H), 5.46 (s, 1H), 3.94 (s, 2H), 0.61-0.52 (m, 2H), 0.49-0.41 (m, 2H).

Example 15

N-(4-(chlorodifluoromethoxy)phenyl)-1-cyclopropyl-2-(difluoromethyl)-7-(pyrimidin-5-yl)-1H-benzo[d]imidazole-5-carboxamide

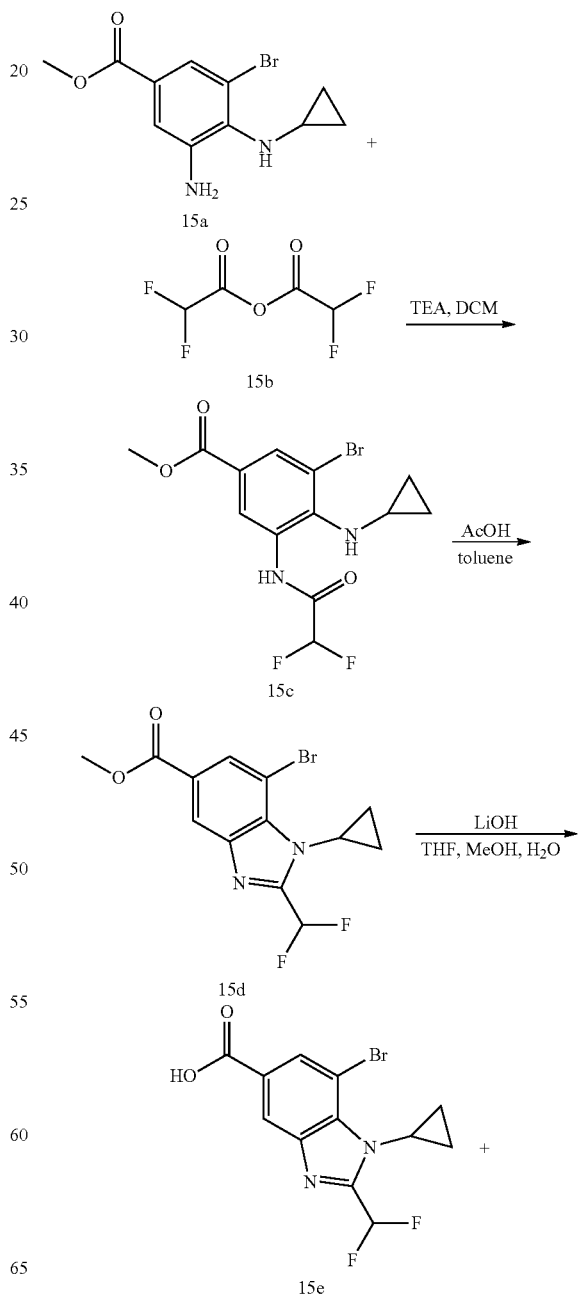

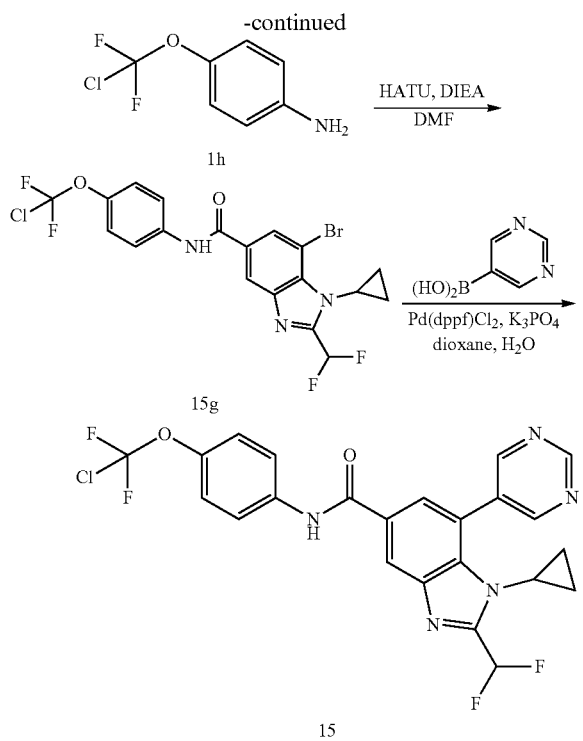

Methyl 3-bromo-4-(cyclopropylamino)-5-(2,2-difluoroacetamido)benzoate (15c). To a solution of methyl 3-amino-5-bromo-4-(cyclopropylamino)benzoate (synthesized in similar fashion to id; 15a, 200 mg, 0.701 mmol, 1 eq) in DCM (8 mL) at 0° C. was added TEA (212.93 mg, 2.10 mmol, 3 eq) and 2,2-difluoroacetic anhydride (15b) (122.08 mg, 0.701 mmol, 1 eq). The mixture was stirred at 15° C. for 2 hr under $N_2$ atmosphere. LCMS showed a peak with desired MS was detected. The reaction mixture was concentrated. The crude product was purified by prep-TLC (petroleum ether:ethyl acetate=3:1, $R_f$=0.4) to give 15c as a yellow solid.

Methyl 7-bromo-1-cyclopropyl-2-(difluoromethyl)-1H-benzo[d]imidazole-5-carboxylate (1d). To a solution of 15d (80 mg, 0.220 mmol, 1 eq) in toluene (3 mL) was added AcOH (1.32 mg, 0.022 mmol, 10 eq). The mixture was stirred at 60° C. for 16 hr. LCMS showed a peak with desired MS. The reaction mixture was concentrated, and the crude product was purified by prep-TLC (petroleum ether:ethyl acetate=1:1, $R_f$=0.4) to give 15d as a yellow solid. $^1$H NMR (400 MHz, CDCl$_3$-d) δ 8.43 (d, J=1.3 Hz, 1H), 8.29 (d, J=1.3 Hz, 1H), 7.18-6.85 (m, 1H), 3.97 (s, 3H), 3.70-3.60 (m, 1H), 1.46-1.39 (m, 2H), 1.39-1.34 (m, 2H)

7-Bromo-1-cyclopropyl-2-(difluoromethyl)-1H-benzo[d]imidazole-5-carboxylic acid (15e). To a solution of 15d (1520 mg, 0.058 mmol, 1 eq) in THF (1 mL), MeOH (1 mL) and H$_2$O (0.5 mL) was added LiOH.H$_2$O (4.86 mg, 0.116 mmol, 2 eq). The mixture was stirred at 50° C. for 2 hr. LCMS showed a peak with desired MS. The mixture was concentrated and poured into H$_2$O (1 mL), and the pH was adjusted to 5 by HCl (1M in H$_2$O). The mixture was concentrated to give 15e as a yellow solid. $^1$H NMR (400 MHz, CDCl$_3$-d) δ 8.49 (s, 1H), 8.32 (d, J=1.3 Hz, 1H), 7.04-6.89 (m, 1H), 3.65 (br dd, J=3.4, 7.2 Hz, 1H), 1.46-1.41 (m, 2H), 1.37 (br s, 2H).

7-Bromo-N-(4-(chlorodifluoromethoxy)phenyl)-1-cyclopropyl-2-(difluoromethyl)-1H-benzo[d]imidazole-5-carboxamide (15g). A mixture of 15e (18 mg, 0.054 mmol, 1 eq), 1h (15.79 mg, 0.082 mmol, 1.5 eq), HATU (31.01 mg, 0.082 mmol, 1.5 eq) and DIEA (21.08 mg, 0.163 mmol, 3 eq) in DMF (1 mL) was stirred at 15° C. for 2 hr. LCMS showed a peak with desired MS. The reaction mixture was concentrated, and the crude product was purified by prep-TLC (petroleum ether:ethyl acetate=2:1, $R_f$=0.5) to give 15g as a yellow solid. $^1$H NMR (400 MHz, CDCl$_3$-d) δ 8.20 (d, J=1.5 Hz, 1H), 8.16 (d, J=1.5 Hz, 1H), 7.85 (s, 1H), 7.72 (d, J=9.0 Hz, 2H), 7.30 (br s, 2H), 7.04 (s, 1H), 3.72 (br s, 1H), 1.47-1.42 (m, 2H), 1.37 (br d, J=4.4 Hz, 2H).

N-(4-(chlorodifluoromethoxy)phenyl)-1-cyclopropyl-2-(difluoromethyl)-7-(pyrimidin-5-yl)-1H-benzo[d]imidazole-5-carboxamide (15). A mixture of 15g (35 mg, 0.069 mmol, 1 eq), pyrimidin-5-ylboronic acid (25.68 mg, 0.207 mmol, 3 eq), Pd(dppf)Cl$_2$ (5.05 mg, 6.91 umol, 0.01 eq), K$_3$PO$_4$ (43.99 mg, 0.207 mmol, 3 eq) in dioxane (2 mL) and H$_2$O (0.2 mL) was degassed and purged with N$_2$ 3 times. The reaction mixture was stirred at 100° C. for 8 hr under N$_2$ atmosphere. LCMS showed a peak with desired MS. The reaction mixture was concentrated, and the crude product was purified by prep-TLC (petroleum ether:ethyl acetate=0:1, $R_f$=0.45) to give the title compound 15 as a white solid. MS mass calculated for [M+H]$^+$ (C$_{23}$H$_{16}$ClF$_4$N$_5$O$_2$) requires m/z 506.1, LCMS found m/z 506.1. $^1$H NMR (400 MHz, CH$_3$OD-d4) δ 9.29 (s, 1H), 9.15 (s, 2H), 8.50 (d, J=1.5 Hz, 1H), 8.02 (d, J=1.5 Hz, 1H), 7.86 (d, J=9.0 Hz, 2H), 7.48-7.21 (m, 3H), 3.45 (td, J=3.3, 7.1 Hz, 1H), 0.80 (br s, 2H), 0.60 (br d, J=6.6 Hz, 2H).

Example 16

N-(4-(chlorodifluoromethoxy)phenyl)-1-(1-hydroxy-2-methylpropan-2-yl)-7-(pyrimidin-5-yl)-1H-benzo[d]imidazole-5-carboxamide

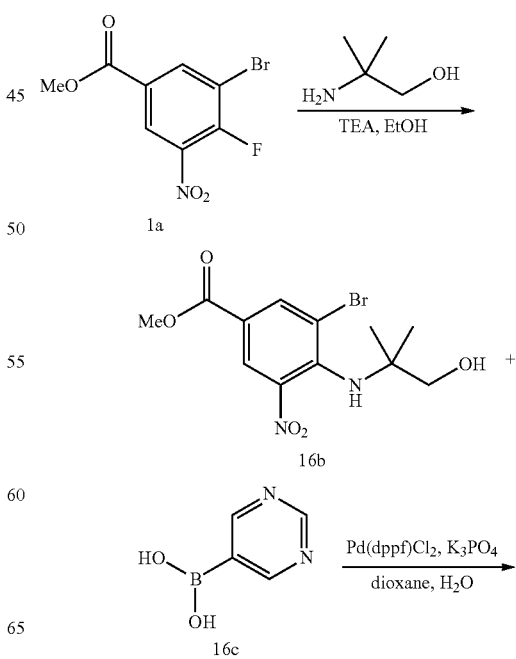

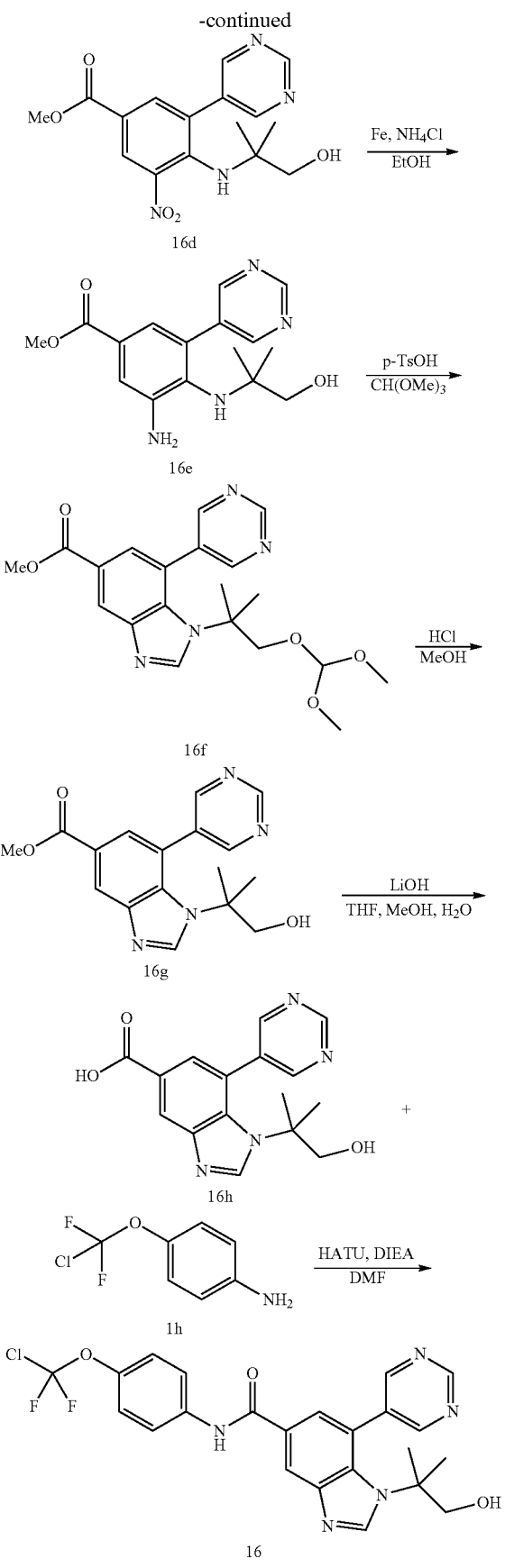

Methyl 3-bromo-4-(1-hydroxy-2-methylpropan-2-yl)amino)-5-nitrobenzoate (16b). A mixture of methyl 3-bromo-4-fluoro-5-nitrobenzoate (1a, 300 mg, 1.08 mmol), 2-amino-2-methyl-propan-1-ol (115.41 mg, 1.29 mmol), TEA (131.02 mg, 1.29 mmol) in EtOH (5 mL) was stirred at 15° C. for 3 hr. The reaction mixture was concentrated, and the crude product was purified by prep-TLC (petroleum ether:ethyl acetate=3:1, $R_f$=0.5) to give 16b as a yellow oil. $^1$H NMR (400 MHz, CDCl$_3$-d) δ 8.41 (d, J=2.0 Hz, 1H), 8.39 (d, J=2.0 Hz, 1H), 5.06 (br s, 1H), 3.95 (s, 3H), 3.48 (s, 2H), 1.19 (s, 6H).

Methyl 4-((1-hydroxy-2-methylpropan-2-yl)amino)-3-nitro-5-(pyrimidin-5-yl)benzoate (16d). A mixture of 16b (200 mg, 0.576 mmol), 16c (142.76 mg, 1.15 mmol), Pd(dppf)Cl$_2$ (21.08 mg, 0.029 mmol), K$_3$PO$_4$ (366.86 mg, 1.73 mmol) in dioxane (4 mL) and H$_2$O (0.4 mL) was degassed and purged with N$_2$ 3 times. The mixture was stirred at 110° C. for 6 hr under a N$_2$ atmosphere. LCMS showed a peak with desired MS. The reaction mixture was concentrated, and the crude product was purified by prep-TLC (petroleum ether:ethyl acetate=0:1, $R_f$=0.4) to give 16d as a yellow solid. $^1$H NMR (400 MHz, CDCl$_3$-d) δ 9.25 (s, 1H), 9.02 (s, 2H), 8.63 (d, J=2.0 Hz, 1H), 8.14 (d, J=2.0 Hz, 1H), 5.79 (s, 1H), 4.02-3.93 (m, 3H), 3.15 (br s, 2H), 0.76 (s, 6H).

Methyl 3-amino-4-((1-hydroxy-2-methylpropan-2-yl)amino)-5-(pyrimidin-5-yl)benzoate (16e). To a solution of 16d (70 mg, 0.202 mmol) in EtOH (4 mL) was added Fe (112.87 mg, 2.02 mmol) and NH$_4$Cl (108.11 mg, 2.02 mmol). The mixture was stirred at 80° C. for 0.5 hr. LCMS showed a peak with desired MS. The mixture was filtered through a Celite® pad and the filtrate was concentrated. The crude product was purified by prep-TLC (petroleum ether:ethyl acetate=10:1, $R_f$=0.3) to give 16e as a yellow solid. $^1$H NMR (400 MHz, CDCl$_3$-d) δ 9.19 (s, 1H), 8.90 (s, 2H), 7.48 (d, J=2.0 Hz, 1H), 7.39 (d, J=2.0 Hz, 1H), 3.91 (s, 3H), 3.50 (s, 2H), 3.25 (s, 2H), 0.76 (s, 6H).

Methyl 1-(1-(dimethoxymethoxy)-2-methylpropan-2-yl)-7-(pyrimidin-5-yl)-1H-benzo[d]imidazole-5-carboxylate (16f). To a solution of 16e (20 mg, 0.063 mmol) in trimethoxymethane (1.94 g, 18.24 mmol) was added PTSA (1.09 mg, 6.32 umol). The mixture was stirred at 80° C. for 1 hr. LCMS showed a peak with desired MS. The reaction mixture was concentrated and the crude residue was purified by prep-TLC (ethyl acetate:methanol=10:1, $R_f$=0.4) to give 16f as a yellow oil. $^1$H NMR (400 MHz, CDCl$_3$-d) δ 9.33 (s, 1H), 8.84 (s, 2H), 8.60 (s, 1H), 8.31 (s, 1H), 7.70 (s, 1H), 4.85 (s, 1H), 3.96 (s, 3H), 3.58 (s, 2H), 3.09 (s, 6H), 1.44 (s, 5H), 1.42 (br s, 1H).

Methyl 1-(1-hydroxy-2-methylpropan-2-yl)-7-(pyrimidin-5-yl)-1H-benzo[d]imidazole-5-carboxylate (16g). To a solution of 16f (10 mg, 0.025 mmol) in MeOH (2 mL) was added HCl (0.1M, 499.47 uL). The mixture was stirred at 15° C. for 3 hr. LCMS showed a peak with desired MS. The reaction mixture was concentrated to give 16g as a yellow oil. The product was used to the next step without purification.

1-(1-Hydroxy-2-methylpropan-2-yl)-7-(pyrimidin-5-yl)-1H-benzo[d]imidazole-5-carboxylic acid (16h). To a solution of 16g (10 mg, 0.031 mmol) in MeOH (1 mL), THF (1 mL) and H$_2$O (0.5 mL) was added LiOH.H$_2$O (3.86 mg, 0.092 mmol). The mixture was stirred at 50° C. for 3 hr. LCMS showed a peak with desired MS. The mixture was concentrated, and the residue was poured into H$_2$O (1 mL). The pH of the solution was adjusted to 4 by addition of HCl (1M in H$_2$O) to give 16h as a white solid. The product was used in the next step without further purification.

N-(4-(chlorodifluoromethoxy)phenyl)-1-(1-hydroxy-2-methylpropan-2-yl)-7-(pyrimidin-5-yl)-1H-benzo[d]imidazole-5-carboxamide (16). A mixture of 16h (10 mg, 0.032 mmol), 4-(chlorodifluoromethoxy)aniline (1h), HATU (18.26 mg, 0.048 mmol) and DIEA (12.41 mg, 0.096 mmol) in DMF (1 mL) was stirred at 15° C. for 3 hr. LCMS showed a peak with desired MS. The reaction mixture was concentrated, and the residue was purified by prep-HPLC (NH$_4$HCO$_3$, column: Agela Durashell C18 150*25 5 u; mobile phase: [water (10 mM NH$_4$HCO$_3$)-ACN]; B %: 35%-65%,10 min) to give the title compound 16 as a white solid. MS mass calculated for [M+1]$^+$ (C$_{23}$H$_{20}$ClF$_2$N$_5$O$_3$) requires m/z 488.1, LCMS found m/z 488.1. $^1$H NMR (400 MHz, MeOD-d$_4$) δ 9.31 (s, 1H), 8.98 (s, 2H), 8.55 (s, 1H), 8.47 (d, J=1.8 Hz, 1H), 7.83 (d, J=9.0 Hz, 2H), 7.71 (d, J=1.8 Hz, 1H), 7.29 (d, J=9.0 Hz, 2H), 3.56 (s, 2H), 1.41 (s, 6H).

Example 17

N-(4-(chlorodifluoromethoxy)phenyl)-7-(4-fluoro-1H-pyrazol-5-yl)-1-isopropyl-1H-benzo[d]imidazole-5-carboxamide

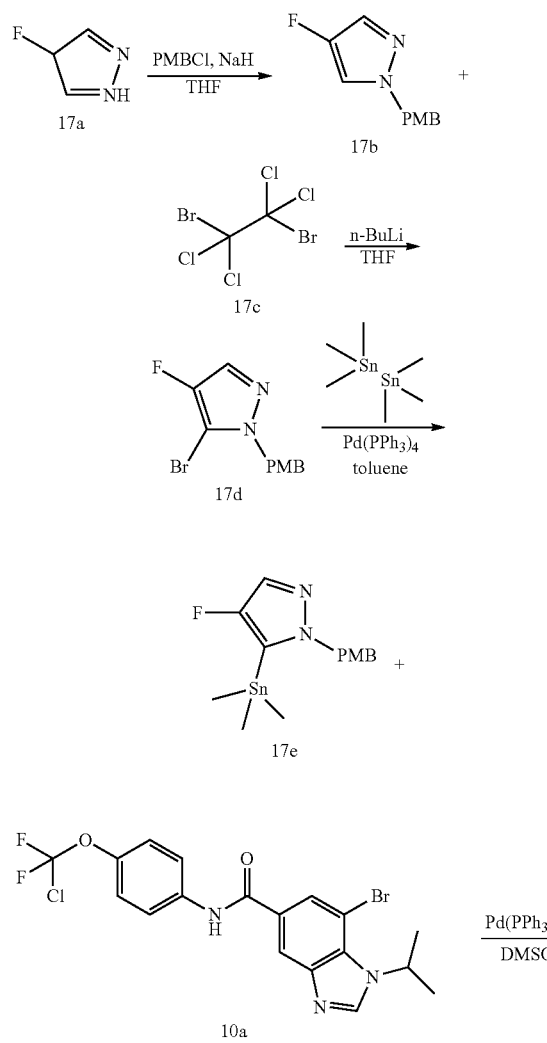

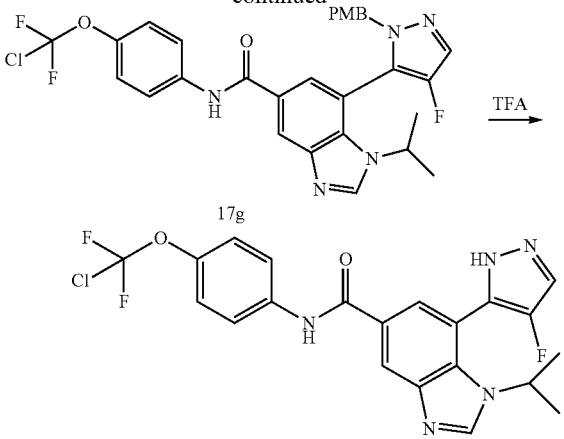

4-Fluoro-1-(4-methoxybenzyl)-1H-pyrazole (17b). To a solution of 4-fluoro-1H-pyrazole (17a, 1 g, 11.62 mmol) in THF (15 mL) at 0° C. was added NaH (697.06 mg, 17.43 mmol, 60% purity). After 10 min stirring, 1-(chloromethyl)-4-methoxy-benzene (2.18 g, 13.94 mmol) was added slowly to the reaction mixture. The resulting solution was stirred for 16 hr at to 15° C. TLC (petroleum ether:ethyl acetate=5:1, R$_f$=0.4) indicated a new spot was generated. LCMS showed a peak with desired MS. The reaction mixture was concentrated. To the residue was added H$_2$O (20 mL) and the aqueous phase was extracted with ethyl acetate (60 mL). The organic layers were washed with brine (5 mL×2), dried over anhydrous Na$_2$SO$_4$, filtered and concentrated in vacuo. The crude product was purified by silica gel column chromatography (petroleum ether:ethyl acetate=50:1-30:1) to give 17b as a yellow oil. $^1$H NMR (400 MHz, CDCl$_3$-d) δ 7.35 (d, J=4.0 Hz, 1H), 7.21-7.17 (m, 3H), 6.91-6.87 (m, 2H), 5.14 (s, 2H), 3.81 (s, 3H).

5-Bromo-4-fluoro-1-(4-methoxybenzyl)-1H-pyrazole (17d). To a solution of 17b (850 mg, 4.12 mmol) in THF (15 mL) at −70° C. was added a solution of n-BuLi (2.5 M, 2.47 mL, 1.5 eq) slowly. The mixture was stirred for 15 min while maintaining the temperature below −60° C. A solution of 1,2-dibromo-1,1,2,2-tetrachloroethane (17c, 1.61 g, 4.95 mmol) in THF (1 mL) was added to the reaction mixture and the resulting solution was continuously stirred for an additional 2 hr. TLC (petroleum ether:ethyl acetate=3:1, R$_f$=0.6) indicated a new spot was generated. LCMS showed a peak with desired MS. The reaction mixture was quenched with the addition of water H$_2$O (20 mL) and followed by the addition of ethyl acetate (80 mL). After quenching the reaction, the reaction mixture was poured into a separatory funnel and separated. The organic layers were concentrated and the crude product was purified by silica gel column chromatography (petroleum ether:ethyl acetate=45:1~10:1) to give 17d as a yellow solid. $^1$H NMR (400 MHz, CDCl$_3$-d) δ 7.43 (d, J=4.8 Hz, 1H), 7.20 (d, J=8.8 Hz, 2H), 6.89-6.85 (m, 2H), 5.23 (s, 2H), 3.80 (s, 3H).

4-Fluoro-1-(4-methoxybenzyl)-5-(trimethylstannyl)-1H-pyrazole (17e). A mixture of 17d (300 mg, 1.05 mmol), trimethyl(trimethylstannyl)stannane (413.68 mg, 1.26 mmol), Pd(PPh$_3$)$_4$ (121.59 mg, 0.105 mmol) in toluene (5 mL) was degassed and purged with N$_2$ 3 times. The mixture was stirred at 130° C. for 16 hr under N$_2$ atmosphere. TLC (petroleum ether:ethyl acetate=3:1, R$_f$=0.7) indicated a new spot was generated. LCMS showed a peak with desired MS was detected. The reaction mixture was quenched by addition of KF (5 mL), followed by the addition of ethyl acetate (40 mL). After quenching the reaction, the reaction mixture was poured into separatory funnel and separated. The organic layers were concentrated and the residue was purified by prep-TLC (petroleum ether:ethyl acetate=3:1, $R_f$=0.7) to give 17e as a yellow oil. $^1$H NMR (400 MHz, CDCl$_3$-d) δ 7.40 (d, J=4.8 Hz, 1H), 6.92 (t, J=8.4 Hz, 2H), 6.88-6.83 (m, 2H), 5.21 (s, 2H), 3.79 (s, 3H), 0.25 (s, 9H).

N-(4-(chlorodifluoromethoxy)phenyl)-7-(4-fluoro-1-(4-methoxybenzyl)-1H-pyrazol-5-yl)-1-isopropyl-1H-benzo[d]imidazole-5-carboxamide (17g). A mixture of 7-bromo-N-(4-(chlorodifluoromethoxy)phenyl)-1-isopropyl-1H-benzo[d]imidazole-5-carboxamide (10a, 74.58 mg, 0.163 mmol), 17e (120.00 mg, 0.325 mmol) and Pd(PPh$_3$)$_4$ (37.58 mg, 0.033 mmol) in DMSO (3 mL) was degassed and purged with N$_2$ 3 times. The mixture was stirred at 100° C. for 16 hr under N$_2$ atmosphere. LCMS showed a peak with desired MS was detected. The mixture was quenched with the addition of water (40 mL) and the mixture was extracted with ethyl acetate (60 mL×3). The combined organic layers were dried over Na$_2$SO$_4$, filtered and concentrated to give the crude product. The crude residue was purified by prep-TLC (ethyl acetate:methanol=10:1, $R_f$=0.6) to give 17g as a yellow oil. $^1$H NMR (400 MHz, CDCl$_3$-d) δ 8.49 (d, J=1.5 Hz, 1H), 8.13-8.08 (m, 1H), 7.87 (s, 1H), 7.72 (s, 2H), 7.61-7.56 (m, 2H), 7.49 (s, 2H), 7.28 (br s, 1H), 6.77 (d, J=8.6 Hz, 2H), 6.70-6.65 (m, 2H), 5.70-5.57 (m, 1H), 5.10-4.92 (m, 3H), 3.91-3.78 (m, 2H), 3.66 (s, 3H), 1.67 (d, J=6.6 Hz, 2H), 1.34 (d, J=6.6 Hz, 3H), 1.15 (d, J=6.6 Hz, 3H).

N-(4-(chlorodifluoromethoxy)phenyl)-7-(4-fluoro-1H-pyrazol-5-yl)-1-isopropyl-1H-benzo[d]imidazole-5-carboxamide (17). A solution of 17g (80 mg, 0.137 mmol) in TFA (2 mL) was stirred at 15° C. for 16 hr. LCMS showed a peak with desired MS was detected. The reaction mixture was concentrated. The crude residue was purified by prep-TLC (ethyl acetate:methanol=10:1, $R_f$=0.4) to give the title compound 17 as a white solid. MS mass calculated for [M+H]$^+$ (C$_{21}$H$_{17}$ClF$_3$N$_5$O$_2$) requires m/z 464.1, LCMS found m/z 464.0. $^1$H NMR (400 MHz, MeOD-d$_4$) δ 8.56 (br s, 1H), 8.43 (br s, 1H), 7.93 (d, J=1.8 Hz, 1H), 7.87-7.80 (m, 3H), 7.29 (d, J=9.0 Hz, 2H), 4.67 (br s, 1H), 1.43 (d, J=6.6 Hz, 6H).

Example 18

N-(4-(chlorodifluoromethoxy)phenyl)-1-cyclopropyl-7-(4-fluoro-1H-pyrazol-5-yl)-1H-benzo[d]imidazole-5-carboxamide

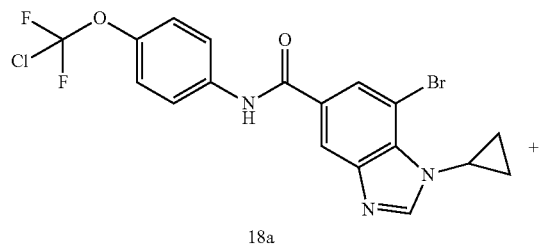

18a

+

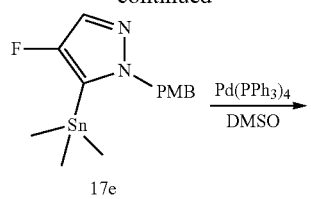

17e

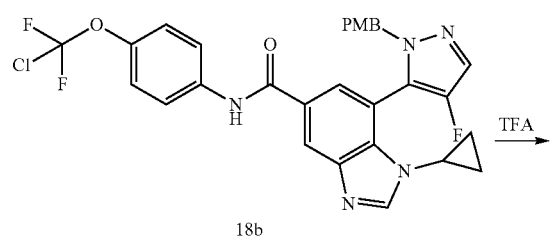

18b

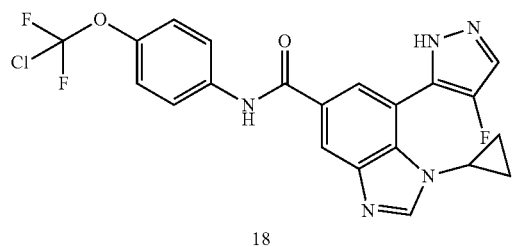

18

N-(4-(chlorodifluoromethoxy)phenyl)-1-cyclopropyl-7-(4-fluoro-1-(4-methoxybenzyl)-1H-pyrazol-5-yl)-1H-benzo[d]imidazole-5-carboxamide (18b). To a mixture of 7-bromo-N-(4-(chlorodifluoromethoxy)phenyl)-1-cyclopropyl-1H-benzo[d]imidazole-5-carboxamide (synthesized in similar fashion to 10a; 18a, 100 mg, 0.219 mmol, 1 eq) and 4-fluoro-1-(4-methoxybenzyl)-5-(trimethylstannyl)-1H-pyrazole (17e, 80.81 mg, 0.219 mmol, 1 eq) in DMSO (1.5 mL) was added Pd(PPh$_3$)$_4$ (12.65 mg, 0.011 mmol, 0.05 eq). The reaction mixture was stirred at 100° C. for 16 hr. LCMS showed a peak with desired MS was detected. The mixture was poured into water (10 mL) and the mixture was extracted with EtOAc (10 mL×2). The combined organic layers were concentrated and purified by prep-TLC (EtOAc:MeOH=10:1, $R_f$=0.6) to give 18b as a yellow oil.

N-(4-(chlorodifluoromethoxy)phenyl)-1-cyclopropyl-7-(4-fluoro-1H-pyrazol-5-yl)-1H-benzo[d]imidazole-5-carboxamide (18). N-(4-(chlorodifluoromethoxy)phenyl)-1-cyclopropyl-7-(4-fluoro-1-(4-methoxybenzyl)-1H-pyrazol-5-yl)-1H-benzo[d]imidazole-5-carboxamide (18b, 120 mg, 0.206 mmol, 1 eq) was dissolved in TFA (3 mL). The reaction mixture was stirred at 20° C. for 2 hr. LCMS showed a peak with desired MS was detected. The solvent was evaporated under vacuum and the residue was dissolved in EtOAc (5 mL). The organic layer was washed with saturated NaHCO$_3$ (2 mL), brine (2 mL) and concentrated to give the crude residue that was purified by prep-TLC (EtOAc:MeOH=10:1, $R_f$=0.3) to give the title compound 18 as a white solid. MS mass calculated for [M+H]$^+$ (C$_{21}$H$_{15}$ClF$_3$N$_5$O$_2$) requires m/z 462.1, LCMS found m/z 462.0. $^1$H NMR (400 MHz, CDCl$_3$-d) δ 9.55 (br s, 1H), 8.31 (s, 1H), 8.01 (s, 1H), 7.92 (s, 1H), 7.82-7.75 (m, 2H), 7.50 (d, J=4.6 Hz, 1H), 7.22 (br d, J=8.8 Hz, 2H), 3.42 (br d, J=3.3 Hz, 1H), 0.80-0.63 (m, 4H).

Example 19

N-(4-(chlorodifluoromethoxy)phenyl)-1-(1,1-dioxidothietan-3-yl)-7-(pyrimidin-5-yl)-1H-benzo[d]imidazole-5-carboxamide

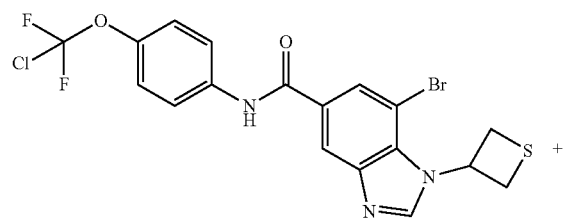

19a

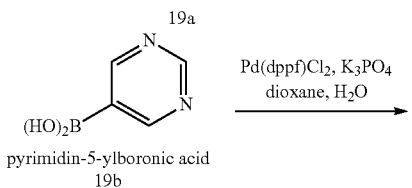

pyrimidin-5-ylboronic acid
19b

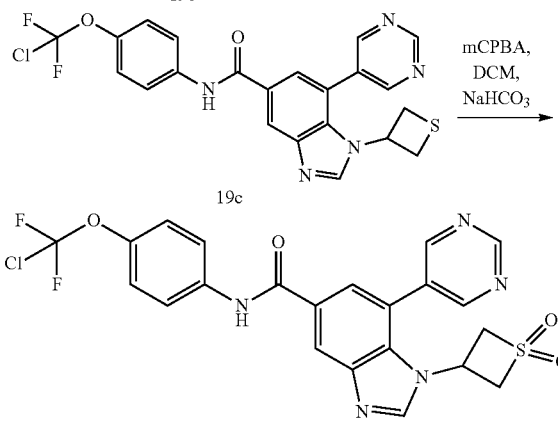

N-(4-(chlorodifluoromethoxy)phenyl)-7-(pyrimidin-5-yl)-1-(thietan-3-yl)-1H-benzo[d]imidazole-5-carboxamide (19c). To a mixture of 7-bromo-N-(4-(chlorodifluoromethoxy)phenyl)-1-(thietan-3-yl)-1H-benzo[d]imidazole-5-carboxamide (19a, 130 mg, 0.266 mmol, 1 eq), pyrimidin-5-ylboronic acid (synthesized in a similar fashion to 2c; 19b, 98.87 mg, 0.798 mmol, 3 eq), $K_3PO_4$ (169.38 mg, 0.798 mmol, 3 eq) in dioxane (2 mL) and $H_2O$ (0.2 mL) under $N_2$ was added Pd(dppf)Cl$_2$ (19.46 mg, 0.27 mmol, 0.1 eq). The mixture was stirred at 100° C. for 16 hours. LCMS showed desired MS. The mixture was poured into water, and then was extracted with EtOAc. The combined organic layers were dried over anhydrous $Na_2SO_4$, filtered and concentrated in vacuo to give the crude product. The residue was purified by prep-TLC (ethyl acetate:methanol=10:1, $R_f$=0.30) to afford 19c as a white solid. $^1$H NMR (400 MHz, CDCl$_3$-d) δ 9.36 (s, 1H), 8.82 (s, 2H), 8.43 (s, 1H), 8.31 (s, 1H), 8.01 (s, 1H), 7.71 (s, 1H), 7.66 (br d, J=8.8 Hz, 2H), 7.22 (br s, 2H), 5.06 (quin, J=8.2 Hz, 1H), 3.63 (t, J=9.0 Hz, 2H), 3.14 (t, J=9.0 Hz, 2H).

N-(4-(chlorodifluoromethoxy)phenyl)-1-(1,1-dioxidothietan-3-yl)-7-(pyrimidin-5-yl)-1H-benzo[d]imidazole-5-carboxamide (19). To a mixture of N-(4-(chlorodifluoromethoxy)phenyl)-7-(pyrimidin-5-yl)-1-(thietan-3-yl)-1H-benzo[d]imidazole-5-carboxamide (19c, 40 mg, 0.082 mmol, 1 eq) was dissolved in DCM (2 mL) at 0° C. was added saturated aqueous sodium hydrogen carbonate and mCPBA (70.74 mg, 0.328 mmol, 80% purity, 4 eq). The reaction mixture was stirred at 15° C. for 16 hours. LCMS showed desired MS. The mixture was poured into water, and then was extracted with EtOAC. The combined organic layers were dried over anhydrous $Na_2SO_4$, filtered and concentrated in vacuo to give the required product. The residue was purified by prep-TLC (ethyl acetate:methanol=10:1, $R_f$=0.37) to afford the title compound 19 as a white solid. MS mass calculated for $[M+1]^+$ ($C_{22}H_{16}ClF_2N_5O_4S$) requires m/z 520.1, LCMS found m/z 520.0. NMR (400 MHz, DMSO-d$_6$) δ 10.50 (s, 1H), 9.38 (s, 1H), 9.03 (s, 2H), 8.83 (s, 1H), 8.55 (s, 1H), 7.95 (br d, J=8.8 Hz, 2H), 7.88-7.77 (m, 1H), 7.38 (br d, J=8.6 Hz, 2H), 4.94-4.83 (m, 1H), 4.74 (br d, J=13.2 Hz, 2H), 4.41-4.26 (m, 2H).

Example 20

N-(4-(chlorodifluoromethoxy)phenyl)-6-fluoro-1-isopropyl-7-(pyrimidin-5-yl)-1H-benzo[d]imidazole-5-carboxamide

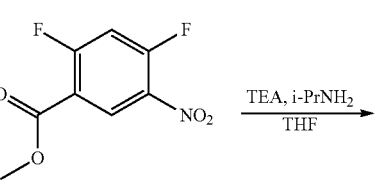

20a

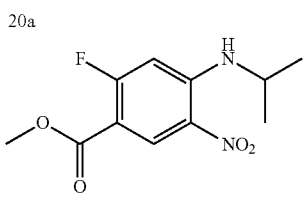

20b

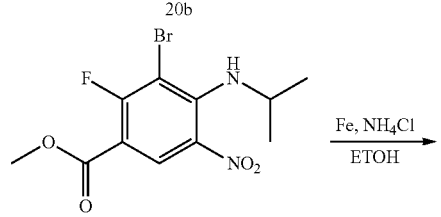

20c

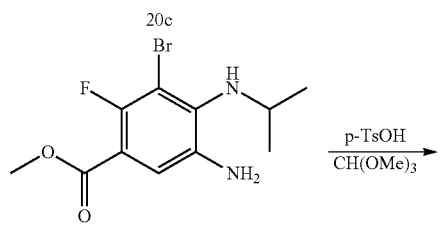

20d

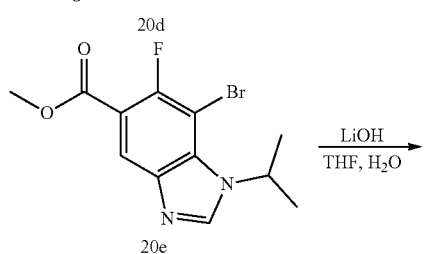

20e

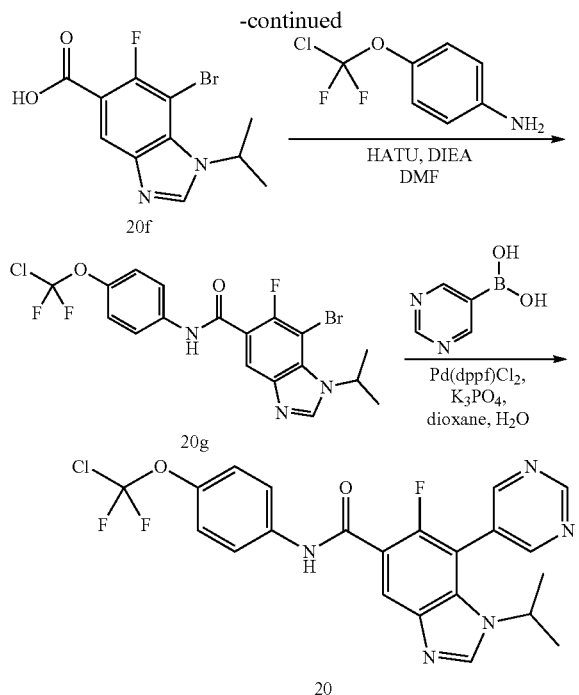

Methyl 2-fluoro-4-(isopropylamino)-5-nitrobenzoate (20b). To a solution of methyl 2,4-difluoro-5-nitrobenzoate (20a, 2 g, 9.21 mmol, 1 eq) in THF (10 mL) at 15° C. was added TEA (2.80 g, 27.63 mmol, 3.85 mL, 3 eq) drop-wise, followed by propan-2-amine (653.37 mg, 11.05 mmol, 949.67 uL, 1.2 eq) drop-wise. The resulting mixture was stirred at 0° C. for 1 hr. TLC (petroleum ether:EtOAc=5:1, $R_f$=0.50) indicated 20a was consumed completely, and one major new spot was detected. The aqueous phase was extracted with EtOAc (20 mL×3). The combined organic layers were washed with brine (30 mL), dried over anhydrous $Na_2SO_4$, filtered and concentrated in vacuo. The product was used in the next step without further purification. Compound 20b was obtained as a yellow solid. $^1$H NMR (400 MHz, $CDCl_3$-d) δ 8.91 (d, J=7.8 Hz, 1H), 8.29 (br d, J=4.9 Hz, 1H), 6.52 (d, J=13.7 Hz, 1H), 3.90 (s, 3H), 3.83-3.70 (m, 1H), 1.36 (d, J=6.4 Hz, 6H).

Methyl 3-bromo-2-fluoro-4-(isopropylamino)-5-nitrobenzoate (20c). To a solution of methyl 2-fluoro-4-(isopropylamino)-5-nitrobenzoate (20b, 2 g, 7.81 mmol, 1 eq) in DCM (5 mL) was added $Br_2$ (2.00 g, 12.51 mmol, 645.16 uL, 1.60 eq). The mixture was stirred at 0° C. for 1 hr. TLC (petroleum ether:EtOAc=5:1, $R_f$=0.50) indicated 20b was consumed completely. The reaction mixture was quenched by the addition of saturated $Na_2SO_3$ (5 mL). The residue was diluted with $H_2O$ (20 mL) and extracted with DCM (10 mL×3). The combined organic layers were washed with brine (30 mL), dried over $Na_2SO_4$, filtered and concentrated under reduced pressure to give the crude product. The residue was purified by silica gel column chromatography ($SiO_2$, petroleum ether:ethyl acetate=10:1) to afford 20c as a yellow solid. $^1$H NMR (400 MHz, $CDCl_3$-d) δ 8.72 (d, J=7.3 Hz, 1H), 4.49-4.34 (m, 1H), 3.93 (s, 3H), 1.29-1.27 (m, 6H).

Methyl 5-amino-3-bromo-2-fluoro-4-(isopropylamino) benzoate (20d). To a solution of methyl 3-bromo-2-fluoro-4-(isopropylamino)-5-nitrobenzoate (20c, 1 g, 2.98 mmol, 1 eq) in EtOH (20 mL) was added Fe (1.67 g, 29.84 mmol, 10 eq) and $NH_4Cl$ (1.60 g, 29.84 mmol, 1.04 mL, 10 eq). The mixture was stirred at 80° C. for 6 hr. TLC (petroleum ether:EtOAc=3:1) indicated 20c was consumed completely. The reaction mixture was concentrated under reduced pressure. The residue was diluted with $H_2O$ (20 mL) and extracted with EtOAc (10 mL×3). The combined organic layers were washed with brine (30 mL), dried over $Na_2SO_4$, filtered and concentrated under reduced pressure to give the crude product. The residue was purified by column chromatography ($SiO_2$, petroleum ether/ethyl acetate=10/1 to 1:1). Compound 20d was obtained as a brown oil. $^1$H NMR (400 MHz, $CDCl_3$-d) δ 7.21 (d, J=6.8 Hz, 1H), 3.90 (s, 3H), 3.80-3.71 (m, 1H), 1.17 (d, J=6.4 Hz, 6H).

Methyl 7-bromo-6-fluoro-1-isopropyl-1H-benzo[d]imidazole-5-carboxylate (20e). To a solution of methyl 5-amino-3-bromo-2-fluoro-4-(isopropylamino)benzoate (20d, 180 mg, 0.590 mmol, 1 eq) in $CH(OMe)_3$ (2 mL) was added p-TsOH (10.16 mg, 0.059 mmol, 0.1 eq). The mixture was stirred at 100° C. for 1.5 hr. TLC (petroleum ether:ethyl acetate=1:1) indicated 20d was consumed completely. The reaction mixture was concentrated under reduced pressure. The residue was diluted with $H_2O$ (20 mL) and extracted with EA (10 mL×3). The combined organic layers were washed with brine (30 mL), dried over $Na_2SO_4$, filtered and concentrated under reduced pressure to give the crude product. The residue was purified by prep-TLC ($SiO_2$, petroleum ether/ethyl acetate=1:1). Compound 20e was obtained as a white solid. $^1$H NMR (400 MHz, $CDCl_3$-d) δ 8.34 (d, J=5.9 Hz, 1H), 8.15 (s, 1H), 5.64 (quind, J=6.7, 13.4 Hz, 1H), 3.97 (s, 3H), 1.65 (d, J=6.4 Hz, 6H).

7-Bromo-6-fluoro-1-isopropyl-1H-benzo[d]imidazole-5-carboxylic acid (20f). To a solution of methyl 7-bromo-6-fluoro-1-isopropyl-1H-benzo[d]imidazole-5-carboxylate (20e, 140 mg, 0.444 mmol, 1 eq) in THF (5 mL), MeOH (5 mL) and $H_2O$ (2 mL) was added $LiOH.H_2O$ (46.60 mg, 1.11 mmol, 2.5 eq). The mixture was stirred at 50° C. for 12 hr. TLC (petroleum ether:ethyl acetate=1:1) indicated 20e was consumed completely. The mixture was adjusted to pH=5 with aqueous HCl (1M) and concentrated to give 20f as a white solid, which was used in the next step without further purification.

7-Bromo-N-(4-(chlorodifluoromethoxy)phenyl)-6-fluoro-1-isopropyl-1H-benzo[d]imidazole-5-carboxamide (20g). To a solution of 7-bromo-6-fluoro-1-isopropyl-1H-benzo[d]imidazole-5-carboxylic acid (20f, 70 mg, 0.232 mmol, 1 eq) in DMF (2 mL) was added HATU (106.07 mg, 0.279 mmol, 1.2 eq), 4-[chloro(difluoro)methoxy]aniline (1h, 49.50 mg, 0.256 mmol, 1.1 eq) and DIEA (90.13 mg, 0.697 mmol, 121.47 uL, 3 eq). The mixture was stirred at 50° C. for 3 hr. TLC (petroleum ether:ethyl acetate=1:1) indicated 20f consumed completely. The reaction mixture was concentrated under reduced pressure. The residue was diluted with $H_2O$ (10 mL) and extracted with EtOAc (10 mL×3). The combined organic layers were washed with brine (10 mL), dried over $Na_2SO_4$, filtered and concentrated under reduced pressure to give the crude product. The residue was purified by column chromatography ($SiO_2$, petroleum ether/ethyl acetate=10/1 to 1:1). Compound 20g was obtained as a white solid. $^1$H NMR (400 MHz, MeOD-$d_4$) δ 8.57 (s, 1H), 8.01 (d, J=6.4 Hz, 1H), 7.82 (d, J=8.8 Hz, 2H), 7.30 (d, J=9.3 Hz, 2H), 5.70 (td, J=6.7, 13.6 Hz, 1H), 1.67 (d, J=6.8 Hz, 6H).

N-(4-(chlorodifluoromethoxy)phenyl)-6-fluoro-1-isopropyl-7-(pyrimidin-5-yl)-1H-benzo[d]imidazole-5-carboxamide (20). To a solution of 7-bromo-N-(4-(chlorodifluoromethoxy)phenyl)-6-fluoro-1-isopropyl-1H-benzo[d] imidazole-5-carboxamide (20g, 50 mg, 0.105 mmol, 1 eq) in dioxane (2.5 mL) and $H_2O$ (0.5 mL) was added $Pd(dppf)Cl_2$ (7.68 mg, 0.01 mmol, 0.1 eq), pyrimidin-5-ylboronic acid (38.99 mg, 0.315 mmol, 3 eq) and K$_3$PO$_4$ (66.80 mg, 0.315 mmol, 3 eq). The mixture was stirred at 100° C. for 6 hr. LC-MS showed 20g was consumed completely and one main peak with desired MS was detected. The mixture was concentrated to give the crude product. The residue was purified by prep-HPLC (NH$_4$HCO$_3$ condition, column: Waters Xbridge 150*50 10 u; mobile phase: [water (10 mM NH$_4$HCO$_3$)-MeOH]; B %: 55%-75%, 12 min) to afford the title compound 20 as a white solid. MS mass calculated for [M+H]$^+$ (C$_{22}$H$_{17}$ClF$_3$N$_5$O$_2$) requires m/z 476.1, LCMS found m/z 476.1; $^1$H NMR (400 MHz, CDCl$_3$-d) δ 9.42 (s, 1H), 8.93 (s, 2H), 8.74 (d, J=7.3 Hz, 1H), 8.44 (br d, J=15.7 Hz, 1H), 8.18 (s, 1H), 7.72 (d, J=8.8 Hz, 2H), 7.25 (d, J=8.8 Hz, 2H), 3.96 (td, J=6.8, 13.3 Hz, 1H), 1.38 (d, J=6.8 Hz, 6H).

Example 21

N-(4-(chlorodifluoromethoxy)phenyl)-1-(2-(cyclopropylamino)-2-oxoethyl)-7-(pyrimidin-5-yl)-1H-benzo[d]imidazole-5-carboxamide

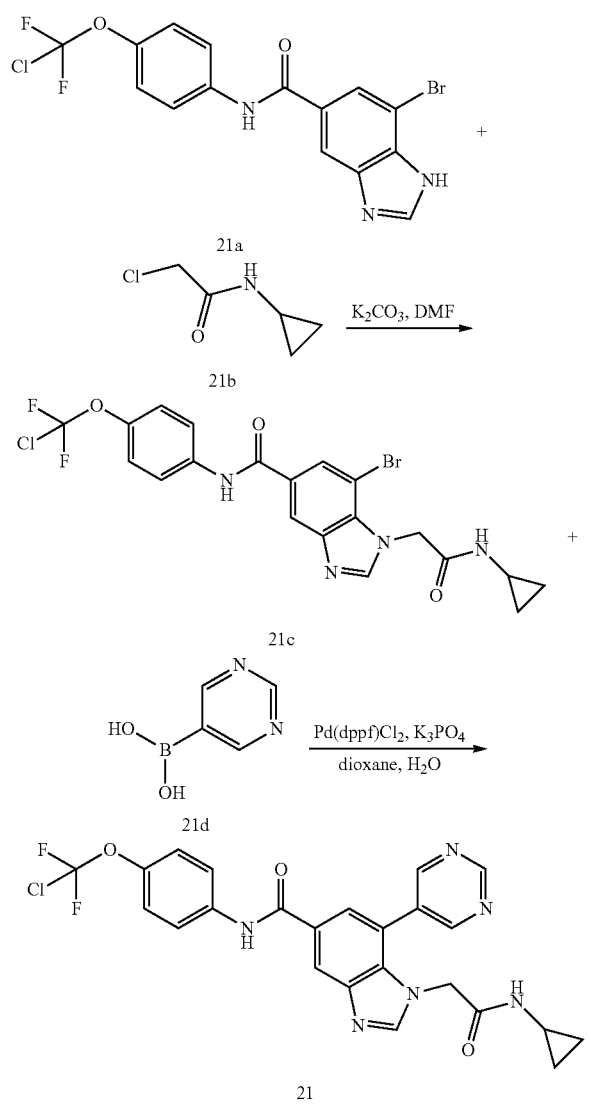 [SMILES: O=C(Nc1ccc(OC(F)(F)Cl)cc1)c1cc(Br)c2[nH]cnc2c1 ; O=C(CCl)NC1CC1 ; O=C(Cn1cnc2cc(C(=O)Nc3ccc(OC(F)(F)Cl)cc3)cc(Br)c21)NC1CC1 ; OB(O)c1cncnc1 ; O=C(Cn1cnc2cc(C(=O)Nc3ccc(OC(F)(F)Cl)cc3)cc(-c3cncnc3)c21)NC1CC1]

7-Bromo-N-(4-(chlorodifluoromethoxy)phenyl)-1-(2-(cyclopropylamino)-2-oxoethyl)-1H-benzo[d]imidazole-5-carboxamide (21c). To a mixture of 7-bromo-N-(4-(chlorodifluoromethoxy)phenyl)-1H-benzo[d]imidazole-5-carboxamide (synthesized in a similar fashion to 2c; 21a, 80 mg, 0.192 mmol, 1 eq) and 2-chloro-N-cyclopropylacetamide (21b, 30.78 mg, 0.230 mmol, 1.2 eq) in DMF (1 mL) under N$_2$ was added K$_2$CO$_3$ (18.58 mg, 0.134 mmol, 0.7 eq). The mixture was stirred at 80° C. for 4 hours. TLC (ethyl acetate:methanol=10:1, R$_f$=0.32) showed the reaction was completed. The mixture was poured into water (20 mL), and then was extracted with EtOAc (20 mL×3). The combined organic layers were dried over anhydrous Na$_2$SO$_4$, filtered and concentrated in vacuo to give the crude product. The residue was purified by prep-TLC (ethyl acetate:methanol=10:1, R$_f$=0.32) to give 21c as a white solid. $^1$H NMR (400 MHz, MeOD-d$_4$) δ 8.21 (d, J=6.2 Hz, 2H), 8.01 (s, 1H), 7.74 (d, J=8.9 Hz, 2H), 7.20 (br d, J=8.9 Hz, 2H), 5.19 (s, 2H), 2.61 (dt, J=3.7, 7.5 Hz, 1H), 0.65 (br d, J=5.1 Hz, 2H), 0.46 (br d, J=2.4 Hz, 2H).

N-(4-(chlorodifluoromethoxy)phenyl)-1-(2-(cyclopropylamino)-2-oxoethyl)-7-(pyrimidin-5-yl)-1H-benzo[d]imidazole-5-carboxamide (21). To a solution of 7-bromo-N-(4-(chlorodifluoromethoxy)phenyl)-1-(2-(cyclopropylamino)-2-oxoethyl)-1H-benzo[d]imidazole-5-carboxamide (21c, 10 mg, 0.019 mmol, 1 eq) and pyrimidin-5-ylboronic acid (21d, 4.82 mg, 0.039 mmol, 2 eq) in dioxane (2 mL) and H$_2$O (0.4 mL) was added Pd(dppf)Cl$_2$ (1.42 mg, 1.95 umol, 0.1 eq) and K$_3$PO$_4$ (12.40 mg, 0.058 mmol, 3 eq). The reaction mixture was stirred at 100° C. for 6 hr. LCMS showed a peak with desired MS was detected. The reaction mixture was concentrated, the residue was dissolved in EtOAc (5 mL) and washed with H$_2$O (2 mL) and brine (5 mL). The organic layer was concentrated and purified by prep-TLC (EtOAc:MeOH=5:1) to afford the title compound 21 as a white solid. MS mass calculated for [M+H]$^+$ (C$_{24}$H$_{19}$ClF$_2$N$_6$O$_3$) requires m/z 513.1, LCMS found m/z 513.1. $^1$H NMR (400 MHz, MeOD-d$_4$) δ 8.91 (s, 1H), 8.54 (s, 2H), 8.08 (d, J=1.5 Hz, 1H), 7.91 (s, 1H), 7.50-7.41 (m, 3H), 6.92 (d, J=9.0 Hz, 2H), 4.32 (s, 2H), 2.05 (tt, J=3.9, 7.2 Hz, 1H), 0.31-0.21 (m, 2H), 0.01-0.00 (m, 2H).

Example 22

General Procedure I

N-(4-(chlorodifluoromethoxy)phenyl)-1-isopropyl-7-(thiazol-4-yl)-1H-benzo[d]imidazole-5-carboxamide The title compound was prepared using an analogous coupling reaction as outlined in Scheme 9. This General Procedure I exemplifies Scheme 9 and provides particular synthetic details as applied to the title compound.

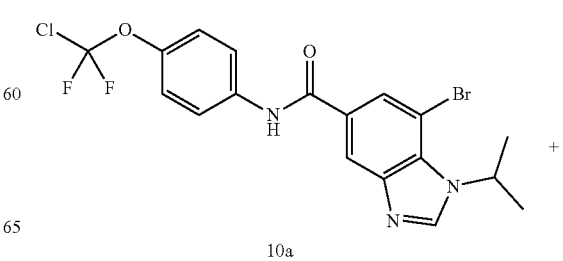

-continued

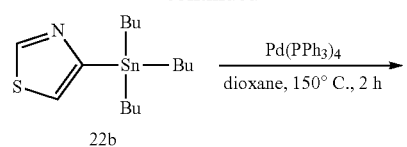

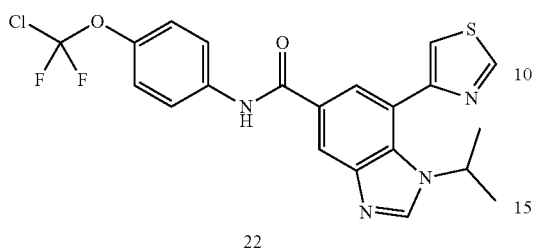

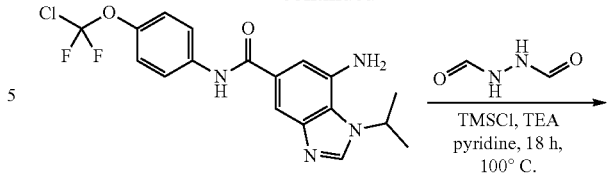

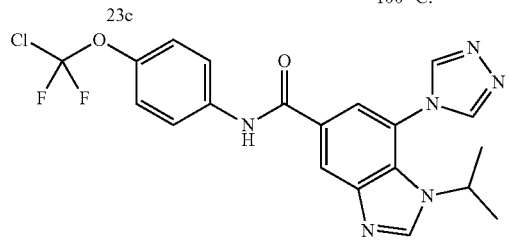

N-(4-(chlorodifluoromethoxy)phenyl)-1-isopropyl-7-(thiazol-4-yl)-1H-benzo[d]imidazole-5-carboxamide (22). 7-Bromo-N-(4-(chlorodifluoromethoxy)phenyl)-1-isopropyl-1H-benzo[d]imidazole-5-carboxamide (10a, 100 mg, 0.218 mmol, 1 eq), tributyl(thiazol-4-yl)stannane (22b, 97.89 mg, 0.262 mmol, 1.2 eq) and Pd(PPh$_3$)$_4$ (25.19 mg, 0.022 mmol, 0.1 eq) were added to a microwave tube in dioxane (4 mL). The sealed tube was heated to 150° C. for 3 hrs under microwave irradiation. Water (5 ml) was added to the reaction mixture, and the extracted with EtOAc (10 mL×2). The combined organic layers were concentrated, and the crude residue was purified by prep-HPLC (TFA condition, column: Luna C18 100*30 5 u; mobile phase: [water (0.1% TFA)-ACN]; B %: 15%-50%, 10 min) to afford the title compound 22 as a yellow solid. MS mass calculated for [M+1]$^+$ (C$_{21}$H$_{17}$ClF$_2$N$_4$O$_2$S) requires m/z 463.1, LCMS found m/z 463.0. $^1$H NMR (400 MHz, CDCl$_3$-d) δ 8.95-8.91 (m, 1H), 8.86 (d, J=1.6 Hz, 1H), 8.40 (s, 1H), 8.03 (s, 1H), 7.84 (s, 1H), 7.74 (br d, J=8.8 Hz, 2H), 7.50 (d, J=1.6 Hz, 1H), 7.24-7.15 (m, 2H), 4.53 (td, J=6.6, 13.3 Hz, 1H), 1.26 (d, J=6.6 Hz, 6H).

Example 23

N-(4-(chlorodifluoromethoxy)phenyl)-1-isopropyl-7-(4H-1,2,4-triazol-4-yl)-1H-benzo[d]imidazole-5-carboxamide

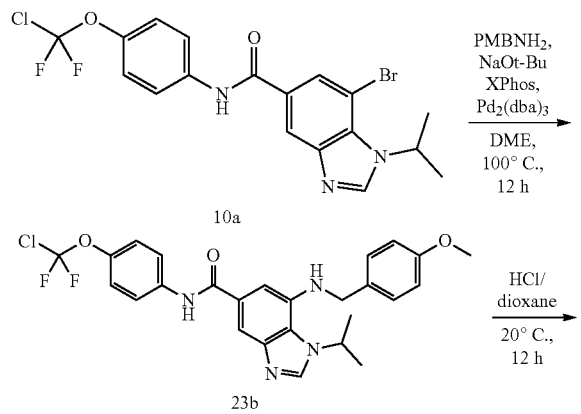

N-(4-(chlorodifluoromethoxy)phenyl)-1-isopropyl-7-((4-methoxybenzyl)amino)-1H-benzo[d]imidazole-5-carboxamide (23b). To a mixture of 7-bromo-N-(4-(chlorodifluoromethoxy)phenyl)-1-isopropyl-1H-benzo[d]imidazole-5-carboxamide (10a, 900 mg, 1.96 mmol) in DME (15 mL) was added PMBNH$_2$ (323.00 mg, 2.35 mmol, 304.71 uL), NaOBu-t (565.70 mg, 5.89 mmol), XPhos (93.54 mg, 0.196 mmol) and Pd$_2$(dba)$_3$ (179.68 mg, 0.196 mmol). The mixture was stirred at 100° C. for 12 hr under N$_2$ atmosphere. LCMS showed a peak with desired MS was detected. The reaction mixture was concentrated under reduced pressure. The residue was diluted with water (5 mL) and extracted with EtOAc (5 mL×3). The combined organic layers were washed with brine (5 mL), dried over anhydrous Na$_2$SO$_4$, filtered and concentrated in vacuo. The residue was purified by silica gel chromatography (petroleum ether/ethyl acetate=3/1, 1/3) to afford 23b as a yellow solid. MS mass calculated for [M+1]$^+$ (C$_{26}$H$_{25}$ClF$_2$N$_4$O$_3$) requires m/z 515.2, LCMS found m/z 515.2. $^1$H NMR (400 MHz, DMSO-d$_6$) δ 10.24 (s, 1H), 8.38-8.36 (m, 1H), 7.93-7.89 (m, 2H), 7.78 (d, J=1.2 Hz, 1H), 7.38 (d, J=8.6 Hz, 2H), 7.33 (br d, J=9.0 Hz, 2H), 7.04 (s, 1H), 6.91 (d, J=8.7 Hz, 2H), 6.01-5.94 (m, 1H), 5.32-5.23 (m, 1H), 4.40 (br d, J=5.3 Hz, 2H), 3.72 (s, 3H), 1.57 (d, J=6.5 Hz, 6H).

7-Amino-N-(4-(chlorodifluoromethoxy)phenyl)-1-isopropyl-1H-benzo[d]imidazole-5-carboxamide (23c). A solution of N-(4-(chlorodifluoromethoxy)phenyl)-1-isopropyl-7-((4-methoxybenzyl)amino)-1H-benzo[d]imidazole-5-carboxamide (23b, 100 mg, 0.194 mmol) in HCl/dioxane (40 mL) was stirred at 20° C. for 12 hr. LCMS showed desired MS was detected. The reaction mixture was concentrated under reduced pressure. The mixture was purified by prep-HPLC (NH$_4$HCO$_3$ condition, column: Agela Durashell C18 150*25 5 u; mobile phase: [water (10 mM NH4HCO3)-ACN]; B %: 35%-65%,10 min) to give 23c as yellow solid. MS mass calculated for [M+1]$^+$ (C$_{18}$H$_{17}$ClF$_2$N$_4$O$_2$) requires m/z 395.1, LCMS found m/z 395.1. $^1$H NMR (400 MHz, MeOD-d$_4$) δ 8.34 (br s, 1H), 7.82 (d, J=9.0 Hz, 2H), 7.69 (d, J=1.6 Hz, 1H), 7.29 (d, J=9.2 Hz, 2H), 7.23 (d, J=1.6 Hz, 1H), 5.25-5.12 (m, 1H), 1.66 (d, J=6.7 Hz, 6H).

N-(4-(chlorodifluoromethoxy)phenyl)-1-isopropyl-7-(4H-1,2,4-triazol-4-yl)-1H-benzo[d]imidazole-5-carboxamide (23). To a solution of 7-amino-N-(4-(chlorodifluoromethoxy)phenyl)-1-isopropyl-1H-benzo[d]imidazole-5-carboxamide (23c, 14 mg, 0.035 mmol) and N-formamidoformamide (9.37 mg, 0.106 mmol) in pyridine (1.5 mL) was added chloro-trimethyl-silane (57.79 mg, 0.532 mmol, 67.51 uL) and TEA (25.12 mg, 0.248 mmol, 34.55 uL). The mixture was stirred at 100° C. for 18 hr. LCMS showed 23c was consumed completely and one main peak with desired mass was detected. The reaction mixture was concentrated under reduced pressure. The residue was purified by prep-HPLC (column: Waters Atlantis T3 150*30*5 um; mobile phase: [water (0.225% FA)-ACN]; B %: 20%-60%, 13 min) to afford the title compound 23 as a white solid. MS mass calculated for $[M+1]^+$ ($C_{20}H_{17}ClF_2N_6O_2$) requires m/z 447.1, LCMS found m/z 447.1. $^1$H NMR (400 MHz, CDCl$_3$-d) δ 8.50-8.45 (m, 3H), 8.23 (s, 2H), 7.91 (d, J=1.0 Hz, 1H), 7.75 (d, J=8.8 Hz, 2H), 7.29 (br d, J=9.3 Hz, 2H), 3.74-3.61 (m, 1H), 1.45 (d, J=6.4 Hz, 6H).

Example 24

General Procedure J (S)—N-(4-(chlorodifluoromethoxy)phenyl)-1-(5-oxopyrrolidin-3-yl)-7-(pyrimidin-5-yl)-1H-benzo[d]imidazole-5-carboxamide This General Procedure J provides particular synthetic details as applied to the title compound. Additional compounds can be prepared according to this method by varying the coupling reagents.

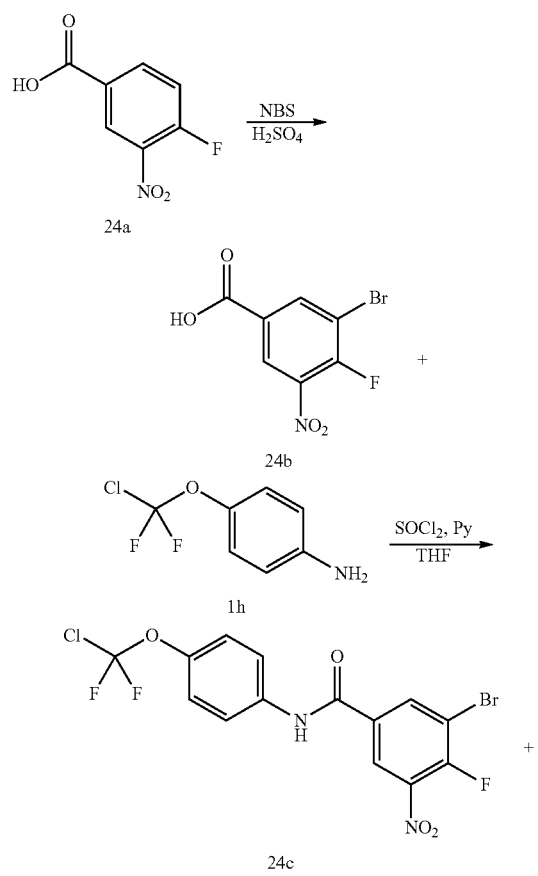

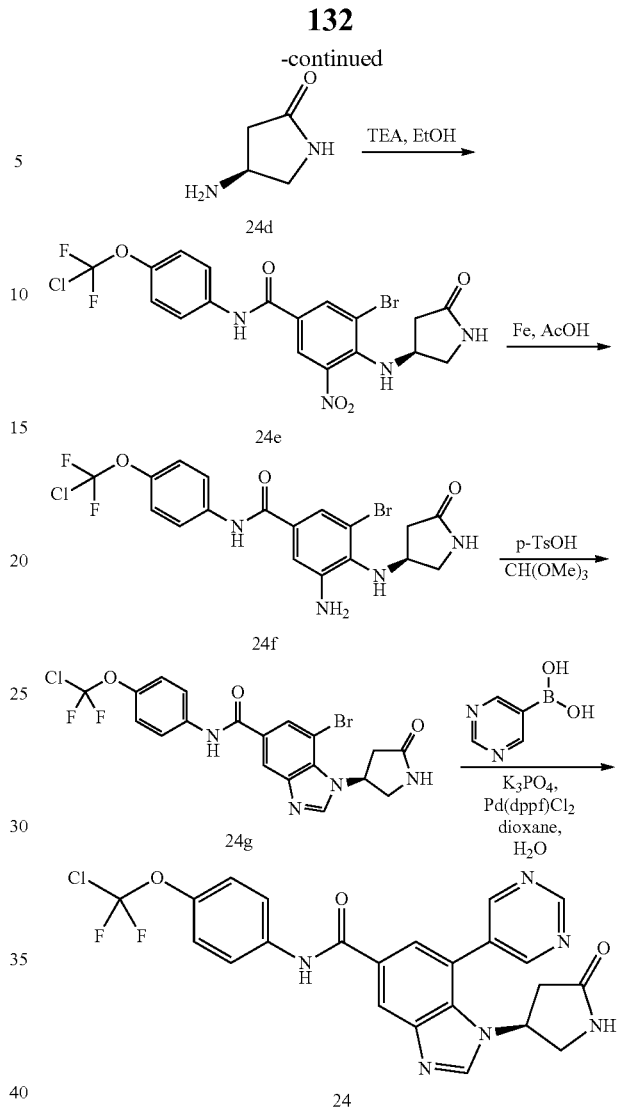

3-Bromo-4-fluoro-5-nitrobenzoic acid (24b). To a solution of 4-fluoro-3-nitrobenzoic acid (24a, 5 g, 27.01 mmol) in H$_2$SO$_4$ (30 mL) was added NBS (5.77 g, 32.41 mmol). The mixture was stirred at 60° C. for 6 hr. The mixture was added to ice-water (2 L) drop-wise with vigorous stirring. The precipitate was filtered to afford 24b as a white solid. $^1$H NMR (400 MHz, CDCl$_3$-d) δ 8.72 (dd, J=2.2, 6.4 Hz, 1H), 8.58 (dd, J=2.2, 5.5 Hz, 1H).

3-Bromo-N-(4-(chlorodifluoromethoxy)phenyl)-4-fluoro-5-nitrobenzamide (24c). A suspension of 3-bromo-4-fluoro-5-nitrobenzoic acid (24b, 150 mg, 0.568 mmol) in SOCl$_2$ (2 mL) was stirred at 60° C. for 3 hours. The mixture was concentrated to obtain 3-bromo-4-fluoro-5-nitro-benzoyl chloride (214 mg, crude) as a white solid. To a mixture of 4-(chlorodifluoromethoxy)aniline (1h, 146.64 mg, 0.758 mmol) and pyridine (89.89 mg, 1.13 mmol, 91.72 uL) in THF (2 mL) under N$_2$ was added 3-bromo-4-fluoro-5-nitro-benzoyl chloride (213.97 mg, 0.758 mmol). The mixture was stirred at 20° C. for 3 hours. LCMS showed the desired MS. The mixture was extracted with ethyl acetate (2 mL×3), the combined organic layers were washed with brine (5 mL×2), dried over anhydrous Na$_2$SO$_4$, filtered and concentrated in vacuo. The residue was purified by prep-TLC (SiO$_2$, petroleum ether:ethyl acetate=1:1, R$_f$=0.3). Compound 24c was obtained as a white solid.

(S)-3-bromo-N-(4-(chlorodifluoromethoxy)phenyl)-5-nitro-4-((5-oxopyrrolidin-3-yl)amino)benzamide (24e). To a mixture of 3-bromo-N-(4-(chlorodifluoromethoxy)phenyl)-4-fluoro-5-nitrobenzamide (24c, 100 mg, 0.228 mmol) and (4S)-4-aminopyrrolidin-2-one (24d, 22.78 mg, 0.228 mmol) in EtOH (2 mL) was added TEA (69.06 mg, 0.682 mmol, 94.99 uL). The mixture was stirred at 50° C. for 3 h. LCMS showed the desired MS. The mixture was concentrated and purified by prep-TLC (SiO$_2$, petroleum ether:ethyl acetate=3:1, R$_f$=0.1) to afford 24e as a yellow solid. $^1$H NMR (400 MHz, MeOD-d$_4$) δ 8.62 (d, J=2.2 Hz, 1H), 8.45 (d, J=2.2 Hz, 1H), 7.84-7.80 (m, 2H), 7.30 (d, J=8.8 Hz, 2H), 4.64 (br s, 1H), 3.80 (dd, J=6.8, 10.7 Hz, 1H), 3.39 (dd, J=4.2, 10.7 Hz, 1H), 2.80 (dd, J=7.9, 17.1 Hz, 1H), 2.41 (dd, J=4.8, 17.1 Hz, 1H).

(S)-3-amino-5-bromo-N-(4-(chlorodifluoromethoxy)phenyl)-4-((5-oxopyrrolidin-3-yl)amino)benzamide (24f). To a mixture of (S)-3-bromo-N-(4-(chlorodifluoromethoxy)phenyl)-5-nitro-4-((5-oxopyrrolidin-3-yl)amino)benzamide (24e, 0.053 g, 0.102 mmol) in AcOH (1 mL) at 20° C. under N$_2$ was added Fe (56.95 mg, 1.02 mmol) in one portion, and the mixture was stirred at 35° C. for 2 hours. LCMS showed the desired MS. The mixture was poured into sat. NaHCO$_3$ and extracted with ethyl acetate (5 mL×2). The combined organic layers were washed with brine (5 mL×2), dried over anhydrous Na$_2$SO$_4$, filtered and concentrated in vacuo to give 24f as a yellow solid.

(S)-7-bromo-N-(4-(chlorodifluoromethoxy)phenyl)-1-(5-oxopyrrolidin-3-yl)-1H-benzo[d]imidazole-5-carboxamide (24g). To a mixture of (S)-3-amino-5-bromo-N-(4-(chlorodifluoromethoxy)phenyl)-4-((5-oxopyrrolidin-3-yl)amino)benzamide (24f, 0.0358 g, 73.11 mmol) in CH(OMe)$_3$ (2 mL) at 20° C. under N$_2$ was added TsOH (1.26 mg, 7.31 umol) in one portion, and the mixture was stirred at 20° C. for 30 min. LCMS showed the desired MS. The mixture was extracted with ethyl acetate (3 mL×2), the combined organic layers were washed with brine (5 mL×2), dried over anhydrous Na$_2$SO$_4$, filtered and concentrated in vacuo to obtain 24g as a yellow solid.

(S)—N-(4-(chlorodifluoromethoxy)phenyl)-1-(5-oxopyrrolidin-3-yl)-7-(pyrimidin-5-yl)-1H-benzo[d]imidazole-5-carboxamide (24). To a mixture of (S)-7-bromo-N-(4-(chlorodifluoromethoxy)phenyl)-1-(5-oxopyrrolidin-3-yl)-1H-benzo[d]imidazole-5-carboxamide (24g, 35.3 mg, 0.071 mmol) and pyrimidin-5-ylboronic acid (17.51 mg, 0.141 mmol) in H$_2$O (0.1 mL) and dioxane (1 mL) under N$_2$ was added Pd(dppf)Cl$_2$ (5.17 mg, 7.06 umol), K$_3$PO$_4$ (29.99 mg, 0.141 mmol) in one portion. The mixture was stirred at 100° C. for 12 hours. LCMS showed the desired MS. The mixture was extracted with ethyl acetate (3 mL×3), the combined organic layers were washed with brine (5 mL×2), dried over anhydrous Na$_2$SO$_4$, filtered and concentrated in vacuo. The residue was purified by prep-TLC (SiO$_2$, petroleum ether: ethyl acetate=1:5, R$_f$=0.1) to afford the title compound 24 as a brown solid. MS mass calculated for [M+1]$^+$ (C$_{23}$H$_{17}$ClF$_2$N$_6$O$_3$) requires m/z 499.1, LCMS found m/z 499.1. $^1$H NMR (400 MHz, DMSO-d$_6$) δ 9.39 (s, 1H), 8.90 (br s, 2H), 8.49 (s, 1H), 8.40 (s, 1H), 8.10 (s, 1H), 7.83 (s, 1H), 7.78 (s, 1H), 7.28 (br s, 2H), 6.12 (br s, 1H), 4.69 (br s, 1H), 3.65 (dd, J=6.5, 11.1 Hz, 1H), 3.51 (br d, J=11.7 Hz, 1H), 2.82-2.60 (m, 2H).

Example 25

N-(4-(chlorodifluoromethoxy)phenyl)-1-isopropyl-7-(5-oxo-4,5-dihydro-1,2,4-oxadiazol-3-yl)-1H-benzo[d]imidazole-5-carboxamide

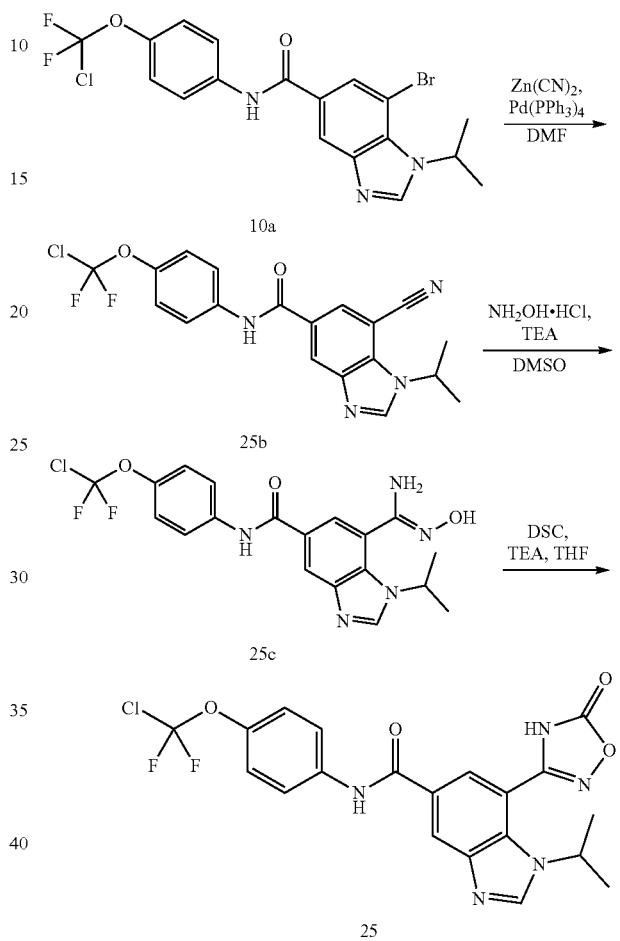

N-(4-(chlorodifluoromethoxy)phenyl)-7-cyano-1-isopropyl-1H-benzo[d]imidazole-5-carboxamide (25b). A solution of 7-bromo-N-(4-(chlorodifluoromethoxy)phenyl)-1-isopropyl-1H-benzo[d]imidazole-5-carboxamide (10a, 0.15 g, 0.327 mmol), Zn(CN)$_2$ (57.60 mg, 0.491 mmol, 31.14 uL) and Pd(PPh$_3$)$_4$ (18.89 mg, 0.016 mmol) in DMF (3 mL) were put into a microwave tube. The sealed tube was heated at 150° C. for 2 h under microwave irradiation. LCMS showed the desired MS. The mixture was extracted with ethyl acetate (2 mL×3), the combined organic layers were washed with brine (5 mL×2), dried over anhydrous Na$_2$SO$_4$, filtered and concentrated in vacuo. The residue was purified by prep-TLC (SiO$_2$, petroleum ether:ethyl acetate=0:1, R$_f$=0.67) to afford 1b as a white solid. $^1$H NMR (400 MHz, CDCl$_3$-d) δ 8.52 (s, 1H), 8.30-8.21 (m, 2H), 8.09 (s, 1H), 7.73 (d, J=8.8 Hz, 2H), 7.28 (d, J=8.6 Hz, 2H), 5.32 (spt, J=6.7 Hz, 1H), 1.72 (d, J=6.6 Hz, 6H).

(Z)—N-(4-(chlorodifluoromethoxy)phenyl)-7-(N'-hydroxycarbamimidoyl)-1-isopropyl-1H-benzo[d]imidazole-5-carboxamide (25c). To a solution of N-(4-(chlorodifluoromethoxy)phenyl)-7-cyano-1-isopropyl-1H-benzo[d]imidazole-5-carboxamide (25b, 20 mg, 0.049 mmol) in DMF (3 mL) was added NH$_2$OH.HCl (34.33 mg, 0.494 mmol) and TEA (49.99 mg, 0.49 mmol, 68.76 uL) The mixture was stirred at 75° C. for 12 hours. LCMS showed the desired MS. The aqueous phase was extracted with ethyl acetate (5 mL×3). The combined organic layers were washed with brine (10 mL×2), dried over anhydrous Na$_2$SO$_4$, filtered and concentrated in vacuo. The residue was purified by prep-TLC (SiO$_2$, petroleum ether:ethyl acetate=0:1, R$_f$=0.5) to afford 25c as a white solid. MS mass calculated for [M+1]$^+$ (C$_{19}$H$_{18}$ClF$_2$N$_5$O$_3$) requires m/z 438.1, LCMS found m/z 438.3.

N-(4-(chlorodifluoromethoxy)phenyl)-1-isopropyl-7-(5-oxo-4,5-dihydro-1,2,4-oxadiazol-3-yl)-1H-benzo[d]imidazole-5-carboxamide (25). To a solution of (Z)—N-(4-(chlorodifluoromethoxy)phenyl)-7-(N'-hydroxycarbamimidoyl)-1-isopropyl-1H-benzo[d]imidazole-5-carboxamide (25c, 0.02 g, 0.046 mmol) in THF (2 mL) under N$_2$ was added bis(2,5-dioxopyrrolidin-1-yl) carbonate (15.21 mg, 0.059 mmol) and TEA (9.24 mg, 0.091 mmol, 12.72 uL). The mixture was stirred at 60° C. for 12 hours. LCMS showed the desired MS. The aqueous phase was extracted with ethyl acetate (3 mL×3), the combined organic layers were washed with brine (5 mL×2), dried over anhydrous Na$_2$SO$_4$, filtered and concentrated in vacuo. The residue was purified by prep-TLC (SiO$_2$, ethyl acetate:methanol=10:1, R$_f$=0.1) to yield the title compound 25 as a yellow solid. MS mass calculated for [M+1]$^+$ (C$_{20}$H$_{16}$ClF$_2$N$_5$O$_4$) requires m/z 464.1, LCMS found m/z 464.1; $^1$H NMR (400 MHz, MeOD-d$_4$) δ 8.55 (s, 1H), 8.43 (d, J=1.6 Hz, 1H), 8.09 (d, J=1.6 Hz, 1H), 7.85 (d, J=9.0 Hz, 2H), 7.29 (d, J=8.9 Hz, 2H), 5.25 (td, J=6.6, 13.3 Hz, 1H), 1.53 (d, J=6.7 Hz, 6H).

Example 26

N$^5$-(4-(chlorodifluoromethoxy)phenyl)-1-isopropyl-1H-benzo[d]imidazole-5,7-dicarboxamide

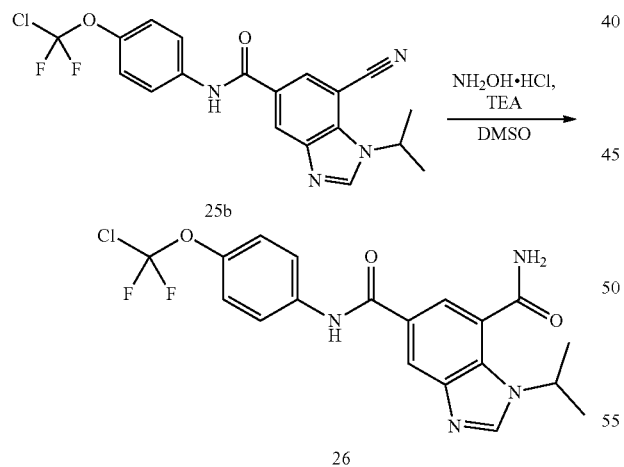

N$^5$-(4-(chlorodifluoromethoxy)phenyl)-1-isopropyl-1H-benzo[d]imidazole-5,7-dicarboxamide (26). To a solution of N-(4-(chlorodifluoromethoxy)phenyl)-7-cyano-1-isopropyl-1H-benzo[d]imidazole-5-carboxamide (25b, 30 mg, 0.074 mmol) in DMSO (3 mL) was added NH$_2$OH.HCl (41.20 mg, 0.593 mmol) and TEA (13.86 mg, 0.137 mmol) The mixture was stirred at 80° C. for 12 hours. LCMS showed the desired MS. The aqueous phase was extracted with ethyl acetate (5 mL×3). The combined organic layers were washed with brine (10 mL×2), dried over anhydrous Na$_2$SO$_4$, filtered and concentrated in vacuo. The residue was purified by prep-TLC (SiO$_2$, petroleum ether:ethyl acetate=0:1, R$_f$=0.5) to afford the title compound 26 as a white solid. MS mass calculated for [M+1]$^+$ (C$_{19}$H$_{17}$ClF$_2$N$_4$O$_3$) requires m/z 423.1, LCMS found m/z 423.0. $^1$H NMR (400 MHz, DMSO-d$_6$) δ 10.48 (s, 1H), 8.62 (s, 1H), 8.48 (d, J=1.6 Hz, 1H), 8.27 (s, 1H), 7.98 (d, J=1.7 Hz, 1H), 7.97-7.94 (m, 2H), 7.78 (s, 1H), 7.37 (d, J=9.0 Hz, 2H), 5.09 (quin, J=6.6 Hz, 1H), 1.52 (s, 3H), 1.50 (s, 3H).

Example 27

N-(4-(chlorodifluoromethoxy)phenyl)-3-isopropyl-4-(pyrimidin-5-yl)-3H-imidazo[4,5-c]pyridine-6-carboxamide

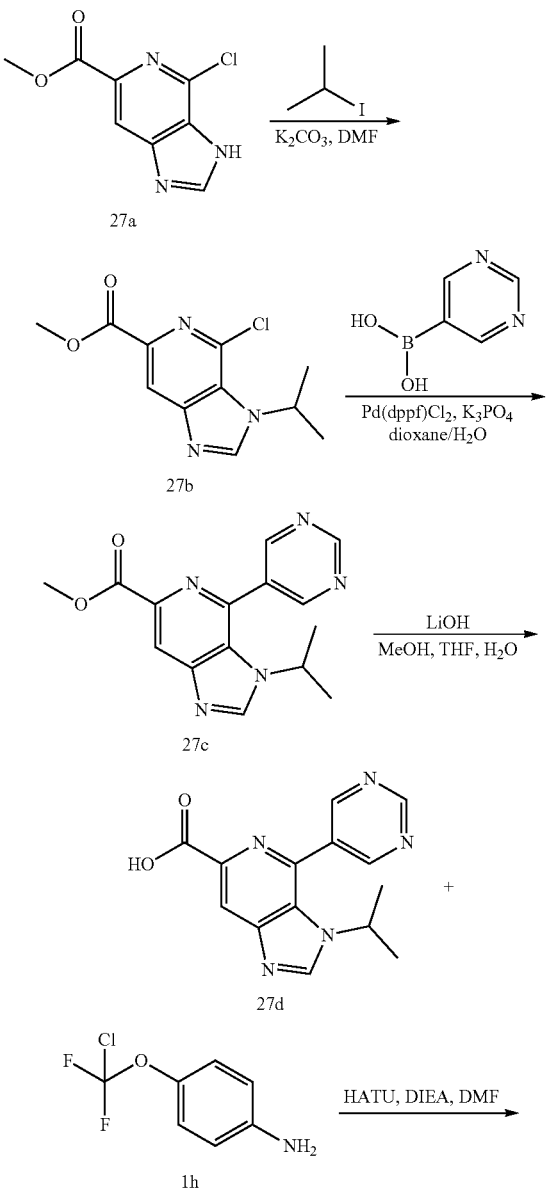

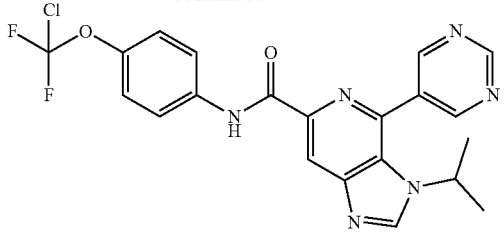

27

Methyl 4-chloro-3-isopropyl-3H-imidazo[4,5-c]pyridine-6-carboxylate (27b). To a solution of methyl 4-chloro-3H-imidazo[4,5-c]pyridine-6-carboxylate (27a, 200 mg, 0.945 mmol) and 2-iodopropane (482.01 mg, 2.84 mmol, 283.53 uL) in DMF (3 mL) was added $K_2CO_3$ (391.88 mg, 2.84 mmol). The mixture was stirred at 30° C. for 16 hr. LCMS showed 27a was consumed completely and desired MS was detected. The mixture was diluted with water (5 mL) and extracted with EtOAc (5 mL×3). The combined organic layers were washed with brine (5 mL), dried over $Na_2SO_4$, filtered and concentrated under reduced pressure to give a residue. The residue was purified by prep-TLC ($SiO_2$, petroleum ether:ethyl acetate=1:2) to afford 27c as a white solid. $^1$H NMR (400 MHz, $CDCl_3$-d) δ 8.54 (s, 1H), 8.30 (s, 1H), 5.60-5.42 (m, 1H), 4.04 (s, 3H), 1.70 (d, J=6.7 Hz, 6H).

Methyl 3-isopropyl-4-(pyrimidin-5-yl)-3H-imidazo[4,5-c]pyridine-6-carboxylate (27c). To a solution of methyl 4-chloro-3-isopropyl-3H-imidazo[4,5-c]pyridine-6-carboxylate (27b, 70 mg, 0.276 mmol) and pyrimidin-5-ylboronic acid (68.38 mg, 0.552 mmol) in dioxane (1 mL) and $H_2O$ (0.1 mL) was added Pd(dppf)$Cl_2$ (20.19 mg, 27.59 umol) and $K_3PO_4$ (175.71 mg, 0.828 mmol). The mixture was stirred at 110° C. for 16 hr under $N_2$. LCMS showed 27b was consumed completely and desired MS was detected. The mixture was diluted with water (5 mL) and extracted with EtOAc (5 mL×3). The combined organic layers were washed with brine (5 mL), dried over $Na_2SO_4$, filtered and concentrated under reduced pressure to give a residue. The residue was purified by prep-TLC ($SiO_2$, ethyl acetate:methanol=10:1) to afford 27c as a white solid. $^1$H NMR (400 MHz, MeOD-$d_4$) δ 9.36 (s, 1H), 9.13 (s, 2H), 8.82 (s, 1H), 8.56 (s, 1H), 4.36-4.23 (m, 1H), 4.01 (s, 3H), 1.45 (d, J=6.6 Hz, 6H).

3-Isopropyl-4-(pyrimidin-5-yl)-3H-imidazo[4,5-c]pyridine-6-carboxylic acid (27d). To a solution of methyl 3-isopropyl-4-(pyrimidin-5-yl)-3H-imidazo[4,5-c]pyridine-6-carboxylate (27c, 35 mg, 0.118 mmol) in THF (0.5 mL), MeOH (0.5 mL) and $H_2O$ (0.25 mL) was added LiOH.$H_2O$ (9.88 mg, 0.235 mmol). The mixture was stirred at 20° C. for 2 hr. TLC (ethyl acetate:methanol=10:1, $R_f$=0.0) showed 27c was consumed completely and one major new spot with more polarity was detected. The mixture was concentrated in vacuo. Then the mixture was added to $H_2O$ (3 mL) and the aqueous phase was acidified with aqueous HCl to pH=5. The mixture was concentrated in vacuo. The product was used in the next step without further purification. Compound 27d was obtained as a white solid. $^1$H NMR (400 MHz, MeOD-$d_4$) δ 9.69 (s, 1H), 9.46 (s, 1H), 9.22 (s, 2H), 8.80-8.67 (m, 1H), 4.42 (s, 1H), 1.50 (d, J=6.6 Hz, 6H).

N-(4-(chlorodifluoromethoxy)phenyl)-3-isopropyl-4-(pyrimidin-5-yl)-3H-imidazo[4,5-c]pyridine-6-carboxamide (27). To a solution of 3-isopropyl-4-(pyrimidin-5-yl)-3H-imidazo[4,5-c]pyridine-6-carboxylic acid (27d, 32 mg, 0.113 mmol) and 1h (32.80 mg, 0.169 mmol) in DMF (2 mL) was added DIEA (43.80 mg, 0.339 mmol, 59.03 uL) and HATU (51.54 mg, 0.136 mmol). The mixture was stirred at 25° C. for 4 hr. LCMS showed 27d was consumed completely and desired MS was detected. The mixture was diluted with water (5 mL) and extracted with EtOAc (5 mL×3). The combined organic layers were washed with brine (5 mL), dried over $Na_2SO_4$, filtered and concentrated under reduced pressure to give a residue. The residue was purified by prep-TLC ($SiO_2$, petroleum ether: ethyl acetate=0:1) to afford 27 as a white solid. MS mass calculated for [M+H]$^+$ ($C_{21}H_{17}O_2N_6ClF_2$) requires m/z 459.1, LCMS found m/z 459.0. $^1$H NMR (400 MHz, DMSO-$d_6$) δ 10.61 (s, 1H), 9.42 (s, 1H), 9.30 (s, 2H), 8.94 (s, 1H), 8.50 (s, 1H), 8.05-7.95 (m, 2H), 7.37 (d, J=9.0 Hz, 2H), 4.38-4.09 (m, 1H), 1.38 (d, J=6.7 Hz, 6H).

Example 28

General Procedure K (R)—N-(4-(chlorodifluoromethoxy)phenyl)-2-(difluoromethyl)-1-(1-fluoropropan-2-yl)-7-(1H-pyrazol-5-yl)-1H-benzo[d]imidazole-5-carboxamide This General Procedure K provides particular synthetic details as applied to the title compound. Additional compounds can be prepared according to this method by varying the coupling reagents.

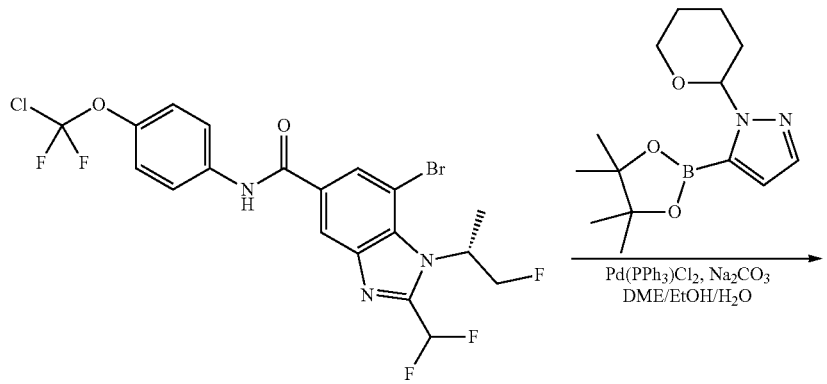

28a

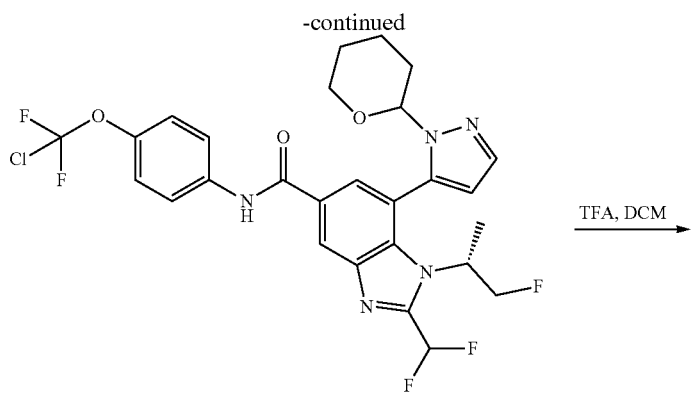

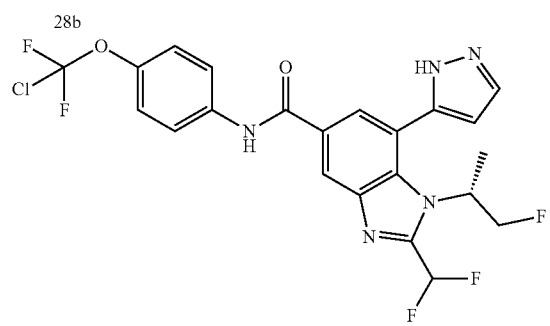

N-(4-(chlorodifluoromethoxy)phenyl)-2-(difluoromethyl)-1-(R)-1-fluoropropan-2-yl)-7-(1-(tetrahydro-2H-pyran-2-yl)-1H-pyrazol-5-yl)-1H-benzo[d]imidazole-5-carboxamide (28b). To a solution of (R)-7-bromo-N-(4-(chlorodifluoromethoxy)phenyl)-2-(difluoromethyl)-1-(1-fluoropropan-2-yl)-1H-benzo[d]imidazole-5-carboxamide (synthesized in a similar fashion to 15g; 28a, 30 mg, 0.057 mmol) and 1-tetrahydropyran-2-yl-5-(4,4,5,5-tetramethyl-1,3,2-dioxaborolan-2-yl)pyrazole (63.38 mg, 0.228 mmol) in DME (1.5 mL), EtOH (1.5 mL) and H$_2$O (0.3 mL) was added Pd(PPh$_3$)$_2$Cl$_2$ (4.00 mg, 5.70 umol), Na$_2$CO$_3$ (12.07 mg, 0.114 mmol). The mixture was stirred at 80° C. for 2 hr. LCMS showed 28a was consumed completely and desired MS was detected. The mixture was diluted with water (5 mL) and extracted with EtOAc (5 mL×3). The combined organic layers were washed with brine (5 mL), dried over Na$_2$SO$_4$, filtered and concentrated under reduced pressure to give a residue. The residue was purified by prep-TLC (SiO$_2$, petroleum ether:ethyl acetate=2:1) to afford 28b as a yellow solid.

(R)—N-(4-(chlorodifluoromethoxy)phenyl)-2-(difluoromethyl)-1-(1-fluoropropan-2-yl)-7-(1H-pyrazol-5-yl)-1H-benzo[d]imidazole-5-carboxamide (28). To a solution of N-(4-(chlorodifluoromethoxy)phenyl)-2-(difluoromethyl)-1-(R)-1-fluoropropan-2-yl)-7-(1-(tetrahydro-2H-pyran-2-yl)-1H-pyrazol-5-yl)-1H-benzo[d]imidazole-5-carboxamide (28b, 25 mg, 0.042 mmol) in DCM (1 mL) was added TFA (1.54 g, 13.51 mmol, 1 mL). The mixture was stirred at 20° C. for 1 hr. LCMS showed 28b was consumed completely and desired MS was detected. The mixture was diluted with water (5 mL) and extracted with EtOAc (5 mL×3). The combined organic layers were washed with brine (5 mL), dried over Na$_2$SO$_4$, filtered and concentrated under reduced pressure to give a residue. The residue was purified by prep-TLC (SiO$_2$, petroleum ether:ethyl acetate=1:1) to afford 28 as a white solid. MS mass calculated for [M+H]$^+$ (C$_{22}$H$_{17}$O$_2$N$_5$ClF$_5$) requires m/z 514.1, LCMS found m/z 514.1. $^1$H NMR (400 MHz, MeOD-d$_4$) δ 8.47 (d, J=1.3 Hz, 1H), 7.98 (d, J=1.7 Hz, 1H), 7.88 (br s, 1H), 7.87-7.81 (m, 2H), 7.44-7.15 (m, 3H), 6.66 (d, J=2.2 Hz, 1H), 4.70-4.67 (m, 1H), 4.63-4.45 (m, 2H), 1.52 (br d, J=7.2 Hz, 3H).

Example 29

N-(4-(chlorodifluoromethoxy)phenyl)-6-(pyrimidin-5-yl)-3,4-dihydro-1H-benzo[4,5]imidazo[2,1-c][1,4]thiazine-8-carboxamide 2,2-dioxide

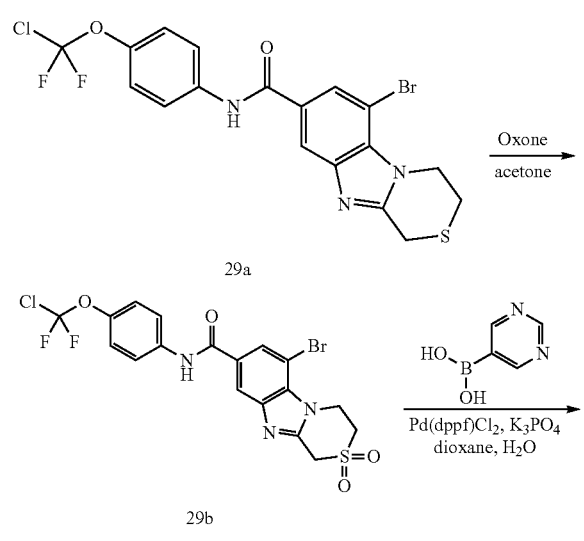

-continued

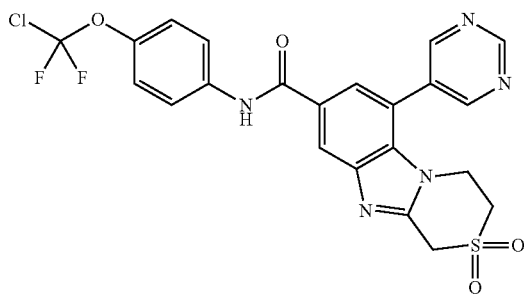

29

6-bromo-N-(4-(chlorodifluoromethoxy)phenyl)-3,4-dihydro-1H-benzo[4,5]imidazo[2,1-c][1,4]thiazine-8-carboxamide 2,2-dioxide (29b). To a solution of 6-bromo-N-(4-(chlorodifluoromethoxy)phenyl)-3,4-dihydro-1H-benzo[4,5]imidazo[2,1-c][1,4]thiazine-8-carboxamide (synthesized in a similar fashion to 8g; 29a, 2 mg, 4.09 umol) in acetone (0.5 mL) and H$_2$O (0.1 mL) was added Oxone (5.03 mg, 8.18 umol). The mixture was stirred at 20° C. for 24 hr. TLC (petroleum ether:ethyl acetate=0:1, R$_f$=0.77) indicated 29a was consumed completely and one major new spot with larger polarity was detected. The reaction was quenched by sodium sulfide. The reaction mixture was concentrated under reduced pressure to remove acetone. The residue was diluted with H$_2$O (10 mL) and extracted with EtOAc (10 mL×3). The combined organic layers were washed with brine (10 mL), dried over Na$_2$SO$_4$, filtered and concentrated under reduced pressure to give a residue. The residue was purified by prep-TLC (SiO$_2$, Petroleum ether:Ethyl acetate=0:1) to afford 29b as a brown solid. $^1$H NMR (400 MHz, MeOD-d$_4$) δ 8.18 (d, J=1.5 Hz, 1H), 8.05 (d, J=1.5 Hz, 1H), 7.73 (d, J=8.8 Hz, 2H), 7.20 (br d, J=8.8 Hz, 2H), 5.17-5.12 (m, 2H), 5.08 (s, 2H), 3.81-3.75 (m, 2H).

N-(4-(chlorodifluoromethoxy)phenyl)-6-(pyrimidin-5-yl)-3,4-dihydro-1H-benzo[4,5]imidazo[2,1-c][1,4]thiazine-8-carboxamide 2,2-dioxide (29). A mixture of 6-bromo-N-(4-(chlorodifluoromethoxy)phenyl)-3,4-dihydro-1H-benzo[4,5]imidazo[2,1-c][1,4]thiazine-8-carboxamide 2,2-dioxide (29b, 6 mg, 0.012 mmol), pyrimidin-5-ylboronic acid (4.28 mg, 0.035 mmol), Pd(dppf)Cl$_2$ (843.09 ug, 1.15 umol), K$_3$PO$_4$ (7.34 mg, 0.035 mmol) in dioxane (1 mL) and H$_2$O (0.1 mL) was degassed and purged with N$_2$ three times, and then the mixture was stirred at 110° C. for 16 hr under N$_2$ atmosphere. TLC (petroleum ether:ethyl acetate=0:1, R$_f$=0.3) indicated 29b was consumed completely and one major new spot with larger polarity was detected. The reaction mixture was concentrated under reduced pressure to remove dioxane. The residue was diluted with H$_2$O (1 mL) and extracted with ethyl acetate (1 mL×3). The combined organic layers were washed with brine (1 mL), dried over Na$_2$SO$_4$, filtered and concentrated under reduced pressure to give a residue. The residue was purified by prep-TLC (petroleum ether:ethyl acetate=0:1) to afford 29 as a white solid. $^1$H NMR (400 MHz, DMSO-d$_6$) δ 10.49 (s, 1H), 9.33 (s, 1H), 9.09 (s, 2H), 8.45 (d, J=1.0 Hz, 1H), 7.91 (d, J=9.3 Hz, 2H), 7.83 (d, J=1.5 Hz, 1H), 7.36 (d, J=8.8 Hz, 2H), 5.09 (s, 2H), 4.12 (br t, J=5.9 Hz, 2H), 3.75 (br t, J=5.6 Hz, 2H).

Example 30

General Procedure L

N-(4-(chlorodifluoromethoxy)phenyl)-1-isopropyl-7-(1H-1,2,3-triazol-5-yl)-1H-benzo[d]imidazole-5-carboxamide This General Procedure L provides particular synthetic details as applied to the title compound. Additional compounds can be prepared according to this method by varying the coupling reagents and/or the deprotection reagents.

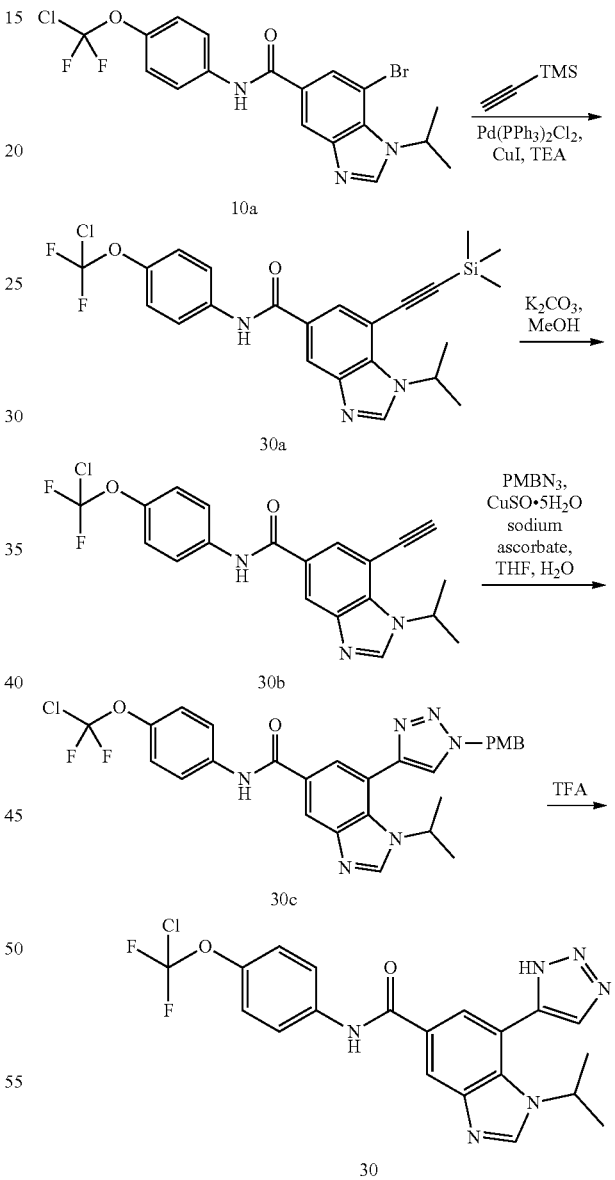

N-(4-(chlorodifluoromethoxy)phenyl)-1-isopropyl-7-(trimethylsilyl)ethynyl)-1H-benzo[d]imidazole-5-carboxamide (30a). To a mixture of 7-bromo-N-(4-(chlorodifluoromethoxy)phenyl)-1-isopropyl-1H-benzo[d]imidazole-5-carboxamide (10a, 80 mg, 0.174 mmol) and ethynyl(trimethyl)silane (85.65 mg, 0.872 mmol, 120.81 uL) in TEA (1 mL) was added CuI (3.32 mg, 0.017 mmol), Pd(PPh$_3$)$_2$Cl$_2$ (12.24 mg, 0.017 mmol) under N$_2$, the mixture was stirred at 80° C. for 2 hours. LCMS showed desired MS. Water was added to the reaction mixture and the mixture was extracted with ethyl acetate (5 mL×3). The combined organic layers were washed with brine (10 mL×2), dried over anhydrous Na$_2$SO$_4$, filtered and concentrated in vacuo. The residue was purified by prep-TLC (SiO$_2$, petroleum ether:ethyl acetate=1:1, R$_f$=0.4) to give 30a as a white solid. $^1$H NMR (400 MHz, CDCl$_3$-d) δ 8.31 (s, 1H), 8.15 (br d, J=7.2 Hz, 2H), 8.00 (s, 1H), 7.75 (br d, J=8.9 Hz, 2H), 7.30-7.27 (m, 2H), 5.65 (td, J=6.8, 13.4 Hz, 1H), 1.66 (d, J=6.7 Hz, 6H), 0.31 (s, 9H).

N-(4-(chlorodifluoromethoxy)phenyl)-7-ethynyl-1-isopropyl-1H-benzo[d]imidazole-5-carboxamide (30b). To a mixture of N-(4-(chlorodifluoromethoxy)phenyl)-1-isopropyl-7-(trimethylsilyl)ethynyl)-1H-benzo[d]imidazole-5-carboxamide (30a, 70 mg, 0.147 mmol) in MeOH (2 mL) was added K$_2$CO$_3$ (40.65 mg, 0.294 mmol, 2 eq). The mixture was stirred at 20° C. for 0.5 hours. TLC (petroleum ether: ethyl acetate=1:1, R$_f$=0.5) indicated 30a was consumed, and one major new spot with larger polarity was detected. The mixture was concentrated and extracted with ethyl acetate (5 mL×3). The combined organic layers were washed with brine (10 mL×2), dried over anhydrous Na$_2$SO$_4$, filtered and concentrated in vacuo. The residue was purified by prep-TLC (SiO$_2$, petroleum ether:ethyl acetate=0:1, R$_f$=0.5) to give 30b as a yellow solid. $^1$H NMR (400 MHz, CDCl$_3$-d) δ 8.33 (d, J=1.6 Hz, 1H), 8.22-8.13 (m, 2H), 8.06 (d, J=1.5 Hz, 1H), 7.78-7.72 (m, 2H), 7.29 (s, 2H), 5.68-5.49 (m, 1H), 3.44 (s, 1H), 1.66 (d, J=6.7 Hz, 6H).

N-(4-(chlorodifluoromethoxy)phenyl)-1-isopropyl-7-(1-(4-methoxybenzyl)-1H-1,2,3-triazol-4-yl)-1H-benzo[d]imidazole-5-carboxamide (30c). To a mixture of N-(4-(chlorodifluoromethoxy)phenyl)-7-ethynyl-1-isopropyl-1H-benzo[d]imidazole-5-carboxamide (30b, 50 mg, 0.124 mmol) and 1-(azidomethyl)-4-methoxy-benzene (22.23 mg, 0.136 mmol) in THF (1 mL), H$_2$O (1 mL) under N$_2$ was added CuSO$_4$.5H$_2$O (1.55 mg, 6.19 umol) and sodium (2R)-2-[(1S)-1,2-dihydroxyethyl]-4-hydroxy-5-oxo-2H-furan-3-olate (2.45 mg, 0.012 mmol). The mixture was stirred at 20° C. for 3 hours. LCMS showed the desired MS. The mixture was extracted with ethyl acetate (3 mL×3). The combined organic layers were washed with brine (5 mL×2), dried over anhydrous Na$_2$SO$_4$, filtered and concentrated in vacuo. The residue was purified by prep-TLC (SiO$_2$, petroleum ether:ethyl acetate=0:1, R$_f$=0.4) to give 30c as a yellow solid. $^1$H NMR (400 MHz, CDCl$_3$-d) δ 8.28 (s, 1H), 8.20 (s, 1H), 8.09 (br s, 1H), 7.79-7.66 (m, 4H), 7.32 (br d, J=8.4 Hz, 2H), 7.26-7.25 (m, 1H), 6.95 (d, J=8.4 Hz, 2H), 5.59 (s, 2H), 5.11-5.02 (m, 1H), 3.84 (s, 3H), 1.36 (d, J=6.7 Hz, 6H).

N-(4-(chlorodifluoromethoxy)phenyl)-1-isopropyl-7-(1H-1,2,3-triazol-5-yl)-1H-benzo[d]imidazole-5-carboxamide (30). The mixture of N-(4-(chlorodifluoromethoxy)phenyl)-1-isopropyl-7-(1-(4-methoxybenzyl)-1H-1,2,3-triazol-4-yl)-1H-benzo[d]imidazole-5-carboxamide (30c, 40 mg, 0.071 mmol) in TFA (3 mL) was stirred at 60° C. for 12 hours. LCMS showed the desired MS. The mixture was concentrated and extracted with ethyl acetate (5 mL×3). The combined organic layers were washed with brine (10 mL×2), dried over anhydrous Na$_2$SO$_4$, filtered and concentrated in vacuo. The residue was purified by prep-TLC (SiO$_2$, petroleum ether:ethyl acetate=0:1, R$_f$=0.3) to give 30 as an off-white solid. MS mass calculated for [M+1]$^+$ (C$_{20}$H$_{17}$ClF$_2$N$_6$O$_2$) requires m/z 447.1, LCMS found m/z 447.0; $^1$H NMR (400 MHz, DMSO-d$_6$) δ 10.47 (s, 1H), 8.62 (s, 1H), 8.48 (d, J=1.3 Hz, 1H), 8.31 (br s, 1H), 7.95 (d, J=9.0 Hz, 2H), 7.85 (d, J=1.3 Hz, 1H), 7.36 (d, J=9.0 Hz, 2H), 4.63 (br s, 1H), 1.32 (d, J=6.6 Hz, 6H).

Example 31 General Procedure M

N-(4-(chlorodifluoromethoxy)phenyl)-7-(4-cyano-1H-pyrazol-3-yl)-1-isopropyl-1H-benzo[d]imidazole-5-carboxamide This General Procedure M provides particular synthetic details as applied to the title compound. Additional compounds can be prepared according to this method by varying the coupling reagents and/or the deprotection reagents.

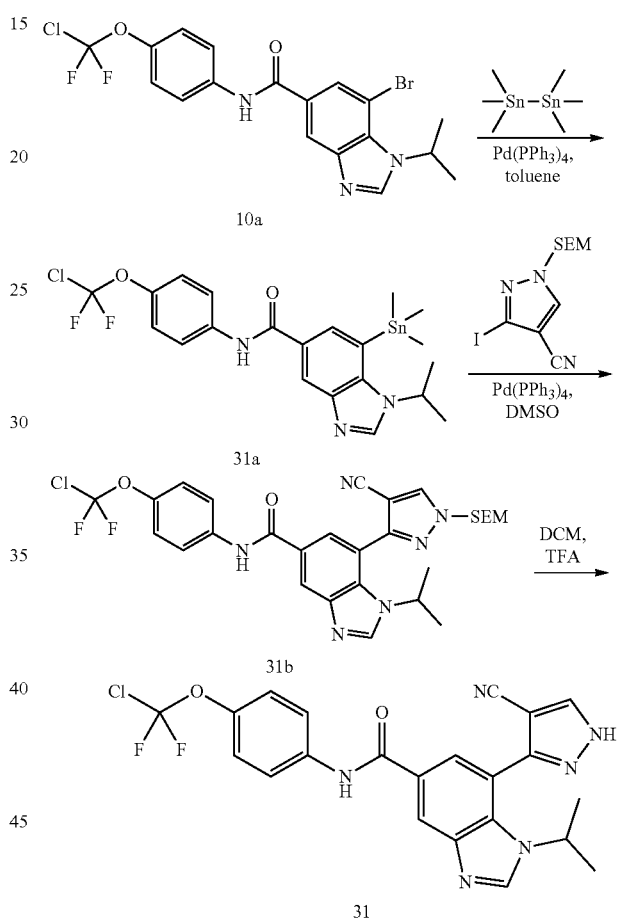

N-(4-(chlorodifluoromethoxy)phenyl)-1-isopropyl-7-(trimethylstannyl)-1H-benzo[d]imidazole-5-carboxamide (31a). To a mixture of 7-bromo-N-(4-(chlorodifluoromethoxy)phenyl)-1-isopropyl-1H-benzo[d]imidazole-5-carboxamide (10a, 94.7 mg, 0.206 mmol) and trimethyl (trimethylstannyl)stannane (270.57 mg, 0.826 mmol, 171.25 uL) in toluene (3 mL) under N$_2$ was added Pd(PPh$_3$)$_4$ (23.86 mg, 0.021 mmol). The mixture was stirred at 130° C. for 12 hours. LCMS showed the desired MS. Water was added to the reaction mixture and the mixture was extracted with ethyl acetate (5 mL×2). The combined organic layers were washed with brine (10 mL×2), dried over anhydrous Na$_2$SO$_4$, filtered and concentrated in vacuo. The residue was purified by prep-TLC (SiO$_2$, petroleum ether:ethyl acetate=1:1, R$_f$=0.4) to give 31a as a colorless oil.

N-(4-(chlorodifluoromethoxy)phenyl)-7-(4-cyano-1-((2-(trimethylsilyl)ethoxy)methyl)-1H-pyrazol-3-yl)-1-isopropyl-1H-benzo[d]imidazole-5-carboxamide (31b). To a mixture of N-(4-(chlorodifluoromethoxy)phenyl)-1-isopropyl-7-(trimethylstannyl)-1H-benzo[d]imidazole-5-carboxamide (31a, 50 mg, 0.92 mmol) and 3-iodo-1-(2-trimethylsilylethoxymethyl)pyrazole-4-carbonitrile (64.37 mg, 0.184 mmol) in DMSO (3 mL) under $N_2$ was added Pd(PPh$_3$)$_4$ (10.65 mg, 9.22 umol). The mixture was stirred at 100° C. for 12 hours. LCMS showed the desired MS. The mixture was filtered and extracted with ethyl acetate (3 mL×3) and water. The combined organic layers were washed with brine (5 mL×2), dried over anhydrous Na$_2$SO$_4$, filtered and concentrated in vacuo. The residue was purified by prep-TLC (SiO$_2$, petroleum ether:ethyl acetate=0:1, R$_f$=0.6) to afford 31b as a yellow oil. MS mass calculated for [M+1]$^+$ (C$_{28}$H$_{31}$ClF$_2$N$_6$O$_3$Si) requires m/z 601.2, LCMS found m/z 601.2.

N-(4-(chlorodifluoromethoxy)phenyl)-7-(4-cyano-1H-pyrazol-3-yl)-1-isopropyl-1H-benzo[d]imidazole-5-carboxamide (31). A mixture of N-(4-(chlorodifluoromethoxy)phenyl)-7-(4-cyano-1-(2-(trimethylsilyl)ethoxy)methyl)-1H-pyrazol-3-yl)-1-isopropyl-1H-benzo[d]imidazole-5-carboxamide (31b, 20 mg, 33.27 mmol) in TFA (0.5 mL) and DCM (0.5 mL) was stirred at 20° C. for 2 hours. LCMS showed the desired MS. The mixture was concentrated under reduced pressure. The residue was purified by prep-TLC (SiO$_2$, petroleum ether:ethyl acetate=0:1, R$_f$=0.4) to give 31 as a yellow solid. MS mass calculated for [M+1]$^+$ (C$_{22}$H$_{17}$ClF$_2$N$_6$O$_2$) requires m/z 471.1, LCMS found m/z 471.0; $^1$H NMR (400 MHz, DMSO-d$_6$) δ 14.16 (br s, 1H), 10.52 (s, 1H), 8.90-8.78 (m, 1H), 8.68 (br s, 1H), 8.59 (br s, 1H), 7.96 (d, J=9.0 Hz, 2H), 7.91 (s, 1H), 7.37 (br d, J=8.8 Hz, 2H), 4.39 (br s, 1H), 1.36 (br d, J=6.7 Hz, 6H).

Example 32

(R)—N$^8$-(4-(chlorodifluoromethoxy)phenyl)-N$^6$,4-dimethyl-3,4-dihydro-1H-benzo[4,5]imidazo[2,1-c][1,4]oxazine-6,8-dicarboxamide

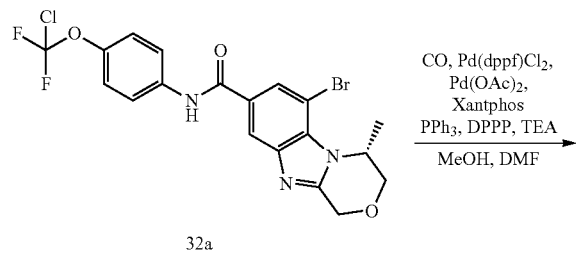

32a

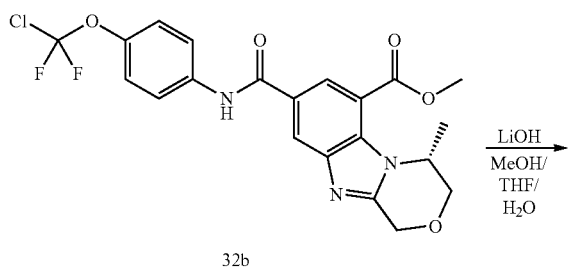

32b

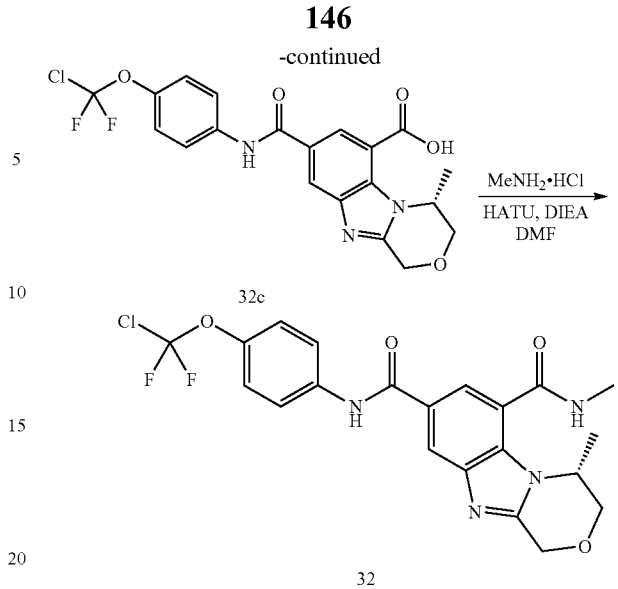

(R)-methyl 8-((4-(chlorodifluoromethoxy)phenyl)carbamoyl)-4-methyl-3,4-dihydro-1H-benzo[4,5]imidazo[2,1-c][1,4]oxazine-6-carboxylate (32b). To a solution of (R)-6-bromo-N-(4-(chlorodifluoromethoxy)phenyl)-4-methyl-3,4-dihydro-1H-benzo[4,5]imidazo[2,1-c][1,4]oxazine-8-carboxamide (synthesized in a similar fashion to 8g; 32a, 50 mg, 0.103 mmol) in MeOH (1 mL) and DMF (3 mL) under N$_2$ was added Pd(dppf)Cl$_2$ (15.03 mg, 0.021 mmol), TEA (51.98 mg, 0.514 mmol, 71.50 uL), Pd(OAc)$_2$ (4.61 mg, 0.021 mmol), Xantphos (11.89 mg, 0.021 mmol), PPh$_3$ (5.39 mg, 0.021 mmol and DPPP (8.47 mg, 0.021 mmol). The suspension was degassed under vacuum and purged with CO several times. The mixture was stirred under CO (2 MPa) at 120° C. for 12 hours. LCMS showed desired ms was detected. The reaction mixture was concentrated under reduced pressure. The residue was diluted with H$_2$O (10 mL) and the mixture was extracted with EtOAc (10 mL×3). The combined organic layers were washed with brine (10 mL), dried over Na$_2$SO$_4$, filtered and concentrated under reduced pressure to give a residue. The residue was purified by prep-TLC (Sift, ethyl acetate: petroleum ether=3:1, R$_f$=0.3) to afford the title compound 32b as a brown solid. $^1$H NMR (400 MHz, MeOD-d$_4$) δ 8.53-8.42 (m, 2H), 7.88-7.81 (m, 2H), 7.30 (d, J=9.0 Hz, 2H), 5.41 (br dd, J=1.8, 6.5 Hz, 1H), 5.18-4.95 (m, 2H), 4.24-4.18 (m, 1H), 4.12-4.08 (m, 1H), 4.04 (s, 3H), 1.40 (d, J=6.5 Hz, 3H).

(R)-8-((4-(chlorodifluoromethoxy)phenyl)carbamoyl)-4-methyl-3,4-dihydro-1H-benzo[4,5]imidazo[2,1-c][1,4]oxazine-6-carboxylic acid (32c). To a solution of (R)-methyl 8-((4-(chlorodifluoromethoxy)phenyl)carbamoyl)-4-methyl-3,4-dihydro-1H-benzo[4,5]imidazo[2,1-c][1,4]oxazine-6-carboxylate (32b, 22 mg, 0.047 mmol) in MeOH (1 mL), THF (1 mL) and H$_2$O (1 mL) was added LiOH.H$_2$O (7.93 mg, 0.189 mmol). The mixture was stirred at 50° C. for 5 hr. LCMS showed desired ms was detected. The reaction mixture was concentrated under reduced pressure to remove solvent. H$_2$O was added, and 1M HCl was added to the mixture drop-wise until pH=5. The mixture was concentrated to give a crude product, which was used in next step without purification. $^1$H NMR (400 MHz, DMSO-d$_6$) δ 10.60 (s, 1H), 8.55 (d, J=1.7 Hz, 1H), 8.38 (d, J=1.7 Hz, 1H), 7.96 (d, J=9.2 Hz, 2H), 7.38 (d, J=9.0 Hz, 2H), 5.38-5.26 (m, 1H), 5.16-4.90 (m, 2H), 4.29-3.98 (m, 2H), 1.31 (d, J=6.5 Hz, 3H).

(R)—N⁸-(4-(chlorodifluoromethoxy)phenyl)-N⁶,4-dimethyl-3,4-dihydro-1H-benzo[4,5]imidazo[2,1-c][1,4]oxazine-6,8-dicarboxamide (32). To a solution of (R)-8-((4-(chlorodifluoromethoxy)phenyl)carbamoyl)-4-methyl-3,4-dihydro-1H-benzo[4,5]imidazo[2,1-c][1,4]oxazine-6-carboxylic acid (32c, 21 mg, 0.046 mmol) and methanamine hydrochloride (31.38 mg, 0.465 mmol) in DMF (2 mL) was added HATU (53.02 mg, 0.139 umol) and DIEA (48.06 mg, 0.372 mmol, 64.77 uL). The mixture was stirred at 20° C. for 24 hr. LCMS showed desired ms was detected. The reaction mixture was concentrated under reduced pressure to remove solvent. The residue was diluted with H₂O (5 mL) and extracted with EtOAc (5 mL×3). The combined organic layers were washed with brine (5 mL), dried over Na₂SO₄, filtered and concentrated under reduced pressure to give a residue. The residue was purified by prep-TLC (SiO₂, petroleum ether:ethyl acetate=0:1, $R_f$=0.60) to afford the title compound 32 as a white solid. MS mass calculated for [M+1]⁺ ($C_{21}H_{19}ClF_2N_4O_4$) requires m/z 465.1, LCMS found m/z 465.1. ¹H NMR (400 MHz, DMSO-d₆) δ 10.50 (s, 1H), 8.85-8.73 (m, 1H), 8.42 (d, J=1.6 Hz, 1H), 8.04-7.90 (m, 3H), 7.37 (d, J=9.0 Hz, 2H), 5.13-4.89 (m, 3H), 4.18-3.95 (m, 2H), 2.87 (d, J=4.6 Hz, 3H), 1.28 (d, J=6.5 Hz, 3H).

Example 33

General Procedure N (R)—N-(4-(chlorodifluoromethoxy)phenyl)-3-methyl-5-(1H-pyrazol-5-yl)-2,3-dihydrobenzo[4,5]imidazo[2,1-b]oxazole-7-carboxamide This General Procedure N provides particular synthetic details as applied to the title compound. Additional compounds can be prepared according to this method by varying the coupling reagents.

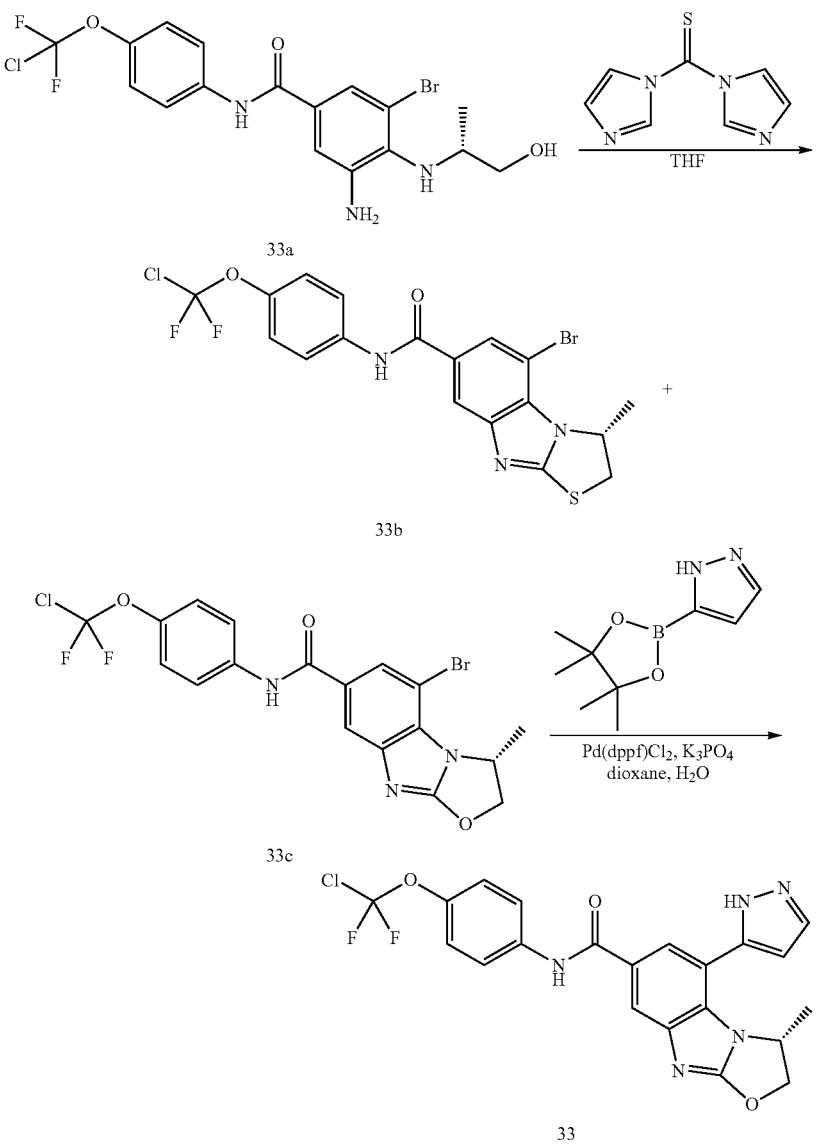

(R)-5-bromo-N-(4-(chlorodifluoromethoxy)phenyl)-3-methyl-2,3-dihydrobenzo[4,5]imidazo[2,1-b]thiazole-7-carboxamide (33b) & (R)-5-bromo-N-(4-(chlorodifluoromethoxy)phenyl)-3-methyl-2,3-dihydrobenzo[4,5]

imidazo[2,1-b]oxazole-7-carboxamide (33c). A solution of (R)-1-(3-amino-5-bromo-4-((1-hydroxypropan-2-yl)amino) phenyl)-2-(4-(chlorodifluoromethoxy)phenyl)ethanone (synthesized in a similar fashion to 6c; 33a, 330 mg, 0.71 mmol) and di(imidazol-1-yl)methane thione (379.68 mg, 2.13 mmol) in THF (15 mL) was stirred at 15° C. for 16 hr. TLC (petroleum ether:ethyl acetate=0:1, $R_f$=0.6) showed two new spots were generated. LCMS showed two peaks with with MS of 33b and 33c was detected. The mixture was concentrated. The crude product was purified by silica gel column chromatography (petroleum ether:ethyl acetate=3: 1~0:1) to give 33b as a yellow solid. $^1$H NMR (400 MHz, CDCl$_3$-d) δ 8.14 (s, 1H), 7.99 (d, J=1.5 Hz, 1H), 7.93 (d, J=1.5 Hz, 1H), 7.77-7.69 (m, 2H), 7.28 (br s, 1H), 7.26 (br s, 1H), 5.39 (quin, J=6.5 Hz, 1H), 4.35-4.24 (m, 1H), 3.48 (d, J=11.1 Hz, 1H), 1.57 (d, J=6.4 Hz, 3H). A batch of crude product was further purified by silica gel column chromatography (petroleum ether:ethyl acetate=3:1~0:1) to give 33c as a colourless solid. $^1$H NMR (400 MHz, CDCl$_3$-d) δ 8.49 (s, 1H), 8.02 (d, J=1.3 Hz, 1H), 7.92 (d, J=1.5 Hz, 1H), 7.79-7.72 (m, 2H), 7.28 (br s, 1H), 7.26 (s, 1H), 5.37 (quin, J=6.6 Hz, 1H), 4.26 (dd, J=7.2, 11.1 Hz, 1H), 4.13 (q, J=7.2 Hz, 1H), 3.46 (d, J=11.0 Hz, 1H), 1.56 (d, J=6.4 Hz, 3H).

(R)—N-(4-(chlorodifluoromethoxy)phenyl)-3-methyl-5-(1H-pyrazol-5-yl)-2,3-dihydrobenzo[4,5]imidazo[2,1-b] oxazole-7-carboxamide (33). A mixture of (R)-5-bromo-N-(4-(chlorodifluoromethoxy)phenyl)-3-methyl-2,3-dihydrobenzo[4,5]imidazo[2,1-b]oxazole-7-carboxamide (33c, 20 mg, 0.042 mmol), 5-(4,4,5,5-tetramethyl-1,3,2-dioxaborolan-2-yl)-1H-pyrazole (32.84 mg, 0.169 mmol), K$_3$PO$_4$ (26.94 mg, 0.127 mmol), Pd(dppf)Cl$_2$ (6.19 mg, 8.46 umol) and Boc$_2$O (4.62 mg, 0.021 umol, 4.86 uL) in dioxane (2 mL) and H$_2$O (0.2 mL) was degassed and purged with N$_2$ 3 times. The mixture was stirred at 110° C. for 16 hr under N$_2$ atmosphere. LCMS showed 33c remained. To this mixture was added 5-(4,4,5,5-tetramethyl-1,3,2-dioxaborolan-2-yl)-1H-pyrazole (24.63 mg, 0.127 mmol), K$_3$PO$_4$ (17.96 mg, 0.085 mmol) and Pd(dppf)Cl$_2$ (6.19 mg, 8.46 umol). The mixture was stirred at 110° C. for 4 hr under N$_2$ atmosphere. LCMS showed a peak with desired MS was detected. TLC (ethyl acetate:methanol=10:1, $R_f$=0.48) showed a new spot was generated. The reaction mixture was concentrated and H$_2$O (10 mL) was added. The mixture was extracted with ethyl acetate (20 mL×3). The combined organic layers were washed with brine (10 mL), dried over anhydrous Na$_2$SO$_4$, filtered and concentrated in vacuo. The crude product was purified by prep-TLC (ethyl acetate: methanol=10:1, $R_f$=0.48) to give a crude product, which was further purified by prep-TLC (DCM:methanol=10:1, $R_f$=0.5) to give 33 as a white solid. MS mass calculated for [M+1]$^+$ (C$_{21}$H$_{16}$ClF$_2$N$_5$O$_3$) requires m/z 460.1, LCMS found m/z 460.1. $^1$H NMR (400 MHz, MeOD-d$_4$) δ 8.00 (br d, J=9.7 Hz, 2H), 7.88-7.81 (m, 3H), 7.29 (d, J=8.8 Hz, 2H), 6.79 (br s, 1H), 5.29 (br d, J=7.9 Hz, 2H), 4.79 (br d, J=5.7 Hz, 1H), 1.00 (br d, J=4.9 Hz, 3H).

Example 34

General Procedure O (R)—N-(4-(chlorodifluoromethoxy)phenyl)-4-(hydroxymethyl)-6-(1H-pyrazol-5-yl)-3,4-dihydro-1H-benzo[4,5]imidazo[2,1-c][1,4]oxazine-8-carboxamide This General Procedure O provides particular synthetic details as applied to the title compound. Additional compounds can be prepared according to this method by varying the coupling reagents and/or deprotection reagents.

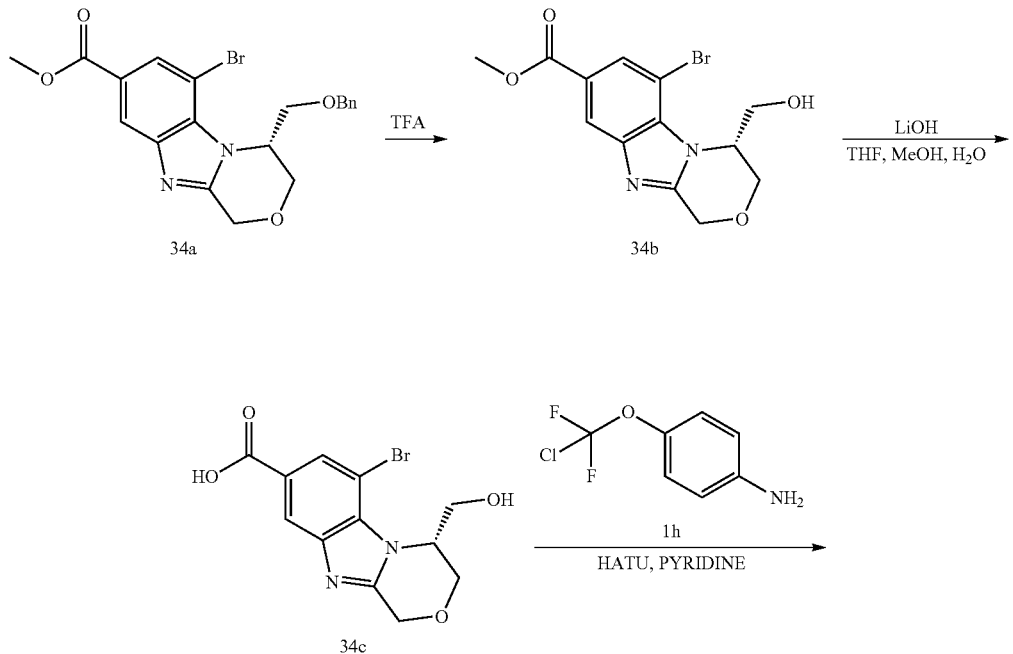

-continued

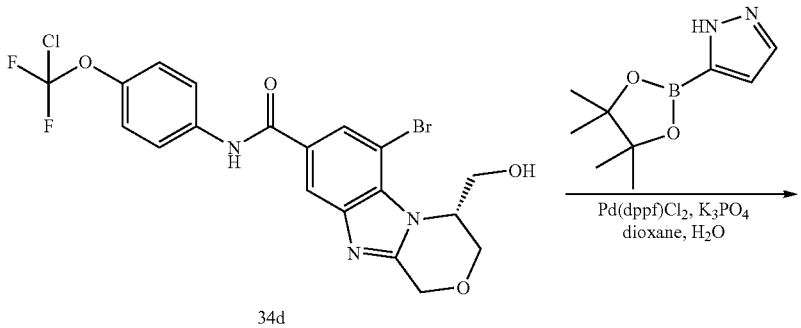

34d

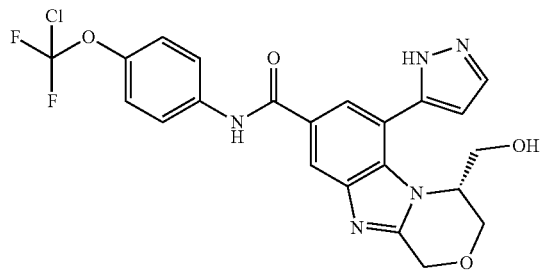

34

(R)-methyl 6-bromo-4-(hydroxymethyl)-3,4-dihydro-1H-benzo[4,5]imidazo[2,1-c][1,4]oxazine-8-carboxylate (34b). A solution of (R)-methyl 4-((benzyloxy)methyl)-6-bromo-3,4-dihydro-1H-benzo[4,5]imidazo[2,1-c][1,4]oxazine-8-carboxylate (synthesized in a similar fashion to 8e; 34a, 1.2 g, 2.78 mmol) in TFA (10 mL) was stirred at 75° C. for 16 hours. LCMS showed the desired MS. The mixture was concentrated to afford 34b as a yellow oil. MS mass calculated for [M+1]$^+$ ($C_{13}H_{13}BrN_2O_4$) requires m/z 341.0, LCMS found m/z 341.0.

(R)-6-bromo-4-(hydroxymethyl)-3,4-dihydro-1H-benzo[4,5]imidazo[2,1-c][1,4]oxazine-8-carboxylic acid (34c). To a solution of (R)-methyl 6-bromo-4-(hydroxymethyl)-3,4-dihydro-1H-benzo[4,5]imidazo[2,1-c][1,4]oxazine-8-carboxylate (34b, 0.95 g, 2.78 mmol) in THF (5 mL), MeOH (5 mL) and H$_2$O (1 mL) was added LiOH.H$_2$O (233.71 mg, 5.57 mmol). The mixture was stirred at 50° C. for 1 hour. LCMS showed the desired MS. The mixture was concentrated and the residue was dissolved in water (5 mL). The suspension was extracted with ethyl acetate (10 mL×2) and to the water phase was added HCl (1M) drop-wise until pH=3. The precipitated solid was collected by filtration and dried to afford 34c as a white solid. $^1$H NMR (400 MHz, DMSO-d$_6$) δ 8.12 (s, 1H), 7.95 (d, J=1.2 Hz, 1H), 5.45-5.36 (m, 1H), 5.13-5.05 (m, 1H), 4.97-4.88 (m, 1H), 4.38 (d, J=12.1 Hz, 1H), 4.02 (br d, J=11.9 Hz, 1H), 3.90 (br d, J=10.1 Hz, 1H), 3.67 (dt, J=5.9, 10.1 Hz, 1H).

(R)-6-bromo-N-(4-(chlorodifluoromethoxy)phenyl)-4-(hydroxymethyl)-3,4-dihydro-1H-benzo[4,5]imidazo[2,1-c][1,4]oxazine-8-carboxamide (34d). To a mixture of (R)-6-bromo-4-(hydroxymethyl)-3,4-dihydro-1H-benzo[4,5]imidazo[2,1-c][1,4]oxazine-8-carboxylic acid (34c, 0.85 g, 2.60 mmol) and 4-(chlorodifluoromethoxy)aniline (1h, 528.13 mg, 2.73 mmol) in pyridine (10 mL) was added HATU (1.48 g, 3.90 mmol). The mixture was stirred at 40° C. for 6 hours. LCMS showed the desired MS. The reaction mixture was poured into water (30 mL) and the mixture was extracted with ethyl acetate (50 mL×3). The combined organic layers were washed with brine (100 mL×2), dried over anhydrous Na$_2$SO$_4$, filtered and concentrated in vacuo. The residue was purified by column chromatography (SiO$_2$, petroleum ether:ethyl acetate=100:1 to 0:1, R$_f$=0.4) give 34d as a white solid. Mass calculated for [M+1]$^+$ ($C_{19}H_{15}BrClF_2N_3O_4$) requires m/z 502.0, LCMS found m/z 502.0; $^1$H NMR (400 MHz, CDCl$_3$-d) δ 8.10 (brs, 1H), 8.04 (d, J=1.3 Hz, 1H), 7.98 (d, J=1.3 Hz, 1H), 7.72 (d, J=9.0 Hz, 2H), 7.28 (s, 2H), 5.16 (d, J=16.5 Hz, 1H), 5.12-5.06 (m, 1H), 4.94 (d, J=16.3 Hz, 1H), 4.57 (d, J=12.3 Hz, 1H), 4.22 (dd, J=2.8, 10.5 Hz, 1H), 4.15-4.08 (m, 2H), 2.27 (br s, 1H).

(R)—N-(4-(chlorodifluoromethoxy)phenyl)-4-(hydroxymethyl)-6-(1H-pyrazol-5-yl)-3,4-dihydro-1H-benzo[4,5]imidazo[2,1-c][1,4]oxazine-8-carboxamid (34). To a mixture of (R)-6-bromo-N-(4-(chlorodifluoromethoxy)phenyl)-4-(hydroxymethyl)-3,4-dihydro-1H-benzo[4,5]imidazo[2,1-c][1,4]oxazine-8-carboxamide (34d, 0.5 g, 0.995 mmol) and pyrimidin-5-ylboronic acid (369.72 mg, 2.98 mmol) in dioxane (5 mL), H$_2$O (0.5 mL) was added K$_3$PO$_4$ (422.27 mg, 1.99 mmol), Pd(dppf)Cl$_2$ (72.78 mg, 0.099 mmol), (Boc)$_2$O (217.08 mg, 0.995 mmol, 228.51 uL) under N$_2$. The mixture was stirred at 110° C. for 16 hours. LCMS showed the desired MS. The mixture was filtered and concentrated. The residue was purified by column chromatography (SiO$_2$, petroleum ether:ethyl acetate=100:1 to 0:1, R$_f$=0.3) to give 34 as a yellow solid. Mass calculated for [M+1]$^+$ ($C_{22}H_{18}ClF_2N_5O_4$) requires m/z 490.1, LCMS found m/z 490.1; $^1$H NMR (400 MHz, MeOD-d$_4$) δ 8.29 (br s, 1H), 7.95 (s, 1H), 7.84 (br d, J=8.6 Hz, 3H), 7.30 (br d, J=8.8 Hz, 2H), 6.71 (br s, 1H), 5.17-4.93 (m, 2H), 4.37 (br d, J=12.2 Hz, 1H), 4.08 (br d, J=11.0 Hz, 1H), 3.60 (s, 1H), 3.53-3.40 (m, 2H).

Example 35

(S)—N-(4-(chlorodifluoromethoxy)phenyl)-4-(fluoromethyl)-6-(1H-pyrazol-5-yl)-3,4-dihydro-1H-benzo[4,5]imidazo[2,1-c][1,4]oxazine-8-carboxamide

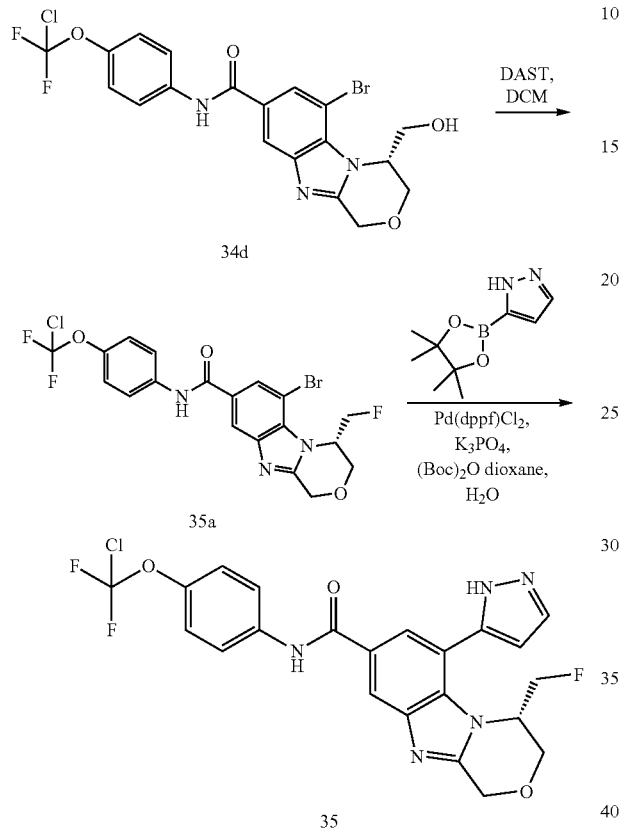

(S)-6-bromo-N-(4-(chlorodifluoromethoxy)phenyl)-4-(fluoromethyl)-3,4-dihydro-1H-benzo[4,5]imidazo[2,1-c][1,4]oxazine-8-carboxamide (35a). To a mixture of (R)-6-bromo-N-(4-(chlorodifluoromethoxy)phenyl)-4-(hydroxymethyl)-3,4-dihydro-1H-benzo[4,5]imidazo[2,1-c][1,4]oxazine-8-carboxamide (34d, 0.03 g, 0.06 mmol) in DCM (2 mL) at 0° C. under $N_2$ was added DAST (19.24 mg, 0.119 mmol, 15.77 uL). The mixture was stirred at 25° C. for 8 hours. LCMS showed the desired MS. The crude product was purified by prep-TLC (SiO$_2$, petroleum ether:ethyl acetate=0:1, $R_f$=0.6) to give 35a as a white solid. MS mass calculated for [M+1]$^+$ ($C_{19}H_{14}BrClF_3N_3O_3$) requires m/z 504.0, LCMS found m/z 504.0.

(S)—N-(4-(chlorodifluoromethoxy)phenyl)-4-(fluoromethyl)-6-(1H-pyrazol-5-yl)-3,4-dihydro-1H-benzo[4,5]imidazo[2,1-c][1,4]oxazine-8-carboxamide (35). To a mixture of (S)-6-bromo-N-(4-(chlorodifluoromethoxy)phenyl)-4-(fluoromethyl)-3,4-dihydro-1H-benzo[4,5]imidazo[2,1-c][1,4]oxazine-8-carboxamide (35a, 10 mg, 0.02 mmol) and 5-(4,4,5,5-tetramethyl-1,3,2-dioxaborolan-2-yl)-1H-pyrazole (11.53 mg, 0.059 mmol) in dioxane (2 mL) and H$_2$O (0.2 mL) was added (Boc)$_2$O (4.32 mg, 0.02 mmol, 4.55 uL), Pd(dppf)Cl$_2$ (1.45 mg, 1.98 umol), K$_3$PO$_4$ (12.62 mg, 0.059 mmol). The mixture was stirred at 110° C. for 12 hours. LCMS showed the desired MS. The mixture was filtered and concentrated. The residue was purified by prep-HPLC (column: Nano-micro Kromasil C18 100*30 mm 5 um; mobile phase: [water (0.1% TFA)-ACN]; B %: 36%-53%,10 min) to give 35 as a white solid. MS mass calculated for [M+1]$^+$ ($C_{22}H_{17}ClF_3N_5O_3$) requires m/z 492.1, LCMS found m/z 492.1; $^1$H NMR (400 MHz, CDCl$_3$-d) δ 8.21 (br s, 1H), 8.11 (br s, 1H), 7.92 (s, 1H), 7.80-7.73 (m, 3H), 7.29 (s, 2H), 6.68 (br s, 1H), 5.33 (br s, 1H), 5.18 (br d, J=16.1 Hz, 1H), 5.05-4.92 (m, 1H), 4.49-4.27 (m, 2H), 4.17-3.98 (m, 2H).

Example 36

(R)—N-(4-(chlorodifluoromethoxy)phenyl)-6-(3-hydroxyazetidin-1-yl)-4-methyl-3,4-dihydro-1H-benzo[4,5]imidazo[2,1-c][1,4]oxazine-8-carboxamide

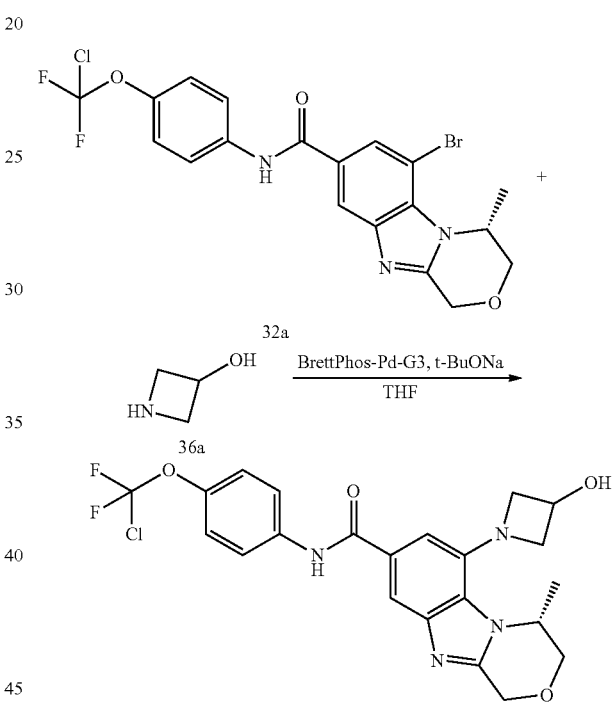

(R)—N-(4-(chlorodifluoromethoxy)phenyl)-6-(3-hydroxyazetidin-1-yl)-4-methyl-3,4-dihydro-1H-benzo[4,5]imidazo[2,1-c][1,4]oxazine-8-carboxamide (36). To a mixture of (R)-6-bromo-N-(4-(chlorodifluoromethoxy)phenyl)-4-methyl-3,4-dihydro-1H-benzo[4,5]imidazo[2,1-c][1,4]oxazine-8-carboxamide (32a, 20 mg, 0.041 mmol), azetidin-3-ol (36a, 15.02 mg, 0.205 mmol) in THF (0.8 mL) under N$_2$ was added BrettPhos Pd G3 (3.73 mg, 4.11 umol) and t-BuONa (2 M, 41.09 uL). The mixture was stirred at 100° C. for 16 hr in a sealed tube. LCMS showed a peak with desired MS. TLC (ethyl acetate:methanol=10:1, $R_f$=0.47) showed a new spot was generated. The reaction mixture was concentrated. The crude product was purified by prep-TLC (ethyl acetate:methanol=10:1, $R_f$=0.47), which was further purified by prep-HPLC (Column: Waters Xbridge 150*25 5 u; mobile phase: [water (10 mM NH$_4$HCO$_3$)-ACN]; B %: 25%-55%, 7 min) to afford 36 as a white solid. MS mass calculated for [M+1]$^+$ ($C_{22}H_{21}ClF_2N_4O_4$) requires m/z 479.1, LCMS found m/z 479.1; $^1$H NMR (400 MHz, MeOD-$d_4$) δ 7.91 (d, J=1.3 Hz, 1H), 7.86-7.81 (m, 2H), 7.54 (d, J=1.3 Hz, 1H), 7.30 (d, J=9.0 Hz, 2H), 5.05-4.99 (m, 2H), 4.95 (s, 1H), 4.72-4.65 (m, 1H), 4.36 (br t, J=6.5 Hz, 1H), 4.22 (dd, J=3.3, 12.0 Hz, 1H), 4.10-4.04 (m, 2H), 4.02-3.96 (m, 1H), 3.54 (t, J=6.3 Hz, 1H), 1.56 (d, J=6.4 Hz, 3H).

Example 37

N-(4-(chlorodifluoromethoxy)phenyl)-9-(1H-pyrazol-5-yl)-1,2,3,4-tetrahydrobenzo[4,5]imidazo[1,2-a]pyridine-7-carboxamide

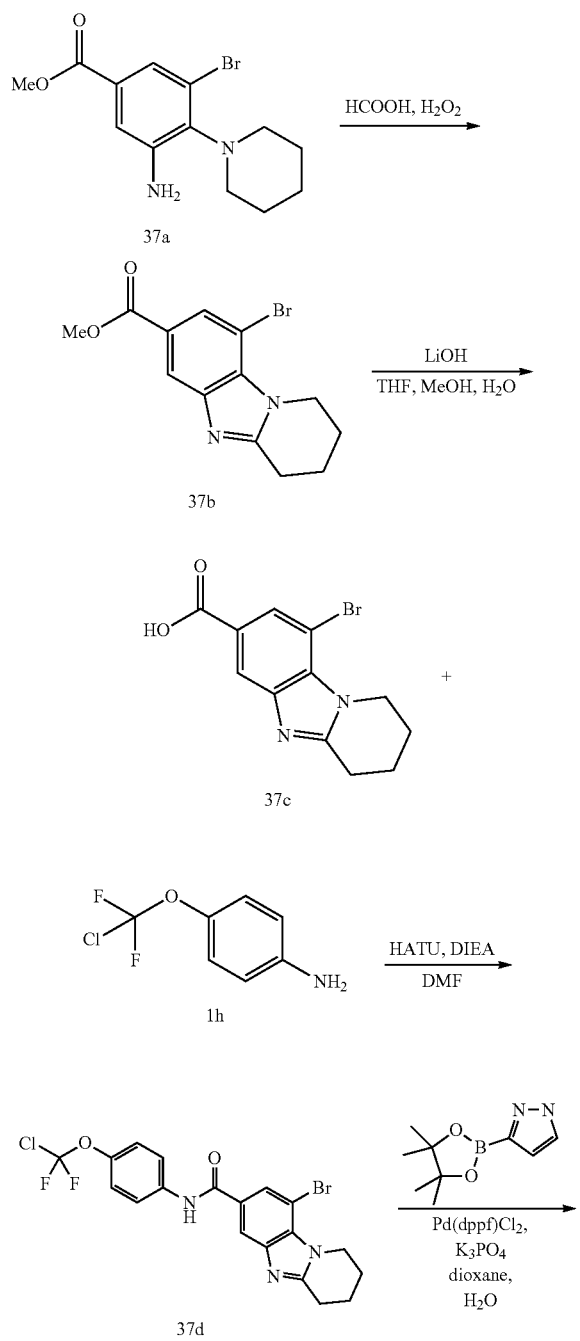

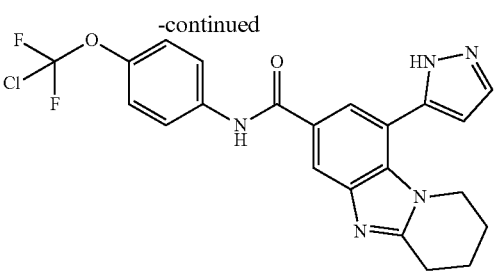

37

Methyl 9-bromo-1,2,3,4-tetrahydrobenzo[4,5]imidazo[1,2-a]pyridine-7-carboxylate (37b). To a solution of methyl 3-amino-5-bromo-4-(piperidin-1-yl)benzoate (synthesized in a similar fashion to 1d; 37a, 160 mg, 0.511 mmol) in formic acid (3 mL) was added $H_2O_2$ (521.32 mg, 4.60 mmol, 441.79 uL, 30% purity). The mixture was heated at reflux temperature for 40 min. LCMS showed 37a was consumed completely and one main peak with desired mass was detected. TLC (petroleum ether:ethyl acetate=2:1, $R_f$=0.20) indicated the reactant was consumed completely and one new spot formed. The mixture was concentrated under reduce pressure. The residue was dissolved in ethyl acetate (30 mL). The organic layers were washed with saturated aq. $NaHCO_3$ (10 mL×3), dried over $Na_2SO_4$, filtered and concentrated. The crude product was purified by prep-TLC (petroleum ether:ethyl acetate=2:1, $R_f$=0.20) to afford 37b as a white solid. $^1$H NMR (400 MHz, $CDCl_3$-d) δ 8.24-8.18 (m, 1H), 8.00 (d, J=1.3 Hz, 1H), 4.61-4.55 (m, 2H), 3.87 (s, 3H), 3.09-3.01 (m, 2H), 2.10-2.03 (m, 2H), 1.99-1.89 (m, 2H).

9-Bromo-1,2,3,4-tetrahydrobenzo[4,5]imidazo[1,2-a]pyridine-7-carboxylic acid (37c). To a solution of methyl 9-bromo-1,2,3,4-tetrahydrobenzo[4,5]imidazo[1,2-a]pyridine-7-carboxylate (37b, 50 mg, 0.162 mmol) in MeOH (1 mL), $H_2O$ (1 mL) and THF (1 mL) was added $LiOH \cdot H_2O$ (13.57 mg, 0.323 mmol). The mixture was stirred at 50° C. for 2 hr. LCMS showed 37b was consumed completely and one main peak with desired mass was detected. The mixture was concentrated to remove THF and MeOH. Then 1M HCl in water was added to the reaction mixture drop-wise until pH=5. The suspension was filtered, and the filter cake was washed with $H_2O$ (1 mL) and dried to afford 37 as white solid. $^1$H NMR (400 MHz, $CDCl_3$-d) δ 8.34 (d, J=1.3 Hz, 1H), 8.31 (d, J=1.2 Hz, 1H), 4.87-4.84 (m, 2H), 3.32-3.32 (m, 2H), 2.28-2.06 (m, 4H).

9-Bromo-N-(4-(chlorodifluoromethoxy)phenyl)-1,2,3,4-tetrahydrobenzo[4,5]imidazo[1,2-a]pyridine-7-carboxamide (37d). To a solution of 9-bromo-1,2,3,4-tetrahydrobenzo[4,5]imidazo[1,2-a]pyridine-7-carboxylic acid (37c, 47 mg, 0.159 mmol) in DMF (4 mL) was added HATU (72.66 mg, 0.191 mmol), DIEA (61.75 mg, 0.478 mmol, 83.22 uL) and 4-(chlorodifluoromethoxy)aniline (1h, 61.66 mg, 0.319 umol). The mixture was stirred at 15° C. for 16 hr. LCMS showed 37c was consumed completely and one main peak with desired mass was detected. TLC (ethyl acetate:methanol=10:1, $R_f$=0.36) indicated 37c was consumed completely and one new spot formed. $H_2O$ (20 mL) was added to the mixture. The mixture was extracted with ethyl acetate (10 mL×3). The combined organic layers were washed with brine (20 mL), dried over $Na_2SO_4$, filtered and concentrated in vacuo. The crude product was purified by prep-TLC (ethyl acetate:methanol=10:1, $R_f$=0.36) to afford 37d as a white oil. $^1$H NMR (400 MHz, $CDCl_3$-d) δ 8.01 (d, J=1.5 Hz, 1H), 7.96 (d, J=1.5 Hz, 1H), 7.75-7.67 (m, 2H), 7.15 (d, J=8.8 Hz, 2H), 4.60 (t, J=6.2 Hz, 2H), 3.02 (t, J=6.5 Hz, 2H), 2.09-2.04 (m, 2H), 1.97-1.88 (m, 2H).

N-(4-(chlorodifluoromethoxy)phenyl)-9-(1H-pyrazol-5-yl)-1,2,3,4-tetrahydrobenzo[4,5]imidazo[1,2-a]pyridine-7-carboxamide (37). A mixture of 9-bromo-N-(4-(chlorodifluoromethoxy)phenyl)-1,2,3,4-tetrahydrobenzo[4,5]imidazo[1,2-a]pyridine-7-carboxamide (37d, 20 mg, 0.042 mmol), 3-(4,4,5,5-tetramethyl-1,3,2-dioxaborolan-2-yl)-1H-pyrazole (24.73 mg, 0.127 mmol), Pd(dppf)Cl$_2$ (3.11 mg, 4.25 umol) and K$_3$PO$_4$ (27.06 mg, 0.127 mmol) in dioxane (1 mL) and H$_2$O (0.1 mL) was degassed and purged with N$_2$ 3 times. The mixture was stirred at 110° C. for 16 hr under N$_2$ atmosphere. LCMS showed 37d was consumed completely and one main peak with desired mass was detected. TLC (dichloromethane:methanol=10:1, R$_f$=0.44) indicated 37d was consumed completely and one new spot formed. The mixture was concentrated and H$_2$O (10 mL) was added. The mixture was extracted with ethyl acetate (10 mL×3). The combined organic layers were washed with brine (10 mL), dried over anhydrous Na$_2$SO$_4$, filtered and concentrated in vacuo. The crude product was purified by prep-TLC (dichloromethane:methanol=10:1, R$_f$=0.30) to afford 37 as a white solid. MS mass calculated for [M+1]$^+$ (C$_{22}$H$_{18}$ClF$_2$N$_5$O$_2$) requires m/z 458.1, LCMS found m/z 458.1; $^1$H NMR (400 MHz, MeOD-d$_4$) δ 8.26-8.23 (m, 1H), 7.86-7.81 (m, 4H), 7.29 (d, 2H, J=9.0 Hz), 6.62 (s, 1H), 3.86 (br s, 2H), 3.12 (br t, 2H, J=6.1 Hz), 1.99 (br s, 4H).

Example 38

General Procedure P (R)—N-(4-(chlorodifluoromethoxy)phenyl)-4-hydroxy-9-(1H-pyrazol-5-yl)-1,2,3,4-tetrahydrobenzo[4,5]imidazo[1,2-a]pyridine-7-carboxamide The title compound was prepared according to Scheme 10. This General Procedure P exemplifies Scheme 10 and provides particular synthetic details as applied to the title compound.

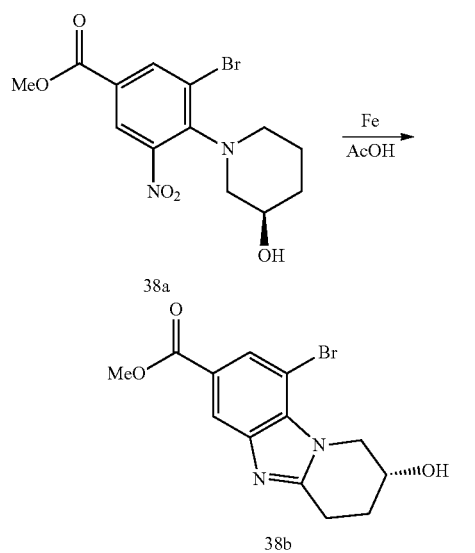

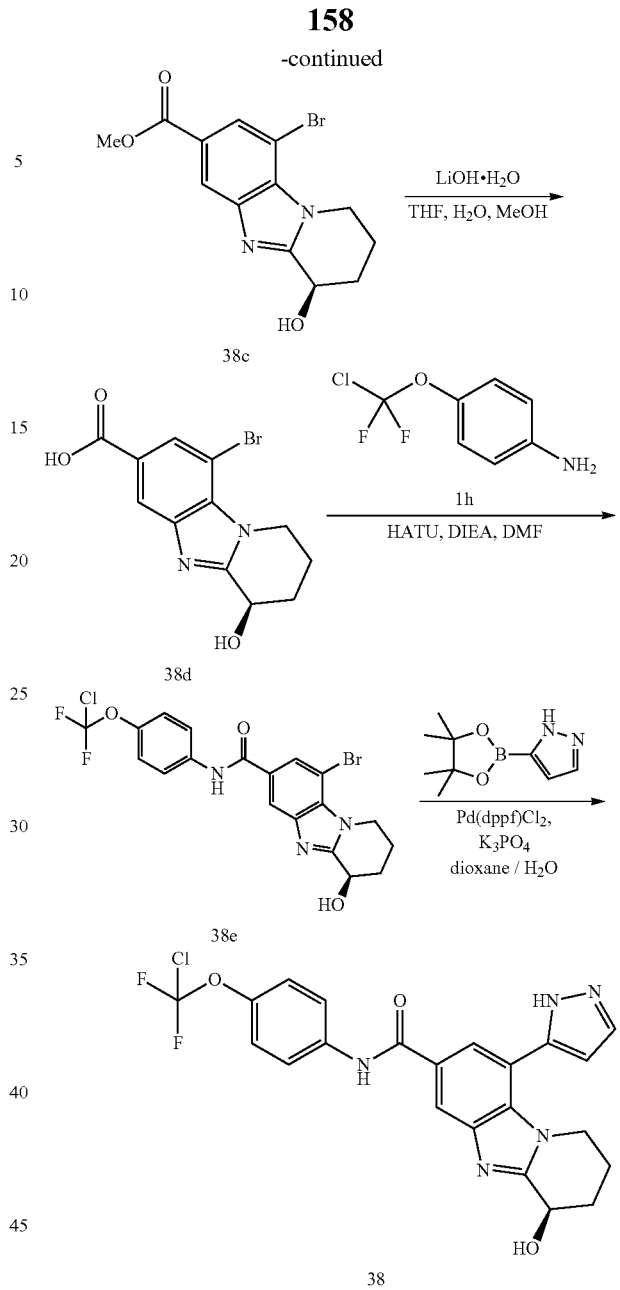

(R)-methyl 9-bromo-2-hydroxy-1,2,3,4-tetrahydrobenzo[4,5]imidazo[1,2-a]pyridine-7-carboxylate (39b) and (R)-methyl 9-bromo-4-hydroxy-1,2,3,4-tetrahydrobenzo[4,5]imidazo[1,2-a]pyridine-7-carboxylate (38c). A solution of methyl (R)-methyl 3-bromo-4-(3-hydroxypiperidin-1-yl)-5-nitrobenzoate (synthesized in a similar fashion to 1d; 38a, 100 mg, 0.278 mmol) in AcOH (3 mL) was stirred at 30° C. Iron powder (155.48 mg, 2.78 mmol) was added slowly to the reaction mixture portion-wise over 32 hrs. TLC (ethyl acetate:methanol=10:1, R$_f$=0.37) showed two new spots were generated. LCMS showed two peaks with desired MS was detected. The reaction mixture was filtered, and the filtrate was partitioned between ethyl acetate (50 mL) and H$_2$O (50 mL). The separated organic layer was washed with water (50 mL×3), and then washed with saturated NaHCO$_3$ aqueous (30 mL×3), dried over Na$_2$SO$_4$ and evaporated to dryness. The crude product was purified by prep-TLC (ethyl acetate:methanol=10:1, R$_f$=0.3) to give 38b as a yellow solid. ¹H NMR (400 MHz, MeOD-d₄) δ 8.16 (d, J=1.1 Hz, 1H), 8.02 (d, J=1.3 Hz, 1H), 4.82-4.74 (m, 1H), 4.69-4.61 (m, 1H), 4.50-4.42 (m, 1H), 3.93 (s, 3H), 3.25 (dd, J=6.7, 9.8 Hz, 1H), 3.13-3.04 (m, 1H), 2.20-2.09 (m, 2H). The crude product was purified by prep-TLC (ethyl acetate:methanol=10:1, R$_f$=0.37) to give 38c was obtained as a yellow solid. ¹H NMR (400 MHz, MeOD-d₄) δ 8.27 (d, J=0.9 Hz, 1H), 8.07 (d, J=1.1 Hz, 1H), 4.97 (t, J=5.4 Hz, 1H), 4.79-4.70 (m, 1H), 4.65-4.52 (m, 1H), 3.94 (s, 3H), 2.38 (br dd, J=6.8, 13.5 Hz, 1H), 2.26-2.04 (m, 3H).

(R)-9-bromo-4-hydroxy-1,2,3,4-tetrahydrobenzo[4,5]imidazo[1,2-a]pyridine-7-carboxylic acid (38d). To a solution of (R)-methyl 9-bromo-4-hydroxy-1,2,3,4-tetrahydrobenzo[4,5]imidazo[1,2-a]pyridine-7-carboxylate (38c, 25 mg, 0.077 mmol) in MeOH (1 mL), H₂O (1 mL) and THF (1 mL) was added LiOH.H₂O (6.45 mg, 0.154 mmol). The mixture stirred at 50° C. for 2 hr. TLC (ethyl acetate:methanol=10:1, R$_f$=0.0) showed a new spot was generated. The mixture was concentrated to remove solvent. To the mixture 1M HCl was added to the reaction mixture dropwise until pH=5. The mixture was concentrated, and the crude product was used into the next step further without purification.

(R)-9-bromo-N-(4-(chlorodifluoromethoxy)phenyl)-4-hydroxy-1,2,3,4-tetrahydrobenzo[4,5]imidazo[1,2-a]pyridine-7-carboxamide (38e). To a solution of (R)-9-bromo-4-hydroxy-1,2,3,4-tetrahydrobenzo[4,5]imidazo[1,2-a]pyridine-7-carboxylic acid (38d, 30 mg, 0.096 mmol) in DMF (2 mL) was added HATU (54.99 mg, 0.145 mmol), DIEA (124.62 mg, 0.964 mmol, 167.95 uL) and 4-[chloro(difluoro)methoxy]aniline (1h, 28.00 mg, 0.145 mmol). The mixture was stirred at 15° C. for 16 hr. TLC (ethyl acetate:methanol=10:1, R$_f$=0.3) indicated a new spot was generated. LCMS showed a peak with desired MS was detected. The mixture was quenched with water (20 mL) and the mixture was extracted with ethyl acetate (30 mL×3). The combined organic layers were washed with brine (20 mL), dried over anhydrous Na₂SO₄, filtered and concentrated in vacuo. The crude product was purified by prep-TLC (ethyl acetate:methanol=10:1, R$_f$=0.3) to give 38e as a yellow solid.

(R)—N-(4-(chlorodifluoromethoxy)phenyl)-4-hydroxy-9-(1H-pyrazol-5-yl)-1,2,3,4-tetrahydrobenzo[4,5]imidazo[1,2-a]pyridine-7-carboxamide (38). A mixture of (R)-9-bromo-N-(4-(chlorodifluoromethoxy)phenyl)-4-hydroxy-1,2,3,4-tetrahydrobenzo[4,5]imidazo[1,2-a]pyridine-7-carboxamide (38e, 15 mg, 0.031 mmol), 5-(4,4,5,5-tetramethyl-1,3,2-dioxaborolan-2-yl)-1H-pyrazole (17.94 mg, 0.092 mmol), Pd(dppf)Cl₂ (4.51 mg, 6.16 umol), K₃PO₄ (19.63 mg, 0.092 mmol) in dioxane (2 mL) and H₂O (0.2 mL) was degassed and purged with N₂ 3 times. The mixture was stirred at 120° C. for 16 hr under N₂ atmosphere. TLC (ethyl acetate:methanol=5:1, R$_f$=0.2) showed a new spot was generated. LCMS showed a peak with desired MS was detected. The mixture was concentrated. The crude product was purified by prep-HPLC (Column: Luna C18 100*30 5 u; mobile phase: [water (0.225% FA)-ACN]; B %: 1%-50%, 12 min) to give 38 as a white solid. Mass calculated for [M+1]⁺ (C₂₂H₁₈ClF₂N₅O₂) requires m/z 474.1, LCMS found m/z 474.1; ¹H NMR (400 MHz, MeOD-d₄) δ 8.34 (s, 1H), 7.88 (d, J=1.6 Hz, 1H), 7.87-7.82 (m, 3H), 7.29 (d, J=8.9 Hz, 2H), 6.62 (d, J=2.1 Hz, 1H), 5.01 (t, J=5.1 Hz, 1H), 3.95-3.76 (m, 2H), 2.19 (br d, J=6.7 Hz, 2H), 2.07-1.88 (m, 2H).

Example 39

General Procedure Q (R)—N-(4-(chlorodifluoromethoxy)phenyl)-6-(4-hydroxypyridin-2-yl)-4-methyl-3,4-dihydro-1H-benzo[4,5]imidazo[2,1-c][1,4]oxazine-8-carboxamide This General Procedure Q provides particular synthetic details as applied to the title compound. Additional compounds can be prepared according to this method by varying the coupling reagents.

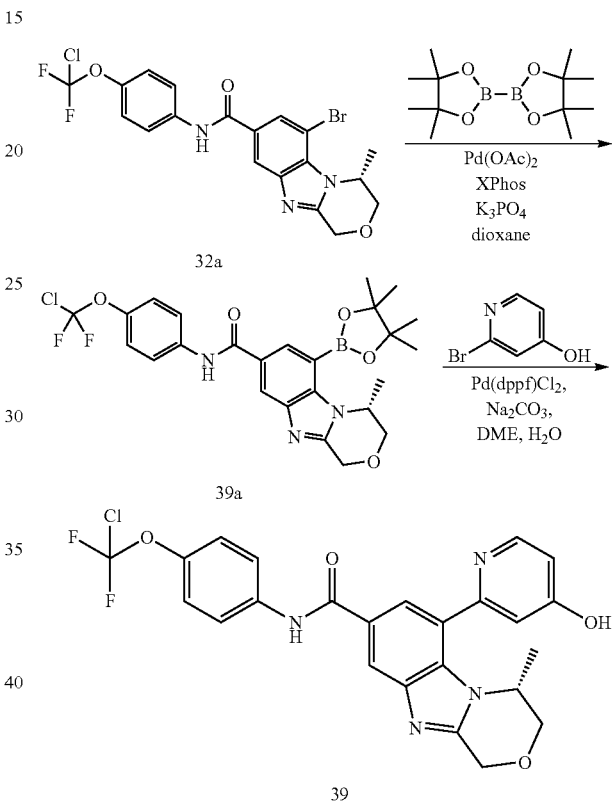

(R)—N-(4-(chlorodifluoromethoxy)phenyl)-4-methyl-6-(4,4,5,5-tetramethyl-1,3,2-dioxaborolan-2-yl)-3,4-dihydro-1H-benzo[4,5]imidazo[2,1-c][1,4]oxazine-8-carboxamide (39a). A mixture of (R)-6-bromo-N-(4-(chlorodifluoromethoxy)phenyl)-4-methyl-3,4-dihydro-1H-benzo[4,5]imidazo[2,1-c][1,4]oxazine-8-carboxamide (32a, 200 mg, 0.411 mmol), 4,4,5,5-tetramethyl-2-(4,4,5,5-tetramethyl-1,3,2-dioxaborolan-2-yl)-1,3,2-dioxaborolane (939.17 mg, 3.70 mmol), Pd(OAc)₂ (9.23 mg, 0.041 mmol), XPhos (48.97 mg, 0.103 mmol) and K₃PO₄ (261.68 mg, 1.23 mmol) in dioxane (6.2 mL) was degassed and purged with N₂ 3 times. The mixture was stirred at 60° C. for 16 hr under N₂ atmosphere under microwave. LCMS showed desired MS was detected. The reaction mixture was concentrated under reduced pressure to remove solvent. The residue was purified by prep-TLC (SiO₂, petroleum ether:ethyl acetate=0:1) to afford 39a as a white solid.

(R)—N-(4-(chlorodifluoromethoxy)phenyl)-6-(4-hydroxypyridin-2-yl)-4-methyl-3,4-dihydro-1H-benzo[4,5]imidazo[2,1-c][1,4]oxazine-8-carboxamide (39). A mixture of (R)—N-(4-(chlorodifluoromethoxy)phenyl)-4-methyl-6-

(4,4,5,5-tetramethyl-1,3,2-dioxaborolan-2-yl)-3,4-dihydro-1H-benzo[4,5]imidazo[2,1-c][1,4]oxazine-8-carboxamide (39a, 5 mg, 9.37 umol), 2-bromopyridin-4-ol (2.44 mg, 0.014 mmol), Pd(dppf)Cl$_2$ (685.43 ug, 9.37 umol), Na$_2$CO$_3$ (2.98 mg, 0.028 mmol) in DME (0.5 mL) and H$_2$O (0.1 mL) was degassed and purged with N$_2$ 3 times. The mixture was stirred at 120° C. for 1 hr under N$_2$ atmosphere in a microwave reactor. LCMS showed 39a was consumed completely and desired MS were detected. The reaction mixture was concentrated under reduced pressure to remove solvent. The residue was purified by prep-HPLC (column: Xtimate C18 150*25 mm*5 um; mobile phase: [water (10 mM NH$_4$HCO$_3$)-ACN]; B %: 25%-55%,10 min) to afford 39 as a white solid. MS mass calculated for [M+1]$^+$ (C$_{24}$H$_{19}$ClF$_2$N$_4$O$_4$) requires m/z 501.1, LCMS found m/z 501.1; $^1$H NMR (400 MHz, MeOD-d$_4$) δ 8.41 (d, J=1.5 Hz, 1H), 8.03 (br d, J=6.8 Hz, 1H), 7.96 (d, J=1.5 Hz, 1H), 7.88-7.81 (m, 2H), 7.29 (d, J=8.8 Hz, 2H), 6.79 (br s, 1H), 6.68 (br d, J=6.8 Hz, 1H), 5.15-4.96 (m, 2H), 4.46 (br s, 1H), 4.13 (br d, J=3.1 Hz, 1H), 3.99 (d, J=12.3 Hz, 1H), 1.14 (d, J=6.6 Hz, 3H).

Example 40

General Procedure R (S)—N-(4-(chlorodifluoromethoxy)phenyl)-2-(1-hydroxyethyl)-1-isopropyl-7-(1H-pyrazol-5-yl)-1H-benzo[d]imidazole-5-carboxamide This General Procedure R provides particular synthetic details as applied to the title compound. Additional compounds can be prepared according to this method by varying the coupling reagents.

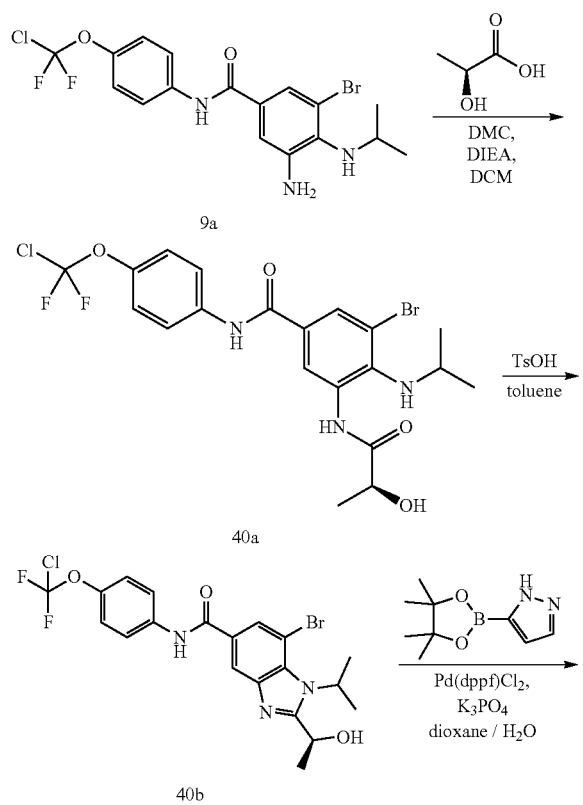

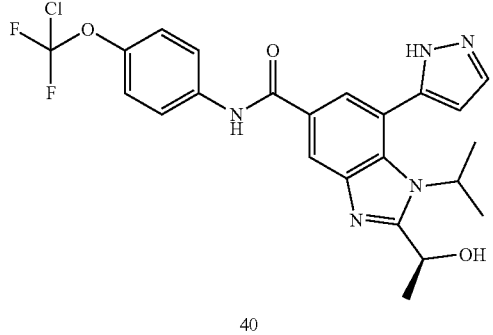

40

(S)-3-bromo-N-(4-(chlorodifluoromethoxy)phenyl)-5-(2-hydroxypropanamido)-4-(isopropylamino)benzamide (40a). To a solution of 3-amino-5-bromo-N-(4-(chlorodifluoromethoxy)phenyl)-4-(isopropylamino)benzamide (9a, 350 mg, 0.78 mmol) in DCM (1 mL) was added DIEA (302.44 mg, 2.34 mmol, 407.60 uL), (2S)-2-hydroxypropanoic acid (140.53 mg, 1.56 mmol, 116.14 uL) and 2-chloro-1,3-dimethylimidazolinium chloride (158.24 mg, 0.936 mmol). The mixture was stirred at 15° C. for 4 hr. TLC (petroleum ether:Ethyl acetate=1:1, R$_f$=0.45) indicated 9a was consumed completely and one major new spot with larger polarity was detected. LCMS detected the desired MS. The reaction mixture was diluted with H$_2$O (20 mL) and extracted with DCM (10 mL×3). The combined organic layers were washed with brine (30 mL), dried over Na$_2$SO$_4$, filtered and concentrated under reduced pressure to give a residue. The residue was purified by prep-TLC (SiO$_2$, petroleum ether:ethyl acetate=1:1) to afford 40b as a white solid. $^1$H NMR (400 MHz, MeOD-d$_4$) δ 8.53 (d, J=2.4 Hz, 1H), 7.99 (d, J=2.0 Hz, 1H), 7.83-7.80 (m, 2H), 7.30 (br d, J=9.3 Hz, 2H), 4.34 (q, J=6.8 Hz, 1H), 3.56 (td, J=6.4, 12.7 Hz, 1H), 1.49 (d, J=6.8 Hz, 3H), 1.24 (d, J=6.4 Hz, 6H).

(S)-7-bromo-N-(4-(chlorodifluoromethoxy)phenyl)-2-(1-hydroxyethyl)-1-isopropyl-1H-benzo[d]imidazole-5-carboxamide (40b). To a solution of (S)-3-bromo-N-(4-(chlorodifluoromethoxy)phenyl)-5-(2-hydroxypropanamido)-4-(isopropylamino)benzamide (40a, 40 mg, 0.077 mmol) in toluene (1 mL) was added 4-methylbenzenesulfonic acid (2.65 mg, 0.015 mmol). The mixture was stirred at 100° C. for 4 hr. TLC (petroleum ether:ethyl acetate=1:1, R$_f$=0.15) indicated 40a was consumed completely and one major new spot with larger polarity was detected. LCMS detected the desired MS. The residue was diluted with H$_2$O (20 mL) and extracted with DCM (10 mL×3). The combined organic layers were washed with brine (30 mL), dried over Na$_2$SO$_4$, filtered and concentrated under reduced pressure to give a residue. The residue was purified by prep-TLC (SiO$_2$, petroleum ether:ethyl acetate=1:1) to afford 40b as a white solid. $^1$H NMR (400 MHz, MeOD-d$_4$) δ 8.29 (s, 1H), 8.14 (br s, 1H), 7.86 (d, J=9.3 Hz, 2H), 7.32 (br d, J=9.3 Hz, 2H), 4.92-4.92 (m, 1H), 4.87-4.86 (m, 1H), 1.91 (br s, 3H), 1.76 (br d, J=6.4 Hz, 6H).

(S)—N-(4-(chlorodifluoromethoxy)phenyl)-2-(1-hydroxyethyl)-1-isopropyl-7-(1H-pyrazol-5-yl)-1H-benzo[d]imidazole-5-carboxamide (40). A mixture of (S)-7-bromo-N-(4-(chlorodifluoromethoxy)phenyl)-2-(1-hydroxyethyl)-1-isopropyl-1H-benzo[d]imidazole-5-carboxamide (40b, 10 mg, 0.02 mmol), 5-(4,4,5,5-tetramethyl-1,3,2-dioxaborolan-2-yl)-1H-pyrazole (11.58 mg, 0.06 mmol), K$_3$PO$_4$ (12.67 mg, 0.06 mmol), Pd(dppf)Cl$_2$ (1.46 mg, 1.99 umol) and 5-(4,4,5,5-tetramethyl-1,3,2-dioxaborolan-2-yl)-1H-pyrazole (11.58 mg, 0.06 mmol) in dioxane (1 mL) and H$_2$O (0.1 mL) was degassed and purged with N$_2$ 3 times. The mixture was stirred at 115° C. for 4 hr under N$_2$ atmosphere. TLC (ethyl acetate:methanol=20:1, R_f=0.24) indicated 40b was consumed completely and one major new spot with larger polarity was detected. LCMS detected the desired MS. The reaction mixture was concentrated under reduced pressure to remove solvent. The residue was diluted with $H_2O$ (20 mL) and extracted with ethyl acetate (10 mL×3). The combined organic layers were washed with brine (30 mL), dried over $Na_2SO_4$, filtered and concentrated under reduced pressure to give a residue. The residue was purified by prep-TLC (ethyl acetate:methanol=20:1) to afford 40 as a white solid. Mass calculated for $[M+1]^+$ ($C_{23}H_{22}ClF_2N_5O_3$) requires m/z 490.1, LCMS found m/z 490.1; $^1H$ NMR (400 MHz, MeOD-$d_4$) δ 8.34 (br s, 1H), 7.92-7.79 (m, 4H), 7.29 (d, J=9.3 Hz, 2H), 6.61 (d, J=2.0 Hz, 1H), 5.29 (q, J=6.0 Hz, 1H), 4.76 (br s, 1H), 1.73 (d, J=6.4 Hz, 3H), 1.45 (dd, J=7.1, 12.0 Hz, 6H).

Example 41

(R)—N-(4-(chlorodifluoromethoxy)phenyl)-4-methyl-6-(pyrrolidin-1-yl)-3,4-dihydro-1H-benzo[4,5]imidazo[2,1-c][1,4]oxazine-8-carboxamide

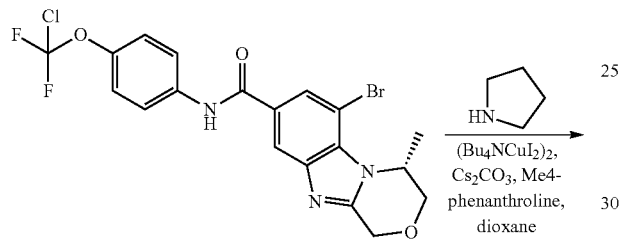

32a

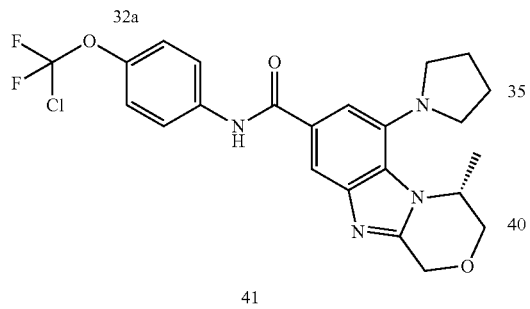

41

(R)—N-(4-(chlorodifluoromethoxy)phenyl)-4-methyl-6-(pyrrolidin-1-yl)-3,4-dihydro-1H-benzo[4,5]imidazo[2,1-c][1,4]oxazine-8-carboxamide (41). A mixture of (R)-6-bromo-N-(4-(chlorodifluoromethoxy)phenyl)-4-methyl-3,4-dihydro-1H-benzo[4,5]imidazo[2,1-c][1,4]oxazine-8-carboxamide (32a, 50 mg, 0.103 mmol), pyrrolidine (438.39 mg, 6.16 mmol, 514.54 uL), $(Bu_4NCuI_2)_2$ (23.00 mg, 0.021 mmol), $Cs_2CO_3$ (66.95 mg, 0.205 mmol) and 3,4,7,8-tetramethyl-1,10-phenanthroline (2.43 mg, 0.01 mmol) in dioxane (2 mL) was degassed and purged with $N_2$ 3 times. The mixture was stirred at 120° C. for 16 hr under $N_2$ atmosphere. LCMS showed desired mass was detected. The reaction mixture was filtered and concentrated under reduced pressure to give a residue. The residue was purified by prep-TLC ($SiO_2$, ethyl acetate:methanol=20:1) to afford 41 as a white solid. Mass calculated for $[M+1]^+$ ($C_{23}H_{23}ClF_2N_4O_3$) requires m/z 477.1, LCMS found m/z 477.1. $^1H$ NMR (400 MHz, $CDCl_3$-d) 8.61 (s, 1H), 7.74 (d, J=9.0 Hz, 2H), 7.25 (s, 1H), 7.22 (d, J=6.6 Hz, 2H), 5.16-4.92 (m, 2H), 4.47 (br s, 1H), 4.15-4.00 (m, 2H), 3.26 (br s, 4H), 2.12 (br s, 4H), 1.63 (d, J=6.6 Hz, 3H).

Example 42

General Procedure S (R)—N-(4-(chlorodifluoromethoxy)phenyl)-3-methyl-5-(pyridazin-3-yl)-2,3-dihydrobenzo[4,5]imidazo[2,1-b]oxazole-7-carboxamide This General Procedure S provides particular synthetic details as applied to the title compound. Additional compounds can be prepared according to this method by varying the coupling reagents.

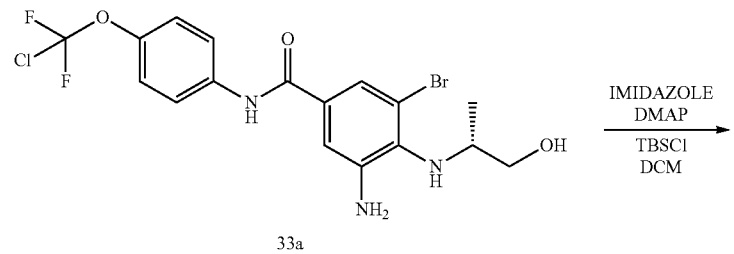

33a

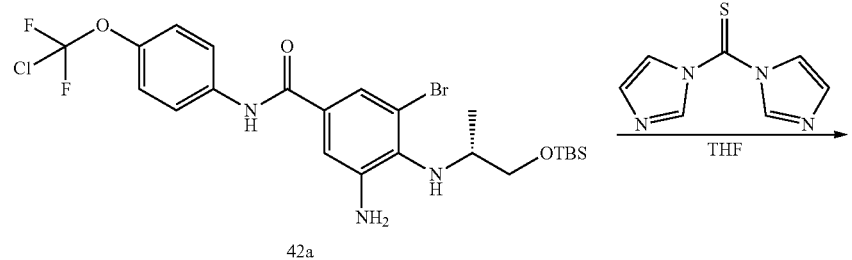

42a

-continued

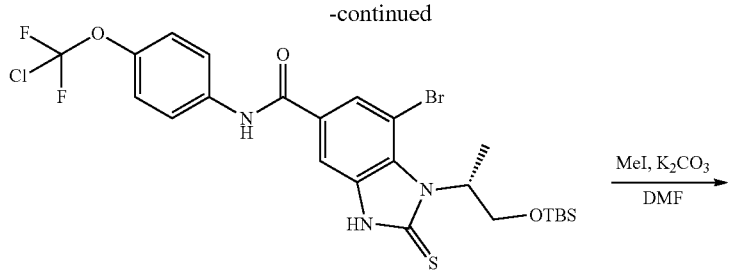
42b

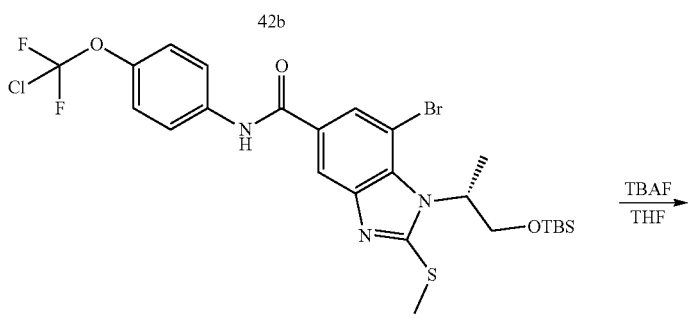
42c

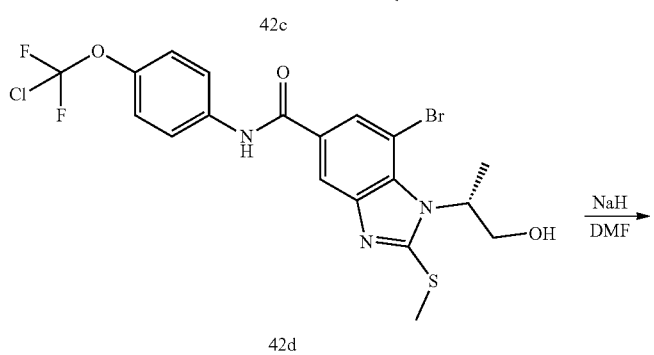
42d

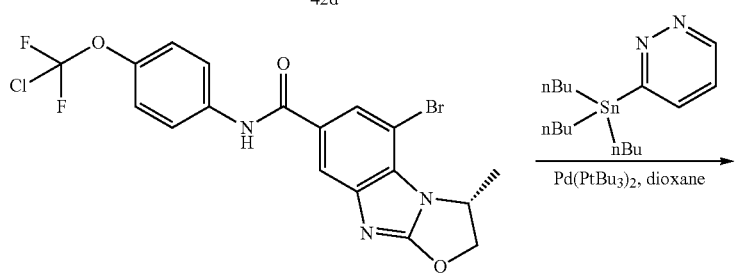
42e

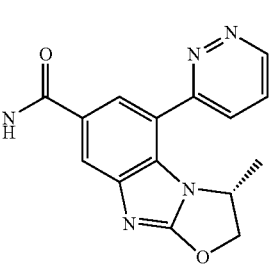
42

(R)-3-amino-5-bromo-4-((1-((tert-butyldimethylsilyloxy)propan-2-yl)amino)-N-(4-(chlorodifluoromethoxy)phenyl)benzamide (42a). A mixture of (R)-3-amino-5-bromo-N-(4-(chlorodifluoromethoxy)phenyl)-4-(1-hydroxypropan-2-yl)amino)benzamide (33a, 2 g, 4.30 mmol), imidazole (439.50 mg, 6.46 mmol), TBSCl (973.05 mg, 6.46 mmol, 791.10 uL) and DMAP (52.58 mg, 430.40 umol) in DCM (30 mL) was degassed and purged with N₂ three times, and then the mixture was stirred at 15° C. for 2 hr under a N₂ atmosphere. TLC (petroleum ether:ethyl acetate=3:1, R$_f$=0.5) showed a new spot was generated. LCMS showed a peak with desired MS was detected. The reaction mixture was concentrated and H₂O (20 mL) was added. The aqueous phase was extracted with ethyl acetate (30 mL×3). The combined organic layers were washed with brine (10 mL), dried over anhydrous $Na_2SO_4$, filtered and concentrated in vacuo. The crude product was purified by silica gel column chromatography (petroleum ether:ethyl acetate=10:1~5:1) to give 42a as a yellow oil. $^1$H NMR (400 MHz, $CDCl_3$-d) δ 7.69 (br s, 1H), 7.66 (d, J=9.0 Hz, 2H), 7.37 (d, J=1.8 Hz, 1H), 7.25 (br d, J=8.8 Hz, 2H), 7.14 (d, J=1.8 Hz, 1H), 4.31 (br s, 2H), 3.78-3.66 (m, 2H), 3.62-3.50 (m, 2H), 1.15 (d, J=6.2 Hz, 3H), 0.94 (s, 9H), 0.11 (s, 6H).

(R)-7-bromo-1-(1-((tert-butyldimethylsilyl)oxy)propan-2-yl)-N-(4-(chlorodifluoromethoxy)phenyl)-2-thioxo-2,3-dihydro-1H-benzo[d]imidazole-5-carboxamide (42b). A mixture of (R)-3-amino-5-bromo-4-((1-((tert-butyldimethylsilyl)oxy)propan-2-yl)amino)-N-(4-(chlorodifluoromethoxy)phenyl)benzamide (42a, 2.4 g, 4.15 mmol), di(imidazol-1-yl)methanethione (2.22 g, 12.44 mmol), DIEA (1.07 g, 8.29 mmol, 1.44 mL) in THF (20 mL) was degassed and purged with $N_2$ three times. The mixture was stirred at 60° C. for 16 hr under a $N_2$ atmosphere. TLC (petroleum ether:ethyl acetate=2:1, $R_f$=0.54) indicated a new spot was generated. LCMS showed a peak with desired MS was detected. The mixture was concentrated and $H_2O$ (50 mL) was added. The aqueous phase was extracted with ethyl acetate (50 mL×3). The combined organic layers were washed with brine (20 mL), dried over anhydrous $Na_2SO_4$, filtered and concentrated in vacuo. The crude product was purified by silica gel column chromatography (petroleum ether:ethyl acetate=8:1~2:1) to give 42b as a yellow solid. $^1$H NMR (400 MHz, $CDCl_3$-d) δ 11.21 (s, 1H), 7.96 (s, 1H), 7.86 (d, J=1.1 Hz, 1H), 7.75-7.67 (m, 3H), 7.28 (s, 1H), 7.26 (s, 1H), 6.11-5.97 (m, 1H), 4.99 (t, J=9.6 Hz, 1H), 3.95 (dd, J=5.1, 10.4 Hz, 1H), 1.86 (d, J=7.1 Hz, 3H), 0.68 (s, 9H), 0.00 (s, 3H), −0.12 (s, 3H).

(R)-7-bromo-1-(1-((tert-butyldimethylsilyl)oxy)propan-2-yl)-N-(4-(chlorodifluoromethoxy)phenyl)-2-(methylthio)-1H-benzo[d]imidazole-5-carboxamide (42c). To a solution of (R)-7-bromo-1-(1-((tert-butyldimethylsilyl)oxy)propan-2-yl)-N-(4-(chlorodifluoromethoxy)phenyl)-2-thioxo-2,3-dihydro-1H-benzo[d]imidazole-5-carboxamide (42b, 2.4 g, 3.86 mmol) in DMF (20 mL) was added MeI (822.82 mg, 5.80 mmol, 360.89 uL) and $K_2CO_3$ (1.07 g, 7.73 mmol). The mixture was stirred at 15° C. for 2 hr. TLC (petroleum ether:ethyl acetate=2:1, $R_f$=0.72) indicated a new spot was generated. LCMS showed a peak with desired MS was detected. The mixture was quenched with water (50 mL) and extracted with ethyl acetate (50 mL×3), the combined organic layers were washed with brine (20 mL), dried over anhydrous $Na_2SO_4$, filtered and concentrated in vacuo. The crude product was purified by silica gel column chromatography (petroleum ether:ethyl acetate=3:1~2:1) to give 42c as a yellow oil. $^1$H NMR (400 MHz, $CDCl_3$-d) δ 8.03 (d, J=1.6 Hz, 1H), 7.97 (d, J=1.6 Hz, 1H), 7.89 (s, 1H), 7.74-7.67 (m, 2H), 7.28 (s, 1H), 7.25 (s, 1H), 6.21-6.05 (m, 1H), 4.28 (dd, J=9.2, 10.4 Hz, 1H), 3.89 (dd, J=5.7, 10.6 Hz, 1H), 2.83 (s, 3H), 1.67 (d, J=7.3 Hz, 3H), 0.67 (s, 9H), −0.04 (s, 3H), −0.18 (s, 3H)

(R)-7-bromo-N-(4-(chlorodifluoromethoxy)phenyl)-1-(1-hydroxypropan-2-yl)-2-(methylthio)-1H-benzo[d]imidazole-5-carboxamide (42d). To a solution of (R)-7-bromo-1-(1-((tert-butyldimethylsilyl)oxy)propan-2-yl)-N-(4-(chlorodifluoromethoxy)phenyl)-2-(methylthio)-1H-benzo[d]imidazole-5-carboxamide (42c, 1 g, 1.57 mmol) in THF (20 mL) was added TBAF (1M, 1.73 mL). The mixture was stirred at 15° C. for 3 hr. TLC (petroleum ether:ethyl acetate=0:1, $R_f$=0.65) showed a new spot was generated. LCMS showed a peak with desired MS was detected. The mixture was quenched with $AcONH_4$ (30 mL) and extracted with ethyl acetate (50 mL×3). The combined organic layers were washed with brine (20 mL), dried over anhydrous $Na_2SO_4$, filtered and concentrated in vacuo. The crude product was purified by silica gel column chromatography (petroleum ether:ethyl acetate=3:1~0:1) to give 42d as a yellow solid. $^1$H NMR (400 MHz, $CDCl_3$-d) δ 8.63 (s, 1H), 7.87 (d, J=9.0 Hz, 2H), 7.62 (d, J=1.7 Hz, 2H), 7.31 (d, J=8.8 Hz, 2H), 6.14 (ddd, J=4.6, 7.4, 10.0 Hz, 1H), 4.59 (dd, J=10.0, 12.7 Hz, 1H), 3.91 (dd, J=4.4, 12.8 Hz, 1H), 2.84 (s, 3H), 1.59 (d, J=7.3 Hz, 3H).

(R)-5-bromo-N-(4-(chlorodifluoromethoxy)phenyl)-3-methyl-2,3-dihydrobenzo[4,5]imidazo[2,1-b]oxazole-7-carboxamide (42e) A solution of (R)-7-bromo-N-(4-(chlorodifluoromethoxy)phenyl)-1-(1-hydroxypropan-2-yl)-2-(methylthio)-1H-benzo[d]imidazole-5-carboxamide (42d, 500 mg, 960.11 umol) in DMF (6 mL) was degassed and purged with $O_2$ three times and the mixture cooled to 0° C. NaH (46.08 mg, 1.15 mmol, 60% purity, 1.2 eq) was added. The mixture was stirred at 0~15° C. for 6 hr under $O_2$. TLC (petroleum ether:ethyl acetate=1:2, $R_f$=0.5) showed a new spot was generated. LCMS showed a peak with desired MS was detected. The mixture was quenched with $NH_4Cl$ (50 mL) and extracted with ethyl acetate (50 mL×3), the combined organic layers were washed with brine (20 mL), dried over anhydrous $Na_2SO_4$, filtered and concentrated in vacuo. The crude product was purified by silica gel column chromatography (petroleum ether:ethyl acetate=2:1-0:1) to give 42e as a white solid. $^1$H NMR (400 MHz, $CDCl_3$-d) δ 8.24 (s, 1H), 7.90 (dd, J=1.3, 15.9 Hz, 2H), 7.74 (d, J=9.0 Hz, 2H), 7.25 (s, 1H), 5.29-5.19 (m, 1H), 5.09-4.98 (m, 1H), 4.78 (dd, J=2.2, 8.6 Hz, 1H), 1.69 (d, J=6.4 Hz, 3H)

(R)—N-(4-(chlorodifluoromethoxy)phenyl)-3-methyl-5-(pyridazin-3-yl)-2,3-dihydrobenzo[4,5]imidazo[2,1-b]oxazole-7-carboxamide (42). A mixture of (R)-5-bromo-N-(4-(chlorodifluoromethoxy)phenyl)-3-methyl-2,3-dihydrobenzo[4,5]imidazo[2,1-b]oxazole-7-carboxamide (42e, 25 mg, 52.89 umol), tributyl(pyridazin-3-yl)stannane (39.05 mg, 105.78 umol, 2 eq), palladium; tritert-butylphosphane (2.70 mg, 5.29 umol, 0.1 eq) in dioxane (2 mL) was degassed and purged with $N_2$ three times, and then the mixture was stirred at 110° C. for 16 hr under $N_2$. TLC (ethyl acetate:methanol=10:1, $R_f$=0.31) showed a new spot was generated. LCMS showed a peak with desired MS was detected. The reaction mixture was concentrated and $H_2O$ (20 mL) was added. The aqueous phase was extracted with ethyl acetate (30 mL×3). The combined organic layers were washed with brine (10 mL), dried over anhydrous $Na_2SO_4$, filtered and concentrated in vacuo. The crude product was purified by prep-TLC (ethyl acetate:methanol=10:1, $R_f$=0.31) to give a crude product, which was further purified by prep-HPLC (Column: Luna C18 100*30 5 u; mobile phase: [water (0.225% FA)-ACN]; B %: 20%-70%, 12 min.) to give 42 as a light yellow solid. MS mass calculated for $[M+1]^+$ ($C_{22}H_{16}ClF_2N_5O_3$) requires m/z 472.1, LCMS found m/z 472.0; $^1$H NMR (400 MHz, MeOD-$d_4$) δ 9.28 (dd, J=1.5, 4.9 Hz, 1H), 8.33 (dd, J=1.5, 8.6 Hz, 1H), 8.21-8.17 (m, 1H), 8.16 (d, J=1.6 Hz, 1H), 7.95 (dd, J=5.0, 8.6 Hz, 1H), 7.88-7.84 (m, 2H), 7.31 (d, J=9.0 Hz, 2H), 5.39-5.26 (m, 2H), 4.83 (dd, J=2.8, 8.4 Hz, 1H), 0.94 (d, J=6.4 Hz, 3H).

Example 43

General Procedure T (S)—N-(4-(chlorodifluoromethoxy)phenyl)-2-hydroxy-9-(pyrimidin-5-yl)-1,2,3,4-tetrahydrobenzo[4,5]imidazo[1,2-a]pyridine-7-carboxamide This General Procedure T provides particular synthetic details as applied to the title compound. Additional compounds can be prepared according to this method by varying the coupling reagents.

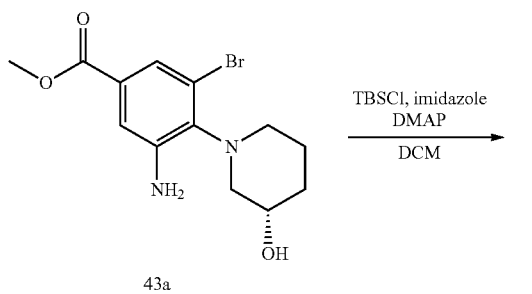
43a

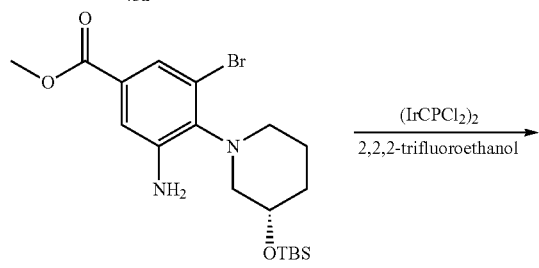
43b

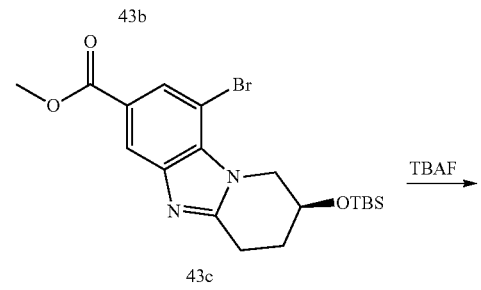
43c

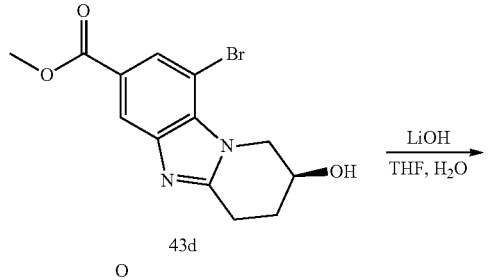
43d

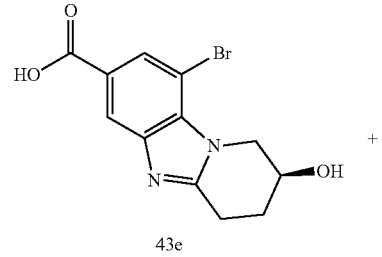
43e

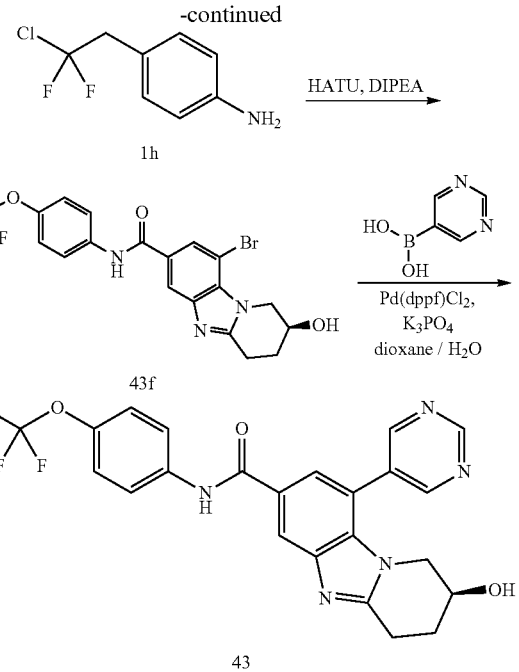
43

(S)-methyl 3-amino-5-bromo-4-(3-((tert-butyldimethylsilyl)oxy)piperidin-1-yl)benzoate (43b). To a mixture of (S)-methyl 3-amino-5-bromo-4-(3-hydroxypiperidin-1-yl)benzoate (synthesized in a similar fashion to 1d; 43a, 970 mg, 2.95 mmol) and imidazole (501.52 mg, 7.37 mmol) in DCM (20 mL) at 20° C. was added TBSCl (666.18 mg, 4.42 mmol) and DMAP (36.00 mg, 0.295 mmol) in one portion under $N_2$. The mixture was stirred at 20° C. for 12 hours. TLC (petroleum ether:ethyl acetate=3:1, $R_f$=0.7) indicated 43a was consumed completely and one new spot formed. The mixture was washed with water (8 mL×3) and brine (8 mL), dried over $Na_2SO_4$, filtered and concentrated to give 43b as a yellow oil, which was used in the next step without further purification.

(S)-methyl 9-bromo-2-((tert-butyldimethylsilyl)oxy)-1,2,3,4-tetrahydrobenzo[4,5]imidazo[1,2-a]pyridine-7-carboxylate (43c). To a solution of (S)-methyl 3-amino-5-bromo-4-(3-((tert-butyldimethylsilyl)oxy)piperidin-1-yl)benzoate (43b, 1.18 g, 2.66 mmol) in 2,2,2-trifluoroethanol (10 mL) at 20° C. under $N_2$ was added chloroiridium; (1Z,5Z)-cycloocta-1,5-diene (268.11 mg, 0.399 mmol) in one portion. The mixture was heated to 85° C. and stirred for 72 hours. LCMS showed 43b was consumed completely and one main peak with desired mass was detected. TLC (petroleum ether:ethyl acetate=1:1, $R_f$=0.4) indicated 43b was consumed completely and one new spot formed. The reaction mixture was concentrated under reduced pressure to remove solvent. The residue was purified by column chromatography ($SiO_2$, petroleum ether/ethyl acetate=20/1 to 2/1) to give 43c as a yellow oil. $^1$H NMR (400 MHz, $CDCl_3$-d) δ 8.30 (s, 1H), 8.08 (s, 1H), 4.69-4.57 (m, 2H), 4.46 (br d, J=3.9 Hz, 1H), 4.15-4.06 (m, 1H), 3.95 (s, 3H), 3.41-3.29 (m, 1H), 3.12-3.07 (m, 1H), 2.13-2.09 (m, 1H), 0.88 (s, 9H), 0.15 (br d, J=6.4 Hz, 6H).

(S)-methyl 9-bromo-2-hydroxy-1,2,3,4-tetrahydrobenzo[4,5]imidazo[1,2-a]pyridine-7-carboxylate (43d). To a solution of (S)-methyl 9-bromo-2-((tert-butyldimethylsilyl)oxy)-1,2,3,4-tetrahydrobenzo[4,5]imidazo[1,2-a]pyridine-7-carboxylate (43c, 550 mg, 1.25 mmol) in THF (10 mL) at 20° C. was added TBAF (1M, 1.38 mL) in one portion. The mixture was stirred at 20° C. for 30 min. TLC (ethyl acetate:methanol=10:1) indicated 43c was consumed completely and one new spot formed. The mixture was concentrated under reduced pressure. The residue was dissolved into EtOAc (20 mL), washed with water (7 mL×3) and brine (5 mL), dried over $Na_2SO_4$, filtered and concentrated to give 43d as a yellow oil, which was used in the next step without further purification. $^1$H NMR (400 MHz, DMSO-$d_6$) δ 8.09 (d, J=1.3 Hz, 1H), 7.90 (d, J=1.5 Hz, 1H), 5.34 (d, J=3.4 Hz, 1H), 4.57 (d, J=3.9 Hz, 2H), 4.37-4.28 (m, 1H), 3.87 (s, 3H), 3.18-2.96 (m, 2H), 2.04-1.99 (m, 2H).

(S)-9-bromo-2-hydroxy-1,2,3,4-tetrahydrobenzo[4,5]imidazo[1,2-a]pyridine-7-carboxylic acid (43e). To a solution of (S)-methyl 9-bromo-2-hydroxy-1,2,3,4-tetrahydrobenzo[4,5]imidazo[1,2-a]pyridine-7-carboxylate (43d, 320 mg, 0.984 mmol) in THF at 20° C. (5 mL) and $H_2O$ (2 mL) was added LiOH.$H_2O$ (61.95 mg, 1.48 mmol) in one portion. The mixture was stirred at 20° C. for 16 hours. LCMS showed 43d was consumed completely and one main peak with desired mass was detected. The reaction mixture was concentrated under reduced pressure to remove solvent. The residue was dissolved into $H_2O$ (1 mL) and the pH was adjusted to 4-5 by HCl (1M). The mixture was filtered and the filter cake was washed with $H_2O$ (0.5 mL) to give 43e as a white solid, which was used in the next step without further purification. $^1$H NMR (400 MHz, DMSO-$d_6$) δ 8.05 (s, 1H), 7.88 (s, 1H), 5.41-5.28 (m, 1H), 4.56 (br s, 2H), 4.38-4.25 (m, 1H), 3.16-2.91 (m, 2H), 1.99 (br s, 2H).

(S)-9-bromo-N-(4-(chlorodifluoromethoxy)phenyl)-2-hydroxy-1,2,3,4-tetrahydrobenzo[4,5]imidazo[1,2-a]pyridine-7-carboxamide (43f). To a mixture of (S)-9-bromo-2-hydroxy-1,2,3,4-tetrahydrobenzo[4,5]imidazo[1,2-a]pyridine-7-carboxylic acid (43e, 280 mg, 899.94 umol) and HATU (376.40 mg, 989.93 umol) in DMF (3 mL) at 20° C. was added 4-(chlorodifluoromethoxy)aniline (1 h, 209.05 mg, 1.08 mmol) and DIPEA (232.62 mg, 1.80 mmol) in one portion. The mixture was stirred at 20° C. for 12 hours. LCMS showed 43e was consumed completely and one main peak with desired mass was detected. TLC (methanol:dichloromethane=10:1, $R_f$=0.41) indicated 43e was consumed completely and one new spot formed. The mixture was poured into EtOAc (20 mL), washed with water (5 mL×4) and brine (5 mL), dried over $Na_2SO_4$, filtered and concentrated. The residue was purified by prep-TLC ($SiO_2$, ethyl acetate:methanol=10:1) to give 43f as a yellow solid. $^1$H NMR (400 MHz, $CDCl_3$-d) δ 10.47 (s, 1H), 8.25 (d, J=1.1 Hz, 1H), 7.99 (d, J=1.2 Hz, 1H), 7.96-7.90 (m, 2H), 7.36 (d, J=8.9 Hz, 2H), 5.37 (d, J=3.4 Hz, 1H), 4.58 (d, J=3.8 Hz, 2H), 4.38-4.30 (m, 1H), 3.22-2.96 (m, 2H), 2.04-1.99 (m, 2H).

(S)—N-(4-(chlorodifluoromethoxy)phenyl)-2-hydroxy-9-(pyrimidin-5-yl)-1,2,3,4-tetrahydrobenzo[4,5]imidazo[1,2-a]pyridine-7-carboxamide (43). To a mixture of (S)-9-bromo-N-(4-(chlorodifluoromethoxy)phenyl)-2-hydroxy-1,2,3,4-tetrahydrobenzo[4,5]imidazo[1,2-a]pyridine-7-carboxamide (43f, 30 mg, 0.062 mmol) and pyrimidin-5-ylboronic acid (15.28 mg, 0.123 mmol) in dioxane (2 mL) and $H_2O$ (0.2 mL) at 20° C. under $N_2$ was added Pd(dppf)$Cl_2$ (4.51 mg, 6.16 umol) and $K_3PO_4$ (39.25 mg, 184.92 umol) in one portion. The mixture was heated to 110° C. and stirred for 12 hours. LCMS showed 43f was consumed completely and one main peak with desired mass was detected. TLC (ethyl acetate:methanol=10:1, $R_f$=0.4) indicated 43f was consumed completely and one new spot formed. The mixture was filtered through a Celite pad. The pad was washed with EtOAc (10 mL) and the filtrate was concentrated to give the crude product. The residue was purified by prep-TLC ($SiO_2$, ethyl acetate:methanol=10:1) to give 43 as a yellow solid. Mass calculated for $[M+1]^+$ ($C_{23}H_{18}ClF_2N_5O_3$) requires m/z 486.1, LCMS found m/z 486.1; $^1$H NMR (400 MHz, DMSO-$d_6$) δ 10.44 (s, 1H), 9.34 (s, 1H), 9.06 (s, 2H), 8.37 (d, J=1.6 Hz, 1H), 7.94 (d, J=9.2 Hz, 2H), 7.76 (d, J=1.5 Hz, 1H), 7.37 (d, J=9.0 Hz, 2H), 5.16 (d, J=3.3 Hz, 1H), 4.12 (br d, J=2.1 Hz, 1H), 3.84 (dd, J=3.7, 11.7 Hz, 1H), 3.45 (br dd, J=4.4, 11.7 Hz, 1H), 3.19-2.97 (m, 2H), 2.02-1.92 (m, 2H).

Example 44

General Procedure U (S)—N-(4-(chlorodifluoromethoxy)phenyl)-3-hydroxy-6-(1H-pyrazol-5-yl)-3,4-dihydro-2H-benzo[4,5]imidazo[2,1-b][1,3]oxazine-8-carboxamide This General Procedure U provides particular synthetic details as applied to the title compound. Additional compounds can be prepared according to this method by varying the coupling reagents.

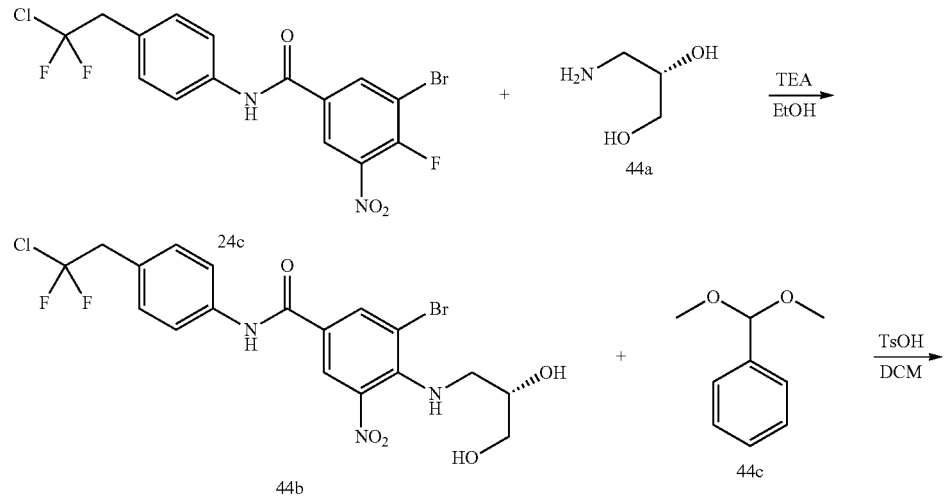

-continued
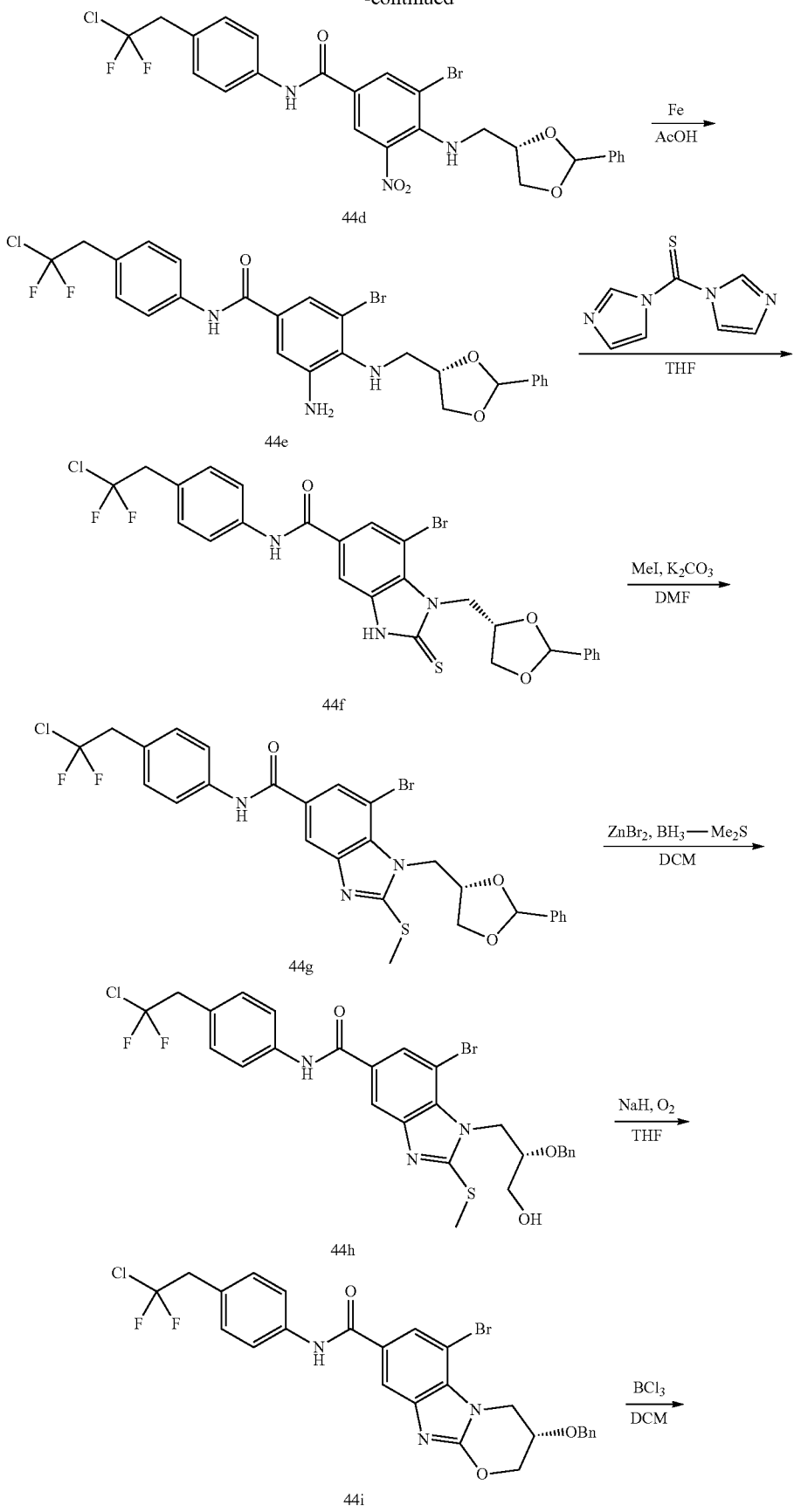

-continued

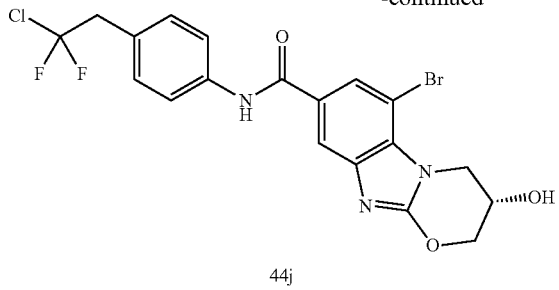

44j

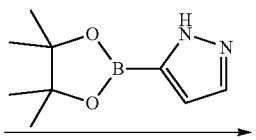

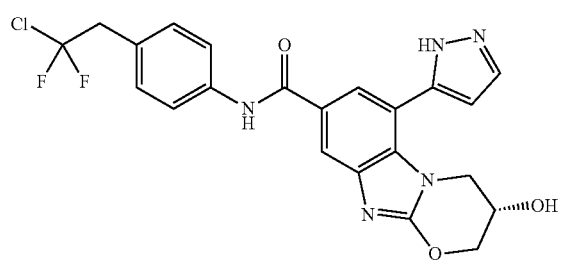

44k (S)-3-bromo-N-(4-(chlorodifluoromethoxy)phenyl)-4-(2,3-dihydroxypropyl)amino)-5-nitrobenzamide (44b). To a mixture of 3-bromo-N-(4-(chlorodifluoromethoxy)phenyl)-4-fluoro-5-nitrobenzamide (24c, 1.2 g, 2.73 mmol) and (S)-3-aminopropane-1,2-diol (44a, 261.16 mg, 2.87 mmol, 221.32 uL) in EtOH (3 mL) was added TEA (552.49 mg, 5.46 mmol, 759.96). The mixture was stirred at 25° C. for 12 hours. LCMS showed the desired MS. The mixture was concentrated and poured into water, filtered to give 44b as a red solid. $^1$H NMR (400 MHz, MeOD-d$_4$) δ 8.53 (d, J=2.1 Hz, 1H), 8.38 (d, J=2.2 Hz, 1H), 7.80 (d, J=9.0 Hz, 2H), 7.28 (br d, J=8.9 Hz, 2H), 3.83-3.75 (m, 1H), 3.61-3.41 (m, 3H), 3.26-3.22 (m, 1H).

3-bromo-N-(4-(chlorodifluoromethoxy)phenyl)-5-nitro-4-((((4S)-2-phenyl-1,3-dioxolan-4-yl)methyl)amino)benzamide (44d). To a mixture of (S)-3-bromo-N-(4-(chlorodifluoromethoxy)phenyl)-4-((2,3-dihydroxypropyl)amino)-5-nitrobenzamide (44b, 1.2 g, 2.35 mmol) and TsOH (40.46 mg, 0.235 mmol) in DCM (10 mL) at 0° C. under N$_2$ was added dimethoxymethylbenzene (44c, 1.07 g, 7.05 mmol, 1.06 mL). The mixture was stirred at 25° C. for 12 hours. TLC (petroleum ether:ethyl acetate=3:1, R$_f$=0.60) indicated 44b was consumed completely and two new spots formed. The mixture was extracted with ethyl acetate (30 mL×3), the combined organic layers were washed with brine (50 mL×2), dried over anhydrous Na$_2$SO$_4$, filtered and concentrated in vacuo. The residue was purified by column chromatography (SiO$_2$, petroleum ether:ethyl acetate=100:1 to 3:1, R$_f$=0.60) to give 44d as a yellow solid. $^1$H NMR (400 MHz, DMSO-d$_6$) δ 10.46 (s, 1H), 10.43 (s, 1H), 8.54 (d, J=2.1 Hz, 1H), 8.47 (d, J=2.1 Hz, 1H), 8.46 (d, J=2.1 Hz, 1H), 8.42 (d, J=2.2 Hz, 1H), 7.89 (d, J=1.3 Hz, 2H), 7.86 (s, 2H), 7.42-7.31 (m, 14H), 6.75 (t, J=5.7 Hz, 1H), 6.67 (t, J=5.7 Hz, 1H), 5.84 (s, 1H), 5.72 (s, 1H), 4.51-4.42 (m, 2H), 4.18 (dd, J=6.6, 8.4 Hz, 1H), 3.94 (dd, J=5.0, 8.5 Hz, 1H), 3.73 (dd, J=6.4, 8.5 Hz, 1H), 3.61-3.53 (m, 1H), 3.49-3.42 (m, 2H).

3-amino-5-bromo-N-(4-(chlorodifluoromethoxy)phenyl)-4-((((4S)-2-phenyl-1,3-dioxolan-4-yl)methyl)amino)benzamide (44e). To a solution of 3-bromo-N-(4-(chlorodifluoromethoxy)phenyl)-5-nitro-4-((((4S)-2-phenyl-1,3-dioxolan-4-yl)methyl)amino)benzamide (44d, 0.7 g, 1.17 mmol) in AcOH (10 mL) was added Fe (652.86 mg, 11.69 mmol). The mixture was stirred at 35° C. for 0.5 hr. TLC indicated 44d was consumed completely and one new spot formed. The mixture was poured into water and extracted with ethyl acetate (10 mL×2). The combined organic layers were washed with sat. NaHCO$_3$, washed with brine (50 mL×2), dried over anhydrous Na$_2$SO$_4$, filtered and concentrated in vacuo to give 44e as a yellow oil.

7-bromo-N-(4-(chlorodifluoromethoxy)phenyl)-1-(((4S)-2-phenyl-1,3-dioxolan-4-yl)methyl)-2-thioxo-2,3-dihydro-1H-benzo[d]imidazole-5-carboxamide (44f). A solution of 3-amino-5-bromo-N-(4-(chlorodifluoromethoxy)phenyl)-4-((((4S)-2-phenyl-1,3-dioxolan-4-yl)methyl)amino)benzamide (44f, 0.9 g, 1.58 mmol), di(imidazol-1-yl)methanethione (845.96 mg, 4.75 mmol) in THF (10 mL) was added DIEA (408.99 mg, 3.16 mmol, 551.20 uL) and the mixture was stirred at 60° C. for 12 hours. LCMS showed the desired MS. The mixture was extracted with ethyl acetate (30 mL×2), the combined organic layers were washed with brine (50 mL×2), dried over anhydrous Na$_2$SO$_4$, filtered and concentrated in vacuo. The residue was purified by prep-TLC (SiO$_2$, petroleum ether:ethyl acetate=1:1, R$_f$=0.30) to give 44f as a yellow solid. $^1$H NMR (400 MHz, DMSO-d$_6$) δ 13.55 (s, 1H), 10.53 (s, 1H), 8.05 (dd, J=1.5, 4.2 Hz, 1H), 7.92-7.85 (m, 2H), 7.78 (d, J=1.2 Hz, 1H), 7.50-7.45 (m, 1H), 7.42-7.33 (m, 6H), 6.11-5.69 (m, 1H), 5.17-4.69 (m, 3H), 4.35-4.27 (m, 1H), 4.08-3.98 (m, 1H).

7-bromo-N-(4-(chlorodifluoromethoxy)phenyl)-2-(methylthio)-1-(((4S)-2-phenyl-1,3-dioxolan-4-yl)methyl)-1H-benzo[d]imidazole-5-carboxamide (44g). To a solution of 7-bromo-N-(4-(chlorodifluoromethoxy)phenyl)-1-(((4S)-2-phenyl-1,3-dioxolan-4-yl)methyl)-2-thioxo-2,3-dihydro-1H-benzo[d]imidazole-5-carboxamide (44f, 0.72 g, 1.18 mmol) in DMF (10 mL) was added MeI (184.03 mg, 1.30 mmol, 80.72 uL) and K$_2$CO$_3$ (325.80 mg, 2.36 mmol). The mixture was stirred at 25° C. for 2 hours. LCMS showed the desired MS. The mixture was extracted with ethyl acetate (20 mL×3). The combined organic layers were washed with brine (50 mL×2), dried over anhydrous Na$_2$SO$_4$, filtered and concentrated in vacuo. The residue was purified by column chromatography (SiO$_2$, petroleum ether:ethyl acetate=100:1 to 1:1) to give 44g as a white solid. $^1$H NMR (400 MHz, DMSO-d$_6$) δ 10.44 (s, 1H), 8.29 (d, J=1.2 Hz, 1H), 8.00 (s, 1H), 7.97-7.90 (m, 2H), 7.52-7.47 (m, 1H), 7.43-7.33 (m, 5H), 6.07-5.70 (m, 1H), 4.85-4.60 (m, 3H), 4.46-3.91 (m, 2H), 2.79-2.71 (m, 3H).

(S)-1-(2-(benzyloxy)-3-hydroxypropyl)-7-bromo-N-(4-(chlorodifluoromethoxy)phenyl)-2-(methylthio)-1H-benzo[d]imidazole-5-carboxamide (44h). To a solution of 7-bromo-N-(4-(chlorodifluoromethoxy)phenyl)-2-(methylthio)-1-(((4S)-2-phenyl-1,3-dioxolan-4-yl)methyl)-1H-benzo[d]imidazole-5-carboxamide (44g, 0.06 g, 0.96 mmol), ZnBr$_2$ (64.87 mg, 0.288 mmol, 14.42 uL) in DCM (2 mL) at 0° C. was added BH$_3$-Me$_2$S (10 M, 11.52 uL, 1.2 eq). The mixture was stirred at 25° C. for 12 hours. LCMS showed the desired MS. The mixture was quenched by sat. NaHCO$_3$ and extracted with DCM (2 mL×2). The combined organic layers were washed with brine (5 mL), dried over anhydrous Na$_2$SO$_4$, filtered and concentrated in vacuo. The residue was purified by prep-TLC (SiO$_2$, petroleum ether:ethyl acetate=0:1, R$_f$=0.40) to give 44h as a white solid. $^1$H NMR (400 MHz, DMSO-d$_6$) δ 10.43 (s, 1H), 8.28 (d, J=1.2 Hz, 1H), 7.97-7.91 (m, 3H), 7.37 (d, J=8.8 Hz, 2H), 7.09-7.04 (m, 3H), 6.89-6.85 (m, 2H), 5.00 (t, J=5.6 Hz, 1H), 4.68-4.59 (m, 1H), 4.47 (d, J=12.2 Hz, 2H), 4.13 (d, J=12.2 Hz, 1H), 3.89 (br dd, J=4.0, 9.5 Hz, 1H), 3.67 (t, J=4.9 Hz, 2H), 2.72 (s, 3H).

(S)-3-(benzyloxy)-6-bromo-N-(4-(chlorodifluoromethoxy)phenyl)-3,4-dihydro-2H-benzo[4,5]imidazo[2,1-b][1,3]oxazine-8-carboxamide (44i). To a mixture of (S)-1-(2-(benzyloxy)-3-hydroxypropyl)-7-bromo-N-(4-(chlorodifluoromethoxy)phenyl)-2-(methylthio)-1H-benzo[d]imidazole-5-carboxamide (44h, 20 mg, 0.032 mmol) in THF (2 mL) at 0° C. under O$_2$ was added NaH (1.78 mg, 0.045 mmol, 60% purity). The mixture was stirred at 25° C. for 12 hours. LCMS showed the desired MS. The mixture was quenched by H$_2$O and extracted with ethyl acetate (2 mL×3). The combined organic layers were washed with brine (5 mL×2), dried over anhydrous Na$_2$SO$_4$, filtered and concentrated in vacuo. The residue was purified by prep-TLC (SiO$_2$, petroleum ether:ethyl acetate=0:1, R$_f$=0.40) to give 44i as a white solid.

(S)-6-bromo-N-(4-(chlorodifluoromethoxy)phenyl)-3-hydroxy-3,4-dihydro-2H-benzo[4,5]imidazo[2,1-b][1,3]oxazine-8-carboxamide (44j). To a mixture of (S)-3-(benzyloxy)-6-bromo-N-(4-(chlorodifluoromethoxy)phenyl)-3,4-dihydro-2H-benzo[4,5]imidazo[2,1-b][1,3]oxazine-8-carboxamide (44i, 30 mg, 0.052 mmol) in DCM (2 mL) at −70° C. under N$_2$ was added BCl$_3$ (1M, 259.16 uL). The mixture was stirred at −70° C. for 1 hour. LCMS showed the desired MS. The reaction was quenched with water and DCM (3 mL×2). The combined organic layers were washed with brine (5 mL×2), dried over anhydrous Na$_2$SO$_4$, filtered and concentrated in vacuo to give 44j as a white solid. $^1$H NMR (400 MHz, DMSO-d$_6$) δ 10.42 (s, 1H), 8.08 (s, 1H), 7.95-7.86 (m, 3H), 7.36 (br d, J=8.8 Hz, 2H), 4.66 (br d, J=11.9 Hz, 1H), 4.58-4.49 (m, 2H), 4.46-4.36 (m, 2H).

(S)—N-(4-(chlorodifluoromethoxy)phenyl)-3-hydroxy-6-(1H-pyrazol-5-yl)-3,4-dihydro-2H-benzo[4,5]imidazo[2,1-b][1,3]oxazine-8-carboxamide (44). To a solution of (S)-6-bromo-N-(4-(chlorodifluoromethoxy)phenyl)-3-hydroxy-3,4-dihydro-2H-benzo[4,5]imidazo[2,1-b][1,3]oxazine-8-carboxamide (44j, 15 mg, 0.031 mmol), 5-(4,4,5,5-tetramethyl-1,3,2-dioxaborolan-2-yl)-1H-pyrazole (17.87 mg, 0.092 mmol) in dioxane (2 mL), H$_2$O (0.2 mL) was added K$_3$PO$_4$ (19.55 mg, 0.092 mmol) and Pd(dppf)Cl$_2$ (2.25 mg, 3.07 umol), (Boc)$_2$O (6.70 mg, 0.031 umol, 7.05 uL). The mixture was stirred at 110° C. for 12 hours. TLC (ethyl acetate:methanol=10:1, R$_f$=0.24) indicated 44j was consumed completely and many new spots formed. The mixture was filtered and poured into water, extracted with ethyl acetate (5 mL×2). The combined organic layers were washed with brine (10 mL×2), dried over anhydrous Na$_2$SO$_4$, filtered and concentrated in vacuo. The residue was purified by prep-TLC (SiO$_2$, ethyl acetate:methanol=10:1) to give 44 as a yellow solid. $^1$H NMR (400 MHz, MeOD-d$_4$) δ 8.06 (s, 1H), 7.85-7.77 (m, 4H), 7.28 (d, J=9.0 Hz, 2H), 6.64 (s, 1H), 4.57-4.44 (m, 2H), 4.28 (br s, 1H), 4.12 (br d, J=13.1 Hz, 1H), 3.73 (br s, 1H).

Example 45

General Procedure V (S)—N-(4-(chlorodifluoromethoxy)phenyl)-4-(hydroxymethyl)-6-(pyridazin-3-yl)-3,4-dihydro-2H-benzo[4,5]imidazo[2,1-b][1,3]oxazine-8-carboxamide This General Procedure V provides particular synthetic details as applied to the title compound. Additional compounds can be prepared according to this method by varying the coupling reagents.

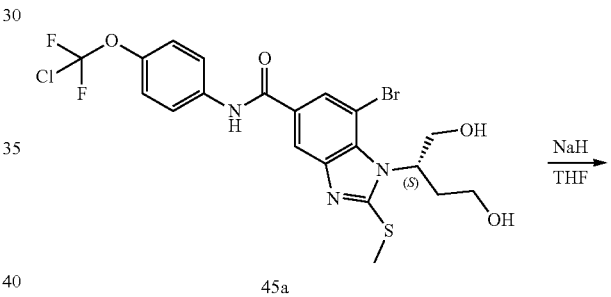

45a

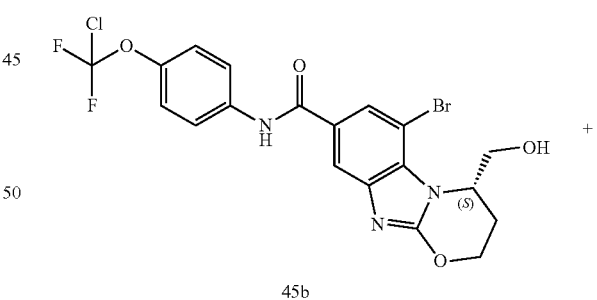

45b

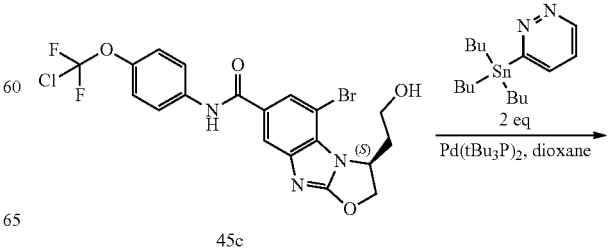

45c

-continued

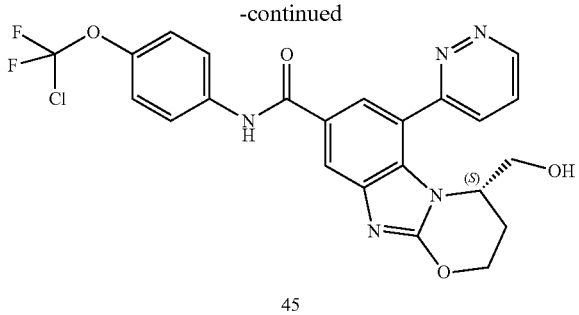

45

(S)-6-bromo-N-(4-(chlorodifluoromethoxy)phenyl)-4-(hydroxymethyl)-3,4-dihydro-2H-benzo[4,5]imidazo[2,1-b][1,3]oxazine-8-carboxamide (45b), (S)-5-bromo-N-(4-(chlorodifluoromethoxy)phenyl)-3-(2-hydroxyethyl)-2,3-dihydrobenzo[4,5]imidazo[2,1-b]oxazole-7-carboxamide (45c). To a solution of (S)-7-bromo-N-(4-(chlorodifluoromethoxy)phenyl)-1-(1,4-dihydroxybutan-2-yl)-2-(methylthio)-1H-benzo[d]imidazole-5-carboxamide (synthesized in a similar fashion to 42d; 45a, 260 mg, 0.472 mmol) in THF (5 mL) at 0° C. was added NaH (28.32 mg, 0.708 mmol, 60% purity). The mixture was stirred at 20° C. for 1 hr under $O_2$. LCMS showed 45a was consumed completely and desired MS was detected. TLC (ethyl acetate:methanol=10:1, $P_1$: $R_f$=0.5, $P_2$: $R_f$=0.4) showed the reaction was completed. The mixture was diluted with aq.$NH_4Cl$ (10 mL) and extracted with EtOAc (20 mL×3). The combined organic layers were washed with brine (10 mL), dried over $Na_2SO_4$, filtered and concentrated under reduced pressure to give a residue. The residue was purified by silica gel chromatography (petroleum ether/ethyl acetate=5/1, 0/1, ethyl acetate:methanol=20/1) to give 45b as a white solid and 45c as a white solid. (45b) $^1$H NMR (400 MHz, MeOD-$d_4$) δ 7.92 (d, J=1.5 Hz, 1H), 7.83-7.77 (m, 2H), 7.62 (d, J=1.8 Hz, 1H), 7.29 (d, J=9.0 Hz, 2H), 6.13-5.99 (m, 1H), 4.22 (q, J=7.6 Hz, 1H), 4.18-4.06 (m, 2H), 3.99 (dt, J=5.1, 8.0 Hz, 1H), 2.75-2.58 (m, 1H), 2.41-2.23 (m, 1H). (45c) $^1$H NMR (400 MHz, DMSO-$d_6$) δ 10.40 (s, 1H), 8.06 (d, J=1.1 Hz, 1H), 7.98-7.85 (m, 3H), 7.35 (br d, J=9.0 Hz, 2H), 5.30-5.22 (m, 1H), 5.15 (dd, J=2.3, 8.7 Hz, 1H), 5.12-5.00 (m, 1H), 4.68 (t, J=4.8 Hz, 1H), 3.52 (td, J=5.8, 11.4 Hz, 2H), 2.27-2.14 (m, 1H), 2.09-2.00 (m, 1H).

(S)—N-(4-(chlorodifluoromethoxy)phenyl)-4-(hydroxymethyl)-6-(pyridazin-3-yl)-3,4-dihydro-2H-benzo[4,5]imidazo[2,1-b][1,3]oxazine-8-carboxamide (45). To a solution of (S)-6-bromo-N-(4-(chlorodifluoromethoxy)phenyl)-4-(hydroxymethyl)-3,4-dihydro-2H-benzo[4,5]imidazo[2,1-b][1,3]oxazine-8-carboxamide (45b, 40 mg, 0.08 mmol) and tributyl(pyridazin-3-yl)stannane (58.74 mg, 0.159 mmol) in dioxane (4 mL) was added palladium; tritert-butylphosphane (4.07 mg, 7.96 umol). The mixture was stirred at 110° C. for 16 hr under $N_2$. LCMS showed 45b was consumed completely and desired MS was detected. The reaction mixture was diluted with $H_2O$ (5 mL) and extracted with EtOAc (10 mL×2). The combined organic layers were dried over $Na_2SO_4$, filtered and concentrated under reduced pressure to give a residue. The mixture was further purification by pre-HPLC (FA, column: Phenomenex Luna C18 200*40 mm*10 um; mobile phase: [water (0.225% FA)-ACN]; B %: 40%-70%,12 min) to give 45 as a white solid. MS mass calculated for [M+1]$^+$ ($C_{23}H_{18}ClF_2N_5O_4$) requires m/z 502.1, LCMS found m/z 502.1; $^1$H NMR (400 MHz, MeOD-$d_4$) δ 9.35 (dd, J=1.5, 5.1 Hz, 1H), 8.17 (dd, J=1.4, 8.5 Hz, 1H), 8.01 (dd, J=5.1, 8.4 Hz, 1H), 7.84-7.78 (m, 3H), 7.76 (d, J=1.8 Hz, 1H), 7.29 (d, J=9.0 Hz, 2H), 4.16-3.99 (m, 3H), 3.91-3.82 (m, 1H), 3.79-3.70 (m, 1H), 2.54-2.43 (m, 1H), 2.01 (br s, 1H)

Example 46

(R)—N-(4-(chlorodifluoromethoxy)phenyl)-4-hydroxy-9-(pyridazin-3-yl)-1,2,3,4-tetrahydrobenzo[4,5]imidazo[1,2-a]pyridine-7-carboxamide

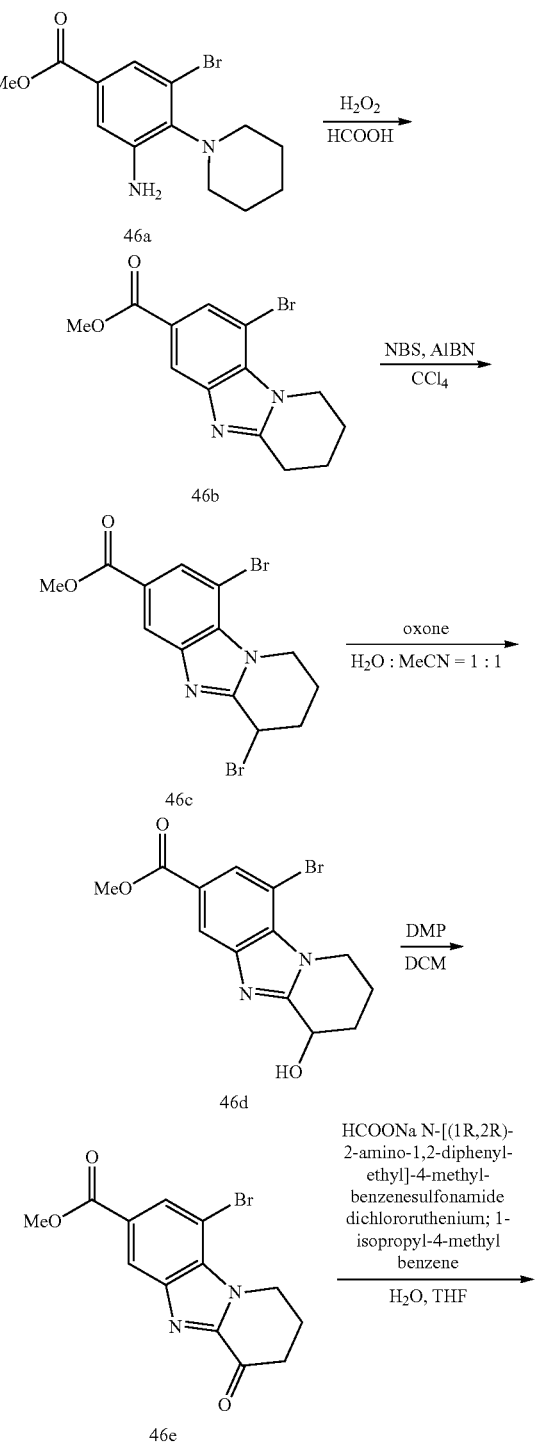

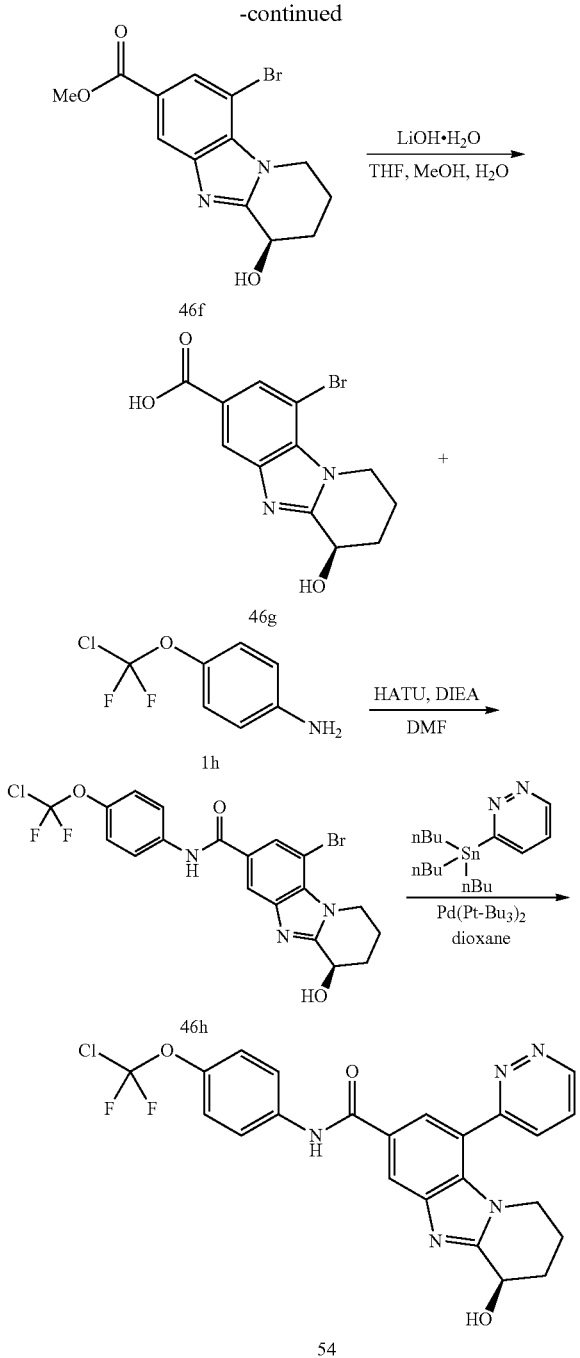

Methyl 9-bromo-1,2,3,4-tetrahydrobenzo[4,5]imidazo[1,2-a]pyridine-7-carboxylate (46b). To a mixture of methyl 3-amino-5-bromo-4-(piperidin-1-yl)benzoate (46a, 1.8 g, 5.75 mmol) in HCOOH (20 mL) was added $H_2O_2$ (5.86 g, 51.73 mmol, 4.97 mL, 30% purity) under $N_2$. The mixture was stirred at 110° C. for 40 mins. LCMS showed the desired MS. The mixture was quenched with sat. $Na_2S_2O_3$, made basic with $NaHCO_3$ (pH=7) and extracted with ethyl acetate (50 mL×3). The combined organic layers were washed with brine (100 mL), dried over anhydrous $Na_2SO_4$, filtered and concentrated in vacuo. The residue was purified by column chromatography ($SiO_2$, petroleum ether:ethyl acetate=100:1 to 0:1, $R_f$=0.20) to give 46b as a brown solid.

Methyl 4,9-dibromo-1,2,3,4-tetrahydrobenzo[4,5]imidazo[1,2-a]pyridine-7-carboxylate (46c). To a solution of methyl 9-bromo-1,2,3,4-tetrahydrobenzo[4,5]imidazo[1,2-a]pyridine-7-carboxylate (46b, 0.7 g, 2.26 mmol), AIBN (37.18 mg, 0.226 umol) in $CCl_4$ (20 mL) was added NBS (402.99 mg, 2.26 mmol). The mixture was stirred at 50° C. for 12 hours. LCMS showed the desired MS. The mixture was quenched by $H_2O$ and extracted with DCM (30 mL×2). The combined organic layers were washed with brine (50 mL×2), dried over anhydrous $Na_2SO_4$, filtered and concentrated in vacuo. The residue was purified by column chromatography ($SiO_2$, petroleum ether:ethyl acetate=100:1 to 1:1, $R_f$=0.50) to give 46c as a brown solid.

Methyl 9-bromo-4-hydroxy-1,2,3,4-tetrahydrobenzo[4,5]imidazo[1,2-a]pyridine-7-carboxylate (46d). To a solution of methyl 4,9-dibromo-1,2,3,4-tetrahydrobenzo[4,5]imidazo[1,2-a]pyridine-7-carboxylate (46c, 0.7 g, 1.80 mmol) in MeCN (5 mL) and $H_2O$ (5 mL) was added Oxone (2.22 g, 3.61 mmol). The mixture was stirred at 50° C. for 12 hours. LCMS showed the desired MS. The mixture was concentrated, poured into water and extracted with ethyl acetate (10 mL×2). The combined organic layers were washed with brine (30 mL×2), dried over anhydrous $Na_2SO_4$, filtered and concentrated in vacuo. The residue was purified by column chromatography ($SiO_2$, petroleum ether:ethyl acetate=100:1 to 0:1) to give 46d as a white solid.

Methyl 9-bromo-4-oxo-1,2,3,4-tetrahydrobenzo[4,5]imidazo[1,2-a]pyridine-7-carboxylate (46e). To a solution of methyl 9-bromo-4-hydroxy-1,2,3,4-tetrahydrobenzo[4,5]imidazo[1,2-a]pyridine-7-carboxylate (46d, 0.3 g, 0.922 mmol) in DCM (5 mL) was added DMP (395.24 mg, 0.932 mmol) at 0° C. The mixture was stirred at 25° C. for 10 mins. TLC (petroleum ether:ethyl acetate=0:1, $R_f$=0.50) indicated 46d was consumed completely and one new spot formed. The mixture was poured into water and extracted with ethyl acetate (3 mL×2). The combined organic layers were washed with brine (5 mL×2), dried over anhydrous $Na_2SO_4$, filtered and concentrated in vacuo. The residue was purified by prep-TLC ($SiO_2$, petroleum ether:ethyl acetate=0:1, $R_f$=0.50) to give 46e as a brown solid.

(R)-methyl 9-bromo-4-hydroxy-1,2,3,4-tetrahydrobenzo[4,5]imidazo[1,2-a]pyridine-7-carboxylate (46f). A solution of dichlororuthenium; 1-isopropyl-4-methyl-benzene (18.00 mg, 29.40 umol), N-[(1R,2R)-2-amino-1,2-diphenyl-ethyl]-4-methyl-benzenesulfonamide (25.86 mg, 70.56 umol) in $H_2O$ (10 mL) was stirred at 70° C. for 1.5 hours. Sodium formate (199.93 mg, 2.94 mmol, 158.68 uL), methyl 9-bromo-4-oxo-1,2,3,4-tetrahydrobenzo[4,5]imidazo[1,2-a]pyridine-7-carboxylate (46e, 0.19 g, 0.588 mmol) in THF (5 mL) was added and the mixture was stirred at 40° C. for 0.5 hours. LCMS showed the desired MS. The mixture was filtered, poured into water and extracted with ethyl acetate (10 mL×2). The combined organic layers were washed with brine (30 mL×1), dried over anhydrous $Na_2SO_4$, filtered and concentrated in vacuo. The residue was purified by prep-TLC ($SiO_2$, petroleum ether:ethyl acetate=0:1, $R_f$=0.20) to give 46f as a yellow solid.

(R)-9-bromo-4-hydroxy-1,2,3,4-tetrahydrobenzo[4,5]imidazo[1,2-a]pyridine-7-carboxylic acid (46g). To a solution of (R)-methyl 9-bromo-4-hydroxy-1,2,3,4-tetrahydrobenzo[4,5]imidazo[1,2-a]pyridine-7-carboxylate (46f, 0.06 g, 0.185 mmol) in MeOH (0.5 mL), THF (0.5 mL) and $H_2O$ (0.1 mL) was added $LiOH \cdot H_2O$ (15.49 mg, 0.369 mmol). The mixture was stirred at 50° C. for 0.5 hours. LCMS showed the desired MS. TLC (ethyl acetate:methanol=10:1, $R_f$=0.05) and indicated 46f was consumed completely. The mixture was concentrated and poured into aq.

HCl (1M) to adjust the pH=5-6. The precipitate was filtered and dried to give 46g as a white solid.

(R)-9-bromo-N-(4-(chlorodifluoromethoxy)phenyl)-4-hydroxy-1,2,3,4-tetrahydrobenzo[4,5]imidazo[1,2-a]pyridine-7-carboxamide (46h). To a solution of (R)-9-bromo-4-hydroxy-1,2,3,4-tetrahydrobenzo[4,5]imidazo[1,2-a]pyridine-7-carboxylic acid (46g, 0.06 g, 0.193 mmol), 4-[chloro(difluoro)methoxy]aniline (1h, 41.06 mg, 0.212 mmol) in DMF (2 mL) was added HATU (87.99 mg, 0.23 mmol) and DIEA (74.77 mg, 0.579 mmol, 100.77 uL). The mixture was stirred at 25° C. for 12 hours. LCMS showed the desired MS. The mixture was extracted with ethyl acetate (3 mL×3). The combined organic layers were washed with brine (5 mL×2), dried over anhydrous Na$_2$SO$_4$, filtered and concentrated in vacuo. The residue was purified by prep-TLC (SiO$_2$, ethyl acetate:methanol=10:1, R$_f$=0.40) to give 46h as a yellow oil.

(R)—N-(4-(chlorodifluoromethoxy)phenyl)-4-hydroxy-9-(pyridazin-3-yl)-1,2,3,4-tetrahydrobenzo[4,5]imidazo[1,2-a]pyridine-7-carboxamide (46). To a solution of (R)-9-bromo-N-(4-(chlorodifluoromethoxy)phenyl)-4-hydroxy-1,2,3,4-tetrahydrobenzo[4,5]imidazo[1,2-a]pyridine-7-carboxamide (46h, 0.05 g, 0.103 mmol), tributyl(pyridazin-3-yl)stannane (75.84 mg, 0.205 mmol) in dioxane (2 mL) was added palladium; tritert-butylphosphane (5.25 mg, 10.27 umol). The mixture was stirred at 120° C. for 12 hours. LCMS showed the desired MS. The mixture was filtered and poured into water and extracted with ethyl acetate (5 mL×2). The combined organic layers were washed with brine (10 mL×1), dried over anhydrous Na$_2$SO$_4$, filtered and concentrated in vacuo. The residue was purified by prep-HPLC (FA, column: Phenomenex Luna C18 200*40 mm*10 um; mobile phase: [water (0.225% FA)-ACN]; B %: 20%-50%, 12 min) to give 46 as a yellow solid. $^1$H NMR (400 MHz, MeOD-d$_4$) δ 9.31 (dd, J=1.4, 5.0 Hz, 1H), 8.45 (d, J=1.3 Hz, 1H), 8.13 (dd, J=1.5, 8.4 Hz, 1H), 7.96 (d, J=1.5 Hz, 1H), 7.93 (dd, J=5.1, 8.4 Hz, 1H), 7.85 (d, J=9.0 Hz, 2H), 7.30 (d, J=9.3 Hz, 2H), 5.06-5.00 (m, 1H), 3.82-3.72 (m, 2H), 2.20 (br d, J=11.5 Hz, 2H), 2.07-2.00 (m, 1H), 1.98-1.86 (m, 1H).

Example 47

(2S,3S)—N-(4-(chlorodifluoromethoxy)phenyl)-2-(hydroxymethyl)-3-methyl-5-(1H-pyrazol-5-yl)-2,3-dihydrobenzo[4,5]imidazo[2,1-b]oxazole-7-carboxamide

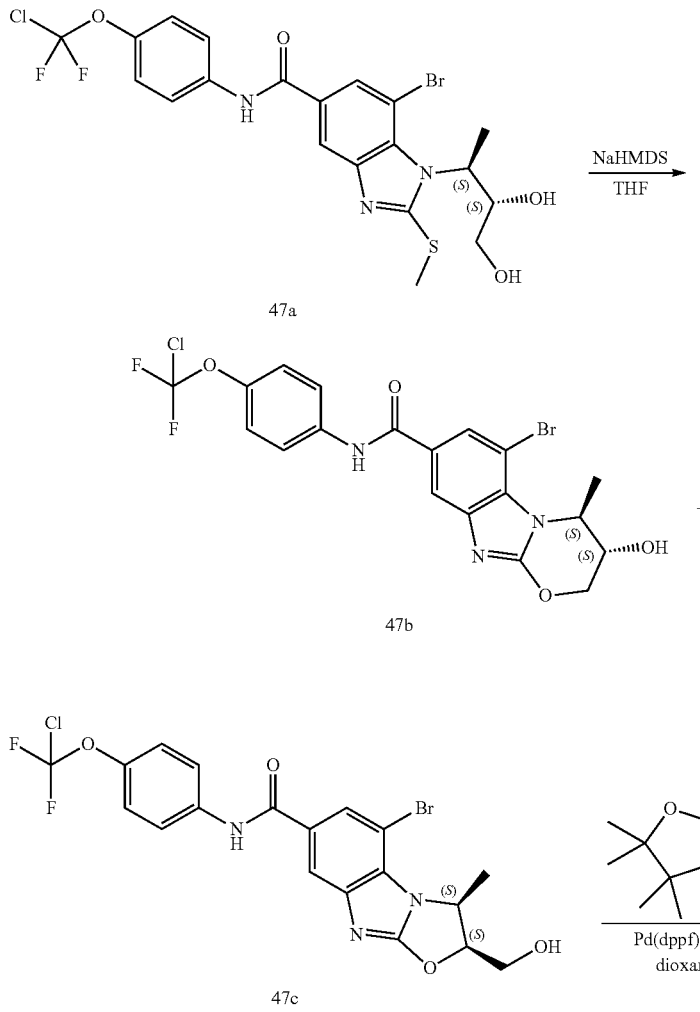

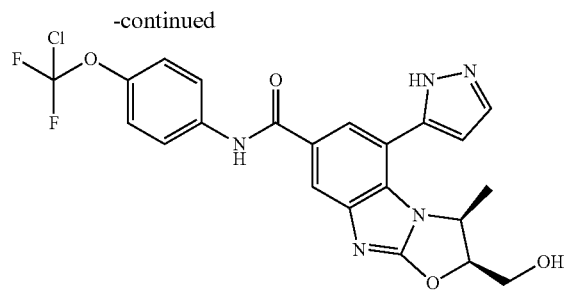

47

(3S,4S)-6-bromo-N-(4-(chlorodifluoromethoxy)phenyl)-3-hydroxy-4-methyl-3,4-dihydro-2H-benzo[4,5]imidazo[2,1-b][1,3]oxazine-8-carboxamide (47b). NaHMDS (1M, 21.79 uL) was added to a solution of 7-bromo-N-(4-(chlorodifluoromethoxy)phenyl)-1-((2S,3S)-3,4-dihydroxybutan-2-yl)-2-(methylthio)-1H-benzo[d]imidazole-5-carboxamide (synthesized in a similar fashion to 45a; 47a, 10 mg, 0.018 mmol) in THF (1 mL) at 0° C. The solution was stirred at 20° C. for 40 min under $O_2$. TLC showed 47a disappeared and four new main spots appeared. LCMS detected the desired MS and showed that the reaction was complete. $NH_4Cl$ (10 mL) was added to the mixture dropwise and the reaction was extracted with ethyl acetate (5 mL×3). The combined organic layers were washed with brine (10 mL), dried over $Na_2SO_4$, filtered and concentrated in vacuo. The residue was purified by prep-TLC (petroleum ether:ethyl acetate=0:1) to give 47b as a white solid. $^1$H NMR (400 MHz, MeOD-$d_4$) δ 8.01 (d, J=1.3 Hz, 1H), 7.96 (d, J=1.5 Hz, 1H), 7.85-7.78 (m, 2H), 7.29 (br d, J=9.0 Hz, 2H), 5.51 (dt, J=5.2, 6.8 Hz, 1H), 5.23-5.14 (m, 1H), 4.14-4.00 (m, 2H), 1.53 (d, J=6.6 Hz, 3H).

(2S,3S)—N-(4-(chlorodifluoromethoxy)phenyl)-2-(hydroxymethyl)-3-methyl-5-(1H-pyrazol-5-yl)-2,3-dihydrobenzo[4,5]imidazo[2,1-b]oxazole-7-carboxamide (47). To a solution of (3S,4S)-6-bromo-N-(4-(chlorodifluoromethoxy)phenyl)-3-hydroxy-4-methyl-3,4-dihydro-2H-benzo[4,5]imidazo[2,1-b][1,3]oxazine-8-carboxamide (47c, 30 mg, 0.06 mmol) and 5-(4,4,5,5-tetramethyl-1,3,2-dioxaborolan-2-yl)-1H-pyrazole (34.74 mg, 0.179 mmol) in dioxane (2 mL) at 20° C. and $H_2O$ (0.2 mL) was added Pd(dppf)$Cl_2$ (4.37 mg, 5.97 umol), $Boc_2O$ (6.51 mg, 0.03 mmol, 6.86 uL) and $K_3PO_4$ (38.00 mg, 0.179 mmol). The reaction was stirred at 120° C. for 16 hr. LCMS detected the desired MS and showed that the reaction was complete. The mixture was concentrated to remove the solvent. The residue was purified by prep-TLC (ethyl acetate:methanol=10:1) to give 47 as a white solid. MS mass calculated for [M+1]$^+$ ($C_{22}H_{18}ClF_2N_5O_4$) requires m/z 490.1, LCMS found m/z 490.1; $^1$H NMR (400 MHz, MeOD-$d_4$) δ 8.02 (s, 2H), 7.87-7.79 (m, 3H), 7.30 (d, J=9.0 Hz, 2H), 6.81 (s, 1H), 5.52-5.44 (m, 1H), 5.37 (br t, J=6.6 Hz, 1H), 4.08-3.91 (m, 2H), 0.93 (br d, J=6.4 Hz, 3H).

Example 48

(S)—N-(4-(chlorodifluoromethoxy)phenyl)-2-hydroxy-2-methyl-9-(1H-pyrazol-5-yl)-1,2,3,4-tetrahydrobenzo[4,5]imidazo[1,2-a]pyridine-7-carboxamide

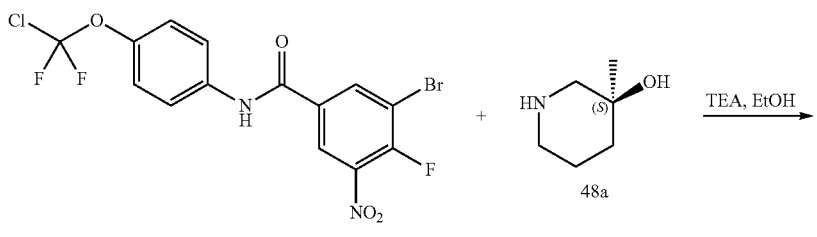

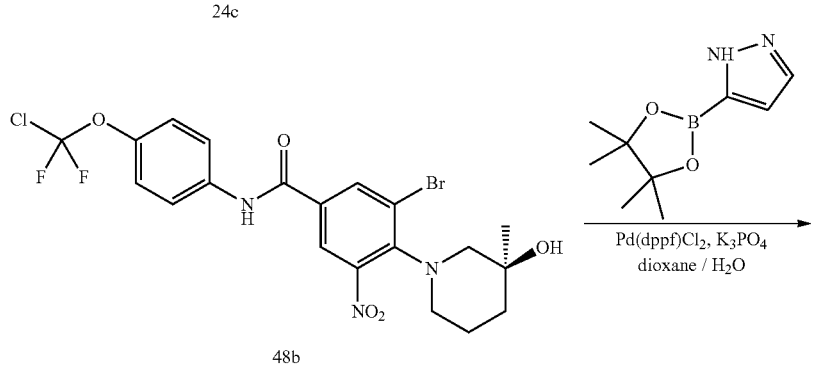

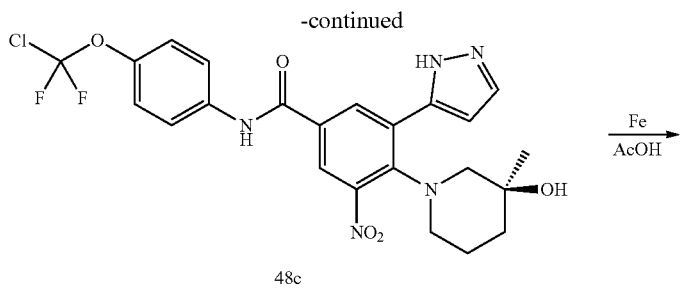

48c

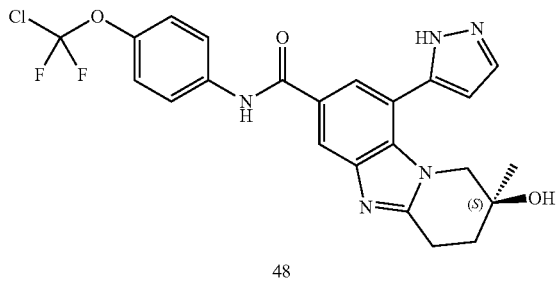

48

(S)-3-bromo-N-(4-(chlorodifluoromethoxy)phenyl)-4-(3-hydroxy-3-methylpiperidin-1-yl)-5-nitrobenzamide (48b). To a solution of 3-bromo-N-(4-(chlorodifluoromethoxy)phenyl)-4-fluoro-5-nitrobenzamide (24c, 500 mg, 1.14 mmol) and (3S)-3-methylpiperidin-3-ol hydrochloride (48a, 206.98 mg, 1.36 mmol) in EtOH (6 mL) was added TEA (345.30 mg, 3.41 mmol, 474.97 uL). The mixture was stirred at 15° C. for 16 hr. LCMS showed the desired ms was detected. TLC (petroleum ether:ethyl acetate=3:1, $R_f$=0.4) showed a new spot was generated. The reaction mixture was concentrated under reduced pressure to remove solvent. The residue was purified by column chromatography (SiO$_2$, petroleum ether/ethyl acetate=60/1 to 1/1) to give 548b as a yellow solid. $^1$H NMR (400 MHz, CDCl$_3$-d) δ 8.33 (s, 1H), 8.11 (s, 1H), 7.76 (s, 1H), 7.69 (d, J=9.0 Hz, 2H), 7.30 (s, 2H), 3.38 (br s, 1H), 3.28-3.00 (m, 1H), 2.93 (br d, J=11.2 Hz, 1H), 2.61 (br s, 1H), 2.20 (br s, 1H), 1.89-1.63 (m, 2H), 1.56 (s, 3H), 1.53-1.39 (m, 1H).

(S)—N-(4-(chlorodifluoromethoxy)phenyl)-4-(3-hydroxy-3-methylpiperidin-1-yl)-3-nitro-5-(1H-pyrazol-5-yl)benzamide (48c). A mixture of (S)-3-bromo-N-(4-(chlorodifluoromethoxy)phenyl)-4-(3-hydroxy-3-methylpiperidin-1-yl)-5-nitrobenzamide (48b, 100 mg, 0.187 mmol), 5-(4,4,5,5-tetramethyl-1,3,2-dioxaborolan-2-yl)-1H-pyrazole (108.86 mg, 0.561 mmol), K$_3$PO$_4$ (119.09 mg, 0.561 mmol), (Boc)$_2$O (20.41 mg, 0.094 mmol, 21.48 uL) and Pd(dppf)Cl$_2$ (27.37 mg, 0.037 mmol) in dioxane (1 mL) and H$_2$O (0.1 mL) was degassed and purged with N$_2$ 3 times The mixture was stirred at 110° C. for 16 hr under a N$_2$ atmosphere. LCMS showed the desired ms were detected. TLC (petroleum ether:ethyl acetate=1:1, $R_f$=0.45) showed a major spot was generated. The reaction mixture was concentrated under reduced pressure to remove solvent. The residue was purified by prep-TLC (SiO$_2$, petroleum ether:ethyl acetate=1:1, $R_f$=0.45) to give 48c as a yellow solid. $^1$H NMR (400 MHz, CDCl$_3$-d) δ 8.09 (d, J=2.0 Hz, 1H), 8.05 (d, J=2.2 Hz, 1H), 7.95 (br s, 1H), 7.73-7.68 (m, 3H), 7.29 (s, 1H), 6.61 (s, 1H), 3.02 (br s, 2H), 2.85 (d, J=11.5 Hz, 1H), 2.70 (br d, J=10.8 Hz, 1H), 1.75 (br d, J=15.0 Hz, 2H), 1.46 (dt, J=4.6, 13.5 Hz, 2H), 1.34 (br s, 1H), 1.25 (s, 3H).

(S)—N-(4-(chlorodifluoromethoxy)phenyl)-2-hydroxy-2-methyl-9-(1H-pyrazol-5-yl)-1,2,3,4-tetrahydrobenzo[4,5]imidazo[1,2-a]pyridine-7-carboxamide (48). To a solution of (S)—N-(4-(chlorodifluoromethoxy)phenyl)-4-(3-hydroxy-3-methylpiperidin-1-yl)-3-nitro-5-(1H-pyrazol-5-yl)benzamide (48c, 20 mg, 0.038 mol) in AcOH (1 mL) was added Fe (21.40 mg, 0.383 mmol). The mixture was stirred at 35° C. for 1 hr. LCMS showed desired ms was detected. The reaction mixture was quenched by addition of EtOAc (15 mL). To the mixture was added NaHCO$_3$ (50 mL) and the mixture was extracted with EtOAc (10 mL×3). The combined organic layers were washed with brine (15 mL), dried over Na$_2$SO$_4$, filtered and concentrated under reduced pressure to give a residue. The residue was purified by prep-HPLC (neutral condition; column: Waters Xbridge BEH C18 100*25 mm*5 um; mobile phase: [water (10 mM NH$_4$HCO$_3$)-ACN]; B %: 30%-45%, 10 min) to give 48 as a white solid. Mass calculated for [M+1]$^+$ (C$_{23}$H$_{20}$ClF$_2$N$_5$O$_3$) requires m/z 488.1, LCMS found m/z 488.1. $^1$H NMR (400 MHz, MeOD-d$_4$) δ 8.25 (br s, 1H), 7.92-7.77 (m, 3H), 7.29 (br d, J=8.9 Hz, 2H), 6.63 (br s, 1H), 3.91-3.65 (m, 2H), 3.28-3.21 (m, 1H), 3.20-3.05 (m, 1H), 2.14-1.94 (m, 2H), 1.30 (s, 3H).

Example 49

General Procedure W (1R,4R)—N-(4-(chlorodifluoromethoxy)phenyl)-4-hydroxy-1-methyl-9-(1H-pyrazol-5-yl)-1,2,3,4-tetrahydrobenzo[4,5]imidazo[1,2-a]pyridine-7-carboxamide This General Procedure W provides particular synthetic details as applied to the title compound. Additional compounds can be prepared according to this method by varying the amines and coupling reagents.

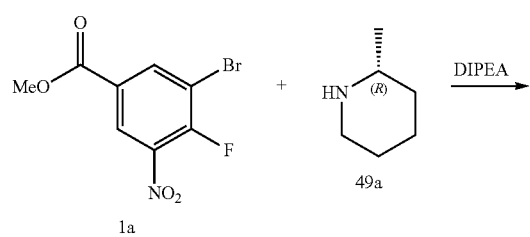
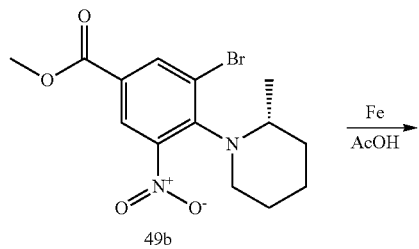
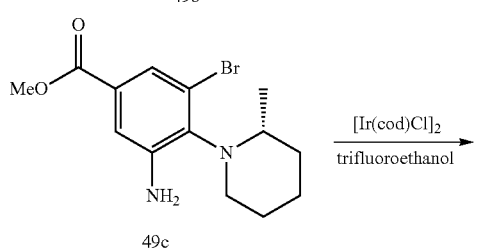
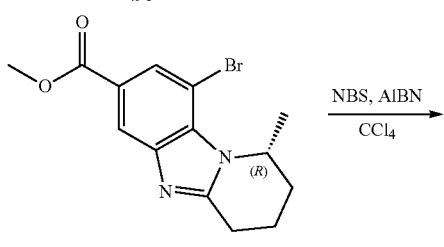
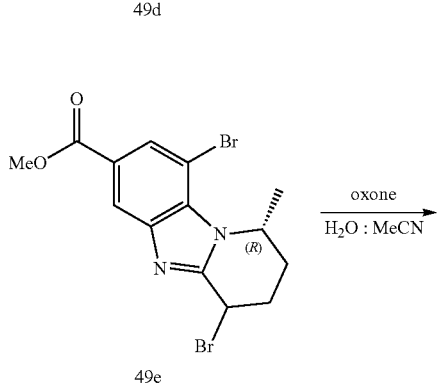
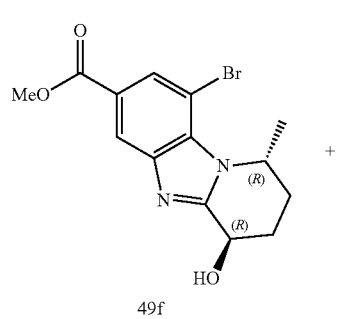
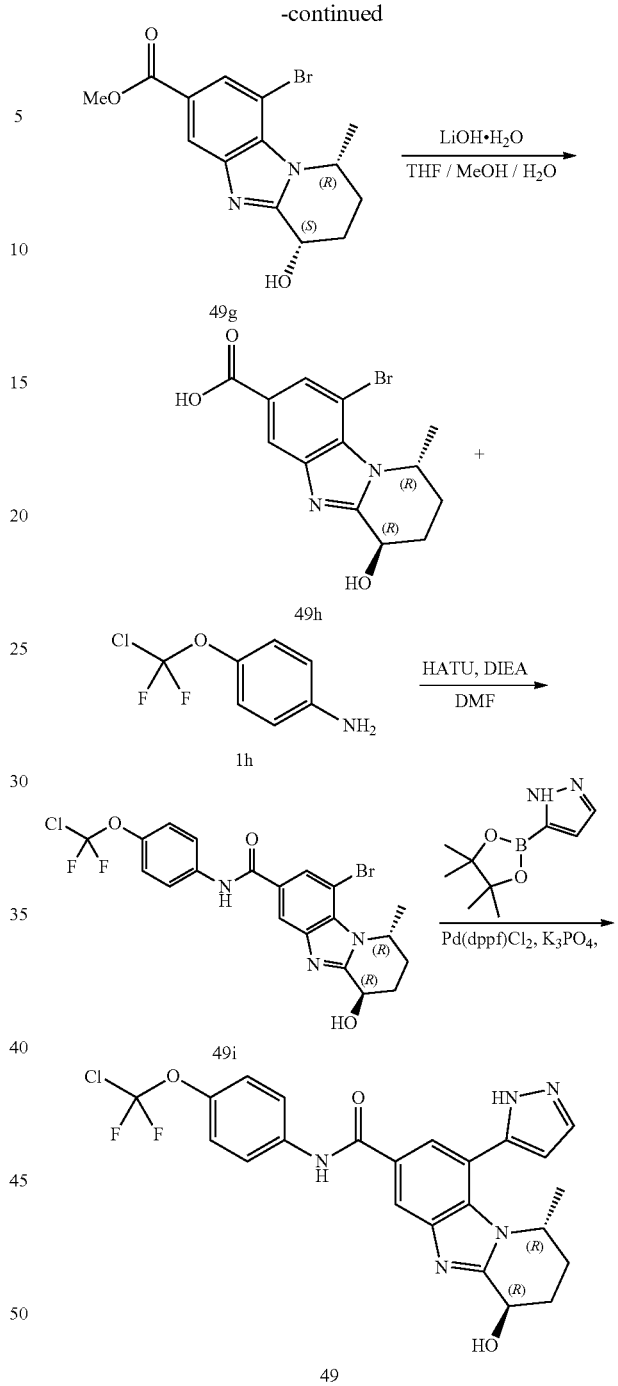

(R)-methyl 3-bromo-4-(2-methylpiperidin-1-yl)-5-nitrobenzoate (49b). To a solution of methyl 3-bromo-4-fluoro-5-nitrobenzoate (1a, 1000 mg, 3.60 mmol) in DIPEA (4.65 g, 35.97 mmol, 6.26 mL) and was added (2R)-2-methylpiperidine (49a, 713.40 mg, 7.19 mmol). The mixture was stirred at 40° C. for 16 hr. LCMS showed desired ms was detected. TLC (petroleum ether:ethyl acetate=5:1, R$_f$=0.60) showed a new major spot was generated. The reaction mixture was concentrated under reduced pressure to remove solvent. The residue was diluted with H$_2$O (5 mL) and extracted with EtOAc (5 mL×3). The combined organic layers were washed with brine (5 mL), dried over Na$_2$SO$_4$, filtered and concentrated under reduced pressure to give a residue. The residue was purified by column chromatography (SiO$_2$, petroleum ether/ethyl acetate=50/1 to 10/1) to give 49b as a white solid. $^1$H NMR (400 MHz, CDCl$_3$) δ 8.38 (br s, 1H), 8.15 (br s, 1H), 3.97-3.92 (m, 1H), 3.95 (s, 2H), 3.11 (br d, J=11.5 Hz, 2H), 1.76 (br d, J=13.1 Hz, 2H), 1.63 (br s, 1H), 1.53-1.41 (m, 1H), 1.39-1.23 (m, 1H), 0.83 (br s, 3H).

(R)-methyl 3-amino-5-bromo-4-(2-methylpiperidin-1-yl) benzoate (49c). To a solution of methyl (R)-methyl 3-bromo-4-(2-methylpiperidin-1-yl)-5-nitrobenzoate (49b, 0.78 g, 2.18 mmol) in AcOH (5 mL) was added Fe (1.22 g, 21.84 mmol). The mixture was stirred at 35° C. for 1 hr. LCMS showed desired ms was detected. The reaction mixture was filtered and concentrated under reduced pressure to give a residue. The mixture was dissolved with EtOAc and washed with NaHCO$_3$. The organic layer was concentrated under reduced pressure to give 49c as brown oil, which was used in the next step without further purification. $^1$H NMR (400 MHz, CDCl$_3$-d) δ=7.49 (d, J=1.8 Hz, 1H), 7.32 (d, J=1.8 Hz, 1H), 4.56 (br s, 2H), 3.88 (s, 3H), 3.74-3.61 (m, 1H), 3.38 (dt, J=2.4, 11.8 Hz, 1H), 2.74 (br d, J=11.7 Hz, 1H), 1.90-1.67 (m, 3H), 1.66-1.38 (m, 3H), 1.35-1.19 (m, 2H), 0.81 (d, J=6.4 Hz, 3H).

(R)-methyl 9-bromo-1-methyl-1,2,3,4-tetrahydrobenzo[4,5]imidazo[1,2-a]pyridine-7-carboxylate (49d). To a solution of methyl (R)-methyl 3-amino-5-bromo-4-(2-methylpiperidin-1-yl) benzoate (49c, 300 mg, 0.917 mmol) in 2,2,2-trifluoroethanol (2 mL) was added chloroiridium;(1Z,5Z)-cycloocta-1,5-diene (92.38 mg, 0.138 mmol). The mixture was stirred at 80° C. for 4 hr under an O$_2$ atmosphere. LCMS showed desired ms was detected. The reaction mixture was filtered and concentrated under reduced pressure to give a residue. The residue was purified by prep-HPLC (neutral condition; column: Waters Xbridge Prep OBD C18 150*40 mm*10 um; mobile phase: [water (10 mM NH$_4$HCO$_3$)-ACN]; B %: 30%-65%, 8 min) to give 49d as a brown solid. $^1$H NMR (400 MHz, CDCl$_3$-d) δ 8.29 (d, J=1.3 Hz, 1H), 8.10 (d, J=1.3 Hz, 1H), 5.45 (br t, J=6.2 Hz, 1H), 3.95 (s, 3H), 3.27 (br dd, J=5.0, 17.3 Hz, 1H), 3.01 (ddd, J=6.4, 11.2, 17.9 Hz, 1H), 2.28-2.06 (m, 3H), 2.03 (s, 1H), 1.52 (d, J=6.6 Hz, 3H).

(1R)-methyl 4,9-dibromo-1-methyl-1,2,3,4-tetrahydrobenzo[4,5]imidazo[1,2-a]pyridine-7-carboxylate (49e). To a solution of (R)-methyl 9-bromo-1-methyl-1,2,3,4-tetrahydrobenzo[4,5]imidazo[1,2-a]pyridine-7-carboxylate (49d, 30 mg, 0.093 mmol) in CCl$_4$ (1 mL) was added NBS (16.52 mg, 0.093 mmol) and AIBN (1.52 mg, 0.0093 mmol). The mixture was stirred at 50° C. for 12 hr. TLC (petroleum ether:ethyl acetate=0:1, R$_f$=0.7) showed a new spot with low polarity was formed. AIBN (5.33 mg, 0.032 mmol) and NBS (8.26 mg, 0.046 mmol) were added. The mixture was stirred at 50° C. for 12 hr. LCMS showed desired ms was detected. TLC (ethyl acetate:petroleum ether=2:1, R$_f$=0.58) showed a new spot was formed. The reaction mixture was concentrated under reduced pressure to remove solvent. The residue was purified by prep-TLC (SiO$_2$, ethyl acetate:petroleum ether=2:1, R$_f$=0.58) to give 49e as a white solid. $^1$H NMR (400 MHz, MeOD-d$_4$) δ 8.27 (d, J=1.3 Hz, 1H), 8.15 (d, J=1.3 Hz, 1H), 5.76 (br s, 1H), 5.66-5.54 (m, 1H), 3.95 (s, 3H), 2.89-2.68 (m, 2H), 2.37 (br d, J=15.4 Hz, 1H), 2.07 (br d, J=13.8 Hz, 1H), 1.66 (d, J=6.5 Hz, 1H), 1.50 (d, J=6.6 Hz, 3H).

(1R,4R)-methyl 9-bromo-4-hydroxy-1-methyl-1,2,3,4-tetrahydrobenzo[4,5]imidazo[1,2-a]pyridine-7-carboxylate (49f). (1R,4S)-methyl 9-bromo-4-hydroxy-1-methyl-1,2,3,4-tetrahydrobenzo[4,5]imidazo[1,2-a]pyridine-7-carboxylate (49g). To a solution of (1R)-methyl 4,9-dibromo-1-methyl-1,2,3,4-tetrahydrobenzo[4,5]imidazo[1,2-a]pyridine-7-carboxylate (49e, 40 mg, 0.099 mmol) in MeCN (2 mL) and H$_2$O (2 mL) was added Oxone (183.48 mg, 0.298 mmol). The mixture was stirred at 50° C. for 16 hr. LCMS showed desired ms was detected. TLC (petroleum ether:ethyl acetate=1:2 R$_f$=0.40) showed a new spot was formed. The reaction mixture was concentrated under reduced pressure to remove solvent. The residue was purified by prep-HPLC (FA condition; column: Phenomenex Luna C18 100*30 mm*5 um; mobile phase: [water (0.2% FA)-ACN]; B %: 15%-45%,10 min) to give 49f as a white solid and 49g as a white solid. (49f) $^1$H NMR (400 MHz, MeOD-d$_4$) δ 8.29 (d, J=1.3 Hz, 1H), 8.12 (d, J=1.3 Hz, 1H), 5.54-5.43 (m, 1H), 5.01 (br s, 1H), 4.61 (br s, 1H), 3.94 (s, 3H), 2.72-2.58 (m, 1H), 2.35 (tt, J=3.5, 14.4 Hz, 1H), 2.07 (br dd, J=2.6, 14.6 Hz, 1H), 1.92 (br d, J=14.6 Hz, 1H), 1.50 (d, J=6.4 Hz, 3H). (49g) $^1$H NMR (400 MHz, MeOD-d4) δ 8.28 (s, 1H), 8.09 (s, 1H), 5.48-5.37 (m, 1H), 4.93 (br s, 2H), 3.93 (s, 3H), 2.44-2.23 (m, 2H), 2.19-2.03 (m, 2H), 1.55 (d, J=6.6 Hz, 3H).

(1R,4R)-9-bromo-4-hydroxy-1-methyl-1,2,3,4-tetrahydrobenzo[4,5]imidazo[1,2-a]pyridine-7-carboxylic acid (49h). To a solution of (1R,4R)-methyl 9-bromo-4-hydroxy-1-methyl-1,2,3,4-tetrahydrobenzo[4,5]imidazo[1,2-a]pyridine-7-carboxylate (49f, 15 mg, 0.044 mmol) in MeOH (1 mL), THF (1 mL) and H$_2$O (1 mL) was added LiOH.H$_2$O (2.78 mg, 0.066 mmol). The mixture was stirred at 15° C. for 16 hr. TLC (petroleum ether:ethyl acetate=0:1) showed 49f remained and a new spot was formed. LiOH.H$_2$O (927.89 ug, 0.022 mmol) was added to the reaction mixture. The mixture was stirred at 15° C. for 16 hr. LCMS showed desired ms were detected. The mixture was adjusted to pH=4 with aqueous HCl (1M) and concentrated to give 49h as a white solid, which was used in the next step without further purification. $^1$H NMR (400 MHz, MeOD-d$_4$) δ 8.40 (d, J=1.1 Hz, 2H), 5.67 (br t, J=4.9 Hz, 1H), 5.20 (br d, J=3.2 Hz, 1H), 2.71-2.40 (m, 2H), 2.18-1.99 (m, 2H), 1.67 (d, J=6.6 Hz, 3H).

(1R,4R)-9-bromo-N-(4-(chlorodifluoromethoxy)phenyl)-4-hydroxy-1-methyl-1,2,3,4-tetrahydrobenzo[4,5]imidazo[1,2-a]pyridine-7-carboxamide (49i). To a solution of (1R,4R)-9-bromo-4-hydroxy-1-methyl-1,2,3,4-tetrahydrobenzo[4,5]imidazo[1,2-a]pyridine-7-carboxylic acid (49h, 10 mg, 0.031 mmol), 4-[chloro(difluoro)methoxy]aniline (1h, 7.14 mg, 0.037 mmol) in DMF (1 mL) was added HATU (14.03 mg, 0.037 mmol) and DIEA (11.92 mg, 0.092 mmol, 16.07 uL). The mixture was stirred at 15° C. for 5 hr. LCMS showed desired ms was detected. TLC (ethyl acetate:methanol=10:1, R$_f$=0.40) showed a new spot was formed. The reaction mixture was concentrated under reduced pressure to remove solvent. The residue was diluted with H$_2$O (10 mL) and extracted with EtAOc (10 mL×3). The combined organic layers were washed with brine, dried over Ns$_2$SO$_4$, filtered and concentrated under reduced pressure to give a residue. The residue was purified by prep-TLC (SiO$_2$, ethyl acetate:methanol=10:1) to give 49i as a white solid. $^1$H NMR (400 MHz, CDCl$_3$-d) δ 8.09 (d, J=1.3 Hz, 1H), 8.00 (d, J=1.3 Hz, 1H), 7.71 (d, J=8.9 Hz, 2H), 7.25 (s, 1H), 5.46 (br t, J=5.8 Hz, 1H), 5.18 (br s, 1H), 2.76-2.60 (m, 1H), 2.39-2.17 (m, 2H), 1.96-1.86 (m, 1H), 1.53 (d, J=6.6 Hz, 3H).

(1R,4R)—N-(4-(chlorodifluoromethoxy)phenyl)-4-hydroxy-1-methyl-9-(1H-pyrazol-5-yl)-1,2,3,4-tetrahydrobenzo[4,5]imidazo[1,2-a]pyridine-7-carboxamide (49). A mixture of (1R,4R)-9-bromo-N-(4-(chlorodifluoromethoxy) phenyl)-4-hydroxy-1-methyl-1,2,3,4-tetrahydrobenzo[4,5] imidazo[1,2-a]pyridine-7-carboxamide (48i, 8 mg, 0.016 mmol), 5-(4,4,5,5-tetramethyl-1,3,2-dioxaborolan-2-yl)-1H-pyrazole (9.30 mg, 0.048 mmol), K₃PO₄ (10.17 mg, 0.048 mmol), Pd(dppf)Cl₂ (1.17 mg, 1.60 umol) in dioxane (2 mL) and H₂O (0.2 mL) was degassed and purged with N₂ 3 times. The mixture was stirred at 120° C. for 16 hr under a N₂ atmosphere. LCMS showed desired ms was detected. The reaction mixture was concentrated under reduced pressure to remove solvent. The residue was purified by prep-HPLC (neutral condition; column: Waters Xbridge BEH C18 100*30 mm*10 um; mobile phase: [water (10 mM NH₄HCO₃)-ACN]; B %: 35%-55%, 10 min) to give 49 as a white solid. Mass calculated for [M+1]⁺ (C₂₃H₂₀ClF₂N₅O₃) requires m/z 488.1, LCMS found m/z 488.1. ¹H NMR (400 MHz, MeOD-d₄) δ 8.34 (br s, 1H), 7.94 (s, 1H), 7.85 (d, J=8.9 Hz, 3H), 7.30 (d, J=8.8 Hz, 2H), 6.69 (br s, 1H), 5.14-4.94 (m, 2H), 2.75-2.55 (m, 1H), 2.25 (br t, J=14.2 Hz, 1H), 2.04 (br d, J=11.9 Hz, 1H), 1.73 (br d, J=13.8 Hz, 1H), 0.88 (br d, J=6.2 Hz, 3H).

The compounds in the table below (Table 1) were made and can be made similarly following the procedures described above.

TABLE 1

| Example | Structure | LCMS m/z | ¹H NMR | General Procedure |
|---|---|---|---|---|
| 50 | 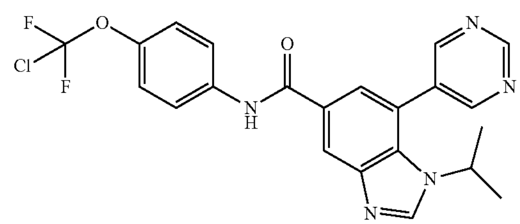 [SMILES: CC(C)n1cnc2cc(C(=O)Nc3ccc(OC(F)(F)Cl)cc3)cc(-c3cncnc3)c21] | 458.1 | ¹H NMR (400 MHz, DMSO-d₆) δ 10.44 (s, 1H), 9.34 (s, 1H), 9.10 (s, 2H), 8.65 (s, 1H), 8.52 (d, J = 1.8 Hz, 1H), 8.14 (s, 1H), 7.98-7.90 (m, 2H), 7.77 (d, J = 1.5 Hz, 1H), 7.36 (d, J = 9.0 Hz, 2H), 4.03 (quin, J = 6.7 Hz, 2H), 1.32 (s, 3H), 1.30 (s, 3H). | A |
| 51 | 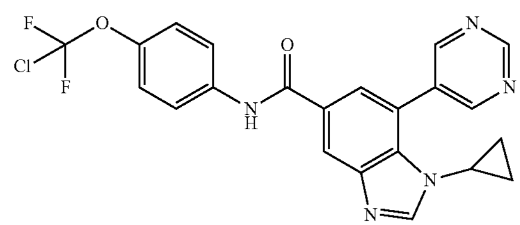 [SMILES: O=C(Nc1ccc(OC(F)(F)Cl)cc1)c1cc(-c2cncnc2)c2c(c1)ncn2C1CC1] | 456.2 | ¹H NMR (400 MHz, DMSO-d₆) δ 10.47 (s, 1H), 9.31 (s, 1H), 9.14 (s, 2H), 8.52-8.44 (m, 2H), 7.95 (d, J = 9.2 Hz, 2H), 7.88 (d, J = 1.6 Hz, 1H), 7.38 (d, J = 9.0 Hz, 2H), 3.29 (dt, J = 3.7, 7.2 Hz, 1H), 0.84-0.75 (m, 2H), 0.49-0.41 (m, 2H). | A |
| 52 | 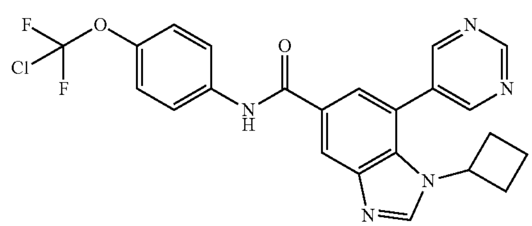 [SMILES: O=C(Nc1ccc(OC(F)(F)Cl)cc1)c1cc(-c2cncnc2)c2c(c1)ncn2C1CCC1] | 470.1 | ¹H NMR (400 MHz, CDCl₃) δ 9.38 (s, 1 H) 8.89 (br s, 2 H) 8.43 (br s, 2 H) 8.22 (br s, 1 H) 7.67-7.88 (m, 3 H) 7.29 (br s, 1 H) 4.38 (br s, 1 H) 2.16-2.37 (m, 2 H) 1.99 (br d, J = 7.0 Hz, 2 H) 1.82 (br d, J = 9.9 Hz, 1 H) 1.63-1.72 (m, 1 H). | A |
| 53 | 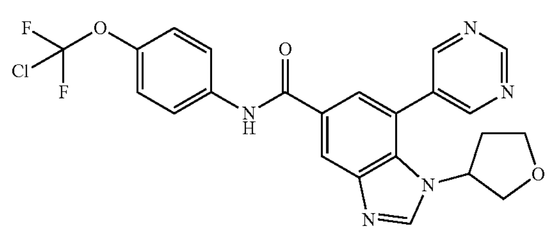 | 486.1 | ¹H NMR (400 MHz, MeOD-d₄) δ 9.35 (s, 1H), 9.07 (s, 2H), 8.88 (s, 1H), 8.50 (d, J = 1.6 Hz, 1H), 7.96 (d, J = 1.6 Hz, 1H), 7.90-7.80 (m, 2H), 7.31 (d, J = 9.0 Hz, 2H), 4.71-4.62 (m, 1H), 4.24-4.08 (m, 2H), 3.86-3.76 (m, 1H), 3.67 (dd, J = 4.8, 10.6 Hz, 1H), 2.28-2.16 (m, 2H). | A |
| 54 | 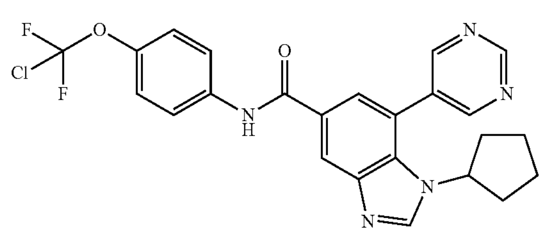 [SMILES: O=C(Nc1ccc(OC(F)(F)Cl)cc1)c1cc(-c2cncnc2)c2c(c1)ncn2C1CCCC1] | 484.1 | ¹H NMR (400 MHz, DMSO-d₆) δ 10.45 (s, 1H), 9.33 (s, 1H), 9.09 (s, 2H), 8.61 (s, 1H), 8.51 (d, J = 1.5 Hz, 1H), 7.93 (d, J = 8.1 Hz, 2H), 7.80 (d, J = 1.3 Hz, 1H), 7.36 (d, J = 8.8 Hz, 2H), 4.22 (quin, J = 6.4 Hz, 1H), 1.86-1.64 (m, 6H), 1.64-1.37 (m, 2H). | A |

TABLE 1-continued

| Example | Structure | LCMS m/z | ¹H NMR | General Procedure |
|---|---|---|---|---|
| 55 | 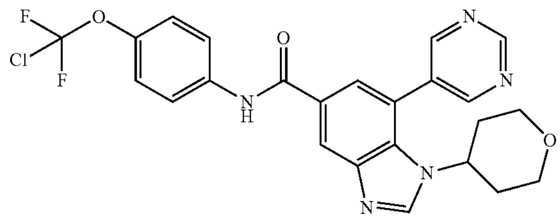 [SMILES: O=C(Nc1ccc(OC(F)(F)Cl)cc1)c1cc(-c2cncnc2)c2c(c1)ncn2C1CCOCC1] | 500.1 | ¹H NMR (400 MHz, DMSO-$d_6$) δ 10.48 (s, 1H), 9.39 (s, 1H), 9.13 (s, 2H), 8.78 (s, 1H), 8.54 (d, J = 1.5 Hz, 1H), 7.94 (d, J = 9.3 Hz, 2H), 7.85 (d, J = 1.5 Hz, 1H), 7.37 (br d, J = 9.0 Hz, 2H), 3.87 (br dd, J = 3.7, 11.2 Hz, 2H), 3.90-3.84 (m, 1H), 2.81 (br t, J = 11.4 Hz, 2H), 2.06-1.93 (m, 2H), 1.80 (br d, J = 14.1 Hz, 2H). | A |
| 56 | 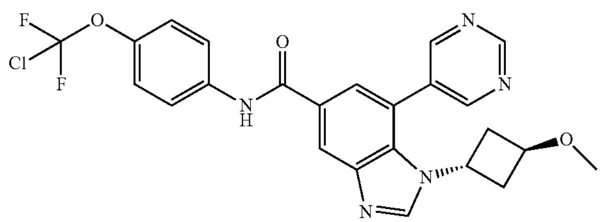 [SMILES: CO[C@H]1C[C@H](n2cnc3cc(C(=O)Nc4ccc(OC(F)(F)Cl)cc4)cc(-c4cncnc4)c32)C1] | 500.1 | ¹H NMR (400 MHz, CDCl$_3$-d) δ 9.37 (s, 1H), 8.86 (s, 2H), 8.45 (br s, 2H), 8.19 (s, 1H), 7.71-7.86 (m, 3H), 7.29 (br s, 1H), 7.27 (s, 1H), 4.51-4.64 (m, 1H), 3.94-4.07 (m, 1H), 3.16 (s, 3H), 2.44 (dt, J = 13.18, 6.53 Hz, 2H), 2.04-2.20 (m, 2H). | A |
| 57 | 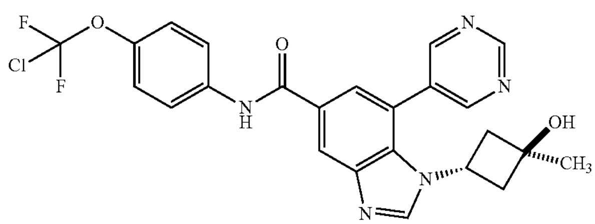 [SMILES: C[C@]1(O)C[C@H](n2cnc3cc(C(=O)Nc4ccc(OC(F)(F)Cl)cc4)cc(-c4cncnc4)c32)C1] | 500.1 | ¹H NMR (400 MHz, DMSO-$d_6$) δ 10.45 (s, 1 H) 9.35 (s, 1H) 9.06 (s, 2 H) 8.63 (s, 1H) 8.51 (d, J = 1.8 Hz, 1 H) 7.94 (d, J = 9.3 Hz, 2 H) 7.81 (d, J = 1.5 Hz, 1 H) 7.36 (d, J = 9.0 Hz, 2 H) 4.85 (s, 1H) 4.61 (t, J = 7.7 Hz, 1 H) 2.21-2.36 (m, 2 H) 1.77-1.88 (m, 2 H) 1.15 (s, 3 H). | A |
| 58 | 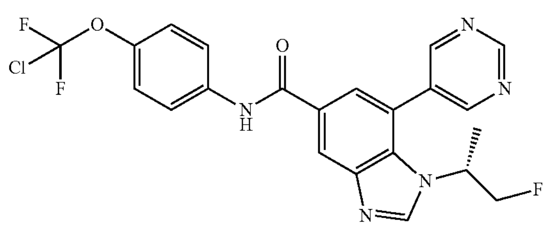 [SMILES: C[C@H](CF)n1cnc2cc(C(=O)Nc3ccc(OC(F)(F)Cl)cc3)cc(-c3cncnc3)c21] | 476.1 | ¹H NMR (400 MHz, MeOD-$d_4$) δ 9.33 (s, 1H), 9.04 (s, 2H), 8.64 (s, 1H), 8.49 (d, J = 1.6 Hz, 1H), 7.91-7.80 (m, 3H), 7.31 (d, J = 8.9 Hz, 2H), 4.63 (d, J = 5.3 Hz, 1H), 4.51 (d, J = 5.1 Hz, 1H), 4.45-4.30 (m, 1H), 1.51 (d, J = 6.2 Hz, 3H). | A |
| 59 | 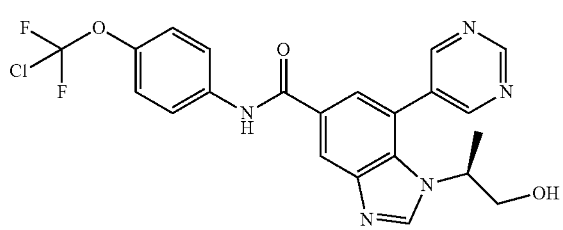 [SMILES: C[C@@H](CO)n1cnc2cc(C(=O)Nc3ccc(OC(F)(F)Cl)cc3)cc(-c3cncnc3)c21] | 474.1 | ¹H NMR (400 MHz, DMSO-$d_6$) δ 9.36 (s, 1H), 9.07 (s, 2H), 8.95 (s, 1H), 8.53 (d, J = 1.3 Hz, 1H), 7.93 (d, J = 9.0 Hz, 2H), 7.86 (d, J = 1.3 Hz, 1H), 7.37 (d, J = 9.0 Hz, 2H), 4.08-4.01 (m, 1H), 3.60-3.47 (m, 2H), 1.35 (d, J = 6.8 Hz, 3H). | A |
| 60 | 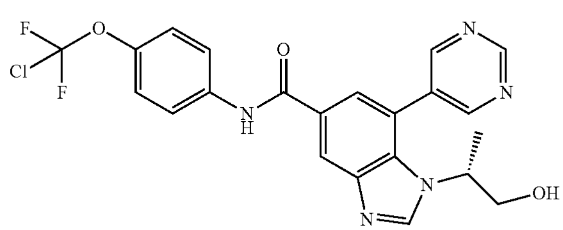 [SMILES: C[C@H](CO)n1cnc2cc(C(=O)Nc3ccc(OC(F)(F)Cl)cc3)cc(-c3cncnc3)c21] | 474.0 | ¹H NMR (400 MHz, DMSO-$d_6$) δ 10.46 (s, 1H), 9.34 (s, 1H), 9.06 (s, 2H), 8.67 (s, 1H), 8.52 (d, J = 1.3 Hz, 1H), 7.94 (d, J = 9.0 Hz, 2H), 7.78 (d, J = 1.1 Hz, 1H), 7.37 (d, J = 9.0 Hz, 2H), 4.07-3.91 (m, 1H), 3.61-3.51 (m, 2H), 1.32 (d, J = 6.8 Hz, 3H). | A |

TABLE 1-continued

| Example | Structure | LCMS m/z | ¹H NMR | General Procedure |
|---|---|---|---|---|
| 61 | 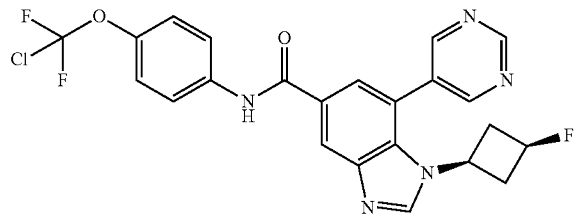 [SMILES: O=C(Nc1ccc(OC(F)(F)Cl)cc1)c1cc(-c2cncnc2)c2c(c1)ncn2[C@H]1C[C@@H](F)C1] | 488.1 | ¹H NMR (400 MHz, DMSO-d$_6$) 10.46 (s, 1H), 9.35 (s, 1H), 9.05 (s, 2H), 8.75 (s, 1H), 8.51 (d, J = 1.5 Hz, 1H), 7.93 (d, J = 9.0 Hz, 2H), 7.81 (d, J = 1.5 Hz, 1H), 7.36 (d, J = 9.0 Hz, 2H), 4.89-4.61 (m, 1H), 4.04 (quin, J = 8.0 Hz, 1H), 2.59 (ddd, J = 3.3, 9.2, 15.3 Hz, 2H), 2.40-2.31 (m, 2H). | A |
| 62 | 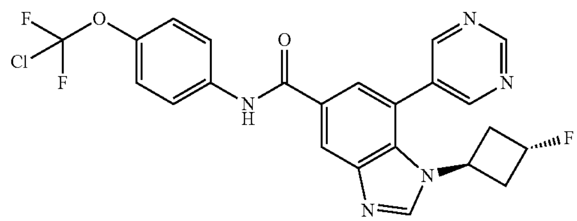 [SMILES: O=C(Nc1ccc(OC(F)(F)Cl)cc1)c1cc(-c2cncnc2)c2c(c1)ncn2[C@H]1C[C@H](F)C1] | 488.1 | ¹H NMR (400 MHz, DMSO-d$_6$) δ 10.48 (s, 1H), 9.37 (s, 1H), 9.07 (s, 2H), 8.80 (s, 1H), 8.53 (d, J = 1.1 Hz, 1H), 7.94 (d, J = 9.0 Hz, 2H), 7.86 (s, 1H), 7.37 (d, J = 8.8 Hz, 2H), 5.34-5.10 (m, 1H), 4.74 (quin, J = 7.2 Hz, 1H), 2.87-2.71 (m, 2H), 2.23-2.07 (m, 2H). | A |
| 63 | 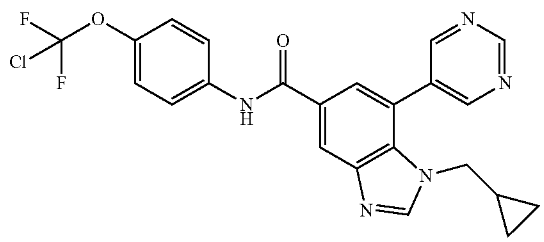 [SMILES: O=C(Nc1ccc(OC(F)(F)Cl)cc1)c1cc(-c2cncnc2)c2c(c1)ncn2CC1CC1] | 470.0 | ¹H NMR (400 MHz, DMSO-d$_6$) δ 10.47 (br s, 1H), 9.36 (s, 1H), 9.13 (s, 2H), 8.53 (d, J = 1.5 Hz, 1H), 8.51 (s, 1H), 7.91-7.97 (m, 2H), 7.83 (d, J = 1.5 Hz, 1H), 7.37 (d, J = 9.0 Hz, 2H), 3.75 (d, J = 7.1 Hz, 2H), 0.63-0.74 (m, 1H), 0.30-0.39 (m, 2H), 0.12-0.22 (m, 2H). | A |
| 64 | 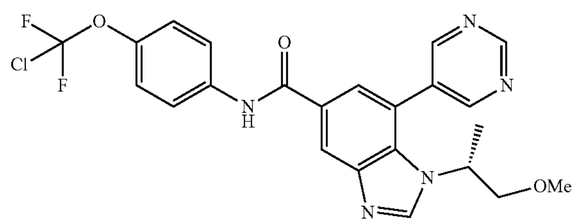 [SMILES: COC[C@@H](C)n1cnc2cc(C(=O)Nc3ccc(OC(F)(F)Cl)cc3)cc(-c3cncnc3)c21] | 488.2 | ¹H NMR (400 MHz, DMSO-d$_6$) δ 10.50 (s, 1H), 9.35 (s, 1H), 9.08 (br s, 2H), 8.85 (s, 1H), 8.53 (d, 1.3 Hz, 1H), 7.93 (d, J = 9.0 Hz, 2H), 7.83 (d, J = 1.5 Hz, 1H), 7.37 (br d, J = 8.9 Hz, 2H), 4.19-4.07 (m, 1H), 3.59-3.40 (m, 2H), 3.06 (s, 3H), 1.38 (d, J = 6.8 Hz, 3H). | A |
| 65 | 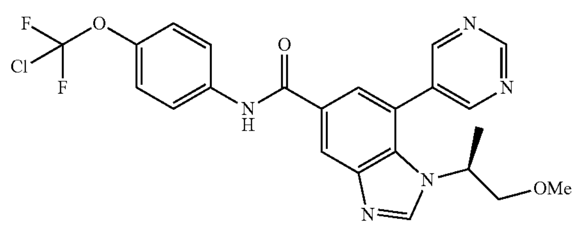 [SMILES: COC[C@H](C)n1cnc2cc(C(=O)Nc3ccc(OC(F)(F)Cl)cc3)cc(-c3cncnc3)c21] | 488.1 | ¹H NMR (400 MHz, MeOD-d$_4$) δ 9.42 (s, 1H), 9.14 (br s, 1H), 9.13 (s, 2H), 8.59 (d, J = 1.5 Hz, 1H), 8.02 (d, J = 1.5 Hz, 1H), 7.93 (d, J = 9.0 Hz, 2H), 7.39 (d, J = 8.9 Hz, 2H), 4.45-4.36 (m, 1H), 3.65-3.61 (m, 2H), 3.41-3.40 (m, 1H), 3.40 (s, 2H), 1.57 (d, J = 6.8 Hz, 3H). | A |
| 66 | 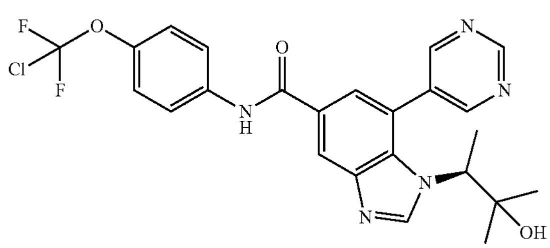 [SMILES: C[C@H](n1cnc2cc(C(=O)Nc3ccc(OC(F)(F)Cl)cc3)cc(-c3cncnc3)c21)C(C)(C)O] | 502.1 | ¹H NMR (400 MHz, DMSO-d$_6$) δ 10.43 (s, 1H), 9.33 (s, 1H), 9.04 (s, 2H), 8.53 (s, 1H), 8.50 (d, J = 1.5 Hz, 1H), 7.92 (d, J = 9.0 Hz, 2H), 7.75 (d, J = 1.5 Hz, 1H), 7.35 (d, J = 8.8 Hz, 2H), 4.84 (s, 1H), 3.73 (q, J = 7.0 Hz, 1H), 1.45 (d, J = 7.1 Hz, 3H), 0.84 (s, 3H), 0.55 (s, 3H). | A |

TABLE 1-continued

| Example | Structure | LCMS m/z | ¹H NMR | General Procedure |
|---|---|---|---|---|
| 67 | 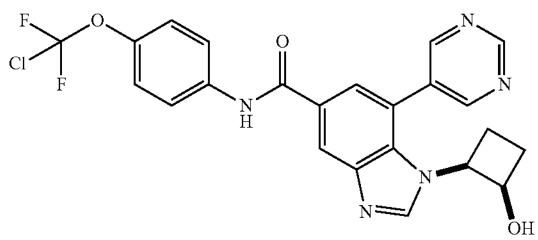 | 486.1 | ¹H NMR (400 MHz, DMSO-d$_6$) δ 10.44 (s, 1 H) 9.33 (s, 1 H) 9.00 (br s, 2 H) 8.63 (s, 1H) 8.50 (d, J = 1.8 Hz, 1 H) 7.88-8.02 (m, 2 H) 7.76 (d, J = 1.5 Hz, 1 H) 7.36 (d, J = 9.0 Hz, 2 H) 5.23 (d, J = 5.1 Hz, 1 H) 4.24-4.45 (m, 1 H) 3.69 (br s, 1 H) 2.68-2.79 (m, 1 H) 2.20 (ddd, J = 11.5, 5.5, 3.1 Hz, 1 H) 1.95 (br dd, J = 12.1, 6.4 Hz, 1 H) 1.69-1.82 (m, 1 H). | A |
| 68 | 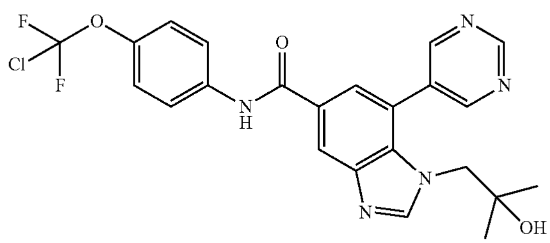 [SMILES: CC(C)(O)Cn1cnc2cc(C(=O)Nc3ccc(OC(F)(F)Cl)cc3)cc(-c3cncnc3)c21] | 488.0 | ¹H NMR (400 MHz, MeOD-d$_4$) δ 9.30 (s, 1H), 8.99 (s, 2H), 8.69 (s, 1H), 8.49 (s, 1H), 7.91 (s, 1H), 7.84 (d, J = 9.0 Hz, 2H), 7.30 (br d, J = 8.8 Hz, 2H), 3.99 (s, 2H), 0.89 (s, 6H). | A |
| 69 | 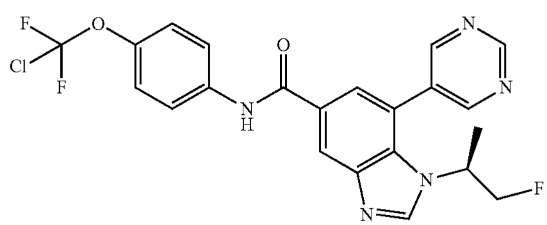 [SMILES: C[C@@H](CF)n1cnc2cc(C(=O)Nc3ccc(OC(F)(F)Cl)cc3)cc(-c3cncnc3)c21] | 476.1 | ¹H NMR (400 MHz, DMSO-d$_6$) δ 10.46 (s, 1 H) 9.35 (s, 1 H) 9.06 (br s, 2 H) 8.69 (s, 1 H) 8.54 (d, J = 1.8 Hz, 1 H) 7.94 (d, J = 9.0 Hz, 2 H) 7.79 (d, J = 1.5 Hz, 1 H) 7.37 (d, J = 8.8 Hz, 2 H) 4.57-4.68 (m, 1 H) 4.45-4.56 (m, 1 H) 4.15-4.29 (m, 1 H) 1.42 (d, J = 6.6 Hz, 3 H). | A |
| 70 | 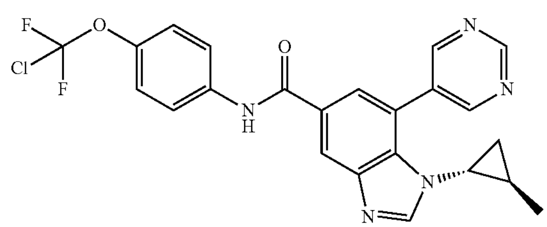 [SMILES: C[C@@H]1C[C@H]1n1cnc2cc(C(=O)Nc3ccc(OC(F)(F)Cl)cc3)cc(-c3cncnc3)c21] | 470.1 | ¹H NMR (400 MHz, MeOD-d$_4$) δ 9.28 (s, 1H), 9.12 (s, 2H), 8.42 (d, J = 1.5 Hz, 1H), 8.40 (s, 1H), 7.89 (d, J = 1.5 Hz, 1H), 7.86-7.82 (m, 2H), 7.30 (d, J = 9.0 Hz, 2H), 3.06 (td, J = 3.5, 6.9 Hz, 1H), 1.18 (tdd, J = 3.2, 6.3, 9.4 Hz, 1H), 1.02 (ddd, J = 3.7, 5.8, 9.6 Hz, 1H), 0.64 (d, J = 6.0 Hz, 3H), 0.39 (q, J = 6.2 Hz, 1H). | A |
| 71 | 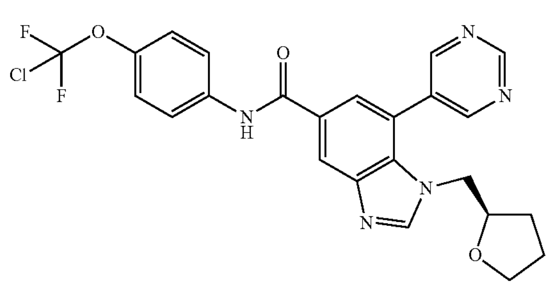 [SMILES: O=C(Nc1ccc(OC(F)(F)Cl)cc1)c1cc(-c2cncnc2)c2c(c1)ncn2C[C@H]1CCCO1] | 500.1 | ¹H NMR (400 MHz, DMSO-d$_6$) δ 10.47 (s, 1H), 9.35 (s, 1H), 9.08 (s, 2H), 8.52 (d, J = 1.6 Hz, 1H), 8.47 (s, 1H), 7.96 (s, 1H), 7.93 (s, 1H), 7.83 (d, J = 1.6 Hz, 1H), 7.37 (d, J = 8.8 Hz, 2H), 4.02-3.96 (m, 1H), 3.93 (d, J = 7.7 Hz, 1H), 3.65 (br s, 1H), 3.57-3.51 (m, 2H), 1.64 (s, 1H), 1.59-1.47 (m, 2H), 1.21 (br d, J = 6.6 Hz, 1H). | A |

TABLE 1-continued

| Example | Structure | LCMS m/z | ¹H NMR | General Procedure |
|---|---|---|---|---|
| 72 | 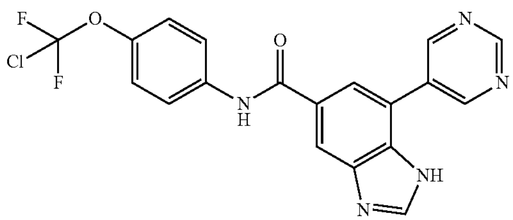 [SMILES: O=C(Nc1ccc(OC(F)(F)Cl)cc1)c1cc(-c2cncnc2)c2[nH]cnc2c1] | 416.0 | ¹H NMR (400 MHz, MeOD-d₄) δ 9.35-9.27 (m, 3H), 9.08 (s, 1H), 8.45 (d, J = 1.3 Hz, 1H), 8.25 (d, J = 1.3 Hz, 1H), 7.87 (d, J = 9.0 Hz, 2H), 7.33 (d, J = 9.0 Hz, 2H). | A |
| 73 | 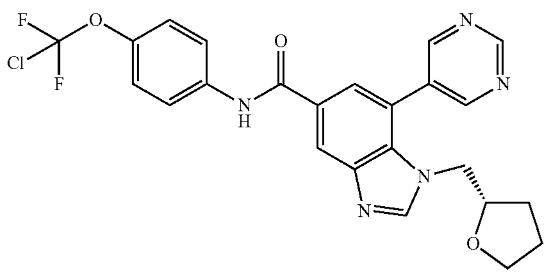 [SMILES: O=C(Nc1ccc(OC(F)(F)Cl)cc1)c1cc(-c2cncnc2)c2c(c1)ncn2C[C@@H]1CCCO1] | 500.1 | ¹H NMR (400 MHz, MeOD-d₄) δ 9.29 (s, 1H), 9.01 (s, 2H), 8.45 (d, J = 1.5 Hz, 1H), 8.38 (s, 1H), 7.86-7.81 (m, 3H), 7.29 (d, J = 9.0 Hz, 2H), 4.07 (dd, J = 3.1, 14.8 Hz, 1H), 3.94 (dd, J = 8.2, 14.8 Hz, 1H), 3.82-3.76 (m, 1H), 3.67-3.54 (m, 2H), 1.79-1.60 (m, 3H), 1.32-1.23 (m, 1H). | A |
| 74 | 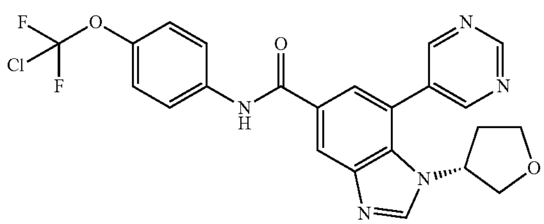 [SMILES: O=C(Nc1ccc(OC(F)(F)Cl)cc1)c1cc(-c2cncnc2)c2c(c1)ncn2[C@@H]1CCOC1] | 486.0 | ¹H NMR (400 MHz, DMSO-d₆) δ 10.48 (s, 1H), 9.35 (s, 1H), 9.09 (s, 2H), 8.53 (s, 2H), 7.94 (d, J = 9.0 Hz, 2H), 7.83 (d, J = 1.3 Hz, 1H), 7.37 (d, J = 8.8 Hz, 2H), 4.53 (br s, 1H), 4.08-3.93 (m, 2H), 3.54 (s, 2H), 2.22-1.94 (m, 2H). | A |
| 75 | 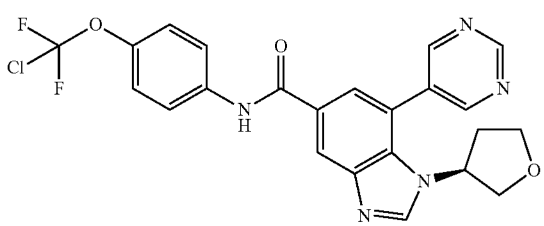 [SMILES: O=C(Nc1ccc(OC(F)(F)Cl)cc1)c1cc(-c2cncnc2)c2c(c1)ncn2[C@H]1CCOC1] | 486.0 | ¹H NMR (400 MHz, DMSO-d₆) δ = 10.47 (s, 1H), 9.35 (s, 1H), 9.08 (s, 2H), 8.56-8.46 (m, 2H), 7.97-7.91 (m, 2H), 7.81 (d, J = 1.5 Hz, 1H), 7.36 (d, J = 8.8 Hz, 2H), 4.52 (br s, 1H), 4.03-3.95 (m, 2H), 3.68 (dt, J = 5.4, 8.8 Hz, 2H), 2.19-2.07 (m, 2H). | A |
| 76 | 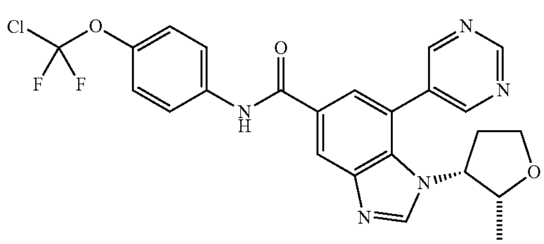 [SMILES: C[C@H]1OCC[C@H]1n1cnc2cc(C(=O)Nc3ccc(OC(F)(F)Cl)cc3)cc(-c3cncnc3)c21] | 500.1 | ¹H NMR (400 MHz, MeOD-d₄) δ 9.25-9.42 (m, 1 H) 9.04 (s, 2 H) 8.48 (d, J = 1.7 Hz, 1 H) 8.36 (s, 1 H) 7.77-7.94 (m, 3 H) 7.30 (d, J = 9.0 Hz, 2 H) 4.50-4.56 (m, 1 H) 4.20-4.31 (m, 1 H) 3.71-3.81 (m, 1 H) 3.65 (dd, J = 6.2, 4.4 Hz, 1 H) 2.54-2.67 (m, 1 H) 2.36-2.49 (m, 1 H) 0.67 (d, J = 6.2 Hz, 3 H). | A |
| 77 | 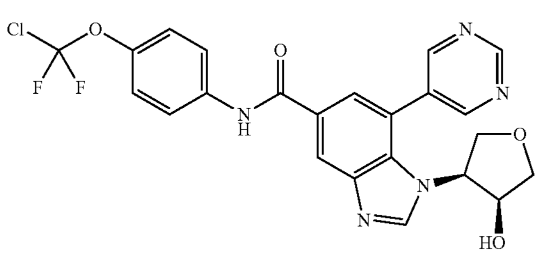 [SMILES: O=C(Nc1ccc(OC(F)(F)Cl)cc1)c1cc(-c2cncnc2)c2c(c1)ncn2[C@H]1COC[C@H]1O] | 502.1 | ¹H NMR (400 MHz, MeOD-d₄) δ 9.32 (s, 1H), 9.06 (s, 2H), 8.49 (s, 1H), 8.47 (d, J = 1.5 Hz, 1H), 7.90-7.79 (m, 3H), 7.30 (d, J = 9.0 Hz, 2H), 4.54-4.47 (m, 1H), 4.26-4.19 (m, 2H), 3.98 (dd, J = 6.5, 10.0 Hz, 1H), 3.89 (dd, J = 6.0, 9.9 Hz, 1H), 3.76 (dd, J = 3.5, 9.7 Hz, 1H). | A |

TABLE 1-continued

| Example | Structure | LCMS m/z | ¹H NMR | General Procedure |
|---|---|---|---|---|
| 78 | 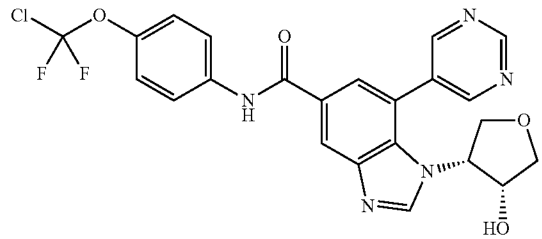 [SMILES: O=C(Nc1ccc(OC(F)(F)Cl)cc1)c1cc(-c2cncnc2)c2c(c1)ncn2[C@@H]1COC[C@@H]1O] | 502.1 | ¹H NMR (400 MHz, MeOD-d$_4$) δ 9.31 (s, 1H), 9.06 (s, 2H), 8.49 (s, 1H), 8.47 (d, J = 1.8 Hz, 1H), 7.88-7.81 (m, 3H), 7.30 (d, J = 9.0 Hz, 2H), 4.53-4.46 (m, 1H), 4.26-4.18 (m, 2H), 3.98 (dd, J = 6.6, 10.1 Hz, 1H), 3.89 (dd, J = 5.7, 9.9 Hz, 1H), 3.76 (dd, J = 3.6, 9.8 Hz, 1H). | A |
| 79 | 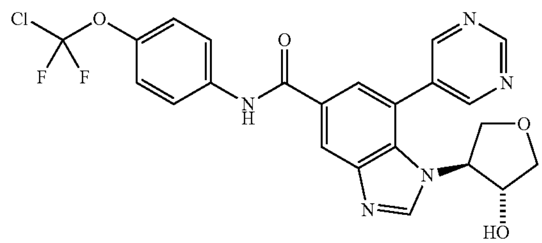 [SMILES: O=C(Nc1ccc(OC(F)(F)Cl)cc1)c1cc(-c2cncnc2)c2c(c1)ncn2[C@H]1COC[C@@H]1O] | 502.0 | ¹H NMR (400 MHz, MeOD-d$_4$) δ 9.31 (s, 1H), 9.05 (s, 2H), 8.47 (d, J = 1.6 Hz, 1H), 8.39 (s, 1H), 7.88-7.83 (m, 3H), 7.30 (d, J = 8.9 Hz, 2H), 4.36 (br d, J = 5.1 Hz, 1H), 4.26 (br d, J = 9.0 Hz, 2H), 4.14 (dd, J = 5.2, 10.2 Hz, 1H), 4.04 (dd, J = 5.2, 10.7 Hz, 1H), 3.61 (dd, J = 2.6, 10.2 Hz, 1H). | A |
| 80 | 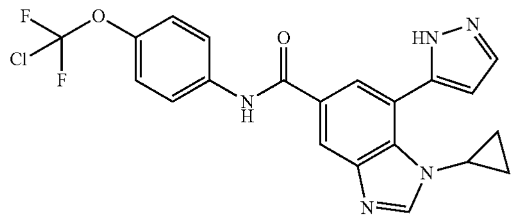 [SMILES: O=C(Nc1ccc(OC(F)(F)Cl)cc1)c1cc(-c2ccn[nH]2)c2c(c1)ncn2C1CC1] | 444.0 | ¹H NMR (400 MHz, MeOD-d$_4$) δ 8.33 (br d, J = 6.2 Hz, 2H), 7.95 (d, J = 1.3 Hz, 1H), 7.84 (br d, J = 9.0 Hz, 3H), 7.31-7.27 (m, 2H), 6.67 (br s, 1H), 3.47 (br s, 1H), 0.78 (br s, 2H), 0.63 (br s, 2H). | B |
| 81 | 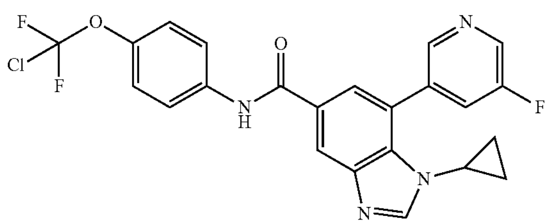 [SMILES: O=C(Nc1ccc(OC(F)(F)Cl)cc1)c1cc(-c2cncc(F)c2)c2c(c1)ncn2C1CC1] | 473.1 | ¹H NMR (400 MHz, DMSO-d$_6$) δ 10.45 (s, 1H), 8.75-8.66 (m, 2H), 8.47 (d, J = 1.3 Hz, 1H), 8.42 (s, 1H), 8.10 (br d, J = 9.0 Hz, 1H), 7.94 (d, J = 9.0 Hz, 2H), 7.84 (d, J = 1.3 Hz, 1H), 7.36 (br d, J = 8.8 Hz, 2H), 3.24 (td, J = 3.4, 6.9 Hz, 1H), 0.75 (br s, 2H), 0.43 (br d, J = 6.4 Hz, 2H). | B |
| 82 | 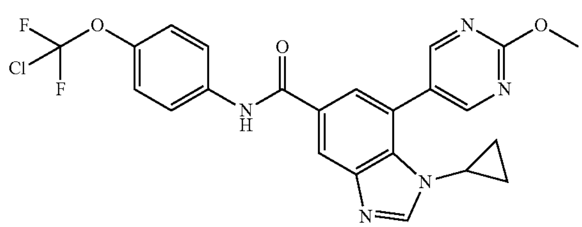 [SMILES: COc1ncc(-c2cc(C(=O)Nc3ccc(OC(F)(F)Cl)cc3)cc3ncn(C4CC4)c23)cn1] | 486.2 | ¹H NMR (400 MHz, MeOD-d$_4$) δ 8.92 (s, 1H), 8.86 (s, 2H), 8.43 (d, J = 1.1 Hz, 1H), 7.99 (d, J = 1.1 Hz, 1H), 7.84 (d, J = 9.0 Hz, 2H), 7.30 (d, J = 8.8 Hz, 2H), 4.11 (s, 3H), 3.39 (tt, J = 3.7, 7.0 Hz, 1H), 1.01-0.92 (m, 2H), 0.77-0.68 (m, 2H). | B |
| 83 | 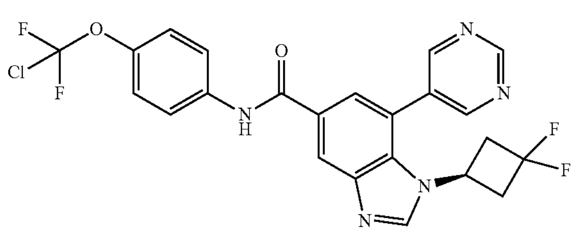 | 506.2 | ¹H NMR (400 MHz, CDCl$_3$-d) δ 9.42 (s, 1H), 8.90 (s, 2H), 8.40 (s, 1H), 8.29 (s, 1H), 7.99 (s, 1H), 7.84 (s, 1H), 7.74 (d, J = 8.8 Hz, 2H), 7.31 (br s, 2H), 4.42 (br s, 1H), 2.99-2.68 (m, B4H). | B |

TABLE 1-continued

| Example | Structure | LCMS m/z | ¹H NMR | General Procedure |
|---|---|---|---|---|
| 84 | 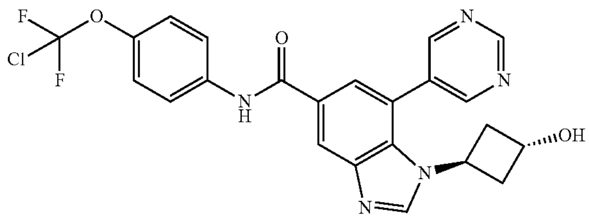 [SMILES: O=C(Nc1ccc(OC(F)(F)Cl)cc1)c1cc(-c2cncnc2)c2c(c1)ncn2[C@H]1C[C@H](O)C1] | 486.0 | ¹H NMR (400 MHz, MeOD-d₄) δ 9.35 (s, 1H), 9.13 (s, 1H), 9.04 (s, 2H), 8.49 (d, J = 1.3 Hz, 1H), 7.98 (d, J = 1.3 Hz, 1H), 7.84 (d, J = 9.0 Hz, 2H), 7.30 (d, J = 8.8 Hz, 2H), 4.78 (quin, J = 7.0 Hz, 1H), 4.43-4.33 (m, 1H), 2.76-2.60 (m, 2H), 2.07-1.93 (m, 2H). | B |
| 85 | 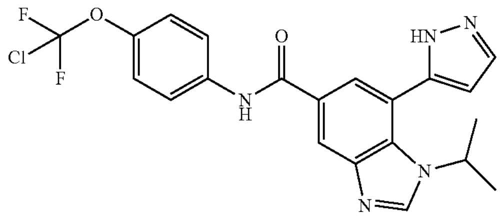 [SMILES: CC(C)n1cnc2cc(C(=O)Nc3ccc(OC(F)(F)Cl)cc3)cc(-c3ccn[nH]3)c21] | 446.1 | ¹H NMR (400 MHz, MeOD-d₄) δ 8.52 (br s, 1H), 8.38 (br s, 1H), 7.91 (s, 1H), 7.84 (br d, J = 8.9 Hz, 3H), 7.29 (br d, J = 8.6 Hz, 2H), 6.65 (br s, 1H), 4.79-4.66 (m, 1H), 1.39 (br d, J = 6.4 Hz, 6H). | B |
| 86 | 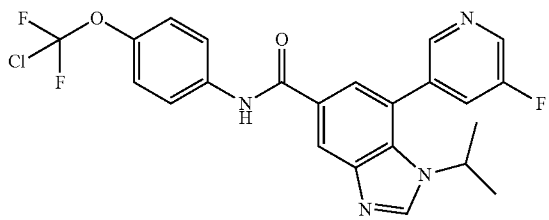 [SMILES: CC(C)n1cnc2cc(C(=O)Nc3ccc(OC(F)(F)Cl)cc3)cc(-c3cncc(F)c3)c21] | 475.1 | ¹H NMR (400 MHz, DMSO-d₆) δ 10.45 (s, 1H), 8.76 (d, J = 2.7 Hz, 1H), 8.68 (d, J = 11.1 Hz, 2H), 8.51 (d, J = 1.5 Hz, 1H), 8.12 (br d, J = 9.8 Hz, 1H), 7.95 (d, J = 9.0 Hz, 2H), 7.77 (s, 1H), 7.37 (d, J = 9.0 Hz, 2H), 4.12-4.03 (m, 1H), 1.32 (d, J = 6.7 Hz, 6H). | B |
| 87 | 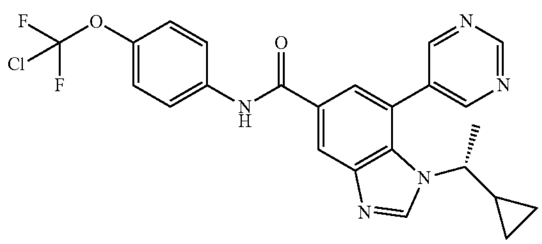 [SMILES: C[C@H](C1CC1)n1cnc2cc(C(=O)Nc3ccc(OC(F)(F)Cl)cc3)cc(-c3cncnc3)c21] | 484.2 | ¹H NMR (400 MHz, DMSO-d₆) δ 10.76 (s, 1H), 9.61 (br s, 1H), 9.32 (s, 1H), 9.09 (s, 2H), 8.56 (s, 1H), 7.99 (s, 1H), 7.91 (br d, J = 8.8 Hz, 2H), 7.32 (br d, J = 8.6 Hz, 2H), 3.32 (br t, J = 7.4 Hz, 1H), 1.38 (br s, 1H), 1.21 (br d, J = 6.6 Hz, 3H), 0.56 (br s, 1H), 0.41 (br s, 1H), 0.20-0.12 (m, 1H), 0.01 (br d, J = 4.0 Hz, 1H). | B |
| 88 | 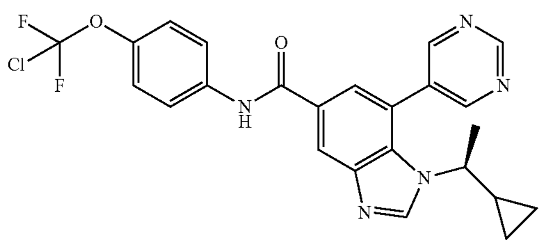 [SMILES: C[C@@H](C1CC1)n1cnc2cc(C(=O)Nc3ccc(OC(F)(F)Cl)cc3)cc(-c3cncnc3)c21] | 484.1 | ¹H NMR (400 MHz, DMSO-d₆) δ 10.76 (s, 1H), 9.61 (br s, 1H), 9.32 (s, 1H), 9.09 (s, 2H), 8.56 (s, 1H), 7.99 (s, 1H), 7.91 (br d, J = 8.8 Hz, 2H), 7.32 (br d, J = 8.6 Hz, 2H), 3.32 (br t, J = 7.4 Hz, 1H), 1.38 (br s, 1H), 1.21 (br d, J = 6.6 Hz, 3H), 0.56 (br s, 1H), 0.41 (br s, 1H), 0.20-0.12 (m, 1H), 0.01 (br d, J = 4.0 Hz, 1H). | B |
| 89 | 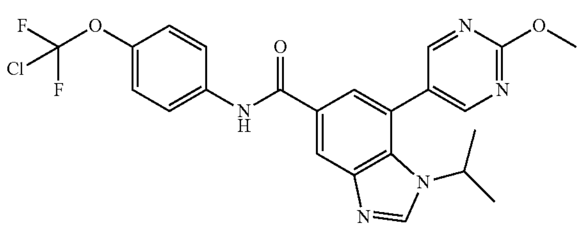 [SMILES: COc1ncc(-c2cc(C(=O)Nc3ccc(OC(F)(F)Cl)cc3)cc3ncn(C(C)C)c23)cn1] | 488.1 | ¹H NMR (400 MHz, MeOD-d₄) δ 8.82 (s, 2H), 8.60 (s, 1H), 8.44 (s, 1H), 7.86 (d, J = 8.9 Hz, 2H), 7.80 (s, 1H), 7.32 (d, J = 8.8 Hz, 2H), 4.37-4.28 (m, 1H), 4.14 (s, 3H), 1.45 (d, J = 6.6 Hz, 6H). | B |

TABLE 1-continued

| Example | Structure | LCMS m/z | ¹H NMR | General Procedure |
|---|---|---|---|---|
| 90 | 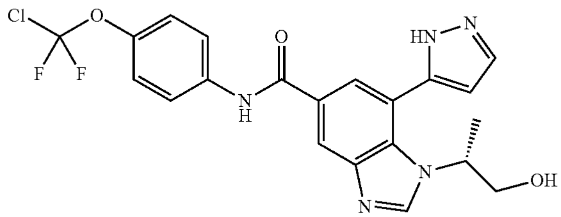 [SMILES: C[C@H](CO)n1cnc2cc(C(=O)Nc3ccc(OC(F)(F)Cl)cc3)cc(-c3ccn[nH]3)c21] | 462.1 | ¹H NMR (400 MHz, MeOD-d₄) δ 8.52 (s, 1 H) 8.37 (s, 1 H) 7.90 (d, J = 1.8 Hz, 1 H) 7.79-7.88 (m, 3 H) 7.29 (d, J = 9.0 Hz, 2 H) 6.65 (d, J = 2.0 Hz, 1 H) 4.71 (br s, 1 H) 3.57-3.75 (m, 2H) 1.44 (d, J = 6.8 Hz, 3 H) | B |
| 91 | 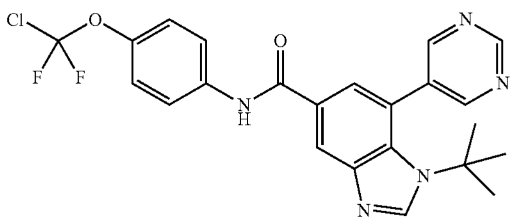 [SMILES: CC(C)(C)n1cnc2cc(C(=O)Nc3ccc(OC(F)(F)Cl)cc3)cc(-c3cncnc3)c21] | 472.1 | ¹H NMR (400 MHz, MeOD-d₄) δ 9.31 (s, 1H), 8.99 (s, 2H), 8.56 (s, 1H), 8.47 (d, J = 1.8 Hz, 1H), 7.85-7.80 (m, 2H), 7.72 (d, J = 2.0 Hz, 1H), 7.29 (d, J = 9.0 Hz, 2H), 1.50 (s, 9H). | B |
| 92 | 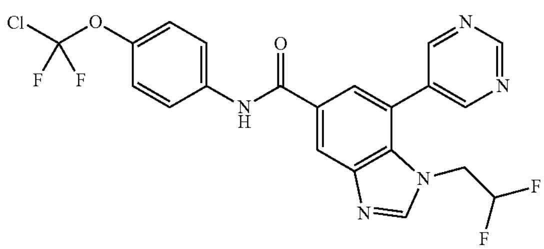 [SMILES: O=C(Nc1ccc(OC(F)(F)Cl)cc1)c1cc(-c2cncnc2)c2c(c1)ncn2CC(F)F] | 480.0 | ¹H NMR (400 MHz, CDCl₃-d) δ 9.31 (s, 1H), 8.80 (s, 2H), 8.34 (d, J = 1.5 Hz, 1H), 8.05-7.96 (m, 2H), 7.74 (d, J = 1.5 Hz, 1H), 7.67 (d, J = 8.9 Hz, 2H), 7.22 (s, 1H), 5.82-5.44 (m, 1H), 4.16 (dt, J = 2.8, 14.7 Hz, 2H). | B |
| 93 | 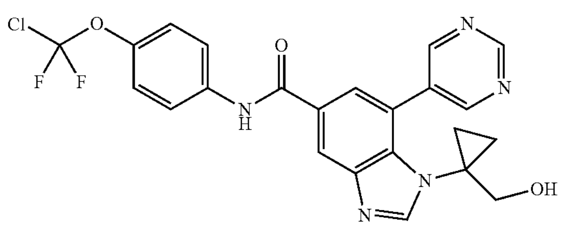 [SMILES: O=C(Nc1ccc(OC(F)(F)Cl)cc1)c1cc(-c2cncnc2)c2c(c1)ncn2C1(CO)CC1] | 486.1 | ¹H NMR (400 MHz, MeOD-d₄) δ 9.30 (s, 1 H) 9.05 (s, 2 H) 8.46 (s, 1 H) 8.40 (s, 1 H) 7.76-7.93 (m, 3 H) 7.30 (d, J = 9.0 Hz, 2 H) 3.64-3.92 (m, 1 H) 2.95 (br d, J = 4.0 Hz, 1 H) 1.30 (br s, 1 H) 1.08 (br s, 2 H) 0.35 (br s, 1 H). | B |
| 94 | 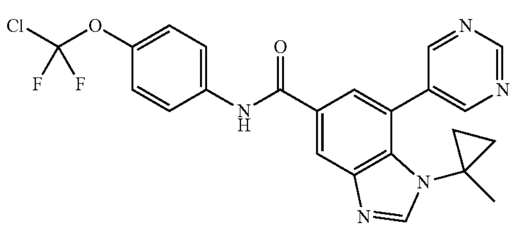 [SMILES: CC1(n2cnc3cc(C(=O)Nc4ccc(OC(F)(F)Cl)cc4)cc(-c4cncnc4)c32)CC1] | 470.1 | ¹H NMR (400 MHz, DMSO-d₆) δ 10.45 (s, 1 H) 9.33 (s, 1 H) 9.10 (s, 2 H) 8.44-8.55 (m, 2 H) 7.94 (d, J = 9.0 Hz, 2 H) 7.80 (d, J = 1.5 Hz, 1 H) 7.36 (d, J = 9.0 Hz, 2 H) 1.22 (s, 3 H) 1.14 (br s, 2 H) 0.53 (br s, 2 H). | B |
| 95 | 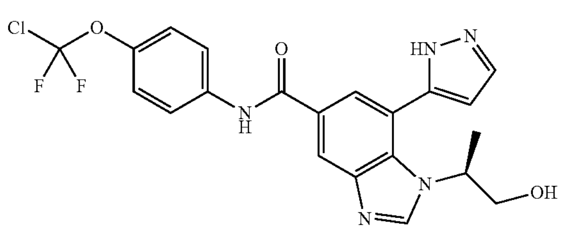 [SMILES: C[C@@H](CO)n1cnc2cc(C(=O)Nc3ccc(OC(F)(F)Cl)cc3)cc(-c3ccn[nH]3)c21] | 462.1 | ¹H NMR (400 MHz, CDCl₃-d)) δ 8.76 9.07 (br s, 1H), 7.93 (s, 1H), 7.72-7.55 (m, 4H), 7.48 (s, 1H), 7.17 (br d, J = 8.7 Hz, 2H), 6.49 (s, 1H), 4.56 (br s, 1H), 3.85 (br d, J = 12.0 Hz, 1H), 3.48 (br d, J = 8.6 Hz, 1H), 1.44 (br d, J = 6.8 Hz, 3H). | B |

TABLE 1-continued

| Example | Structure | LCMS m/z | ¹H NMR | General Procedure |
|---|---|---|---|---|
| 96 | 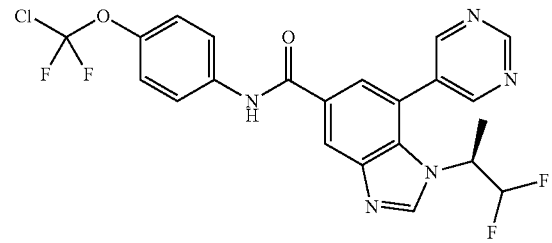 [SMILES: C[C@@H](C(F)F)n1cnc2cc(C(=O)Nc3ccc(OC(F)(F)Cl)cc3)cc(-c3cncnc3)c21] | 494.1 | ¹H NMR (400 MHz, MeOD-d$_4$) δ 9.32 (s, 1H), 9.00 (br s, 2H), 8.60 (s, 1H), 8.48 (d, J = 1.8 Hz, 1H), 7.85-7.84 (m, 1H), 7.84-7.81 (m, 2H), 7.29 (d, J = 9.3 Hz, 2H), 6.14-5.83 (m, 1H), 4.45-4.32 (m, 1H), 1.66 (d, J = 7.1 Hz, 3H). | B |
| 97 | 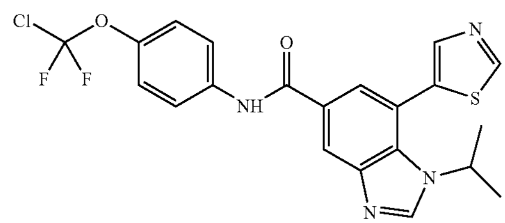 [SMILES: CC(C)n1cnc2cc(C(=O)Nc3ccc(OC(F)(F)Cl)cc3)cc(-c3cncs3)c21] | 463..1 | ¹H NMR (400 MHz, MeOD-d$_4$) δ 9.23 (s, 1H), 8.60 (s, 1H), 8.44 (d, J = 1.8 Hz, 1H), 8.08 (s, 1H), 7.90 (d, J = 1.8 Hz, 1H), 7.87-7.82 (m, 2H), 7.30 (d, J = 9.2 Hz, 2H), 4.42-4.34 (m, 1H), 1.45 (d, J = 6.6 Hz, 6H). | B |
| 98 | 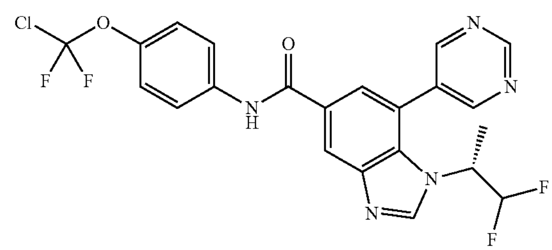 [SMILES: C[C@H](C(F)F)n1cnc2cc(C(=O)Nc3ccc(OC(F)(F)Cl)cc3)cc(-c3cncnc3)c21] | 494.0 | ¹H NMR (400 MHz, MeOD-d$_4$) δ 9.32 (s, 1H), 9.00 (br s, 2H), 8.59 (d, J = 0.7 Hz, 1H), 8.48 (d, J = 1.5 Hz, 1H), 7.86-7.84 (m, 3H), 7.29 (d, J = 9.0 Hz, 2H), 6.15-5.82 (m, 1H), 4.47-4.32 (m, 1H), 1.66 (d, J = 7.1 Hz, 3H). | B |
| 99 | 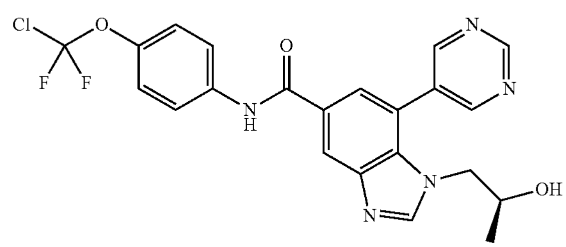 [SMILES: C[C@H](O)Cn1cnc2cc(C(=O)Nc3ccc(OC(F)(F)Cl)cc3)cc(-c3cncnc3)c21] | 474.1 | ¹H NMR (400 MHz, MeOD-d$_4$) δ 9.31 (s, 1H), 9.03 (s, 2H), 8.45 (d, J = 1.5 Hz, 1H), 8.33 (s, 1H), 7.88-7.80 (m, 3H), 7.29 (d, J = 8.8 Hz, 2H), 3.93-3.81 (m, 2H), 3.59-3.51 (m, 1H), 0.83 (d, J = 6.4 Hz, 2H). | B |
| 100 | 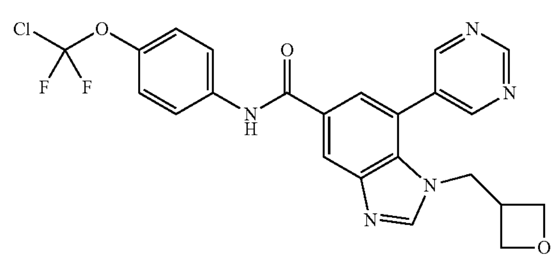 [SMILES: O=C(Nc1ccc(OC(F)(F)Cl)cc1)c1cc(-c2cncnc2)c2c(c1)ncn2CC1COC1] | 486.1 | ¹H NMR (400 MHz, MeOD-d$_4$) δ 9.31 (s, 1 H) 9.08 (s, 2 H) 8.37-8.54 (m, 2 H) 7.80-7.94 (m, 3 H) 7.30 (d, J = 9.0 Hz, 2 H) 4.55 (dd, J = 7.5, 6.6 Hz, 2 H) 4.31 (d, J = 7.5 Hz, 2 H) 4.24 (t, J = 6.2 Hz, 2 H) 3.00-3.11 (m, 1 H). | B |
| 101 | 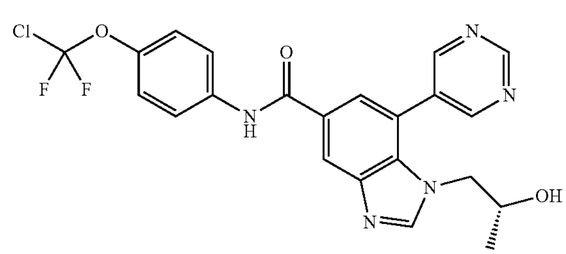 [SMILES: C[C@@H](O)Cn1cnc2cc(C(=O)Nc3ccc(OC(F)(F)Cl)cc3)cc(-c3cncnc3)c21] | 474.1 | ¹H NMR (400 MHz, MeOD-d$_4$) δ = 9.05 (s, 1H), 8.78 (s, 2H), 8.20 (d, J = 1.5 Hz, 1H), 8.08 (s, 1H), 7.62-7.56 (m, 3H), 7.04 (br d, J = 8.8 Hz, 2H), 3.65-3.58 (m, 2H), 3.33-3.25 (m, 1H), 0.57 (d, J = 6.4 Hz, 3H). | B |

TABLE 1-continued

| Example | Structure | LCMS m/z | ¹H NMR | General Procedure |
|---|---|---|---|---|
| 102 | 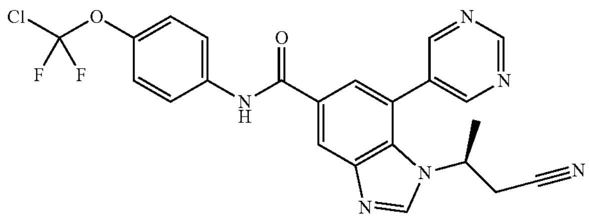 [SMILES: C[C@@H](CC#N)n1cnc2cc(C(=O)Nc3ccc(OC(F)(F)Cl)cc3)cc(-c3cncnc3)c21] | 483.1 | ¹H NMR (400 MHz, MeOD-d$_4$) δ = 9.34 (s, 1H), 9.08 (br s, 2H), 8.69 (s, 1H), 8.49 (d, J = 1.5 Hz, 1H), 7.87-7.82 (m, 3H), 7.30 (d, J = 8.8 Hz, 2H), 4.47-4.38 (m, 1H), 3.06-2.87 (m, 2H), 1.64 (d, J = 6.8 Hz, 3H). | B |
| 103 | 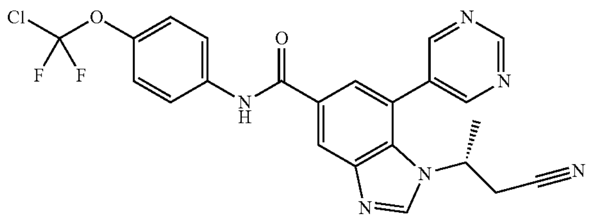 [SMILES: C[C@H](CC#N)n1cnc2cc(C(=O)Nc3ccc(OC(F)(F)Cl)cc3)cc(-c3cncnc3)c21] | 483.0 | ¹H NMR (400 MHz, MeOD-d$_4$) δ 9.34 (s, 1H), 9.07 (br s, 2H), 8.69 (s, 1H), 8.48 (d, J = 1.5 Hz, 1H), 7.86-7.82 (m, 3H), 7.29 (d, J = 8.8 Hz, 2H), 4.45-4.39 (m, 1H), 3.03-2.86 (m, 2H), 1.63 (d, J = 6.8 Hz, 3H). | B |
| 104 | 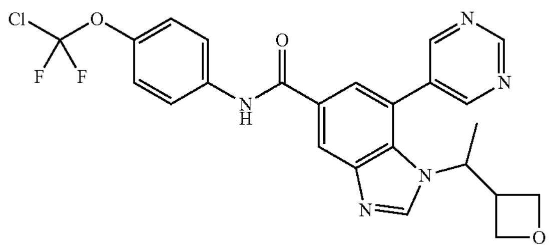 [SMILES: CC(C1COC1)n1cnc2cc(C(=O)Nc3ccc(OC(F)(F)Cl)cc3)cc(-c3cncnc3)c21] | 500.1 | ¹H NMR (400 MHz, MeOD-d$_4$) δ 9.37 (s, 1 H) 9.12 (s, 2H) 8.35-8.61 (m, 2 H) 7.82-7.90 (m, 3 H) 7.30 (d, J = 8.9 Hz, 2 H) 4.77 (t, J = 7.1 Hz, 1 H) 4.56-4.63 (m, 1 H) 4.41 (dd, J = 9.8, 6.5 Hz, 1 H) 4.11 (dt, J = 15.3, 6.1 Hz, 2 H) 3.57 (br s, 1 H) 1.33 (d, J = 6.7 Hz, 3 H). | B |
| 105 | 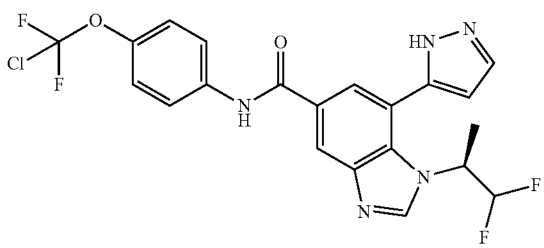 [SMILES: C[C@@H](C(F)F)n1cnc2cc(C(=O)Nc3ccc(OC(F)(F)Cl)cc3)cc(-c3ccn[nH]3)c21] | 482.0 | ¹H NMR (400 MHz, MeOD-d$_4$) δ 8.54 (s, 1H), 8.40 (s, 1H), 7.98 (s, 1H), 7.89 (br s, 1H), 7.85 (d, J = 8.9 Hz, 2H), 7.30 (d, J = 8.6 Hz, 2H), 6.69 (s, 1H), 6.00 (s, 1H), 5.18 (br s, 1H), 1.65 (d, J = 7.2 Hz, 3H). | B |
| 106 | 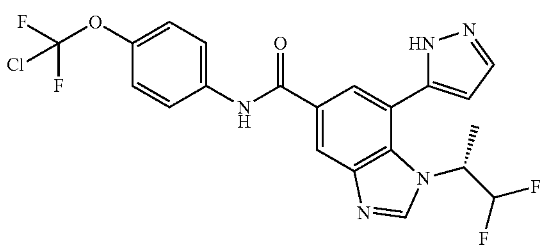 [SMILES: C[C@H](C(F)F)n1cnc2cc(C(=O)Nc3ccc(OC(F)(F)Cl)cc3)cc(-c3ccn[nH]3)c21] | 482.0 | ¹H NMR (400 MHz, MeOD-d$_4$) δ 8.54 (s, 1H), 8.40 (brs, 1H), 7.98 (s, 1H), 7.93-7.77 (m, 2H), 7.92-7.74 (m, 1H), 7.30 (d, J = 9.0Hz, 2H), 6.69 (br s, 1H), 6.00 (br d, J = 2.2 Hz, 1H), 6.12-5.90 (m, 1H), 5.19 (br s, 1H), 1.65 (d, J = 7.1 Hz, 3H). | B |
| 107 | 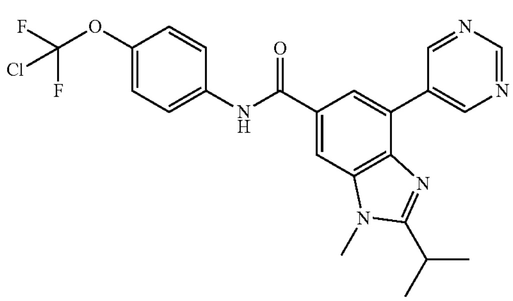 [SMILES: CC(C)c1nc2c(-c3cncnc3)cc(C(=O)Nc3ccc(OC(F)(F)Cl)cc3)cc2n1C] | 472.2 | ¹H NMR (400 MHz, DMSO-d$_6$) δ 10.44 (s, 1H), 9.63 (s, 2H), 9.21 (s, 1H), 8.24 (d, J = 10.4 Hz, 2H), 7.92 (d, J = 8.8 Hz, 2H), 7.38 (br d, J = 8.8 Hz, 2H), 3.91 (s, 3H), 3.45-3.37 (m, 1H), 1.36 (d, J = 6.6 Hz, 6H). | C |

TABLE 1-continued

| Example | Structure | LCMS m/z | ¹H NMR | General Procedure |
|---|---|---|---|---|
| 108 | 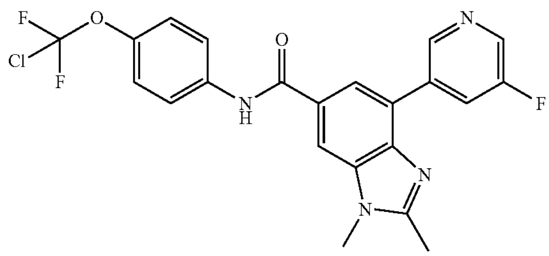 [SMILES: Cc1nc2c(-c3cncc(F)c3)cc(C(=O)Nc3ccc(OC(F)(F)Cl)cc3)cc2n1C] | 461.1 | ¹H NMR (400 MHz, DMSO-$d_6$) δ 10.47 (s, 1H), 9.30 (s, 1H), 8.63-8.51 (m, 2H), 8.20 (d, J = 8.8 Hz, 2H), 7.92 (d, J = 9.0 Hz, 2H), 7.38 (d, J = 8.8 Hz, 2H), 3.87 (s, 3H), 2.64 (s, 3H). | C |
| 109 | 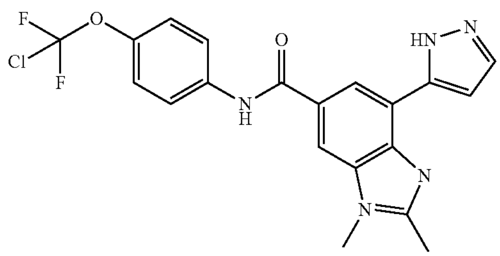 | 432.1 | ¹H NMR (400 MHz, DMSO-$d_6$) δ 8.15 (br s, 1H), 7.99 (br s, 1H), 7.77 (br d, J = 8.6 Hz, 2H), 7.63 (br s, 1H), 7.21 (br d, J = 8.4 Hz, 2H), 7.00 (br s, 1H), 3.79 (br s, 3H), 2.65-2.52 (m, 3H). | C |
| 110 | 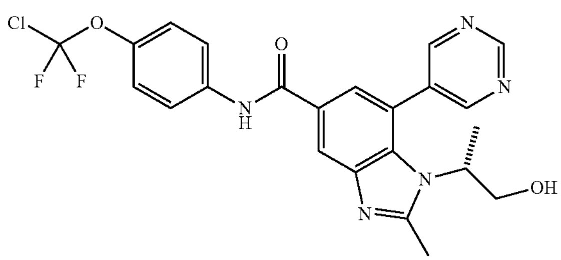 [SMILES: Cc1nc2cc(C(=O)Nc3ccc(OC(F)(F)Cl)cc3)cc(-c3cncnc3)c2n1[C@H](C)CO] | 488.1 | ¹H NMR (400 MHz, DMSO-$d_6$) δ 10.39 (s, 1 H) 9.33 (s, 1 H) 9.02 (s, 2 H) 8.35 (d, J = 1.8 Hz, 1 H) 7.92 (d, J = 9.0 Hz, 2 H) 7.66 (d, J = 1.5 Hz, 1 H) 7.36 (d, J = 8.8 Hz, 2 H) 4.95 (t, J = 5.3 Hz, 1 H) 4.14-4.27 (m, 1 H) 3.66 (br s, 1 H) 3.41-3.56 (m, 1 H) 2.67 (s, 3H) 1.29 (br d, J = 7.1 Hz, 3 H). | D |
| 111 | 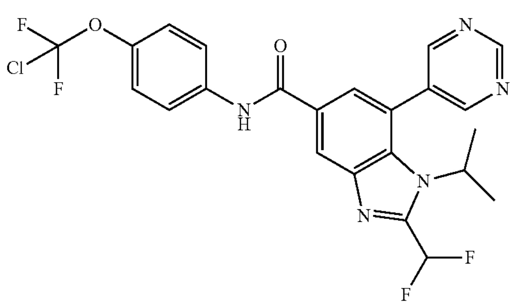 [SMILES: CC(C)n1c(C(F)F)nc2cc(C(=O)Nc3ccc(OC(F)(F)Cl)cc3)cc(-c3cncnc3)c21] | 508.1 | ¹H NMR (400 MHz, DMSO-$d_6$) δ 10.50 (s, 1 H) 9.37 (s, 1 H) 9.12 (s, 2 H) 8.59 (d, J = 1.5 Hz, 1 H) 7.89-7.97 (m, 2 H) 7.86 (d, J = 1.5 Hz, 1 H) 7.43-7.73 (m, 1 H) 7.37 (d, J = 9.0 Hz, 2 H) 4.26-4.57 (m, 1 H) 1.36 (d, J = 7.1 Hz, 6 H). | D |
| 112 | 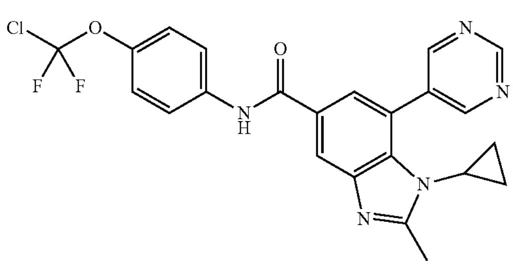 [SMILES: Cc1nc2cc(C(=O)Nc3ccc(OC(F)(F)Cl)cc3)cc(-c3cncnc3)c2n1C1CC1] | 470.1 | ¹H NMR (400 MHz, DMSO-$d_6$) δ 9.28 (s, 1H), 9.12 (s, 2H), 8.33 (d, 1.5 Hz, 1H), 7.93 (d, J = 9.0 Hz, 2H), 7.83 (d, J = 1.5 Hz, 1H), 7.36 (d, J = 9.0 Hz, 2H), 3.30-3.24 (m, 1H), 2.75-2.60 (m, 3H), 0.63-0.55 (m, 2H), 0.47-0.39 (m, 2H). | D |

TABLE 1-continued

| Example | Structure | LCMS m/z | ¹H NMR | General Procedure |
|---|---|---|---|---|
| 113 | 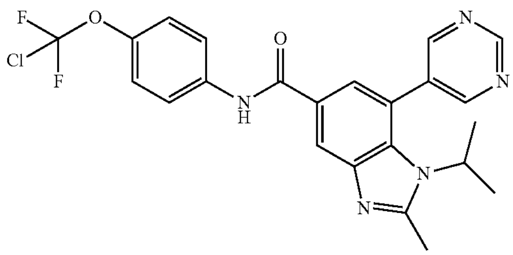 [SMILES: Cc1nc2cc(C(=O)Nc3ccc(OC(F)(F)Cl)cc3)cc(-c3cncnc3)c2n1C(C)C] | 472.1 | ¹H NMR (400 MHz, DMSO-d$_6$) δ 10.40 (s, 1 H) 9.35 (s, 1 H) 9.07 (s, 2 H) 8.36 (d, J = 1.5 Hz, 1 H) 7.92 (d, J = 9.3 Hz, 2 H) 7.69 (d, J = 1.5 Hz, 1 H) 7.36 (d, J = 9.0 Hz, 2 H) 4.13-4.34 (m, 1 H) 2.70 (s, 3 H) 1.34 (d, J = 1.1 Hz, 6 H). | D |
| 114 | 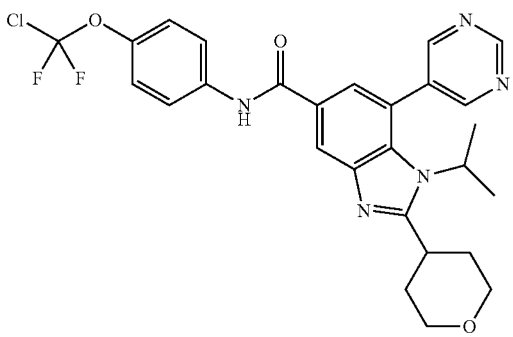 [SMILES: CC(C)n1c(C2CCOCC2)nc2cc(C(=O)Nc3ccc(OC(F)(F)Cl)cc3)cc(-c3cncnc3)c21] | 542.1 | ¹H NMR (400 MHz, MeOD-d$_4$) δ 9.31 (s, 1 H) 9.03 (s, 2 H) 8.35 (s, 1 H) 7.83 (br d, J = 8.9 Hz, 2 H) 7.73 (s, 1H) 7.29 (br d, J = 8.7 Hz, 2 H) 4.45 (dt, J = 14.1, 6.9 Hz, 1 H) 4.10 (br dd, J = 11.5, 3.4 Hz, 2 H) 3.64 (br t, J = 11.8 Hz, 2 H) 3.43 (br t, 11.5 Hz, 1 H) 2.13-2.32 (m, 2 H) 1.91 (br d, J = 12.3 Hz, 2H) 1.48 (br d, J = 7.1 Hz, 6 H). | D |
| 115 | 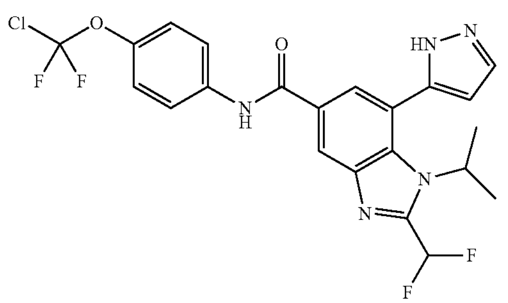 [SMILES: CC(C)n1c(C(F)F)nc2cc(C(=O)Nc3ccc(OC(F)(F)Cl)cc3)cc(-c3ccn[nH]3)c21] | 496.1 | ¹H NMR (400 MHz, DMSO-d$_6$) δ 13.23 (br s, 1H), 10.52 (s, 1H), 8.50 (br s, 1H), 7.99-7.87 (m, 4H), 7.68-7.67 (m, 1H), 7.36 (d, J = 9.3 Hz, 2H), 6.62 (d, J = 2.0 Hz, 1H), 4.89 (br s, 1H), 1.36 (d, J = 6.8 Hz, 6H). | D |
| 116 | 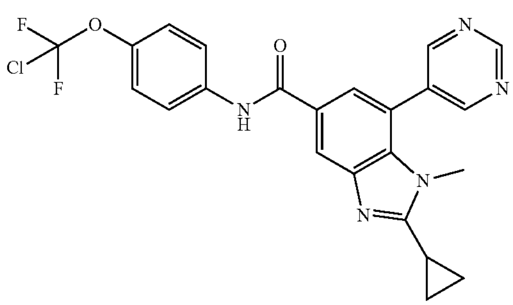 [SMILES: Cn1c(C2CC2)nc2cc(C(=O)Nc3ccc(OC(F)(F)Cl)cc3)cc(-c3cncnc3)c21] | 470.1 | ¹H NMR (400 MHz, DMSO-d$_6$) δ 10.36 (s, 1H), 9.30 (s, 1H), 9.05 (s, 2H), 8.29 (d, J = 1.3 Hz, 1H), 7.90 (d, J = 9.3 Hz, 2H), 7.70 (d, J = 1.3 Hz, 1H), 7.33 (d, J = 9.0 Hz, 2H), 3.48 (s, 3H), 2.27-2.19 (m, 1H), 1.18-0.97 (m, 4H). | E |
| 117 | 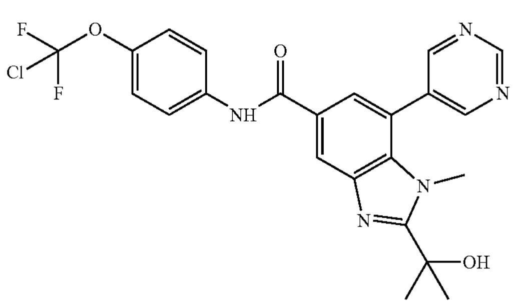 [SMILES: Cn1c(C(C)(C)O)nc2cc(C(=O)Nc3ccc(OC(F)(F)Cl)cc3)cc(-c3cncnc3)c21] | 488.1 | ¹H NMR (400 MHz, DMSO-d$_6$) δ 10.44 (s, 1H), 9.34 (s, 1H), 9.08 (s, 2H), 8.46 (d, J = 1.7 Hz, 1H), 7.94 (d, J = 9.2 Hz, 2H), 7.82 (d, J = 1.6 Hz, 1H), 7.37 (d, J = 9.0 Hz, 2H), 3.70 (s, 3H), 1.69 (s, 6H). | E |

TABLE 1-continued

| Example | Structure | LCMS m/z | ¹H NMR | General Procedure |
|---|---|---|---|---|
| 118 | 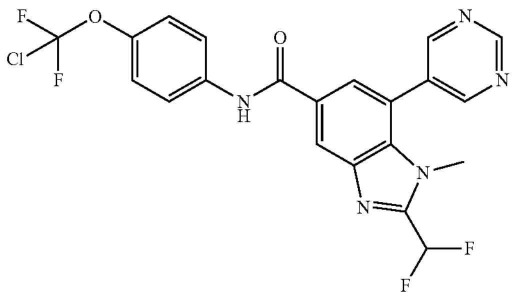 [SMILES: Cn1c(C(F)F)nc2cc(C(=O)Nc3ccc(OC(F)(F)Cl)cc3)cc(-c3cncnc3)c21] | 480.0 | ¹H NMR (400 MHz, DMSO-d$_6$) δ 10.52 (s, 1H), 9.34 (s, 1H), 9.12 (s, 2H), 8.57 (s, 1H), 7.93 (dd, J = 3.9, 5.1 Hz, 3H), 7.66-7.33 (m, 3H), 3.57 (s, 3H). | E |
| 119 | 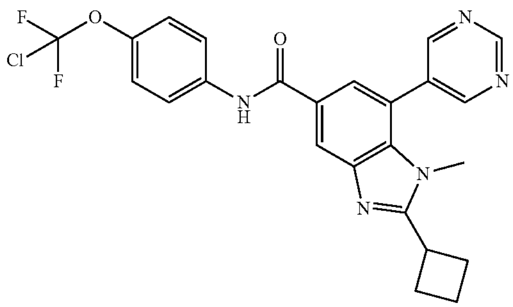 [SMILES: Cn1c(C2CCC2)nc2cc(C(=O)Nc3ccc(OC(F)(F)Cl)cc3)cc(-c3cncnc3)c21] | 484.1 | ¹H NMR (400 MHz, DMSO-d$_6$) δ 10.42 (s, 1H), 9.32 (s, 1H), 9.07 (s, 2H), 8.44 (d, J = 1.3 Hz, 1H), 7.95 (d, J = 9.2 Hz, 2H), 7.76 (d, J = 1.5 Hz, 1H), 7.37 (d, J = 8.9 Hz, 2H), 3.88 (quin, J = 8.3 Hz, 1H), 3.30 (s, 3H), 2.45 (br d, J = 8.9 Hz, 4H), 2.16-2.05 (m, 1H), 2.02-1.89 (m, 1H). | E |
| 120 | 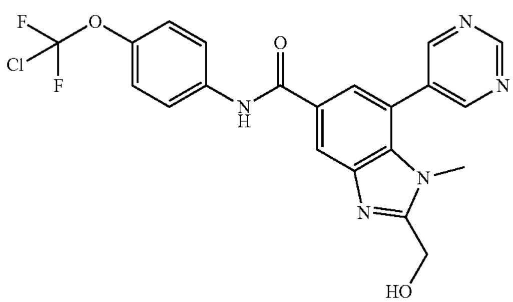 [SMILES: Cn1c(CO)nc2cc(C(=O)Nc3ccc(OC(F)(F)Cl)cc3)cc(-c3cncnc3)c21] | 460.2 | ¹H NMR (400 MHz, MeOD-d$_4$) δ 9.35 (s, 1H), 9.08 (s, 2H), 8.47 (s, 1H), 8.05 (s, 1H), 7.85 (d, J = 9.0 Hz, 2H), 7.32 (d, J = 8.8 Hz, 2H), 5.09 (s, 2H), 3.57 (s, 3H). | F |
| 121 | 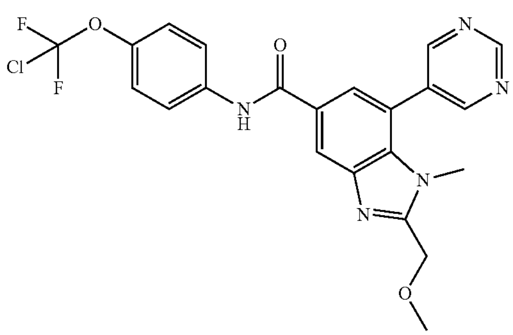 [SMILES: COCc1nc2cc(C(=O)Nc3ccc(OC(F)(F)Cl)cc3)cc(-c3cncnc3)c2n1C] | 474.1 | ¹H NMR (400 MHz, MeOD-d$_4$) δ 9.34 (s, 1H), 9.07 (s, 2H), 8.46 (d, J = 1.3 Hz, 1H), 8.00 (d, J = 1.3 Hz, 1H), 7.85 (d, J = 9.0 Hz, 2H), 7.31 (d, J = 8.8 Hz, 2H), 4.92 (s, 2H), 3.56 (d, J = 4.3 Hz, 6H). | F |
| 122 | 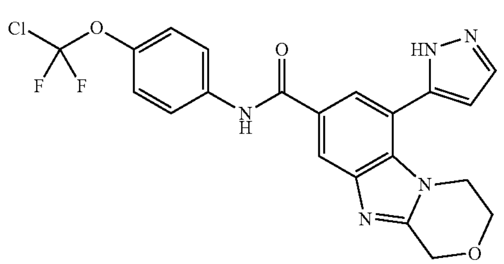 [SMILES: O=C(Nc1ccc(OC(F)(F)Cl)cc1)c1cc(-c2ccn[nH]2)c2c(c1)nc1n2CCOC1] | 460.0 | ¹H NMR (400 MHz, DMSO)-d$_6$) δ 13.14 (br s, 1H), 10.48 (s, 1H), 8.32 (br s, 1H), 7.96 (s, 1H), 7.93 (s, 2H), 7.88 (s, 1H), 7.36 (d, J = 8.6 Hz, 2H), 6.67 (br s, 1H), 5.02 (s, 2H), 4.04 (br s, 4H). | G |

TABLE 1-continued

| Example | Structure | LCMS m/z | ¹H NMR | General Procedure |
|---|---|---|---|---|
| 123 | 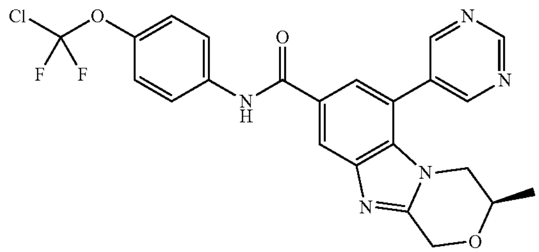 [SMILES: C[C@@H]1Cn2c(nc3cc(C(=O)Nc4ccc(OC(F)(F)Cl)cc4)cc(-c4cncnc4)c32)CO1] | 486.1 | ¹H NMR (400 MHz, MeOD-d₄) δ 9.30 (s, 1 H) 9.06 (s, 2 H) 8.37 (d, J = 1.3 Hz, 1H) 7.80-7.88 (m, 3 H) 7.29 (d, J = 9.0 Hz, 2 H) 4.98-5.20 (m, 2 H) 3.95-4.05 (m, 1H) 3.61-3.72 (m, 2 H) 1.26 (d, J = 6.1 Hz, 3 H). | G |
| 124 | 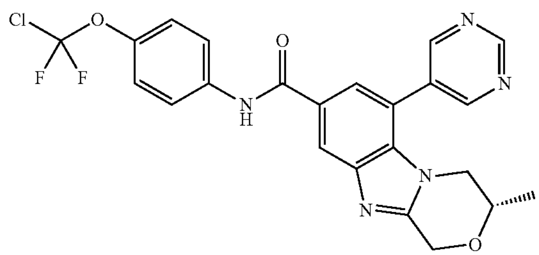 [SMILES: C[C@H]1Cn2c(nc3cc(C(=O)Nc4ccc(OC(F)(F)Cl)cc4)cc(-c4cncnc4)c32)CO1] | 486.0 | ¹H NMR (400 MHz, CDCl₃-d) δ 9.37 (s, 1H), 8.91 (s, 2H), 8.28 (s, 1H), 8.13 (s, 1H), 7.81-7.69 (m, 3H), 7.29 (s, 1H), 5.21 (d, J = 16.3 Hz, 1H), 4.99 (d, J = 16.3 Hz, 1H), 3.99-3.89 (m, 1H), 3.63-3.54 (m, 1H), 3.50-3.44 (m, 1H), 1.31 (d, J = 6.2 Hz, 3H). | G |
| 125 | 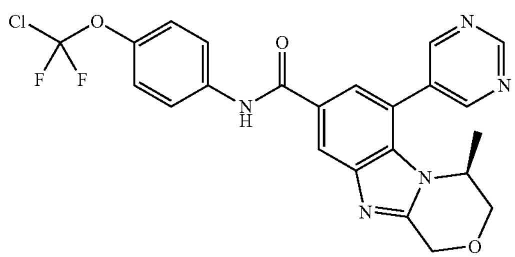 [SMILES: C[C@H]1COCc2nc3cc(C(=O)Nc4ccc(OC(F)(F)Cl)cc4)cc(-c4cncnc4)c3n21] | 486.1 | ¹H NMR (400 MHz, MeOD-d₄) δ 9.32 (s, 1H), 9.11 (s, 2H), 8.39 (d, J = 1.5 Hz, 1H), 7.87-7.82 (m, 3H), 7.30 (d, J = 9.0 Hz, 2H), 5.16-4.96 (m, 2H), 4.19-4.11 (m, 2H), 3.95 (d, J = 11.2 Hz, 1H), 1.00 (d, J = 6.8 Hz, 3H). | G |
| 126 | 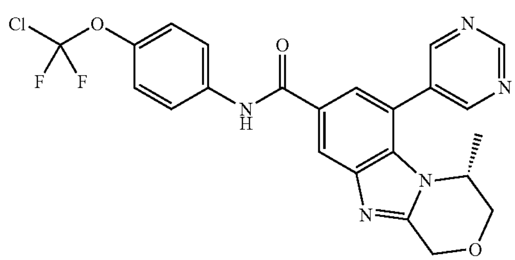 [SMILES: C[C@@H]1COCc2nc3cc(C(=O)Nc4ccc(OC(F)(F)Cl)cc4)cc(-c4cncnc4)c3n21] | 486.1 | ¹H NMR (400 MHz, MeOD-d₄) δ 9.32 (s, 1H), 9.11 (s, 2H), 8.39 (d, J = 1.6 Hz, 1H), 7.88-7.81 (m, 3H), 7.30 (d, J = 9.0 Hz, 2H), 5.19-4.97 (m, 2H), 4.18-4.12 (m, 2H), 3.95 (d, J = 11.4 Hz, 1H), 1.00 (d, J = 6.8 Hz, 3H). | G |
| 127 | 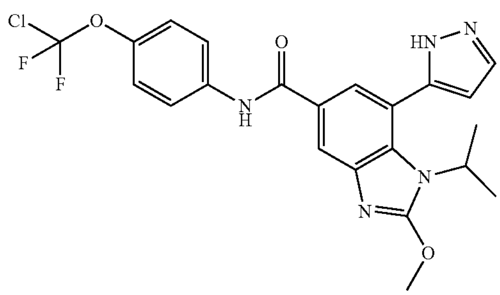 [SMILES: COc1nc2cc(C(=O)Nc3ccc(OC(F)(F)Cl)cc3)cc(-c3ccn[nH]3)c2n1C(C)C] | 476.0 | ¹H NMR (400 MHz, DMSO-d₆) δ 12.96 (br s, 1H), 10.17 (s, 1H), 8.13 (br s, 1H), 7.97-7.83 (m, 3H), 7.71 (s, 1H), 7.31 (d, J = 9.0 Hz, 2H), 6.53 (br s, 1H), 4.53 (br s, 1H), 4.18 (s, 3H), 1.31 (d, J = 6.8 Hz, 6H). | H |

TABLE 1-continued

| Example | Structure | LCMS m/z | ¹H NMR | General Procedure |
|---|---|---|---|---|
| 128 | 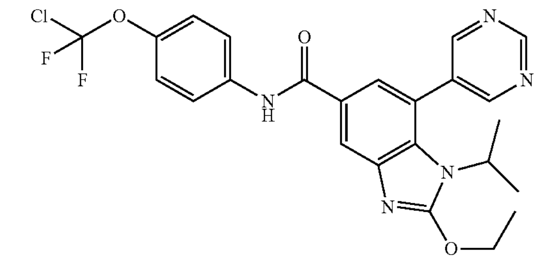 [SMILES: CCOc1nc2cc(C(=O)Nc3ccc(OC(F)(F)Cl)cc3)cc(-c3cncnc3)c2n1C(C)C] | 502.1 | ¹H NMR (400 MHz, MeOD-$d_4$) δ 9.29 (s, 1H), 9.01 (s, 2H), 8.16 (d, J = 1.8 Hz, 1H), 7.85-7.80 (m, 2H), 7.65 (d, J = 1.8 Hz, 1H), 7.29 (d, J = 9.0 Hz, 2H), 4.66 (q, J = 7.2 Hz, 2H), 4.06 (quin, J = 6.8 Hz, 1H), 1.54 (t, J = 7.1 Hz, 3H), 1.40 (d, J = 6.8 Hz, 6H). | H |
| 129 | 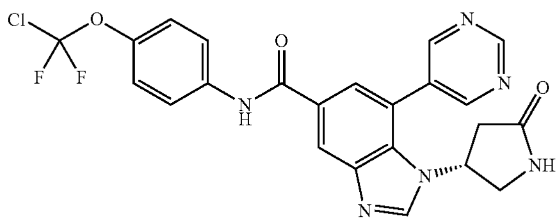 [SMILES: O=C1C[C@@H](n2cnc3cc(C(=O)Nc4ccc(OC(F)(F)Cl)cc4)cc(-c4cncnc4)c32)CN1] | 499.0 | ¹H NMR (400 MHz, CDCl$_3$-d) δ 9.39 (s, 1H), 8.90 (s, 2H), 8.45 (s, 1H), 8.40 (d, J = 1.5 Hz, 1H), 8.10 (s, 1H), 7.83 (d, J = 1.5 Hz, 1H), 7.80-7.74 (m, 2H), 7.29 (s, 2H), 6.03 (s, 1H), 4.69 (br t, J = 7.1 Hz, 1H), 3.71-3.47 (m, 2H), 2.81-2.58 (m, 2H), 1.26 (s, 2H). | J |
| 130 | 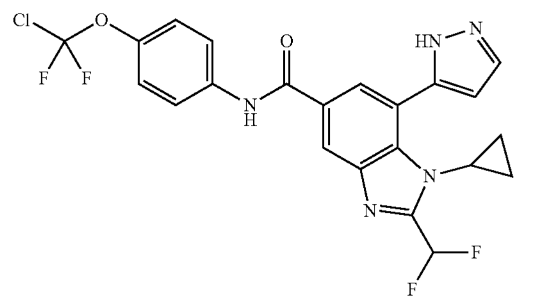 [SMILES: O=C(Nc1ccc(OC(F)(F)Cl)cc1)c1cc(-c2ccn[nH]2)c2c(c1)nc(C(F)F)n2C1CC1] | 494.0 | ¹H NMR (400 MHz, MeOD-$d_4$) δ 8.41 (br s, 1H), 8.06 (d, J = 1.5 Hz, 1H), 7.88-7.83 (m, 2H), 7.48-7.18 (m, 4H), 6.72 (br s, 1H), 3.49 (td, J = 3.3, 7.2 Hz, 1H), 0.77 (br s, 2H), 0.66 (br d, J = 5.7 Hz, 2H). | E |
| 131 | 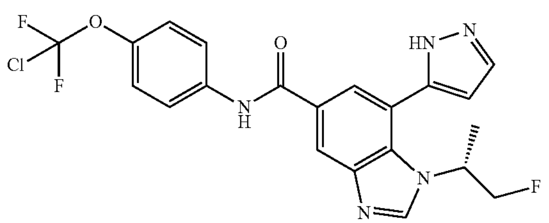 [SMILES: C[C@H](CF)n1cnc2cc(C(=O)Nc3ccc(OC(F)(F)Cl)cc3)cc(-c3ccn[nH]3)c21] | 464.1 | ¹H NMR (400 MHz, MeOD-$d_4$) δ 8.53 (s, 1H), 8.40 (s, 1H), 7.95 (s, 1H), 7.89 (s, 1H), 7.87-7.83 (m, 2H), 7.30 (d, J = 9.0 Hz, 2H), 6.67 (d, J = 2.1 Hz, 1H), 5.23-5.05 (m, 1H), 4.58 (d, J = 4.2 Hz, 1H), 4.46 (d, J = 4.0 Hz, 1H), 1.53 (d, J = 7.0 Hz, 3H). | E |
| 132 | 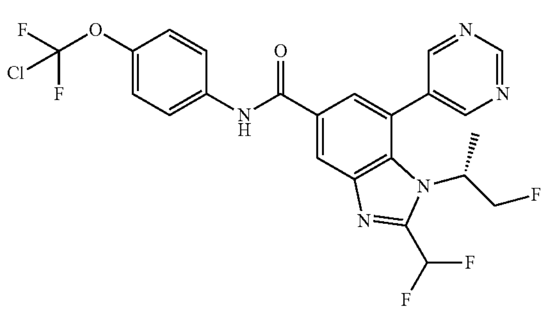 [SMILES: C[C@H](CF)n1c(C(F)F)nc2cc(C(=O)Nc3ccc(OC(F)(F)Cl)cc3)cc(-c3cncnc3)c21] | 526.1 | ¹H NMR (400 MHz, DMSO-$d_6$) δ 10.53 (s, 1H), 9.37 (s, 1H), 9.06 (br s, 2H), 8.60 (d, J = 1.1 Hz, 1H). 7.97-7.84 (m, 3H), 7.70-7.50 (m, 1H), 7.44-7.33 (m, 2H), 4.74-4.48 (m, 3H). 1.44 (br d, J = 6.0 Hz, 3H) | E |

TABLE 1-continued

| Example | Structure | LCMS m/z | ¹H NMR | General Procedure |
|---|---|---|---|---|
| 133 | 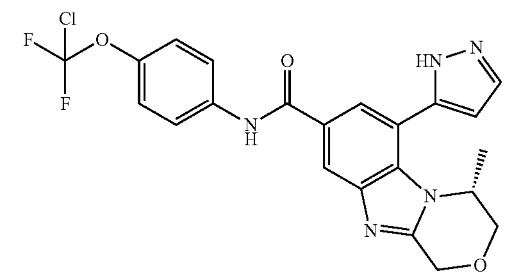 [SMILES: C[C@@H]1COCc2nc3cc(C(=O)Nc4ccc(OC(F)(F)Cl)cc4)cc(-c4ccn[nH]4)c3n21] | 474.0 | ¹H NMR (400 MHz, DMSO-d$_6$) δ 13.16 (br s, 1H), 10.48 (s, 1H), 8.31 (s, 1H), 7.94 (br d, J = 9.0 Hz, 3H), 7.89 (d, J = 1.2 Hz, 1H), 7.36 (br d, J = 8.7 Hz, 2H), 6.70 (s, 1H), 5.13-4.91 (m, 3H), 4.14 (br dd, J = 2.9, 11.9 Hz, 1H), 3.96 (br d, J = 11.9 Hz, 1H), 0.86 (br d, J = 6.5 Hz, 3H). | G |
| 134 | 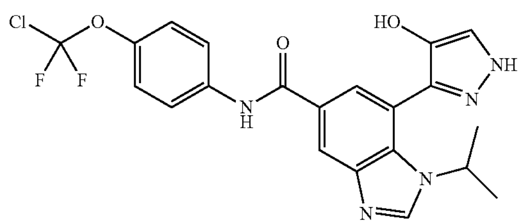 [SMILES: CC(C)n1cnc2cc(C(=O)Nc3ccc(OC(F)(F)Cl)cc3)cc(-c3n[nH]cc3O)c21] | 462.0 | ¹H NMR (400 MHz, MeOD-d$_4$) δ 9.07 (s, 1H), 8.44 (d, J = 1.7 Hz, 1H), 8.05 (d, J = 1.6 Hz, 1H), 7.90-7.83 (m, 2H), 7.42 (s, 1H), 7.32 (d, J = 9.2 Hz, 2H), 4.95-4.92 (m, 1H), 1.48 (d, J = 6.6 Hz, 6H). | M |
| 135 | 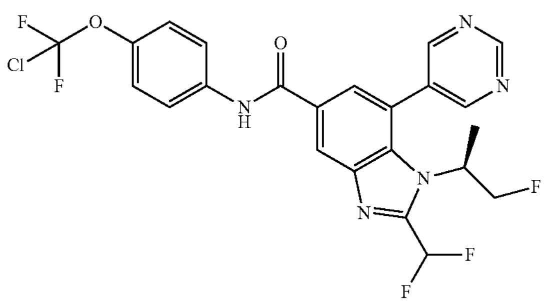 [SMILES: C[C@@H](CF)n1c(C(F)F)nc2cc(C(=O)Nc3ccc(OC(F)(F)Cl)cc3)cc(-c3cncnc3)c21] | 526.1 | ¹H NMR (400 MHz, MeOD-d$_4$) δ 9.32 (s, 1H), 9.01 (br s, 2H), 8.53 (d, J = 1.8 Hz, 1H), 7.90-7.81 (m, 3H), 7.45-7.16 (m, 3H), 4.83-4.67 (m, 2H), 4.64-4.43 (m, 1H), 1.50 (br d, 7.1 Hz, 3H). | E |
| 136 | 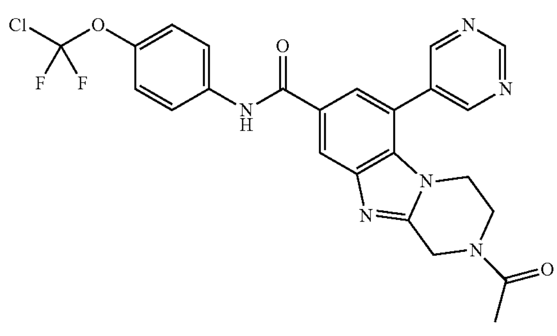 [SMILES: CC(=O)N1CCn2c(nc3cc(C(=O)Nc4ccc(OC(F)(F)Cl)cc4)cc(-c4cncnc4)c32)C1] | 513.1 | ¹H NMR (400 MHz, MeOD-d$_4$) δ 8.24 (s, 1H), 8.08 (s, 1H), 7.83 (d, J = 9.0 Hz, 2H), 7.30 (d, J = 9.0 Hz, 2H), 5.17-5.12 (m, 2H), 5.10-5.03 (m, 4H), 4.20-4.10 (m, 2H), 2.30-2.25 (m, 3H) | G |
| 137 | 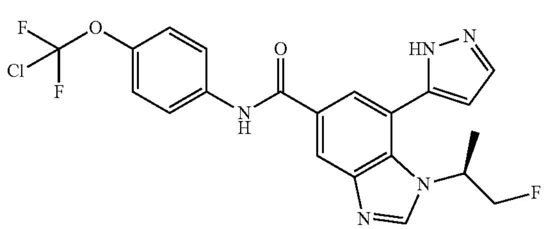 [SMILES: C[C@@H](CF)n1cnc2cc(C(=O)Nc3ccc(OC(F)(F)Cl)cc3)cc(-c3ccn[nH]3)c21] | 464.1 | ¹H NMR (400 MHz, MeOD-d$_4$) δ 8.56-8.50 (m, 1H), 8.43-8.35 (m, 1H), 7.96-7.92 (m, 1H), 7.89-7.80 (m, 3H), 7.34-7.26 (m, 2H), 6.70-6.63 (m, 1H), 5.03-4.89 (m, 1H), 4.58 (d, J = 4.2 Hz, 1H), 4.46 (d, J = 4.0 Hz, 1H), 1.52 (d, J = 7.1 Hz, 3H). | E |

TABLE 1-continued

| Example | Structure | LCMS m/z | ¹H NMR | General Procedure |
|---|---|---|---|---|
| 138 | 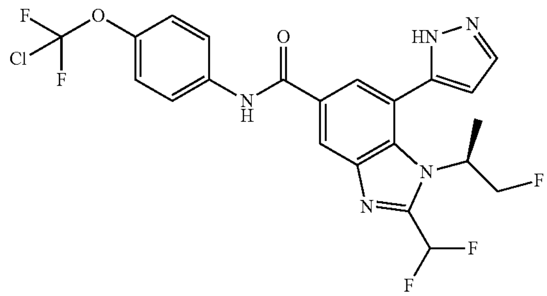 [SMILES: C[C@@H](CF)n1c(C(F)F)nc2cc(C(=O)Nc3ccc(OC(F)(F)Cl)cc3)cc(-c3ccn[nH]3)c21] | 514.1 | ¹H NMR (400 MHz, MeOD-d₄) δ 8.48 (s, 1H), 8.00 (d, J = 1.7 Hz, 1H), 7.92 (s, 1H), 7.89-7.83 (m, 2H), 7.45-7.15 (m, 3H), 6.67 (d, J = 2.1 Hz, 1H), 5.14 (br dd, J = 6.2, 12.8 Hz, 1H), 4.75-4.46 (m, 2H), 1.53 (br d, J = 6.7 Hz, 3H). | E, K |
| 139 | 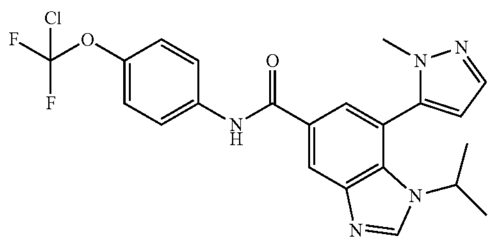 [SMILES: CC(C)n1cnc2cc(C(=O)Nc3ccc(OC(F)(F)Cl)cc3)cc(-c3ccnn3C)c21] | 460.1 | ¹H NMR (400 MHz, DMSO-d₆) δ 10.45 (s, 1H), 8.68 (s, 1H), 8.54 (d, J = 1.6 Hz, 1H), 7.95 (d, J = 9.0 Hz, 2H), 7.83 (d, J = 1.5 Hz, 1H), 7.64 (d, J = 1.8 Hz, 1H), 7.37 (br d, J = 8.9 Hz, 2H), 6.58 (d, J = 1.8 Hz, 1H), 3.87 (td, J = 6.6, 13.2 Hz, 1H), 3.61 (s, 3H), 1.38 (br d, J = 6.6 Hz, 3H), 1.30 (br d, J = 6.5 Hz, 3H). | E |
| 140 | 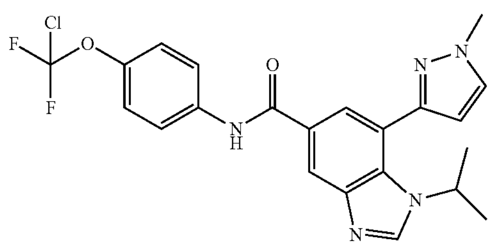 [SMILES: CC(C)n1cnc2cc(C(=O)Nc3ccc(OC(F)(F)Cl)cc3)cc(-c3ccn(C)n3)c21] | 460.1 | ¹H NMR (400 MHz, DMSO-d₆) δ 10.46 (s, 1 H) 8.59 (s, 1H) 8.41 (d, J = 1.5 Hz, 1H) 7.95 (d, J = 9.0 Hz, 2 H) 7.89-7.81 (m, 2 H) 7.36 (d, J = 8.8 Hz, 2 H) 6.59 (d, J = 2.0 Hz, 1 H) 4.90-4.71 (m, 1 H) 3.95 (s, 3 H) 1.35 (d, J = 6.6 Hz, 6 H). | E |
| 141 | 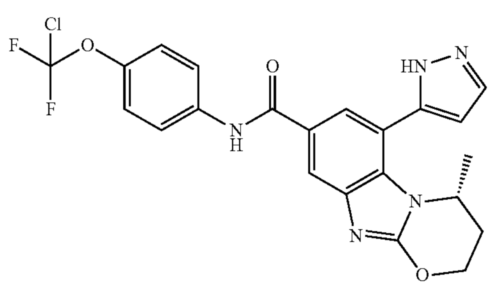 [SMILES: C[C@@H]1CCOc2nc3cc(C(=O)Nc4ccc(OC(F)(F)Cl)cc4)cc(-c4ccn[nH]4)c3n21] | 474.1 | ¹H NMR (400 MHz, MeOD-d₄) δ 8.16 (d, J = 1.7 Hz, 1H), 8.03 (d, J = 1.7 Hz, 1H), 7.91 (d, J = 2.3 Hz, 1H), 7.88-7.82 (m, 2H), 7.32 (d, J = 9.0 Hz, 2H), 6.77 (d, J = 2.3 Hz, 1H), 5.30-5.22 (m, 1H), 4.86-4.81 (m, 2H), 2.65 (dt, J = 6.3, 15.5 Hz, 1H), 2.15 (dd, J = 2.4, 15.1 Hz, 1H), 1.08 (d, J = 6.6 Hz, 3H). | N |
| 142 | 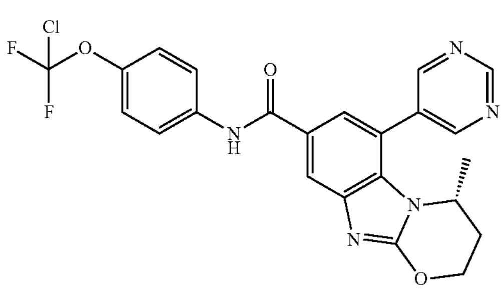 [SMILES: C[C@@H]1CCOc2nc3cc(C(=O)Nc4ccc(OC(F)(F)Cl)cc4)cc(-c4cncnc4)c3n21] | 486.1 | ¹H NMR (400 MHz, CDCl₃-d) δ 9.35 (s, 1H), 8.93 (br s, 2H), 8.08 (br s, 2H), 7.73 (br d, J = 9.0 Hz, 2H), 7.64 (s, 1H), 7.30-7.27 (m, 2H), 4.56 (br d, J = 9.5 Hz, 2H), 4.22 (br s, 1H), 2.55 (br s, 1H), 1.90 (br d, J = 14.1 Hz, 1H), 0.98 (d, J = 6.4 Hz, 3H). | N |

TABLE 1-continued

| Example | Structure | LCMS m/z | ¹H NMR | General Procedure |
|---|---|---|---|---|
| 143 | 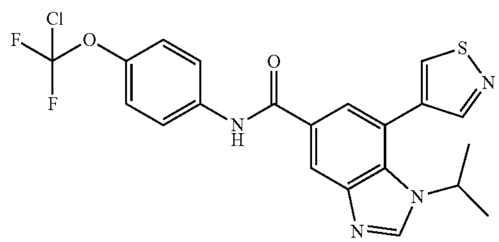 [SMILES: CC(C)n1cnc2cc(C(=O)Nc3ccc(OC(F)(F)Cl)cc3)cc(-c3cnsc3)c21] | 463.0 | ¹H NMR (400 MHz, MeOD-d₄) δ 9.13 (s, 1 H) 8.74 (s, 1 H) 8.55 (s, 1 H) 8.40 (d, J = 1.7 Hz, 1 H) 7.84 (d, J = 9.2 Hz, 2 H) 7.81 (d, J= 1.7 Hz, 1 H) 7.29 (d, J = 9.0 Hz, 2 H) 4.33-4.16 (m, 1 H) 1.40 (d, J = 6.7 Hz, 6 H) | E, I |
| 144 | 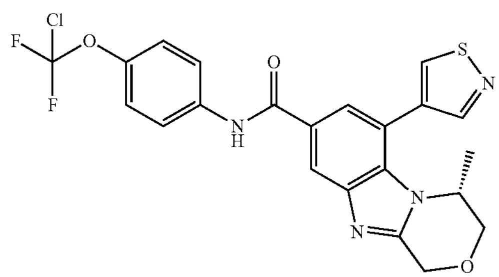 [SMILES: C[C@@H]1COCc2nc3cc(C(=O)Nc4ccc(OC(F)(F)Cl)cc4)cc(-c4cnsc4)c3n21] | 491.0 | ¹H NMR (400 MHz, MeOD-d₄) δ 9.17 (s, 1 H) 8.79 (s, 1H) 8.32 (d, J = 1.7 Hz, 1H) 7.87-7.84 (m, 1 H) 7.83-7.80 (m, 2H) 7.29 (d, J = 9.0 Hz, 2 H) 5.13-5.04 (m, 1H) 5.02-4.94 (m, 1 H) 4.27-4.18 (m, 1 H) 4.16-4.07 (m, 1 H) 3.95 (d, J = 12.1 Hz, 1 H) 1.02 (d, J = 6.5 Hz, 3 H) | G, I |
| 145 | 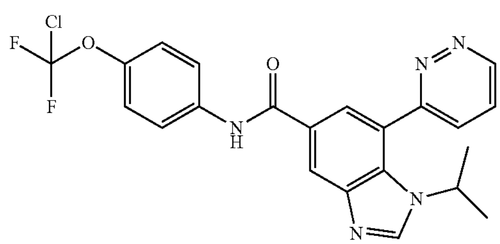 [SMILES: CC(C)n1cnc2cc(C(=O)Nc3ccc(OC(F)(F)Cl)cc3)cc(-c3cccnn3)c21] | 458.1 | ¹H NMR (400 MHz, MeOD-d₄) δ 9.34 (dd, J = 5.0, 1.5 Hz, 1 H) 8.61 (s, 1 H) 8.51 (d, J = 1.6 Hz, 1 H) 8.17 (dd, J = 8.4, 1.5 Hz, 1 H) 8.00-7.94 (m, 2 H) 7.88-7.83 (m, 2 H) 7.31 (d, J = 9.0 Hz, 2H) 4.49-4.34 (m, 1 H) 1.38 (d, 6.7 Hz, 6 H) | M |
| 146 | 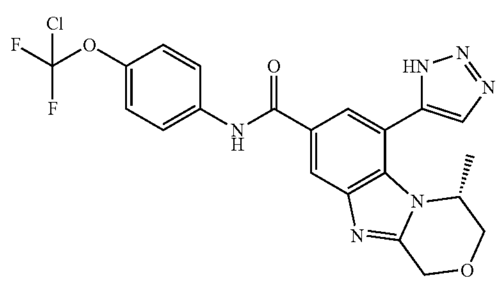 [SMILES: C[C@@H]1COCc2nc3cc(C(=O)Nc4ccc(OC(F)(F)Cl)cc4)cc(-c4cnn[nH]4)c3n21] | 475.1 | ¹H NMR (400 MHz, DMSO-d₆) δ 10.49 (s, 1 H) 8.39 (d, J = 1.6 Hz, 2 H) 8.05-7.80 (m, 3 H) 7.37 (d, J = 9.0 Hz, 2 H) 5.13-4.94 (m, 2 H) 4.94-4.82 (m, 1 H) 4.00 (s, 2 H) 0.87 (d, J = 6.5 Hz, 3 H). | G, L |
| 147 | 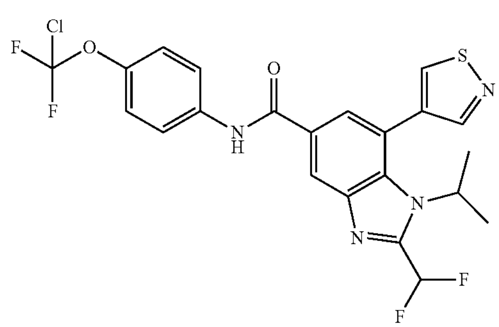 [SMILES: CC(C)n1c(C(F)F)nc2cc(C(=O)Nc3ccc(OC(F)(F)Cl)cc3)cc(-c3cnsc3)c21] | 513.1 | ¹H NMR (400 MHz, CDCl₃-d) δ 8.67 (s, 1H), 8.54 (s, 1H), 8.26 (d, J = 1.8 Hz, 1H), 7.91 (s, 1H), 7.71 (d, J = 1.5 Hz, 1H), 7.68-7.61 (m, 2H), 7.21 (s, 1H), 7.19-7.18 (m, 1H), 7.11-6.78 (m, 1H), 4.51 (td, J = 6.9, 14.0 Hz, 1H), 1.35 (d, J = 7.1 Hz, 6H). | E |

TABLE 1-continued

| Example | Structure | LCMS m/z | ¹H NMR | General Procedure |
|---|---|---|---|---|
| 148 | 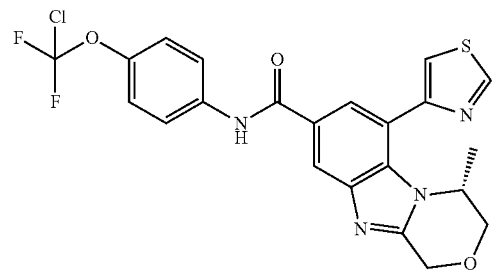 [SMILES: C[C@@H]1COCc2nc3cc(C(=O)Nc4ccc(OC(F)(F)Cl)cc4)cc(-c4cscn4)c3n21] | 491.1 | ¹H NMR (400 MHz, DMSO-$d_6$) δ 10.49 (s, 1H), 9.33 (d, J = 1.6 Hz, 1H), 8.38 (s, 1H), 8.15 (d, J = 1.6 Hz, 1H), 8.01-7.89 (m, 3H), 7.36 (br d, J = 8.6 Hz, 2H), 5.10-4.92 (m, 2H), 4.86-4.78 (m, 1H), 4.18-3.87 (m, 2H), 0.84 (br d, J = 6.5 Hz, 3H) | G |
| 149 | 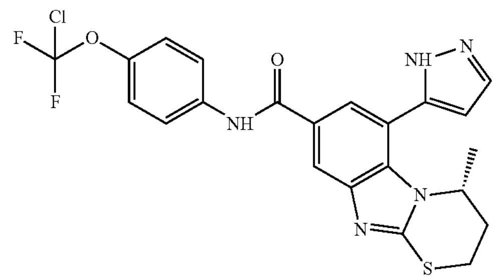 [SMILES: C[C@@H]1CCSc2nc3cc(C(=O)Nc4ccc(OC(F)(F)Cl)cc4)cc(-c4ccn[nH]4)c3n21] | 490.1 | ¹H NMR (400 MHz, MeOD-$d_4$) δ 8.25 (s, 1H), 8.06 (s, 1H), 7.92 (d, J = 1.3 Hz, 1H), 7.84 (d, J = 8.8 Hz, 2H), 7.30 (d, J = 8.8 Hz, 2H), 6.76 (s, 1H), 5.39 (br d, J = 5.7 Hz, 1H), 3.66-3.55 (m, 1H), 3.39 (br d, J = 12.7 Hz, 1H), 2.46 (br d, J = 3.5 Hz, 2H), 1.13 (d, J = 6.6 Hz, 3H). | N |
| 150 | 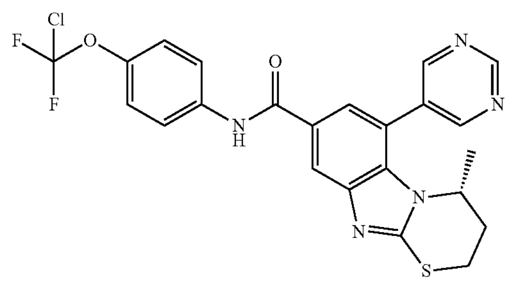 | 502.1 | ¹H NMR (400 MHz, MeOD-$d_4$) δ 9.30 (d, J = 1.1 Hz, 1H), 9.08 (br s, 2H), 8.20 (s, 1H), 7.86-7.78 (m, 2H), 7.68 (s, 1H), 7.28 (br d, J = 8.2 Hz, 2H), 4.36 (br s, 1H), 3.58-3.42 (m, 1H), 3.12 (br d, J = 13.5 Hz, 1H), 2.49-2.35 (m, 1H), 2.33-2.21 (m, 1H), 1.04 (d, J = 6.6 Hz, 3H). | N |
| 151 | 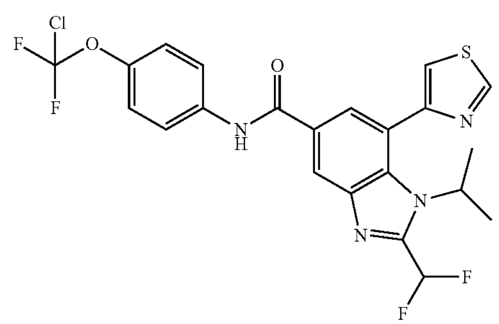 [SMILES: CC(C)n1c(C(F)F)nc2cc(C(=O)Nc3ccc(OC(F)(F)Cl)cc3)cc(-c3cscn3)c21] | 513.1 | ¹H NMR (400 MHz, CDCl$_3$-d) δ 8.98 (br s, 1H), 8.34 (s, 1H), 7.96 (br s, 1H), 7.89 (br s, 1H), 7.71 (br d, J = 7.1 Hz, 2H), 7.59 (br s, 1H), 7.26 (s, 2H), 7.17-6.88 (m, 1H), 4.72-4.58 (m, 1H), 1.46-1.39 (m, 1H), 1.44 (br d, J = 6.4 Hz, 6H) | E, I |
| 152 | 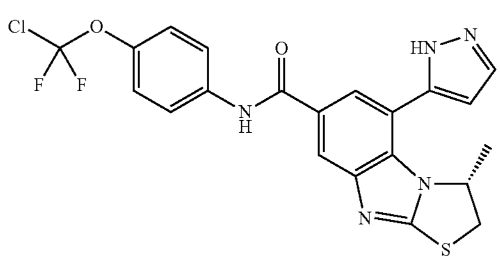 [SMILES: C[C@@H]1CSc2nc3cc(C(=O)Nc4ccc(OC(F)(F)Cl)cc4)cc(-c4ccn[nH]4)c3n21] | 476.0 | ¹H NMR (400 MHz, MeOD-$d_4$) δ 8.13 (s, 1H), 7.95 (s, 1H), 7.87-7.79 (m, 3H), 7.33-7.26 (m, 2H), 6.75 (d, J = 2.2 Hz, 1H), 5.52-5.38 (m, 1H), 4.33 (dd, J = 7.5, 11.2 Hz, 1H), 3.60-3.51 (m, 1H), 0.99-0.93 (m, 3H). | N |

TABLE 1-continued

| Example | Structure | LCMS m/z | ¹H NMR | General Procedure |
|---|---|---|---|---|
| 153 | 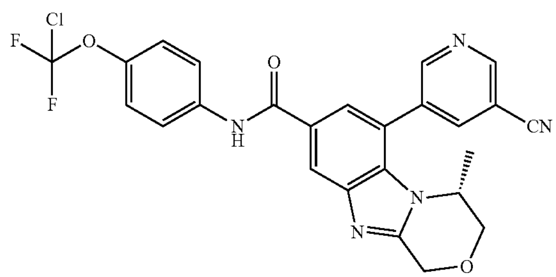 [SMILES: C[C@@H]1COCc2nc3cc(C(=O)Nc4ccc(OC(F)(F)Cl)cc4)cc(-c4cncc(C#N)c4)c3n21] | 510.1 | ¹H NMR (400 MHz, DMSO-d₆) δ 10.45 (s, 1H), 9.21-9.13 (m, 2H), 8.75-8.62 (m, 1H), 8.43 (d, J = 1.3 Hz, 1H), 7.97-7.90 (m, 2H), 7.80 (s, 1H), 7.37 (d, J = 8.8 Hz, 2H), 5.12-4.90 (m, 2H), 4.14-3.95 (m, 2H), 3.90 (d, J = 11.2 Hz, 1H), 0.83 (br d, J = 6.4 Hz, 3H). | G |
| 154 | 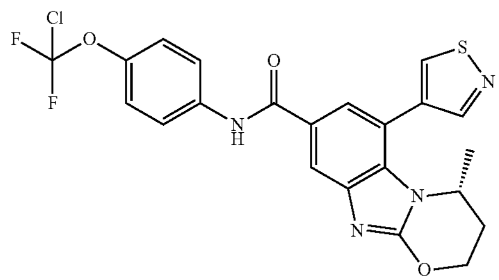 [SMILES: C[C@@H]1CCOc2nc3cc(C(=O)Nc4ccc(OC(F)(F)Cl)cc4)cc(-c4cnsc4)c3n21] | 491.1 | ¹H NMR (400 MHz, MeOD-d₄) δ 9.14 (s, 1 H) 8.78 (s, 1H) 8.08 (d, J = 1.5 Hz, 1 H) 7.91-7.77 (m, 2 H) 7.69 (d, J = 1.8 Hz, 1 H) 7.28 (d, J = 9.3 Hz, 2 H) 4.67-4.53 (m, 2 H) 4.39 (td, J = 6.0, 2.3 Hz, 1 H) 2.63-2.44 (m, 1 H) 1.99-1.93 (m, 1 H) 1.00 (d, J = 6.4 Hz, 3 H) | N |
| 155 | 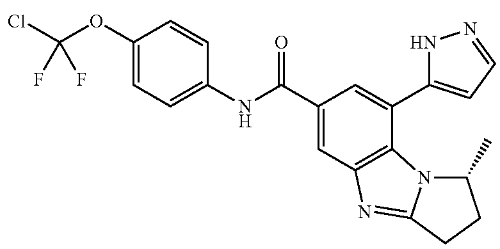 [SMILES: C[C@@H]1CCc2nc3cc(C(=O)Nc4ccc(OC(F)(F)Cl)cc4)cc(-c4ccn[nH]4)c3n21] | 458.1 | ¹H NMR (400 MHz, MeOD-d₄) δ 8.23 (s, 1H), 7.98 (s, 1H), 7.89-7.82 (m, 3H), 7.30 (d, J = 8.8 Hz, 2H), 6.73 (d, J = 2.0 Hz, 1H), 5.06 (br s, 1H), 3.22-2.91 (m, 3H), 2.36-2.26 (m, 1H), 0.86 (d, J = 6.6 Hz, 3H). | G |
| 156 | 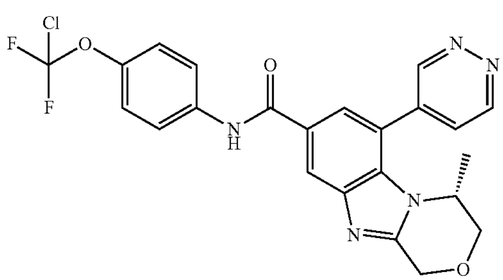 [SMILES: C[C@@H]1COCc2nc3cc(C(=O)Nc4ccc(OC(F)(F)Cl)cc4)cc(-c4ccnnc4)c3n21] | 486.1 | ¹H NMR (400 MHz, DMSO-d₆) δ 10.48 (s, 1H), 9.61 (s, 1H), 9.42 (d, J = 5.1 Hz, 1H), 8.46 (d, J = 1.5 Hz, 1H), 8.05 (dd, J = 2.3, 5.2 Hz, 1H), 7.93 (d, J = 9.0 Hz, 2H), 7.84 (d, J = 1.5 Hz, 1H), 7.37 (d, J = 9.0 Hz, 2H), 5.16-4.87 (m, 2H), 4.23-4.02 (m, 2H), 3.97-3.86 (m, 1H), 0.79 (d, J = 6.6 Hz, 3H). | G, I |
| 157 | 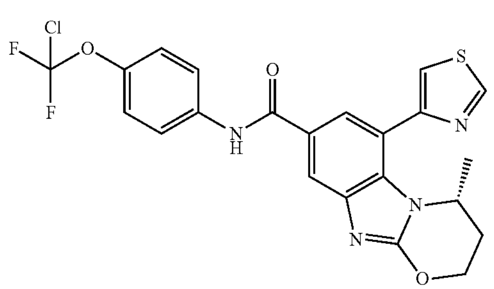 [SMILES: C[C@@H]1CCOc2nc3cc(C(=O)Nc4ccc(OC(F)(F)Cl)cc4)cc(-c4cscn4)c3n21] | 491.1 | ¹H NMR (400 MHz, DMSO-d6) δ 10.41 (s, 1H), 9.32 (d, J = 1.5 Hz, 1H), 8.17-8.08 (m, 2H), 7.93 (br d, J = 9.3 Hz, 2H), 7.78 (s, 1H), 7.35 (br d, J = 8.3 Hz, 2H), 4.89 (br s, 1H), 4.60-4.45 (m, 2H), 2.33 (br s, 1H), 1.92 (br d, J = 12.2 Hz, 1H), 0.83 (br d, J = 6.4 Hz, 3H). | N, I |

TABLE 1-continued

| Example | Structure | LCMS m/z | ¹H NMR | General Procedure |
|---|---|---|---|---|
| 158 | 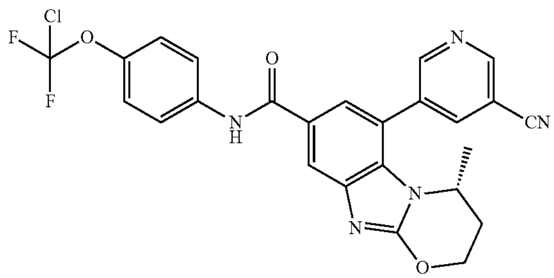 [SMILES: C[C@@H]1CCOc2nc3cc(C(=O)Nc4ccc(OC(F)(F)Cl)cc4)cc(-c4cncc(C#N)c4)c3n21] | 510.2 | ¹H NMR (400 MHz, MeOD-d$_4$) δ 9.12-9.03 (m, 2H), 8.52 (br s, 1H), 8.11 (d, J = 1.7 Hz, 1H), 7.87-7.78 (m, 2H), 7.67 (d, J = 1.6 Hz, 1H), 7.28 (d, J = 9.0 Hz, 2H), 4.70-4.52 (m, 2H), 4.26 (br s, 1H), 2.65-2.45 (m, 1H), 2.08-1.90 (m, 1H), 0.96 (d, J = 6.5 Hz, 3H) | N |
| 159 | 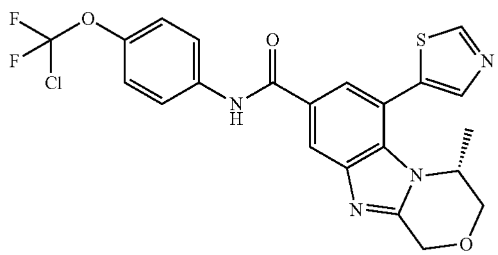 [SMILES: C[C@@H]1COCc2nc3cc(C(=O)Nc4ccc(OC(F)(F)Cl)cc4)cc(-c4cncs4)c3n21] | 491.0 | ¹H NMR (400 MHz, MeOD-d$_4$) δ 9.21 (s, 1 H) 8.36 (d, J = 1.6 Hz, 1 H) 8.12 (s, 1H) 7.90 (d, J = 1.6 Hz, 1 H) 7.84 (d, J = 9.0 Hz, 2 H) 7.30 (d, J = 8.9 Hz, 2 H) 5.14-5.08 (m, 1 H) 5.01 (s, 1 H) 4.45-4.34 (m, 1 H) 4.13 (dd, J = 12.2, 2.9 Hz, 1 H) 3.97 (d, J = 12.1 Hz, 1 H) 1.12 (d, J = 6.6 Hz, 3 H) | G |
| 160 | 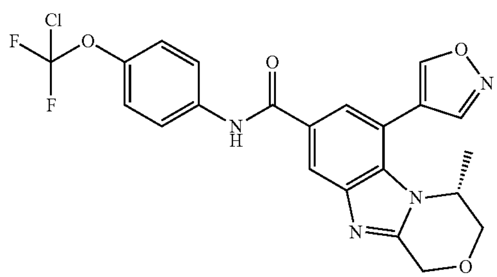 | 475.2 | ¹H NMR (400 MHz, MeOD-d$_4$) δ 9.09 (s, 1 H) 8.81 (s, 1H) 8.32 (d, J = 1.3 Hz, 1 H) 7.90-7.77 (m, 3 H) 7.30 (d, J = 8.9 Hz, 2 H) 5.09 (s, 1 H) 5.00 (s, 1 H) 4.37 (br dd, J = 6.8, 2.1 Hz, 1 H) 4.14 (br dd, J = 12.2, 2.8 Hz, 1 H) 4.01 (d, J = 12.0 Hz, 1 H) 1.16 (d, J = 6.6 Hz, 3 H) | G |
| 161 | 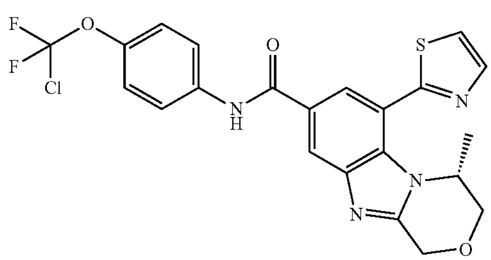 [SMILES: C[C@@H]1COCc2nc3cc(C(=O)Nc4ccc(OC(F)(F)Cl)cc4)cc(-c4nccs4)c3n21] | 491.1 | ¹H NMR (400 MHz, MeOD-d$_4$) δ = 8.42 (d, J = 1.5 Hz, 1H), 8.13 (d, J = 1.5 Hz, 1H), 8.05 (d, J = 3.4 Hz, 1H), 7.87 (s, 1H), 7.86-7.83 (m, 2H), 7.31 (br d, J = 8.8 Hz, 2H), 5.23-5.20 (m, 1H), 5.15-4.99 (m, 2H), 4.20 (dd, J = 3.2, 12.5 Hz, 1H), 4.02 (d, J = 12.2 Hz, 1H), 0.99 (d, J = 6.4 Hz, 3H) | G, M |
| 162 | 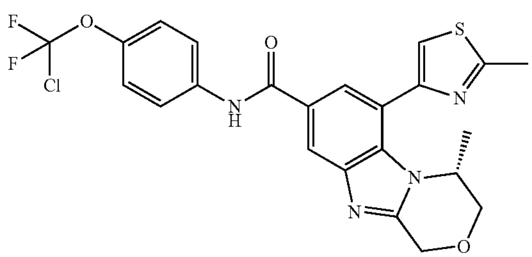 [SMILES: Cc1nc(-c2cc(C(=O)Nc3ccc(OC(F)(F)Cl)cc3)cc3nc4n(c23)[C@H](C)COC4)cs1] | 505.1 | ¹H NMR (400 MHz, MeOD-d$_4$) δ 8.33 (s, 1H), 7.96 (s, 1H), 7.85 (br d, J = 9.2 Hz, 2H), 7.72 (s, 1H), 7.31 (br d, J = 8.2 Hz, 2H), 5.13-5.00 (m, 2H), 4.65-4.54 (m, 1H), 4.16 (br d, J = 9.9 Hz, 1H), 4.02-3.97 (m, 1H), 2.82 (s, 3H), 1.04-0.99 (m, 3H). | G |

TABLE 1-continued

| Example | Structure | LCMS m/z | ¹H NMR | General Procedure |
|---|---|---|---|---|
| 163 | 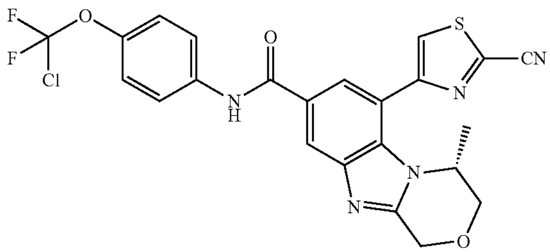 [SMILES: C[C@@H]1COCc2nc3cc(C(=O)Nc4ccc(OC(F)(F)Cl)cc4)cc(-c4csc(C#N)n4)c3n21] | 516.1 | ¹H NMR (400 MHz, MeOD-d$_4$) δ 8.43 (s, 1H), 8.38 (d, J = 1.3 Hz, 1H), 8.01 (d, J = 1.8 Hz, 1H), 7.85 (d, J = 9.2 Hz, 2H), 7.31 (d, J = 8.8 Hz, 2H), 5.14-4.97 (m, 2H), 4.80-4.74 (m, 1H), 4.19 (dd, J = 3.1, 12.3 Hz, 1H), 4.02 (d, J = 12.3 Hz, 1H), 1.03 (d, J = 6.6 Hz, 3H) | G, M |
| 164 | 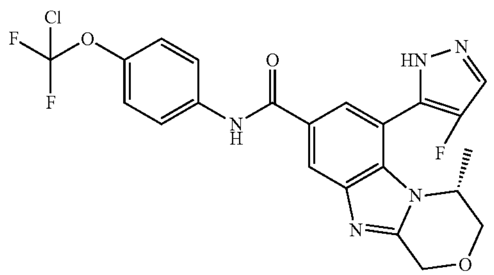 [SMILES: C[C@@H]1COCc2nc3cc(C(=O)Nc4ccc(OC(F)(F)Cl)cc4)cc(-c4[nH]ncc4F)c3n21] | 492.0 | ¹H NMR (400 MHz, MeOD-d$_4$) δ 8.35 (d, J = 1.3 Hz, 1H), 7.97 (s, 1H), 7.87-7.80 (m, 3H), 7.29 (d, J = 8.8 Hz, 2H), 5.16-4.95 (m, 2H), 4.76 (br s, 1H), 4.14 (dd, J = 3.2, 12.5 Hz, 1H), 4.00 (d, J = 12.1 Hz, 1H), 1.09 (d, J = 6.4 Hz, 3H). | G, M |
| 165 | 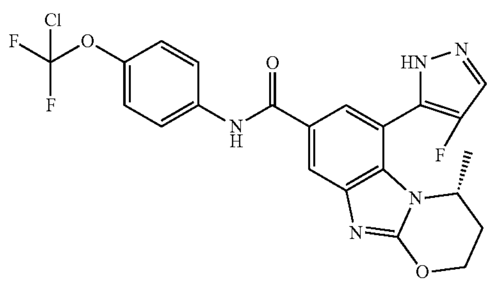 [SMILES: C[C@@H]1CCOc2nc3cc(C(=O)Nc4ccc(OC(F)(F)Cl)cc4)cc(-c4[nH]ncc4F)c3n21] | 492.0 | ¹H NMR (400 MHz, MeOD-d$_4$) δ 8.17 (s, 1H), 7.98 (s, 1H), 7.87 (d, J = 4.6 Hz, 1H), 7.83 (d, J = 9.0 Hz, 2H), 7.30 (br d, J = 8.6 Hz, 2H), 5.04 (br s, 1H), 4.80 (br d, J = 7.7 Hz, 2H), 2.61 (br d, J = 8.2 Hz, 1H), 2.13 (br d, J = 14.8 Hz, 1H), 1.14 (d, J = 6.4 Hz, 3H). | N, M |
| 166 | 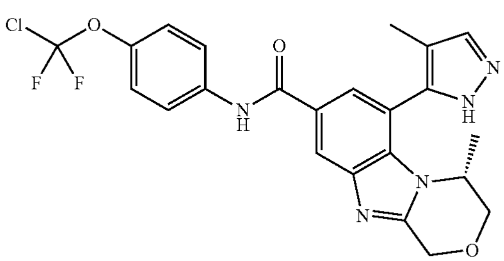 [SMILES: Cc1cn[nH]c1-c1cc(C(=O)Nc2ccc(OC(F)(F)Cl)cc2)cc2nc3n(c12)[C@H](C)COC3] | 488.1 | ¹H NMR (400 MHz, MeOD-d$_4$) δ 8.33 (s, 1H), 7.88-7.81 (m, 3H), 7.66 (br s, 1H), 7.29 (d, J = 8.8 Hz, 2H), 5.15-4.95 (m, 2H), 4.49 (br s, 1H), 4.10 (dd, J = 2.9, 12.1Hz, 1H), 3.95 (d, J= 12.1 Hz, 1H), 2.10 (br s, 3H), 1.03 (br d, J = 6.4 Hz, 3H). | G |
| 167 | 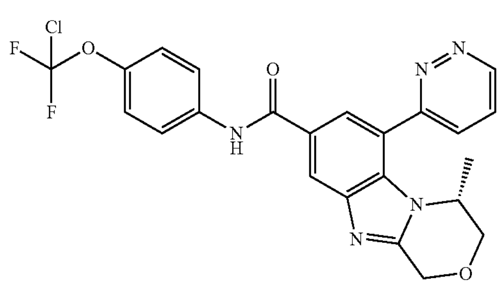 [SMILES: C[C@@H]1COCc2nc3cc(C(=O)Nc4ccc(OC(F)(F)Cl)cc4)cc(-c4cccnn4)c3n21] | 486.1 | ¹H NMR (400 MHz, MeOD-d$_4$) δ 9.33 (dd, J = 1.5, 4.9 Hz, 1H), 8.44 (d, J = 1.6 Hz, 1H), 8.23 (dd, J = 1.5, 8.6 Hz, 1H), 8.03 (d, J = 1.6 Hz, 1H), 7.97 (dd, J = 5.0, 8.6 Hz, 1H), 7.85 (d, J = 9.2 Hz, 2H), 7.30 (d, J = 9.2 Hz, 2H), 5.07 (q, J = 16.1 Hz, 2H), 4.78 (br s, 1H), 4.30-3.88 (m, 2H), 0.88 (d, J = 6.6 Hz, 3H). | G, Q |

TABLE 1-continued

| Example | Structure | LCMS m/z | ¹H NMR | General Procedure |
|---|---|---|---|---|
| 168 | 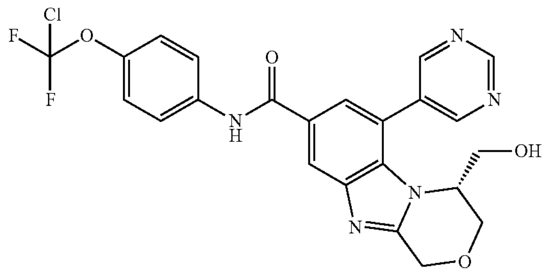 [SMILES: O=C(Nc1ccc(OC(F)(F)Cl)cc1)c1cc(-c2cncnc2)c2c(c1)nc1n2[C@H](CO)COC1] | 502.1 | ¹H NMR (400 MHz, CDCl₃-d) δ 9.37-9.31 (m, 1H), 9.04-8.84 (m, 2H), 8.22 (d, J = 1.5 Hz, 1H), 8.12 (s, 1H), 7.76-7.71 (m, 2H), 7.29 (br s, 1H), 7.27-7.25 (m, 1H), 5.20-5.10 (m, 1H), 5.03-4.92 (m, 1H), 4.32 (d, J = 12.3 Hz, 1H), 4.05 (dd, J = 2.6, 12.5 Hz, 1H), 3.92 (br d, J = 3.5 Hz, 1H), 3.67-3.57 (m, 1H), 3.43 (br d, J = 10.1 Hz, 1H). | O |
| 169 | 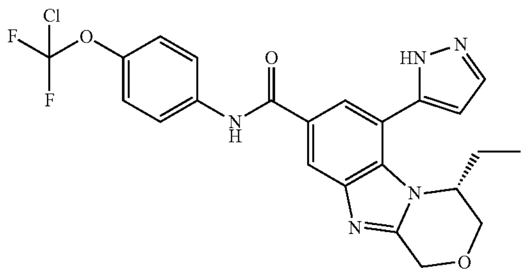 [SMILES: CC[C@@H]1COCc2nc3cc(C(=O)Nc4ccc(OC(F)(F)Cl)cc4)cc(-c4ccn[nH]4)c3n21] | 488.1 | ¹H NMR (400 MHz, MeOD-d₄) δ 8.16-8.22 (m, 1H), 7.83 (d, J = 1.0 Hz, 1H), 7.79-7.71 (m, 3H), 7.19 (d, J = 8.9 Hz, 2H), 6.61-6.56 (m, 1H), 5.00-4.84 (m, 2H), 4.64-4.43 (m, 1H), 4.11-4.05 (m, 1H), 4.00-3.91 (m, 1H), 1.60-1.44 (m, 1H), 1.22-1.02 (m, 1H), 0.48-0.39 (m, 3H) | G |
| 170 | 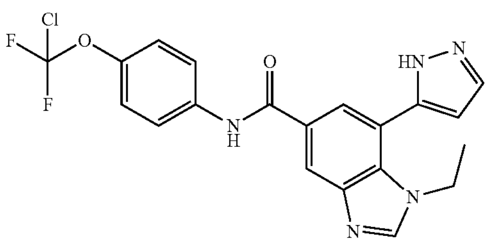 [SMILES: CCn1cnc2cc(C(=O)Nc3ccc(OC(F)(F)Cl)cc3)cc(-c3ccn[nH]3)c21] | 432.1 | ¹H NMR (400 MHz, MeOD-d₄) δ 8.47-8.28 (m, 2H), 7.94 (s, 1H), 7.90-7.77 (m, 3H), 7.37-7.20 (m, 2H), 6.73-6.54 (m, 1H), 4.38-4.02 (m, 2H), 1.10-0.98 (m, 3H). | E |
| 171 | (Stereochemistry is arbitrarily assigned*) | 474.1 | ¹H NMR (400 MHz, MeOD-d₄) δ 8.22 (s, 1H), 7.86-7.76 (m, 4H), 7.25 (d, J = 9.3 Hz, 2H), 6.59 (d, J = 2.0 Hz, 1H), 5.34-5.25 (m, 1H), 4.33 (br d, J = 4.9 Hz, 1H), 2.18-2.12 (m, 1H), 2.10-2.04 (m, 1H), 2.02-1.90 (m, 2H). | P |
| 172 | (Stereochemistry is arbitrarily assigned) | 474.1 | ¹H NMR (400 MHz, MeOD-d₄) δ 8.16 (s, 1H), 7.77-7.72 (m, 2H), 7.71 (br s, 1H), 7.19 (d, J = 9.3 Hz, 2H), 6.52 (d, J = 2.0 Hz, 1H), 5.27-5.21 (m, 1H), 4.26 (br d, J = 4.9 Hz, 1H), 3.00 (dd, J = 4.9, 17.1 Hz, 1H), 2.12-2.07 (m, 1H), 2.05-1.98 (m, 1H), 1.98-1.91 (m, 2H) | P |

TABLE 1-continued

| Example | Structure | LCMS m/z | ¹H NMR | General Procedure |
|---|---|---|---|---|
| 173 | 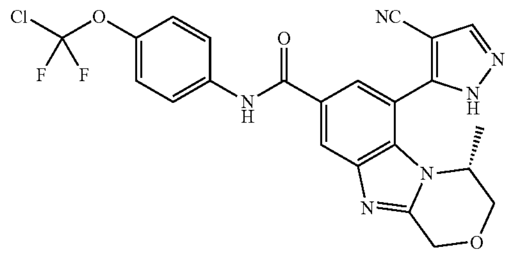 [SMILES: C[C@@H]1COCc2nc3cc(C(=O)Nc4ccc(OC(F)(F)Cl)cc4)cc(-c4[nH]ncc4C#N)c3n21] | 499.1 | ¹H NMR (400 MHz, MeOD-d₄) δ 8.62-8.47 (m, 1H), 8.41 (s, 1H), 8.05 (s, 1H), 7.85 (d, J = 9.0 Hz, 2H), 7.30 (d, J = 9.0 Hz, 2H), 5.21-4.94 (m, 2H), 4.78-4.63 (m, 1H), 4.23-3.93 (m, 2H), 1.05 (d, J = 6.6 Hz, 3H). | G, M |
| 174 | 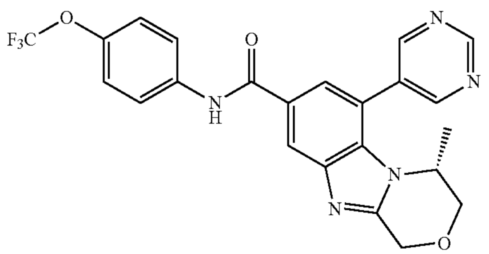 [SMILES: C[C@@H]1COCc2nc3cc(C(=O)Nc4ccc(OC(F)(F)F)cc4)cc(-c4cncnc4)c3n21] | 470.1 | ¹H NMR (400 MHz, MeOD-d₄) δ 9.31 (s, 1H), 9.11 (s, 2H), 8.38 (d, J = 1.5 Hz, 1H), 7.89-7.79 (m, 3H), 7.29 (d, J = 8.4 Hz, 2H), 5.17-4.94 (m, 2H), 4.21-4.09 (m, 2H), 3.95 (d, J = 11.5 Hz, 1H), 1.04-0.95 (m, 3H). | G |
| 175 | 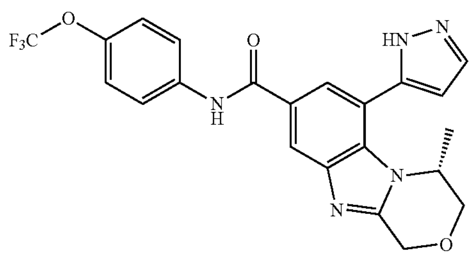 [SMILES: C[C@@H]1COCc2nc3cc(C(=O)Nc4ccc(OC(F)(F)F)cc4)cc(-c4ccn[nH]4)c3n21] | 458.2 | ¹H NMR (400 MHz, MeOD-d₄) δ 8.29 (s, 1H), 7.95 (s, 1H), 7.90-7.80 (m, 3H), 7.29 (d, J = 8.4 Hz, 2H), 6.71 (d, J = 2.0 Hz, 1H), 5.13-4.93 (m, 3H), 4.16 (br dd, J = 3.0, 12.0 Hz, 1H), 3.98 (d, J = 12.1 Hz, 1H), 1.00 (br d, J = 6.4 Hz, 3H). | G |
| 176 | 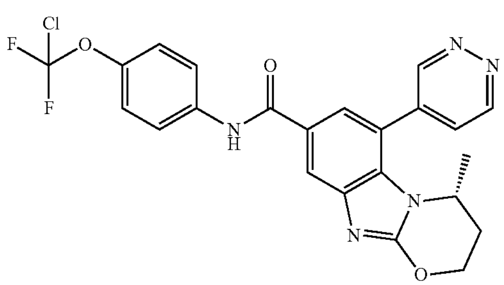 [SMILES: C[C@@H]1CCOc2nc3cc(C(=O)Nc4ccc(OC(F)(F)Cl)cc4)cc(-c4ccnnc4)c3n21] | 486.1 | ¹H NMR (400 MHz, MeOD-d₄) δ 9.44 (d, J = 1.0 Hz, 1H), 9.27 (dd, J = 1.0, 5.3 Hz, 1H), 8.06 (d, J = 1.7 Hz, 1H), 7.91 (dd, J = 2.3, 5.3 Hz, 1H), 7.76-7.69 (m, 2H), 7.62 (d, J = 1.7 Hz, 1H), 7.19 (d, J = 9.0 Hz, 2H), 4.61-4.42 (m, 2H), 4.25 (dt, J = 3.0, 6.2 Hz, 1H), 2.58-2.39 (m, 1H), 1.94-1.83 (m, 1H), 0.87-0.78 (m, 3H). | N, I |
| 177 | 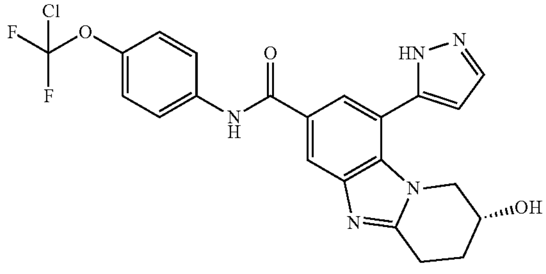 [SMILES: O=C(Nc1ccc(OC(F)(F)Cl)cc1)c1cc(-c2ccn[nH]2)c2c(c1)nc1n2C[C@H](O)CC1] | 474.1 | ¹H NMR (400 MHz, MeOD-d₄) δ 8.25 (s, 1H), 7.86-7.80 (m, 4H), 7.28 (d, J = 8.7 Hz, 2H), 6.63 (d, J = 1.7 Hz, 1H), 4.25 (br t, J = 4.0 Hz, 1H), 4.00 (br dd, J = 3.4, 13.0 Hz, 1H), 3.75 (br dd, J = 3.4, 13.2 Hz, 1H), 3.28-3.22 (m, 1H), 3.17-3.04 (m, 1H), 2.15-2.05 (m, 2H). | P |

TABLE 1-continued

| Example | Structure | LCMS m/z | ¹H NMR | General Procedure |
|---|---|---|---|---|
| 178 | 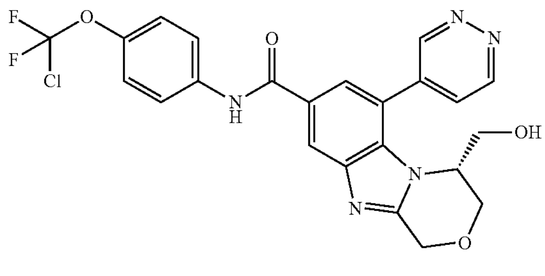 [SMILES: O=C(Nc1ccc(OC(F)(F)Cl)cc1)c1cc(-c2ccnnc2)c2c(c1)nc1n2[C@H](CO)COC1] | 502.1 | ¹H NMR (400 MHz, CDCl₃-d) δ 9.22 (d, J = 5.1 Hz, 2H), 9.04 (s, 1H), 8.14 (s, 1H), 7.75 (d, J = 9.0 Hz, 2H), 7.70 (d, J = 1.3 Hz, 2H), 7.21 (d, J = 8.9 Hz, 2H), 5.08-5.00 (m, 1H), 4.89 (d, J = 16.3 Hz, 1H), 4.30 (br d, J = 11.5 Hz, 1H), 4.05 (br d, J = 10.1 Hz, 2H), 3.56 (br dd, J = 7.1, 10.8 Hz, 1H), 3.47-3.36 (m, 1H). | O, I |
| 179 | 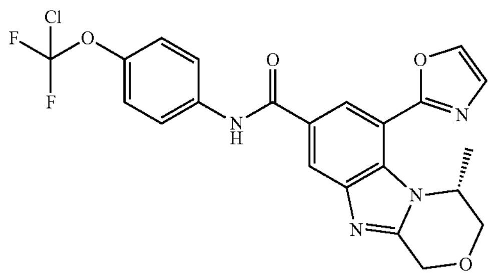 [SMILES: C[C@@H]1COCc2nc3cc(C(=O)Nc4ccc(OC(F)(F)Cl)cc4)cc(-c4ncco4)c3n21] | 475.1 | ¹H NMR (400 MHz, MeOD-d₄) δ 8.40 (dd, J = 2.0, 11.2 Hz, 2H), 8.16 (s, 1H), 7.87-7.84 (m, 2H), 7.45 (d, J = 1.0 Hz, 1H), 7.30 (d, J = 9.3 Hz, 2H), 5.67 (br dd, J = 2.0, 6.8 Hz, 1H), 5.14-4.98 (m, 2H), 4.23 (dd, J = 3.4, 12.2 Hz, 1H), 4.07 (d, J = 12.2 Hz, 1H), 1.16 (d, J = 6.4 Hz, 3H). | G, I |
| 180 | 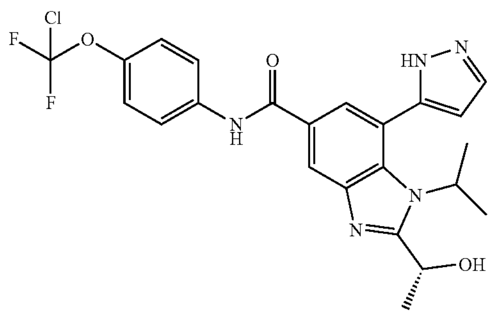 [SMILES: CC(C)n1c([C@@H](C)O)nc2cc(C(=O)Nc3ccc(OC(F)(F)Cl)cc3)cc(-c3ccn[nH]3)c21] | 490.1 | ¹H NMR (400 MHz, MeOD-d₄) δ 8.34 (br s, 1H), 7.90-7.79 (m, 4H), 7.30 (d, J = 8.8 Hz, 2H), 6.61 (d, J = 2.4 Hz, 1H), 5.30 (q, J = 6.4 Hz, 1H), 4.76-4.76 (m, 1H), 4.77 (br s, 1H), 1.73 (d, J = 6.4 Hz, 3H), 1.46 (dd, J = 7.1, 12.0 Hz, 6H). | R |
| 181 | 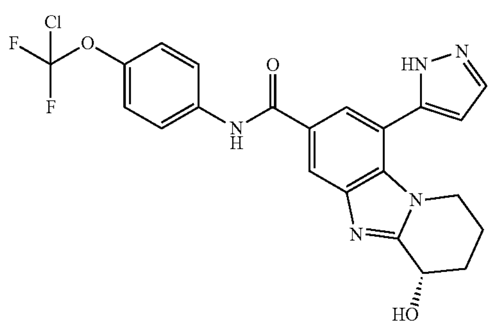 [SMILES: O=C(Nc1ccc(OC(F)(F)Cl)cc1)c1cc(-c2ccn[nH]2)c2c(c1)nc1n2CCC[C@@H]1O] | 474.1 | ¹H NMR (400 MHz, MeOD-d₄) δ 8.39-8.29 (m, 1H), 7.92-7.80 (m, 4H), 7.29 (d, J = 9.2 Hz, 2H), 6.63 (s, 1H), 5.01 (dd, J = 4.3, 6.1 Hz, 1H), 3.96-3.65 (m, 2H), 2.25-1.90 (m, 4H). | P |
| 182 | 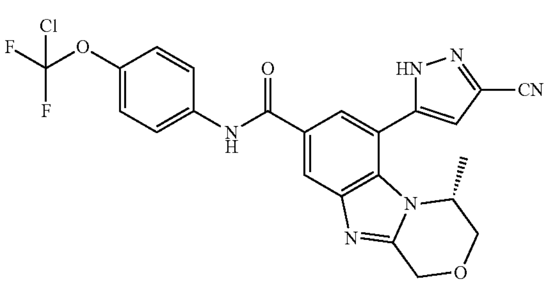 [SMILES: C[C@@H]1COCc2nc3cc(C(=O)Nc4ccc(OC(F)(F)Cl)cc4)cc(-c4cc(C#N)n[nH]4)c3n21] | 499.1 | ¹H NMR (400 MHz, MeOD-d₄) δ 8.40 (s, 1H), 7.94 (d, J = 1.3 Hz, 1H), 7.85 (d, J = 9.0 Hz, 2H), 7.30 (d, J = 9.0 Hz, 2H), 7.22 (s, 1H), 5.16-4.95 (m, 2H), 4.49-4.35 (m, 1H), 4.14 (dd, J = 2.8, 12.2 Hz, 1H), 4.05-3.97 (m, 1H), 1.07 (d, J = 6.4 Hz, 3H). | G, Q |

TABLE 1-continued

| Example | Structure | LCMS m/z | ¹H NMR | General Procedure |
|---|---|---|---|---|
| 183 | 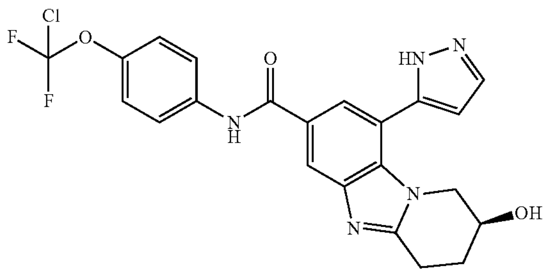 [SMILES: O=C(Nc1ccc(OC(F)(F)Cl)cc1)c1cc(-c2ccn[nH]2)c2c(c1)nc1n2C[C@@H](O)CC1] | 474.1 | ¹H NMR (400 MHz, MeOD-d₄) δ 8.25 (s, 1H), 7.87-7.78 (m, 4H), 7.32-7.25 (m, 2H), 6.63 (d, J = 2.0 Hz, 1H), 4.29-4.21 (m, 1H), 4.06-3.94 (m, 1H), 3.81-3.70 (m, 1H), 3.29-3.22 (m, 1H), 3.15-3.05 (m, 1H), 2.16-2.05 (m, 2H). | P |
| 184 | 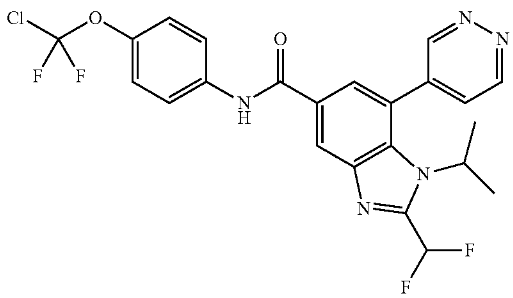 [SMILES: CC(C)n1c(C(F)F)nc2cc(C(=O)Nc3ccc(OC(F)(F)Cl)cc3)cc(-c3ccnnc3)c21] | 508.0 | ¹H NMR (400 MHz, MeOD-d₄) δ 9.53 (dd, J = 1.2, 2.2 Hz, 1H), 9.42 (dd, J = 1.2, 5.1 Hz, 1H), 8.56 (d, J = 2.0 Hz, 1H), 8.03 (dd, J = 2.4, 5.4 Hz, 1H), 7.91 (d, J = 1.5 Hz, 1H), 7.89-7.84 (m, 2H), 7.51-7.36 (m, 1H), 7.32 (d, J = 9.3 Hz, 2H), 4.49 (td, J = 7.2, 13.9 Hz, 1H), 1.54-1.43 (m, 6H). | D, I |
| 185 | 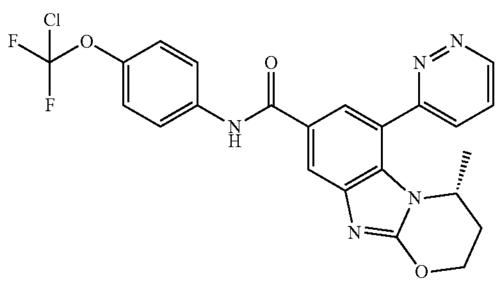 [SMILES: C[C@@H]1CCOc2nc3cc(C(=O)Nc4ccc(OC(F)(F)Cl)cc4)cc(-c4cccnn4)c3n21] | 486.1 | ¹H NMR (400 MHz, MeOD-d₄) δ 9.22 (dd, J = 1.4, 5.0 Hz, 1H), 8.11 (d, J = 1.3 Hz, 1H), 8.09 (d, J = 1.7 Hz, 1H), 7.86 (dd, J = 5.0, 8.6 Hz, 1H), 7.77 (d, J = 1.6 Hz, 1H), 7.76-7.71 (m, 2H), 7.19 (d, J = 9.0 Hz, 2H), 4.79 (br d, J = 2.7 Hz, 1H), 4.60-4.40 (m, 2H), 2.55-2.39 (m, 1H), 1.95-1.79 (m, 1H), 0.76 (d, J = 6.6 Hz, 3H). | N, Q |
| 186 | 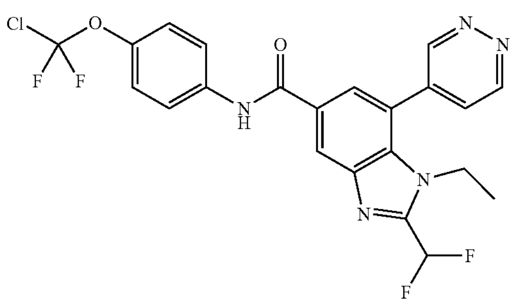 [SMILES: CCn1c(C(F)F)nc2cc(C(=O)Nc3ccc(OC(F)(F)Cl)cc3)cc(-c3ccnnc3)c21] | 494.0 | ¹H NMR (400 MHz, MeOD-d₄) δ 9.60-9.56 (m, 1H), 9.42 (dd, J = 1.2, 5.1 Hz, 1H), 8.58 (d, J = 1.5 Hz, 1H), 8.06 (dd, J = 2.2, 5.1 Hz, 1H), 7.97 (d, J = 1.5 Hz, 1H), 7.90-7.84 (m, 2H), 7.32 (d, J = 9.3 Hz, 2H), 7.26-7.10 (m, 1H), 4.19 (q, J = 7.3 Hz, 2H), 0.99 (t, J = 7.1 Hz, 3H). | I |
| 187 | 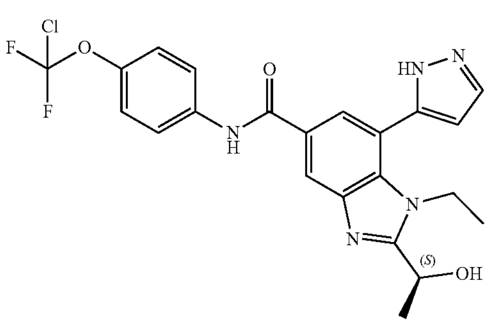 | 476.1 | ¹H NMR (400 MHz, MeOD-d₄) δ 8.33 (s, 1H), 7.89 (s, 1H), 7.87-7.81 (m, 3H), 7.30 (d, J = 8.6 Hz, 2H), 6.66 (s, 1H), 5.18 (q, J = 6.3 Hz, 1H), 4.58-4.29 (m, 2H), 1.74 (d, J = 6.6 Hz, 3H), 0.96 (br t, J = 7.2 Hz, 3H). | R |

TABLE 1-continued

| Example | Structure | LCMS m/z | ¹H NMR | General Procedure |
|---|---|---|---|---|
| 188 | 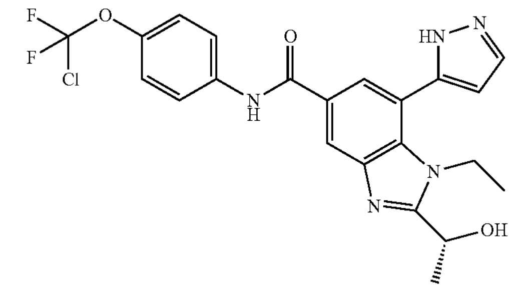 [SMILES: CCn1c([C@@H](C)O)nc2cc(C(=O)Nc3ccc(OC(F)(F)Cl)cc3)cc(-c3ccn[nH]3)c21] | 476.1 | ¹H NMR (400 MHz, MeOD-d₄) δ 8.33 (s, 1H), 7.89 (s, 1H), 7.87-7.81 (m, 3H), 7.30 (d, J = 8.6 Hz, 2H), 6.66 (s, 1H), 5.18 (q, J = 6.3 Hz, 1H), 4.58-4.29 (m, 2H), 1.74 (d, 6.6 Hz, 3H), 0.96 (br t, J = 7.2 Hz, 3H). | R |
| 189 | 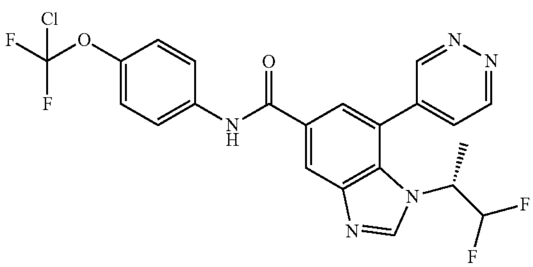 [SMILES: C[C@H](C(F)F)n1cnc2cc(C(=O)Nc3ccc(OC(F)(F)Cl)cc3)cc(-c3ccnnc3)c21] | 493.1 | ¹H NMR (400 MHz, MeOD-d₄) δ 9.46 (s, 1H), 9.39 (d, J = 5.3 Hz, 1H), 8.62 (s, 1H), 8.51 (d, J = 1.5 Hz, 1H), 7.96 (dd, J = 2.3, 5.2 Hz, 1H), 7.87-7.82 (m, 2H), 7.30 (d, J = 9.0 Hz, 2H), 6.13-5.82 (m, 1H), 4.39 (br s, 1H), 1.68 (d, J = 7.1 Hz, 3H) | J |
| 190 | 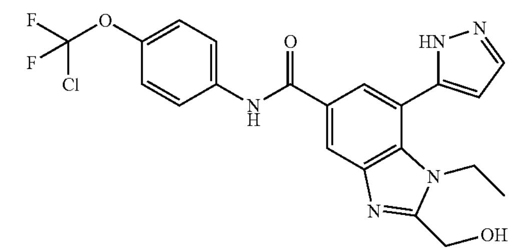 [SMILES: CCn1c(CO)nc2cc(C(=O)Nc3ccc(OC(F)(F)Cl)cc3)cc(-c3ccn[nH]3)c21] | 462.1 | ¹H NMR (400 MHz, MeOD-d₄) δ 8.34 (s, 1H), 7.91 (d, J = 1.5 Hz, 1H), 7.84 (br d, J = 9.0 Hz, 3H), 7.29 (d, J = 9.0 Hz, 2H), 6.66 (d, J = 2.0 Hz, 1H), 4.89 (s, 2H), 4.37 (br d, J = 15.2 Hz, 2H), 0.99 (t, J = 6.9 Hz, 3H) | R |
| 191 | 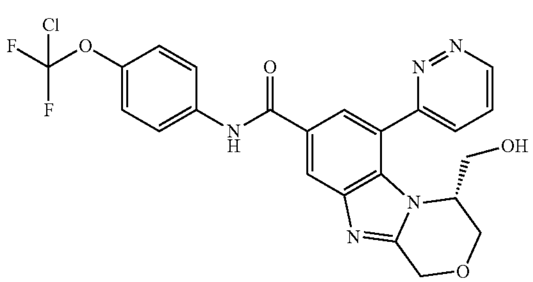 [SMILES: O=C(Nc1ccc(OC(F)(F)Cl)cc1)c1cc(-c2cccnn2)c2c(c1)nc1n2[C@H](CO)COC1] | 502.1 | ¹H NMR (400 MHz, MeOD-d₄) δ 9.29 (dd, J = 1.3, 5.1 Hz, 1H), 8.42 (d, J = 1.5 Hz, 1H), 8.19 (dd, J = 1.4, 8.5 Hz, 1H), 8.00 (d, J = 1.5 Hz, 1H), 7.95 (dd, J = 5.1, 8.6 Hz, 1H), 7.85 (d, J = 9.0 Hz, 2H), 7.30 (d, J = 8.8 Hz, 2H), 5.15-4.99 (m, 2H), 4.67 (br s, 1H), 4.28 (d, J = 12.6 Hz, 1H), 4.12 (dd, J = 3.0, 12.5 Hz, 1H), 3.45 (dd, J = 8.3, 10.9 Hz, 1H), 3.20 (dd, J = 5.1, 10.8 Hz, 1H). | O |
| 192 | 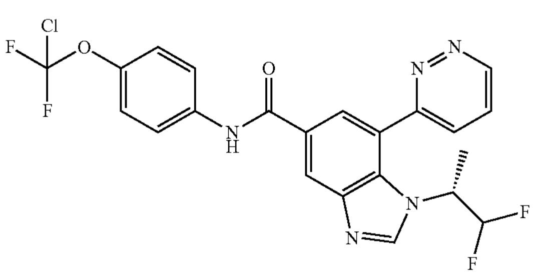 [SMILES: C[C@H](C(F)F)n1cnc2cc(C(=O)Nc3ccc(OC(F)(F)Cl)cc3)cc(-c3cccnn3)c21] | 493.1 | ¹H NMR (400 MHz, MeOD-d₄) δ 9.36-9.32 (m, 1H), 8.64 (s, 1H), 8.54 (d, J = 1.5 Hz, 1H), 8.19 (dd, J = 1.5, 8.6 Hz, 1H), 8.06 (d, J = 1.5 Hz, 1H), 7.87 (d, J = 9.0 Hz, 2H), 7.32 (d, J = 9.0 Hz, 2H), 6.16-5.88 (m, 2H), 4.95 (br d, J = 7.5 Hz, 1H), 1.72 (d, J = 7.1 Hz, 3H) | J, I |

TABLE 1-continued

| Example | Structure | LCMS m/z | ¹H NMR | General Procedure |
|---|---|---|---|---|
| 193 | 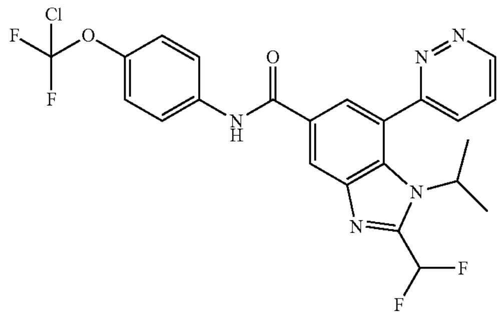 [SMILES: CC(C)n1c(C(F)F)nc2cc(C(=O)Nc3ccc(OC(F)(F)Cl)cc3)cc(-c3cccnn3)c21] | 508.1 | ¹H NMR (400 MHz, MeOD-d₄) δ 9.36 (dd, J = 1.5, 4.9 Hz, 1H), 8.56 (d, J = 2.0 Hz, 1H), 8.16-8.12 (m, 1H), 8.01-7.95 (m, 2H), 7.87-7.83 (m, 2H), 7.51-7.22 (m, 3H), 4.50-4.41 (m, 1H), 1.43 (d, J = 7.3 Hz, 6H) | J, I |
| 194 | 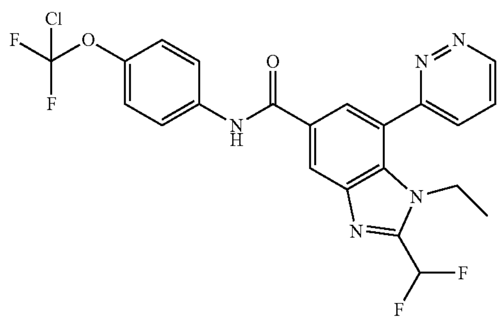 [SMILES: CCn1c(C(F)F)nc2cc(C(=O)Nc3ccc(OC(F)(F)Cl)cc3)cc(-c3cccnn3)c21] | 490.1 | ¹H NMR (400 MHz, MeOD-d₄) δ 9.36 (dd, J = 1.4, 5.0 Hz, 1H), 8.59 (d, J = 1.5 Hz, 1H), 8.21 (dd, J = 1.5, 8.6 Hz, 1H), 8.10 (d, J = 1.5 Hz, 1H), 7.99 (dd, J = 5.1, 8.6 Hz, 1H), 7.89-7.83 (m, 2H), 7.38-7.11 (m, 3H), 4.40-4.32 (m, 2H), 0.89 (t, J = 7.2 Hz, 3H). | J, I |
| 195 | 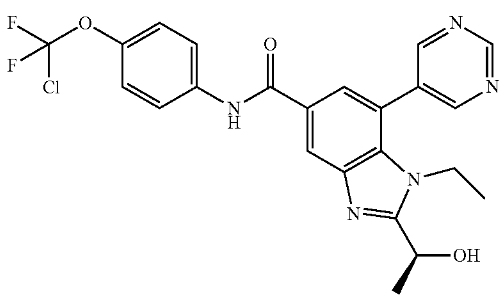 [SMILES: CCn1c([C@H](C)O)nc2cc(C(=O)Nc3ccc(OC(F)(F)Cl)cc3)cc(-c3cncnc3)c21] | 488.1 | ¹H NMR (400 MHz, MeOD-d₄) δ 9.32 (s, 1H), 9.08 (s, 2H), 8.41 (d, J = 1.5 Hz, 1H), 7.91-7.76 (m, 3H), 7.30 (br d, J = 8.8 Hz, 2H), 5.19 (q, J = 6.4 Hz, 1H), 4.28-4.00 (m, 2H), 1.75 (d, J = 6.6 Hz, 3H), 0.96 (t, J = 7.2 Hz, 3H) | R |
| 196 | 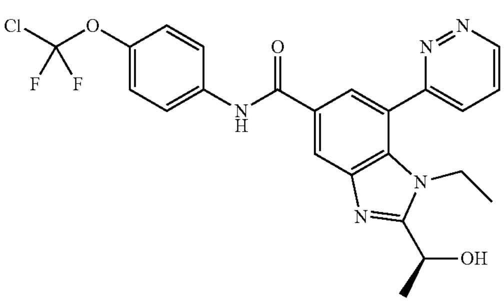 [SMILES: CCn1c([C@H](C)O)nc2cc(C(=O)Nc3ccc(OC(F)(F)Cl)cc3)cc(-c3cccnn3)c21] | 488.1 | ¹H NMR (400 MHz, MeOD-d₄) δ 9.34 (dd, J = 1.5, 5.0 Hz, 1H), 8.46 (d, J = 1.7 Hz, 1H), 8.18 (dd, J = 1.6, 8.4 Hz, 1H), 8.00-7.93 (m, 2H), 7.85 (d, J = 9.0 Hz, 2H), 7.30 (d, J = 9.0 Hz, 2H), 5.21 (q, J = 6.4 Hz, 1H), 4.50-4.19 (m, 2H), 1.76 (d, J = 6.6 Hz, 3H), 0.85 (t, J = 7.1 Hz, 3H) | R, I |
| 197 | 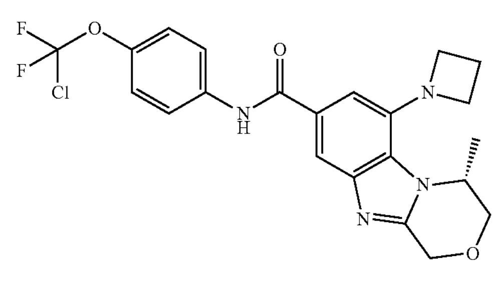 [SMILES: C[C@@H]1COCc2nc3cc(C(=O)Nc4ccc(OC(F)(F)Cl)cc4)cc(N4CCC4)c3n21] | 463.2 | ¹H NMR (400 MHz, MeOD-d₄) δ 7.88-7.82 (m, 3H), 7.49 (d, J = 1.3 Hz, 1H), 7.32 (d, J = 9.0 Hz, 2H), 5.07-4.93 (m, 3H), 4.29-4.22 (m, 3H), 4.11-4.05 (m, 1H), 3.79 (q, J = 6.9 Hz, 2H), 2.39 (q, J = 7.2 Hz, 2H), 1.58 (d, J = 6.5 Hz, 3H) | G |

TABLE 1-continued

| Example | Structure | LCMS m/z | ¹H NMR | General Procedure |
|---|---|---|---|---|
| 198 | 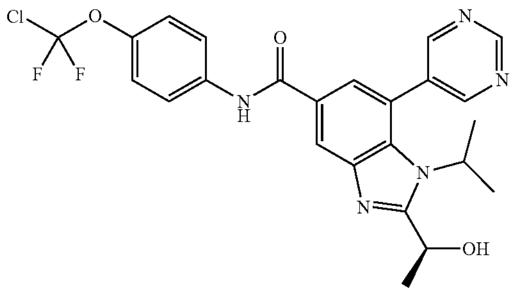 [SMILES: CC(C)n1c([C@H](C)O)nc2cc(C(=O)Nc3ccc(OC(F)(F)Cl)cc3)cc(-c3cncnc3)c21] | 502.1 | ¹H NMR (400 MHz, MeOD-d$_4$) δ 9.31 (s, 1H), 9.03 (s, 2H), 8.40 (d, J = 1.7 Hz, 1H), 7.88-7.80 (m, 2H), 7.75 (d, J = 1.7 Hz, 1H), 7.29 (d, J = 9.0 Hz, 2H), 5.29 (q, J = 6.4 Hz, 1H), 4.59-4.44 (m, 1H), 1.75 (d, J = 6.4 Hz, 3H), 1.46 (t, J = 7.2 Hz, 6H) | R |
| 199 | 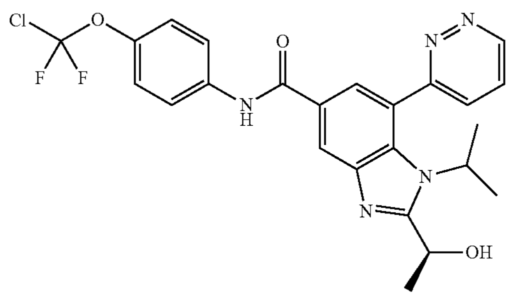 [SMILES: CC(C)n1c([C@H](C)O)nc2cc(C(=O)Nc3ccc(OC(F)(F)Cl)cc3)cc(-c3cccnn3)c21] | 502.1 | ¹H NMR (400 MHz, MeOD-d$_4$) δ 9.34 (d, J = 3.7 Hz, 1H), 8.44 (s, 1H), 8.16-8.06 (m, 1H), 7.95 (dd, J = 5.1, 8.4 Hz, 1H), 7.89-7.80 (m, 3H), 7.29 (d, J = 8.8 Hz, 2H), 5.30 (q, J = 6.1 Hz, 1H), 4.37 (br s, 1H), 1.75 (d, J = 6.4 Hz, 3H), 1.44 (br t, J = 6.7 Hz, 6H) | R, I |
| 200 | 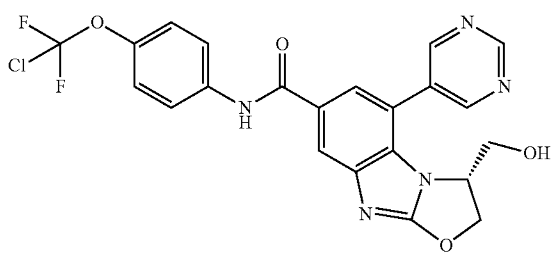 [SMILES: O=C(Nc1ccc(OC(F)(F)Cl)cc1)c1cc(-c2cncnc2)c2c(c1)nc1n2[C@H](CO)CO1] | 488.1 | ¹H NMR (400 MHz, MeOD-d$_4$) δ 9.18 (s, 1H), 9.02 (s, 2H), 8.04 (d, J = 1.6 Hz, 1H), 7.79-7.70 (m, 3H), 7.20 (d, J = 9.0 Hz, 2H), 5.21 (t, J = 8.5 Hz, 1H), 4.97 (dd, J = 3.1, 8.9 Hz, 1H), 4.56 (br dd, J = 3.2, 8.2 Hz, 1H), 3.16 (dd, J = 2.9, 12.2 Hz, 1H), 2.79 (dd, J = 3.3, 12.1 Hz, 1H) | S |
| 201 | 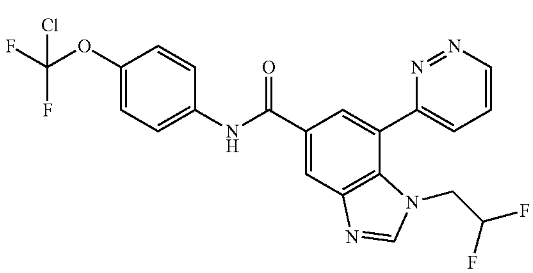 [SMILES: O=C(Nc1ccc(OC(F)(F)Cl)cc1)c1cc(-c2cccnn2)c2c(c1)ncn2CC(F)F] | 480.0 | ¹H NMR (400 MHz, MeOD-d$_4$) δ 9.32 (br d, J = 4.9 Hz, 1H), 8.53 (s, 1H), 8.43 (s, 1H), 8.22 (br d, J = 8.6 Hz, 1H), 8.14-8.07 (m, 1H), 7.97 (br dd, J = 5.0, 8.5 Hz, 1H), 7.87 (br d, J = 8.8 Hz, 2H), 7.31 (br d, J = 8.4 Hz, 2H), 6.13-5.84 (m, 1H), 4.87-4.78 (m, 2H) | J, I |
| 202 | 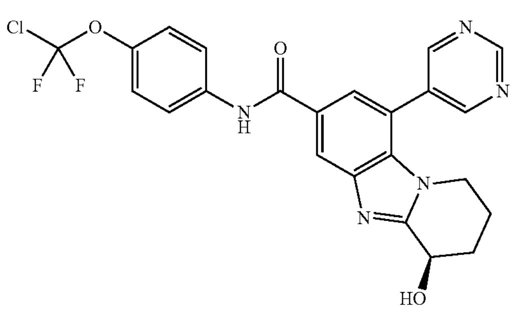 [SMILES: O=C(Nc1ccc(OC(F)(F)Cl)cc1)c1cc(-c2cncnc2)c2c(c1)nc1n2CCC[C@H]1O] | 486.1 | ¹H NMR (400 MHz, CDCl$_3$-d) δ 9.34 (s, 1H), 8.89 (s, 2H), 8.29 (br s, 1H), 8.17 (br s, 1H), 7.72 (br d, J = 10.1 Hz, 3H), 7.23 (s, 2H), 5.14 (br s, 1H), 3.63 (br dd, J = 7.2, 12.1 Hz, 2H), 2.35-2.19 (m, 2H), 2.07 (br d, J = 9.4 Hz, 1H), 1.95 (br s, 1H) | P |

TABLE 1-continued

| Example | Structure | LCMS m/z | ¹H NMR | General Procedure |
|---|---|---|---|---|
| 203 | 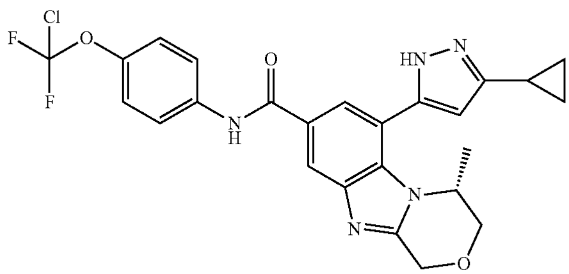 [SMILES: C[C@@H]1COCc2nc3cc(C(=O)Nc4ccc(OC(F)(F)Cl)cc4)cc(-c4cc(C5CC5)n[nH]4)c3n21] | 514.2 | ¹H NMR (400 MHz, MeOD-d$_4$) δ 8.28 (s, 1H), 7.91 (br d, J = 1.3 Hz, 1H), 7.84 (br d, J = 9.0 Hz, 2H), 7.30 (br d, J = 8.8 Hz, 2H), 6.33 (s, 1H), 5.12-4.95 (m, 3H), 4.22-3.92 (m, 2H), 2.10-1.97 (m, 1H), 1.12-0.97 (m, 5H), 0.83 (br d, J = 2.4 Hz, 2H) | J, Q |
| 204 | 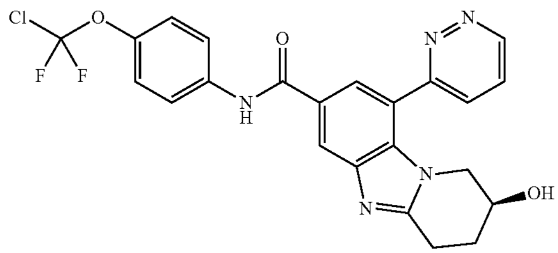 [SMILES: O=C(Nc1ccc(OC(F)(F)Cl)cc1)c1cc(-c2cccnn2)c2c(c1)nc1n2C[C@@H](O)CC1] | 485.11 | ¹H NMR (400 MHz, DMSO-d$_6$) δ 10.50 (s, 1H), 9.37 (dd, J = 1.4, 5.0 Hz, 1H), 8.40 (d, J = 1.3 Hz, 1H), 8.11 (dd, J = 1.5, 8.6 Hz, 1H), 7.99-7.83 (m, 4H), 7.36 (br d, J = 8.8 Hz, 2H), 5.16 (br d, J = 2.8 Hz, 1H), 4.10 (br d, J = 1.5 Hz, 1H), 3.89-3.77 (m, 1H), 3.45 (br dd, J = 3.9, 12.6 Hz, 1H), 3.21-3.11 (m, 1H), 3.10-2.99 (m, 1H), 2.05-1.90 (m, 2H) | T, I |
| 205 | 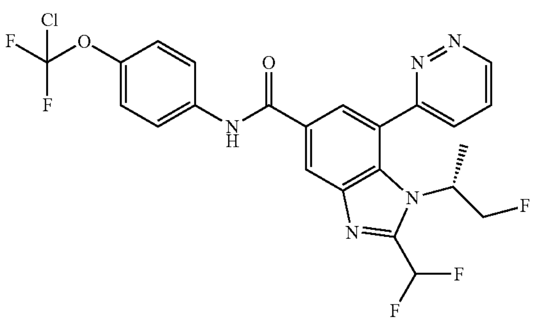 [SMILES: C[C@H](CF)n1c(C(F)F)nc2cc(C(=O)Nc3ccc(OC(F)(F)Cl)cc3)cc(-c3cccnn3)c21] | 525.1 | ¹H NMR (400 MHz, MeOD-d$_4$) δ 9.35 (br d, J = 4.2 Hz, 1H), 8.58 (s, 1H), 8.14 (br d, J = 8.2 Hz, 1H), 8.06-7.94 (m, 2H), 7.85 (br d, J = 8.6 Hz, 2H), 7.35-7.28 (m, 3H), 4.77 (br s, 3H), 1.53 (br d, J = 5.5 Hz, 3H) | J, I |
| 206 | 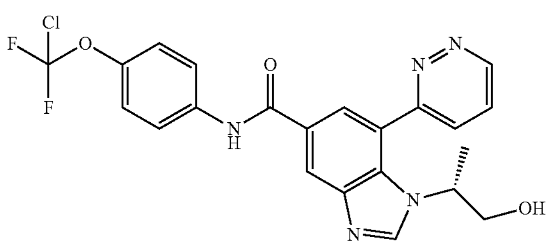 [SMILES: C[C@H](CO)n1cnc2cc(C(=O)Nc3ccc(OC(F)(F)Cl)cc3)cc(-c3cccnn3)c21] | 473.1 | ¹H NMR (400 MHz, MeOD-d$_4$) δ 9.34 (d, J = 4.9 Hz, 1H), 8.63 (s, 1H), 8.52 (d, J = 1.3 Hz, 1H), 8.16 (dd, J = 1.2, 8.6 Hz, 1H), 8.02-7.94 (m, 2H), 7.87 (d, J = 9.0 Hz, 2H), 7.32 (d, J = 8.8 Hz, 2H), 4.46-4.30 (m, 1H), 3.67-3.61 (m, 2H), 1.47 (d, J = 7.0 Hz, 3H) | J, I |
| 207 | 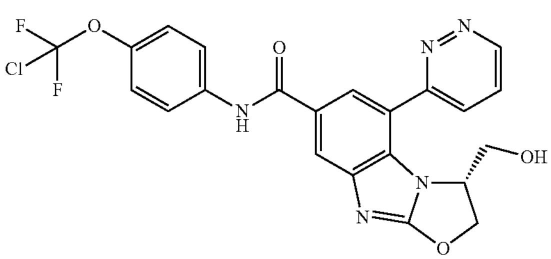 [SMILES: O=C(Nc1ccc(OC(F)(F)Cl)cc1)c1cc(-c2cccnn2)c2c(c1)nc1n2[C@H](CO)CO1] | 488.1 | ¹H NMR (400 MHz, MeOD-d$_4$) δ 9.25 (dd, J = 1.4, 5.0 Hz, 1H), 8.31 (dd, J = 1.3, 8.6 Hz, 1H), 8.16 (dd, J = 1.7, 8.5 Hz, 2H), 7.92 (dd, J = 5.0, 8.7 Hz, 1H), 7.85 (d, J = 9.3 Hz, 2H), 7.30 (d, J = 9.0 Hz, 2H), 5.36-5.28 (m, 1H), 5.23 (dd, J = 2.9, 8.2 Hz, 1H), 5.09 (dd, J = 2.6, 8.6 Hz, 1H), 3.36 (dd, J = 2.8, 12.2 Hz, 1H), 2.99 (dd, J = 3.4, 12.0 Hz, 1H). | S |

TABLE 1-continued

| Example | Structure | LCMS m/z | ¹H NMR | General Procedure |
|---|---|---|---|---|
| 208 | (Stereochemistry is arbitrarily assigned) | 486.2 | ¹H NMR (400 MHz, MeOD-d₄) δ 9.30 (s, 1H), 9.04 (s, 1H), 8.34 (d, J = 1.5 Hz, 1H), 7.85 (d, J = 9.0 Hz, 2H), 7.79 (d, J = 1.5 Hz, 1H), 7.30 (br d, J = 8.8 Hz, 2H), 4.39 (br d, J = 4.2 Hz, 1H), 3.96-3.84 (m, 1H), 3.76-3.65 (m, 1H), 3.35 (br s, 1H), 3.13 (br dd, J = 5.0, 17.3 Hz, 1H), 2.16-2.02 (m, 2H) | T |
| 209 | (Stereochemistry is arbitrarily assigned) | 486.1 | ¹H NMR (400 MHz, MeOD-d₄) δ 9.29 (s, 1H). 9.08-9.01 (m, 1H), 9.04 (s, 1H), 8.33 (d, J = 1.5 Hz, 1H), 7.84 (d, J = 9.0 Hz, 2H), 7.79 (d, J = 1.5 Hz, 1H), 7.30 (br d, J = 8.8 Hz, 2H), 4.38 (br d, J = 4.4 Hz, 1H), 3.96-3.82 (m, 1H), 3.70 (td, J = 5.6, 11.5 Hz, 1H), 3.35 (br d, J = 4.2 Hz, 1H), 3.12 (br dd, J = 5.0, 17.3 Hz, 1H), 2.17-2.01 (m, 2H) | T |
| 210 | (Stereochemistry is arbitrarily assigned) | 486.2 | ¹H NMR (400 MHz, MeOD-d₄) δ 9.32 (dd, J = 1.2, 5.0 Hz, 1H), 8.38 (d, J = 1.3 Hz, 1H), 8.14 (dd, J = 1.2, 8.5 Hz, 1H), 7.98-7.91 (m, 2H), 7.85 (d, J = 9.0 Hz, 2H), 7.30 (br d, J = 8.8 Hz, 2H), 4.38 (br d, J = 4.4 Hz, 1H), 3.99-3.89 (m, 1H), 3.84-3.75 (m, 1H), 3.39-3.34 (m, 1H), 3.14 (br dd, J = 5.0, 17.5 Hz, 1H), 2.15-2.00 (m, 2H) | T, I |
| 211 | (Stereochemistry is arbitrarily assigned) | 486.1 | ¹H NMR (400 MHz, MeOD-d₄) δ 9.36-9.26 (m, 1H), 8.37 (d, J = 1.3 Hz, 1H), 8.13 (dd, J = 1.3, 8.6 Hz, 1H), 7.96-7.90 (m, 2H), 7.84 (d, J = 9.0 Hz, 2H), 7.29 (br d, J = 9.0 Hz, 2H), 4.37 (br d, J = 4.4 Hz, 1H), 3.98-3.86 (m, 1H), 3.85-3.73 (m, 1H), 3.39-3.33 (m, 1H), 3.13 (br dd, J = 5.1, 17.2 Hz, 1H), 2.16-1.97 (m, 2H) | T, I |

TABLE 1-continued

| Example | Structure | LCMS m/z | ¹H NMR | General Procedure |
|---|---|---|---|---|
| 212 | 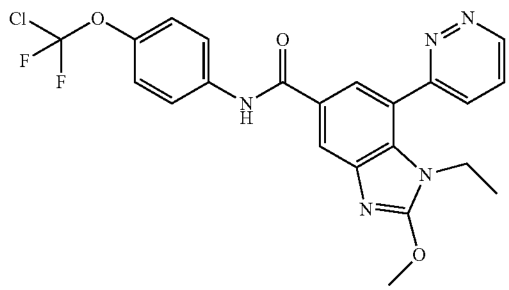 [SMILES: CCn1c(OC)nc2cc(C(=O)Nc3ccc(OC(F)(F)Cl)cc3)cc(-c3cccnn3)c21] | 474.1 | ¹H NMR (400 MHz, MeOD-d$_4$) δ 9.32 (br s, 1H), 8.25 (br d, J = 4.9 Hz, 1H), 8.15 (br s, 1H), 7.94 (br d, J = 13.9 Hz, 1H), 7.90-7.80 (m, 2H), 7.31 (br s, 2H), 4.27 (br d, J = 5.7 Hz, 3H), 3.91 (br d, J = 7.1 Hz, 2H), 0.90 (br d, J = 6.6 Hz, 3H) | H, I |
| 213 | 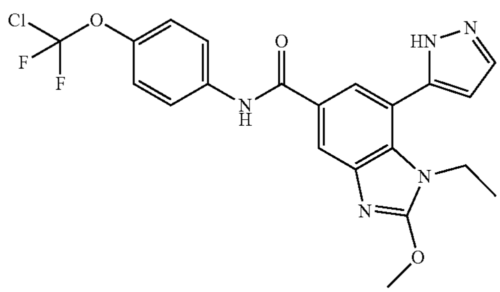 [SMILES: CCn1c(OC)nc2cc(C(=O)Nc3ccc(OC(F)(F)Cl)cc3)cc(-c3ccn[nH]3)c21] | 462.1 | ¹H NMR (400 MHz, MeOD-d$_4$) δ 8.12 (s, 1H), 7.91-7.75 (m, 4H), 7.29 (d, J = 8.9 Hz, 2H), 6.64 (s, 1H), 4.24 (s, 3H), 4.09-3.95 (m, 2H), 0.94 (br t, J = 7.0 Hz, 3H) | H |
| 214 | 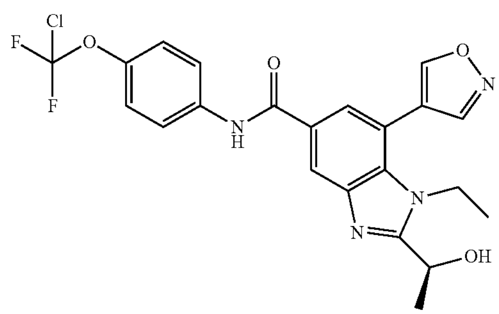 [SMILES: CCn1c([C@H](C)O)nc2cc(C(=O)Nc3ccc(OC(F)(F)Cl)cc3)cc(-c3cnoc3)c21] | 477.1 | ¹H NMR (400 MHz, MeOD-d$_4$) δ = 9.05 (s, 1H), 8.77 (s, 1H), 8.34 (d, J = 1.8 Hz, 1H), 7.86-7.80 (m, 2H), 7.78 (d, J = 1.8 Hz, 1H), 7.29 (d, J = 9.0 Hz, 2H), 5.18 (q, J = 6.6 Hz, 1H), 4.39-4.16 (m, 2H), 1.74 (d, J = 6.6 Hz, 3H), 1.09 (t, J = 7.2 Hz, 3H) | R |
| 215 | 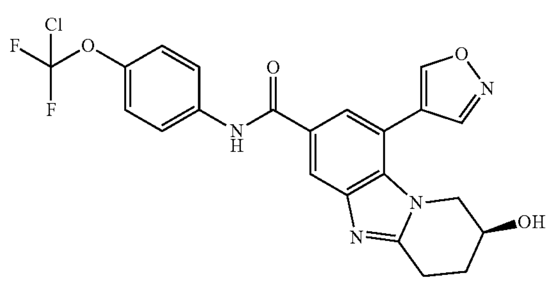 [SMILES: O=C(Nc1ccc(OC(F)(F)Cl)cc1)c1cc(-c2cnoc2)c2c(c1)nc1n2C[C@@H](O)CC1] | 475.1 | ¹H NMR (400 MHz, MeOD-d$_4$) δ 8.98 (s, 1H), 8.72 (s, 1H), 8.24 (d, J = 1.5 Hz, 1H), 7.82 (d, J = 9.0 Hz, 2H), 7.75 (d, J = 1.5 Hz, 1H), 7.28 (d, J = 9.0 Hz, 2H), 4.32 (br dd, J = 3.0, 5.4 Hz, 1H), 4.07 (dd, J = 3.6, 12.5 Hz, 1H), 3.83 (dd, J = 3.9, 12.5 Hz, 1H), 3.26 (dd, J = 7.2, 9.4 Hz, 1H), 3.15-3.04 (m, 1H), 2.19-2.07 (m, 2H) | T |
| 216 | 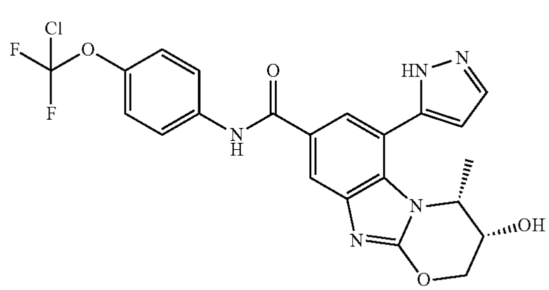 | 489.1 | ¹H NMR (400 MHz, MeOD-d$_4$) δ 8.07 (s, 1H), 7.86-7.80 (m, 3H), 7.78 (d, J = 1.5 Hz, 1H), 7.28 (d, J = 9.0 Hz, 2H), 6.65 (d, J = 2.2 Hz, 1H), 4.94 (br s, 1H), 4.63 (d, J = 11.9 Hz, 1H), 4.47 (br d, J = 12.1 Hz, 1H), 4.03 (s, 1H), 0.99 (br d, J = 6.7 Hz, 3H) | U |

(Stereochemistry is arbitrarily assigned)

TABLE 1-continued

| Example | Structure | LCMS m/z | ¹H NMR | General Procedure |
|---|---|---|---|---|
| 217 | 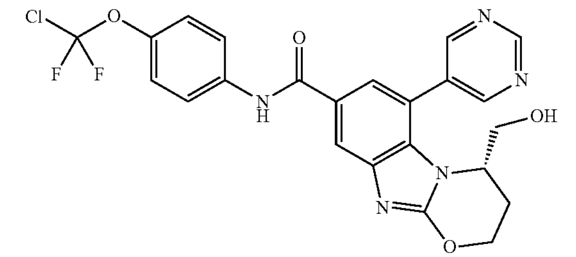 [SMILES: O=C(Nc1ccc(OC(F)(F)Cl)cc1)c1cc(-c2cncnc2)c2c(c1)nc1n2[C@H](CO)CCO1] | 502.2 | ¹H NMR (400 MHz, MeOD-d₄) δ 9.30 (s, 1H), 9.02 (s, 2H), 7.84-7.72 (m, 3H), 7.62 (s, 1H), 7.28 (br d, J = 8.8 Hz, 2H), 4.30-4.18 (m, 1H), 4.15-4.01 (m, 2H), 3.83-3.72 (m, 2H), 2.56-2.37 (m, 1H), 2.10-1.92 (m, 1H) | V |
| 218 | 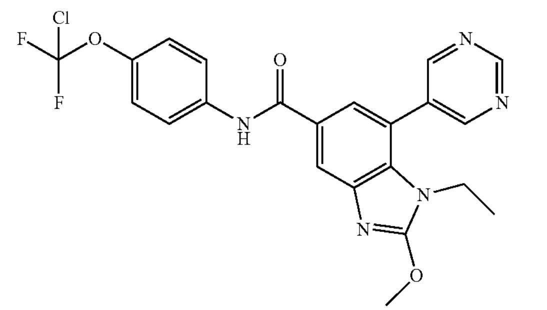 [SMILES: CCn1c(OC)nc2cc(C(=O)Nc3ccc(OC(F)(F)Cl)cc3)cc(-c3cncnc3)c21] | 474.1 | ¹H NMR (400 MHz, MeOD-d₄) δ 9.30 (s, 1H), 9.04 (s, 2H), 8.19 (d, J = 1.5 Hz, 1H), 7.83 (br d, J = 9.3 Hz, 2H), 7.69 (d, J = 1.5 Hz, 1H), 7.29 (br d, J = 8.8 Hz, 2H), 4.25 (s, 3H), 3.75 (q, J = 7.3 Hz, 2H), 1.00-0.90 (m, 3H) | H |
| 219 | 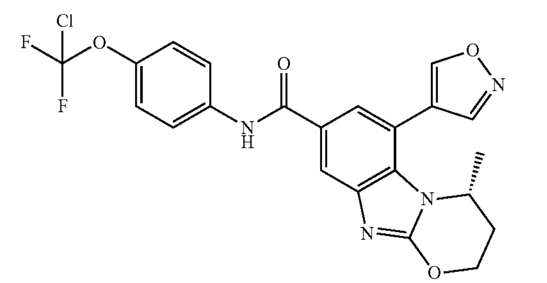 | 474.1 | ¹H NMR (400 MHz, MeOD-d₄) δ 9.06 (s, 1H), 8.79 (s, 1H), 8.07 (s, 1H), 7.82 (br d, J = 8.9 Hz, 2H), 7.68 (s, 1H), 7.29 (br d, J = 8.6 Hz, 2H), 4.70-4.47 (m, 3H), 2.55 (br s, 1H), 2.07-1.96 (m, 1H), 1.15 (br d, J = 6.1 Hz, 3H) | G |
| 220 | 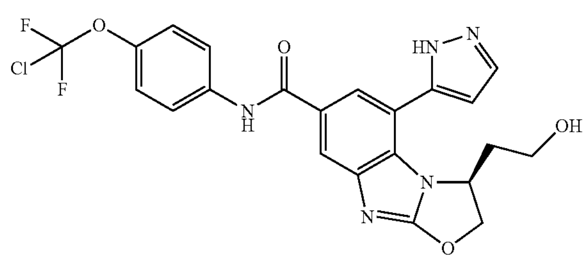 [SMILES: O=C(Nc1ccc(OC(F)(F)Cl)cc1)c1cc(-c2ccn[nH]2)c2c(c1)nc1n2[C@@H](CCO)CO1] | 490.1 | ¹H NMR (400 MHz, MeOD-d₄) δ 8.03 (br s, 2H), 7.86 (br d, J = 8.9 Hz, 3H), 7.31 (br d, J = 8.7 Hz, 2H), 6.81 (br s, 1H), 5.31 (br d, J = 4.8 Hz, 2H), 5.13 (br d, J = 5.7 Hz, 1H), 3.53-3.39 (m, 2H), 1.60 (br d, J = 6.1 Hz, 1H), 1.55-1.45 (m, 1H) | V |
| 221 | 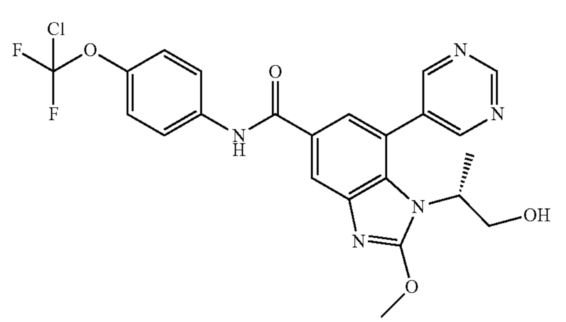 [SMILES: COc1nc2cc(C(=O)Nc3ccc(OC(F)(F)Cl)cc3)cc(-c3cncnc3)c2n1[C@H](C)CO] | 503.1 | ¹H NMR (400 MHz, MeOD-d₄) δ 9.28 (s, 1H), 9.02 (s, 2H), 8.18 (d, J = 1.7 Hz, 1H), 7.86-7.79 (m, 2H), 7.65 (d, J = 1.7 Hz, 1H), 7.29 (br d, J = 9.0 Hz, 2H), 4.25 (s, 3H), 4.09-3.93 (m, 2H), 3.53 (dd, J = 4.9, 11.1 Hz, 1H), 2.02 (s, 1H), 1.32 (d, J = 7.0 Hz, 3H). | H |

TABLE 1-continued

| Example | Structure | LCMS m/z | ¹H NMR | General Procedure |
|---|---|---|---|---|
| 222 | 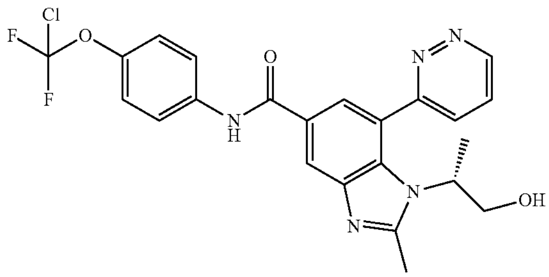 [SMILES: Cc1nc2cc(C(=O)Nc3ccc(OC(F)(F)Cl)cc3)cc(-c3cccnn3)c2n1[C@H](C)CO] | 488.1 | ¹H NMR (400 MHz, MeOD-d₄) δ 9.37-9.29 (m, 1H), 8.35 (d, J = 1.5 Hz, 1H), 8.11 (dd, J = 1.3, 8.6 Hz, 1H), 7.95 (dd, J = 5.0, 8.5 Hz, 1H), 7.87-7.80 (m, 3H), 7.29 (br d, J = 9.0 Hz, 2H), 4.27 (br d, J = 7.1 Hz, 1H), 3.81 (dd, J = 8.8, 11.7 Hz, 1H), 3.61 (br dd, J = 5.6, 11.8 Hz, 1H), 2.79 (s, 3H), 1.44 (br d, 6.4 Hz, 3H) | J, I |
| 223 | 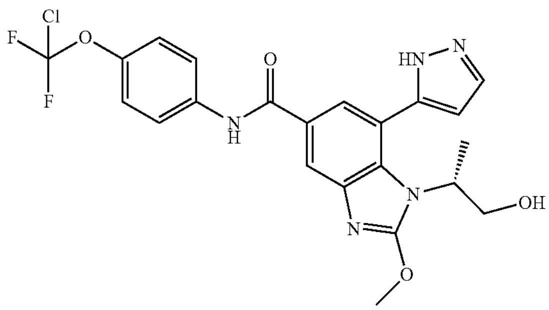 [SMILES: COc1nc2cc(C(=O)Nc3ccc(OC(F)(F)Cl)cc3)cc(-c3ccn[nH]3)c2n1[C@H](C)CO] | 492.0 | ¹H NMR (400 MHz, MeOD-d₄) δ 8.11 (br s, 1H), 7.82 (br d, J = 9.0 Hz, 3H), 7.76 (s, 1H), 7.29 (br d, J = 8.8 Hz, 2H), 6.64 (br s, 1H), 4.45 (br s, 1H), 4.23 (s, 3H), 3.91 (br s, 1H), 3.61 (br s, 1H), 1.33 (d, J = 7.0 Hz, 3H). | H |
| 224 | 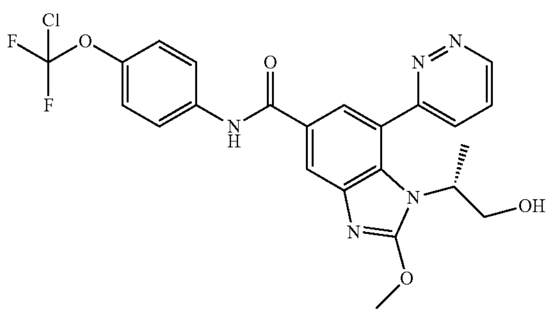 [SMILES: COc1nc2cc(C(=O)Nc3ccc(OC(F)(F)Cl)cc3)cc(-c3cccnn3)c2n1[C@H](C)CO] | 504.0 | ¹H NMR (400 MHz, MeOD-d₄) δ 9.30 (dd, J = 1.5, 5.1 Hz, 1H), 8.22 (d, J = 1.7 Hz, 1H), 8.11 (dd, J = 1.6, 8.4 Hz, 1H), 7.93 (dd, J = 5.0, 8.4 Hz, 1H), 7.86-7.78 (m, 3H), 7.29 (d, J = 8.9 Hz, 2H), 4.25 (s, 3H), 3.96-3.89 (m, 2H), 3.52 (br d, J = 5.9 Hz, 1H), 1.37 (d, J = 6.6 Hz, 3H). | H, I |
| 225 | 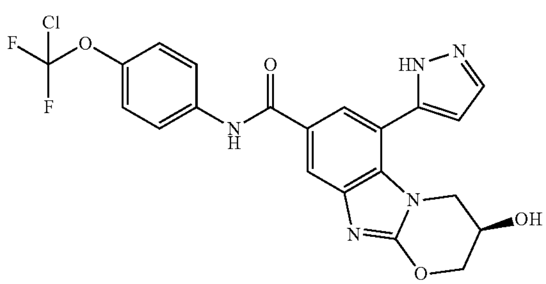 [SMILES: O=C(Nc1ccc(OC(F)(F)Cl)cc1)c1cc(-c2ccn[nH]2)c2c(c1)nc1n2C[C@@H](O)CO1] | 476.1 | ¹H NMR (400 MHz, MeOD-d₄) δ 8.07 (s, 1H), 7.87-7.79 (m, 4H), 7.29 (br d, J = 8.6 Hz, 2H), 6.65 (s, 1H), 4.51 (q, J = 11.4 Hz, 2H), 4.30 (br s, 1H), 4.12 (br s, 1H), 3.75 (br s, 1H) | U |
| 226 | 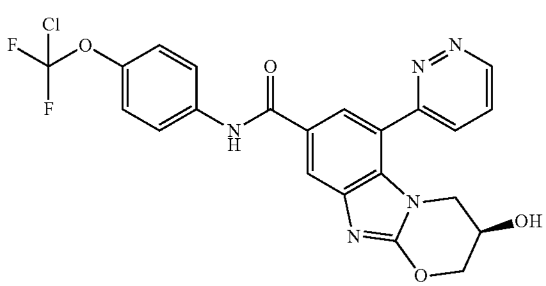 [SMILES: O=C(Nc1ccc(OC(F)(F)Cl)cc1)c1cc(-c2cccnn2)c2c(c1)nc1n2C[C@@H](O)CO1] | 488.1 | ¹H NMR (400 MHz, MeOD-d₄) δ 9.31 (d, J = 5.0 Hz, 1H), 8.22-8.15 (m, 2H), 7.98-7.89 (m, 2H), 7.84 (d, J = 8.8 Hz, 2H), 7.30 (d, J = 8.6 Hz, 2H), 4.63-4.57 (m, 1H), 4.54-4.47 (m, 1H), 4.29 (br s, 1H), 4.18 (dd, 3.8, 12.8 Hz, 1H), 3.55 (br d, J = 12.8 Hz, 1H) | U |

TABLE 1-continued

| Example | Structure | LCMS m/z | ¹H NMR | General Procedure |
|---|---|---|---|---|
| 227 | 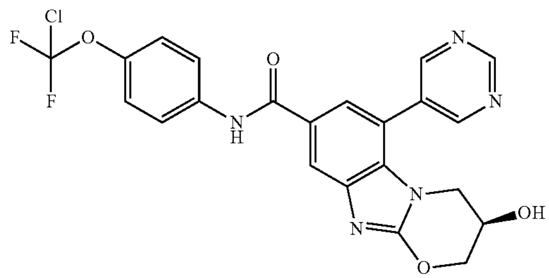 [SMILES: O=C(Nc1ccc(OC(F)(F)Cl)cc1)c1cc(-c2cncnc2)c2c(c1)nc1n2C[C@@H](O)CO1] | 488.1 | ¹H NMR (400 MHz, MeOD-$d_4$) δ 9.29 (s, 1H), 9.05 (s, 2H), 8.15 (d, J = 1.6 Hz, 1H), 7.83 (d, J = 9.0 Hz, 2H), 7.73 (d, J = 1.6 Hz, 1H), 7.29 (br d, J = 9.0 Hz, 2H), 4.59-4.46 (m, 2H), 4.29 (br s, 1H), 4.06 (dd, J = 3.5, 11.7 Hz, 1H), 3.51-3.46 (m, 1H) | U |
| 228 | 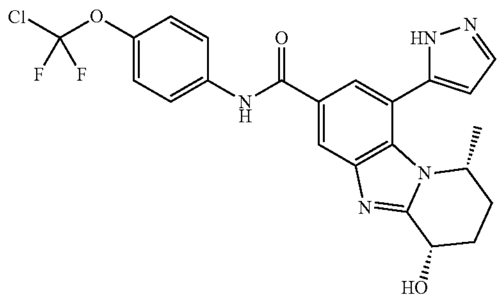 [SMILES: C[C@@H]1CC[C@H](O)c2nc3cc(C(=O)Nc4ccc(OC(F)(F)Cl)cc4)cc(-c4ccn[nH]4)c3n21] | 488.1 | ¹H NMR (400 MHz, MeOD-$d_4$) δ 8.32 (br s, 1H), 7.91 (s, 1H), 7.84 (br d, J = 8.9 Hz, 3H), 7.30 (d, J = 8.8 Hz, 2H), 6.69 (br s, 1H), 4.96 (br dd, J = 6.4, 10.4 Hz, 2H), 2.39-2.18 (m, 2H), 2.11-1.89 (m, 2H), 0.92 (br d, J = 5.9 Hz, 3H) | W |
| 229 | 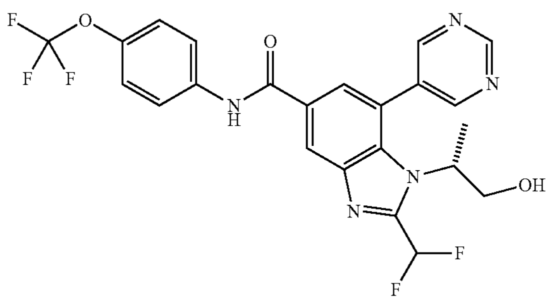 [SMILES: C[C@H](CO)n1c(C(F)F)nc2cc(C(=O)Nc3ccc(OC(F)(F)F)cc3)cc(-c3cncnc3)c21] | 507.1 | ¹H NMR (400 MHz, DMSO-$d_6$) δ 10.48 (s, 1H), 9.35 (s, 1H), 9.06 (s, 2H), 8.57 (s, 1H), 7.95-7.89 (m, J = 8.9 Hz, 2H), 7.84 (s, 1H), 7.69-7.41 (m, 1H), 7.38 (br d, 8.8 Hz, 2H), 5.10 (t, J = 5.0 Hz, 1H), 4.40-4.31 (m, 1H), 3.61-3.44 (m, 2H), 1.37 (br d, J = 7.0 Hz, 3H) | J |
| 230 | 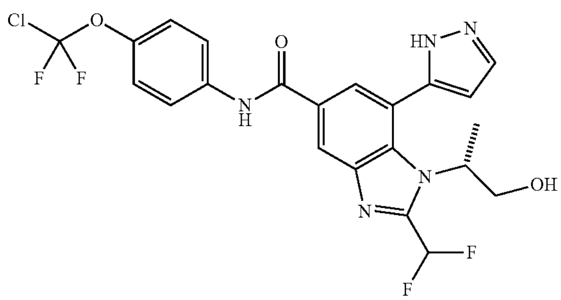 [SMILES: C[C@H](CO)n1c(C(F)F)nc2cc(C(=O)Nc3ccc(OC(F)(F)Cl)cc3)cc(-c3ccn[nH]3)c21] | 511.1 | ¹H NMR (400 MHz, DMSO-$d_6$) δ 13.31-13.18 (m, 1H), 10.52 (s, 1H), 8.48 (s, 1H), 7.99-7.88 (m, 4H), 7.56 (br t, J = 52.1 Hz, 1H), 7.36 (br d, J = 8.9 Hz, 2H), 6.62 (br s, 1H), 5.21-5.12 (m, 1H). 4.86 (br dd, J = 5.2, 10.7 Hz, 1H), 3.59-3.54 (m, 2H), 1.39 (br d, J = 6.8 Hz, 3H) | J |
| 231 | 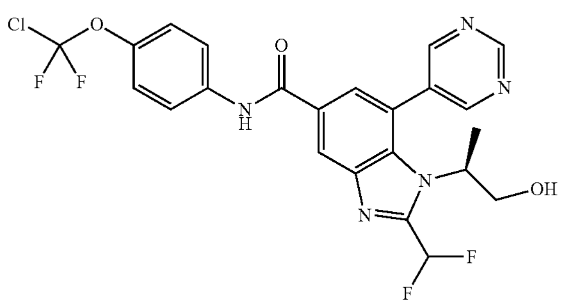 [SMILES: C[C@@H](CO)n1c(C(F)F)nc2cc(C(=O)Nc3ccc(OC(F)(F)Cl)cc3)cc(-c3cncnc3)c21] | 524.0 | ¹H NMR (400 MHz, MeOD-$d_4$) δ 9.31 (s, 1H), 9.03 (s, 2H), 8.52 (s, 1H), 7.85 (br d, J = 9.3 Hz, 3H), 7.54-7.26 (m, 3H), 4.53 (br d, J = 5.6 Hz, 1H), 3.78-3.70 (m, 1H), 3.66-3.59 (m, 1H), 1.45 (br d, J = 7.2 Hz, 3H) | J |

TABLE 1-continued

| Example | Structure | LCMS m/z | $^1$H NMR | General Procedure |
|---|---|---|---|---|
| 232 | [Structure image] | 500.1 | $^1$H NMR (400 MHz, MeOD-d$_4$) δ 9.31 (s, 1H), 9.10 (br s, 2H), 8.43 (d, J = 1.5 Hz, 1H), 7.85 (dd, J = 3.7, 5.3 Hz, 3H), 7.30 (br d, J = 8.8 Hz, 2H), 5.03 (br s, 1H), 4.32 (br t, J = 6.1 Hz, 1H), 2.79-2.57 (m, 1H), 2.25 (br t, J = 14.3 Hz, 1H), 2.05 (br d, J = 11.7 Hz, 1H), 1.73 (br d, J = 14.7 Hz, 1H), 0.86 (d, J = 6.6 Hz, 3H) | W |

*Biological data reported in Table 2 for the compounds whose stereochemistry is noted as arbitrarily assigned in Table 1 can be associated with the appropriate compound of Table 1 by reference to the corresponding $^1$H NMR data. It is thus possible that the compound associated with a given $^1$H NMR and biological data set will have the same absolute stereochemistry or a different absolute stereochemistry from the compound whose stereochemistry is noted as arbitrarily assigned in Table 1.

Biological Examples

Biological Assays
ABL1 Biochemical Kinase Assay

ABL1 WT protein (64-515aa) containing an N-terminal His tag was produced by co-expression with YopH in Sf9 insect cells. Cells were harvested by centrifugation and resuspended in 50 mM Tris, 500 mM NaCl, 5 mM β-ME, pH 8.2. Cells were lysed by sonication and clarified by centrifugation. ABL1 was purified by affinity chromatography using a HisTrap column with a wash step in 4% wash buffer (50 mM Tris, 500 mM NaCl, 500 mM imidazole, 5 mM β-ME, pH 8.2) and eluted in a linear gradient of the same buffer. Fractions containing ABL1 were pooled, concentrated and further purified using an ion exchange column washed with 50 mM Tris, pH 8.3 and eluted with a linear gradient of elution buffer (50 mM Tris, 1M NaCl, pH 8.3). Purified protein was stored at −80° C. in 50 mM Tris (pH 8.2), 300 mM NaCl, 1 mM DTT and 20% glycerol.

The activity of the enzyme and compound inhibition was tested using an EZ reader microfluidic mobility shift assay (PerkinElmer, Waltham, Mass.). For inhibition studies, compounds were serially diluted in DMSO, using an 11-point 3-fold format, from a 1000 μM top compound concentration. 20 nL per well of serial diluted compounds were transferred to Greiner polypropylene flat-bottom 384-well assay plates using an acoustic transfer system (Echo 550). A 15 μL reaction mixture containing fluorescent peptide, enzyme, buffer, co-factors and detergent was added to each well and incubated at room temperature (RT) for 30 minutes. 5 μL per well of an ATP solution was then added and reactions were carried out for 90 minutes before being quenched with 70 μL of stopping buffer containing 500 mM EDTA. The reactions were read on an EZ Reader (PerkinElmer, Waltham, Mass.) using a mobility shift readout. The final concentrations in each reaction were 1.5 μM FL-Peptide 2 (PerkinElmer, Waltham, Mass.), 1 nM ABL1 WT (64-515 aa) enzyme, 50 mM HEPES (pH 7.5), 1 mM EGTA, 2 mM DTT, 0.05% BSA, 10 mM MgCl2, 0.01% Triton-X100 and 20 μM ATP. The final DMSO concentration was 0.1% and the final inhibitor concentration ranged from 1000 nM to 0.017 nM. Each compound was tested in duplicate and the inhibitor dose response curves analyzed using IC$_{50}$ regression curve fitting using GraphPad Prism.

ABL1 K562 Assay

Compound activity was tested using the Cell Titer Glo assay (CTG, Promega). K562 cells (Chronic Myeloid Leukemia) were maintained in IMDM+10% FBS. One day prior to testing compound activity, 800 K562 cells per well were plated in culture medium at 16K cells/mL and incubated overnight at 37° C., 5% CO$_2$. Compounds were serially diluted in IMDM+10% FBS, using a 9-point 3-fold format, from a 2000 nM top compound concentration. DMSO concentration was kept constant at 0.4%. 50 μL per well of serial diluted compounds were transferred to the plates containing K562 cells and incubated at 37° C., 5% CO$_2$ for 72 h (final DMSO concentration of 0.2%). After 72 h plates and CTG reagent were equilibrated to room temperature for 30 minutes before addition of 25 μL per well CTG reagent. Plates were shaken for 2 minutes and then incubated at room temperature for 10 minutes. The reactions were read on an EnVision luminescence reader (PerkinElmer, Waltham, Mass.). Each compound was tested in duplicate and the inhibitor dose response curves analyzed using IC$_{50}$ regression curve fitting using GraphPad Prism.

The results are tabulated below in Table 2.

TABLE 2

| Example | Abl WT IC$_{50}$ (nM) | Abl K562 CC$_{50}$ (nM) |
|---|---|---|
| 1 | ND | 28.36 |
| 2 | 0.37 | 11.64 |
| 3 | 1.07 | 55.29 |
| 4 | 0.27 | 15.11 |
| 5 | 0.38 | 8.91 |
| 6 | 0.63 | 30.27 |
| 7 | 0.33 | 14.11 |
| 8 | ND | 9.27 |
| 9 | 0.33 | 8.89 |
| 10 | 0.63 | 29.25 |
| 11 | 0.16 | 8.73 |
| 12 | 0.38 | 14.85 |
| 13 | 0.71 | 24.41 |
| 14 | 0.86 | 41.08 |
| 15 | 0.41 | 5.22 |
| 16 | 0.58 | 13.80 |
| 17 | 0.34 | 8.32 |
| 18 | 0.51 | 8.19 |
| 19 | 1.02 | 60.18 |
| 20 | 0.50 | 59.12 |
| 21 | 0.64 | 95.95 |
| 22 | 0.31 | 11.21 |
| 23 | 0.72 | 48.25 |
| 24 | 0.40 | 40.23 |

TABLE 2-continued

| Example | Abl WT IC$_{50}$ (nM) | Abl K562 CC$_{50}$ (nM) |
|---|---|---|
| 25 | 20.69 | 1000.00 |
| 26 | 2.31 | 114.56 |
| 27 | 4.78 | 383.74 |
| 28 | 0.57 | 69.05 |
| 29 | 0.62 | 31.34 |
| 30 | 0.80 | 52.02 |
| 31 | 0.66 | 30.96 |
| 32 | 0.37 | 9.23 |
| 33 | 0.60 | 19.36 |
| 34 | 0.74 | 12.60 |
| 35 | 0.32 | 6.11 |
| 36 | 4.20 | 352.61 |
| 37 | 0.54 | 20.45 |
| 38 | 0.63 | 17.67 |
| 39 | 1.11 | 28.77 |
| 40 | 0.48 | 6.76 |
| 41 | 281.23 | >1000 |
| 42 | 0.56 | 14.41 |
| 43 | 0.38 | 9.15 |
| 44 | 0.65 | 60.78 |
| 45 | 0.41 | 53.21 |
| 46 | 0.67 | 39.85 |
| 47 | 3.17 | 277.52 |
| 48 | 1.30 | 35.28 |
| 49 | ND | 6.55 |
| 50 | 0.27 | 9.93 |
| 51 | 0.26 | 9.37 |
| 52 | 0.37 | 10.46 |
| 53 | 0.54 | 14.02 |
| 54 | 0.51 | 6.70 |
| 55 | ND | 15.16 |
| 56 | ND | 14.75 |
| 57 | ND | 8.25 |
| 58 | 0.43 | 11.62 |
| 59 | 0.47 | 18.27 |
| 60 | 0.36 | 8.00 |
| 61 | 0.47 | 13.76 |
| 62 | 0.45 | 17.28 |
| 63 | 0.59 | 15.35 |
| 64 | 0.48 | 7.32 |
| 65 | 0.77 | 41.05 |
| 66 | 0.56 | 16.83 |
| 67 | 0.61 | 25.94 |
| 68 | 1.21 | 59.15 |
| 69 | 0.49 | 8.33 |
| 70 | 0.39 | 8.65 |
| 71 | 0.78 | 46.84 |
| 72 | 0.79 | 54.13 |
| 73 | 0.83 | 42.01 |
| 74 | 0.32 | 7.04 |
| 75 | 0.41 | 15.88 |
| 76 | 0.55 | 27.44 |
| 77 | 0.71 | 34.04 |
| 78 | 1.03 | 98.87 |
| 79 | 0.41 | 15.20 |
| 80 | 0.31 | 10.72 |
| 81 | 0.40 | 7.28 |
| 82 | 0.52 | 13.67 |
| 83 | 0.40 | 19.48 |
| 84 | 0.57 | 13.48 |
| 85 | 0.52 | 8.61 |
| 86 | 0.51 | 6.76 |
| 87 | 0.44 | 12.53 |
| 88 | 0.62 | 16.36 |
| 89 | 0.61 | 21.73 |
| 90 | 0.32 | 8.65 |
| 91 | 0.50 | 6.85 |
| 92 | 0.50 | 6.37 |
| 93 | 0.52 | 23.27 |
| 94 | 0.52 | 14.25 |
| 95 | 0.33 | 25.07 |
| 96 | 0.47 | 11.19 |
| 97 | 0.59 | 9.35 |
| 98 | 0.42 | 4.20 |
| 99 | 0.41 | 22.67 |
| 100 | 0.46 | 26.49 |
| 101 | 0.63 | 22.29 |
| 102 | 0.61 | 33.13 |
| 103 | 0.46 | 16.88 |
| 104 | 0.71 | 22.39 |
| 105 | 0.86 | 30.61 |
| 106 | 0.29 | 6.84 |
| 107 | 0.77 | 35.25 |
| 108 | 0.73 | 51.59 |
| 109 | 1.74 | 236.76 |
| 110 | 0.51 | 7.82 |
| 111 | 0.60 | 6.48 |
| 112 | 0.30 | 4.30 |
| 113 | 0.40 | 6.43 |
| 114 | 0.25 | 8.34 |
| 115 | 0.54 | 7.55 |
| 116 | 0.46 | 18.58 |
| 117 | 0.43 | 26.60 |
| 118 | 0.34 | 12.02 |
| 119 | 0.48 | 17.50 |
| 120 | 0.48 | 23.09 |
| 121 | ND | 21.59 |
| 122 | 0.42 | 15.45 |
| 123 | 0.58 | 12.86 |
| 124 | 0.83 | 36.29 |
| 125 | 1.35 | 106.48 |
| 126 | 0.25 | 1.32 |
| 127 | 0.36 | 8.94 |
| 128 | 0.48 | 15.39 |
| 129 | 1.07 | 145.79 |
| 130 | 0.45 | 6.56 |
| 131 | 0.36 | 10.46 |
| 132 | 0.54 | 8.06 |
| 133 | 0.31 | 4.34 |
| 134 | 0.65 | 23.11 |
| 135 | 0.36 | 4.22 |
| 136 | ND | 178.51 |
| 137 | 0.56 | 5.96 |
| 138 | 0.52 | 20.01 |
| 139 | 2.49 | 141.67 |
| 140 | 1.26 | 61.82 |
| 141 | 0.34 | 5.22 |
| 142 | 0.30 | 2.25 |
| 143 | 0.36 | 15.50 |
| 144 | 0.35 | 3.38 |
| 145 | 0.57 | 17.00 |
| 146 | 0.33 | 15.95 |
| 147 | 0.39 | 5.26 |
| 148 | 0.54 | 7.89 |
| 149 | 0.36 | 4.11 |
| 150 | 0.36 | 1.85 |
| 151 | 0.77 | 13.71 |
| 152 | 0.56 | 8.21 |
| 153 | 0.28 | 1.94 |
| 154 | 0.43 | 6.88 |
| 155 | 0.97 | 17.09 |
| 156 | 0.35 | 3.92 |
| 157 | 0.35 | 8.93 |
| 158 | 0.34 | 2.72 |
| 159 | 0.28 | 2.31 |
| 160 | 0.52 | 10.62 |
| 161 | 0.55 | 17.54 |
| 162 | 0.73 | 15.22 |
| 163 | 0.63 | 20.80 |
| 164 | 0.81 | 9.75 |
| 165 | 0.38 | 4.94 |
| 166 | 0.45 | 6.60 |
| 167 | 2.51 | 22.71 |
| 168 | 0.33 | 2.24 |
| 169 | 0.53 | 5.12 |
| 170 | 0.49 | 9.79 |
| 171 | ND | 19.33 |
| 172 | ND | 40.17 |
| 173 | 0.76 | 38.92 |
| 174 | 0.47 | 7.40 |
| 175 | 0.46 | 11.74 |
| 176 | 0.51 | 14.07 |
| 177 | 0.62 | 22.15 |
| 178 | 0.70 | 28.10 |
| 179 | 1.52 | 130.86 |
| 180 | 1.13 | 37.62 |

TABLE 2-continued

| Example | Abl WT IC$_{50}$ (nM) | Abl K562 CC$_{50}$ (nM) |
|---|---|---|
| 181 | 0.76 | 47.14 |
| 182 | 0.59 | 7.22 |
| 183 | 0.38 | 11.31 |
| 184 | 0.59 | 22.35 |
| 185 | 0.31 | 8.00 |
| 186 | 0.45 | 14.96 |
| 187 | 0.33 | 4.17 |
| 188 | 0.48 | 11.42 |
| 189 | 0.49 | 16.35 |
| 190 | 0.87 | 17.51 |
| 191 | 0.46 | 7.72 |
| 192 | 0.62 | 7.46 |
| 193 | 0.53 | 12.75 |
| 194 | 0.57 | 10.40 |
| 195 | 0.54 | 3.41 |
| 196 | 0.44 | 14.93 |
| 197 | 2.37 | 149.53 |
| 198 | 0.47 | 7.06 |
| 199 | 0.47 | 15.92 |
| 200 | 0.48 | 15.32 |
| 201 | 0.49 | 16.03 |
| 202 | 0.66 | 13.36 |
| 203 | 0.77 | 17.71 |
| 204 | 0.41 | 42.03 |
| 205 | 0.97 | >1000 |
| 206 | 0.55 | 26.56 |
| 207 | 1.41 | 101.03 |
| 208 | 0.37 | 10.84 |
| 209 | 0.45 | 18.55 |
| 210 | 0.51 | 36.62 |
| 211 | 0.55 | 56.46 |
| 212 | 0.73 | 22.02 |
| 213 | 0.44 | 9.77 |
| 214 | 0.45 | 17.46 |
| 215 | 1.03 | 45.52 |
| 216 | 0.99 | 194.06 |
| 217 | 0.56 | 23.54 |
| 218 | 0.34 | 6.53 |
| 219 | 0.93 | 23.67 |
| 220 | 2.55 | 170.95 |
| 221 | 0.28 | 6.71 |
| 222 | 0.67 | 29.06 |
| 223 | 0.26 | 4.46 |
| 224 | 1.00 | 45.33 |
| 225 | 8.71 | 54.91 |
| 226 | 27.98 | 192.62 |
| 227 | 9.67 | 38.88 |
| 228 | ND | 13.93 |
| 229 | ND | 36.82 |
| 230 | ND | 6.98 |
| 231 | ND | 13.52 |
| 232 | ND | 1.32 |

ND = not determined

In Vivo Efficacy In KCL-22 Xenograft Model—Dual Agent Treatment 6-8 week old female nude mice are implanted subcutaneously with 2×10⁶ KCL-22 cells in 50% matrigel (BD Biosciences) in the right dorsal axillary region. Drug treatment is initiated when tumor volume reached an average of 189 mm³ (about 9 days post tumor implantation). Compounds provided herein, in a phosphate-buffered saline solution are prepared weekly and dosed by oral gavage at about 25-35 mg/kg twice daily, and Nilotinib solution is dosed at 75 mg/kg twice daily. Animals receive either single agent alone or combination of both simultaneously. Tumor volume is determined by twice weekly digital calipering and calculated as Length×Width²/2. Animals treated with nilotinib alone can achieve tumor regression after 4 week daily treatment, but tumors can relapse, e.g., to >500 mm³ thereafter. Animals with nilotinib resistant tumors then receive daily treatment of a compound provided herein, and are monitored for tumor response.

What is claimed is:
1. A compound of formula (I) or formula (Ia):

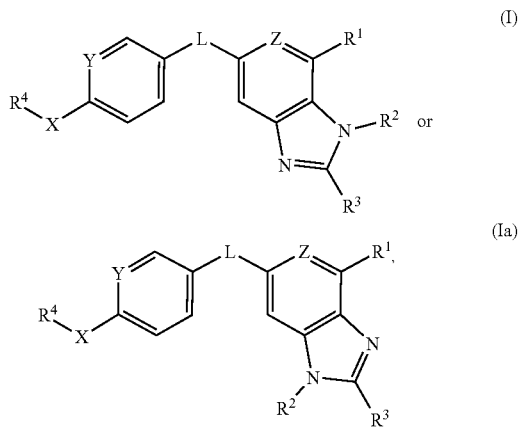

or a pharmaceutically acceptable salt or tautomer thereof, wherein:
L is —C(O)NH—, —NHC(O)—, —NHS(O)$_2$—, or —S(O)$_2$NH—;
X is —O— or —S—;
Y is CH, C(halo), C(C$_1$-C$_2$ alkyl), or N;
Z is CR$^5$ or N;
R$^1$ is C(O)NR$^6$R$^7$, C(O)OR$^6$, NR$^6$C(O)R$^7$, NR$^6$S(O)$_2$R$^7$, S(O)$_2$NR$^6$R$^7$, 4-10 membered heterocyclyl, C$_6$-C$_{10}$ aryl, or 5-10 membered heteroaryl, wherein the 4-10 membered heterocyclyl, C$_6$-C$_{10}$ aryl, and 5-10 membered heteroaryl are each optionally substituted with 1, 2, or 3 substituents independently selected from the group consisting of halo, CN, C$_1$-C$_6$ alkyl, OH, OC$_1$—C$_6$ alkyl, and C$_3$-C$_6$ cycloalkyl;
R$^2$ is H, C$_1$-C$_6$ alkyl, C$_2$-C$_6$ alkenyl, C$_2$-C$_6$ alkynyl, C$_3$-C$_8$ cycloalkyl, 4-10 membered heterocycloalkyl, C$_6$-C$_{10}$ aryl, or 5-10 membered heteroaryl, wherein the C$_1$-C$_6$ alkyl, C$_2$-C$_6$ alkenyl, C$_2$-C$_6$ alkynyl, C$_3$-C$_8$ cycloalkyl, 4-10 membered heterocycloalkyl, C$_6$-C$_{10}$ aryl, and 5-10 membered heteroaryl are each optionally substituted with 1, 2, or 3 substituents independently selected from the group consisting of oxo, halo, CN, C$_1$-C$_6$ alkyl, C(O)NHC$_1$—C$_6$ alkyl, C(O)NHC$_3$—C$_6$ cycloalkyl, OH, OC$_1$—C$_6$ alkyl, C$_3$-C$_6$ cycloalkyl, and 4- to 6-membered heterocyclyl;
R$^3$ is H, C$_1$-C$_6$ alkyl, C$_2$-C$_6$ alkenyl, C$_2$-C$_6$ alkynyl, NR$^6$R$^7$, OR$^6$, cycloalkyl, heterocycloalkyl, aryl, or heteroaryl, wherein the C$_1$-C$_6$ alkyl, C$_2$-C$_6$ alkenyl, C$_2$-C$_6$ alkynyl, cycloalkyl, heterocycloalkyl, aryl, and heteroaryl are each optionally substituted with 1, 2, or 3 substituents independently selected from the group consisting of halo, C$_1$-C$_6$ alkyl, OH, and OC$_1$—C$_6$ alkyl; or
R$^2$ and R$^3$, together with the intervening atoms to which they are attached, form a 4-10 membered heterocycloalkyl, wherein the 4-10 membered heterocycloalkyl is optionally substituted with 1, 2, or 3 substituents independently selected from the group consisting of oxo, C$_1$-C$_6$ alkyl, C$_1$-C$_6$ haloalkyl, C$_1$-C$_6$ alkyl-OH, C(O)C$_1$-C$_6$ alkyl, and OH;
R$^4$ is C$_1$-C$_6$ alkyl, C$_2$-C$_6$ alkenyl, or C$_2$-C$_6$ alkynyl, wherein the C$_1$-C$_6$ alkyl, C$_2$-C$_6$ alkenyl, and C$_2$-C$_6$ alkynyl are each optionally substituted with 1, 2, or 3 independently selected halo substituents;

$R^5$ is H or halo;

$R^6$ is H, $C_1$-$C_6$ alkyl, $C_3$-$C_8$ cycloalkyl, 4-10 membered heterocycloalkyl, $C_6$-$C_{10}$ aryl, or 5-10 membered heteroaryl, wherein the $C_1$-$C_6$ alkyl, $C_3$-$C_8$ cycloalkyl, 4-10 membered heterocycloalkyl, $C_6$-$C_{10}$ aryl, and 5-10 membered heteroaryl are each optionally substituted with 1, 2, or 3 substituents independently selected from the group consisting of halo, $C_1$-$C_6$ alkyl, and OH; and $R^7$ is H, $C_1$-$C_6$ alkyl, $C_3$-$C_8$ cycloalkyl, 4-10 membered heterocycloalkyl, $C_6$-$C_{10}$ aryl, or 5-10 membered heteroaryl, wherein the $C_1$-$C_6$ alkyl, $C_3$-$C_8$ cycloalkyl, 4-10 membered heterocycloalkyl, $C_6$-$C_{10}$ aryl, and 5-10 membered heteroaryl are each optionally substituted with 1, 2, or 3 substituents independently selected from the group consisting of halo, $C_1$-$C_6$ alkyl, and OH; or $R^6$ and $R^7$, together with the nitrogen atom to which they are attached, form a 4-7 membered heterocyclyl, wherein the 4-7 membered heterocyclyl is optionally substituted with 1, 2, or 3 substituents independently selected from the group consisting of halo, $C_1$-$C_6$ alkyl, and OH;

with the proviso that the compound is not:

(i)

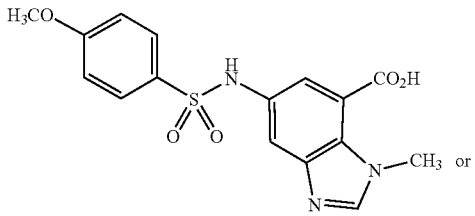

or (ii)

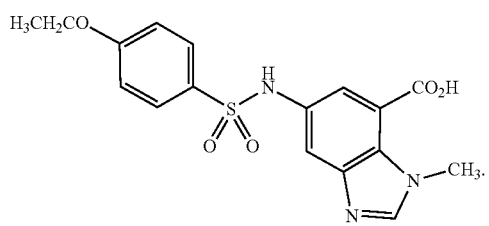

2. The compound of claim 1, wherein the compound is of formula (IA-1):

(IA-1)

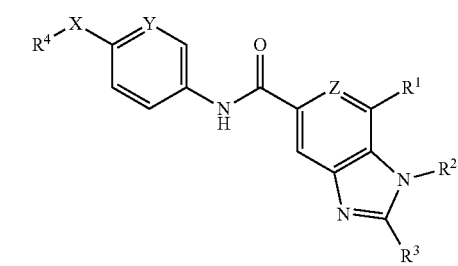

or a pharmaceutically acceptable salt or tautomer thereof.

3. The compound of claim 2, wherein the compound is of formula (IIA), formula (IIB), formula (IIC), formula (IID), formula (IIE), formula (IIF), formula (IIG), or formula (IIH):

(IIA)

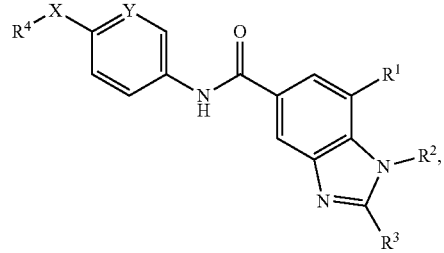

(IIB)

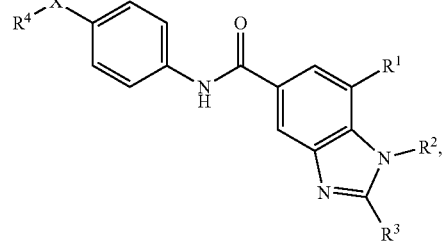

(IIC)

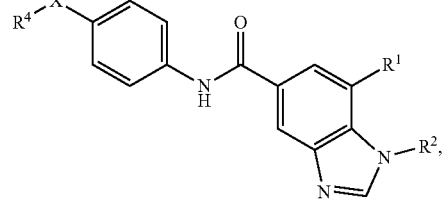

(IID)

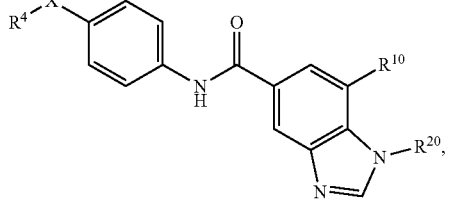

(IIE)

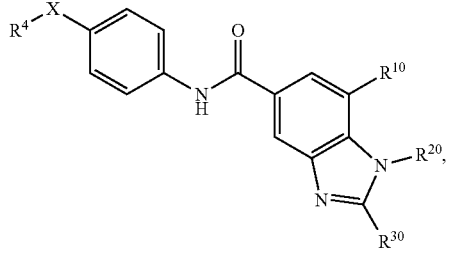

(IIF)

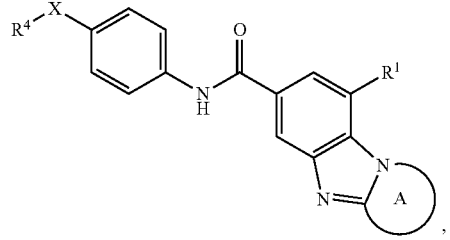

(IIG)

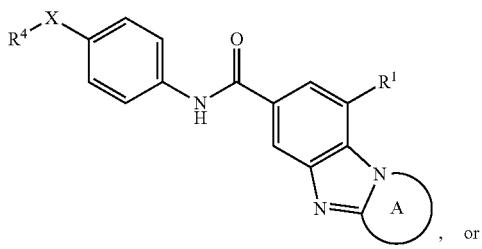

, or (IIH)

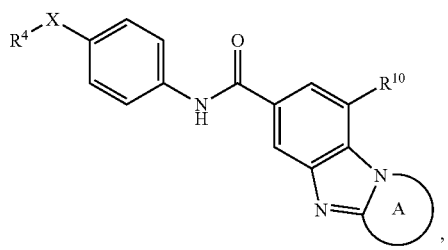

, or a pharmaceutically acceptable salt or tautomer thereof, wherein:
- $R^{10}$ is 5-6 membered heteroaryl, optionally substituted with 1, 2, or 3 substituents independently selected from the group consisting of halo, CN, $C_1$-$C_6$ alkyl, OH, $OC_1$—$C_6$ alkyl, and $C_3$-$C_6$ cycloalkyl;
- $R^{20}$ is $C_1$-$C_3$ alkyl, $C_3$-$C_4$ cycloalkyl, or 4-6 membered heterocycloalkyl, wherein the $C_1$-$C_3$ alkyl, $C_3$-$C_4$ cycloalkyl, and 4-6 membered heterocycloalkyl are each optionally substituted with 1, 2, or 3 substituents independently selected from the group consisting of oxo, halo, CN, $C_1$-$C_6$ alkyl, $C(O)NHC_1$—$C_6$ alkyl, $C(O)NHC_3$—$C_6$ cycloalkyl, OH, $OC_1$—$C_6$ alkyl, $C_3$-$C_6$ cycloalkyl, and 4- to 6-membered heterocyclyl;
- $R^{30}$ is H, $C_1$-$C_3$ alkyl, $C_3$-$C_4$ cycloalkyl, or 5-6 membered heterocycloalkyl, wherein the $C_1$-$C_3$ alkyl, $C_3$-$C_4$ cycloalkyl, or 5-6 membered heterocycloalkyl are each optionally substituted with 1, 2, or 3 substituents independently selected from the group consisting of halo, $C_1$-$C_6$ alkyl, and OH; and
- Ring A is 5-6 membered heterocycloalkyl, optionally substituted with 1, 2, or 3 substituents independently selected from the group consisting of oxo, $C_1$-$C_6$ alkyl, $C_1$-$C_6$ haloalkyl, $C_1$-$C_6$ alkyl-OH, $C(O)C_1$-$C_6$ alkyl, and OH.

4. The compound of claim 3, or a pharmaceutically acceptable salt or tautomer thereof, wherein $R^{30}$ is $C_1$-$C_3$ alkyl, $C_3$-$C_4$ cycloalkyl, or 5-6 membered heterocycloalkyl, wherein the $C_1$-$C_3$ alkyl, $C_3$-$C_4$ cycloalkyl, or 5-6 membered heterocycloalkyl are each optionally substituted with 1, 2, or 3 substituents independently selected from the group consisting of halo, $C_1$-$C_6$ alkyl, and OH.

5. The compound of claim 2, or a pharmaceutically acceptable salt or tautomer thereof, wherein X is —O—.

6. The compound of claim 2, or a pharmaceutically acceptable salt or tautomer thereof, wherein Y is CH.

7. The compound of claim 3, or a pharmaceutically acceptable salt or tautomer thereof, wherein $R^1$ is 4-10 membered heterocyclyl or 5-10 membered heteroaryl, wherein the 4-10 membered heterocyclyl and 5-10 membered heteroaryl are each optionally substituted with 1, 2, or 3 substituents independently selected from the group consisting of halo, CN, $C_1$-$C_6$ alkyl, OH, $OC_1$—$C_6$ alkyl, and $C_3$-$C_6$ cycloalkyl.

8. The compound of claim 2, or a pharmaceutically acceptable salt or tautomer thereof, wherein $R^1$ is —C(O)NH$_2$, C(O)NHCH$_3$, C(O)NH(cyclopropyl),

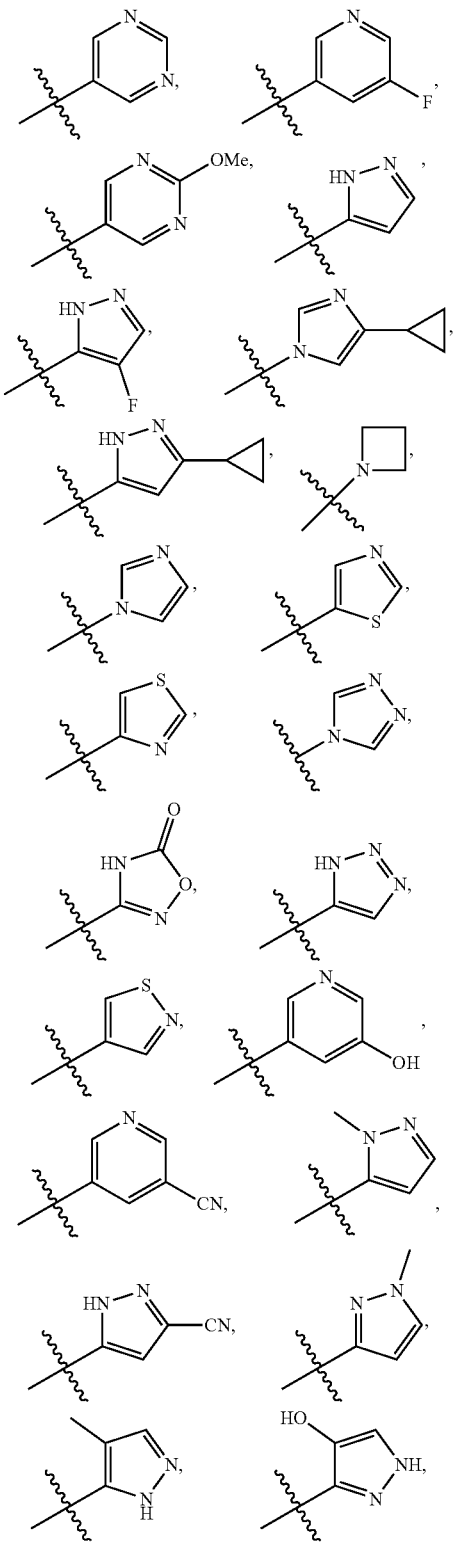

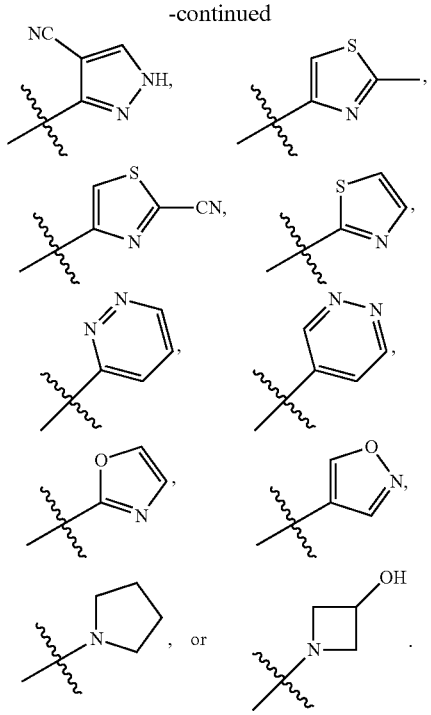

9. The compound of claim 2, or a pharmaceutically acceptable salt or tautomer thereof, wherein $R^1$ is pyrazolyl or pyrimidinyl, wherein the pyrazolyl and pyrimidinyl are each optionally substituted with 1, 2, or 3 substituents independently selected from the group consisting of halo, CN, $C_1$-$C_6$ alkyl, OH, $OC_1$—$C_6$ alkyl, and $C_3$-$C_6$ cycloalkyl.

10. The compound of claim 2, or a pharmaceutically acceptable salt or tautomer thereof, wherein $R^2$ is $C_1$-$C_3$ alkyl or $C_3$-$C_4$ cycloalkyl, wherein the $C_1$-$C_3$ alkyl and $C_3$-$C_4$ cycloalkyl are each optionally substituted with 1, 2, or 3 substituents independently selected from the group consisting of oxo, halo, CN, $C_1$-$C_6$ alkyl, C(O)NHC$_1$—C$_6$ alkyl, C(O)NHC$_3$—C$_6$ cycloalkyl, OH, $OC_1$—$C_6$ alkyl, $C_3$-$C_6$ cycloalkyl, and 4- to 6-membered heterocyclyl.

11. The compound of claim 2, or a pharmaceutically acceptable salt or tautomer thereof, wherein $R^2$ is $CH_3$, $CH_2CH_3$, $CH(CH_3)_2$, $C(CH_3)_3$, cyclopropyl, cyclobutyl, cyclopentyl, tetrahydrofuranyl, tetrahydropyranyl,

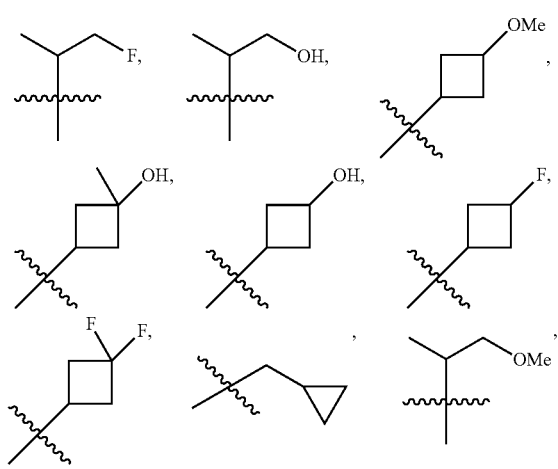

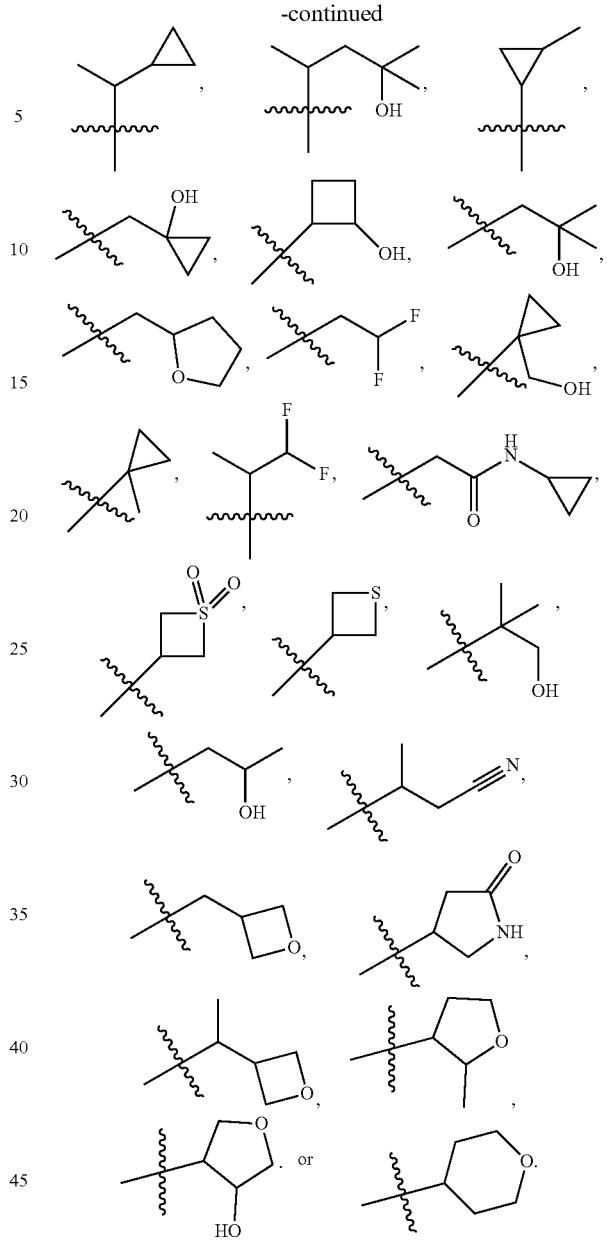

12. The compound of claim 2, or a pharmaceutically acceptable salt or tautomer thereof, wherein $R^3$ is H, $CH_3$, $CHF_2$, $CH_2OH$, $CH_2OCH_3$, $CH_2CH_2OH$, $CH(CH_3)OH$, $CH(CH_3)_2$, $C(CH_3)_2OH$, $OCH_3$, $OCH_2CH_3$, cyclopropyl, cyclobutyl, or tetrahydropyranyl.

13. The compound of claim 2, or a pharmaceutically acceptable salt or tautomer thereof, wherein $R^2$ and $R^3$ together form

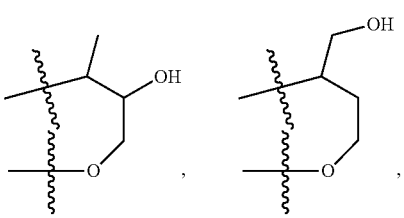

-continued

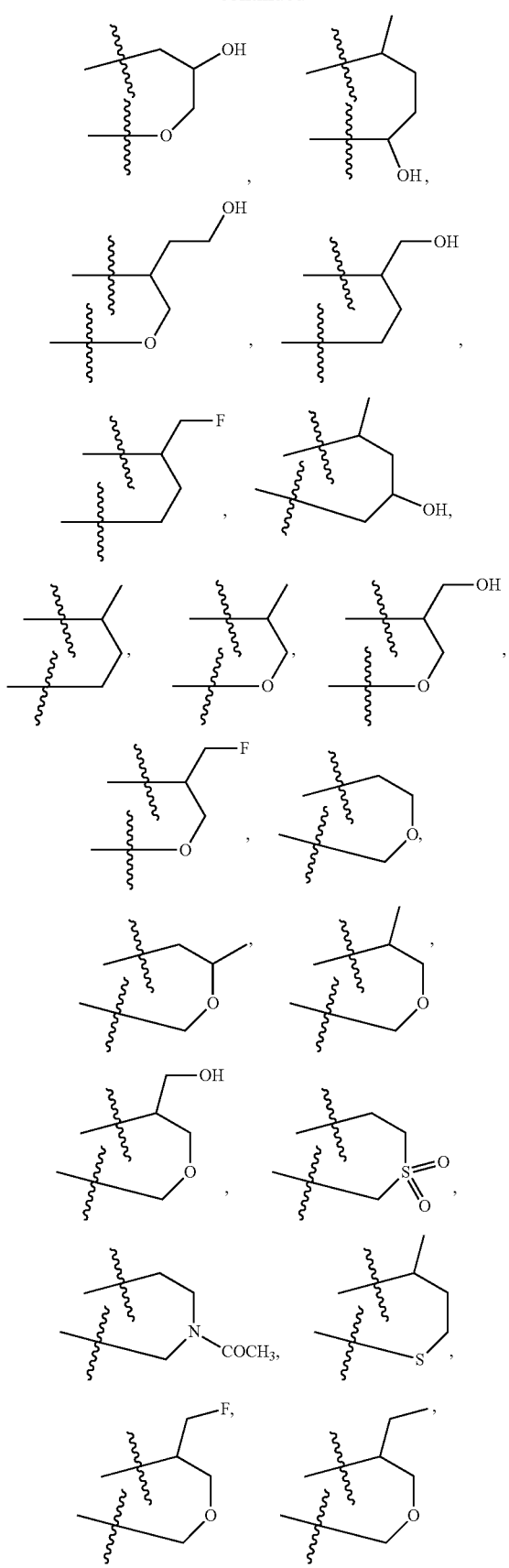

-continued

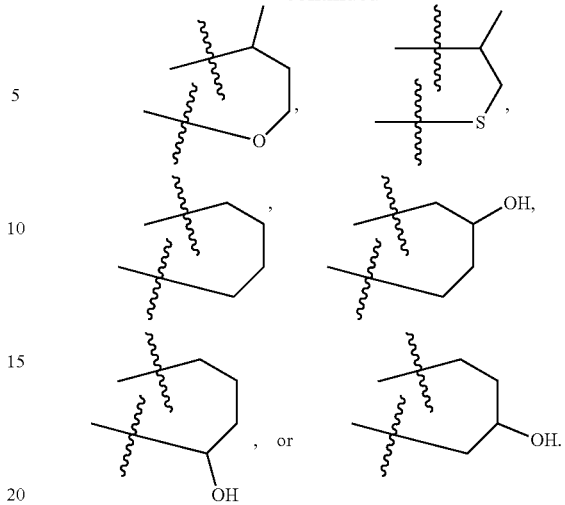

14. The compound of claim 2, or a pharmaceutically acceptable salt or tautomer thereof, wherein $R^4$ is $C_1$-$C_3$ alkyl, optionally substituted with 1, 2, or 3 independently selected halo substituents.

15. The compound of claim 2, or a pharmaceutically acceptable salt or tautomer thereof, wherein $R^4$ is $CF_3$ or $CF_2Cl$.

16. The compound of claim 2, or a pharmaceutically acceptable salt or tautomer thereof, wherein $R^5$ is H.

17. The compound of claim 2, wherein the compound is of formula (Id) or formula (Ie):

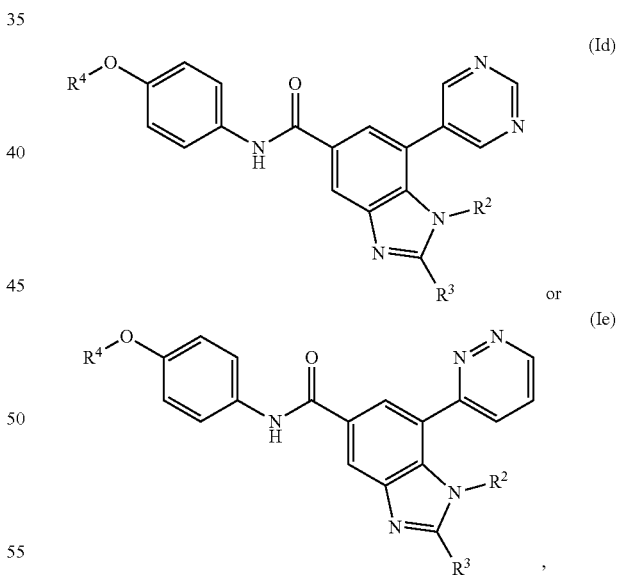

or a pharmaceutically acceptable salt or tautomer thereof.

18. The compound of claim 1, or a pharmaceutically acceptable salt or tautomer thereof, wherein:

$R^1$ is 4-10 membered heterocyclyl, $C_6$-$C_{10}$ aryl, or 5-10 membered heteroaryl, each optionally substituted with 1, 2, or 3 substituents independently selected from the group consisting of halo, CN, $C_1$-$C_6$ alkyl, OH, $OC_1$—$C_6$ alkyl, and $C_3$-$C_6$ cycloalkyl;

$R^2$ is $C_1$-$C_6$ alkyl, $C_2$-$C_6$ alkenyl, $C_2$-$C_6$ alkynyl, $C_3$-$C_8$ cycloalkyl, 4-10 membered heterocycloalkyl, $C_6$-$C_{10}$ aryl, or 5-10 membered heteroaryl, wherein the $C_1$-$C_6$ alkyl, $C_2$-$C_6$ alkenyl, $C_2$-$C_6$ alkynyl, $C_3$-$C_8$ cycloalkyl, 4-10 membered heterocycloalkyl, $C_6$-$C_{10}$ aryl, and 5-10 membered heteroaryl are each optionally substituted with 1, 2, or 3 substituents independently selected from the group consisting of oxo, halo, CN, $C_1$-$C_6$ alkyl, C(O)NH$C_1$—$C_6$ alkyl, C(O)NH$C_3$—$C_6$ cycloalkyl, OH, O$C_1$—$C_6$ alkyl, $C_3$-$C_6$ cycloalkyl, and 4- to 6-membered heterocyclyl;

$R^3$ is $C_1$-$C_6$ alkyl, $C_2$-$C_6$ alkenyl, $C_2$-$C_6$ alkynyl, $C_3$-$C_6$ cycloalkyl, 4- to 6-membered heterocycloalkyl, $C_6$-$C_{10}$ aryl, or 5- to 10-membered heteroaryl, wherein the $C_1$-$C_6$ alkyl, $C_2$-$C_6$ alkenyl, $C_2$-$C_6$ alkynyl, $C_3$-$C_6$ cycloalkyl, 4- to 6-membered heterocycloalkyl, $C_6$-$C_{10}$ aryl, and 5- to 10-membered heteroaryl are each optionally substituted with 1, 2, or 3 substituents independently selected from the group consisting of halo, $C_1$-$C_6$ alkyl, and OH; or $R^2$ and $R^3$, together with the intervening atoms to which they are attached, form a 4-10 membered heterocycloalkyl, wherein the 4-10 membered heterocycloalkyl is optionally substituted with 1, 2, or 3 substituents independently selected from the group consisting of oxo, $C_1$-$C_6$ alkyl, $C_1$-$C_6$ alkyl-OH, C(O)$C_1$-$C_6$ alkyl, and OH;

$R^4$ is $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, and $C_2$-$C_6$ alkynyl are each optionally substituted with 1, 2, or 3 independently selected halo substituents;

$R^6$ is $C_1$-$C_6$ alkyl, $C_3$-$C_8$ cycloalkyl, 4-10 membered heterocycloalkyl, $C_6$-$C_{10}$ aryl, or 5-10 membered heteroaryl, wherein the $C_1$-$C_6$ alkyl, $C_3$-$C_8$ cycloalkyl, 4-10 membered heterocycloalkyl, $C_6$-$C_{10}$ aryl, and 5-10 membered heteroaryl are each optionally substituted with 1, 2, or 3 substituents independently selected from the group consisting of halo, $C_1$-$C_6$ alkyl, and OH; and $R^7$ is $C_1$-$C_6$ alkyl, $C_3$-$C_8$ cycloalkyl, 4-10 membered heterocycloalkyl, $C_6$-$C_{10}$ aryl, or 5-10 membered heteroaryl, wherein the $C_1$-$C_6$ alkyl, $C_3$-$C_8$ cycloalkyl, 4-10 membered heterocycloalkyl, $C_6$-$C_{10}$ aryl, and 5-10 membered heteroaryl are each optionally substituted with 1, 2, or 3 substituents independently selected from the group consisting of halo, $C_1$-$C_6$ alkyl, and OH; or $R^6$ and $R^7$, together with the nitrogen atom to which they are attached, form a 4-7 membered heterocyclyl, wherein the 4-7 membered heterocyclyl is optionally substituted with 1, 2, or 3 substituents independently selected from the group consisting of halo, $C_1$-$C_6$ alkyl, and OH.

19. A pharmaceutical composition comprising a compound of claim 1, or a pharmaceutically acceptable salt or tautomer thereof, and at least one pharmaceutically acceptable excipient.

20. A method for inhibiting tyrosine kinase activity in a cell, comprising contacting the cell with an effective amount of a compound of claim 1, or a pharmaceutically acceptable salt or tautomer thereof, wherein the tyrosine kinase is selected from the group consisting of Abelson homolog 1, Abelson homolog 2, and breakpoint cluster region-Abelson homolog 1.

21. A method for inhibiting tyrosine kinase activity in a patient, comprising administering to the patient in need thereof a therapeutically effective amount of a compound of claim 1, or a pharmaceutically acceptable salt or tautomer thereof, wherein the tyrosine kinase is selected from the group consisting of Abelson protein, Abelson-related protein, and breakpoint cluster region-Abelson protein.

22. The method of claim 21, wherein the patient has a disease selected from the group consisting of leukemia, Alzheimer's disease, and Parkinson's disease.

23. A method for treating leukemia in a patient, comprising administering to the patient in need thereof a therapeutically effective amount of a compound of claim 1, or a pharmaceutically acceptable salt or tautomer thereof, wherein the leukemia is selected from the group consisting of acute lymphoblastic leukemia, acute myeloid leukemia, and chronic myeloid leukemia.

24. The method of claim 23, wherein:
(a) the leukemia is selected from the group consisting of acute lymphoblastic leukemia and chronic myeloid leukemia; and
(b) the method further comprising administering to the patient in need thereof a therapeutically effective amount of a compound selected from the group consisting of bafetinib, bosutinib, dasatinib, imatinib, nilotinib, and ponatinib.

25. The method of claim 23, wherein the chronic myeloid leukemia is resistant to standard-of-care treatment.

26. The method of claim 23, wherein the chronic myeloid leukemia is resistant to treatment with a compound selected from the group consisting of dasatinib, imatinib, and nilotinib, or a combination thereof.

27. The method of claim 23, wherein the acute myeloid leukemia is secondary acute myeloid leukemia.

28. A compound selected from the group consisting of:

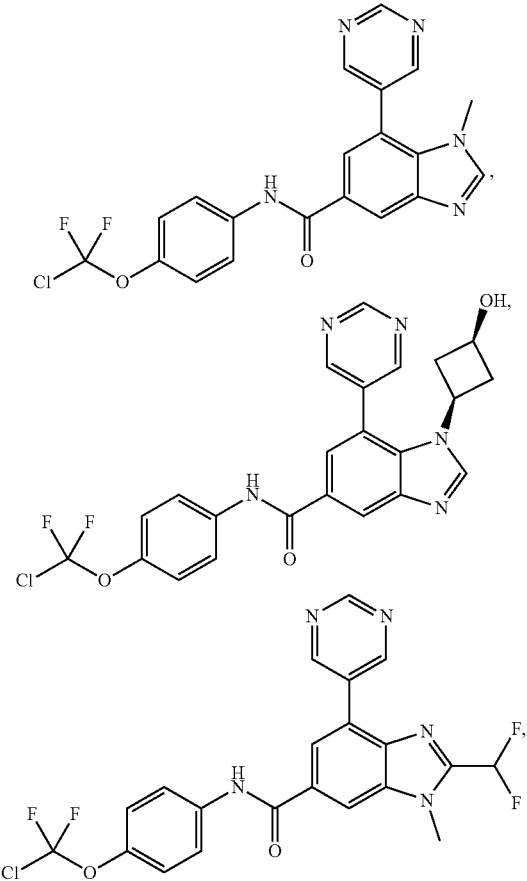

279
-continued
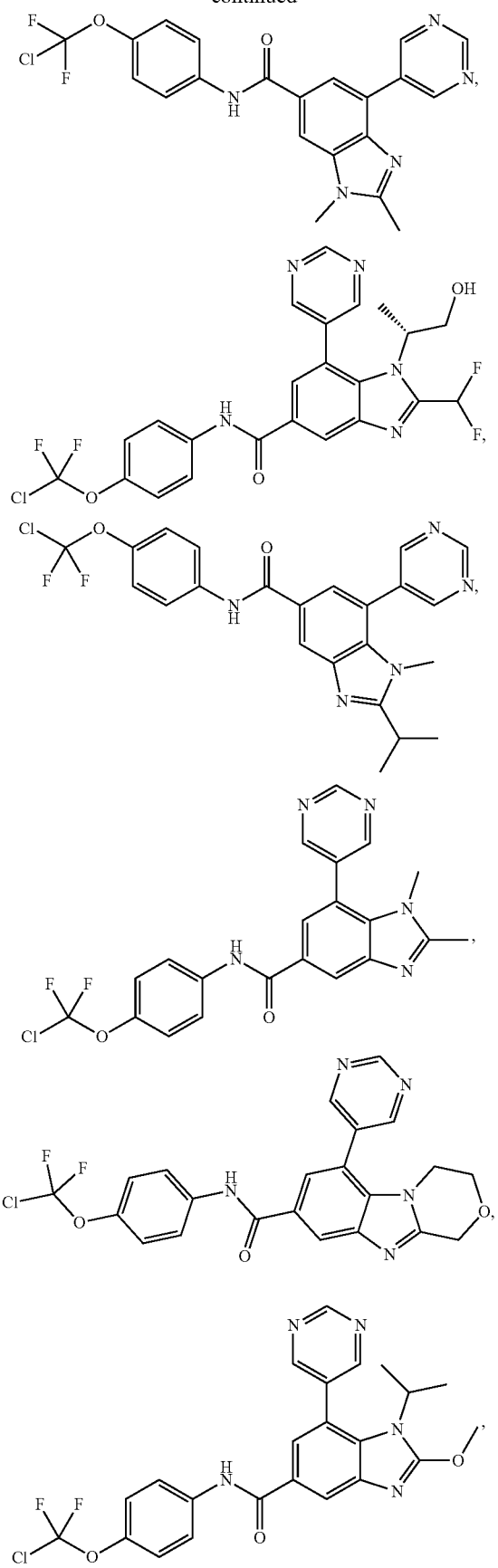
280
-continued
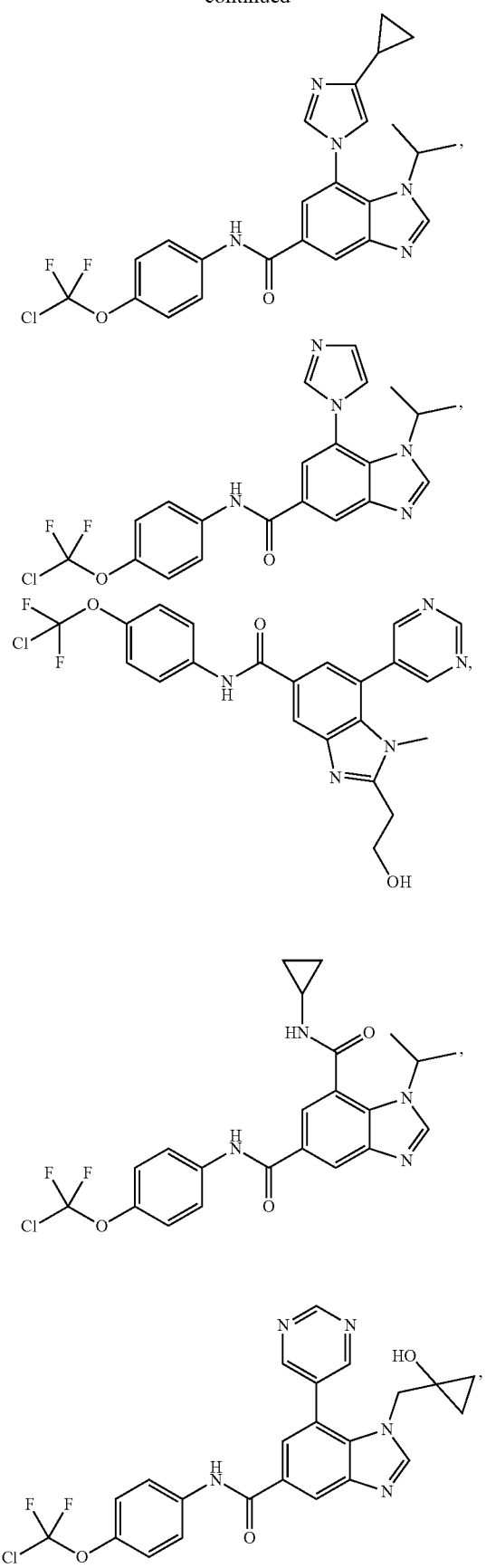

281
-continued
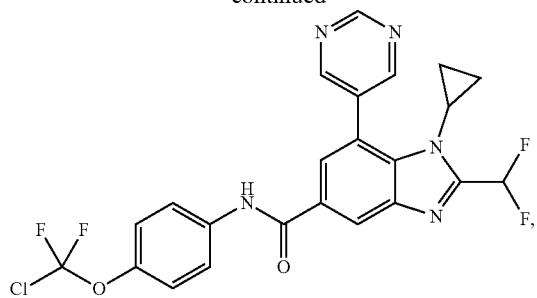
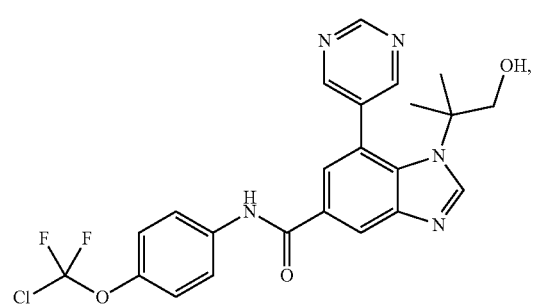
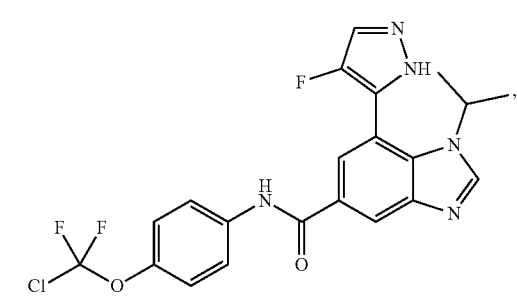
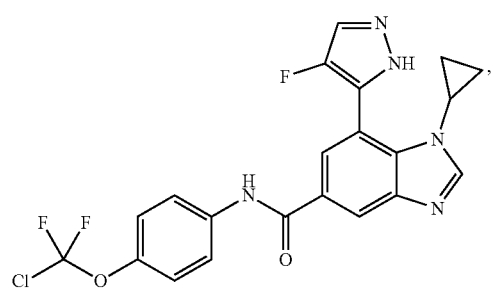
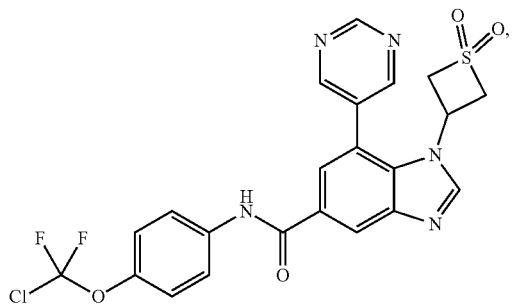
282
-continued
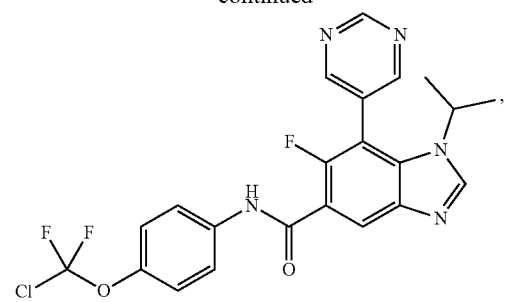
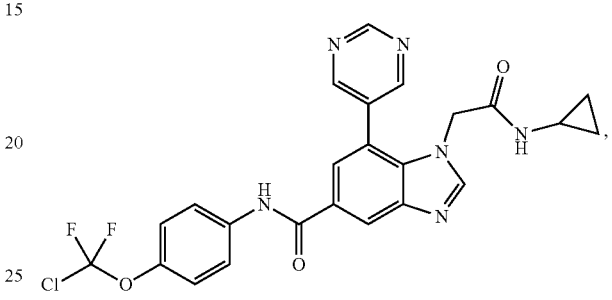
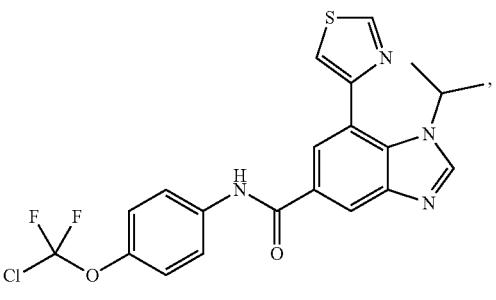
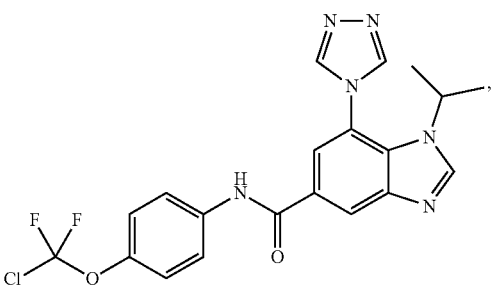
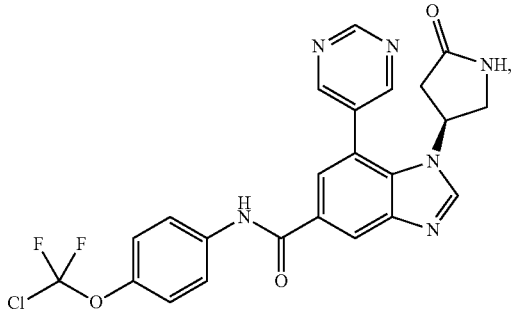

283
-continued
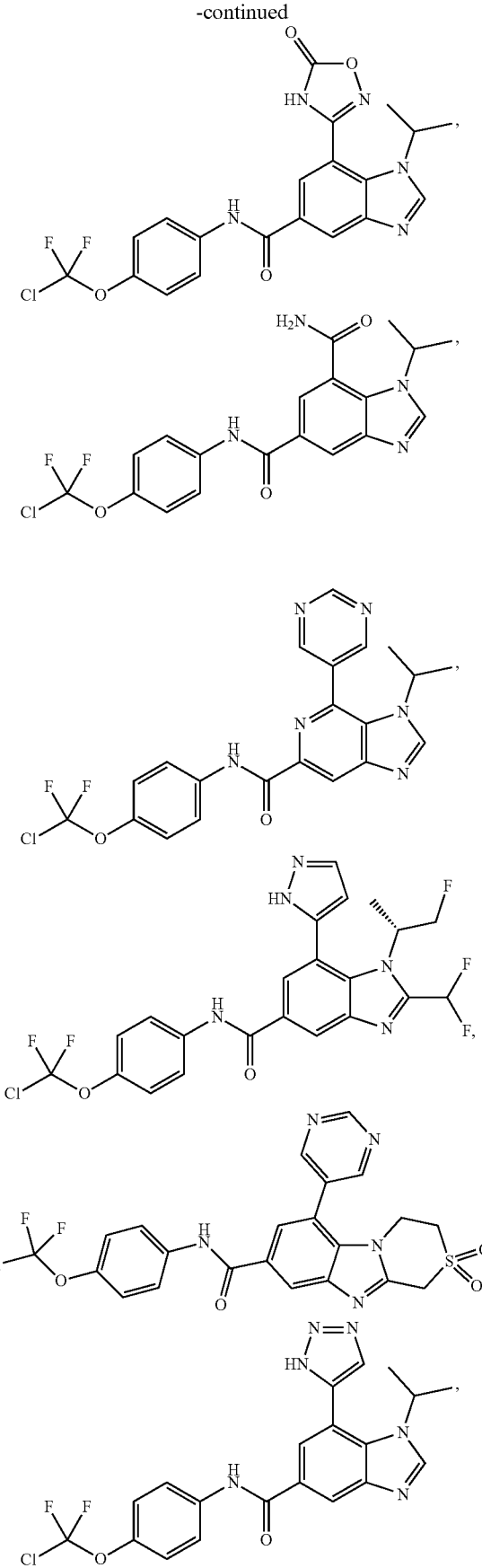
284
-continued
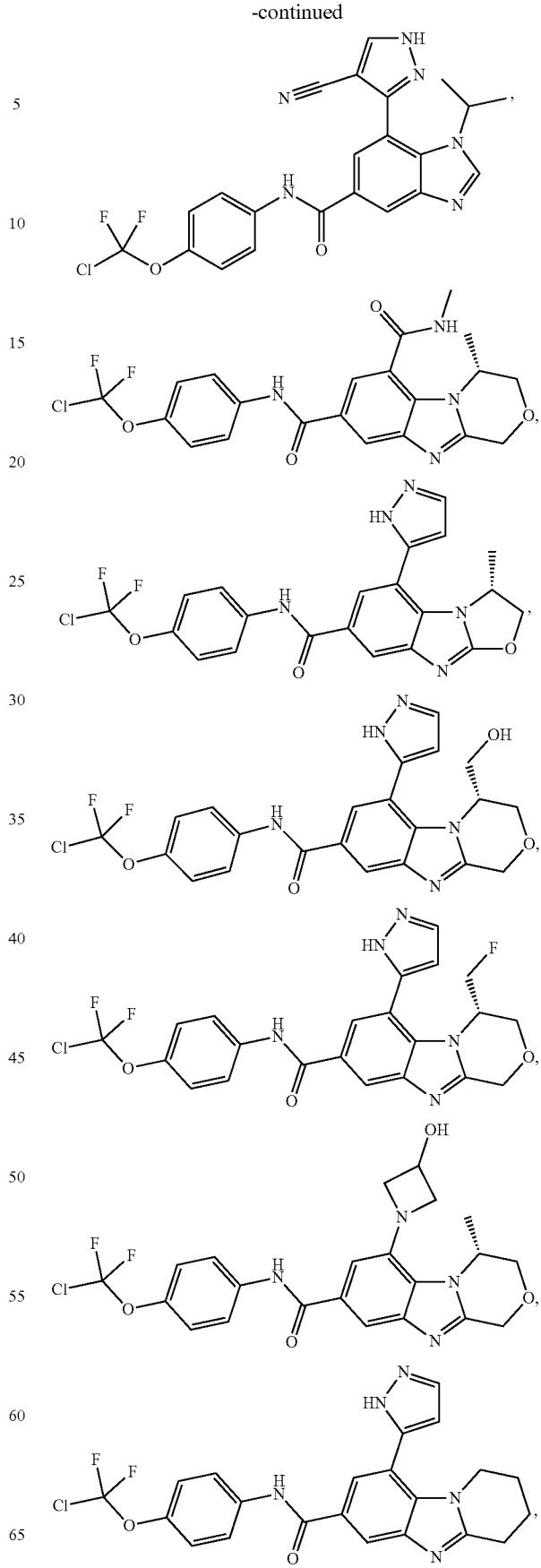

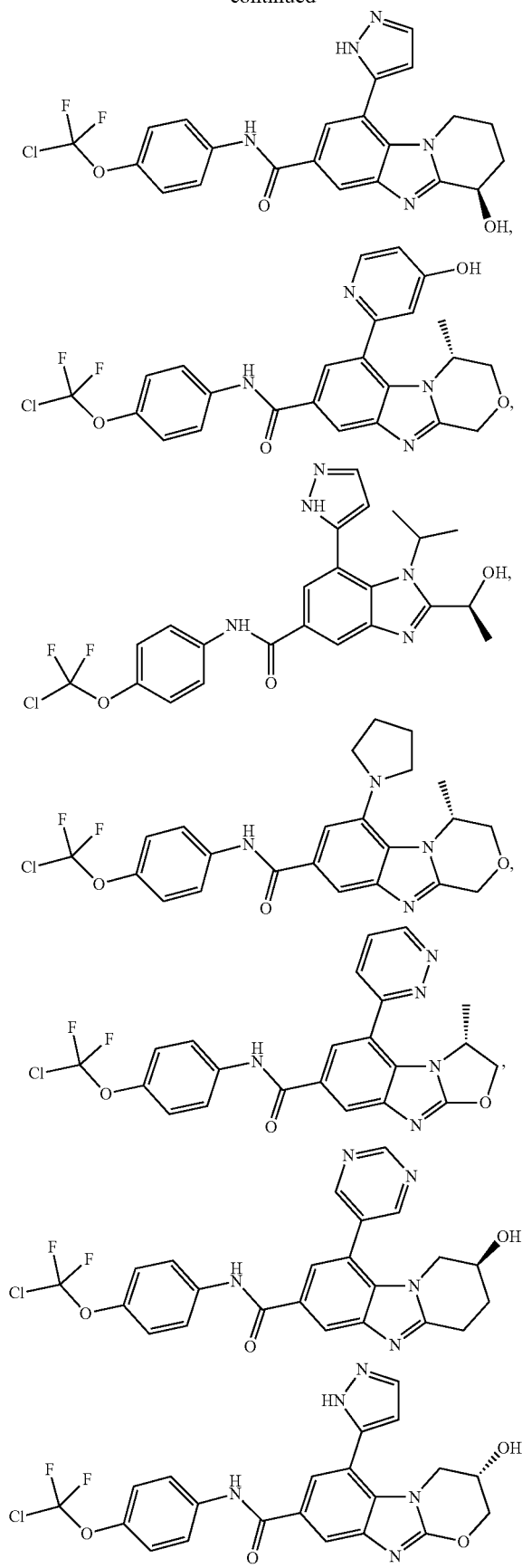
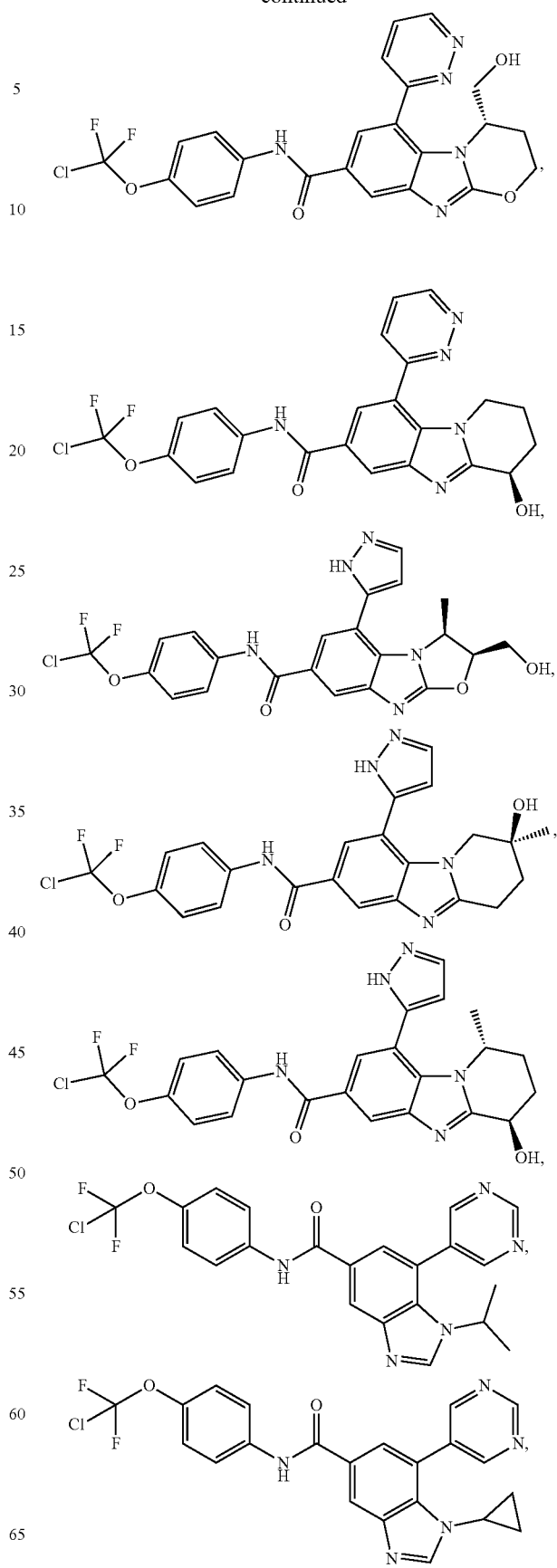

287
-continued
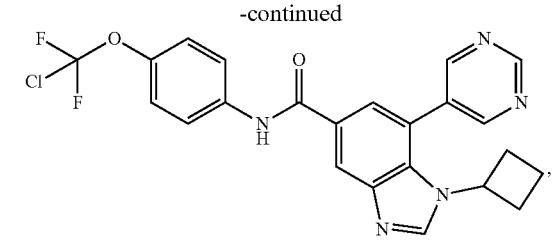
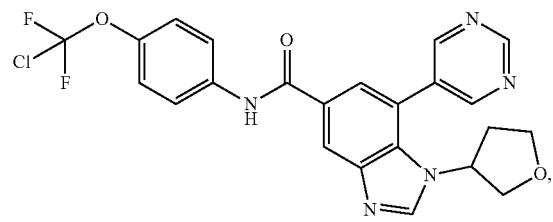
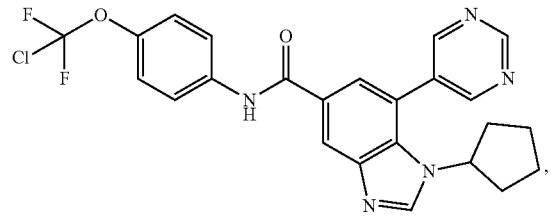
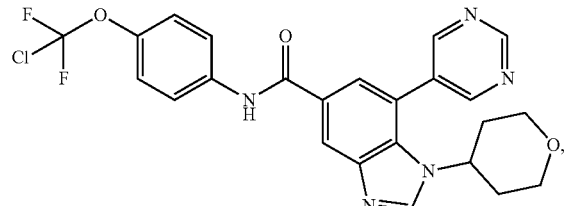
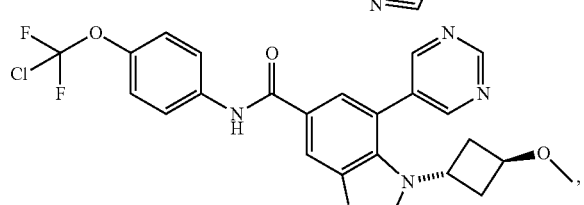
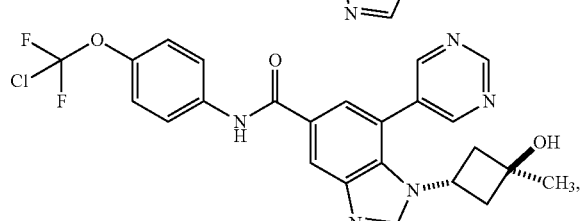
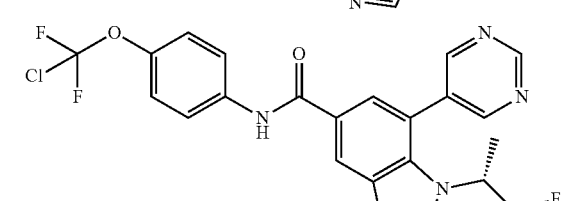
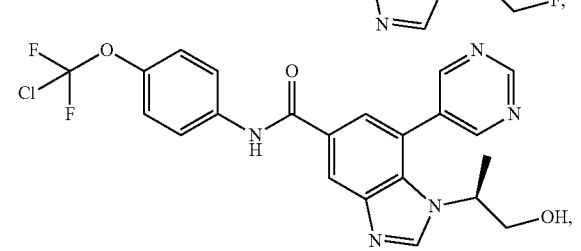
288
-continued
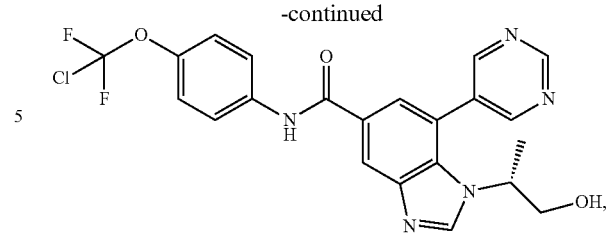
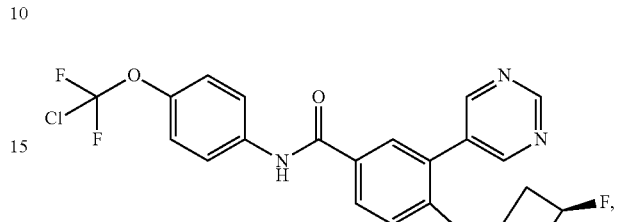
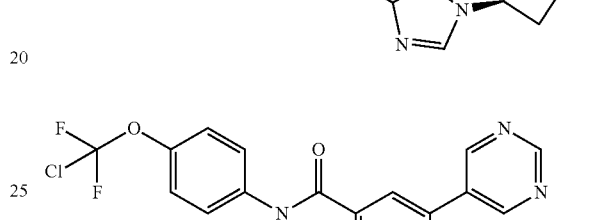
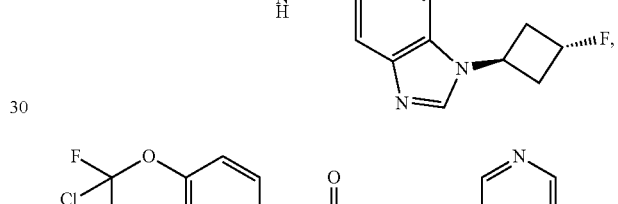
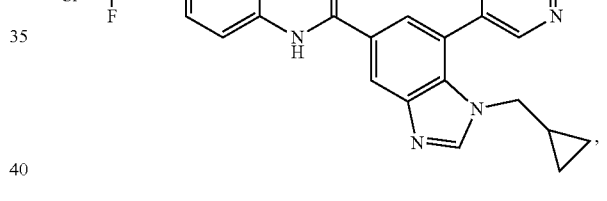
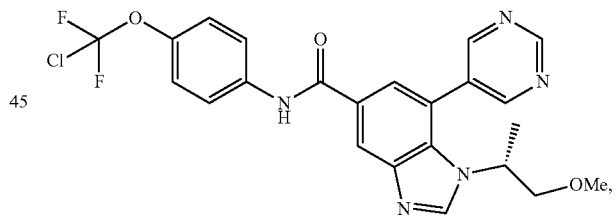
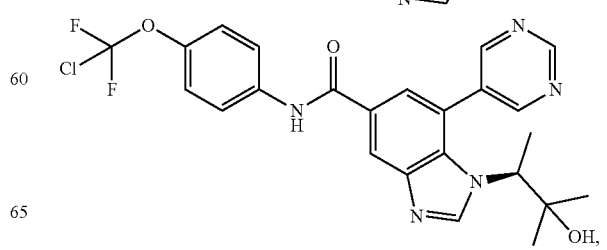

289
-continued
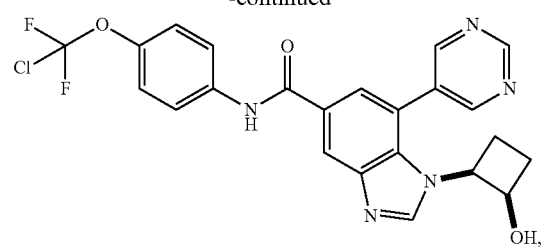
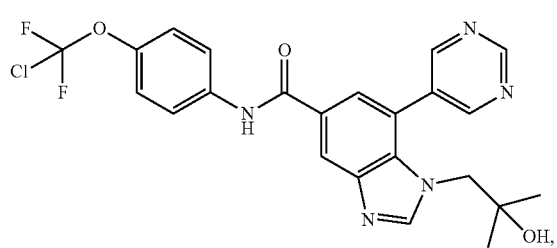
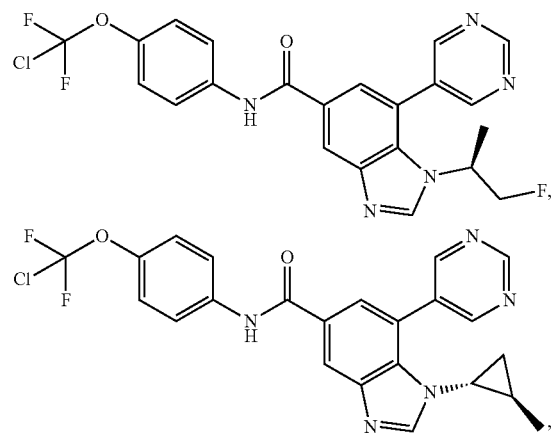
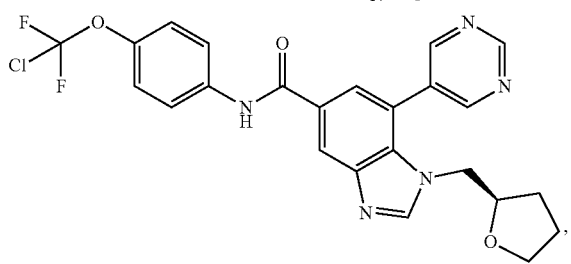
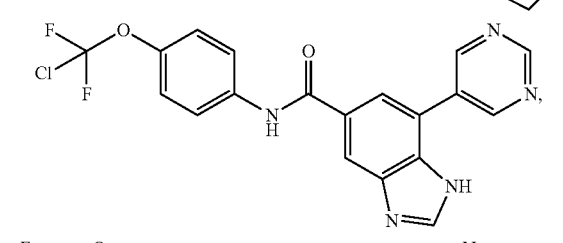
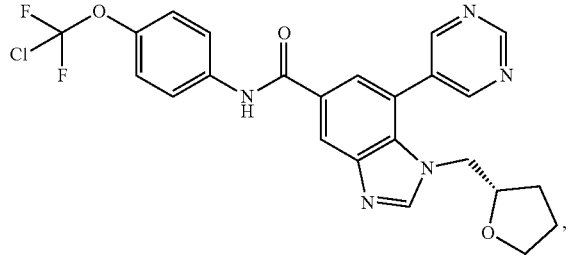
290
-continued
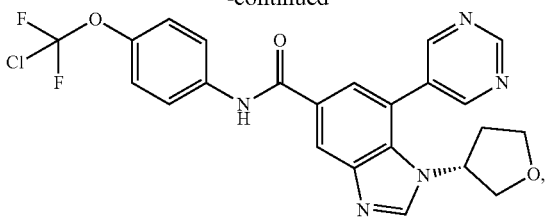
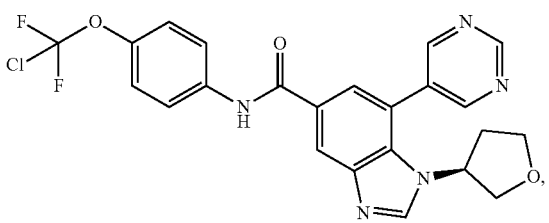
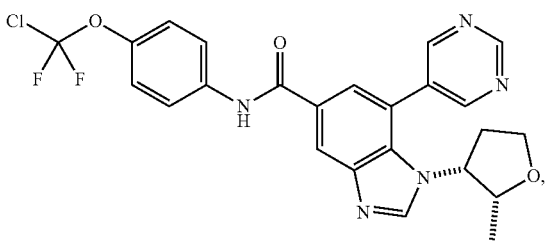
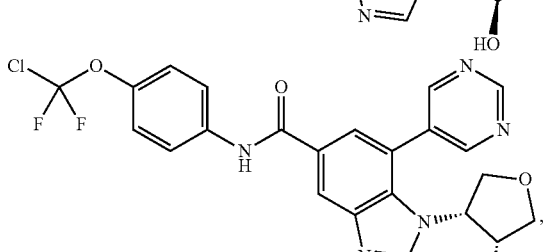
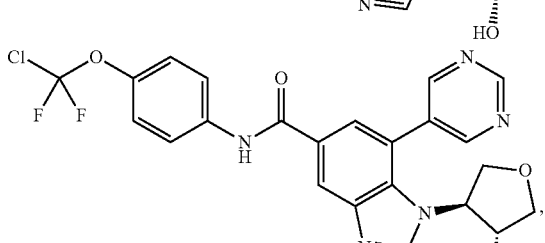
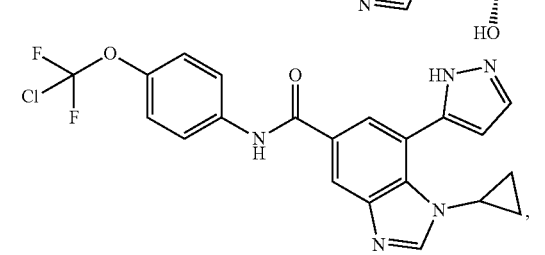

-continued
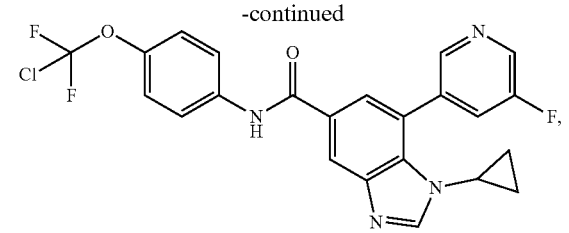
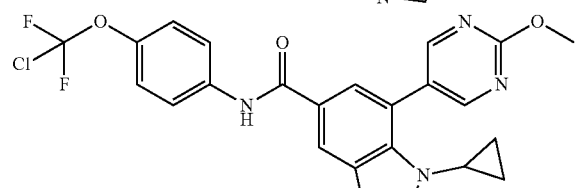
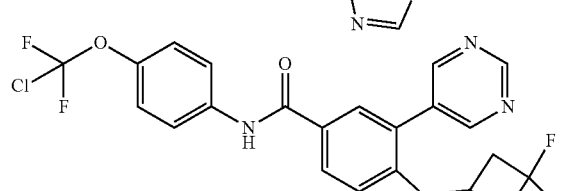
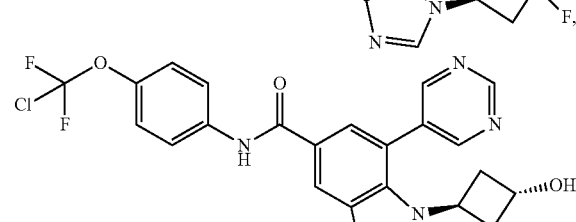
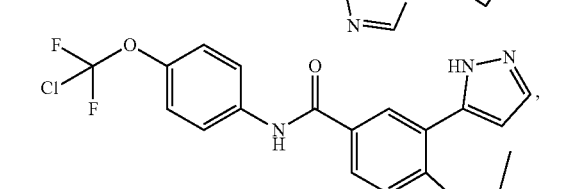
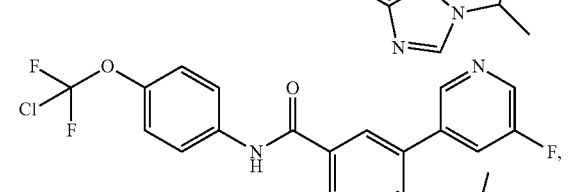
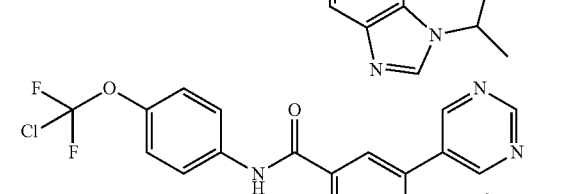
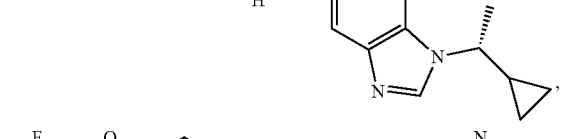
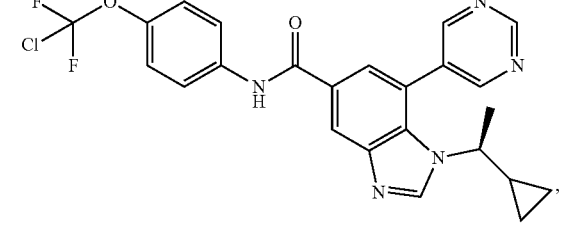
-continued
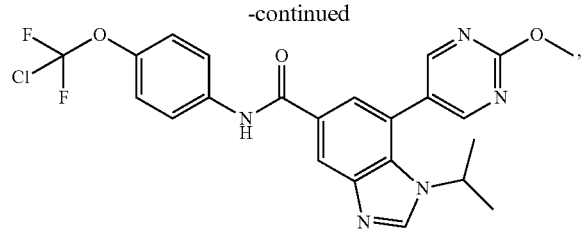
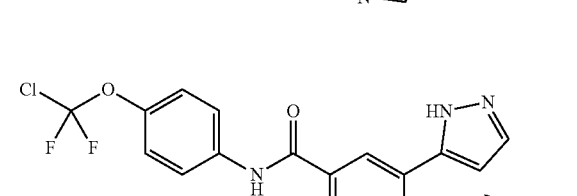
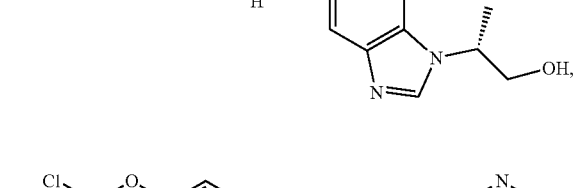
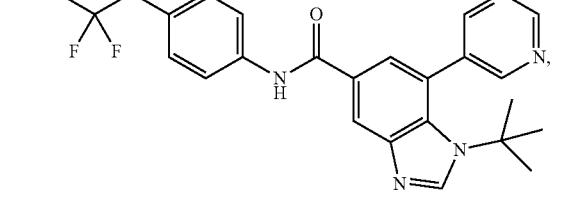
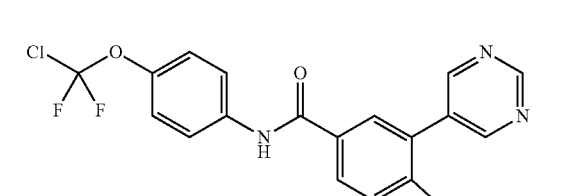
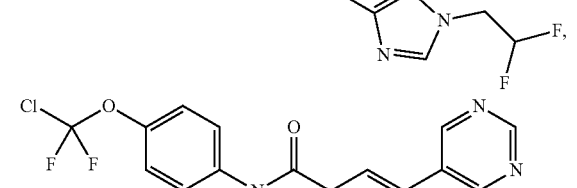
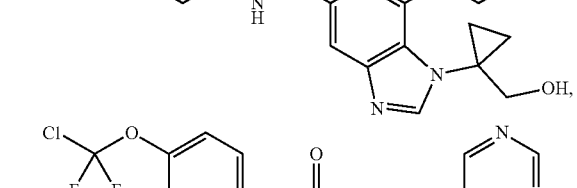
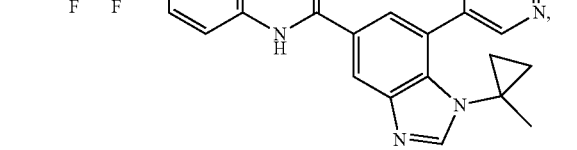
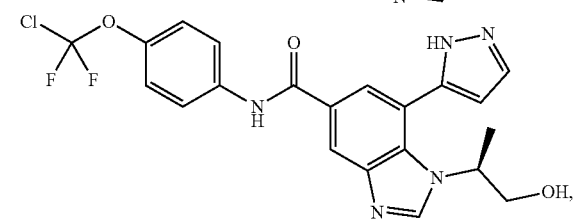

293
-continued
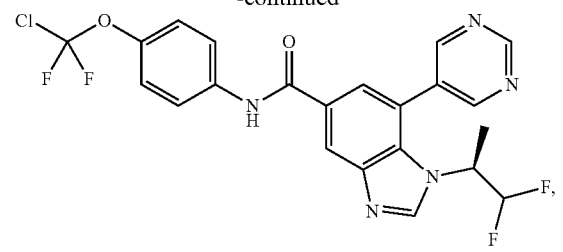
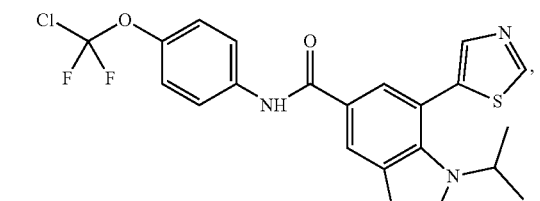
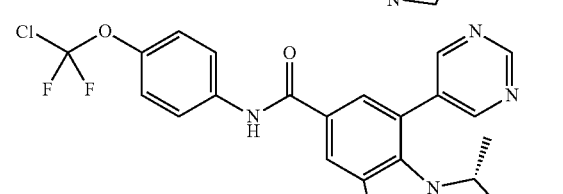
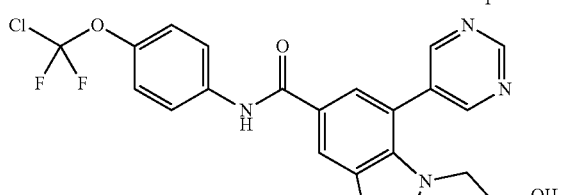
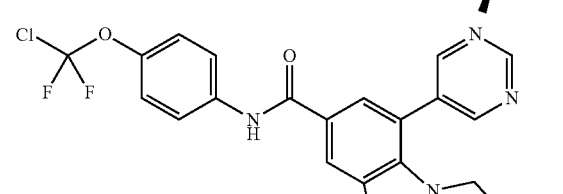
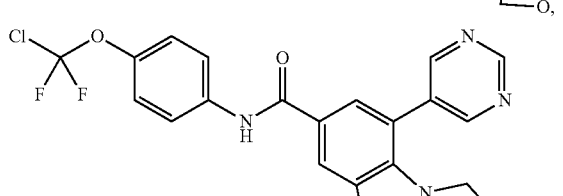
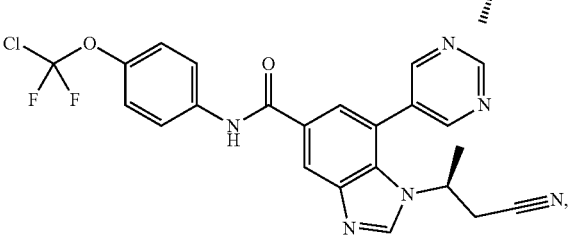
294
-continued
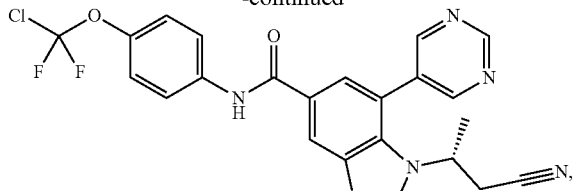
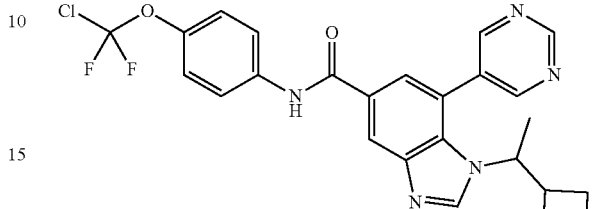
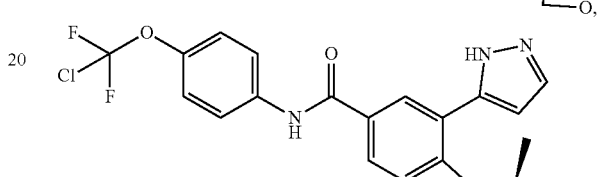
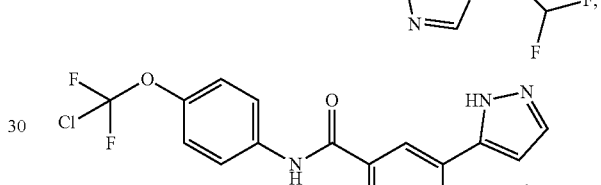
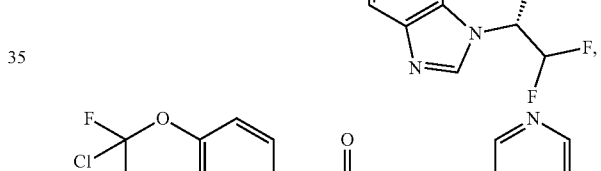
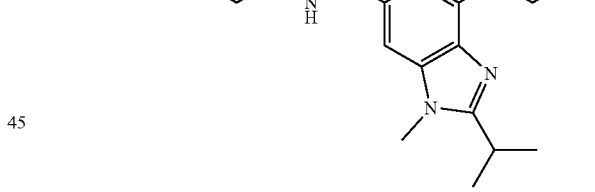
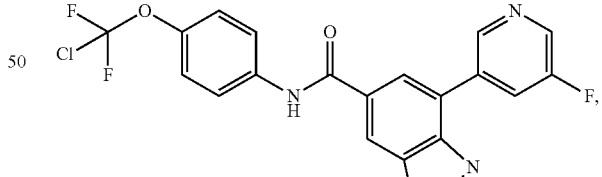
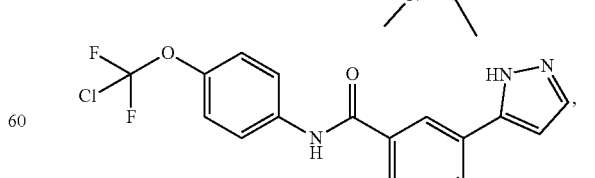

295
-continued
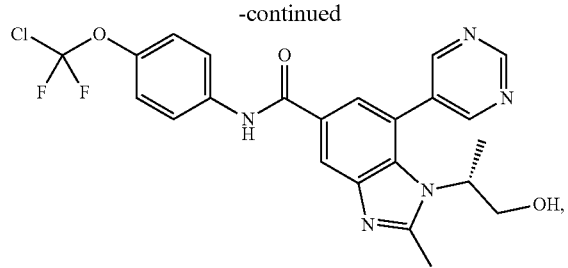
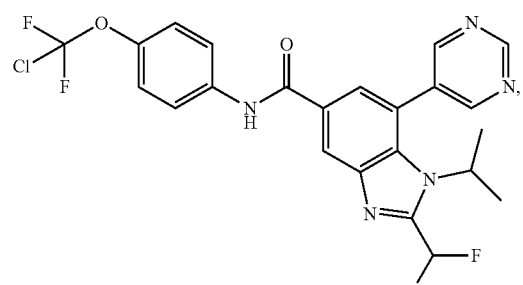
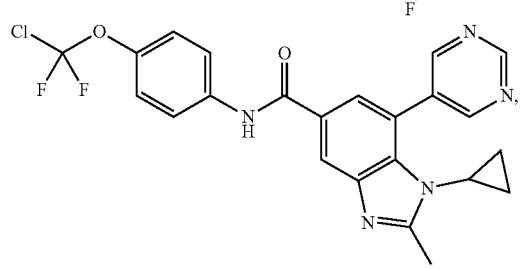
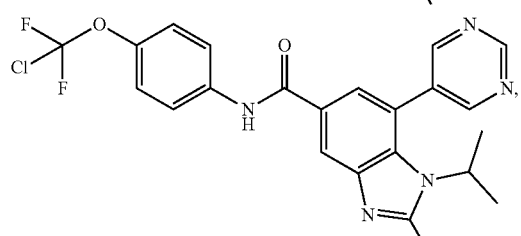
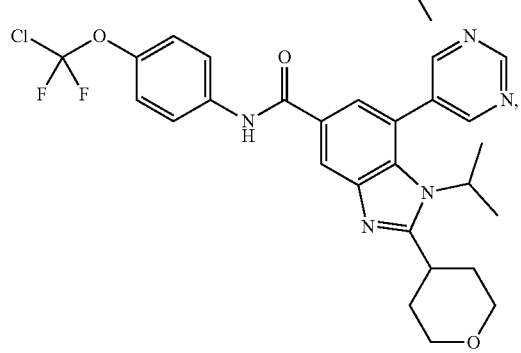
296
-continued
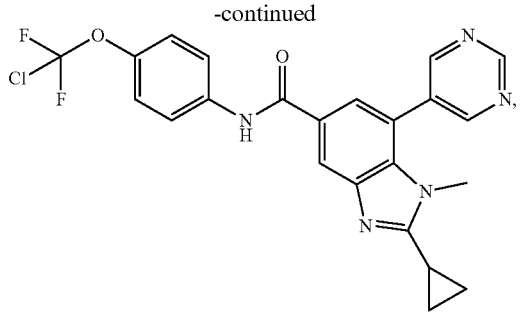
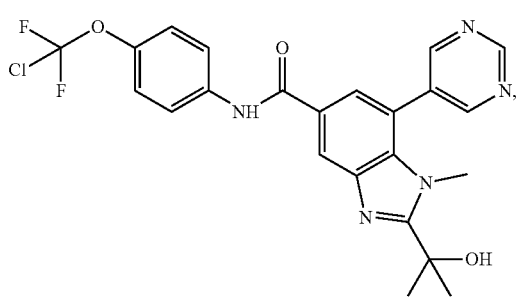
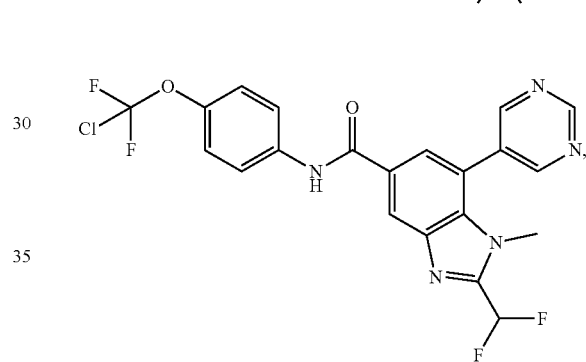
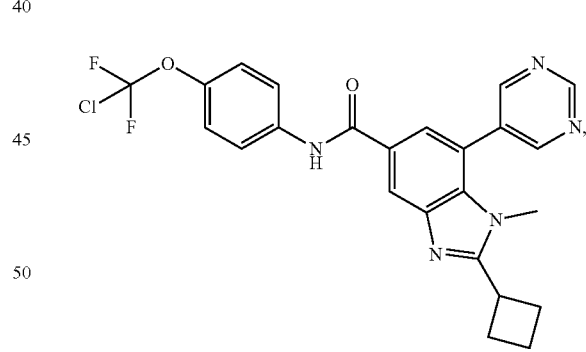
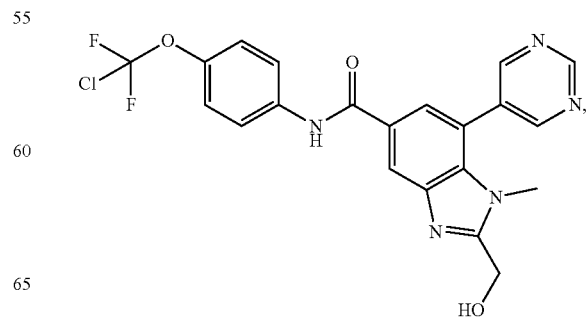

-continued
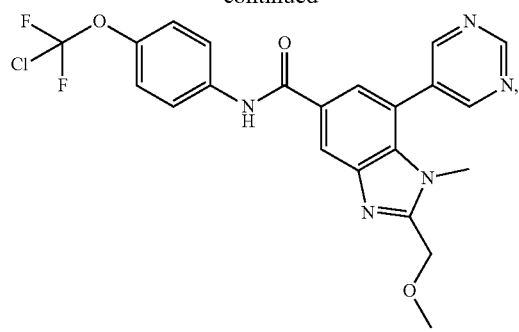
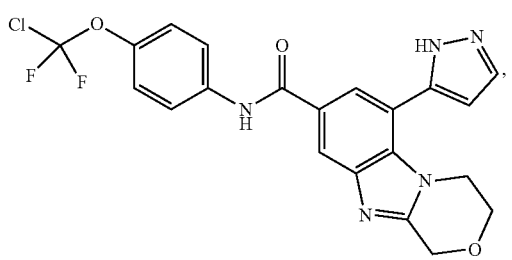
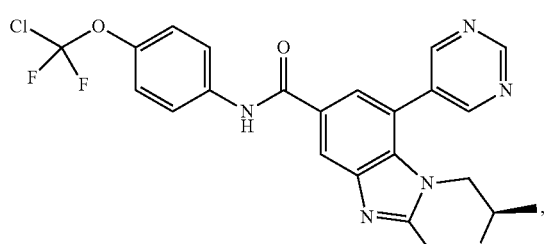
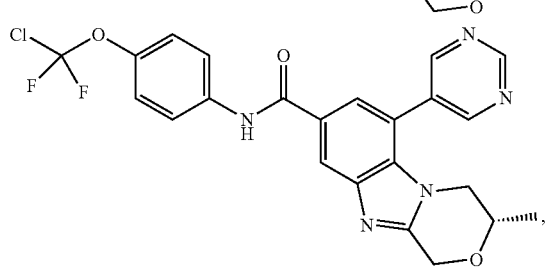
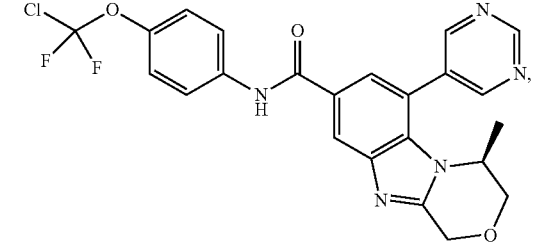
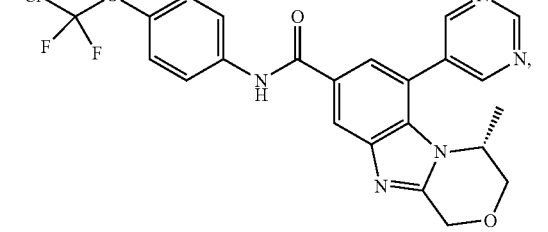
-continued
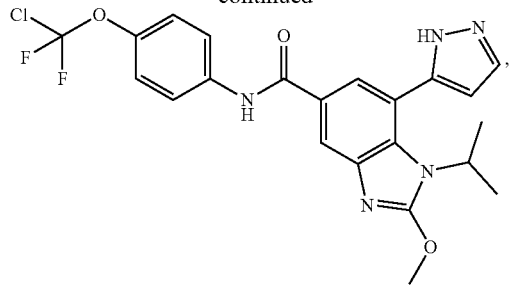
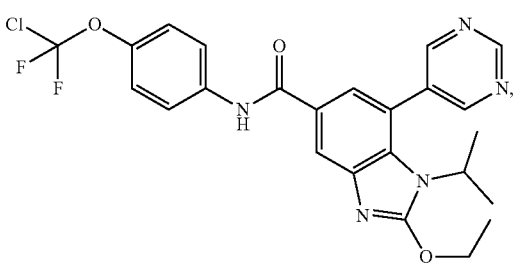
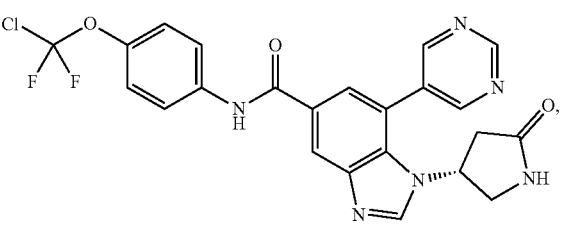
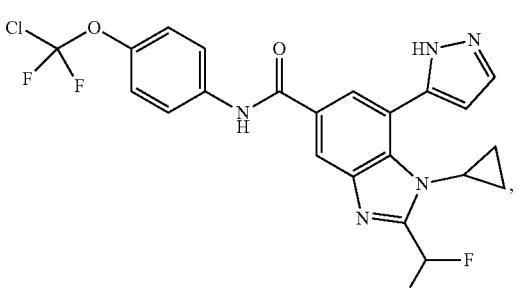
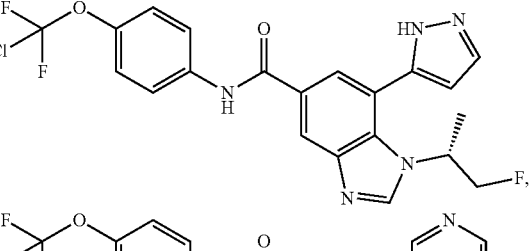
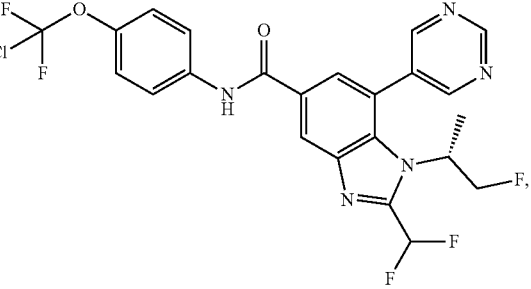

299
-continued
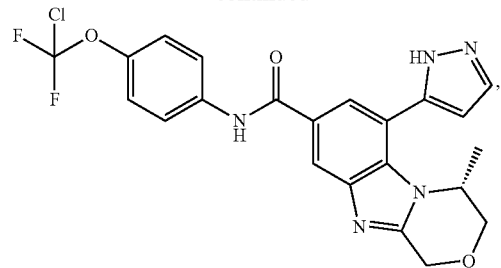
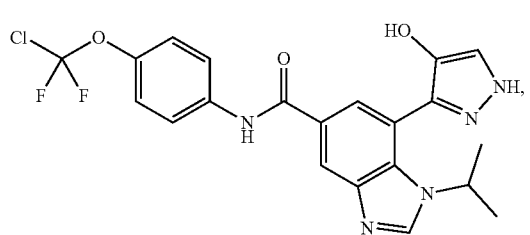
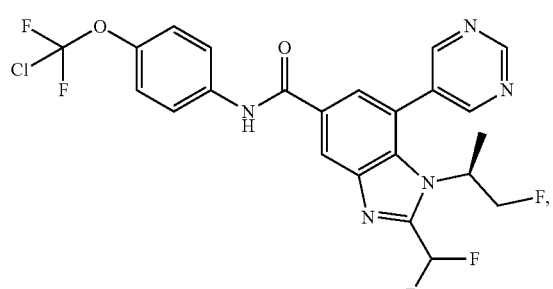
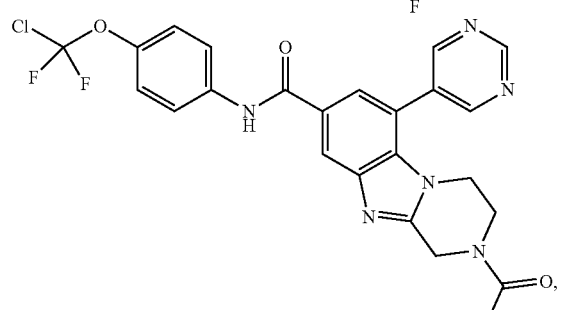
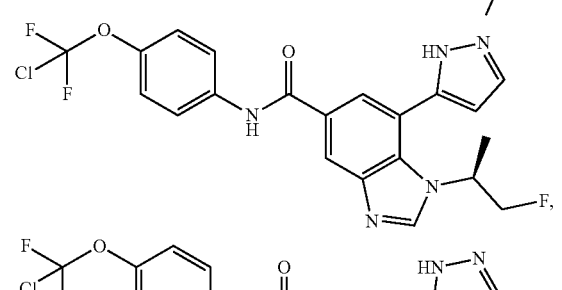
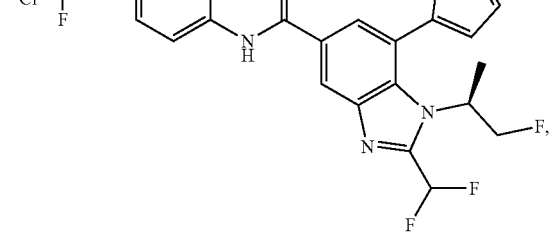
300
-continued
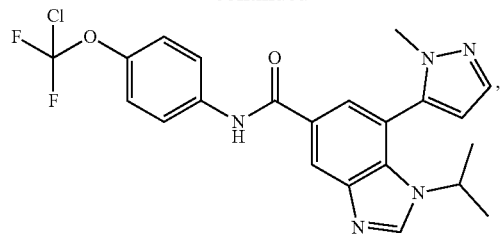
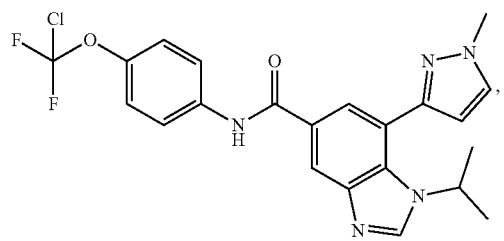
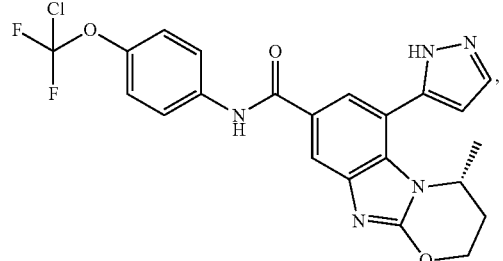
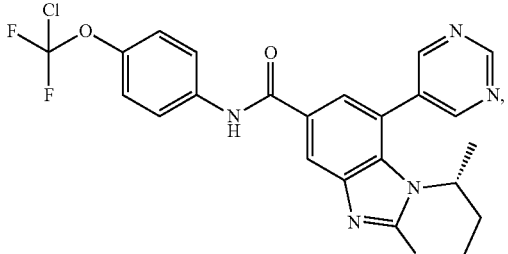
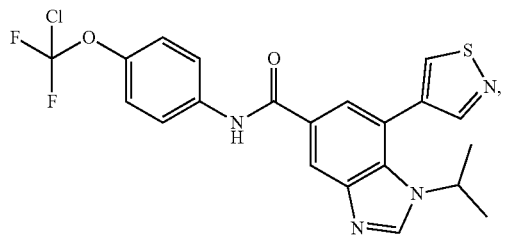
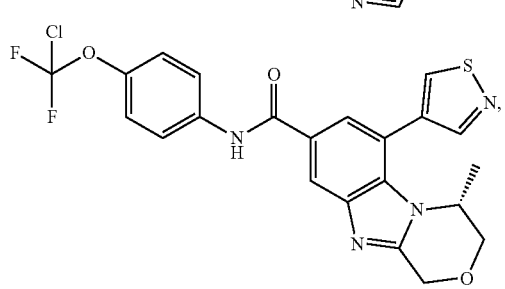

301
-continued
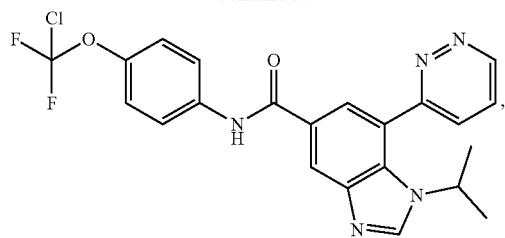
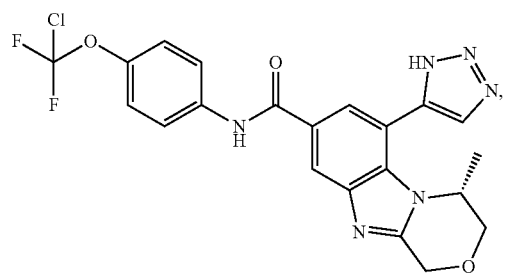
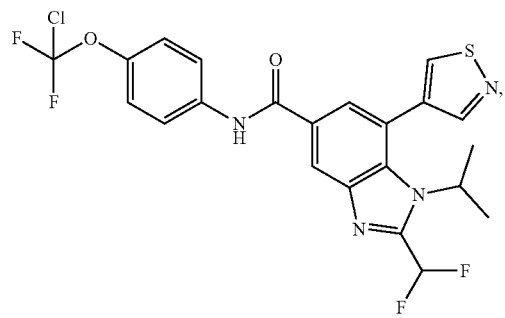
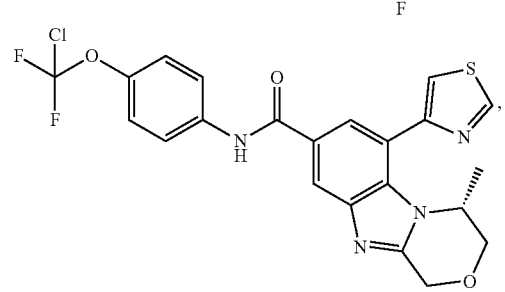
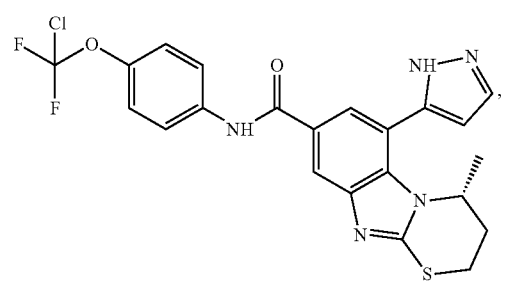
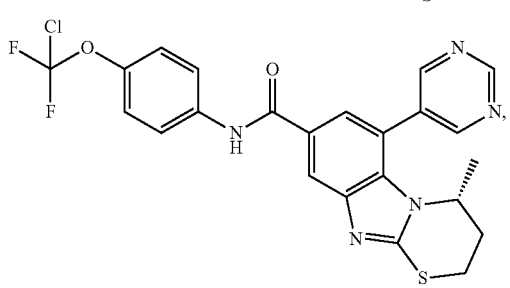
302
-continued
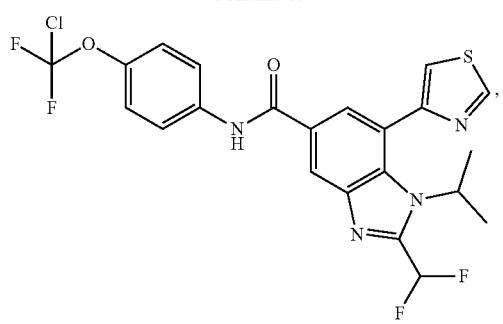
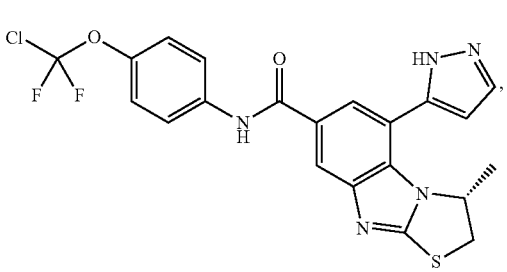
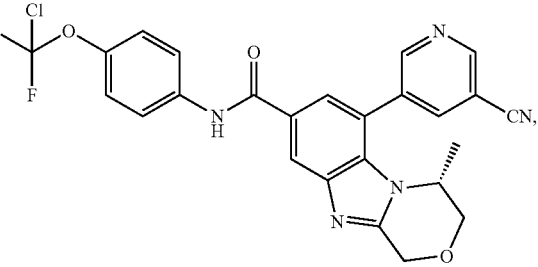
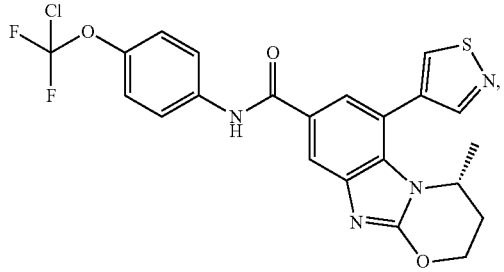
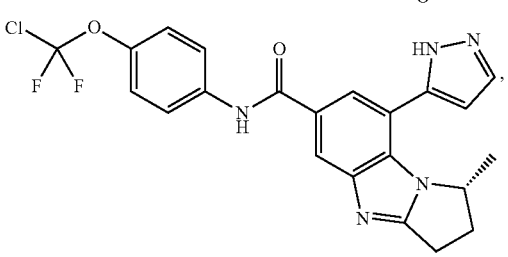
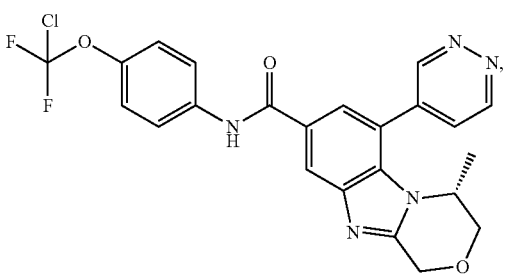

303
-continued
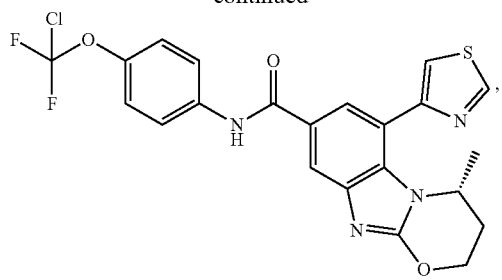
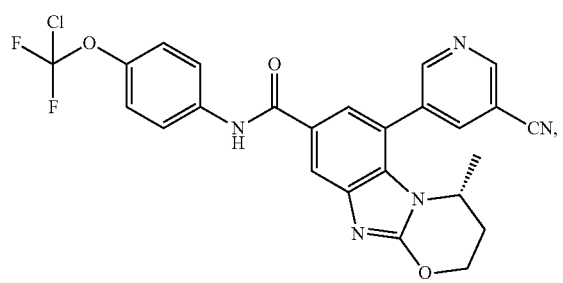
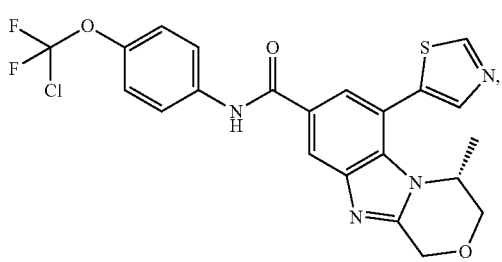
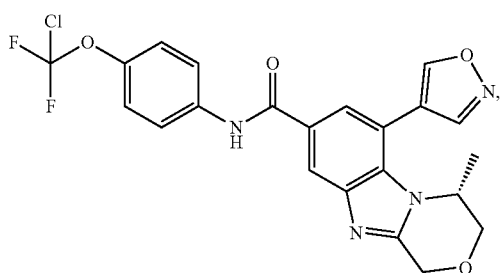
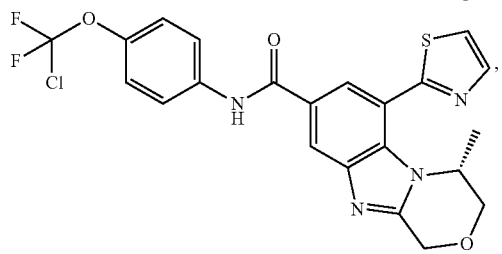
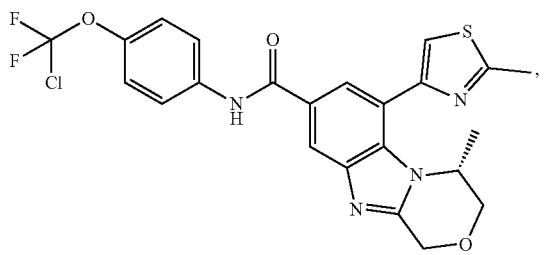
304
-continued
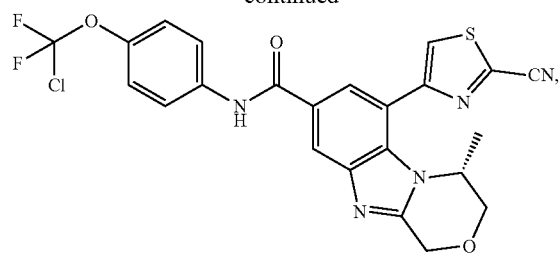
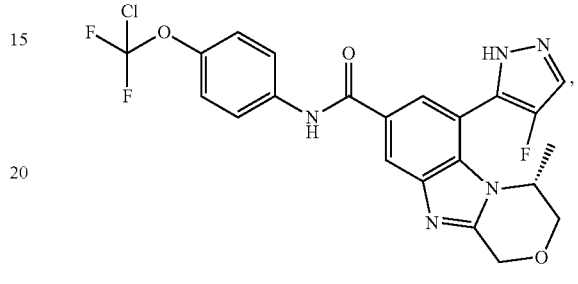
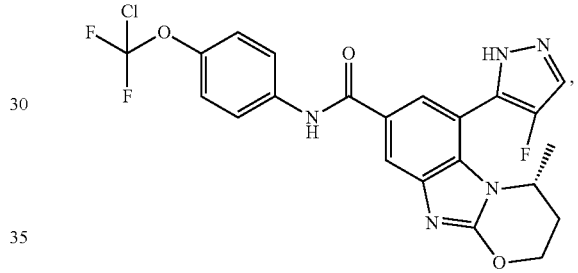
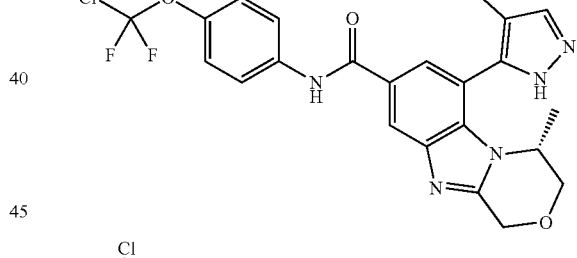
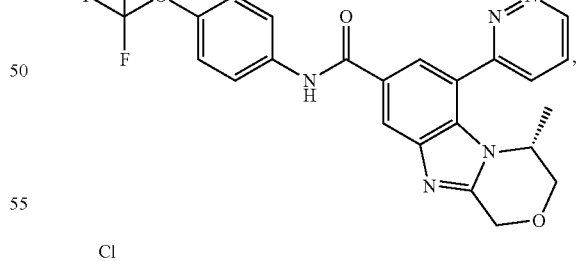
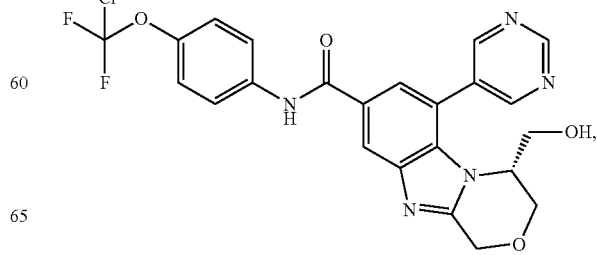

305
-continued
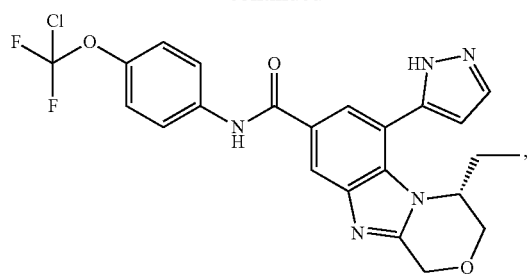
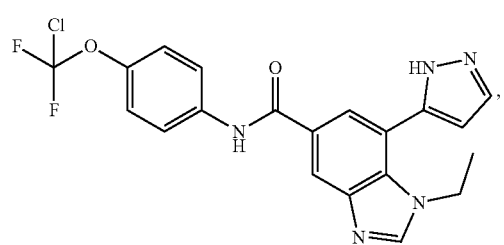
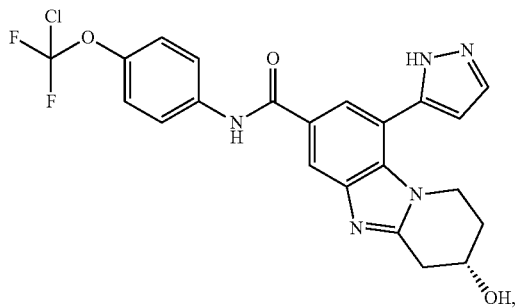
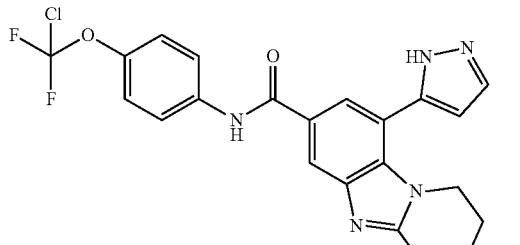
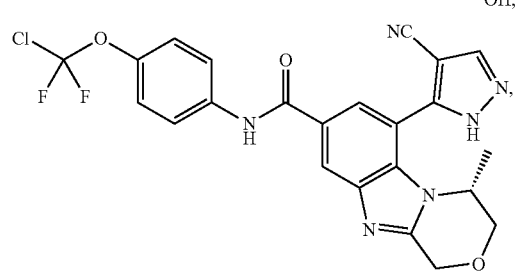
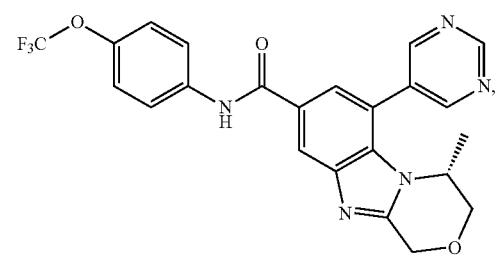
306
-continued
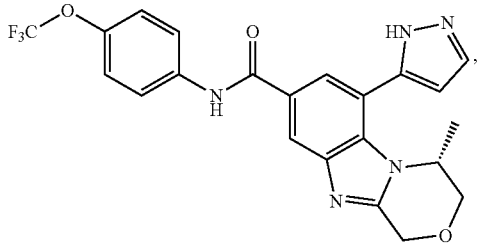
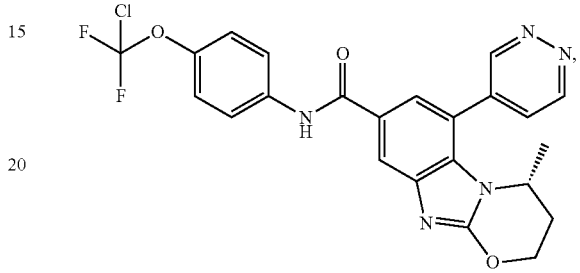
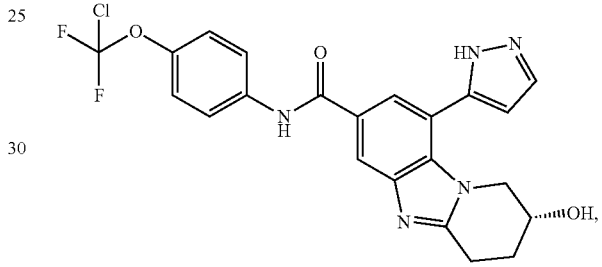
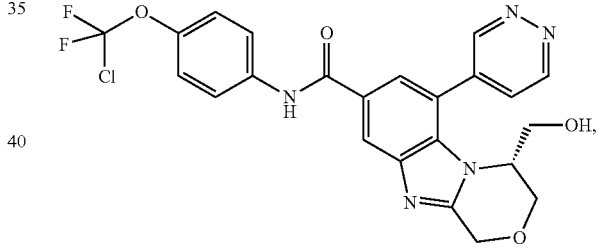
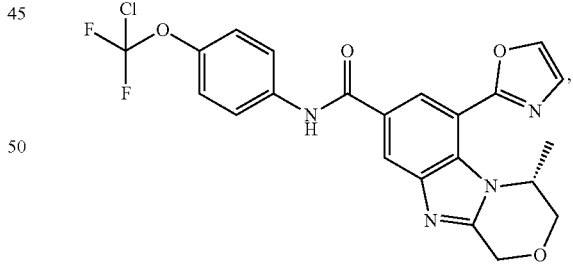
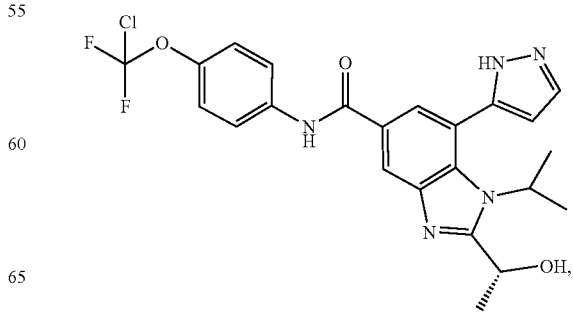

307
-continued
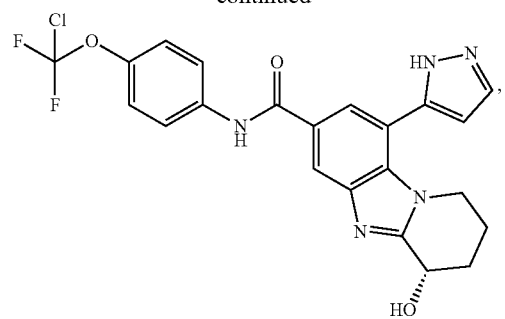
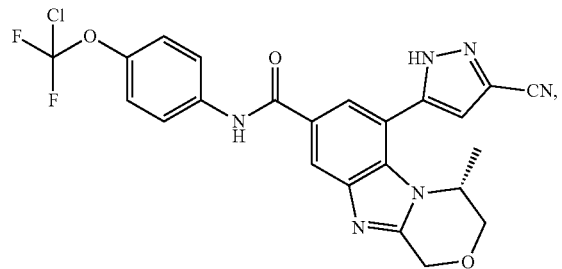
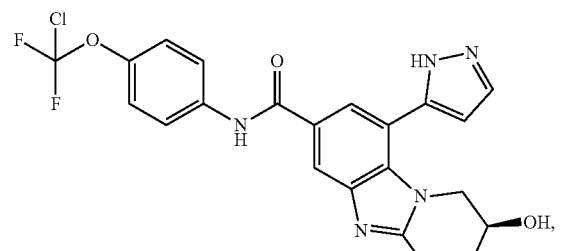
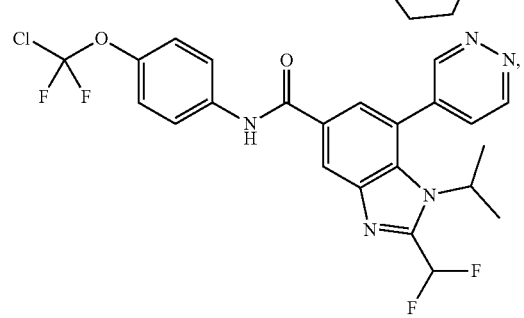
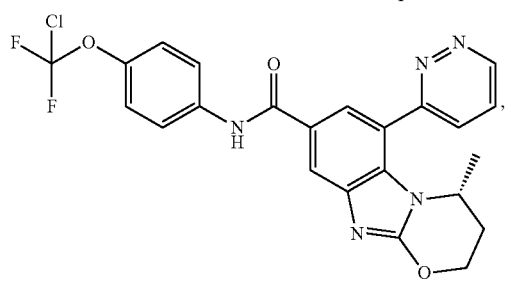
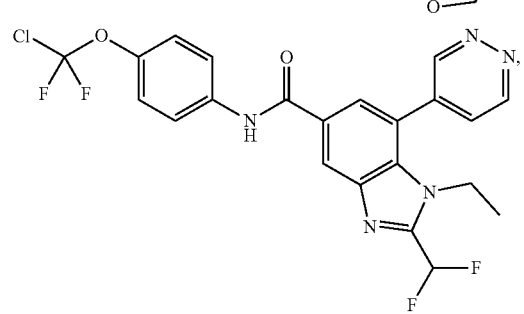
308
-continued
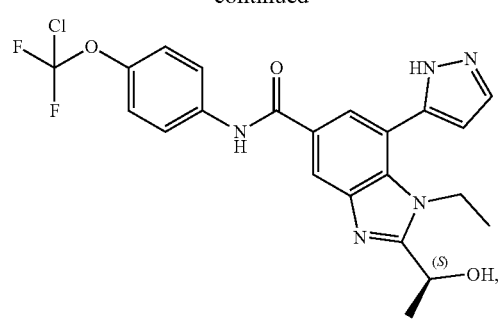
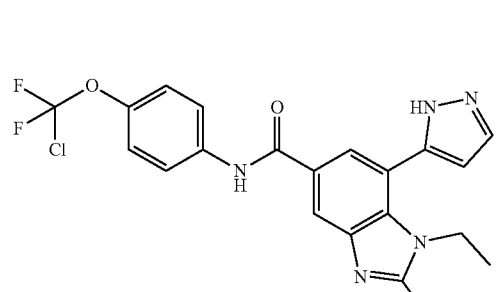
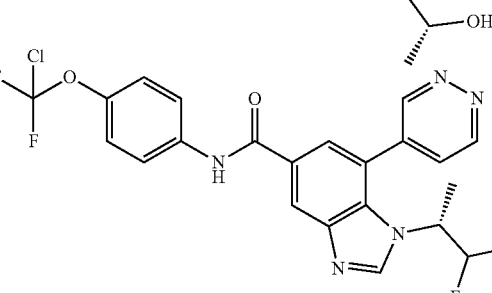
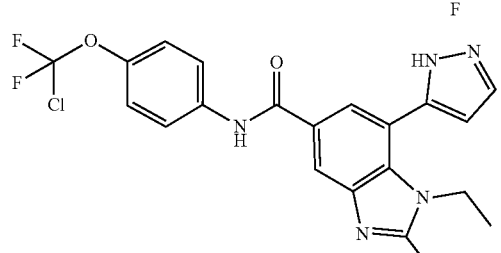
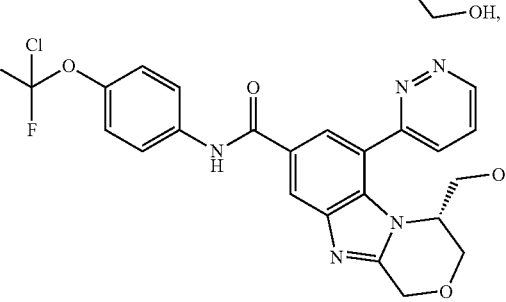
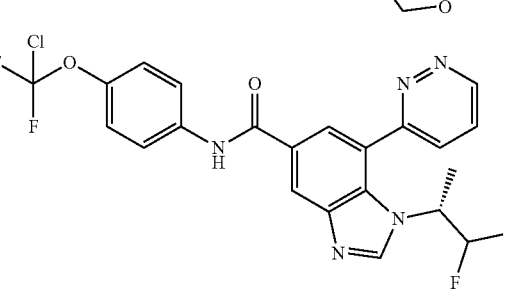

309
-continued
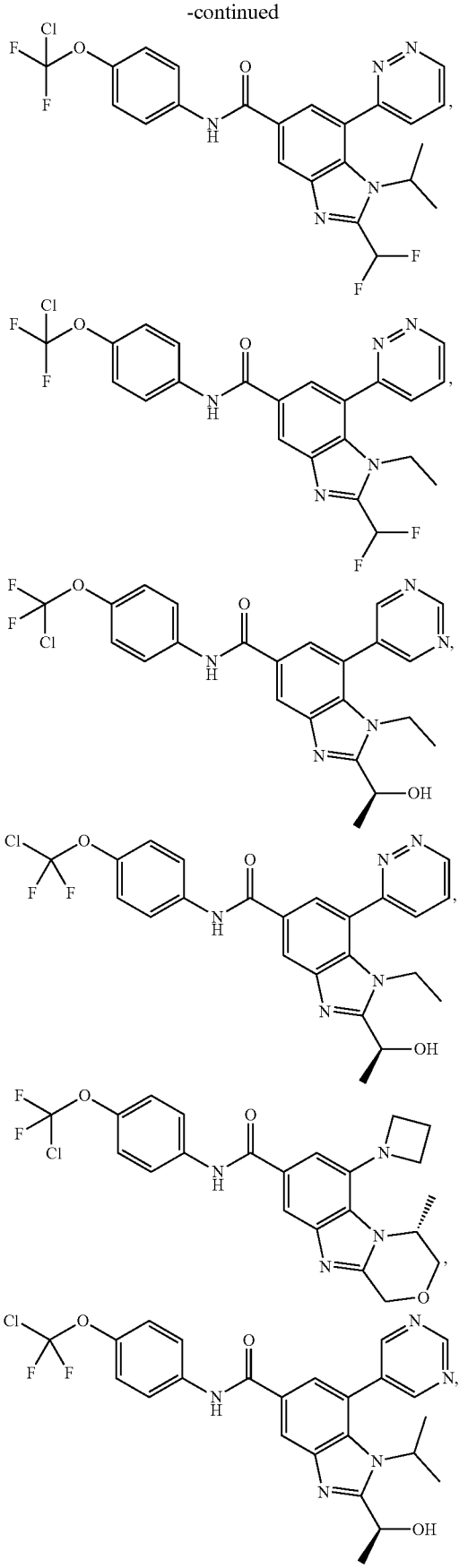
310
-continued
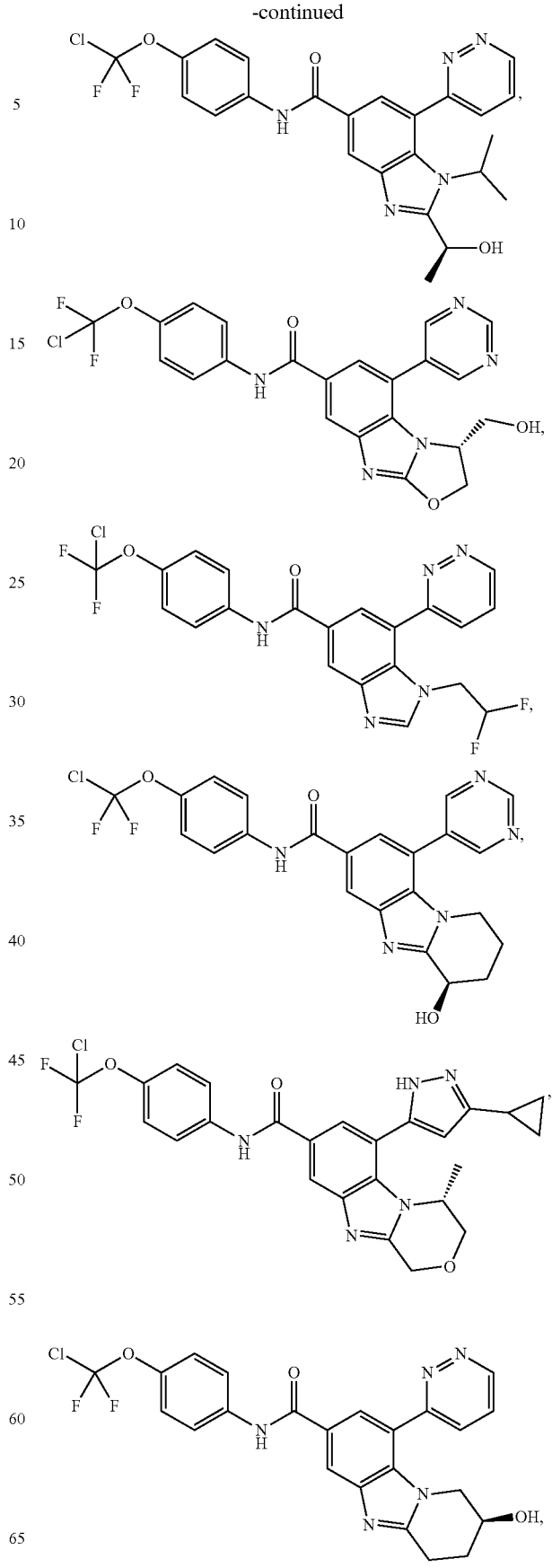

-continued
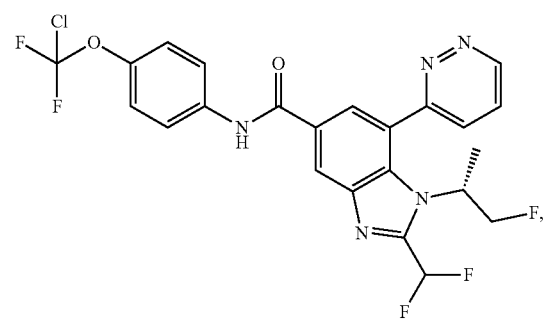
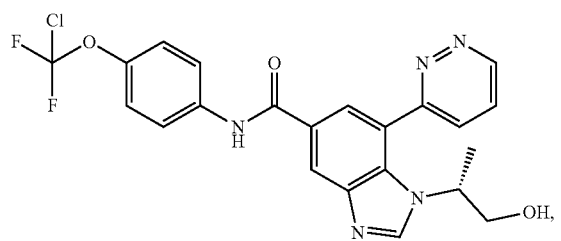
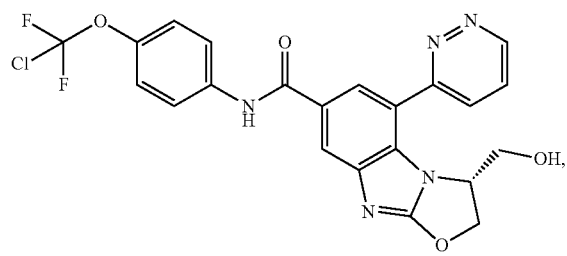
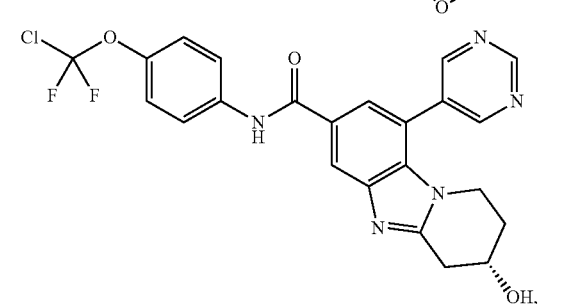
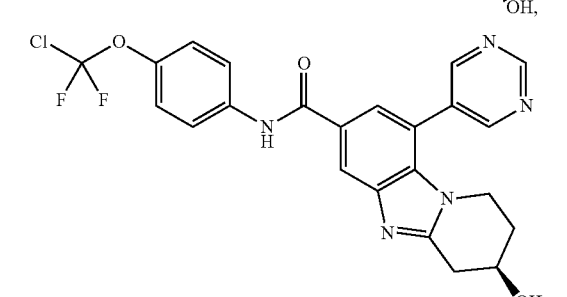
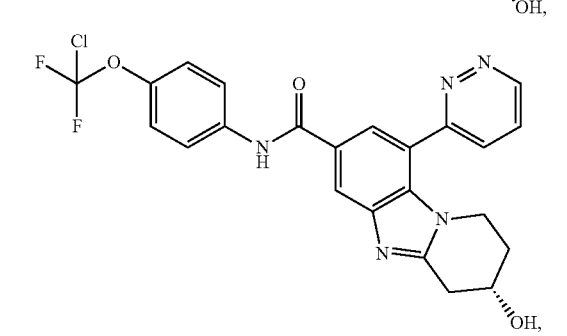
-continued
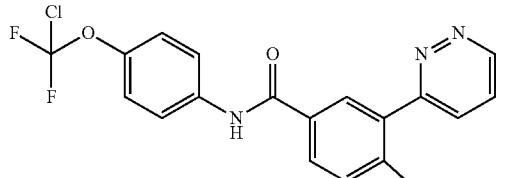
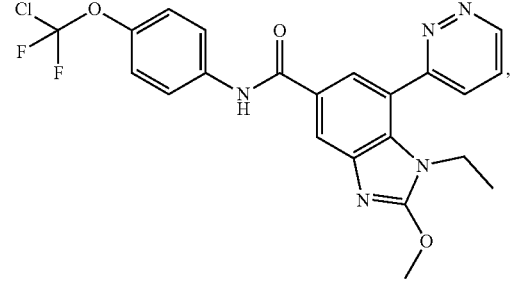
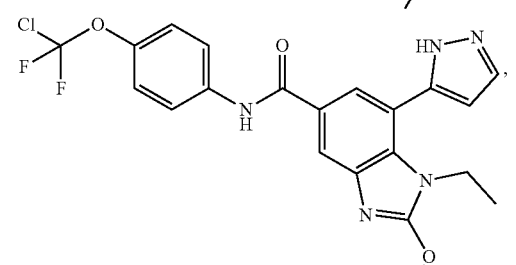
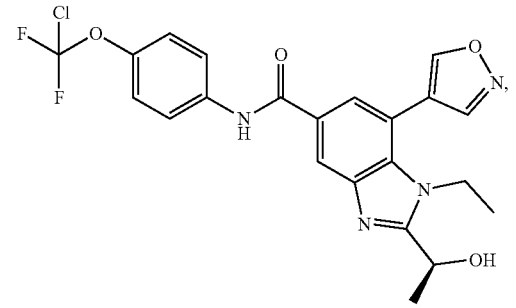
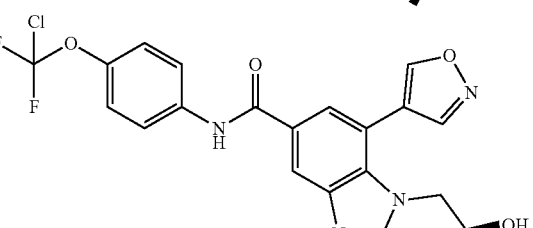
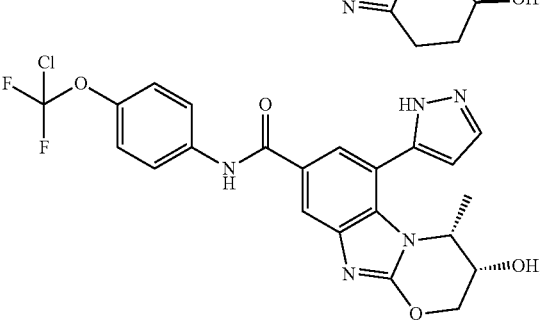

313
-continued
314
-continued
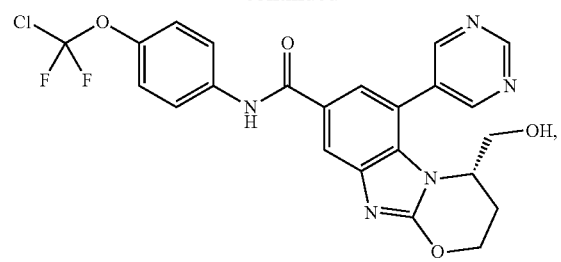
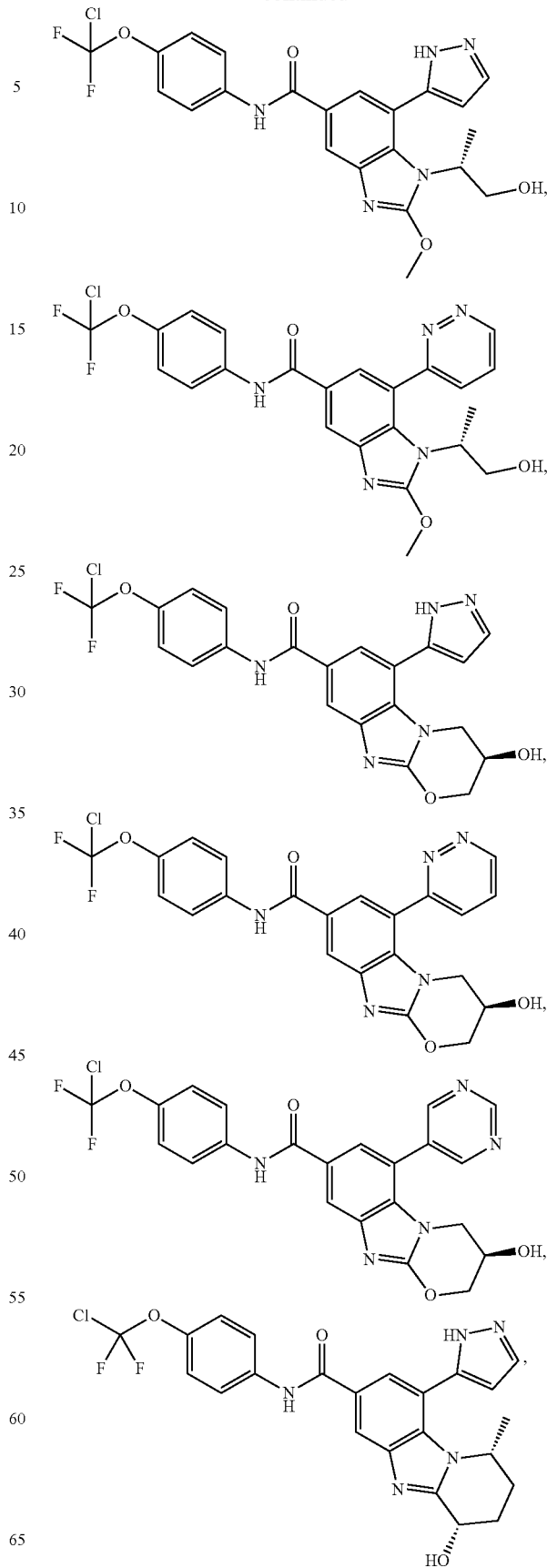

-continued
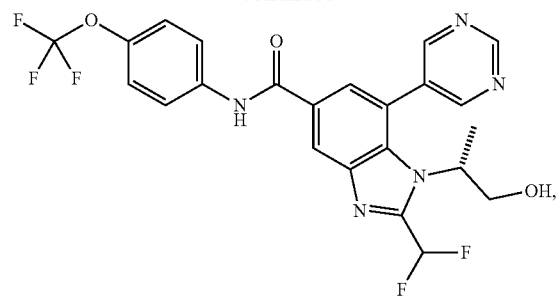
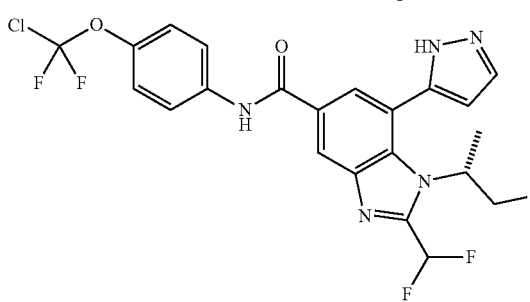
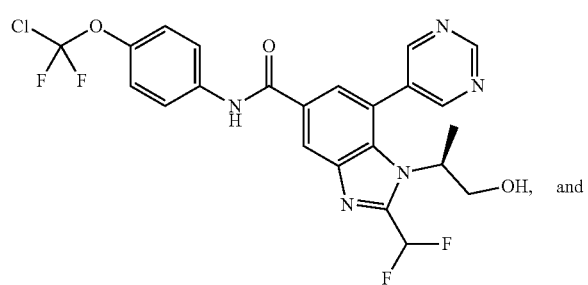
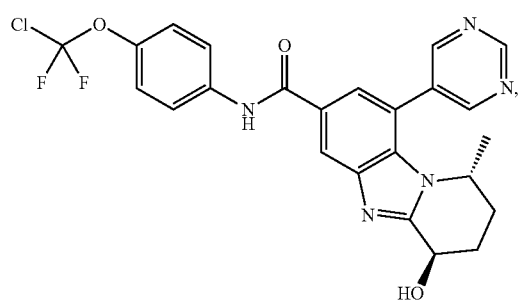
or a pharmaceutically acceptable salt or tautomer thereof.
29. The compound of claim 28, wherein the compound is selected from the group consisting of:
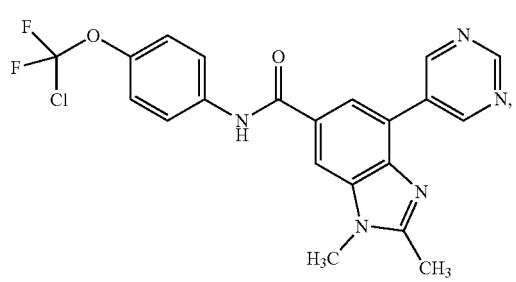
-continued
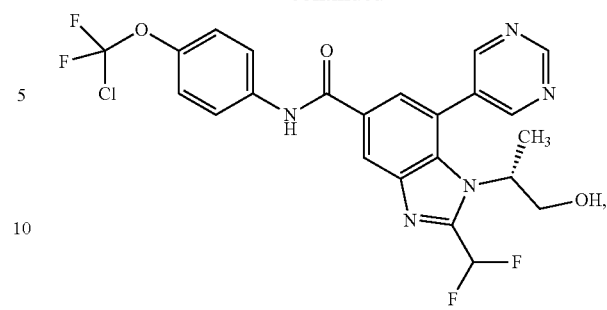
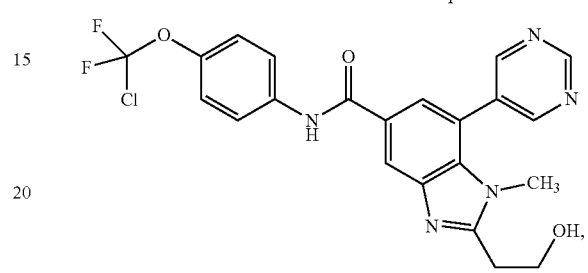
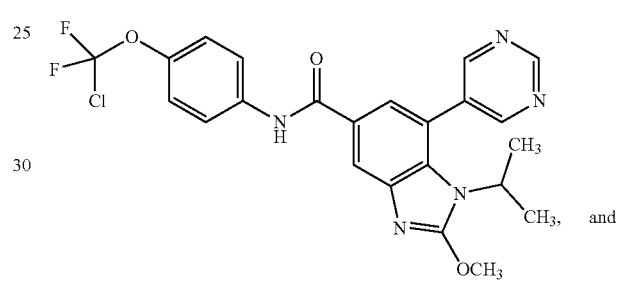
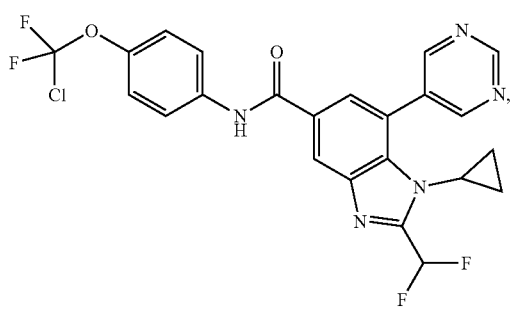
or a pharmaceutically acceptable salt or tautomer thereof.
30. The compound of claim 29, wherein the compound is:
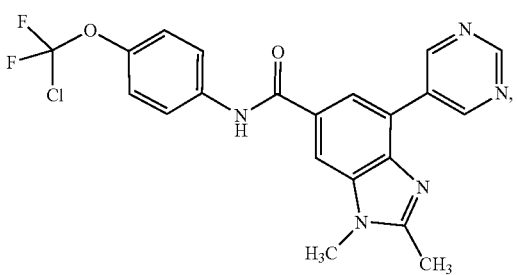 [SMILES: Cc1nc2c(-c3cncnc3)cc(C(=O)Nc3ccc(OC(F)(F)Cl)cc3)cc2n1C]
or a pharmaceutically acceptable salt or tautomer thereof.

31. The compound of claim 29, wherein the compound is:

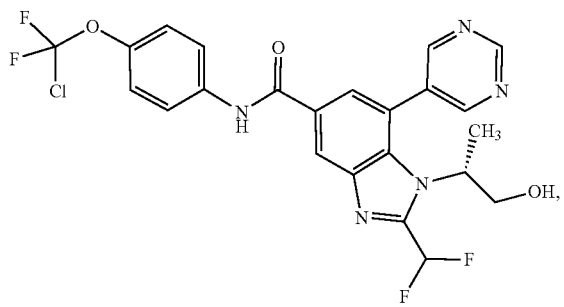 [SMILES: C[C@H](CO)n1c(C(F)F)nc2cc(C(=O)Nc3ccc(OC(F)(F)Cl)cc3)cc(-c3cncnc3)c21]

or a pharmaceutically acceptable salt or tautomer thereof.

32. The compound of claim 29, wherein the compound is:

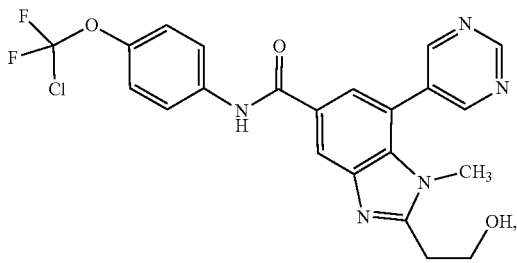 [SMILES: Cn1c(CCO)nc2cc(C(=O)Nc3ccc(OC(F)(F)Cl)cc3)cc(-c3cncnc3)c21]

or a pharmaceutically acceptable salt or tautomer thereof.

33. The compound of claim 29, wherein the compound is:

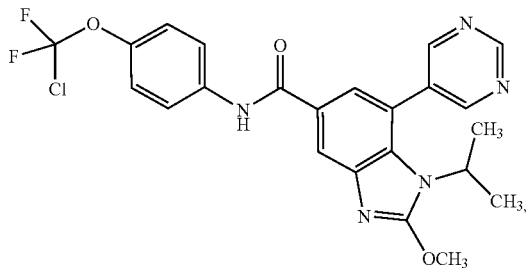 [SMILES: COc1nc2cc(C(=O)Nc3ccc(OC(F)(F)Cl)cc3)cc(-c3cncnc3)c2n1C(C)C]

or a pharmaceutically acceptable salt or tautomer thereof.

34. The compound of claim 29, wherein the compound is:

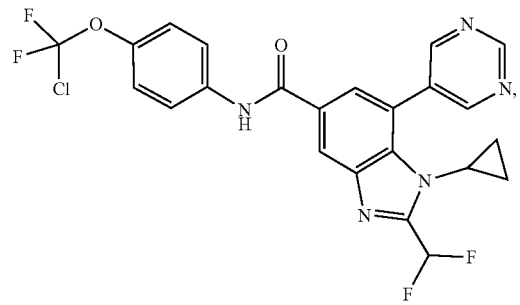 [SMILES: O=C(Nc1ccc(OC(F)(F)Cl)cc1)c1cc(-c2cncnc2)c2c(c1)nc(C(F)F)n2C1CC1]

or a pharmaceutically acceptable salt or tautomer thereof.

* * * * *